US011702472B2

(12) United States Patent
Adusumilli et al.

(10) Patent No.: US 11,702,472 B2
(45) Date of Patent: Jul. 18, 2023

(54) METHOD OF REDUCING MESOTHELIN-EXPRESSING TUMOR BURDEN BY ADMINISTRATION OF T CELLS COMPRISING MESOTHELIN-TARGETED CHIMERIC ANTIGEN RECEPTORS

(71) Applicants: MEMORIAL SLOAN-KETTERING CANCER CENTER, New York, NY (US); The U.S.A. as Represented by the Secretary, Department of Health and Human Services, Bethesda, MD (US)

(72) Inventors: Prasad S. Adusumilli, New York, NY (US); Michel Sadelain, New York, NY (US); Dimiter S. Dimitrov, Frederick, MD (US); Yang Feng, Frederick, MD (US)

(73) Assignees: MEMORIAL SLOAN-KETTERING CANCER CENTER, New York, NY (US); THE U.S.A. AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 424 days.

(21) Appl. No.: 16/821,674

(22) Filed: Mar. 17, 2020

(65) Prior Publication Data
US 2020/0239569 A1 Jul. 30, 2020

Related U.S. Application Data

(60) Division of application No. 15/368,278, filed on Dec. 2, 2016, now Pat. No. 10,633,441, which is a continuation of application No. PCT/US2015/034552, filed on Jun. 5, 2015.

(60) Provisional application No. 62/008,851, filed on Jun. 6, 2014.

(51) Int. Cl.
| | |
|---|---|
| C07K 16/28 | (2006.01) |
| C07K 14/725 | (2006.01) |
| C07K 16/30 | (2006.01) |
| C07K 14/705 | (2006.01) |
| C07K 14/47 | (2006.01) |
| A61K 39/00 | (2006.01) |
| A61K 38/00 | (2006.01) |
| A61K 35/00 | (2006.01) |

(52) U.S. Cl.
CPC .......... *C07K 16/28* (2013.01); *C07K 14/4748* (2013.01); *C07K 14/705* (2013.01); *C07K 14/7051* (2013.01); *C07K 14/70517* (2013.01); *C07K 14/70521* (2013.01); *C07K 16/30* (2013.01); *A61K 35/00* (2013.01); *A61K 38/00* (2013.01); *A61K 2039/505* (2013.01); *C07K 2317/21* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/73* (2013.01); *C07K 2317/92* (2013.01); *C07K 2319/02* (2013.01); *C07K 2319/03* (2013.01)

(58) Field of Classification Search
CPC ............ C07K 14/4748; C07K 14/7051; C07K 16/30
See application file for complete search history.

(56) References Cited

U.S. PATENT DOCUMENTS

| | | |
|---|---|---|
| 8,357,783 B2 | 1/2013 | Dimitrov et al. |
| 2003/0157132 A1 | 8/2003 | Itami et al. |
| 2011/0020361 A1 | 1/2011 | Dimitrov |
| 2014/0099309 A1 | 4/2014 | Powell, Jr. et al. |
| 2014/0099340 A1 | 4/2014 | June et al. |

FOREIGN PATENT DOCUMENTS

| | | |
|---|---|---|
| WO | WO 2009/045957 | 4/2009 |
| WO | WO 2009/120769 A1 | 10/2009 |
| WO | WO 2013/063419 A2 | 5/2013 |
| WO | WO 2013/142034 A1 | 9/2013 |
| WO | WO 2013/185552 | 12/2013 |
| WO | WO 2014/100385 A1 | 6/2014 |
| WO | WO 2015/090230 A1 | 6/2015 |

OTHER PUBLICATIONS

U.S. Appl. No. 15/368,278 (U.S. Pat. No. 10,633,441), filed Dec. 2, 2016 (Apr. 28, 2020).
U.S. Appl. No. 15/368,278, Dec. 4, 2017 Restriction Requirement.
U.S. Appl. No. 15/368,278, Mar. 27, 2018 Response to Restriction Requirement.
U.S. Appl. No. 15/368,278, Jul. 23, 2018 Non-Final Office Action.
U.S. Appl. No. 15/368,278, Oct. 23, 2018 Response to Non-Final Office Action.
U.S. Appl. No. 15/368,278, Nov. 26, 2018 Final Office Action.
U.S. Appl. No. 15/368,278, Mar. 26, 2019 Amendment and Request for Continued Examination (RCE).
U.S. Appl. No. 15/368,278, May 3, 2019 Non-Final Office Action.
U.S. Appl. No. 15/368,278, Jul. 17, 2019 Response to Non-Final Office Action.
U.S. Appl. No. 15/368,278, Jul. 31, 2019 Applicant Initiated Interview Summary.

(Continued)

*Primary Examiner* — Elly-Gerald Stoica
(74) *Attorney, Agent, or Firm* — Baker Botts L.L.P.

(57) ABSTRACT

The presently disclosed subject matter provides for methods and compositions for enhancing the immune response toward cancers and pathogens. It relates to chimeric antigen receptors (CARs) that specifically target human mesothelin, and immunoresponsive cells comprising such CARs. The presently disclosed mesothelin-targeted CARs have enhanced immune-activating properties, including anti-tumor activity.

31 Claims, 108 Drawing Sheets
Specification includes a Sequence Listing.

(56) References Cited

OTHER PUBLICATIONS

U.S. Appl. No. 15/368,278, Sep. 13, 2019 Non-Final Office Action.
U.S. Appl. No. 15/368,278, Dec. 3, 2019 Response to Non-Final Office Action.
U.S. Appl. No. 15/368,278, Dec. 18, 2019 Notice of Allowance.
U.S. Appl. No. 15/368,278, Mar. 17, 2020 Issue Fee Payment.
Adusumilli et al., "Imaging and Therapy of Malignant Pleural Mesothelioma using Replication-competent Herpes Simplex Viruses," J Gene Med. 8(5):603-615 (2006).
Adusumilli et al., "Intraoperative localization of lymph node metastases with a replication-competent herpes simplex virus," J Thorac Cardiovasc Surg 132:1179-1188 (2006).
Adusumilli et al., "Real-time diagnostic imaging of tumors and metastases by use of a replication-competent herpes vector to facilitate minimally invasive oncological surgery," FASEB J 20:726-728 (2006).
Adusumilli et al., "Regional delivery of mesothelin-targeted CAR T cell therapy generates potent and long-lasting CD4-dependent tumor immunity," Science Translational Medicine 6:261ra151 (2014).
Adusumilli et al., "Virally-directed fluorescent imaging (VFI) can facilitate endoscopic staging," Surg. Endosc. 20:628-635 (2006).
Adusumilli, "Translational Immunotherapeutics: Chemoimmunotherapy for Malignant Pleural Mesothelioma," Cancer 3268-3271 (2014).
Amati et al., "Profiling Tumor-Associated Markers for Early Detection of Malignant Mesothelioma: an Epidemiologic Study," Cancer Epidemiol Biomarkers Prev 17(1):163-170 (2008).
Anraku et al., "Impact of tumor-infiltrating T cells on survival in patients with malignant pleural mesothelioma," J Thorac Cardiovasc Surg 135:823-829 (2008).
Antony et al., "Management of malignant pleural effusions," Eur Respir J 18:402-419 (2001).
Argani et al., "Mesothelin is Overexpressed in the Vast Majority of Ductal Adenocarcinomas of the Pancreas: Identification of a New Pancreatic Cancer Marker by Serial Analysis of Gene Expression (SAGE)," Clin Cancer Res 7:3862-3868 (2001).
Barber et al., "Restoring function in exhausted CD8 T cells during chronic viral infection," Nature 439:682-687 (2006).
Baselga et al., "Randomized Phase II Study of the Anti-Epidermal Growth Factor Receptor Monoclonal Antibody Cetuximab with Cisplatin Versus Cisplatin Alone in Patients With Metastatic Triple-Negative Breast Cancer," J Clin Oncol 31(20):2586-2592 (2013).
Beatty et al., "Mesothelin-Specific Chimeric Antigen Receptor mRNA-Engineered T cells Induce Anti-Tumor Activity in Solid Malignancies," Cancer Immunol Res 2(2):112-120 (2013).
Bekaii-Saab et al., "A phase I trial of paclitaxel and trastuzumab in combination with interleukin-1 2 in patients with HER2/neu-expressing malignancies," Mol. Cancer Ther 8(11):2983-2991 (2009).
Bera et al., "Mesothelin Is Not Required for Normal Mouse Development or Reproduction," Mol. Cell Biol. 20(8):2902-2906 (2000).
Bharadwaj et al., "Mesothelin-Induced Pancreatic Cancer Cell Proliferation Involves Alteration of Cyclin E via Activation of Signal Transducer and Activator of Transcription Protein 3," Mol Cancer Res 6(11):1755-1765 (2008).
Boggio et al., "Ability of Systemic Interleukin-12 to Hamper Progressive Stages of Mammary Carcinogenesis in HER2/neu Transgenic Mice," Cancer Res 60:359-364 (2000).
Bograd et al., "Immune responses and immunotherapeutic interventions in malignant pleural mesothelioma," Cancer Immunol Immunother 60:1509-1527 (2011).
Bollard et al., "Adapting a transforming growth factor β-related tumor protection strategy to enhance antitumor immunity," Blood 99:3179-3187 (2002).
Bramson et al., "Direct Intratumoral Injection of an Adenovirus Expressing Interleukin-12 Induces Regression and Long-Lasting Immunity That Is Associated with Highly Localized Expression of Interleukin-12," Hum Gene Ther 7:1995-2002 (1996).
Brentjens et al., "CD19-Targeted T cells Rapidly Induce Molecular Remissions in Adults with Chemotherapy-Refractory Acute Lymphoblastic Leukemia," Science Translational Medicine 5:177ra38 (2013).
Brentjens et al., "Eradication of systemic B-cell tumors by genetically targeted human T lymphocytes co-stimulated by CD80 and interleukin-15," Nat Med 9(3):279-86 (2003).
Brentjens et al., "Genetically Targeted T Cells Eradicate Systemic Acute Lymphoblastic Leukemia Xenografts," Clin Cancer Res 13(18):5426-5435 (2007).
Brentjens et al., "Safety and persistence of adoptively transferred autologous CD19-targeted T cells in patients with relapsed or chemotherapy refractory B-cell leukemias," Blood 118(18):4817-4828 (2011).
Brown et al., "Blockade of Programmed Death-1 Ligands on Dendritic Cells Enhances T Cell Activation and Cytokine Production," Journal of Immunology 170:1257-1266 (2003).
Brunda et al., "Antitumor and Antimetastatic Activity of Interleukin 12 against Murine Tumors," J. Exp. Med. 178:1223-1230 (1993).
Carey et al., "Triple-negative breast cancer: disease entity or title of convenience?" Nat. Rev. Clin. Oncol. 7:683-692 (2010).
Carpenito et al., "Control of large, established tumor xenografts with genetically retargeted human T cells containing CD28 and CD137 domains," PNAS USA 106(9):3360-3365 (2009).
Carpenter et al., "Regional Liver Therapy Using Oncolytic Virus to Target Hepatic Colorectal Metastases," Semin Oncol 37:160-169 (2010).
Carter et al., "PD-1:PD-L inhibitory pathway affects both CD4(+) and CD8(+) T cells and is overcome by IL-2," Eur. J. Immunol. 32:634-643 (2002).
Chmielewski et al., "IL-12 Release by Engineered T Cells Expressing Chimeric Antigen Receptors Can Effectively Muster an Antigen-Independent Macrophage Response on Tumor Cells That Have Shut Down Tumor Antigen Expression," Cancer Res 71(17):5697-5706 (2011).
Chmielewski et al., "T Cell Activation by Antibody-Like Immunoreceptors: Increase in Affinity of the Single-Chain Fragment Domain above Threshold Does Not Increase T cell Activation against Antigen-Positive Target Cells but Decreases Selectivity," Journal of Immunology 173:7647-7653 (2004).
Cooper et al., "Manufacturing of gene-modified cytotoxic T lymphocytes for autologous cellular therapy for lymphoma," Cytotherapy 8(2):105-117 (2006).
Crane et al., "PI(3) kinase is associated with a mechanism of immunoresistance in breast and prostate cancer," Oncogene 28:306-312 (2009).
Curran et al., "Systemic 4-1BB activation induces a novel T cell phenotype driven by high expression of Eomesodermin," J. Exp. Med. 210(4):743-755 (2013).
Curtsinger et al., "Signal 3 Determines Tolerance versus Full Activation of Naive CD8 T Cells: Dissociating Proliferation and Development of Effector Function," J. Exp. Med. 197(9):1141-1151 (2003).
Czerniecki et al., "Targeting HER-2/neu in Early Breast Cancer Development Using Dendritic Cells with Staged Interleukin-12 Burst Secretion," Cancer Res 67(4):1842-1852 (2007).
Davila et al., "CD19 CAR-Targeted T Cells Induce Long-Term Remission and B Cell Aplasia in an Immunocompetent Mouse Model of B Cell Acute Lymphoblastic Leukemia," PLoS ONE 8(4):e61338 (2013).
Davila et al., "Efficacy and Toxicity Management of 19-28z CAR T Cell Therapy in B Cell Acute Lymphoblastic Leukemia," Science Translational Medicine 6:224ra225 (2014).
Del Vecchio et al., "Interleukin-12: Biological Properties and Clinical Application," Clin Cancer Res 13(16):4677-4685 (2007).
Dent et al., "Triple-Negative Breast Cancer: Clinical Features and Patterns of Recurrence," Clin Cancer Res 13(15):4429-4434 (2007).
Di Stasi et al., "Inducible Apoptosis as a Safety Switch for Adoptive Cell Therapy," N Engl J Med 365:1673-1683 (2011).
Dong et al., "Tumor-associated B7-H1 promotes T-cell apoptosis: A potential mechanism of immune evasion," Nature Medicine 8(8):793-800 (2002).

(56) References Cited

OTHER PUBLICATIONS

Dudley et al., "Adoptive Cell Therapy for Patients With Metastatic Melanoma: Evaluation of Intensive Myeloablative Chemoradiation Preparative Regimens," J Clin Oncol 26:5233-5239 (2008).
Einama et al., "Luminal membrane expression of mesothelin is a prominent poor prognostic factor for gastric cancer," Br J Cancer 107:137-142 (2012).
Eisenberg et al., "Real-Time Intraoperative Detection of Breast Cancer Axillary Lymph Node Metastases Using a Green Fluorescent Protein-Expressing Herpes Virus," Ann. Surg. 243:824-832 (2006).
Eliopoulos et al., "Neo-Organoid of Marrow Mesenchymal Stromal Cells Secreting Interleukin-12 for Breast Cancer Therapy," Cancer Res 68(12):4810-4818 (2008).
Engels et al., "Long-term Persistence of CD4(+) but Rapid Disappearance of CD8(+) T Cells Expressing an MHC Class I-restricted TCR of Nanomolar Affinity," Mol Ther. 20(3):652-660 (2012).
Estep et al., "High throughput solution-based measurement of antibody-antigen affinity and epitope binning," mAbs, 5(2):270-278 (2013).
Fedorov et al., "Novel Approaches to Enhance the Specificity and Safety of Engineered T Cells," Cancer 120:160-165 (2014).
Fedorov et al., "PD-1- and CTLA-4-Based Inhibitory Chimeric Antigen Receptors (iCARs) Divert Off-Target Immunotherapy Responses," Science Translational Medicine 5:215ra172 (2013).
Feng et al., "A novel human monoclonal antibody that binds with high affinity to mesothelin-expressing cells and kills them by antibody-dependent cell-mediated cytotoxicity," Mol Cancer Ther 8(5):1113-1118 (2009).
Formenti et al., "Systemic effects of local radiotherapy," Lancet Oncol 10:718-726 (2009).
Foster et al., "Antitumor Activity of EBV-specific T Lymphocytes Transduced With a Dominant Negative TGF-β Receptor," J Immunother 31:500-505 (2008).
Freeman et al., "Engagement of the PD-1 Immunoinhibitory Receptor by a Novel B7 Family Member Leads to Negative Regulation of Lymphocyte Activation," J. Exp. Med. 192(7):1027-1034 (2000).
Frierson et al., "Large-Scale Molecular and Tissue Microarray Analysis of Mesothelin Expression in Common Human Carcinomas," Hum Pathol 34:605-609 (2003).
Gade et al., "Targeted Elimination of Prostate Cancer by Genetically Directed Human T Lymphocytes," Cancer Res 65(19):9080-9088 (2005).
Ge et al., "Blockade of PD-1/PD-L1 immune checkpoint during DC vaccination induces potent protective immunity against breast cancer in hu-SCID mice," Cancer Letters 336:253-259 (2013).
Ghebeh et al., "FOXP3+ Tregs and B7-H1+/PD-I+ T lymphocytes co-infiltrate the tumor tissues of high-risk breast cancer patients: Implication for immunotherapy," BMC Cancer 8:57 (2008).
Ghebeh et al., "The B7-H1 (PD-L1) T Lymphocyte-Inhibitory Molecule is Expressed in Breast Cancer Patients with Infiltrating Ductal Carcinoma: Correlation with Important High-Risk Prognostic Factors," Neoplasia 8(3):190-198 (2006).
Gong et al., "Cancer Patient T cells Genetically Targeted to Prostate-Specific Membrane Antigen Specifically Lyse Prostate Cancer Cells and Release Cytokines in Response to Prostate-Specific Membrane Antigen," Neoplasia. 1(2): 123-127 (1999).
Grupp et al., "Chimeric Antigen Receptor-Modified T cells for Acute Lymphoid Leukemia," N Engl J Med 368:1509-1518 (2013).
Gubbels et al., "Mesothelin-MUC 16 binding is a high affinity, N-glycan dependent interaction that facilitates peritoneal metastasis of ovarian tumors," Molecular Cancer 5:50 (2006).
Gyorffy et al., "Combined Treatment of a Murine Breast Cancer Model with Type 5 Adenovirus Vectors Expressing Murine Angiostatin and IL-12: A Role for Combined Anti-Angiogenesis and Immunotherapy," J Immunol 166:6212-6217 (2001).
Hamid et al., "A prospective phase II trial exploring the association between tumor microenvironment biomarkers and clinical activity of ipilimumab in advanced melanoma," Journal of Translational Medicine 9:204 (2011).
Hamid et al., "Safety and Tumor Responses with Lambrolizumab (Anti-PD-1) in Melanoma," N Engl J Med 369:134-144 (2013).
Hassan et al., "Phase II Clinical Trial of Amatuximab, a Chimeric Anti-Mesothelin Antibody with Pemetrexed and Cisplatin in Advanced Unresectable Pleural Mesothelioma," Clin Cancer Res 20(23):5927-5936 (2014).
Hassan et al., "Major Cancer Regressions in Mesothelioma After Treatment with an Anti-Mesothelin Immunotoxin and Immune Suppression," Science Translational Medicine 5:208ra147 (2013).
Hassan et al., "Mesothelin is Overexpressed in Pancreaticobiliary Adenocarcinomas but Not in Normal Pancreas and Chronic Pancreatitis," Am J Clin Pathol 124:838-845 (2005).
Hassan et al., "Mesothelin targeted cancer immunotherapy," Eur J Cancer 44:46-53 (2008).
Hassan et al., "Phase I Clinical Trial of the Chimeric Anti-Mesothelin Monoclonal Antibody MORAb-009 in Patients with Mesothelin-Expressing Cancers," Clin Cancer Res 16(24):6132-6138 (2010).
Hassan et al., "Phase I Study of SS1P, a Recombinant Anti-Mesothelin Immunotoxin Given as a Bolus I.V. Infusion to Patients with Mesothelin-Expressing Mesothelioma, Ovarian, and Pancreatic Cancers," Clin Cancer Res 13(17):5144-5149 (2007).
Hirschhom-Cymerman et al., "Induction of tumoricidal function in CD4+ T cells is associated with concomitant memory and terminally differentiated phenotype," J. Exp. Med. 209(11):2113-2126 (2012).
Ho et al., "Humoral Immune Response to Mesothelin in Mesothelioma and Ovarian Cancer Patients," Clin Cancer Res 11(10):3814-3820 (2005).
Hodi et al., "Improved Survival with Ipilimumab in Patients with Metastatic Melanoma," N Engl J Med 363:711-723 (2010).
Hollyman et al., "Manufacturing Validation of Biologically Functional T cells Targeted to CD19 Antigen for Autologous Adoptive Cell Therapy," J Immunother 32:169-180 (2009).
Hombach et al., "T Cell Activation by Antibody-Like Immunoreceptors: The Position of the Binding Epitope within the Target Molecule Determines the Efficiency of Activation of Redirected T Cells," Journal of Immunology 178:4650-4657 (2007).
Hunder et al., "Treatment of Metastatic Melanoma with Autologous CD4+ T Cells against NY-ESO-1," N Engl J Med 358:2698-2703 (2008).
International Search Report dated Dec. 4, 2015 in International Application No. PCT/US15/34552.
James et al., "Antigen Sensitivity of CD22-Specific Chimeric TCR Is Modulated by Target Epitope Distance from the Cell Membrane," Journal of Immunology 180:7028-7038 (2008).
James et al., "Mathematical Modeling of Chimeric TCR Triggering Predicts the Magnitude of Target Lysis and Its Impairment by TCR Downmodulation," Journal of Immunology 184:4284-4294 (2010).
Jensen et al., "Design and implementation of adoptive therapy with chimeric antigen receptor-modified T cells," Immunol Rev. 257:127-144 (2014).
Ji et al., "An immune-active tumor microenvironment favors clinical response to ipilimumab," Cancer Immunol Immunother 61:1019-1031 (2012).
John et al., "Anti-PD-1 Antibody Therapy Potently Enhances the Eradication of Established Tumors by Gene-Modified T cells," Clin Cancer Res 19(20):5636-5646 (2013).
Kachala et al., "Mesothelin Overexpression is a Marker of Tumor Aggressiveness and Is Associated with Reduced Recurrence-Free and Overall Survival in Early-Stage Lung Adenocarcinoma," Clin Cancer Res 20(4):1020-1028 (2014).
Kalos et al., "T cells with Chimeric Antigen Receptors have Potent Antitumor Effects and Can Establish Memory in Patients with Advanced Leukemia," Science Translational Medicine 3:95ra73 (2011).
Kaneko et al., "A Binding Domain on Mesothelin for CA125/MUC16," J Biol Chem 284(6):3739-3749 (2009).
Kang et al., "Interleukin 12 Gene Therapy of Cancer by Peritumoral Injection of Transduced Autologous Fibroblasts: Outcome of a Phase I Study," Hum Gene Ther 12:671-684 (2001).

(56) References Cited

OTHER PUBLICATIONS

Kao et al., "Transcription factor T-bet represses expression of the inhibitory receptor PD-1 and sustains virus-specific CD8+ T cell responses during chronic infection," Nature Immunology 12(7):663-671 (2011).

Kawamata et al., "Intracellular localization of mesothelin predicts patient prognosis of extrahepatic bile duct cancer," Int J Oncol. 41:2109-2118 (2012).

Kelly et al., "Mesothelin-Targeted Agents in Clinical Trials and in Preclinical Development," Mol. Cancer Ther 11(3):517-525 (2012).

Kershaw et al., "Gene-Engineered T cells as a Superior Adjuvant Therapy for Metastatic Cancer," J Immunol 173:2143-2150 (2004).

Kim et al., "Tumor-infiltrating Lymphocytes, Tumor Characteristics, and Recurrence in Patients With Early Breast Cancer," Am J Clin Oncol 36(3):224-231 (2012).

Kitahara et al., "Establishment of interleukin 2 dependent cytotoxic T lymphocyte cell line specific for autologous brain tumor and its intracranial administration for therapy of the tumor," Journal of Neuro-Oncology 4:329-336 (1987).

Kloss et al., "Combinatorial antigen recognition with balanced signaling promotes selective tumor eradication by engineered T cells," Nat Biotechnol. 31(1):71-75 (2013).

Kochenderfer et al., "Donor-derived CD 19-targeted T cells cause regression of malignancy persisting after allogeneic hematopoietic stem cell transplantation," Blood 122(25):4129-4139 (2013).

Koehler et al., "CD28 Costimulation Overcomes Transforming Growth Factor-β-Mediated Repression of Proliferation of Redirected Human CD4+ and CD8+ T Cells in an Antitumor Cell Attack," Cancer Res 67(5):2265-2273 (2007).

Krause et al., "Antigen-dependent CD28 Signaling Selectively Enhances Survival and Proliferation in Genetically Modified Activated Human Primary T Lymphocytes," J. Exp. Med. 188(4):619-626 (1998).

Kuo et al., "Molecular Characteristics and Metastasis Predictor Genes of Triple-Negative Breast Cancer: A Clinical Study of Triple-Negative Breast Carcinomas," PLoS ONE 7(9):e45831 (2012).

Lanitis et al., "Redirected Antitumor Activity of Primary Human Lymphocytes Transduced With a Fully Human Anti-mesothelin Chimeric Receptor," Mol Ther., 20(3):633-643 (2012).

Latouche et al., "Induction of human cytotoxic T lymphocytes by artificial antigen-presenting cells," Nat. Biotechnol. 18:405-409 (2000).

Lee et al., "In vivo Inhibition of Human CD19-Targeted Effector T cells by Natural T Regulatory Cells in a Xenotransplant Murine Model of B cell Malignancy," Cancer Res 71(8):2871-2881 (2011).

Lenzi et al., "Phase I Study of Intraperitoneal Recombinant Human Interleukin 12 in Patients with Mullerian Carcinoma, Gastrointestinal Primary Malignancies, and Mesothelioma," Clin. Cancer Res. 8:3686-3695 (2002).

Lenzi et al., "Phase II study of intraperitoneal recombinant interleukin-12 (rhIL-12) in patients with peritoneal carcinomatosis (residual disease < 1 cm) associated with ovarian cancer or primary peritoneal carcinoma," J Transl. Med 5:66 (2007).

Li et al., "Activation of regulatory T cells instigates functional down-regulation of cytotoxic T lymphocytes in human breast cancer," Immunologic Research 51:71-79 (2011).

Li et al., "Mesothelin is a malignant factor and therapeutic vaccine target for pancreatic cancer," Mol Cancer Ther 7(2):286-296 (2008).

Liedtke et al., "Response to Neoadjuvant Therapy and Long-Term Survival in Patients With Triple-Negative Breast Cancer," J Clin Oncol 26:1275-1281 (2008).

Lloyd et al., "Modelling the human immune response: performance of a $10^{11}$ human antibody repertoire against a broad panel of therapeutically relevant antigens," Protein Engineering, Design & Selection, 22(3):159-168 (2009).

Long et al., "4-1BB Costimulation Ameliorates T cell Exhaustion Induced by Tonic Signaling of Chimeric Antigen Receptors," Nat Med 21(6):581-590 (2015).

Louis et al., "Antitumor activity and long-term fate of chimeric antigen receptor-positive T cells in patients with neuroblastoma," Blood 118(23):6050-6056 (2011).

Lyddane et al., "Cutting Edge: CD28 Controls Dominant Regulatory T Cell Activity during Active Immunization," J. Immunol. 176:3306-3310 (2006).

Maher et al., "Human T-lymphocyte cytotoxicity and proliferation directed by a single chimeric TCRξ/CD28 receptor," Nat. Biotechnol. 20:70-75 (2002).

Mahvi et al., "Intratumoral injection of IL-12 plasmid DNA—results of a phase I/IB clinical trial," Cancer Gene Therapy 14:717-723 (2007).

Markley et al., "IL-7 and IL-21 are superior to IL-2 and IL-15 in promoting human T cell-mediated rejection of systemic lymphoma in immunodeficient mice," Blood 115(17):3508-3519 (2010).

Maus et al., "T Cells Expressing Chimeric Antigen Receptors Can Cause Anaphylaxis in Humans," Cancer Immunol Res 1(1):26-31 (2013).

McCoy et al., "Chromium-Release Assay for Cell-Mediated Cytotoxicity of Human Leukemia and Lymphoid Tissue-Culture Cells," Natl Cancer Inst Monogr 37:59-67 (1973).

McGray et al., "Immunotherapy-induced CD8(+) T Cells Instigate Immune Suppression in the Tumor," Molecular Therapy 22(1):206-218 (2014).

Moon et al., "Expression of a Functional CCR2 Receptor Enhances Tumor Localization and Tumor Eradication by Retargeted Human T cells Expressing a Mesothelin-Specific Chimeric Antibody Receptor," Clin Cancer Res 17(14):4719-4730 (2011).

Moon et al., "Multifactorial T-cell Hypofunction That Is Reversible Can Limit the Efficacy of Chimeric Antigen Receptor-Transduced Human T cells in Solid Tumors," Clin Cancer Res 20(16):4262-4273 (2014).

Mueller et al., "High antigen levels are the cause of T cell exhaustion during chronic viral infection," PNAS USA 106(21):8623-8628 (2009).

Na et al., "Concurrent visualization of trafficking, expansion, and activation of T lymphocytes and T-cell precursors in vivo," Blood 116(11):e18-e25 (2010).

Nanni et al., "Combined Allogeneic Tumor Cell Vaccination and Systemic Interleukin 12 Prevents Mammary Carcinogenesis in HER-2/neu Transgenic Mice," J. Exp. Med. 194(9):1195-1205 (2001).

Nesbeth et al., "CD4+ T Cells Elicit Host Immune Responses to MHC Class II—Ovarian Cancer through CCL5 Secretion and CD40-Mediated Licensing of Dendritic Cells," Journal of Immunology 184:5654-5662 (2010).

Palumbo et al., "Molecular Targets and Targeted Therapies for Malignant Mesothelioma," Current Medicinal Chemistry 15:855-867 (2008).

Papanicolaou et al., "Rapid expansion of cytomegalovirus-specific cytotoxic T lymphocytes by artificial antigen-presenting cells expressing a single HLA allele," Blood 102:2498-2505 (2003).

Papapetrou et al., "Stoichiometric and temporal requirements of Oct4, Sox2, Klf4, and c-Myc expression for efficient human iPSC induction and differentiation," PNAS USA 106(31):12759-12764 (2009).

Park et al., "Soluble Mesothelin-related Protein in an Asbestos-exposed Population: The Dust Diseases Board Cohort Study," Am J Respir Crit Care Med 178:832-837 (2008).

Pass et al., "Soluble Mesothelin-Related Peptide Level Elevation in Mesothelioma Serum and Pleural Effusions," Ann Thorac Surg 85:265-272; discussion 272 (2008).

Pastan et al., "Discovery of Mesothelin and Exploiting It as a Target for Immunotherapy," Cancer Res. 74(11):2907-2912 (2014).

Pegram et al., "Tumor-targeted T cells modified to secrete TL-12 eradicate systemic tumors without need for prior conditioning," Blood 119(18):4133-4141 (2012).

Pogoda et al., "Analysis of pattern, time and risk factors influencing recurrence in triplenegative breast cancer patients," Med Oncol 30:388 (2013).

Ponomarev et al., "Imaging TCR-Dependent NFAT-Mediated T-cell Activation with Positron Emission Tomography In Vivo," Neoplasia 3(6):480-488 (2001).

(56) References Cited

OTHER PUBLICATIONS

Rabinovich et al., "Visualizing fewer than 10 mouse T cells with an enhanced firefly luciferase in immunocompetent mouse models of cancer," PNAS USA 105(38):14342-14346 (2008).
Rakha et al., "Basal-Like Breast Cancer: A Critical Review," J Clin Oncol 26:2568-2581 (2008).
Reits et al., "Radiation modulates the peptide repertoire, enhances MHC class I expression, and induces successful antitumor immunotherapy," J Exp Med. 203(5):1259-1271 (2006).
Riese et al., "Enhanced Effector Responses in Activated CD8+ T Cells Deficient in Diacylglycerol Kinases," Cancer Res 73(12):3566-3577 (2013).
Riviere et al., "Novel Strategies for Cancer Therapy: The Potential of Genetically Modified T Lymphocytes," Curr Hematol Rep 3:290-297 (2004).
Rizk et al., "Tissue and Serum Mesothelin Are Potential Markers of Neoplastic Progression in Barrett's Associated Esophageal Adenocarcinoma," Cancer Epidemiol Biomarkers Prev 21(3):482-486 (2012).
Rizvi et al., "Cancer immunology: Mutational landscape determines sensitivity to PD-1 blockade in non-small cell lung cancer," Science 348(6230):124-128 (2015).
Robinson et al., "Malignant mesothelioma," Lancet 366:397-408 (2005).
Robinson et al., "Soluble mesothelin-related protein—A blood test for mesothelioma," Lung Cancer 49 Suppl 1:S109-S111 (2005).
Rodriguez Portal et al., "Serum Levels of Soluble Mesothelin-Related Peptides in Malignant and Nonmalignant Asbestos-Related Pleural Disease: Relation with Past Asbestos Exposure," Cancer Epidemiol Biomarkers Prev 18(2):646-650 (2009).
Roe et al., "Mesothelin-related predictive and prognostic factors in malignant mesothelioma: a nested case-control study," Lung Cancer 61:235-243 (2008).
Rosenberg et al., "Adoptive cell transfer: a clinical path to effective cancer immunotherapy," Nat. Rev. Cancer 8:299-308 (2008).
Sabel et al., "Intratumoral delivery of encapsulated TL-12, IL-18 and TNF-$\alpha$ in a model of metastatic breast cancer," Breast Cancer Res Treat 122:325-336 (2010).
Sadelain et al., "Targeting Tumours With Genetically Enhanced T Lymphocytes," Nat Rev Cancer 3:35-45 (2003).
Sadelain et al., "The Basic Principles of Chimeric Antigen Receptor Design," Cancer Discov 3(4):388-398 (2013).
Sadelain et al., "The promise and potential pitfalls of chimeric antigen receptors," Curr Opin Immunol 21:215-223 (2009).
Sallusto et al., "Two subsets of memory T lymphocytes with distinct homing potentials and effector functions," Nature 401:708-712 (1999).
Santos et al., "Sensitive in vivo imaging of T cells using a membrane-bound *Gaussia princeps luciferase*," Nat Med 15(3):338-344 (2009).
Schietinger et al., "Rescued Tolerant CD8 T Cells Are Preprogrammed to Reestablish the Tolerant State," Science 335:723-727 (2012).
Segawa et al., "MESOMARK kit detects C-ERC/mesothelin, but not SMRP with C-terminus," Biochem Biophys Res Commun 369:915-918 (2008).
Servais et al., "An In Vivo Platform for Tumor Biomarker Assessment," PLoS ONE 6(10):e26722 (2011).
Servais et al., "Mesothelin Overexpression Promotes Mesothelioma Cell Invasion and MMP-9 Secretion in an Orthotopic Mouse Model and in Epithelioid Pleural Mesothelioma Patients," Clin Cancer Res 18(9):2478-2489 (2012).
Servais et al., "Pre-Clinical Mouse Models of Primary and Metastatic Pleural Cancers of the Lung and Breast and the Use of Bioluminescent Imaging to Monitor Pleural Tumor Burden," Curr. Protoc. Pharmacol. 54:14.21.1-14.21.18 (2011).
Sigurdson et al., "Tumor and Liver Drug Uptake Following Hepatic Artery and Portal Vein Infusion," J Clin Oncol 5:1836-1840 (1987).
Smid et al., "Subtypes of Breast Cancer Show Preferential Site of Relapse," Cancer Res 68(9):3108-3114 (2008).
Song et al., "A Semiparametric Likelihood Approach to Joint Modeling of Longitudinal and Time-To-Event Data," Biometrics 58:742-753 (2002).
Song et al., "Eomesodermin is required for antitumor immunity mediated by 4-1BB-agonist immunotherapy," OncoImmunology 3(2):e27680 (2014).
Spear et al., "Collaboration of chimeric antigen receptor (CAR)-expressing T cells and host T cells for optimal elimination of established ovarian tumors," OncoImmunology 2(4):e23564 (2013).
Spranger et al., "Up-Regulation of PD-L1, IDO, and T(regs) in the Melanoma Tumor Microenvironment Is Driven by CD8(+) T Cells," Science Translational Medicine 5:200ra116 (2013).
Stamatopoulos et al., "Immunoglobulin light chain repertoire in chronic lymphocytic leukemia," Blood 106(10):3575-3583 (2005).
Stephan et al., "T cell-encoded CD80 and 4-1BBL induce auto- and transcostimulation, resulting in potent tumor rejection," Nat.Med 13(12):1440-1449 (2007).
Stiles et al., "Minimally invasive localization of oncolytic herpes simplex viral therapy of metastatic pleural cancer," Cancer Gene Therapy 13:53-64 (2006).
Stone et al., "A sensitivity scale for targeting T cells with chimeric antigen receptors (CARs) and bispecific T-cell engagers (BiTEs)," OncoImmunology. 1(6):863-873 (2012).
Strome et al., "B7-H1 Blockade Augments Adoptive T-cell Immunotherapy for Squamous Cell Carcinoma," Cancer Research 63:6501-6505 (2003).
Supplementary European Search Report dated Oct. 2, 2017 in Application No. EP 15803100.
Suzuki et al., "Chronic inflammation in tumor stroma is an independent predictor of prolonged survival in epithelioid malignant pleural mesothelioma patients," Cancer Immunol Immunother. 60:1721-1728 (2011).
Suzuki et al., "Palliation and Pleurodesis in Malignant Pleural Effusion: The Role for Tunneled Pleural Catheters," J Thorac Oncol. 6:762-767 (2011).
Tajima et al., "ERC/Mesothelin as a Marker for Chemotherapeutic Response in Patients with Mesothelioma," Anticancer Res 28:3933-3936 (2008).
Tchou et al., "Mesothelin, a novel immunotherapy target for triple negative breast cancer," Breast Cancer Res Treat 133:799-804 (2012).
Thom et al., "Cytokine Levels and Systemic Toxicity in Patients Undergoing Isolated Limb Perfusion With High-Dose Tumor Necrosis Factor, Interferon Gamma, and Melphalan," J Clin Oncol 13:264-273 (1995).
Thomas et al., "Mesothelin-specific CD8(+) T Cell Responses Provide Evidence of In Vivo Cross-Priming by Antigen-Presenting Cells in Vaccinated Pancreatic Cancer Patients," J. Exp. Med. 200(3):297-306 (2004).
Topalian et al., "Safety, Activity, and Immune Correlates of Anti-PD-1 Antibody in Cancer," The New England Journal of Medicine 366(26):2443-2454 (2012).
Tozbikian et al., "Mesothelin Expression in Triple Negative Breast Carcinomas Correlates Significantly with Basal-Like Phenotype, Distant Metastases and Decreased Survival," PLoS ONE 9(12):e114900 (2014).
Uehara et al., "Mesothelin Promotes Anchorage-Independent Growth and Prevents Anoikis via Extracellular Signal-Regulated Kinase Signaling Pathway in Human Breast Cancer Cells," Mol Cancer Res 6(2):186-193 (2008).
Van den Heuvel et al., "Non-invasive diagnosis of pleural malignancies: The role of tumour markers," Lung Cancer 59:350-354 (2008).
Van Herpen et al., "Intratumoral Recombinant Human Interleukin-12 Administration in Head and Neck Squamous Cell Carcinoma Patients Modifies Locoregional Lymph Node Architecture and Induces Natural Killer Cell Infiltration in the Primary Tumor," Clin Cancer Res. 11:1899-1909 (2005).
Villena-Vargas et al., "Mesothelin-targeted immunotherapies for malignant pleural mesothelioma," Ann Cardiothorac Surg 1(4):466-471 (2012).
Voest et al., "Inhibition of Angiogenesis In Vivo by Interleukin 12," J Natl Cancer Inst 87(8):581-586 (1995).

(56) References Cited

OTHER PUBLICATIONS

Wang et al., "A transgene-encoded cell surface polypeptide for selection, in vivo tracking, and ablation of engineered cells," Blood 118(5):1255-1263 (2011).
Wang et al., "Clinicopathological Significance of Mesothelin Expression in Invasive Breast Cancer," J Int Med Res 40:909-916 (2012).
Wang et al., "Mesothelin Promotes Invasion and Metastasis in Breast Cancer Cells," J Int Med Res 40:2109-2116 (2012).
Wang et al., "Targeting Fibroblast Activation Protein in Tumor Stroma with Chimeric Antigen Receptor T Cells Can Inhibit Tumor Growth and Augment Host Immunity without Severe Toxicity," Cancer Immunology Research, 2(2):154-166 (2014).
Watanabe et al., "Target Antigen Density Governs the Efficacy of Anti-CD20-CD28-CD3 ξ Chimeric Antigen Receptor-Modified Effector CD8+ T Cells," Journal of Immunology 194:911-920 (2015).
Wesa et al., "Polarized Type-I Dendritic Cells (DC1) Producing High Levels of IL-12 Family Members Rescue Patient TH1-type Antimelanoma CD4+ T cell Responses In Vitro," J Immunother 30(1):75-82 (2007).
Wolchok et al., "Nivolumab plus Ipilimumab in Advanced Melanoma," N Engl J Med 369:122-133 (2013).
Wu et al., "Heterogeneity of Breast Cancer Metastases: Comparison of Therapeutic Target Expression and Promoter Methylation Between Primary Tumors and Their Multifocal Metastases," Clin Cancer Res 14(7):1938-1946 (2008).
Yamada et al., "CD8+ tumor-infiltrating lymphocytes predict favorable prognosis in malignant pleural mesothelioma after resection," Cancer Immunol Immunother 59:1543-1549 (2010).
Yau et al., "A multigene predictor of metastatic outcome in early stage hormone receptornegative and triple-negative breast cancer," Breast Cancer Res 12:R85 (2010).
Yokokawa et al., "Identification of Novel Human CTL Epitopes and Their Agonist Epitopes of Mesothelin," Clin Cancer Res 11(17):6342-6351 (2005).
Zamarin et al., "Localized Oncolytic Virotherapy Overcomes Systemic Tumor Resistance to Immune Checkpoint Blockade Immunotherapy," Science Translational Medicine 6:226ra232 (2014).
Zervos et al., "Malignant mesothelioma 2008," Curr Opin Pulm Med 14:303-309 (2008).
Zhao et al., "High-Affinity TCRs Generated by Phage Display Provide CD4+ T Cells with the Ability to Recognize and Kill Tumor Cell Lines," J Immunol. 179:5845-5854 (2007).
Zhao et al., "Multiple Injections of Electroporated Autologous T cells Expressing a Chimeric Antigen Receptor Mediate Regression of Human Disseminated Tumor," Cancer Res 70(22):9053-9061 (2010).
Zhong et al., "Chimeric Antigen Receptors Combining 4-1BB and CD28 Signaling Domains Augment PI3kinase/AKT/Bcl-XL Activation and CD8+ T Cell-mediated Tumor Eradication," Mol Ther 18(2):413-420 (2010).
Bergan et al., "Development and in vitro validation of anti-mesothelin biobodies that prevent CA125/Mesothelin-dependent cell attachment," Elsevier, Cancer Letters, 255:263-274 (2007).
Extended European Search Report dated Apr. 17, 2020 in Application No. EP 20158336.
Wan, et al., "T cell-mediated cellular immune response," Pathogens and Immunology, Fourth Military Medical University Press, pp. 99 (2011) (with full English translation).

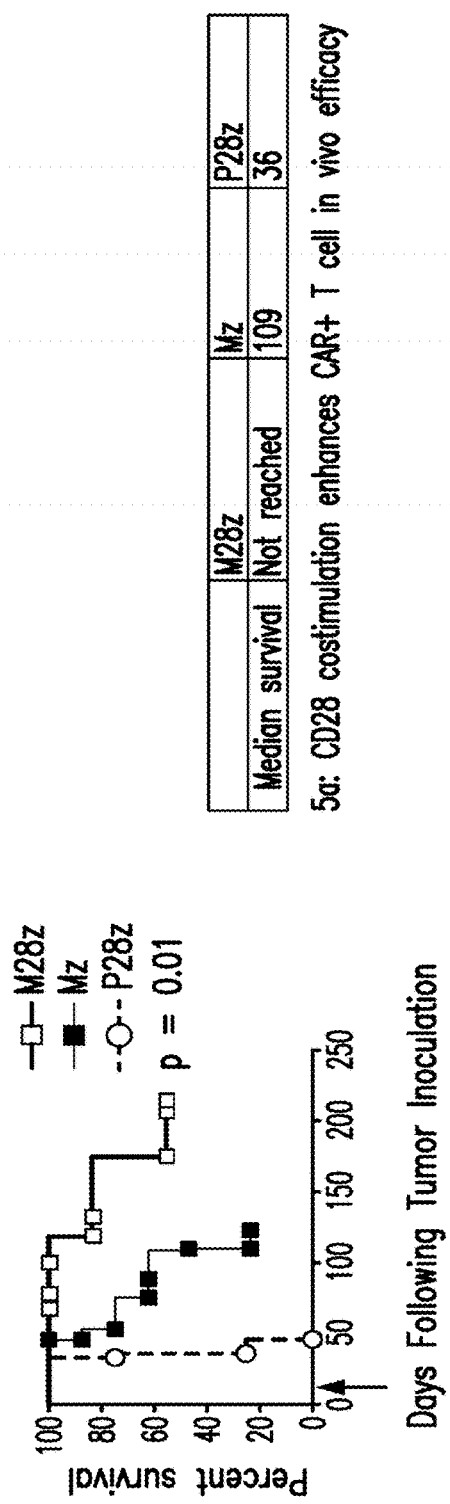
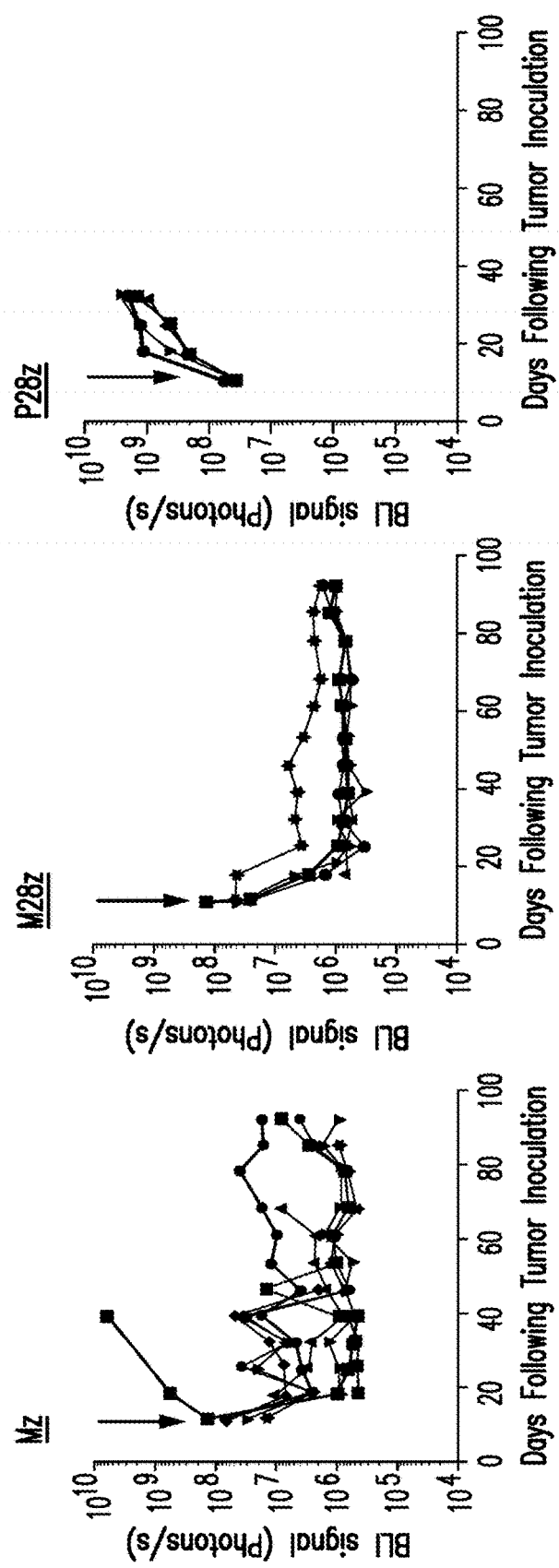
FIG. 5A

5b: CD28 costimulation enhances CAR+ Tcell persistence

5c: Persisting CAR+ T cells are predominantly CD4+

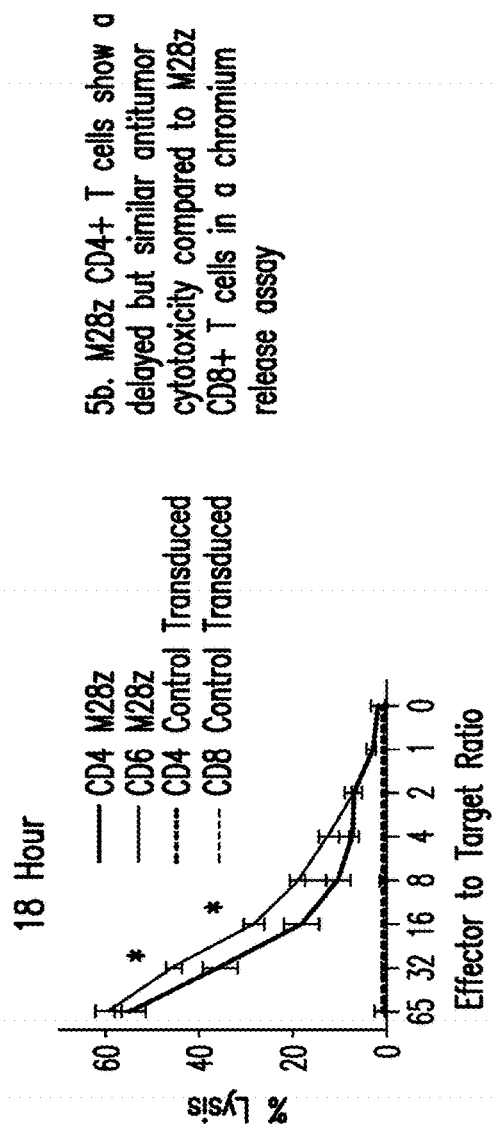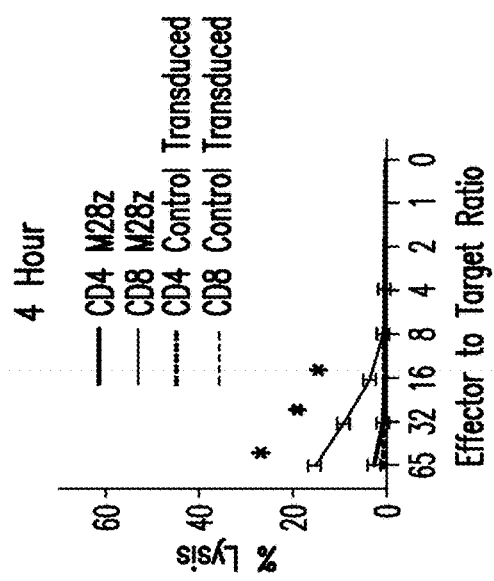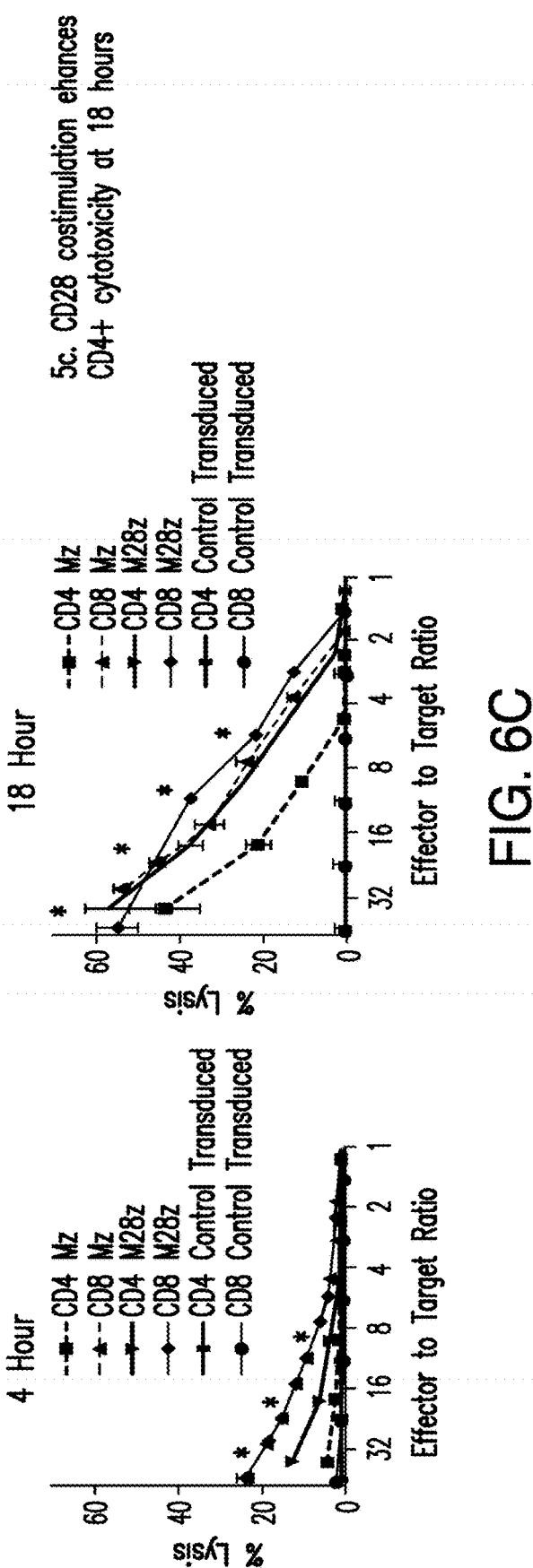
FIG. 6B
FIG. 6C

6a: Fas/FasL and cytokines do not mediate CAR+ T cell cytotoxicity

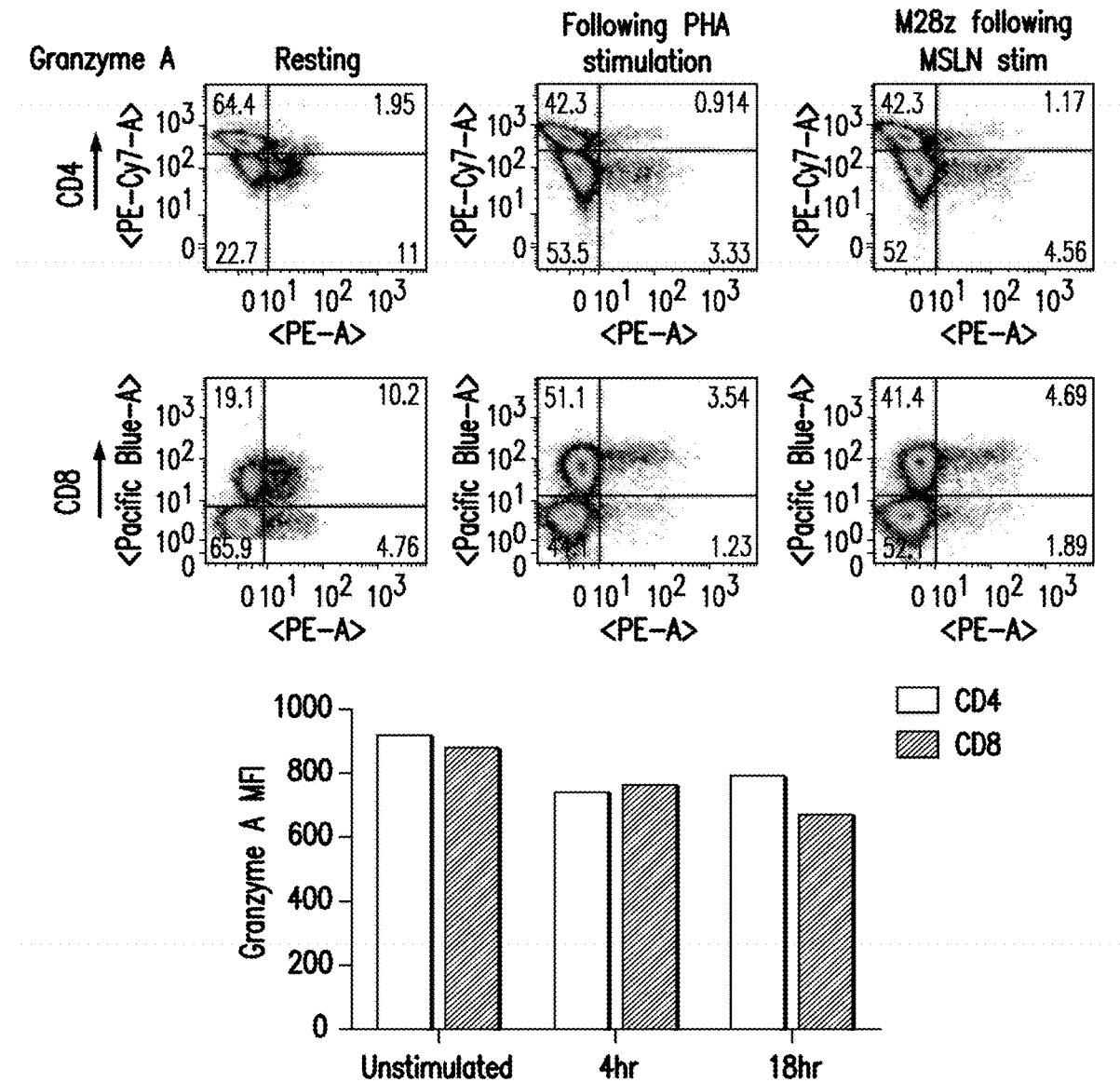

6c: Resting CD8+ T cell human PBMCs express granzymes A and B. Granzyme A expression is not significantly altered following CAR+ T cell stimulation whereas granzyme B expression is inducible in both Cd4 and CD8 CAR+ T cells upon PHA stimulation, and is further upregulated following stimulation with mesothelin. CD4+ CAR+ T cells induced to upregulate granzyme B expression with slower kinetics when compared to CD8+ CAR+ T cells

FIG. 7C

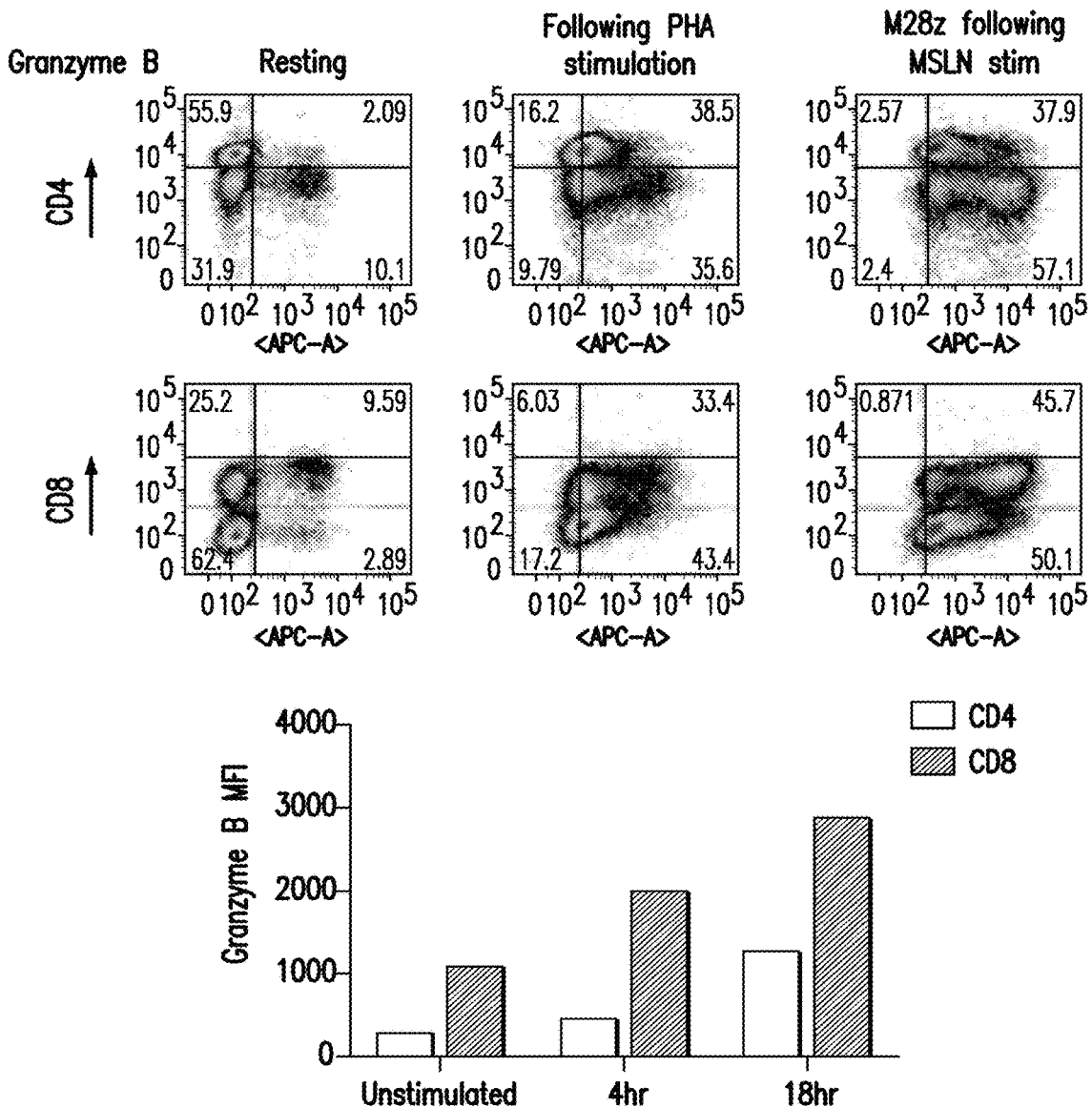

6c: Resting CD8+ T cell human PBMCs express granzymes A and B. Granzyme A expression is not significantly altered following CAR+ T cell stimulation whereas granzyme B expression is inducible in both Cd4 and CD8 CAR+ T cells upon PHA stimulation, and is further upregulated following stimulation with mesothelin. CD4+ CAR+ T cells induced to upregulate granzyme B expression with slower kinetics when compared to CD8+ CAR+ T cells

FIG. 7C continued

6d: Both CD4 and CD8 with M28z CAR T cells express a greater amount of granzyme B when compared to Mz CD4 M28z CAR T cells are efficacious alone in vivo and mediate enhanced efficacy when compared to CD8 M28z CAR T cells

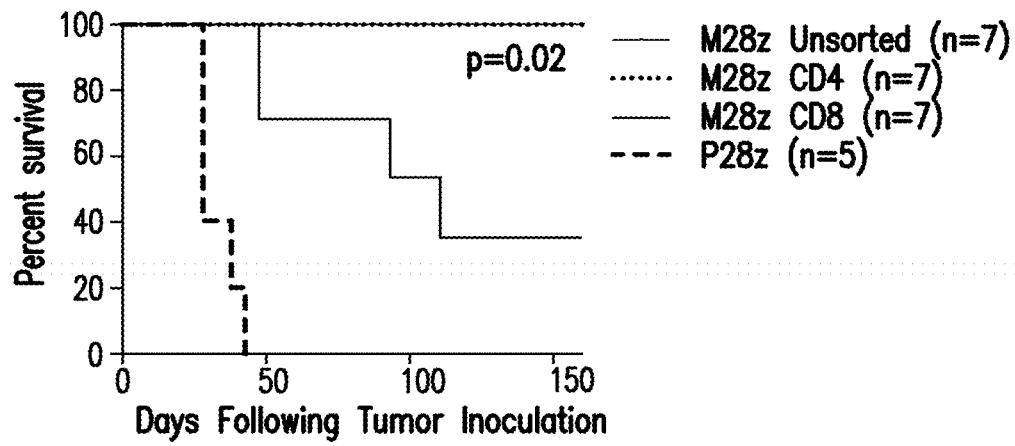
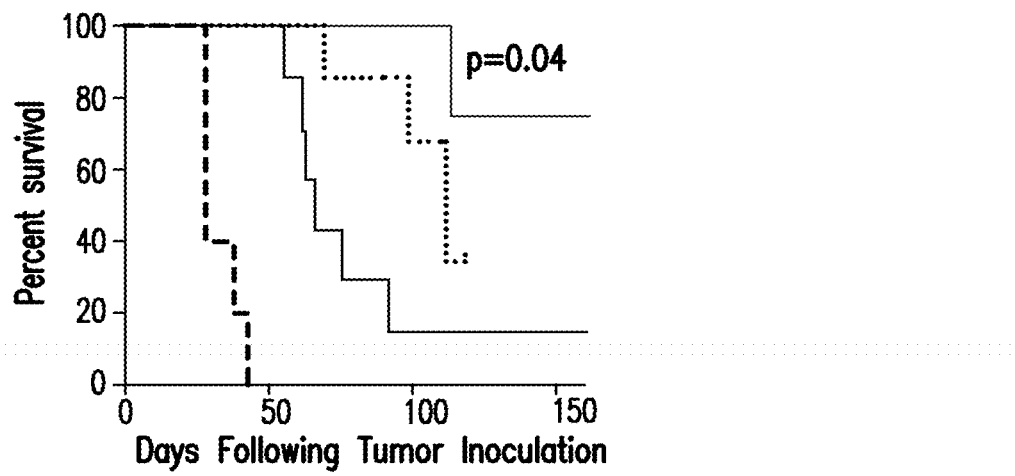
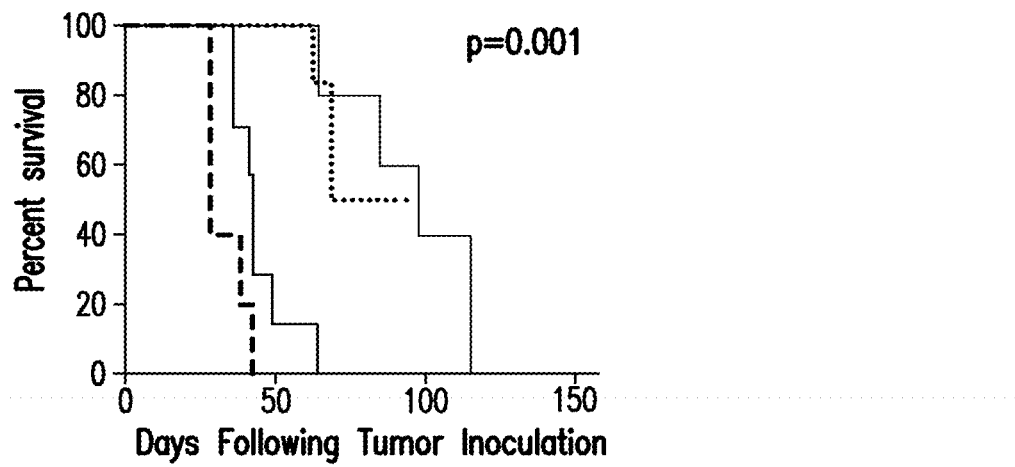
FIG. 9B

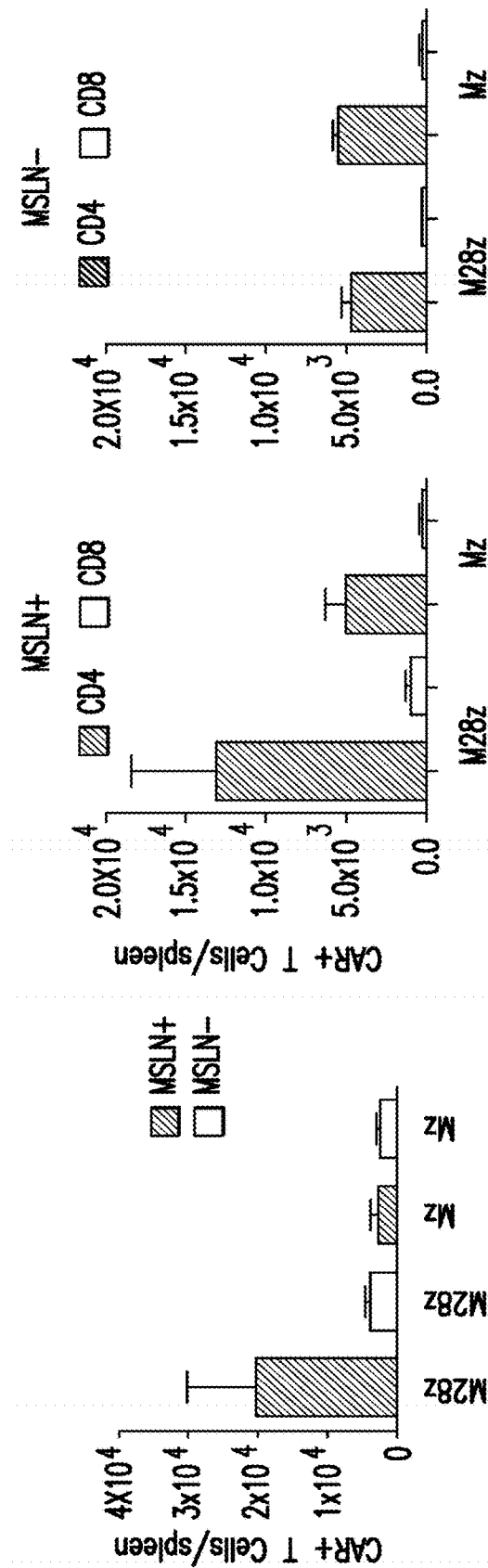
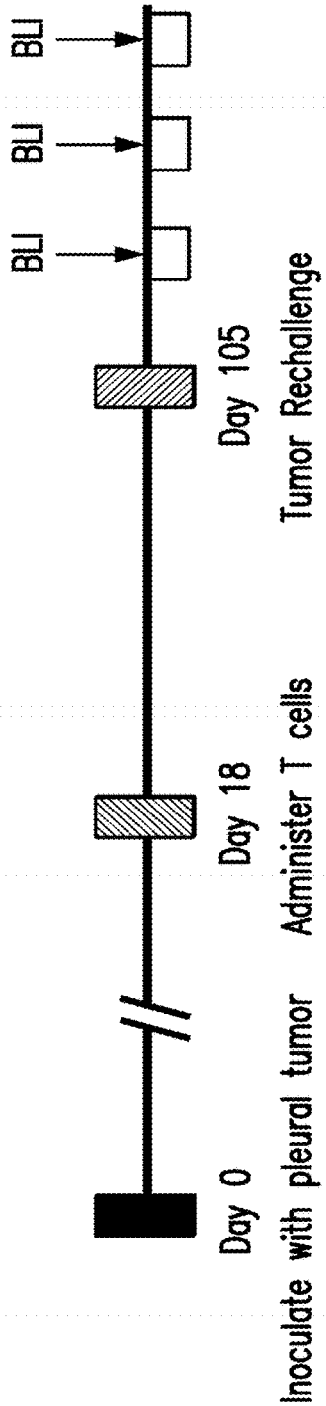
FIG. 10C
FIG. 10D
FIG. 10E

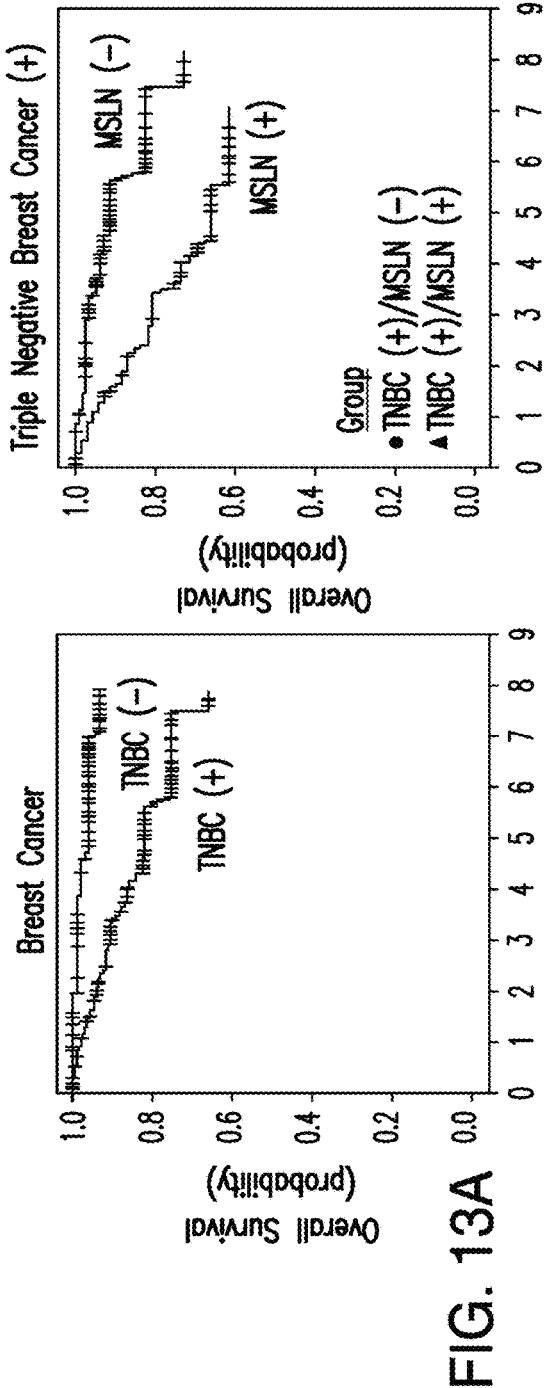
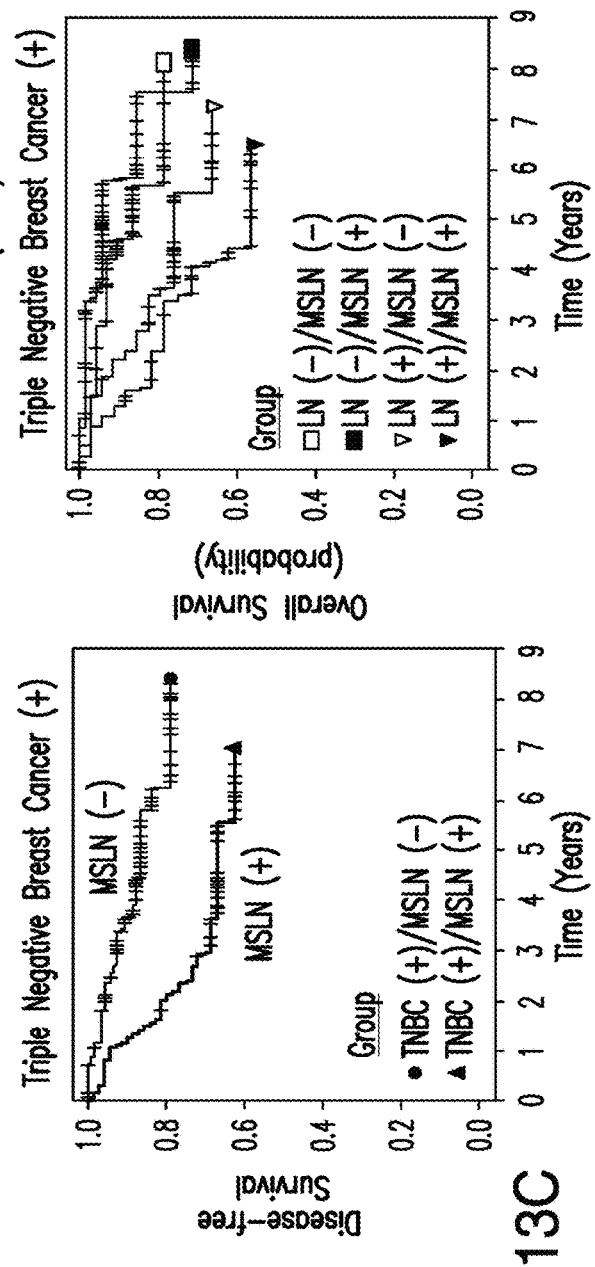
FIG. 13A, FIG. 13B, FIG. 13C, FIG. 13D

Graph of Overall Survival Comparing Mesothelin Negative TNCa Mesothelin Positive TNCa and Tumor Controls.

Graph of Disease Specific Survival, Comparing Mesothelin Negative TNCa Mesothelin Positive TNCa and Tumor Controls (DOD)

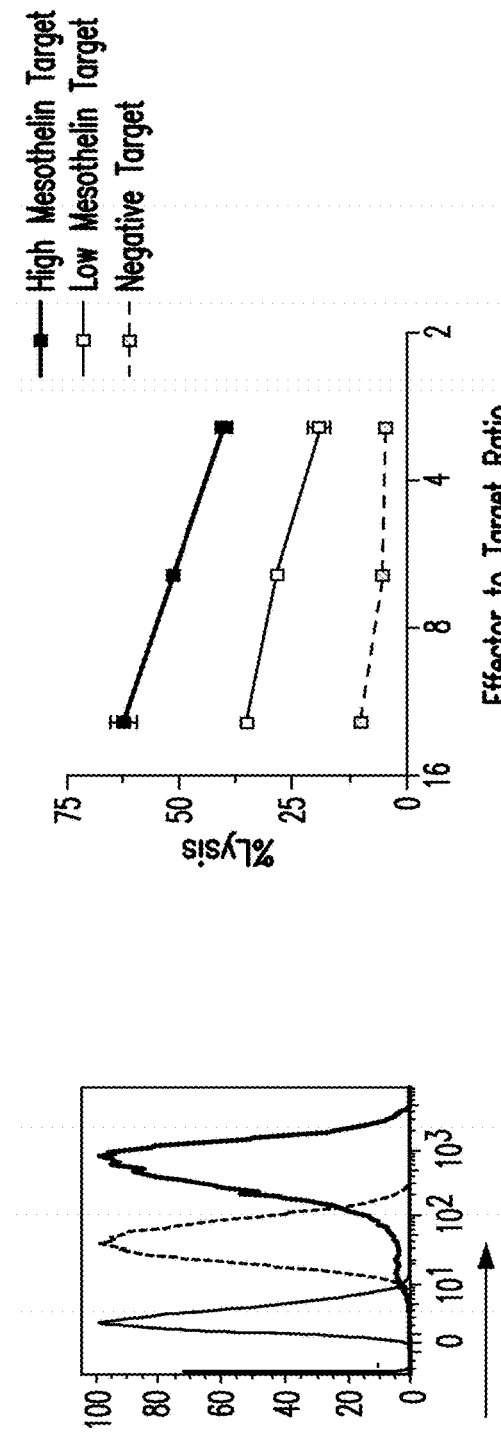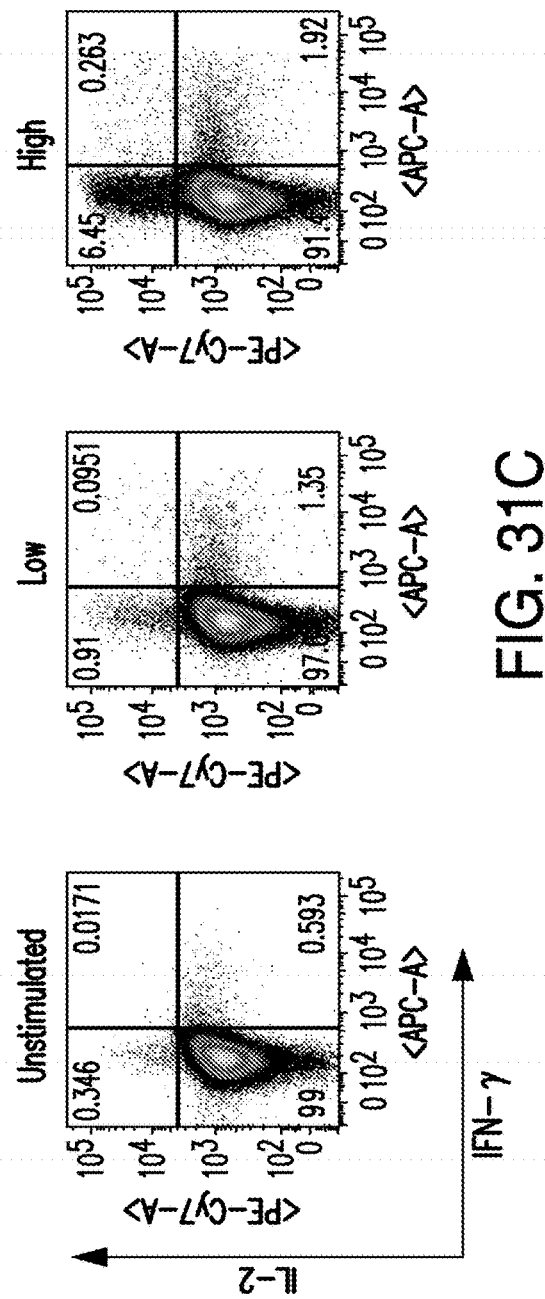
FIG. 31A  FIG. 31B  FIG. 31C

Chemokine and cytokine secretion in *vitro* (A) and *in vivo* (B) 72 h following exposure to hemi thoracic radiation exposure to hemi thoracic radiation therapy (HTRT) in mice with thoracic tumors

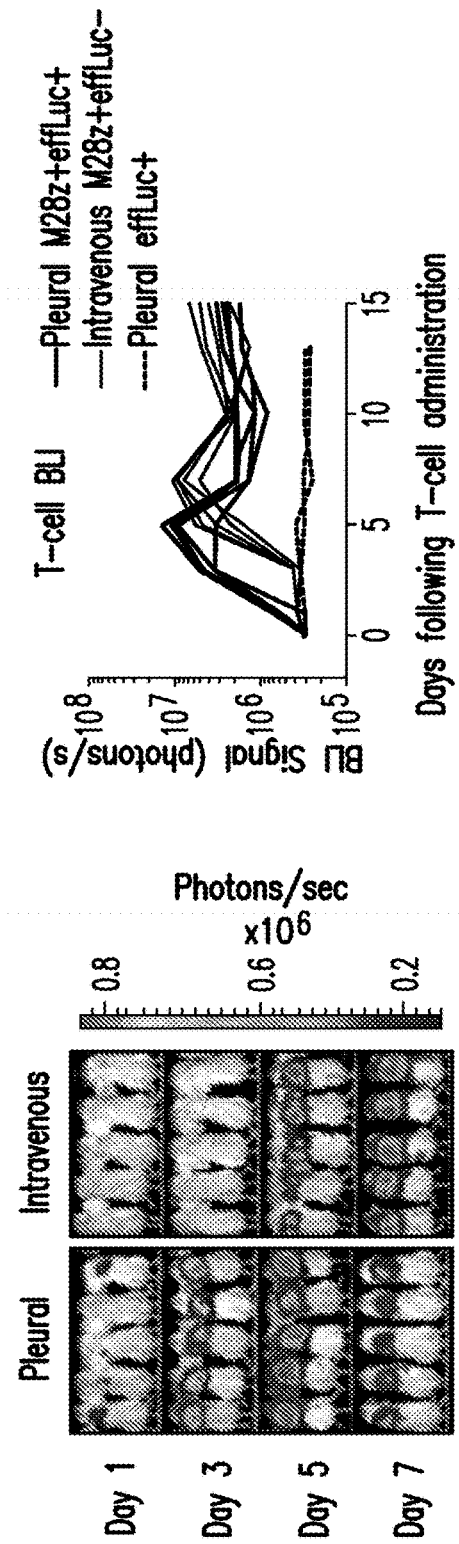
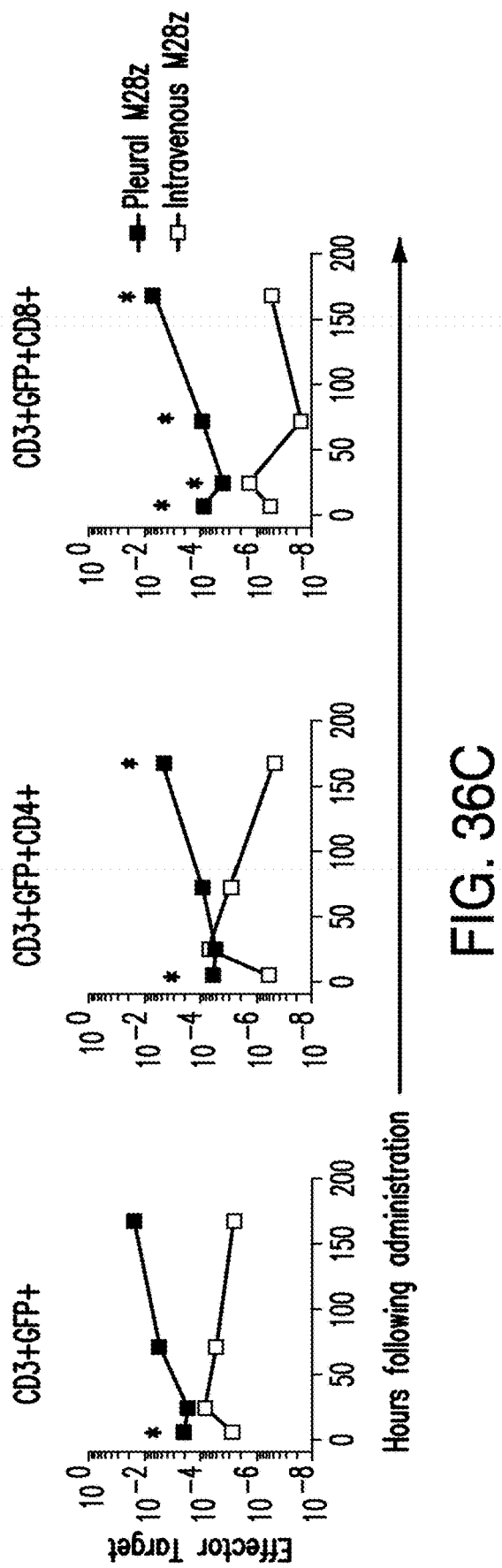
FIG. 36A
FIG. 36B
FIG. 36C

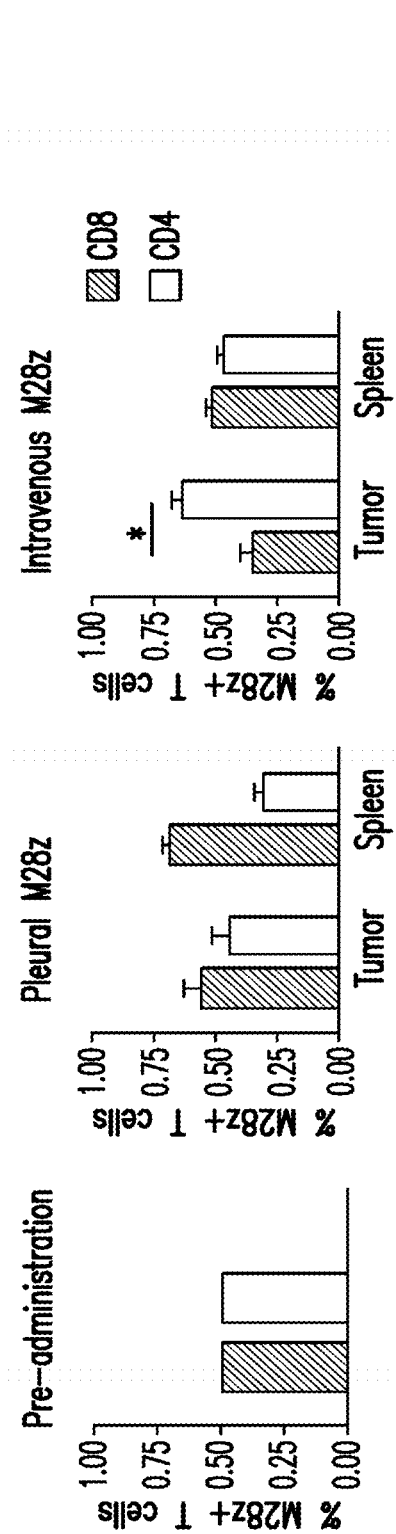
FIG. 36D
FIG. 36E

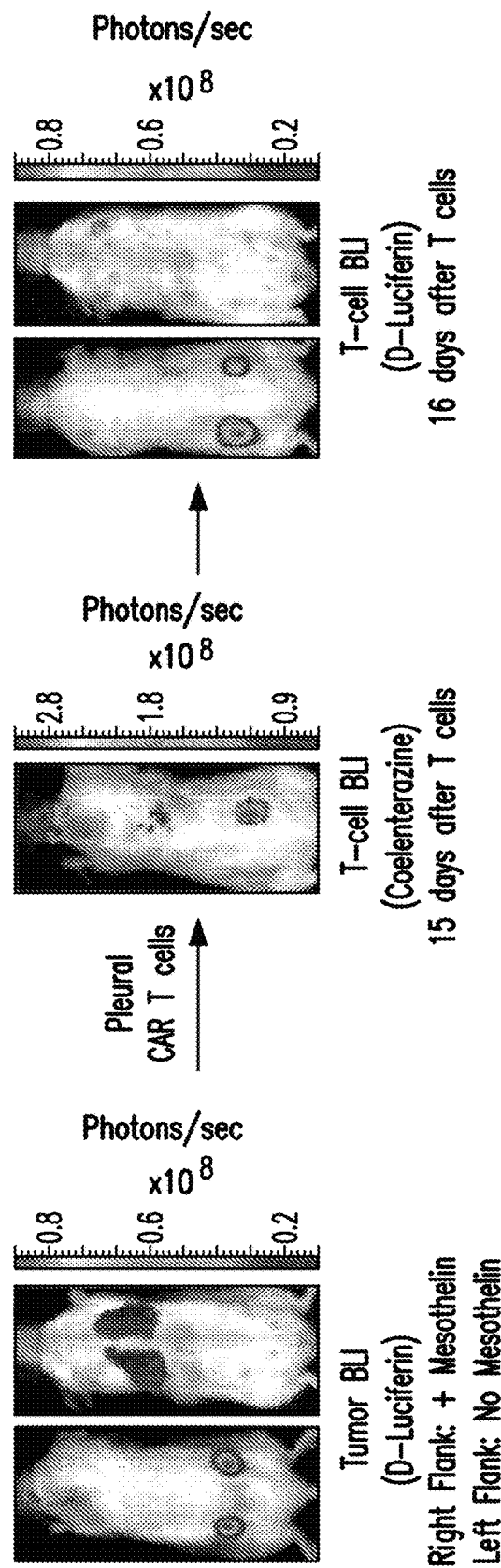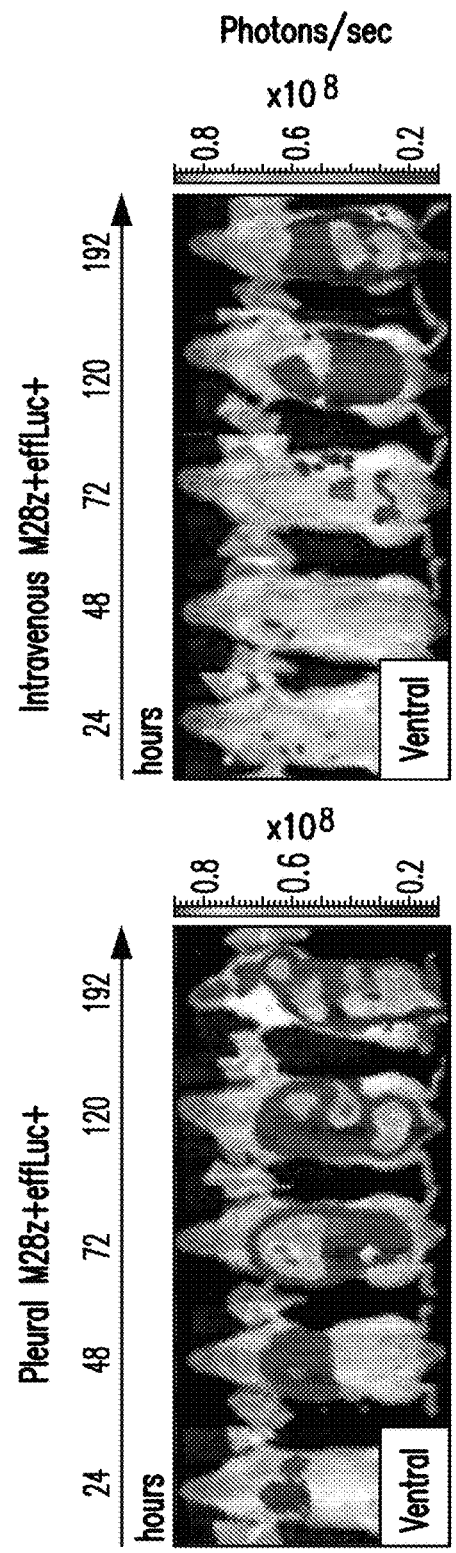
FIG. 37A
FIG. 37B

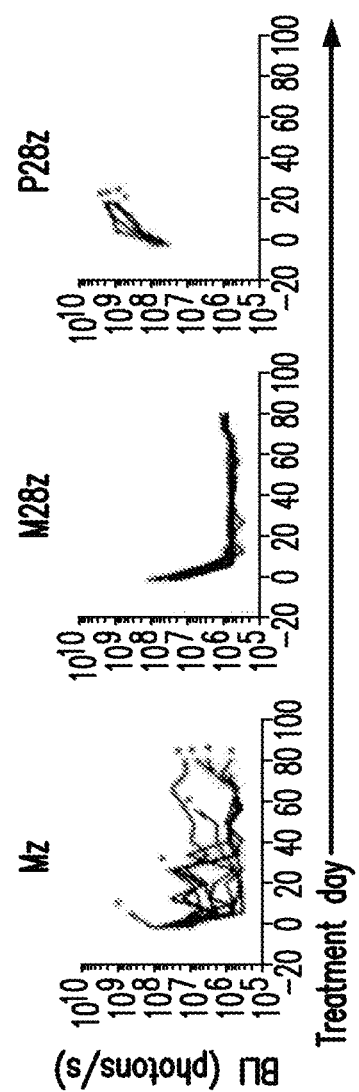
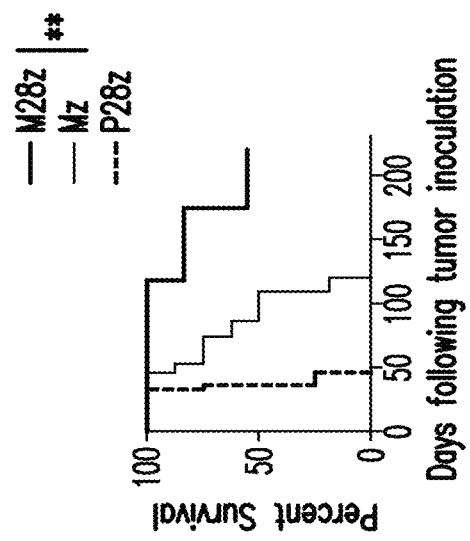
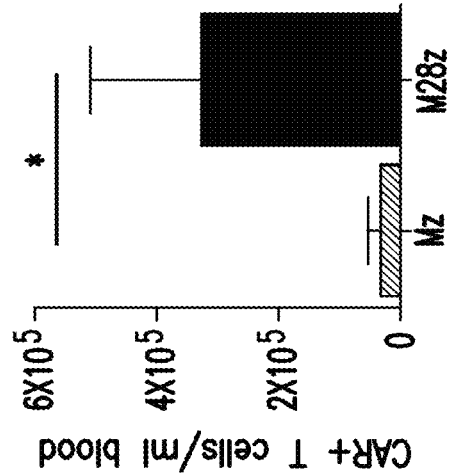
FIG. 38A
FIG. 38B

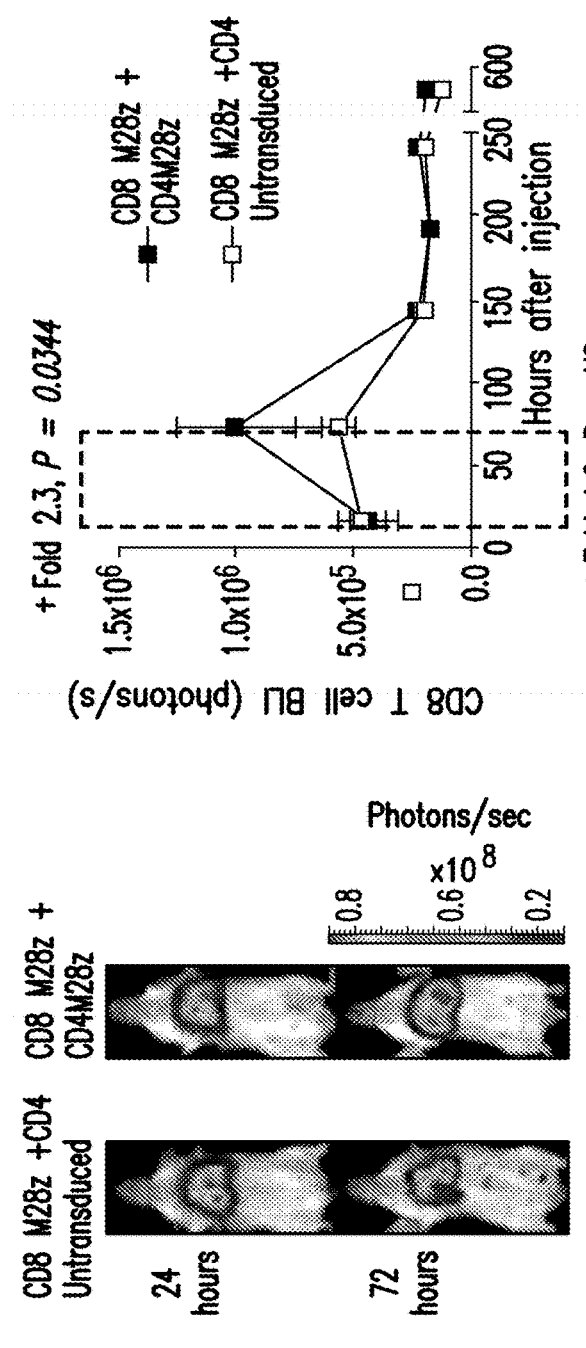
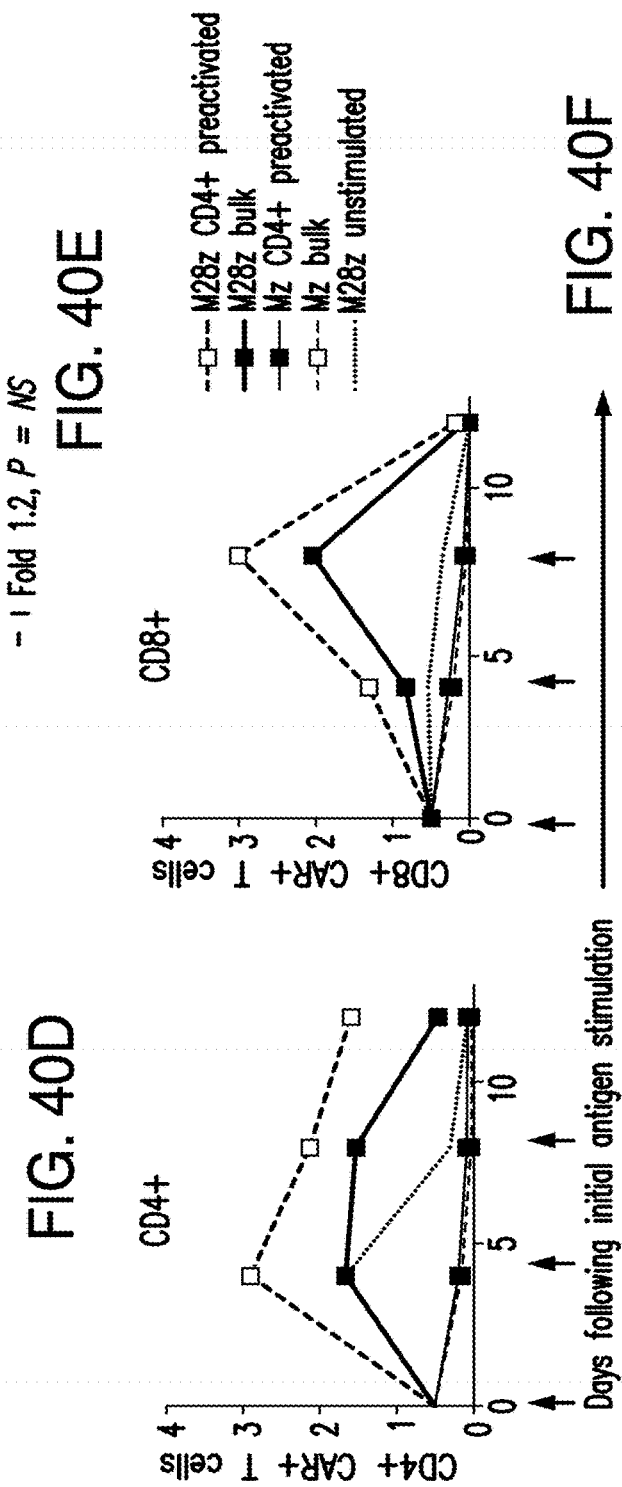

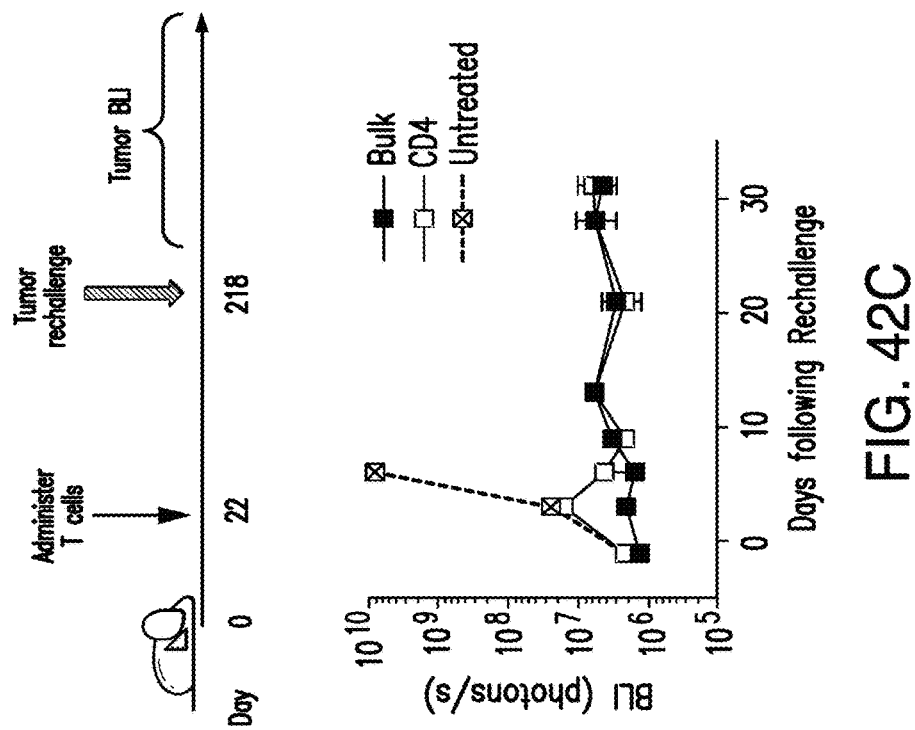
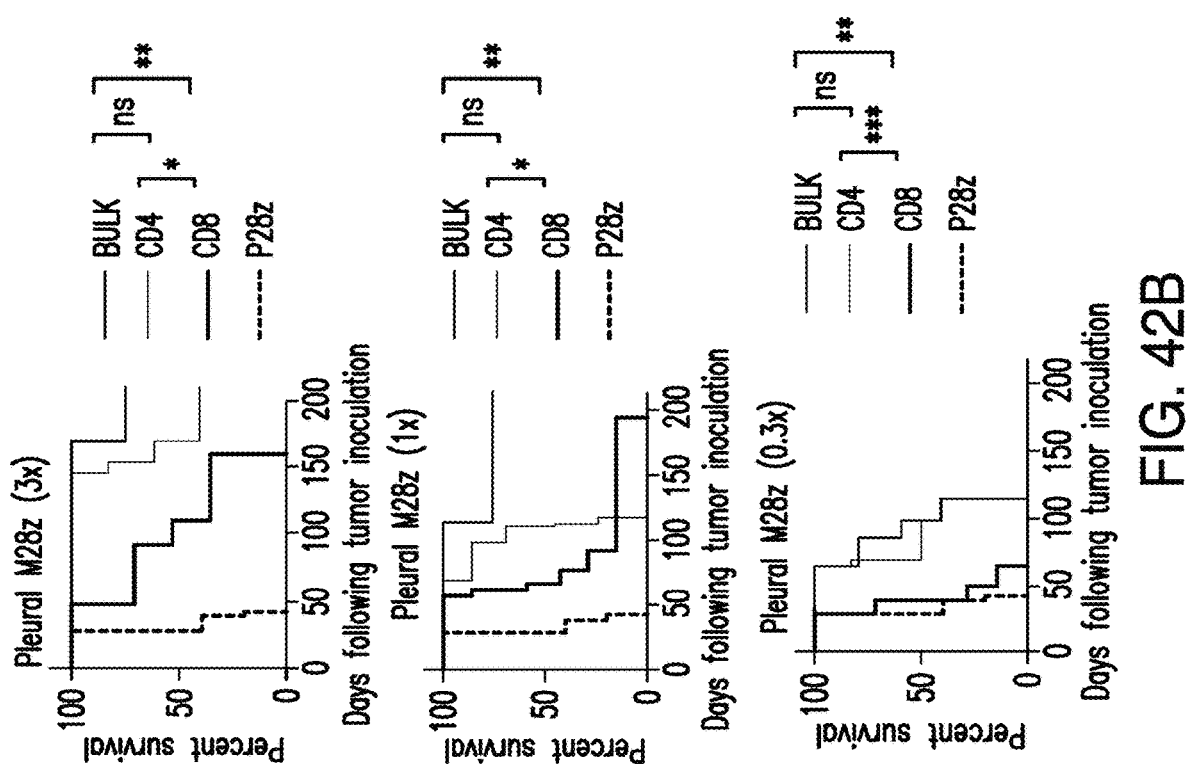
FIG. 42B
FIG. 42C

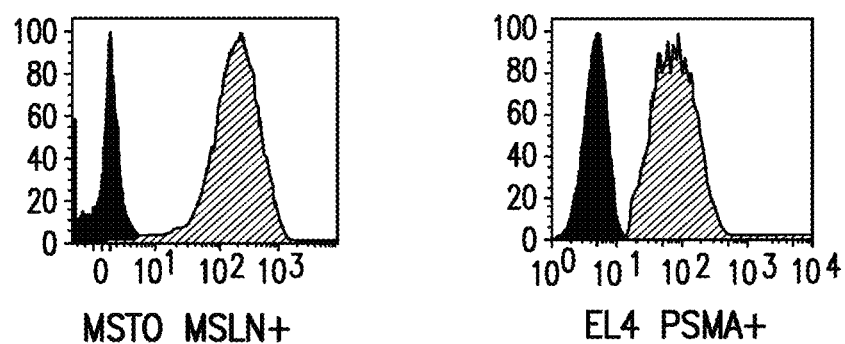
FIG. 43A
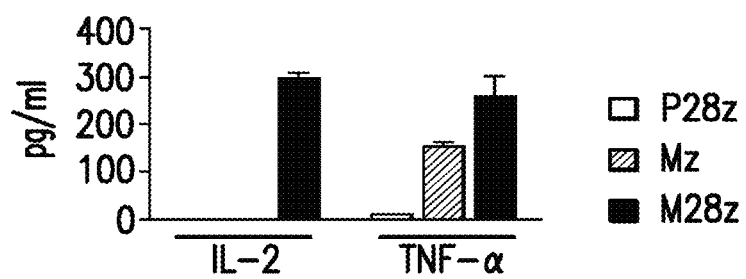
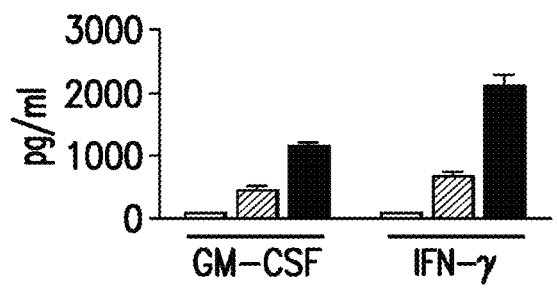
FIG. 43B

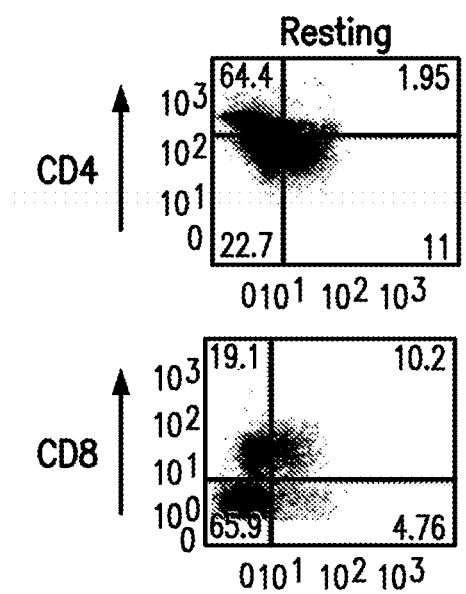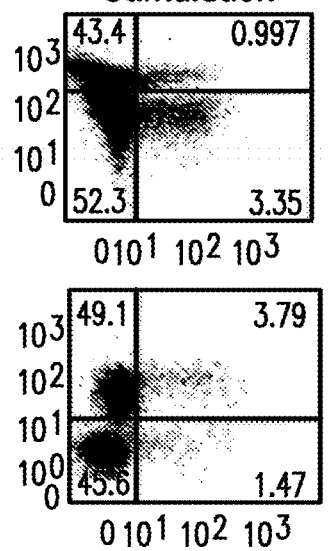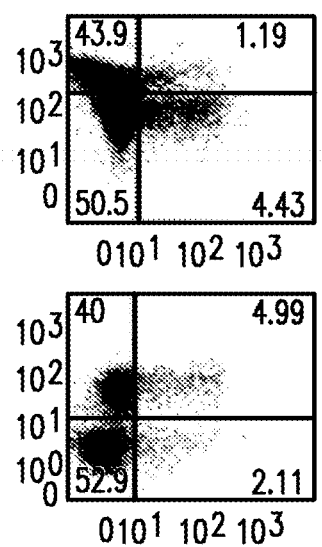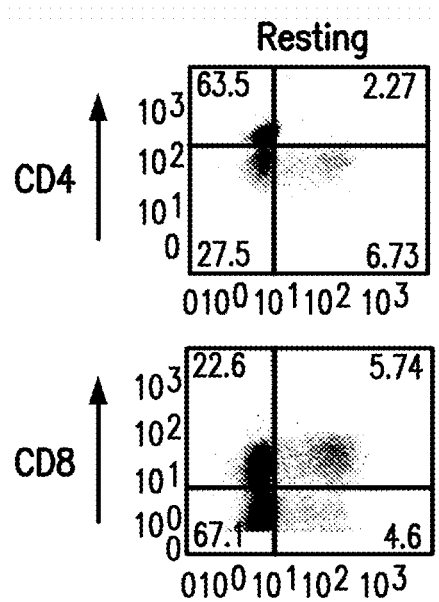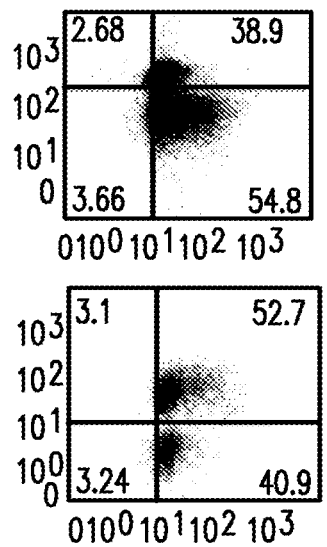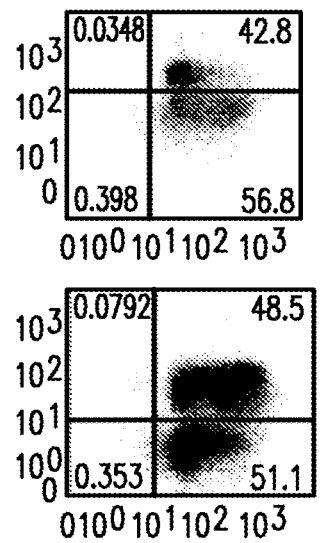
FIG. 44

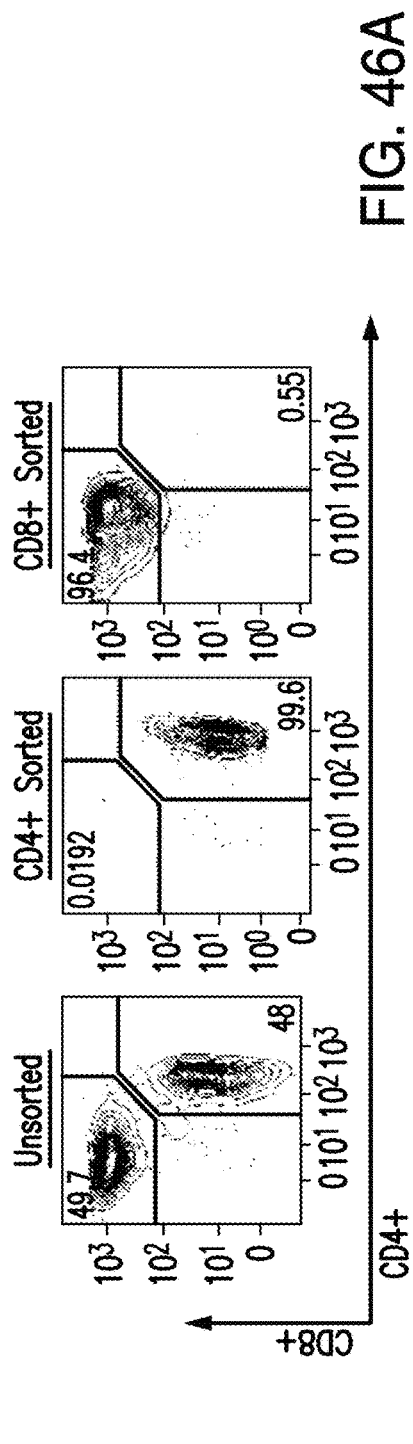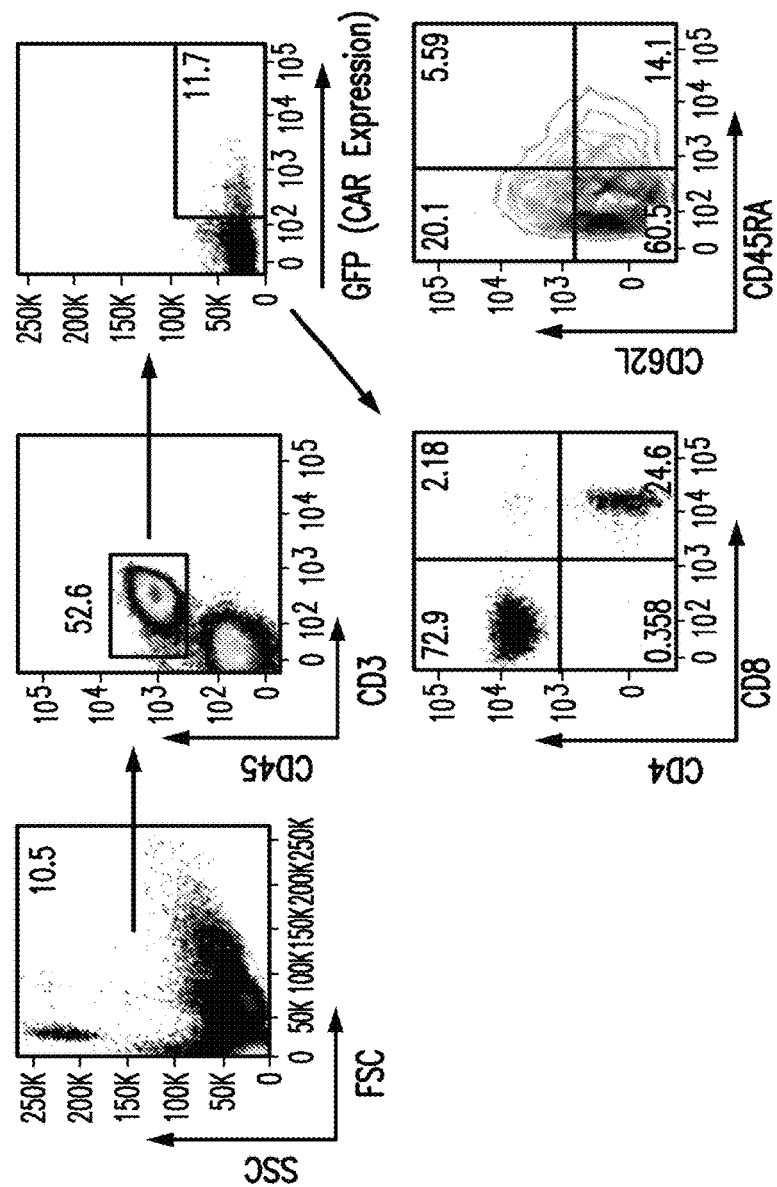
FIG. 46A
FIG. 46B

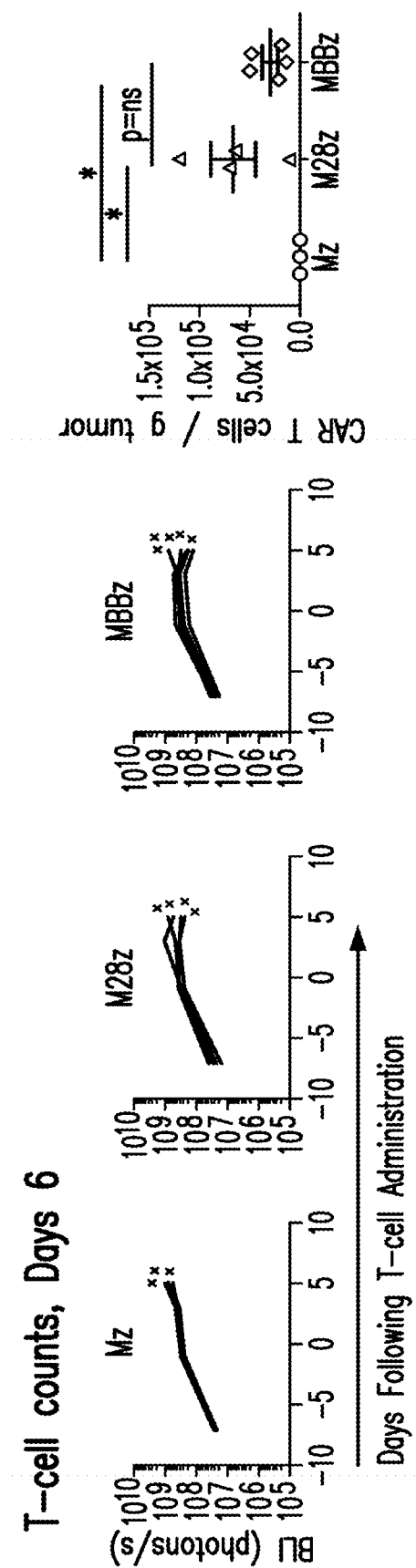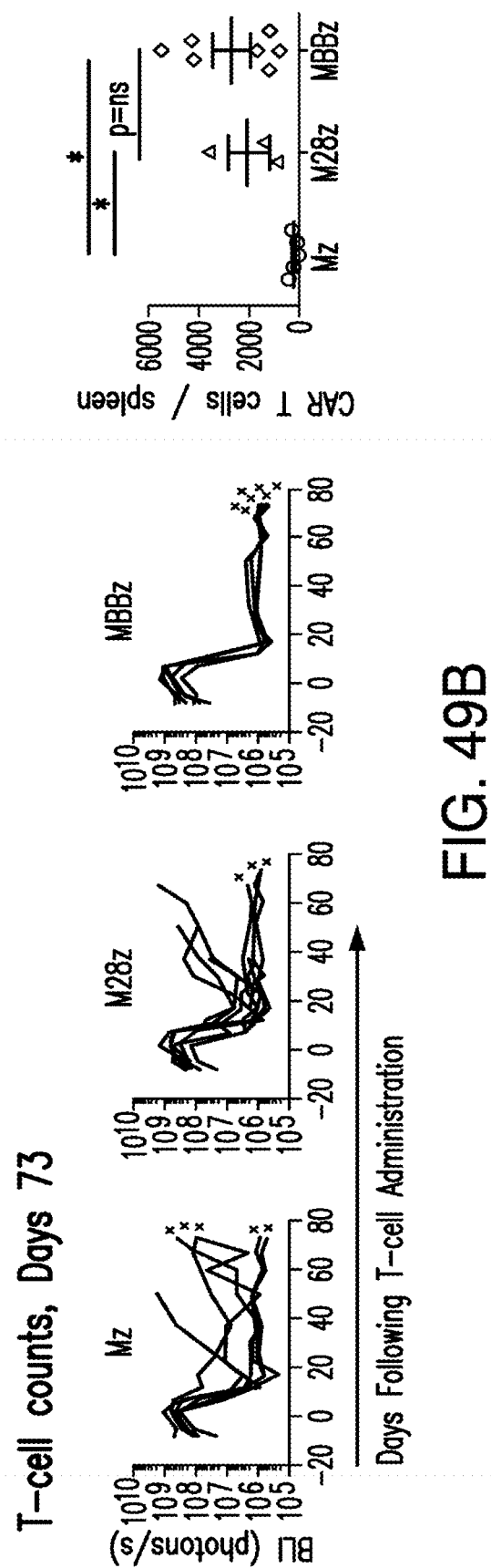
FIG. 49A
FIG. 49B

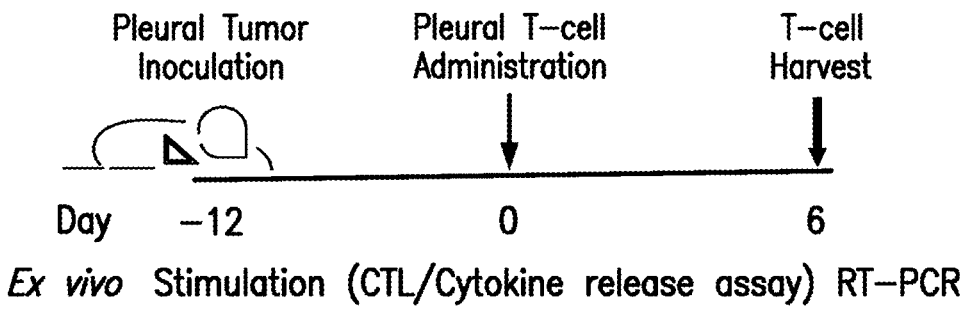
FIG. 50A
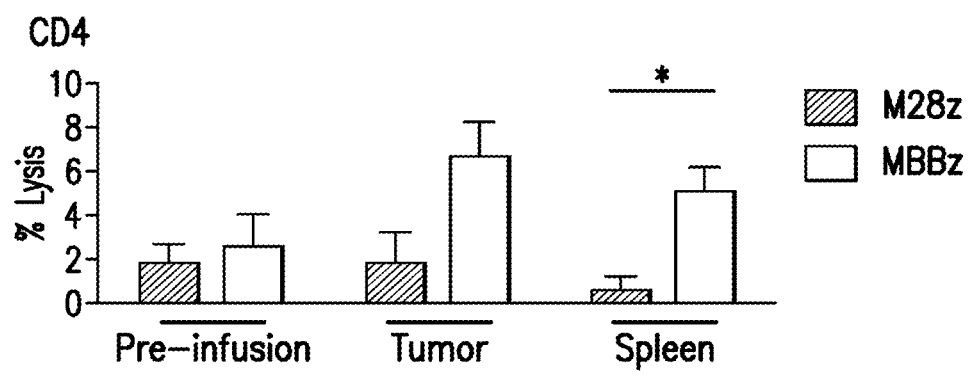
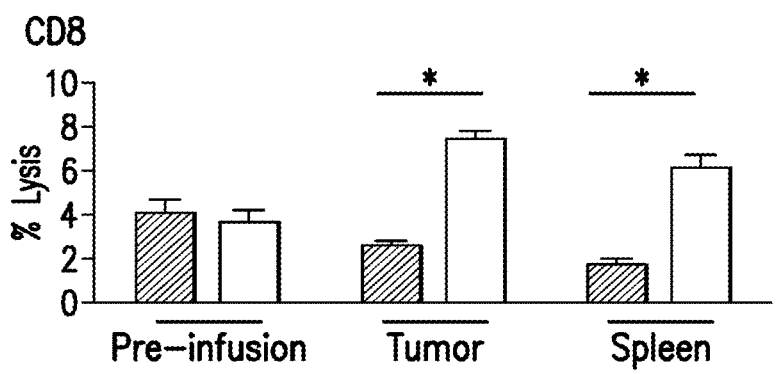
FIG. 50B

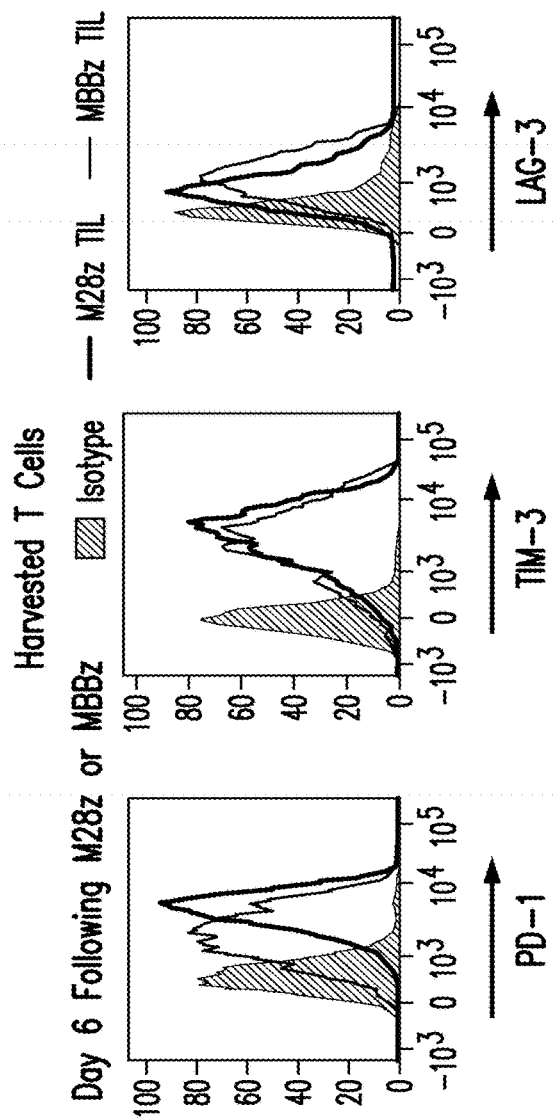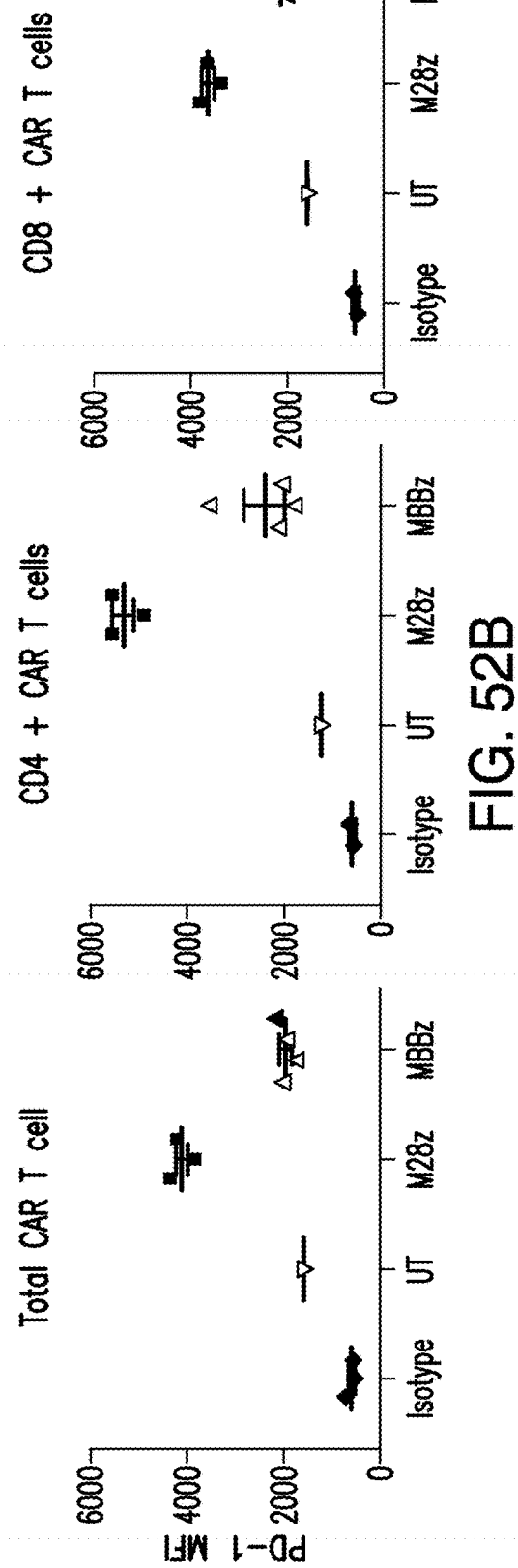
FIG. 52A
FIG. 52B

Tumor cells

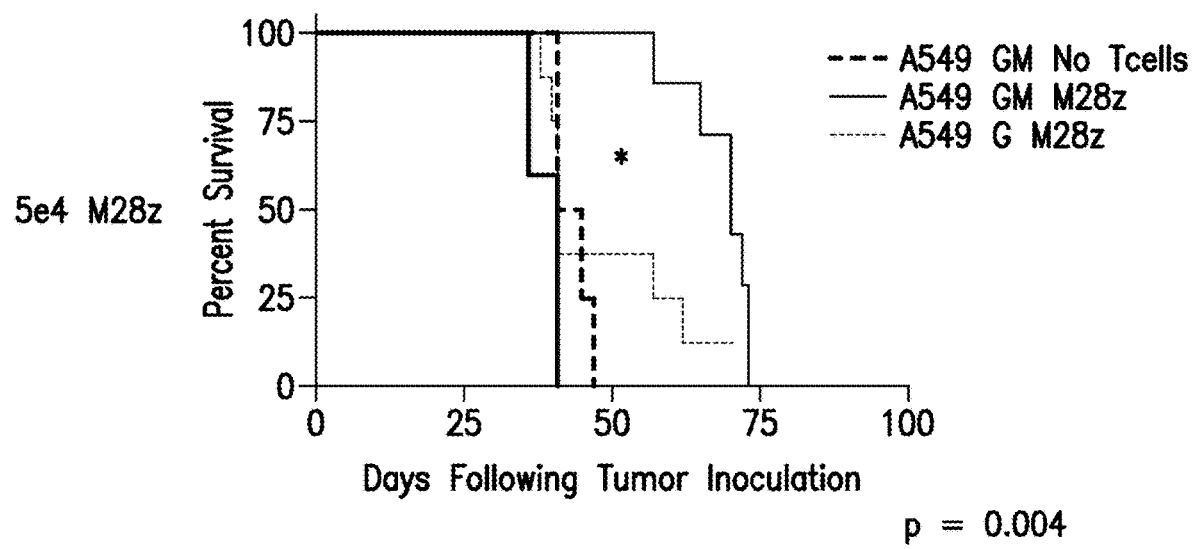
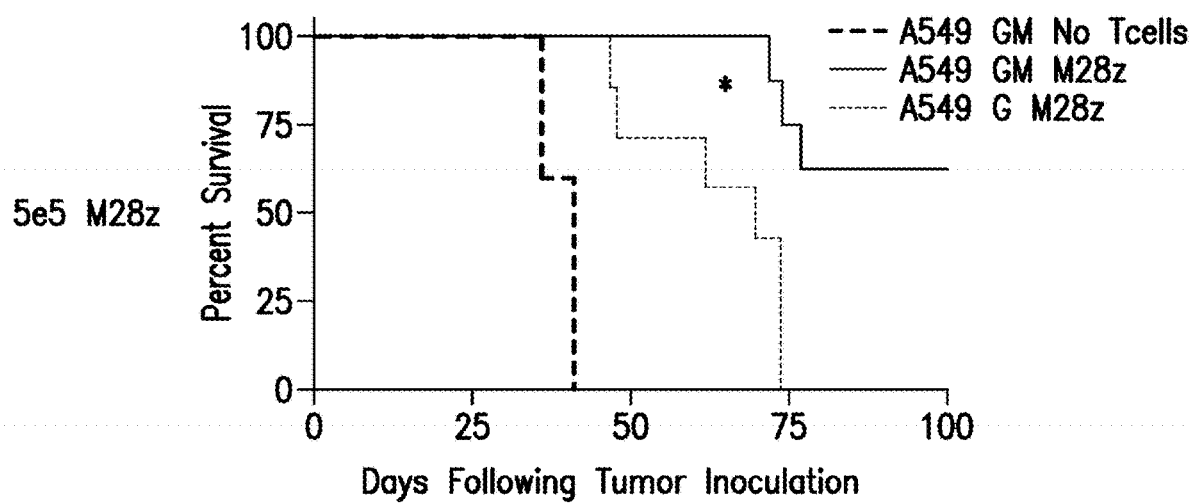
FIG. 63C

Fold change

| | Day 1 | Day 3 | Day 5 | Day 7 |
|---|---|---|---|---|
| A549 M effluc alone | 1 | 2.19 ± 0.34 | 2.89 ± 0.27 | 1.3 ± 0.27 |
| A549 E M28z effluc | 1 | 3.86 ± 0.92 | 9.34 ± 2.5 | 18.30 ± 4.2 |
| A549 M M28z effluc | 1 | 10.13 ± 3.6 | 23.37 ± 6.9 | 6.58 ± 1 |

SEQUENCE LISTING

```
<160> NUMBER OF SEQ ID NOS: 45

<210> SEQ ID NO 1
<211> LENGTH: 230
<212> TYPE: PRT
<213> ORGANISM: Homo sapiens

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80
```

Ser Leu Lys Leu Ser Ser Val Thr Ala Ala Asp Thr Ala Val Tyr Tyr
            85                  90                  95

Cys Ala Arg Glu Gly Lys Asn Gly Ala Phe Asp Ile Trp Gly Gln Gly
        100                 105                 110

Thr Met Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr Ser Gly Gln Ala Gly
225                 230

<210> SEQ ID NO 2
<211> LENGTH: 693
<212> TYPE: DNA
<213> ORGANISM: Homo sapiens

<400> SEQUENCE: 2
caggtgcagc tgcaggagtc cggcccagga ctggtgaagc cttcggagac cctgtccctc    60
acctgcactg tctctggtgg ctccgtcagc agtggtagtt actactggag ctggatccgg   120
cagcccccag ggaagggact ggagtggatt gggtatatct attacagtgg gagcaccaac   180
tacaacccct ccctcaagag tcgagtcacc atatcagtag acacgtccaa gaaccagttc   240
tccctgaagc tgagctctgt gaccgctgcg gacacggccg tgtattactg tgcgagagag   300
gggaagaatg ggcttttgat atctggggc caagggacaa tggtcaccgt ctcttcagcc   360
tccaccaagg gcccatcggt cttccccctg gcaccctcct ccaagagcac ctctgggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagaaagt tgagcccaaa   660
tcttgtgaca aaactagtgg ccaggccggc cac                                 693

<210> SEQ ID NO 3
<211> LENGTH: 214
<212> TYPE: PRT
<213> ORGANISM: Homo sapiens

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

```
Tyr Ala Ala Ser Ser Leu Gln Ser Gly Val Pro Ser Gly Phe Ser Gly
        50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ser Thr Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 4
<211> LENGTH: 640
<212> TYPE: DNA
<213> ORGANISM: Homo sapiens

<400> SEQUENCE: 4
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
gggttcagtg gcagtggatc tgggacagat ttcactctca ccatcagcag tctgcaacct    240
gaagattttg caacttacta ctgtcaacag agttacagta ccccgctcac tttcggcgga    300
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctact gcctcagcag cacccctgacg   540
ctgagcaaag cagactacga gaaacacaaa gtctacgcct gcgaagtcac ccatcagggc    600
ctgagctcgc ccgtcacaaa gagcttcaac aggggagagt                         640

<210> SEQ ID NO 5
<211> LENGTH: 214
<212> TYPE: PRT
<213> ORGANISM: Homo sapiens

<400> SEQUENCE: 5

Arg His Gln Met Thr Gln Ser Pro Ser Ser Leu Ser Ala Ser Val Gly
 1               5                  10                  15
Asp Arg Val Thr Ile Thr Cys Arg Ala Ser Gln Ser Ile Ser Ser Tyr
            20                  25                  30
```

```
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Gly Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 120
<212> TYPE: PRT
<213> ORGANISM: Homo sapiens

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Lys Asn Gly Ala Phe Asp Ile Trp Gly Gln Gly
            100                 105                 110

Thr Met Val Thr Val Ser Ser
        115                 120

<210> SEQ ID NO 7
<211> LENGTH: 262
<212> TYPE: PRT
<213> ORGANISM: Homo sapiens

<400> SEQUENCE: 7

Gln Val Gln Leu Gln Glu Ser Gly Pro Gly Leu Val Lys Pro Ser Glu
1               5                   10                  15
```

-continued

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Glu Gly Lys Asn Gly Ala Phe Asp Ile Trp Gly Gln Gly
            100                 105                 110

Thr Met Val Thr Val Ser Ser Gly Gly Gly Gly Ser Gly Gly Gly
            115                 120                 125

Gly Ser Gly Gly Gly Gly Ser Arg His Gln Met Thr Gln Ser Pro Ser
 130                 135                 140

Ser Leu Ser Ala Ser Val Gly Asp Arg Val Thr Ile Thr Cys Arg Ala
145                 150                 155                 160

Ser Gln Ser Ile Ser Ser Tyr Leu Asn Trp Tyr Gln Gln Lys Pro Gly
            165                 170                 175

Lys Ala Pro Lys Leu Leu Ile Tyr Ala Ala Ser Ser Leu Gln Ser Gly
            180                 185                 190

Val Pro Ser Arg Phe Ser Gly Ser Gly Ser Gly Thr Asp Phe Thr Leu
            195                 200                 205

Thr Ile Ser Ser Leu Gln Pro Glu Asp Phe Ala Thr Tyr Tyr Cys Gln
        210                 215                 220

Gln Ser Tyr Ser Thr Pro Leu Thr Phe Gly Gly Gly Thr Lys Val Glu
225                 230                 235                 240

Ile Lys Gly Gln Ala Gly His His His His His Gly Asp Tyr Lys
            245                 250                 255

Asp Asp Asp Asp Lys Gly
            260

<210> SEQ ID NO 8
<211> LENGTH: 801
<212> TYPE: DNA
<213> ORGANISM: Homo sapiens

<400> SEQUENCE: 8

```
atggccttac cagtgaccgc cttgctcctg ccgctggcct tgctgctcca cgccgccagg    60
ccgcaggtgc agctgcagga gtccggccca ggactggtga agccttcgga cccctgtcc   120
ctcacctgca ctgtctctgg tggctccgtc agcagtggta gttactactg gagctggatc   180
cggcagcccc cagggaaggg actggagtgg attgggtata tctattacag tgggagcacc   240
aactacaacc cctccctcaa gagtcgagtc accatatcag tagacacgtc caagaaccag   300
ttctccctga agctgagctc tgtgaccgct gcggacacgg ccgtgtatta ctgtgcgaga   360
gaggggaaga atggggcttt tgatatctgg ggccaaggga caatggtcac cgtctcttca   420
ggtggaggcg gttcaggcgg aggtggctct ggcggtggcg gatcacgaca tcagatgacc   480
cagtctccat cctccctgtc tgcatctgta ggagacagag tcaccatcac ttgccgggca   540
agtcagagca ttagcagcta tttaaattgg tatcagcaga aaccagggaa agcccctaag   600
ctcctgatct atgctgcatc cagtttgcaa agtggggtcc catcaaggtt cagtggcagt   660
```

| | |
|---|---|
| ggatctggga cagatttcac tctcaccatc agcagtctgc aacctgaaga ttttgcaact | 720 |
| tactactgtc aacagagtta cagtaccccg ctcactttcg gcggagggac caaggtggag | 780 |
| atcaaacgga ctgcggccgc a | 801 |

<210> SEQ ID NO 9
<211> LENGTH: 801
<212> TYPE: DNA
<213> ORGANISM: Homo sapiens

<400> SEQUENCE: 9

| | |
|---|---|
| atggcgctgc cggtgaccgc gctgctgctg ccgctggcgc tgctgctgca tgcggcgcgc | 60 |
| ccgcaggtgc agctgcagga aagcggcccg ggcctggtga aaccgagcga aaccctgagc | 120 |
| ctgacctgca ccgtgagcgg cggcagcgtg agcagcggca gctattattg gagctggatt | 180 |
| cgccagccgc cgggcaaagg cctggaatgg attggctata tttattatag cggcagcacc | 240 |
| aactataacc cgagcctgaa aagccgcgtg accattagcg tggataccag caaaaaccag | 300 |
| tttagcctga aactgagcag cgtgaccgcg gcggataccg cggtgtatta ttgcgcgcgc | 360 |
| gaaggcaaaa acggcgcgtt tgatatttgg ggccagggca ccatggtgac cgtgagcagc | 420 |
| ggcggcggcg gcagcggcgg cggcggcagc ggcggcggcg gcagccgcca tcagatgacc | 480 |
| cagagcccga gcagcctgag cgcgagcgtg ggcgatcgcg tgaccattac ctgccgcgcg | 540 |
| agccagagca ttagcagcta tctgaactgg tatcagcaga accgggcaa agcgccgaaa | 600 |
| ctgctgattt atgcggcgag cagcctgcag agcggcgtgc cgagccgctt tagcggcagc | 660 |
| ggcagcggca ccgattttac cctgaccatt agcagcctgc agccggaaga ttttgcgacc | 720 |
| tattattgcc agcagagcta tagcaccccg ctgacctttg gcggcggcac caaagtggaa | 780 |
| attaaacgca ccgcggcggc g | 801 |

<210> SEQ ID NO 10
<211> LENGTH: 801
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

| | |
|---|---|
| atggccctcc cggtaacggc tctgctgctt ccactcgcac tgctcttgca tgctgccaga | 60 |
| ccacaggtcc agctgcagga gagtgggcct ggactggtta agccgagtga gacactttcc | 120 |
| ttgacgtgca ctgtgagcgg gggaagtgtg tcctcaggta gttattactg gtcctggatt | 180 |
| cgccagccac caggaaaggg actggagtgg ataggttata tctattattc tggcagcact | 240 |
| aattacaatc cttctctcaa aagtagggtg acaatttcag tggatacttc caaaaatcag | 300 |
| tttagtctga agctcagctc tgtgacagct gctgatactg cagtttacta ctgcgccagg | 360 |
| gaggggaaga atggcgcctt cgatatttgg ggacagggca ctatggtgac tgtatcaagc | 420 |
| ggaggcggtg gcagcggcgg gggagggagt ggaggcggcg gtctcgaca tcagatgaca | 480 |
| cagagcccat catcacttag cgccagcgtt ggcgaccggg ttacgataac atgcagggct | 540 |
| tcccaatcta tcagttctta tctgaactgg tatcagcaga accaggtaa ggccccaag | 600 |
| ctgctcatct acgcagcctc atccctgcag agcggcgtcc ctagtcgatt tccggtagt | 660 |

```
gggtcaggga cagattttac cctgactatc agttcactgc agcccgagga cttcgcgaca    720
tactattgcc aacagtccta tagtacaccc ttgacatttg gcggcgggac taaagtagaa    780
attaaacgca ccgcggccgc a                                              801
```

<210> SEQ ID NO 11
<211> LENGTH: 10
<212> TYPE: PRT
<213> ORGANISM: Homo sapiens

<400> SEQUENCE: 11

Gly Gly Ser Val Ser Ser Gly Ser Tyr Tyr
1               5                   10

<210> SEQ ID NO 12
<211> LENGTH: 7
<212> TYPE: PRT
<213> ORGANISM: Homo sapiens

<400> SEQUENCE: 12

Ile Tyr Tyr Ser Gly Ser Thr
1               5

<210> SEQ ID NO 13
<211> LENGTH: 12
<212> TYPE: PRT
<213> ORGANISM: Homo sapiens

<400> SEQUENCE: 13

Ala Arg Glu Gly Lys Asn Gly Ala Phe Asp Ile Trp
1               5                   10

<210> SEQ ID NO 14
<211> LENGTH: 6
<212> TYPE: PRT
<213> ORGANISM: Homo sapiens

<400> SEQUENCE: 14

Gln Ser Ile Ser Ser Tyr
1               5

<210> SEQ ID NO 15
<211> LENGTH: 4
<212> TYPE: PRT
<213> ORGANISM: Homo sapiens

<400> SEQUENCE: 15

Ala Ala Ser Ser
1

<210> SEQ ID NO 16
<211> LENGTH: 10
<212> TYPE: PRT
<213> ORGANISM: Homo sapiens

<400> SEQUENCE: 16

Gln Gln Ser Tyr Ser Thr Pro Leu Thr Phe
1               5                   10

<210> SEQ ID NO 17
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 17

Gly Gly Gly Gly Ser Gly Gly Gly Gly Ser Gly Gly Gly Gly Ser
1               5                   10                  15

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggaggtggag gctcaggagg aggaggcagt ggaggtggtg ggtca              45

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggtggaggcg gttcaggcgg aggtggctct ggcggtggcg gatca              45

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Ala Leu Pro Val Thr Ala Leu Leu Leu Pro Leu Ala Leu Leu Leu
1               5                   10                  15

His Ala Ala Arg Pro
            20

<210> SEQ ID NO 21
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atggccctgc cagtaacggc tctgctgctg ccacttgctc tgctcctcca tgcagccagg   60
cc                                                                  62

<210> SEQ ID NO 22
<211> LENGTH: 235
<212> TYPE: PRT
<213> ORGANISM: Homo sapiens

<400> SEQUENCE: 22

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30
```

```
Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
 50                  55                  60

Ala Ser Pro Thr Phe Leu Leu Tyr Leu Ser Gln Asn Lys Pro Lys Ala
 65                  70                  75                  80

Ala Glu Gly Leu Asp Thr Gln Arg Phe Ser Gly Lys Arg Leu Gly Asp
                 85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235

<210> SEQ ID NO 23
<211> LENGTH: 220
<212> TYPE: PRT
<213> ORGANISM: Homo sapiens

<400> SEQUENCE: 23

Met Leu Arg Leu Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
 50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                 85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160
```

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 24
<211> LENGTH: 321
<212> TYPE: DNA
<213> ORGANISM: Homo sapiens

<400> SEQUENCE: 24
attgaagtta tgtatcctcc tccttaccta gacaatgaga agagcaatgg aaccattatc     60
catgtgaaag ggaaacacct ttgtccaagt cccctatttc ccggaccttc taagcccttt    120
tgggtgctgg tggtggttgg tggagtcctg gcttgctata gcttgctagt aacagtggcc    180
tttattattt tctgggtgag gagtaagagg agcaggctcc tgcacagtga ctacatgaac    240
atgactcccc gccgccccgg gcccacccgc aagcattacc agccctatgc cccaccacgc    300
gacttcgcag cctatcgctc c                                              321

<210> SEQ ID NO 25
<211> LENGTH: 164
<212> TYPE: PRT
<213> ORGANISM: Homo sapiens

<400> SEQUENCE: 25

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 26
<211> LENGTH: 339
<212> TYPE: DNA
<213> ORGANISM: Homo sapiens

<400> SEQUENCE: 26

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga agataagat ggcggaggcc tacagtgaga ttgggatgaa aggcgagcgc    240
cggaggggca aggggcacga tggcctttac cagggtctca gtacagccac caaggacacc   300
tacgacgccc ttcacatgca ggccctgccc cctcgctaa                          339
```

<210> SEQ ID NO 27
<211> LENGTH: 255
<212> TYPE: PRT
<213> ORGANISM: Homo sapiens

<400> SEQUENCE: 27

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 28
<211> LENGTH: 277
<212> TYPE: PRT
<213> ORGANISM: Homo sapiens

<400> SEQUENCE: 28

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275
```

<210> SEQ ID NO 29
<211> LENGTH: 199
<212> TYPE: PRT
<213> ORGANISM: Homo sapiens

<400> SEQUENCE: 29

```
Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80
```

```
Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
            115                 120                 125

His Ile Tyr Glu Ser Gln Leu Cys Cys Gln Leu Lys Phe Trp Leu Pro
130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
            195

<210> SEQ ID NO 30
<211> LENGTH: 223
<212> TYPE: PRT
<213> ORGANISM: Homo sapiens

<400> SEQUENCE: 30

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 31
<211> LENGTH: 288
<212> TYPE: PRT
```

<213> ORGANISM: Homo sapiens

<400> SEQUENCE: 31

Met Gln Ile Pro Gln Ala Pro Trp Pro Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gly Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 32
<211> LENGTH: 525
<212> TYPE: PRT
<213> ORGANISM: Homo sapiens

<400> SEQUENCE: 32

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

-continued

```
His Gln Pro Asp Ser Gly Pro Pro Ala Ala Ala Pro Gly His Pro Leu
 65                  70                  75                  80

Ala Pro Gly Pro His Pro Ala Ala Pro Ser Trp Gly Pro Arg Pro
             85                  90                  95

Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
                115                 120                 125

Arg Gly Asp Phe Ser Leu Trp Leu Arg Pro Ala Arg Arg Ala Asp Ala
            130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
            195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Pro Gly Gly Gly
            290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
            370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Leu Leu Phe Leu Ile Leu Gly Val Leu Ser Leu Leu Leu Leu
            450                 455                 460

Val Thr Gly Ala Phe Gly Phe His Leu Trp Arg Arg Gln Trp Arg Pro
465                 470                 475                 480
```

-continued

```
Arg Arg Phe Ser Ala Leu Glu Gln Gly Ile His Pro Pro Gln Ala Gln
            485                 490                 495
Ser Lys Ile Glu Glu Leu Glu Gln Glu Pro Glu Pro Glu Pro Glu Pro
            500                 505                 510
Glu Pro Glu Pro Glu Pro Glu Pro Glu Pro Glu Gln Leu
            515                 520                 525

<210> SEQ ID NO 33
<211> LENGTH: 370
<212> TYPE: PRT
<213> ORGANISM: Homo sapiens

<400> SEQUENCE: 33

Met Leu Gly Gln Val Val Thr Leu Ile Leu Leu Leu Leu Lys Val
1               5                   10                  15
Tyr Gln Gly Lys Gly Cys Gln Gly Ser Ala Asp His Val Val Ser Ile
                20                  25                  30
Ser Gln Val Pro Leu Gln Leu Gln Pro Asn Ser Ile Gln Thr Lys Val
            35                  40                  45
Asp Ser Ile Ala Trp Lys Lys Leu Leu Pro Ser Gln Asn Gly Phe His
        50                  55                  60
His Ile Leu Lys Trp Glu Asn Gly Ser Leu Pro Ser Asn Thr Ser Asn
65                  70                  75                  80
Asp Arg Phe Ser Phe Ile Val Lys Asn Leu Ser Leu Leu Ile Lys Ala
                85                  90                  95
Ala Gln Gln Gln Asp Ser Gly Leu Tyr Cys Leu Glu Val Thr Ser Ile
            100                 105                 110
Ser Gly Lys Val Gln Thr Ala Thr Phe Gln Val Phe Val Phe Glu Ser
        115                 120                 125
Leu Leu Pro Asp Lys Val Glu Lys Pro Arg Leu Gln Gly Gln Gly Lys
    130                 135                 140
Ile Leu Asp Arg Gly Arg Cys Gln Val Ala Leu Ser Cys Leu Val Ser
145                 150                 155                 160
Arg Asp Gly Asn Val Ser Tyr Ala Trp Tyr Arg Gly Ser Lys Leu Ile
                165                 170                 175
Gln Thr Ala Gly Asn Leu Thr Tyr Leu Asp Glu Glu Val Asp Ile Asn
            180                 185                 190
Gly Thr His Thr Tyr Thr Cys Asn Val Ser Asn Pro Val Ser Trp Glu
        195                 200                 205
Ser His Thr Leu Asn Leu Thr Gln Asp Cys Gln Asn Ala His Gln Glu
    210                 215                 220
Phe Arg Phe Trp Pro Phe Leu Val Ile Ile Val Ile Leu Ser Ala Leu
225                 230                 235                 240
Phe Leu Gly Thr Leu Ala Cys Phe Cys Val Trp Arg Arg Lys Arg Lys
                245                 250                 255
Glu Lys Gln Ser Glu Thr Ser Pro Lys Glu Phe Leu Thr Ile Tyr Glu
            260                 265                 270
Asp Val Lys Asp Leu Lys Thr Arg Arg Asn His Glu Gln Glu Gln Thr
        275                 280                 285
Phe Pro Gly Gly Gly Ser Thr Ile Tyr Ser Met Ile Gln Ser Gln Ser
    290                 295                 300
Ser Ala Pro Thr Ser Gln Glu Pro Ala Tyr Thr Leu Tyr Ser Leu Ile
305                 310                 315                 320
Gln Pro Ser Arg Lys Ser Gly Ser Arg Lys Arg Asn His Ser Pro Ser
                325                 330                 335
```

-continued

Phe Asn Ser Thr Ile Tyr Glu Val Ile Gly Lys Ser Gln Pro Lys Ala
                340                 345                 350

Gln Asn Pro Ala Arg Leu Ser Arg Lys Glu Leu Glu Asn Phe Asp Val
            355                 360                 365

Tyr Ser
    370

<210> SEQ ID NO 34
<211> LENGTH: 289
<212> TYPE: PRT
<213> ORGANISM: Homo sapiens

<400> SEQUENCE: 34

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
        275                 280                 285

Ser

<210> SEQ ID NO 35
<211> LENGTH: 183
<212> TYPE: PRT
<213> ORGANISM: Homo sapiens

<400> SEQUENCE: 35

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180
```

<210> SEQ ID NO 36
<211> LENGTH: 9071
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
catgctcgag ggagtgcagg tggagactat ctccccagga cgggcgca ccttccccaa      60 gcgcggccag acctgcgtgg tgcactacac cgggatgctt gaagatggaa agaaagttga    120
ttcctcccgg acagaaaaca agccctttaa gtttatgcta ggcaagcagg aggtgatccg    180
aggctgggaa aaggggttg cccagatgag tgtgggtcag agagccaaac tgactatatc     240
tccagattat gcctatggtg ccactgggca cccaggcatc atcccaccac atgccactct    300
cgtcttcgat gtggagcttc taaaactgga atctggcggt ggatccggag tcgacggatt    360
tggtgatgtc ggtgctcttg agagtttgag gggaaatgca gatttggctt acatcctgag    420
catggagccc tgtggccact gcctcattat caacaatgtg aacttctgcc gtgagtccgg    480
gctccgcacc cgcactggct ccaacatcga ctgtgagaag ttgcggcgtc gcttctcctc    540
gctgcatttc atggtggagg tgaagggcga cctgactgcc aagaaaatgg tgctggcttt    600
gctggagctg gcgcggcagg accacggtgc tctggactgc tgcgtggtgg tcattctctc    660
tcacggctgt caggccagcc acctgcagtt cccaggggct gtctacggca cagatggatg    720
ccctgtgtcg gtcgagaaga ttgtgaacat cttcaatggg accagctgcc ccagcctggg    780
agggaagccc aagctctttt tcatccaggc ctgtggtggg gagcagaaag accatgggtt    840
tgaggtggcc tccacttccc ctgaagacga gtccctggc agtaaccccg agccagatgc     900
```

```
caccccgttc caggaaggtt tgaggacctt cgaccagctg gacgccatat ctagtttgcc      960
cacacccagt gacatctttg tgtcctactc tactttccca ggttttgttt cctggaggga     1020
ccccaagagt ggctcctggt acgttgagac cctggacgac atctttgagc agtgggctca     1080
ctctgaagac ctgcagtccc tcctgcttag ggtcgctaat gctgtttcgg tgaaagggat     1140
ttataaacag atgcctggtt gctttaattt cctccggaaa aaacttttct ttaaaacatc     1200
aggatctgga gcaacaaact tctcactact caaacaagca ggtgacgtgg aggagaatcc     1260
cggcccaatg gccctgccag taacggctct gctgctgcca cttgctctgc tcctccatgc     1320
agccaggcct caggttcagc ttcaggagag tgggcccaggc ctggtgaagc caagtgagac     1380
tctcagcttg acttgcacag tttctggagg cagtgtctcc tcaggcagct attattggtc     1440
ctggattcgg cagcccctg ggaaaggcct ggagtggatt gggtacatat attacagtgg     1500
cagcacaaat acaatccat ccctgaagtc tcgagtaact atcagtgtgg acacaagcaa      1560
gaatcagttt tcactcaaac tgtcttctgt gactgctgct gacactgctg tttattattg     1620
tgccagggag gggaaaaatg gggcatttga tatttgggt cagggcacaa tggtgacagt      1680
cagctctgga ggtggaggct caggaggagg aggcagtgga ggtggtgggt cacgccatca     1740
gatgactcag tccccctcca gtctttctgc ctcagttggg gatagagtga ccatcacatg     1800
cagagcaagt cagagcatat catcctatct gaactggtac cagcagaagc cagggaaagc     1860
ccccaaattg ctgatttatg cagcctcaag tctccagagt ggggtgccaa gcaggttctc     1920
aggcagtggc agtgggacag atttcacatt gacaatcagc tccctccaac ctgaagattt     1980
tgccacctac tattgccagc aatcctacag cacgcccctg acttttggag gtggcacaaa     2040
ggtagagatc aagaggactg cggccgcaat tgaagttatg tatcctcctc cttacctaga     2100
caatgagaag agcaatggaa ccattatcca tgtgaaaggg aaacacctt gtccaagtcc      2160
cctatttccc ggaccttcta gcccttttg ggtgctggtg gtggttggtg gagtcctggc      2220
ttgctatagc ttgctagtaa cagtggcctt tattatttc tgggtgagga gtaagaggag      2280
caggctcctg cacagtgact acatgaacat gactccccgc cgccccgggc cacccgcaa      2340
gcattaccag ccctatgccc caccacgcga cttcgcagcc tatcgctcca gagtgaagtt     2400
cagcaggagc gcagacgccc ccgcgtacca gcagggccag aaccagctct ataacgagct     2460
caatctagga cgaagagagg agtacgatgt tttggacaag agacgtggcc gggaccctga     2520
gatggggga aagccgagaa ggaagaaccc tcaggaaggc ctgtacaatg aactgcagaa      2580
agataagatg gcgaaggcct acagtgagat tgggatgaaa ggcgagcgcc ggaggggcaa     2640
ggggcacgat ggcctttacc agggtctcag tacagccacc aaggacacct acgacgccct     2700
tcacatgcag gccctgcccc ctcgctaaca gccactcgag gatccggatt agtccaattt     2760
gttaaagaca ggatatcagt ggtccaggct ctagttttga ctcaacaata tcaccagctg     2820
aagcctatag agtacgagcc atagataaaa taaaagattt tatttagtct ccagaaaaag     2880
gggggaatga agacccccac ctgtaggttt ggcaagctag cttaagtaac gccatttgc      2940
aaggcatgga aaaatacata actgagaata gagaagttca gatcaaggtc aggaacagat     3000
ggaacagctg aatatgggcc aaacaggata tctgtggtaa gcagttcctg ccccggctca     3060
gggccaagaa cagatggaac agctgaatat gggccaaaca ggatatctgt ggtaagcagt     3120
tcctgccccg gctcagggcc aagaacagat ggtcccagat gcggtccag ccctcagcag      3180
tttctagaga accatcagat gtttccaggg tgccccaagg acctgaaatg accctgtgcc     3240
```

-continued

```
ttatttgaac taaccaatca gttcgcttct cgcttctgtt cgcgcgcttc tgctccccga      3300
gctcaataaa agagcccaca acccctcact cggggcgcca gtcctccgat tgactgagtc      3360
gcccgggtac ccgtgtatcc aataaaccct cttgcagttg catccgactt gtggtctcgc      3420
tgttccttgg gagggtctcc tctgagtgat tgactacccg tcagcggggg tctttcacat      3480
gcagcatgta tcaaaattaa tttggttttt tttcttaagt atttacatta aatggccata      3540
gtacttaaag ttacattggc ttccttgaaa taaacatgga gtattcagaa tgtgtcataa      3600
atatttctaa ttttaagata gtatctccat tggctttcta cttttcttt tatttttttt       3660
gtcctctgtc ttccatttgt tgttgttgtt gtttgtttgt ttgtttgttg gttggttggt      3720
taatttttt ttaaagatcc tacactatag ttcaagctag actattagct actctgtaac       3780
ccagggtgac cttgaagtca tgggtagcct gctgttttag ccttcccaca tctaagatta      3840
caggtatgag ctatcatttt tggtatattg attgattgat tgattgatgt gtgtgtgtgt      3900
gattgtgttt gtgtgtgtga ttgtgtatat gtgtgtatgg ttgtgtgtga ttgtgtgtat      3960
gtatgtttgt gtgtgattgt gtgtgtgtga ttgtgcatgt gtgtgtgtgt gattgtgttt      4020
atgtgtatga ttgtgtgtgt gtgtgtgtgt gtgtgtgtgt gtgtgtgtgt gtgtgtgttg      4080
tgtatatata tttatggtag tgagaggcaa cgctccggct caggtgtcag gttggttttt      4140
gagacagagt ctttcactta gcttggaatt cactggccgt cgttttacaa cgtcgtgact      4200
gggaaaaccc tggcgttacc caacttaatc gccttgcagc acatcccct ttcgccagct       4260
ggcgtaatag cgaagaggcc cgcaccgatc gcccttccca acagttgcgc agcctgaatg      4320
gcgaatggcg cctgatgcgg tattttctcc ttacgcatct gtgcggtatt tcacaccgca      4380
tatggtgcac tctcagtaca atctgctctg atgccgcata gttaagccag ccccgacacc      4440
cgccaacacc cgctgacgcg ccctgacggg cttgtctgct cccggcatcc gcttacagac      4500
aagctgtgac cgtctccggg agctgcatgt gtcagaggtt ttcaccgtca tcaccgaaac      4560
gcgcgagacg aaagggcctc gtgatacgcc tatttttata ggttaatgtc atgataataa      4620
tggtttctta gacgtcaggt ggcacttttc ggggaaatgt gcgcggaacc cctatttgtt      4680
tatttttcta aatacattca aatatgtatc cgctcatgag acaataaccc tgataaatgc      4740
ttcaataata ttgaaaaagg aagagtatga gtattcaaca tttccgtgtc gcccttattc      4800
ccttttttgc ggcattttgc cttcctgttt ttgctcaccc agaaacgctg gtgaaagtaa      4860
aagatgctga agatcagttg ggtgcacgag tgggttacat cgaactggat ctcaacagcg      4920
gtaagatcct tgagagtttt cgccccgaag aacgttttcc aatgatgagc acttttaaag      4980
ttctgctatg tggcgcggta ttatcccgta ttgacgccgg gcaagagcaa ctcggtcgcc      5040
gcatacacta ttctcagaat gacttggttg agtactcacc agtcacagaa aagcatctta      5100
cggatggcat gacagtaaga gaattatgca gtgctgccat aaccatgagt gataacactg      5160
cggccaactt acttctgaca acgatcggag gaccgaagga gctaaccgct ttttgcaca      5220
acatggggga tcatgtaact cgccttgatc gttgggaacc ggagctgaat gaagccatac      5280
caaacgacga gcgtgacacc acgatgcctg tagcaatggc aacaacgttg cgcaaactat      5340
taactggcga actacttact ctagcttccc ggcaacaatt aatagactgg atggaggcgg      5400
ataaagttgc aggaccactt ctgcgctcgg cccttccggc tggctggttt attgctgata      5460
aatctggagc cggtgagcgt gggtctcgcg gtatcattgc agcactgggg ccagatggta      5520
agccctcccg tatcgtagtt atctacacga cggggagtca gcaactatg gatgaacgaa       5580
atagacagat cgctgagata ggtgcctcac tgattaagca ttggtaactg tcagaccaag      5640
```

```
tttactcata tatactttag attgatttaa aacttcattt ttaatttaaa aggatctagg   5700
tgaagatcct ttttgataat ctcatgacca aaatcccctta acgtgagttt tcgttccact  5760
gagcgtcaga ccccgtagaa aagatcaaag gatcttcttg agatcctttt tttctgcgcg   5820
taatctgctg cttgcaaaca aaaaaaccac cgctaccagc ggtggtttgt ttgccggatc   5880
aagagctacc aactctttt  ccgaaggtaa ctggcttcag cagagcgcag ataccaaata   5940
ctgttcttct agtgtagccg tagttaggcc accacttcaa gaactctgta gcaccgccta   6000
catacctcgc tctgctaatc ctgttaccag tggctgctgc cagtggcgat aagtcgtgtc   6060
ttaccgggtt ggactcaaga cgatagttac cggataaggc gcagcggtcg ggctgaacgg   6120
ggggttcgtg cacacagccc agcttggagc gaacgaccta caccgaactg agatacctac   6180
agcgtgagct atgagaaagc gccacgcttc ccgaagggag aaaggcggac aggtatccgg   6240
taagcggcag ggtcggaaca ggagagcgca cgagggagct tccaggggga aacgcctggt   6300
atctttatag tcctgtcggg tttcgccacc tctgacttga gcgtcgattt ttgtgatgct   6360
cgtcaggggg gcggagccta tggaaaaacg ccagcaacgc ggcctttta  cggttcctgg   6420 ccttttgctg gccttttgct cacatgttct ttcctgcgtt atcccctgat tctgtggata   6480
accgtattac cgcctttgag tgagctgata ccgctcgccg cagccgaacg accgagcgca   6540
gcgagtcagt gagcgaggaa gcggaagagc gcccaatacg caaaccgcct ctccccgcgc   6600
gttggccgat tcattaatgc agctggcacg acaggtttcc cgactggaaa gcgggcagtg   6660
agcgcaacgc aattaatgtg agttagctca ctcattaggc accccaggct ttacacttta   6720
tgcttccggc tcgtatgttg tgtggaattg tgagcggata acaatttcac acaggaaaca   6780
gctatgacca tgattacgcc aagctttgct cttaggagtt tcctaataca tcccaaactc   6840
aaatatataa agcatttgac ttgttctatg ccctaggggg cgggggggaag ctaagccagc   6900 tttttttaac atttaaaatg ttaattccat tttaaatgca cagatgtttt tatttcataa   6960
gggtttcaat gtgcatgaat gctgcaatat tcctgttacc aaagctagta taaataaaaa   7020
tagataaacg tggaaattac ttagagtttc tgtcattaac gtttccttcc tcagttgaca   7080
acataaatgc gctgctgaga agccagtttg catctgtcag gatcaatttc ccattatgcc   7140
agtcatatta attactagtc aattagttga ttttttatttt tgacatatac atgtgaaaga   7200
ccccacctgt aggtttggca agctagctta agtaacgcca ttttgcaagg catggaaaaa   7260
tacataactg agaatagaaa agttcagatc aaggtcagga acagatggaa cagctgaata   7320
tgggccaaac aggatatctg tggtaagcag ttcctgcccc ggctcagggc caagaacaga   7380
tggaacagct gaatatgggc caaacaggat atctgtggta agcagttcct gccccggctc   7440
agggccaaga acagatggtc cccagatgcg gtccagccct cagcagtttc tagagaacca   7500
tcagatgttt ccagggtgcc ccaaggacct gaaatgaccc tgtgccttat ttgaactaac   7560
caatcagttc gcttctcgct tctgttcgcg cgcttctgct ccccgagctc aataaaagag   7620
cccacaaccc ctcactcggc gcgccagtcc tccgattgac tgagtcgccc gggtacccgt   7680
gtatccaata aaccctcttg cagttgcatc cgacttgtgg tctcgctgtt ccttgggagg   7740
gtctcctctg agtgattgac tacccgtcag cggggggtctt tcatttgggg gctcgtccgg   7800
gatcgggaga cccctgccca ggaccaccg  acccaccacc gggaggtaag ctggccagca   7860
acttatctgt gtctgtccga ttgtctagtg tctatgactg attttatgcg cctgcgtcgg   7920
tactagttag ctaactagct ctgtatctgg cggacccgtg gtggaactga cgagttcgga   7980
```

```
acacccggcc gcaaccctgg gagacgtccc agggacttcg ggggccgttt ttgtggcccg    8040
acctgagtcc taaaatcccg atcgtttagg actctttggt gcaccccct tagaggaggg     8100
atatgtggtt ctggtaggag acgagaacct aaaacagttc ccgcctccgt ctgaattttt    8160
gctttcggtt tgggaccgaa gccgcgccgc gcgtcttgtc tgctgcagca tcgttctgtg    8220
ttgtctctgt ctgactgtgt tctgtatttt gtctgaaaat atgggcccgg gctagcctgt    8280
taccactccc ttaagtttga ccttaggtca ctggaaagat gtcgagcgga tcgctcacaa    8340
ccagtcggta gatgtcaaga agagacgttg ggttaccttc tgctctgcag aatggccaac    8400
ctttaacgtc ggatggccgc gagacggcac ctttaaccga gacctcatca cccaggttaa    8460
gatcaaggtc ttttcacctg gcccgcatgg acacccagac caggtcccct acatcgtgac    8520
ctgggaagcc ttggcttttg accccctcc ctgggtcaag ccctttgtac accctaagcc     8580
tccgcctcct cttcctccat ccgcccgtc tctccccctt gaacctcctc gttcgacccc      8640
gcctcgatcc tccctttatc cagccctcac tccttctcta ggcgccccca tatgccata     8700
tgagatctta tatggggcac ccccgcccct tgtaaacttc cctgaccctg acatgacaag    8760
agttactaac agcccctctc tccaagctca cttacaggct ctctacttag tccagcacga    8820
agtctggaga cctctggcgg cagcctacca agaacaactg gaccgaccgg tggtacctca    8880
cccttaccga gtcggcgaca cagtgtgggt ccgccgacac cagactaaga acctagaacc    8940
tcgctggaaa ggaccttaca cagtcctgct gaccaccccc accgccctca agtagacgg     9000
catcgcagct tggatacacg ccgcccacgt gaaggctgcc gaccccgggg gtggaccatc    9060
ctctagactg c                                                         9071
```

```
<210> SEQ ID NO 37
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcgctccgga aaaacttttt ctttaaaaca tcaggatctg gagcaacaaa cttc          54

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggtgtttccc tttcacatgg                                                20

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Thr Asn Phe Ser Leu Leu Lys Gln Ala Gly Asp Val Glu Glu Asn
1               5                   10                  15

Pro Gly Pro
```

<210> SEQ ID NO 40
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gcaacaaact tctcactact caaacaagca ggtgacgtgg aggagaatcc cggccc        56

<210> SEQ ID NO 41
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcgcgcgcgc acgtttgccc gggagatggg ggaggctaac ggatctggag caacaaactt    60
c                                                                   61

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggtgtttccc tttcacatgg                                                20

<210> SEQ ID NO 43
<211> LENGTH: 622
<212> TYPE: PRT
<213> ORGANISM: Homo sapiens

<400> SEQUENCE: 43

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr His Phe Phe Ser Arg Ile
    130                 135                 140

Thr Lys Ala Asn Val Asp Leu Leu Pro Arg Gly Ala Pro Glu Arg Gln
145                 150                 155                 160

```
Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
210                 215                 220

Ala Ala Leu Gln Gly Gly Pro Pro Tyr Gly Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575
```

```
Gly Leu Gln Gly Gly Ile Pro Asn Gly Tyr Leu Val Leu Asp Leu Ser
            580                 585                 590

Val Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
        610                 615                 620

<210> SEQ ID NO 44
<211> LENGTH: 4
<212> TYPE: PRT
<213> ORGANISM: Homo sapiens

<400> SEQUENCE: 44

Tyr Val Lys Met
1

<210> SEQ ID NO 45
<211> LENGTH: 4
<212> TYPE: PRT
<213> ORGANISM: Homo sapiens

<400> SEQUENCE: 45

Gln Val Gln Leu
1
```

METHOD OF REDUCING MESOTHELIN-EXPRESSING TUMOR BURDEN BY ADMINISTRATION OF T CELLS COMPRISING MESOTHELIN-TARGETED CHIMERIC ANTIGEN RECEPTORS

CROSS-REFERENCE TO RELATED APPLICATIONS

This application is a Divisional of U.S. patent application Ser. No. 15/368,278, filed Dec. 2, 2016, which is a Continuation of International Patent Application No. PCT/US2015/034552, filed Jun. 5, 2015, which claims priority to U.S. Provisional Patent Application Ser. No. 62/008,851, filed Jun. 6, 2014, the contents of each of which are incorporated by reference in their entirety, and to each of which priority is claimed.

GRANT INFORMATION

This invention was made with government support under Grant Nos. W81XWH-11-1-0783 and W81XWH-12-1-0230 from Department of Defense. The government has certain rights in the invention.

SEQUENCE LISTING

The specification incorporates by reference the Sequence Listing submitted herewith via EFS on Mar. 17, 2020. Pursuant to 37 C.F.R. § 1.52(e)(5), the Sequence Listing text file, identified as 0727341027SL.txt, is 65,730 bytes and was created on Mar. 17, 2020. The Sequence Listing, electronically filed herewith, does not extend beyond the scope of the specification and thus does not contain new matter.

INTRODUCTION

The presently disclosed subject matter provides for methods and compositions for enhancing the immune response toward cancers and pathogens. It relates to chimeric antigen receptors (CARs) that specifically target human mesothelin, and immunoresponsive cells comprising such CARs. The presently disclosed mesothelin-targeted CARs have enhanced immune-activating properties, including anti-tumor activity, while possessing features to minimize CAR-induced toxicity and immunogenicity.

BACKGROUND OF THE INVENTION

Cell-based immunotherapy is a therapy with curative potential for the treatment of cancer. T cells and other immune cells may be modified to target tumor antigens through the introduction of genetic material coding for artificial or synthetic receptors for antigen, termed Chimeric Antigen Receptors (CARs), specific to selected antigens. Targeted T cell therapy using CARs has shown recent clinical success in treating some hematologic malignancies. However, translating CAR-expressing T cell therapy to solid tumors poses several obstacles that must be overcome to achieve clinical benefit. Malignant cells adapt to generate an immunosuppressive microenvironment to protect themselves from immune recognition and elimination. This tumor microenvironment poses a challenge to methods of treatment involving stimulation of an immune response, such as targeted T cell therapies. Solid tumors may also be restricted within anatomical compartments that impede efficient T cell trafficking, lack expression of agonistic costimulatory ligands and/or express negative regulators of T cell function. The successful elimination of solid tumors thus requires effective tumor infiltration and overcoming tumor-induced immunosuppression. In addition, solid tumors pose a challenge for selecting optimal immune targets—antigens whose targeting would enable tumor eradication by potent T cells, with minimal or tolerable toxicity to non-tumor tissues. Accordingly, there are needs for novel therapeutic strategies to design CARs for treating cancers, particularly, solid tumors, which strategies capable of inducing potent tumor eradication with minimal toxicity and immunogenicity (CAR immunogenicity may result in reduced efficacy or acute toxicity exemplified in the setting of anaphylactic response to suboptimal CARs).

SUMMARY OF THE INVENTION

The presently disclosed subject matter generally provides chimeric antigen receptors (CARs) that specifically target human mesothelin, immunoresponsive cells comprising such CARs, and uses of these CARs and immunoresponsive cells for treating cancers, pathogen infections, etc.

The presently disclosed subject matter provides CARs. In one non-limiting example, the CAR comprises an extracellular antigen-binding domain, a transmembrane domain and an intracellular domain, where the extracellular antigen-binding domain specifically binds to human mesothelin with a binding affinity of from about 1 nM to about 25 nM. In certain embodiments, the CAR recognizes human mesothelin with a mesothelin expression level of about 1,000 or more mesothelin binding sites/cell.

In some embodiments, the extracellular antigen-binding domain comprises a heavy chain variable region comprising amino acids 1-119 of SEQ ID NO:1. In some embodiments, the extracellular antigen-binding domain comprises a light chain variable region comprising amino acids 1-107 of SEQ ID NO:5. In some embodiments, the extracellular antigen-binding domain comprises a light chain variable region comprising amino acids 1-107 of SEQ ID NO:3. In some embodiments, the extracellular antigen-binding domain comprises a heavy chain variable region CDR1 comprising amino acids having the sequence set forth in SEQ ID NO: 11 or conservative modifications thereof, a heavy chain variable region CDR2 comprising amino acids having the sequence set forth in SEQ ID NO: 12 or conservative modifications thereof, and a heavy chain variable region CDR3 comprising amino acids having the sequence set forth in SEQ ID NO: 13 or conservative modifications thereof. In some embodiments, the extracellular antigen-binding domain comprises a light chain variable region CDR1 comprising amino acids having the sequence set forth in SEQ ID NO:14 or conservative modifications thereof, a light chain variable region CDR2 comprising amino acids having the sequence set forth in SEQ ID NO:15 or conservative modifications thereof, and a light chain variable region CDR3 comprising amino acids having the sequence set forth in SEQ ID NO: 16 or conservative modifications thereof. In certain non-limiting embodiments, the extracellular antigen-binding domain comprises both of said heavy and light chains, optionally with a linker sequence, for example a linker peptide, between the heavy chain variable region and the light chain variable region. For example, in certain non-limiting embodiments, the extracellular antigen-binding domain comprises (i) a heavy chain variable region comprising amino acids 1-119 of SEQ ID NO:1 and (ii) a light chain variable region comprising amino acids 1-107 of SEQ ID NO:5, optionally with (iii) a linker sequence, for example a linker peptide, between the heavy chain variable region and the light chain variable region. In some embodiments, the extracellular antigen-binding domain comprises (i) a heavy chain variable region comprising amino acids 1-119 of SEQ ID NO:1 and (ii) a light chain variable region comprising amino acids 1-107 of SEQ ID NO:3, optionally with (iii) a linker sequence, for example a linker peptide, between the heavy chain variable region and the light chain variable region. For example, in certain non-limiting embodiments, the extracellular antigen-binding domain comprises (i) a heavy chain variable region CDR1 comprising amino acids having the sequence set forth in SEQ ID NO:11 or conservative modifications thereof, a heavy chain variable region CDR2 comprising amino acids having the sequence set forth in SEQ ID NO: 12 or conservative modifications thereof, and a heavy chain variable region CDR3 comprising amino acids having the sequence set forth in SEQ ID NO:13 or conservative modifications thereof, and (ii) a light chain variable region CDR1 comprising amino acids having the sequence set forth in SEQ ID NO: 14 or conservative modifications thereof, a light chain variable region CDR2 comprising amino acids having the sequence set forth in SEQ ID NO:15 or conservative modifications thereof, and a light chain variable region CDR3 comprising amino acids having the sequence set forth in SEQ ID NO: 16 or conservative modifications thereof, optionally with (iii) a linker sequence, for example a linker peptide, between the heavy chain variable region and the light chain variable region. In a specific non-limiting embodiment, the extracellular antigen-binding domain is a scFv. In a specific non-limiting embodiment, the extracellular antigen-binding domain is a Fab, which is optionally crosslinked. In a specific non-limiting embodiment, the extracellular binding domain is a F(ab)$_2$. In a specific non-limiting embodiment, any of the foregoing molecules can be comprised in a fusion protein with a heterologous sequence to form the extracellular antigen-binding domain.

In accordance with the presently disclosed subject matter, the extracellular antigen-binding domain is covalently joined to a transmembrane domain. The extracellular antigen-binding domain of the CAR can comprise a linker between a heavy chain variable region and a light chain variable region of the extracellular antigen-binding domain. The extracellular antigen-binding domain can comprise a leader that is covalently joined to the 5' terminus of the extracellular antigen-binding domain. In one embodiment, the leader comprises a CD8 polypeptide. In some embodiments, the transmembrane domain of the CAR comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof. In one embodiment, the transmembrane domain comprises a CD8 polypeptide. In one embodiment, the transmembrane domain comprises a CD28 polypeptide.

In accordance with the presently disclosed subject matter, the intracellular domain comprises a CD3 ζ polypeptide. In some embodiments, the intracellular domain further comprises at least one co-stimulatory signaling region. In some embodiments, the at least one co-stimulatory signaling region comprises a CD28 polypeptide, a 4-1BB polypeptide, an OX40 polypeptide, an ICOS polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof. In one embodiment, the transmembrane domain comprises a CD8 polypeptide and the intracellular domain comprises a CD3ζ polypeptide. In another embodiment, the transmembrane domain comprises a CD28 polypeptide and the intracellular domain comprises a CD3ζ polypeptide and a co-stimulatory signaling domain comprising a CD28 polypeptide. In yet another embodiment, the transmembrane domain comprises a CD8 polypeptide and the intracellular domain comprises a CD3ζ polypeptide and a co-stimulatory signaling domain comprising a 4-1BB polypeptide.

In one embodiment, the CAR is Mz. Mz comprises a transmembrane domain comprising a CD8 polypeptide, and an intracellular domain comprising a CD3ζ polypeptide. In one embodiment, the CAR is M28z. M28z comprises a transmembrane domain comprising a CD28 polypeptide, and an intracellular domain comprising a CD3ζ polypeptide and a co-stimulatory signaling region comprising a CD28 polypeptide. In one embodiment, the CAR is MBBz. MBBz includes a transmembrane domain comprising a CD8 polypeptide, and an intracellular domain comprising a CD3ζ polypeptide and a co-stimulatory signaling region comprising a 4-1BB polypeptide.

In certain embodiments, the CAR is recombinantly expressed. The CAR can be expressed from a vector. In one embodiment, the vector is a γ-retroviral rector.

The presently disclosed subject matter also provides isolated immunoresponsive cells comprising the above-described CARs. In certain embodiments, the isolated immunoresponsive cell further comprises at least one exogenous co-stimulatory ligand. In some embodiments, the at least one co-stimulatory ligand is selected from the group consisting of 4-1BBL, CD80, CD86, CD70, OX40L, CD48, TNFRSF14, and combinations thereof. In one embodiment, the co-stimulatory ligand is 4-1BBL. In certain embodiments, the isolated immunoresponsive cell further comprises at least one exogenous cytokine. In some embodiments, the at least cytokine is selected from the group consisting of IL-2, IL-3, IL-6, IL-7, IL-11, IL-12, IL-15, IL-17, IL-21, and combinations thereof. In one embodiment, the cytokine is IL-12. In some embodiments, the isolated immunoresponsive cell is selected from the group consisting of a T cell, a Natural Killer (NK) cell, a cytotoxic T lymphocyte (CTL), a regulatory T cell, a human embryonic stem cell, and a pluripotent stem cell from which lymphoid cells may be differentiated. In one embodiment, the cell is a T cell. In certain embodiments, the immunoresponsive cell expresses from about 1 to about 4 vector copy numbers/cell of the CAR. In certain embodiments, the isolated immunoresponsive cell further comprises an antigen recognizing receptor that binds to an antigen different than human mesothelin. The antigen can be a tumor or pathogen antigen. In some embodiments, the tumor antigen is selected from the group consisting of carbonic anhydrase IX (CA1X), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, an antigen of a cytomegalovirus (CMV) infected cell (e.g., a cell surface antigen), epithelial glycoprotein2 (EGP 2), epithelial glycoprotein-40 (EGP-40), epithelial cell adhesion molecule (EpCAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1CAM), melanoma antigen family A, 1 (MAGE-AI), Mucin 16 (Muc-16), Mucin 1 (Muc-1), NKG2D ligands, cancer-testis antigen NY-ESO-1, oncofetal antigen (h5T4), prostate stem cell antigen (PSCA), prostate-specific membrane antigen (PSMA), tumor-associated glycoprotein 72 (TAG-72), vascular endothelial growth factor R2 (VEGF-R2), Wilms tumor protein (WT-1), type 1 tyrosine-protein kinase transmembrane receptor (ROR1), and a combination thereof. In some embodiments, the immunoresponsive cell expresses one or more adhesion molecules. The adhesion molecule can increase the avidity of the CAR. In some embodiments, the adhesion molecule is selected from the group consisting of CD2, VLA-4, and combinations thereof.

Furthermore, the presently disclosed subject matter provides various methods of using the above-described immunoresponsive cell. For example, the presently disclosed subject matter provides methods of reducing tumor burden in a subject, where the method comprises administering an effective amount of the presently disclosed immunoresponsive cell to the subject, thereby inducing tumor cell death in the subject. In one embodiment, the method reduces the number of tumor cells. In another embodiment, the method reduces tumor size. In yet another embodiment, the method eradicates the tumor in the subject. In some embodiments, the tumor is a solid tumor. In some embodiments, the solid tumor is selected from the group consisting of mesothelioma, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, cholangiocarcinoma, and a combination thereof.

The presently disclosed subject matter also provides methods of increasing or lengthening survival of a subject having neoplasia, where the method comprises administering an effective amount of the presently disclosed immunoresponsive cell to the subject, thereby increasing or lengthening survival of the subject. In certain embodiments, the neoplasia is selected from the group consisting of mesothelioma, lung cancer, pancreatic cancer, ovarian cancer, breast cancer, colon cancer, pleural cancer, glioblastoma, esophageal cancer, gastric cancer, synovial sarcoma, thymic carcinoma, endometrial carcinoma, stomach cancer, cholangiocarcinoma, and a combination thereof. The method can reduce or eradicate tumor burden in the subject.

Additionally, the presently disclosed subject matter provides methods of increasing immune-activating cytokine production in response to a cancer cell or a pathogen in a subject, where the method comprises administering the presently disclosed immunoresponsive cell to the subject. In certain embodiments, the immune-activating cytokine is selected from the group consisting of granulocyte macrophage colony stimulating factor (GM-CSF), IFN-α, IFN-β, IFN-γ, TNF-α, IL-2, IL-3, IL-6, IL-11, IL-7, IL-12, IL-15, IL-21, interferon regulatory factor 7 (IRF7), and combinations thereof.

In accordance with the presently disclosed subject matter, the above-described various methods can comprise administering at least one immunomodulatory agent. In certain embodiments, the at least one immunomodulatory agent is selected from the group consisting of immunostimulatory agents, checkpoint immune blockade agents, radiation therapy agents, chemotherapy agents, and combinations thereof. In some embodiments, the immunostimulatory agents are selected from the group consisting of IL-12, an agonist costimulatory monoclonal antibody, and combinations thereof. In one embodiment, the immunostimulatory agent is IL-12. In some embodiments, the agonist costimulatory monoclonal antibody is selected from the group consisting of an anti-4-1BB antibody, an anti-OX40 antibody, an anti-ICOS antibody, and combinations thereof. In one embodiment, the agonist costimulatory monoclonal antibody is an anti-4-1BB antibody. In some embodiments, the checkpoint immune blockade agents are selected from the group consisting of anti-PD-L1 antibodies, anti-CTLA-4 antibodies, anti-PD-1 antibodies, anti-LAG3 antibodies, anti-B7-H3 antibodies, anti-TIM3 antibodies, and combinations thereof. In one embodiment, the checkpoint immune blockade agent is an anti-PD-L1 antibody. In certain embodiments, the subject is a human. In certain embodiments, the immunoresponsive cell is pleurally administered to the subject.

The presently disclosed subject matter also provides methods for producing an immunoresponsive cell that binds to human mesothelin. In one non-limiting example, the method comprises introducing into the immunoresponsive cell a nucleic acid sequence that encodes a chimeric antigen receptor (CAR), which comprises an extracellular antigen-binding domain, a transmembrane domain and an intracellular domain, wherein the extracellular antigen-binding domain specifically binds to human mesothelin with a binding affinity of from about 1 nM to about 25 nM. In a specific non-limiting embodiment, the extracellular antigen-binding domain is a scFv. In a specific non-limiting embodiment, the extracellular antigen-binding domain is a Fab, which is optionally crosslinked. In a specific non-limiting embodiment, the extracellular binding domain is a F(ab)$_2$. In a specific non-limiting embodiment, any of the foregoing molecules may be comprised in a fusion protein with a heterologous sequence to form the extracellular antigen-binding domain.

The presently disclosed subject matter further provides nucleic acids encoding the presently disclosed CARs, and vectors comprising the nucleic acids. In one embodiment, the vector is a γ-retroviral vector.

The presently disclosed subject matter further provides pharmaceutical compositions comprising an effective amount of the presently disclosed immunoresponsive cells and a pharmaceutically acceptable excipient. Also provided are pharmaceutical compositions for treating a neoplasia, comprising an effective amount of the presently disclosed immunoresponsive cells and a pharmaceutically acceptable excipient. In some embodiments, the neoplasia is selected from the group consisting of mesothelioma, lung cancer, pancreatic cancer, ovarian cancer, breast cancer, colon cancer, pleural cancer, glioblastoma, esophageal cancer, gastric cancer, synovial sarcoma, thymic carcinoma, endometrial carcinoma, stomach cancer, cholangiocarcinoma, and a combination thereof.

The presently disclosed subject matter further provides kits for treating or preventing a neoplasia, a pathogen infection, an autoimmune disorder, an inflammatory disease, an allogeneic transplant, or graft rejection, comprising the presently disclosed immunoresponsive cells. Also provided are kits for treating or preventing a neoplasia, a pathogen infection, an autoimmune disorder, an inflammatory disease, an allogeneic transplant, or graft rejection, comprising nucleic acids comprising the presently disclosed CARs. In some embodiments, the kit further include written instructions for using the immunoresponsive cell for treating a subject having a neoplasia, a pathogen infection, an autoimmune disorder, an inflammatory disease, an allogeneic transplant, or graft rejection.

The presently disclosed subject matter further provides a method of preventing or treating an inflammatory disease in a subject. In one non-limiting example, the method comprises administering the presently disclosed immunoresponsive cell to the subject. In one embodiment, the immunoresponsive cell is an immunoinhibitory cell. In one non-limiting embodiment, the immunoinhibitory cell is a regulatory T cell. In one embodiment, the inflammatory disease is pancreatitis. In one embodiment, the subject is a human. In one embodiment, the subject is a recipient of an organ transplant. In one specific embodiment, the subject is a recipient of a pancreas transplant.

The presently disclosed subject matter further provides a method of preventing graft rejection in a subject who is a recipient of an organ transplant. In one non-limiting example, the method comprises administering the presently disclosed immunoresponsive cell to the subject. In one embodiment, the immunoresponsive cell is an immunoinhibitory cell. In one non-limiting embodiment, the immunoinhibitory cell is a regulatory T cell. In one embodiment, the subject is a human. In one embodiment, the subject is a recipient of an pancreas transplant.

BRIEF DESCRIPTION OF THE FIGURES

The following Detailed Description, given by way of example, but not intended to limit the invention to specific embodiments described, may be understood in conjunction with the accompanying drawings.

FIGS. 5A-5C depict CD28 co-stimulation enhances CAR+ T-cell in vivo persistence and efficacy. (A) CD28 co-stimulation enhances CAR+ T-cell efficacy as measured by median survival and facilitates tumor eradication following a single T cell dose. $1\times10^5$ CAR+ Mz, M28z, or P28z (negative control) T cells were pleurally administered into mice bearing established pleural MSTO MSLN+ GFP/Luc+ tumors. Tumor burden was measured weekly by BLI. Left, Kaplan Meier survival curve. Statistical significance comparing median survival of Mz and M28z groups (at least 9 mice per group) was determined using a logrank test. Right, tumor burden as quantified by BLI for each individual mouse using units of photons per second. (B) CD28 co-stimulation enhances CAR+ T cell persistence. Absolute CAR+ T cells per mL peripheral blood are shown at 40 and 50 d following pleural administration of $3\times10^6$ CAR+ T cells. Shown bar graphs represent mean±s.e.m. of three mice. t tests were performed, and statistical significance was determined using a Bonferroni correction for multiple corrections. *p<0.05. (C) Persisting CAR+ T cells are predominantly CD4+. Left, representative multicolor flow cytometric analysis of peripheral blood in mice treated with either Mz or M28z CAR T cells. Gating strategy shows lymphocyte gate and CD3+CD45+ T-cell gate after removal of dead cells. For each mouse, CD4+ and CD8+ phenotype analysis was performed after gating for live cells, CD3+CD45+ T cells, and GFP+ (CAR+) T cells. Right, bar graphs depicting CD4:CD8 ratios determined using serial flow cytometric analysis of peripheral blood drawn at successive time points following T cell administration. Pre-infusion CD4:CD8 ratio was approximately 0.5 for all in vivo experiments. Results shown are similar across a range of T cell dose ($3\times10^6$, $1\times10^6$, and $3\times10^5$ CAR+). t tests comparing mean CD4+ to CD8+ ratios (n=3 at each time point) demonstrated statistical significance (after Bonferroni correction for multiple comparisons) at d 30, 40, and 50 post T-cell infusion in the Mz treated mice and at d 30 and 40 for M28z treated mice.

FIGS. 6A-6E depict CD4+ CAR+ T cells with CD28 co-stimulation demonstrate delayed, but efficient cytotoxicity. (A) Negative selection bead sorting achieved >98% purity for experiments analyzing CD4+ and CD8+ T cell populations. (B) CD4+ M28z T cells show a delayed but similar antitumor cytotoxicity compared to CD8+ M28z T cells. Mesothelin-specific or control transduced CAR+ T cells were incubated at indicated effector/target ratios with $^{51}$Cr-loaded MSTO211H target cells transduced to overexpress mesothelin (MSTO MSLN+) and target cell lysis (chromium release) was measured. Error bars represent s.e.m. of the mean of three replicates. *p<0.05 comparing CD8 M28z with CD4 M28z CAR+ T cells. (C) CD28 co-stimulation is necessary for optimal CD4+ mediated cytotoxicity. Following bead purification of CD4+ and CD8+ T cell subsets, mesothelin-specific or control transduced CAR+ T cells were incubated at indicated effector/target ratios with $^{51}$Cr-loaded MSTO211H target cells transduced to over-express mesothelin (MSTO MSLN+) and target cell lysis (chromium release) was measured. *p<0.05 comparing CD4 M28z with CD4 Mz CAR+ T cells. (D) Cytokine-rich supernatant does not directly cause tumor cell lysis. Supernatants obtained following 18 h co-incubation of CD4+ M28z or CD4+ P28z (as a negative control) with MSTO MSLN+ or MSTO empty target cells were mixed with freshly plated $^{51}$Cr labeled targets and target cell lysis was measured at the indicated time points. CD4+ M28z CAR T cells demonstrated antigen-specific lysis (positive control). (E) CAR+ T cell secreted cytokines enhance CAR+ mediated cytotoxicity. Supernatants obtained following mesothelin-specific stimulation of CD4+ M28z CAR+ T cells enhance cytotoxicity in 18 h co-cultures of both CD8M28z and CD4M28z with MSTO MSLN+ target cells. Error bars represent s.e.m. of the mean of three replicates. *p<0.05 comparing CAR+ T cells with and without added supernatant.

FIGS. 7A-7D depict mesothelin-specific CAR+ T cell cytotoxicity is primarily mediated by perforin/granzyme. (A) Left and middle demonstrates no influence on cytotoxicity on M28z transduced T cells upon Fas ligand blockade. Sorted CD4, CD8 and unsorted CD4/8 M28z+ T cells were co-cultivated in the presence of the anti-Fas-L mAb NOK-1 or an IgG1 isotype control mAb (each 10 ug/ml) and MSTO MSLN+ in 18 h $^{51}$Cr-release assays. Figure on the right shows the susceptibility of target cells for Fas L mediated cell death (for details see Methods section). *p<0.05. (B) Mesothelin specific CAR transduced T cells lysis of tumor targets is dependent on release of cytotoxic granules. 18 h $^{51}$Cr-release assays of sorted CD4+, CD8+ subpopulations and unsorted bulk populations of M28z or Mz transduced T cells were co-cultured for 18 h in 96-well tissue culture plates in the presence or absence of the chelating agent ethylene glycol tetraacetic acid (EGTA), with MSTO MSLN+ tumor cells. *p<0.05. (C) CD4+ CAR T cells express granzyme B upon stimulation but with delayed kinetics when compared to CD8+ CAR T cells. Intracellular flow cytometry for granzymes A and B were performed on resting PBMCs, PHA stimulated blasts, and MSTO MSLN+ stimulated (2:1 effector to target ratio) CAR transduced (M28z, Mz, and P28z as a negative control) T cells. Cells were stimulated for 4 or 18 h in order to compare to the two time points at which chromium release was assessed in cytotoxicity assays. After gating for CD3+ and GFP+ events, granzyme positive events were determined using fluorescence minus one stained cells. Antibody isotype control was negative for all stains. Left, representative FACS dot plots for both CD4+ and CD8+ T cell subsets. Right, bar graphs of one representative experiment of a total of 3 total experiments performed. (D) M28z CAR T cells express a greater amount of granzyme B than Mz CAR T cells. Cells were stained as in (c) and representative histograms are shown 18 h following stimulation with MSTO MSLN+ stimulation.

Figure 9A:
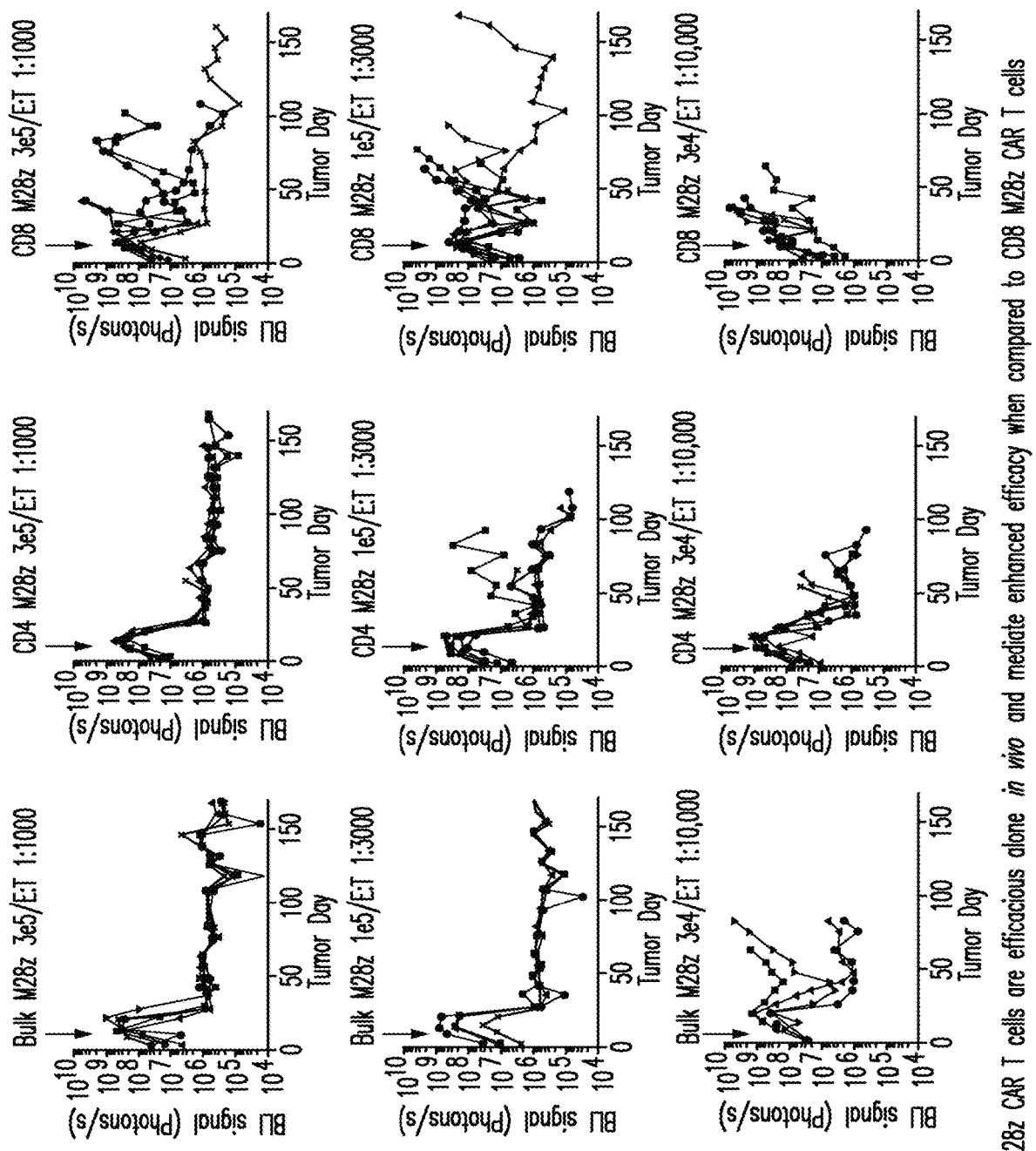

FIGS. 9A and 9B depict CD4$^+$ M28z CAR T cells are efficacious when administered alone in vivo and mediate enhanced efficacy when compared to CD8$^+$ M28z CAR T cells. (A) In vivo bioluminescence imaging performed weekly tracking tumor burden of MSTO MSLN$^+$ GFP/Luc+ tumors inoculated into the pleural cavity of NSG mice (time of inoculation d 0). At 18 d post tumor infusion, mice received either $3 \times 10^5$, $1 \times 10^5$, or $3 \times 10^4$ CAR$^+$ T cells of bulk M28z (n=5), sorted CD4$^+$ or CD8$^+$ M28z (n=7). An equal number of T cells expressing the human PSMA-targeting CAR P28z were injected in the control group (n=4). BLI signal intensities are shown as photons/second and represent the average of ventral and dorsal signals. (B) Kaplan-Meier survival curves of T-cell treated mice described in (a). P values shown were calculated using logrank statistical tests. At all doses CD4$^+$ M28z CAR$^+$ T-cells are efficacious compared to CD8$^+$ CAR$^+$ T cells. CD4$^+$ CAR$^+$ T cells antitumor efficacy is comparable to unsorted CAR+ T cells.

FIGS. 10A-10E depict the functional persistence of adoptively transferred, mesothelin-redirected T cells is predominantly CD4$^+$ mediated and is augmented by CD28 co-stimulation. (A) Multicolor flow cytometric analysis of a splenic single-cell suspension prepared from one representative NSG mouse (n=3) sacrificed 202 d after T cells were administered intrapleurally. 184 d after the eradication of established MSTO MSLN$^+$ intrapleural tumor by the infusion of $3 \times 10^5$ M28z T cells (data not shown). M28z T cell subpopulations following gating for CAR$^+$ (CD3$^+$GFP$^+$) events show a predominance of CD4$^+$ T cells. (B) In vivo BLI of MSTO MSLN$^+$ and MSTO-211H-MSLN-tumor rechallenged NSG mice. 87 d after pleural tumor eradication following administration of either $1 \times 10^5$ M28z or Mz transduced T cells; $1 \times 10^6$ MSLN$^+$ or MSLN-MSTO tumor cells where injected into the peritoneal cavity of mice. At the indicated time points, luc$^+$ tumor cells were monitored by bioluminescence imaging. Three NSG mice were imaged per treatment group. Each line represents the mean±s.e.m. of each group of mice with each dot showing the average photon count measured over the entire mouse both ventrally and dorsally. Two weeks following tumor rechallenge in mice injected with MSTO MSLN$^+$ peritoneal tumor, both the Mz and M28z CAR$^+$ T cells injected 87 days prior demonstrated antitumor efficacy. M28z CAR$^+$ T cells were more efficacious in reducing tumor burden compared to Mz CAR$^+$ T cells. (C and D). Absolute M28z or Mz T cell numbers accumulated in the spleen after tumor rechallenge. Shown bar graphs represent the transduced T cell mean±s.e.m. from the spleen of NSG mice rechallenged with either MSLN$^+$ (n=6) or MSLN$^-$ (n=6) tumor and sacrificed 16 d post tumor rechallenge. Only the M28z T cell treated mice rechallenged with MSTO-211H-MSLN$^+$ showed a robust accumulation of CAR$^+$ T cells in the spleen. T cell subpopulations were also quantified by flow cytometry (see Methods section for details) and showed that the majority of the T cells seen in the M28z group are CD4$^+$ T cells. (E) Treatment of animals after tumor inoculation.

Figure 11A:
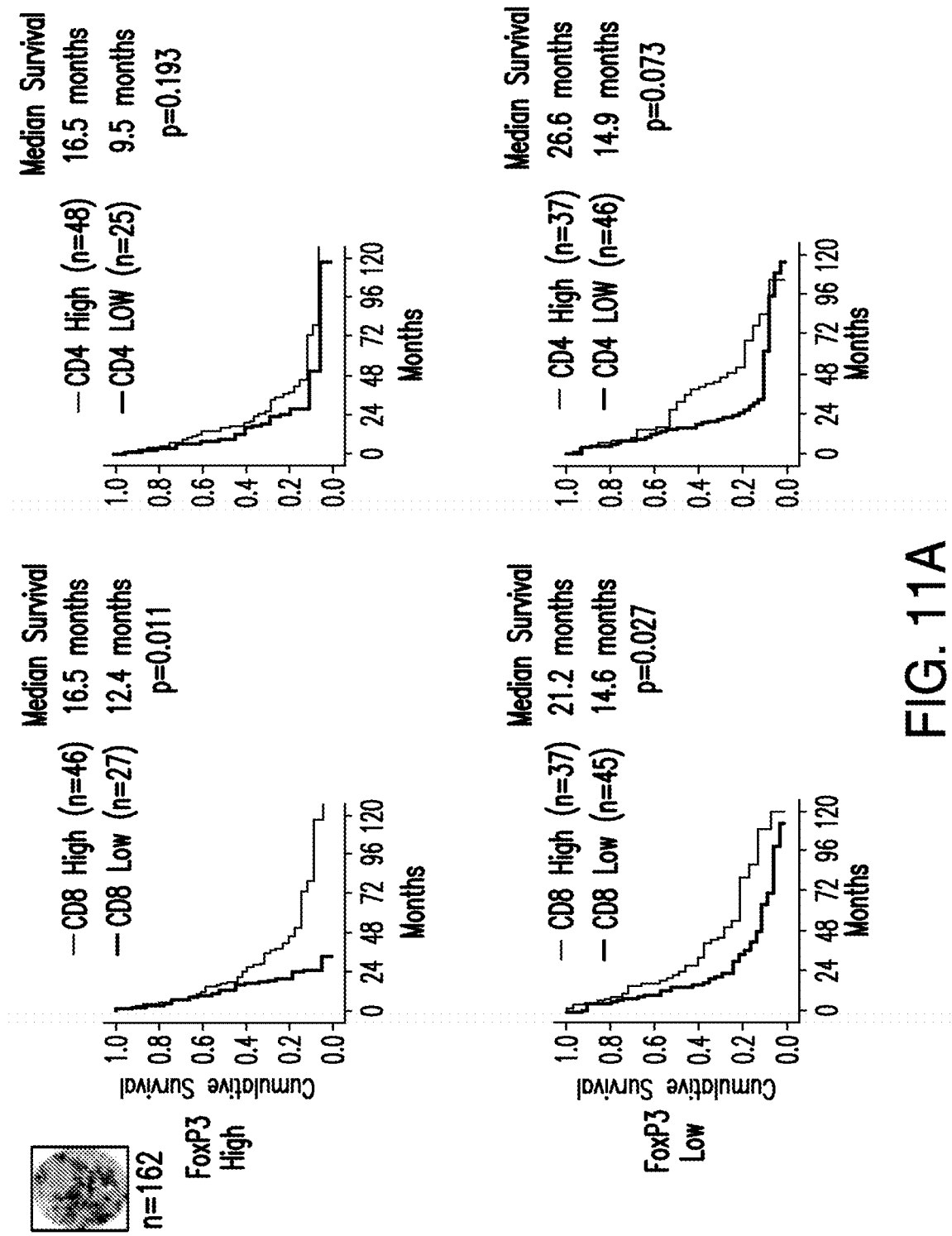
Figure 11B:
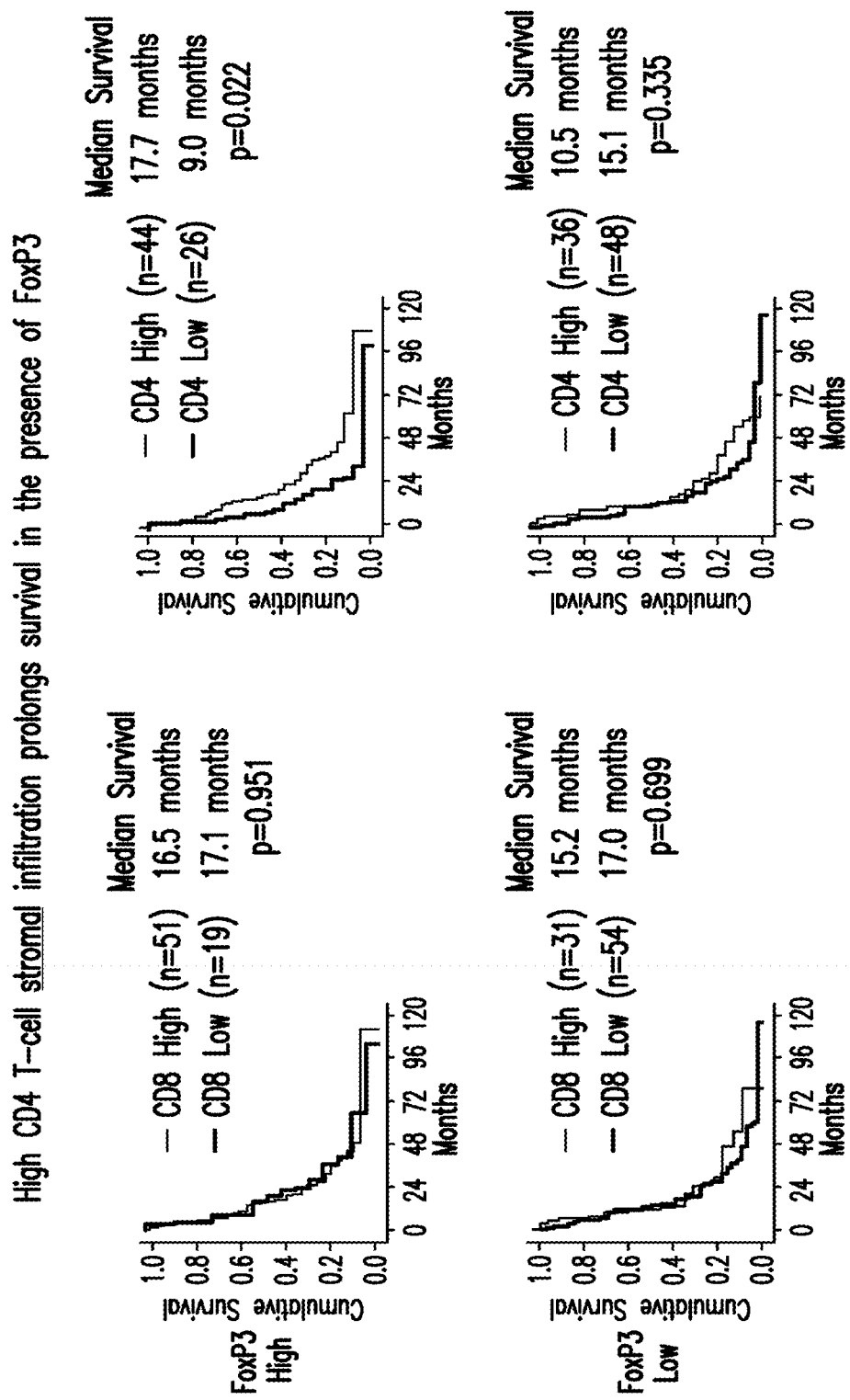

FIGS. 11A and 11B depict CD4$^+$ and CD8$^+$ tumor/stromal infiltration in a FoxP3 rich tumor microenvironment is associated with prolonged survival. (A) High CD8$^+$ T-cell tumor infiltration is associated with prolonged survival even in the presence of FoxP3. Patients diagnosed with epitheloid MPM between 1989 and 2009 at Memorial Sloan-Kettering Cancer Center were included. For each of the 162 patients with available specimens, all H&E slides (median 9, range 1-43) were reviewed. Representative blocks were selected to construct a tissue microarray (TMA) by taking 9 representative cores (0.6 mm) from each patient tumor block and ensuring at least 6 complete tumor cores. Five micrometer-sections were cut from the TMA and stained by specific antibodies (CD8: Mouse Monoclonal, Dako, 1:200 dilution, FoxP3: Mouse Monoclonal, Abcam, 1:2,000 dilution). Grading of CD8 and FoxP3 intensity was carried out on separate occasions by a pathologist who was blinded to the clinical data as follows: For each patient, immune-cell infiltration was defined by a score of 1 (average, 1 to 1.67), 2 (average, 1.67 to 2.33), or 3 (average, >2.33). For statistical analysis, a score of 1 was considered to be low, and 2 and 3 were considered to be high. (B) High CD4$^+$ T-cell stromal infiltration is associated with prolonged survival in the presence of FoxP3. As described in a. using Goat Polyclonal, R&D Systems at a 1:100 dilution to stain CD4$^+$ cells.

Figure 12:
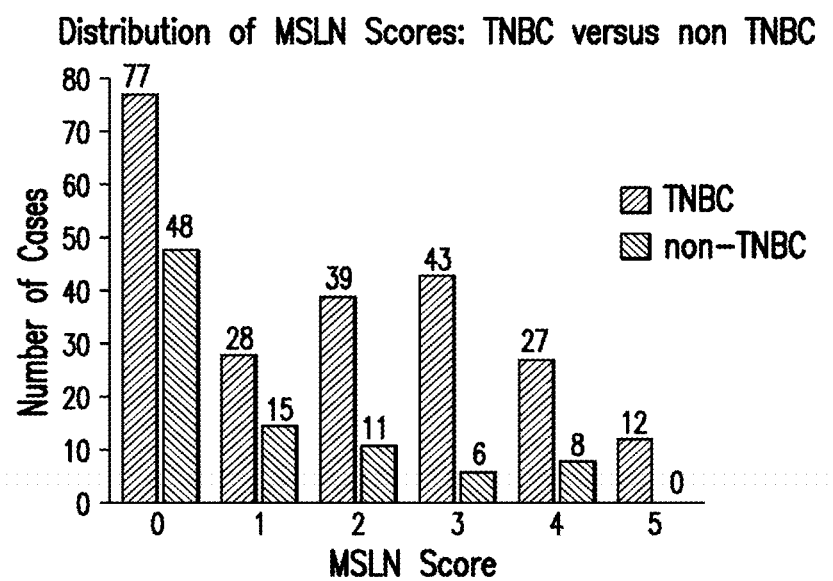

FIG. 12 depicts distribution of MSLN scores: triple-negative breast cancer (TNBC) versus non-TNBC.

FIGS. 13A-13F depict survival profile: MSLN$^+$ TNBC versus NSLN$^-$ TNBC.

Figure 14:
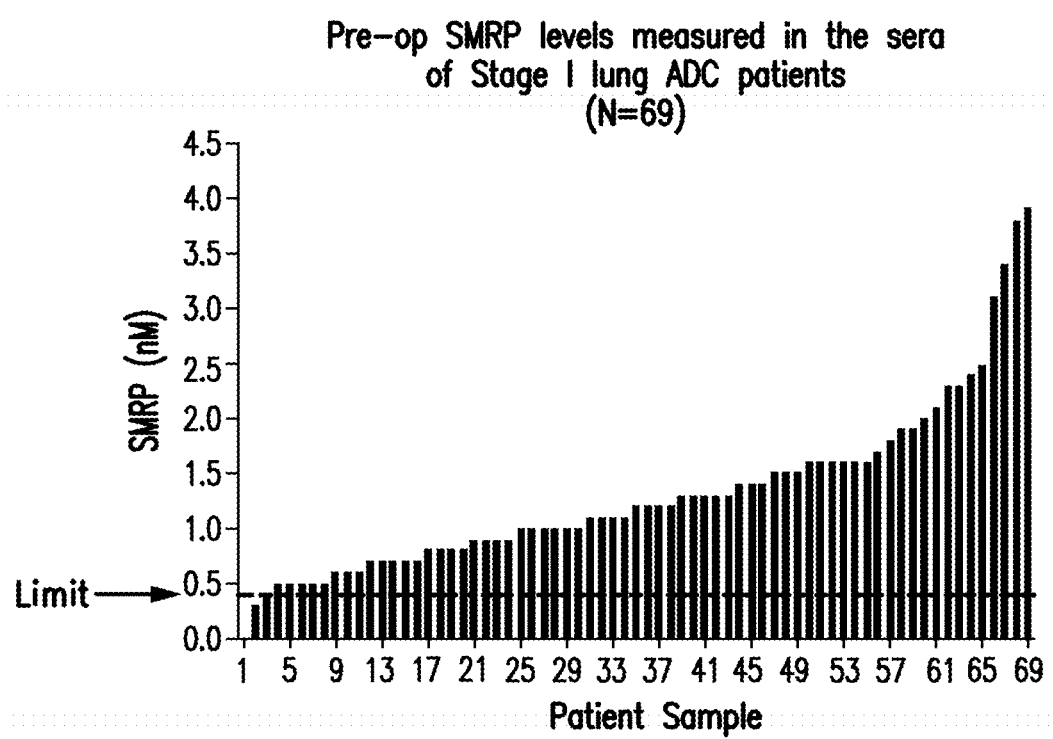

FIG. 14 depicts measurement of pre-op soluble MSLN-related peptide (SMRP) levels in the sera of stage I lung ADC patients.

Figures 15A, 15B, 15C:
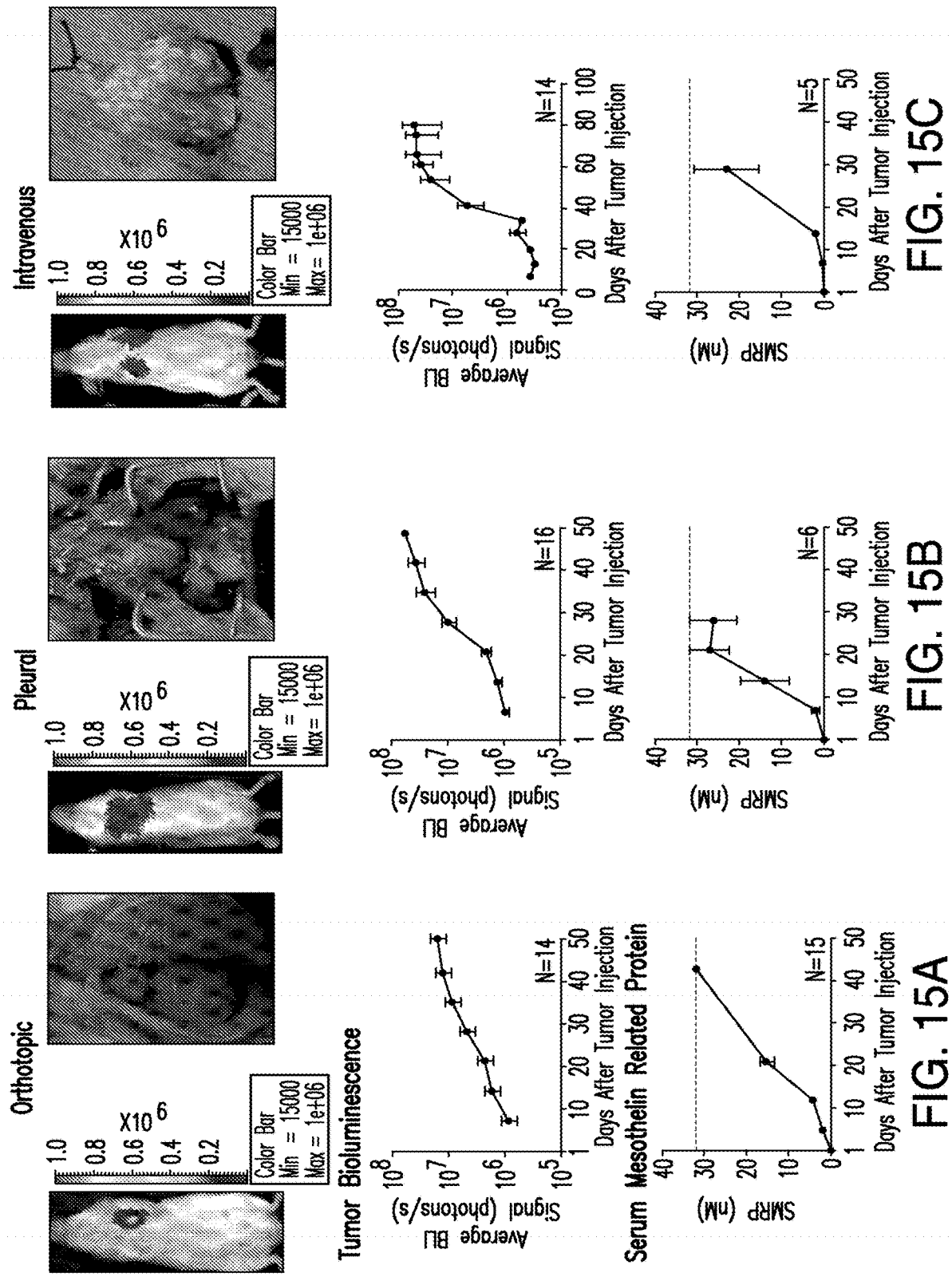

FIGS. 15A-15C depict development of mouse models.

Figure 16:
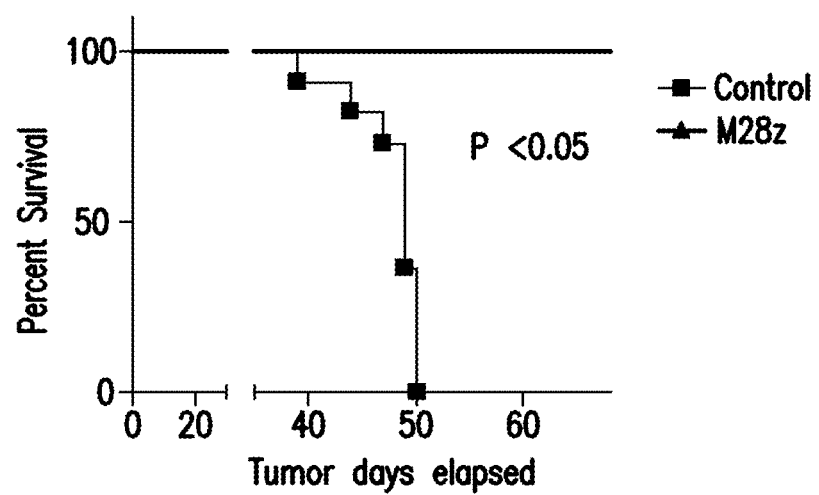

FIG. 16 depicts effectiveness of M28z for decreasing tumor burden in a lung metastasis mouse model.

FIGS. 17A-17D depict M28z T cells on antigen-specific bystander killing of low-MSLN-expressing targets compared to high-MSLN-expressing targets.

Figure 18:
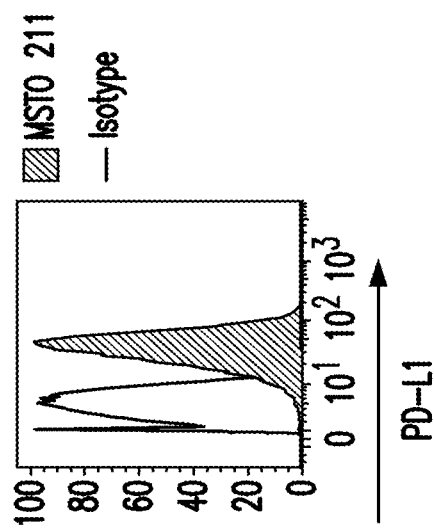

FIG. 18 depicts PD-L1-expressing MSTO-211H (human pleural mesothelioma) cells.

Figure 19:
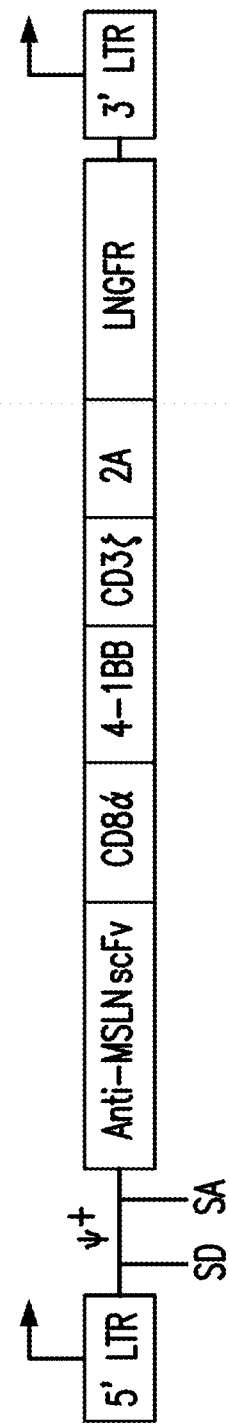

FIG. 19 depicts the structure of MBBz.

Figures 20A, 20B, 20C:
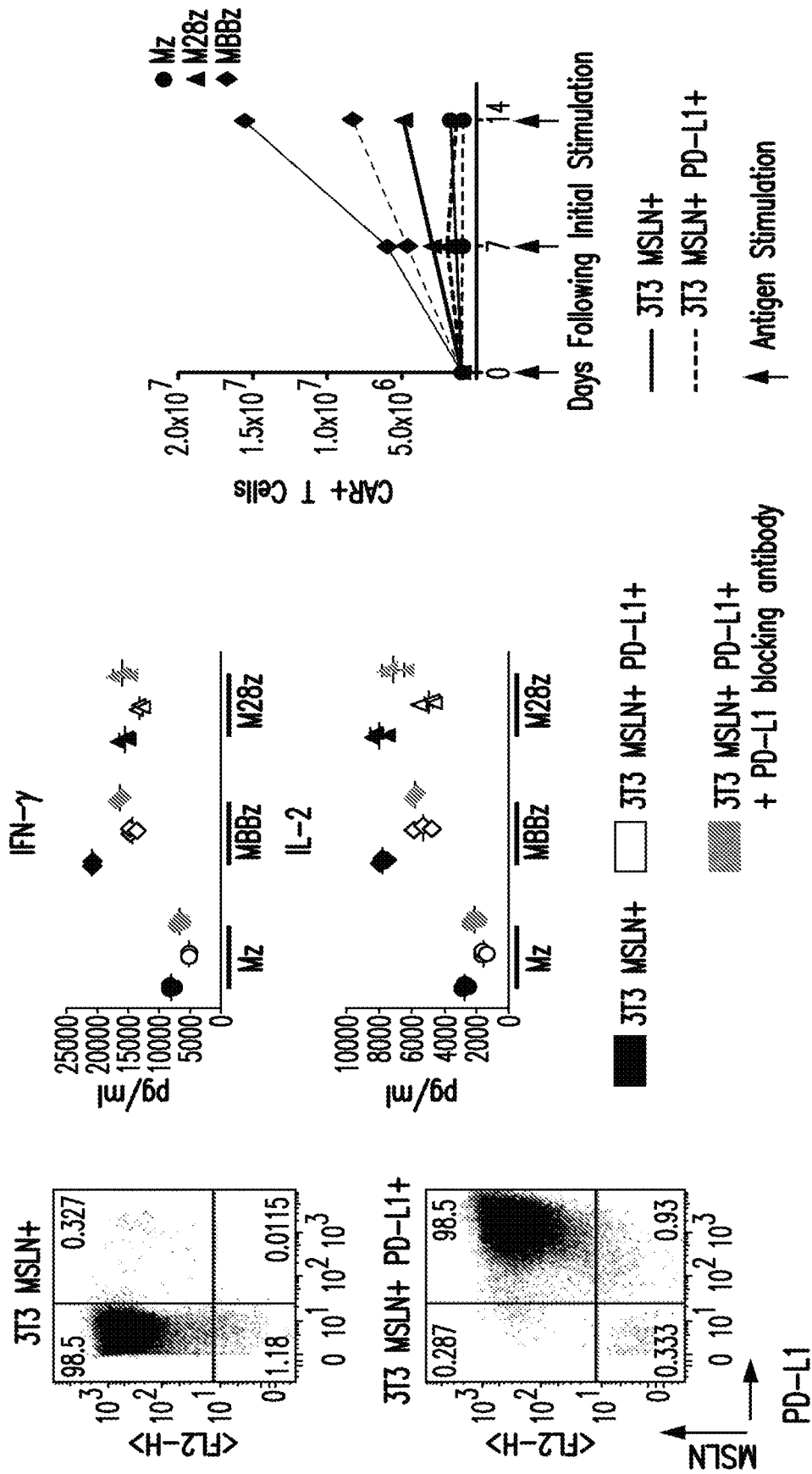

FIGS. 20A-20C depict that MSLN-targeted CD28 and 4-1BB co-stimulation enhanced CAR T cell function in the presence of tumor-secreted immunosuppressive proteins.

Figure 21A:
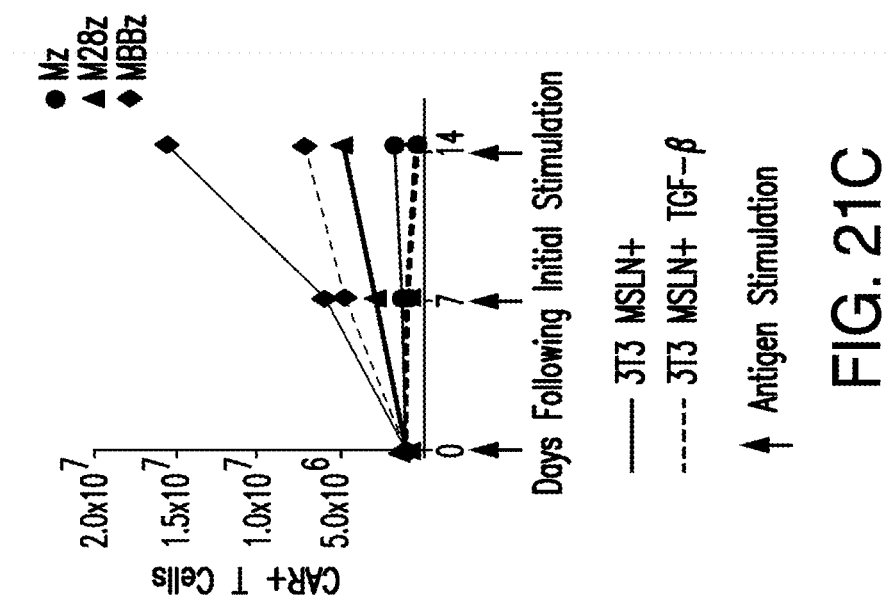
Figure 21B:
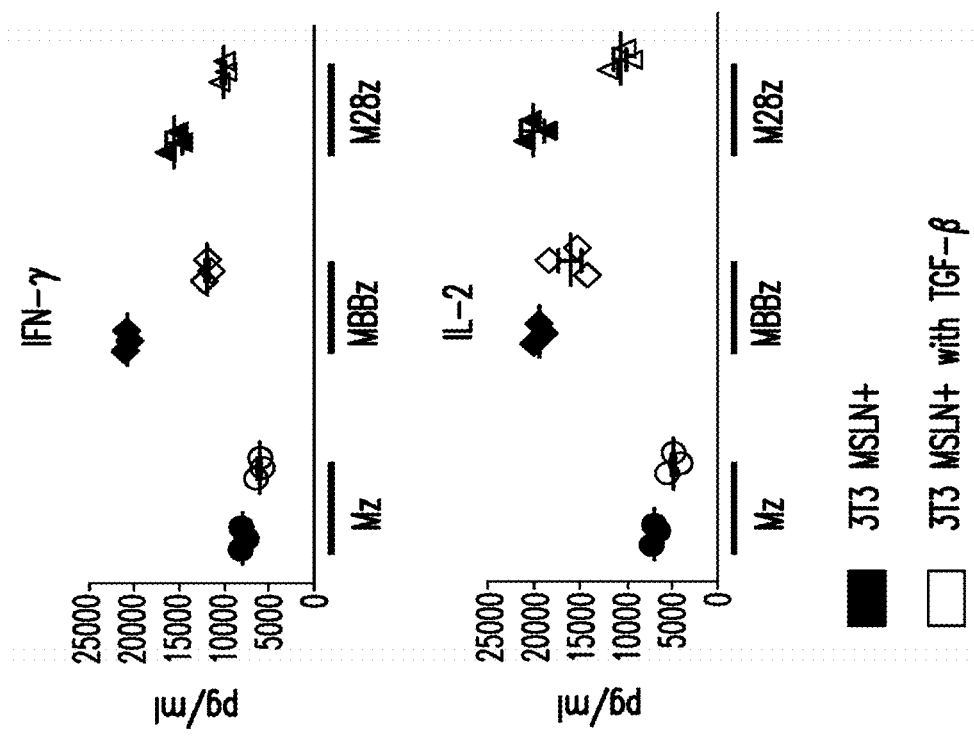
Figure 21C:
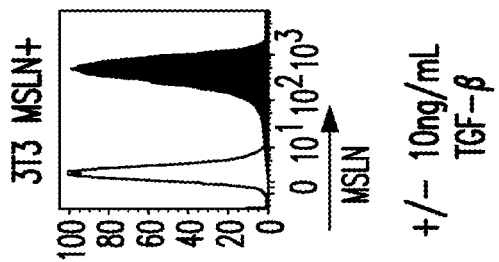

FIGS. 21A-21C depict that MSLN-targeted CD28 and 4-1BB co-stimulation enhanced CAR T cell function in the presence of tumor-secreted immunosuppressive proteins.

Figure 22:
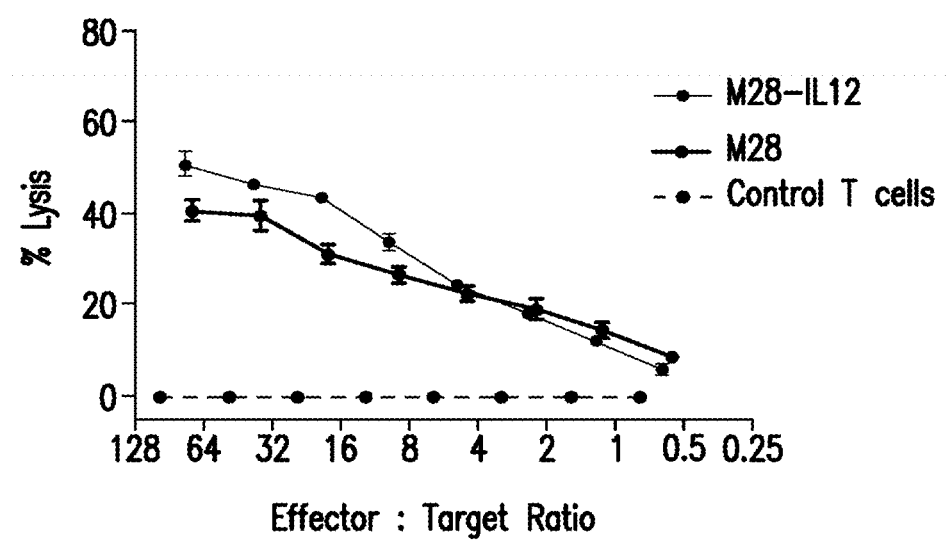

FIG. 22 depicts cytotoxicity of M28-IL12 and M28z on MSLN$^+$ cancer cells.

Figure 23:
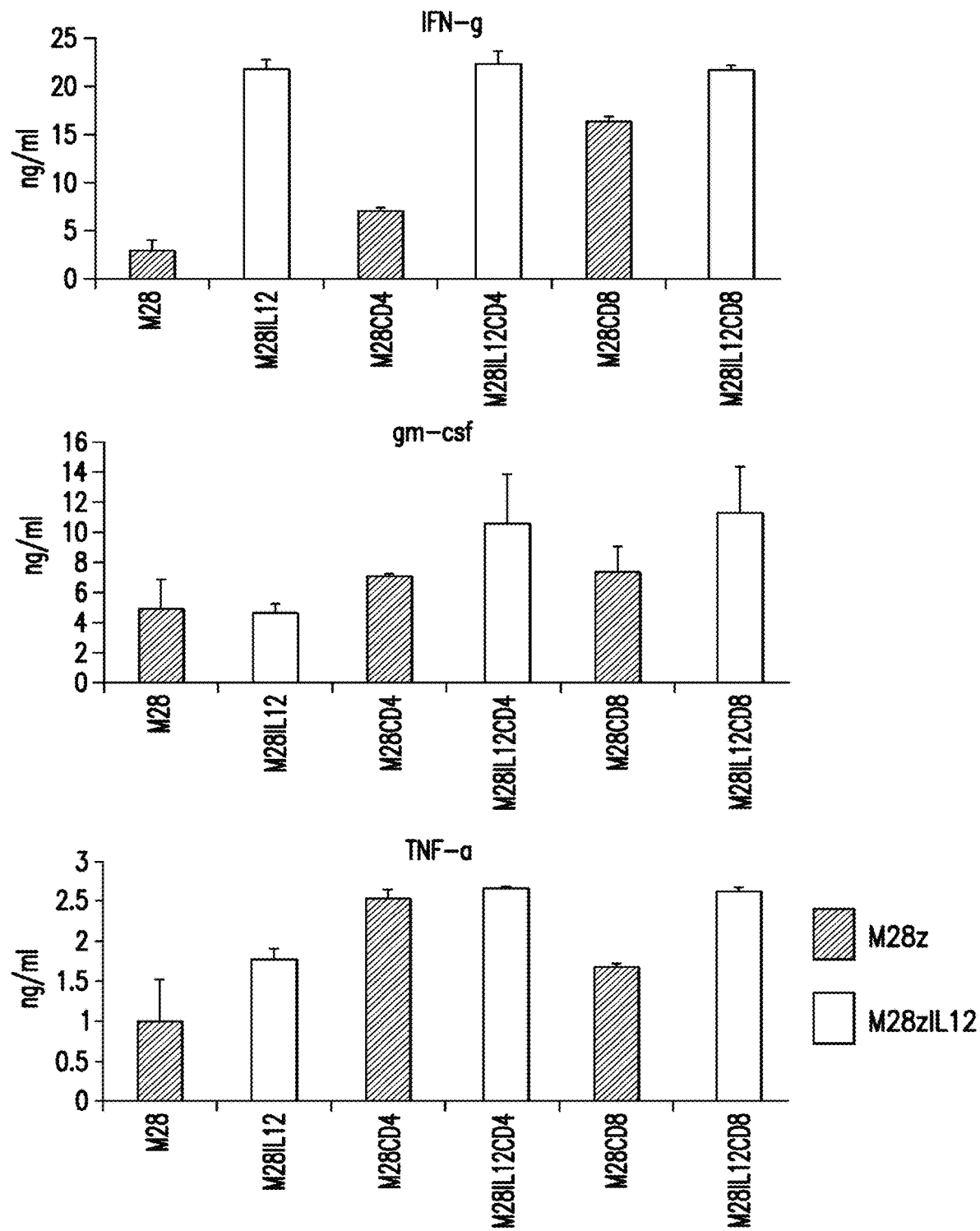

FIG. 23 depicts impact of IL-12 on M28z-induced cytokine expression.

FIGS. 24A-24E depict CARs in accordance with the presently disclosed subject matter. (A) the structure of SFG-M28z is displayed. (BB the structure of SFG-MBBz is displayed. (C) the structure of SFG-M28z-4-1BBL is displayed. (D) the structure of SFG-4-1BBL-M28z is displayed. (E) the structure of SFG-M28z-IRES-Flexi-IL-12 is displayed (where IRES may be alternatively expressed under the control of a NFAT or interferon responsive element).

Figure 25:
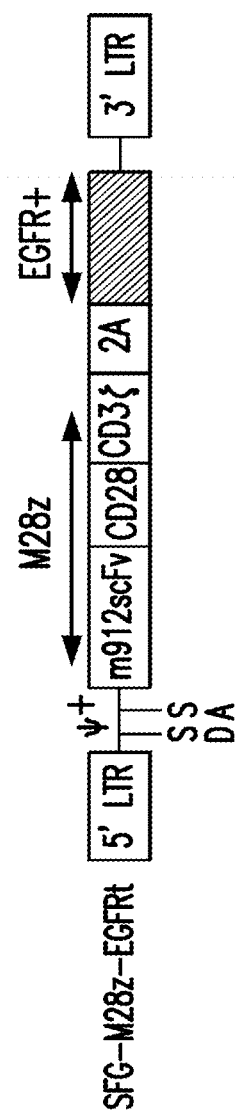

FIG. 25 depicts the structure of SFG-M28z-EGFRt.

Figure 26:
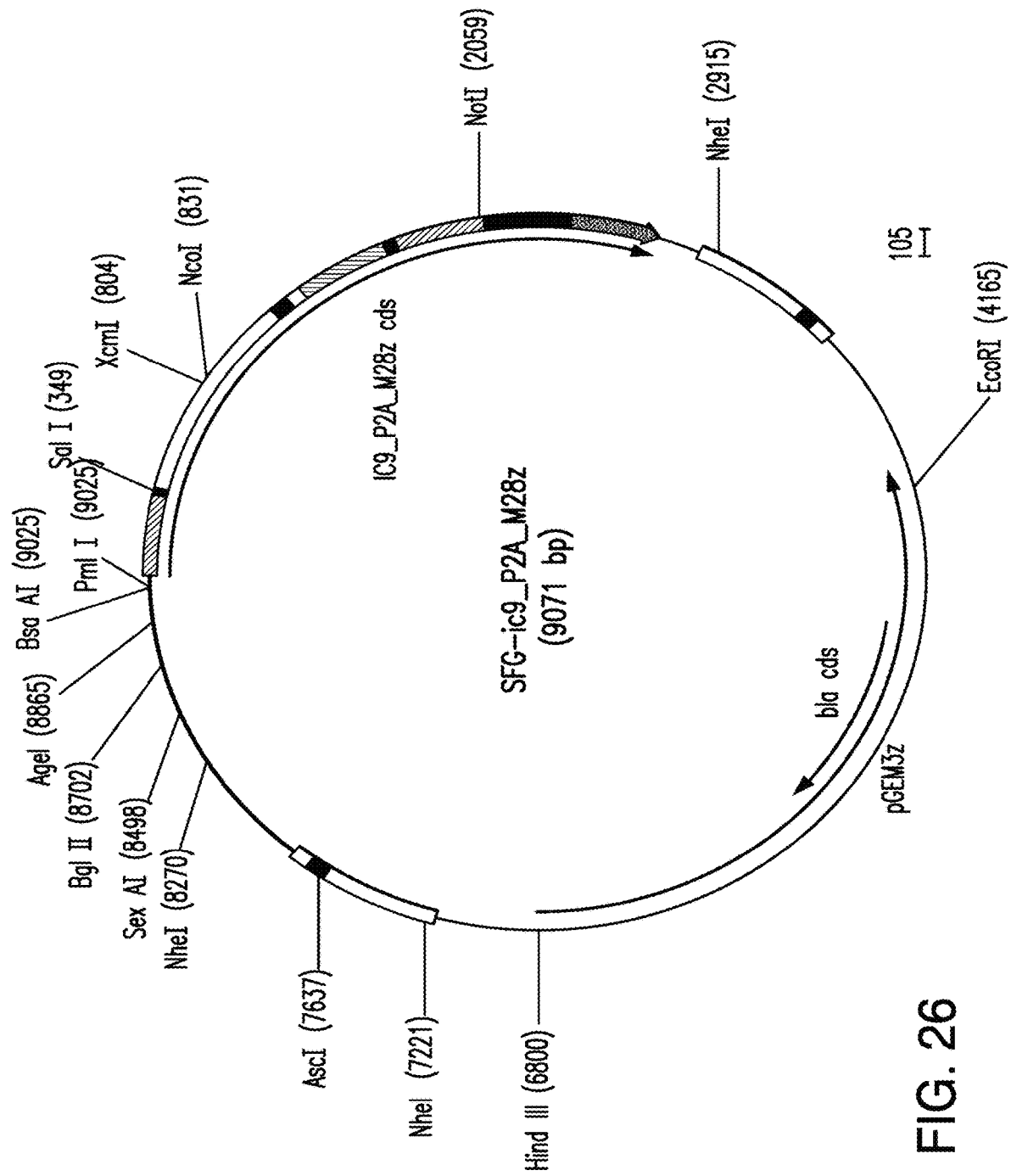

FIG. 26 depicts the restriction map of SFG-iC9-M28z.

Figure 27A:
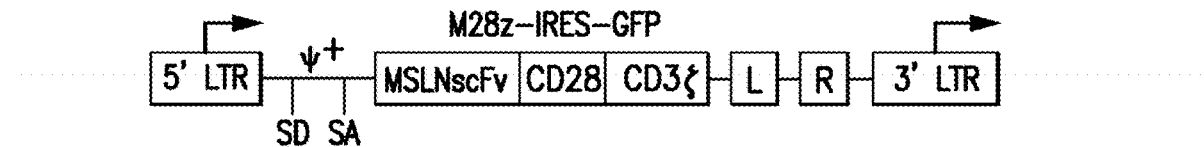
Figure 27B:
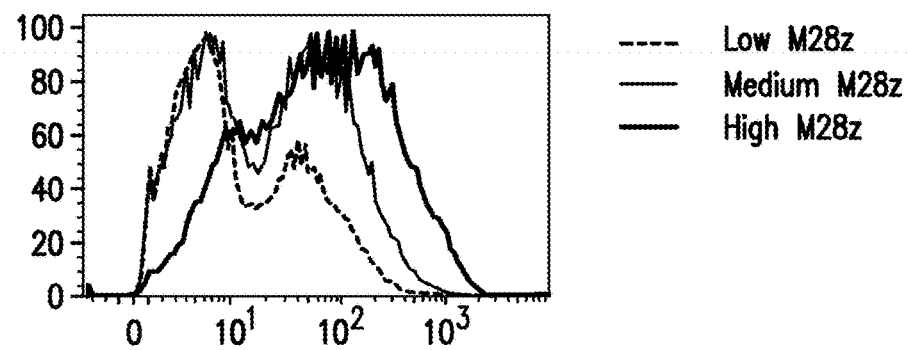
Figure 27C:
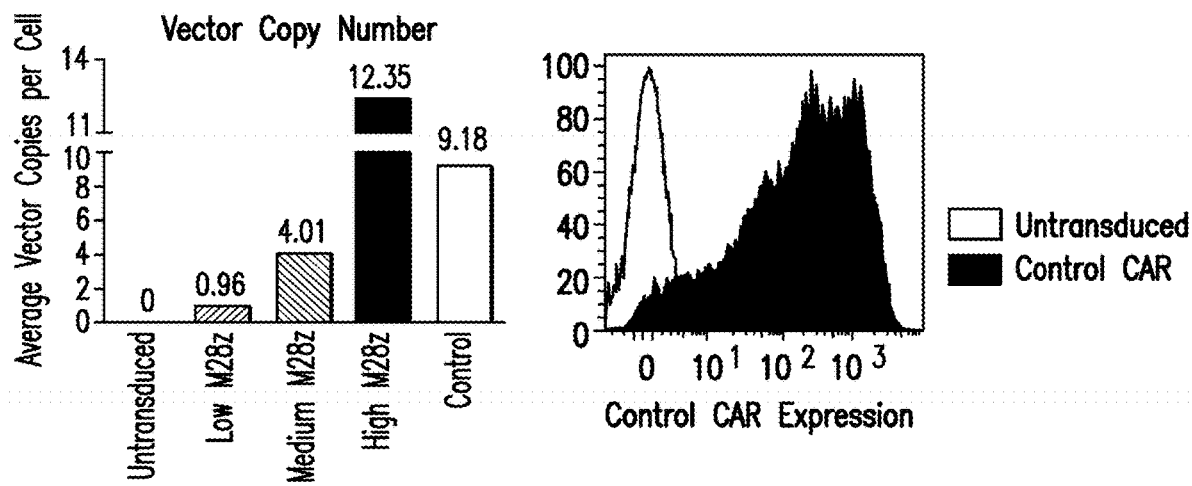

FIGS. 27A-27C depict human T cells expressing varying levels of M28z.

Figure 28:
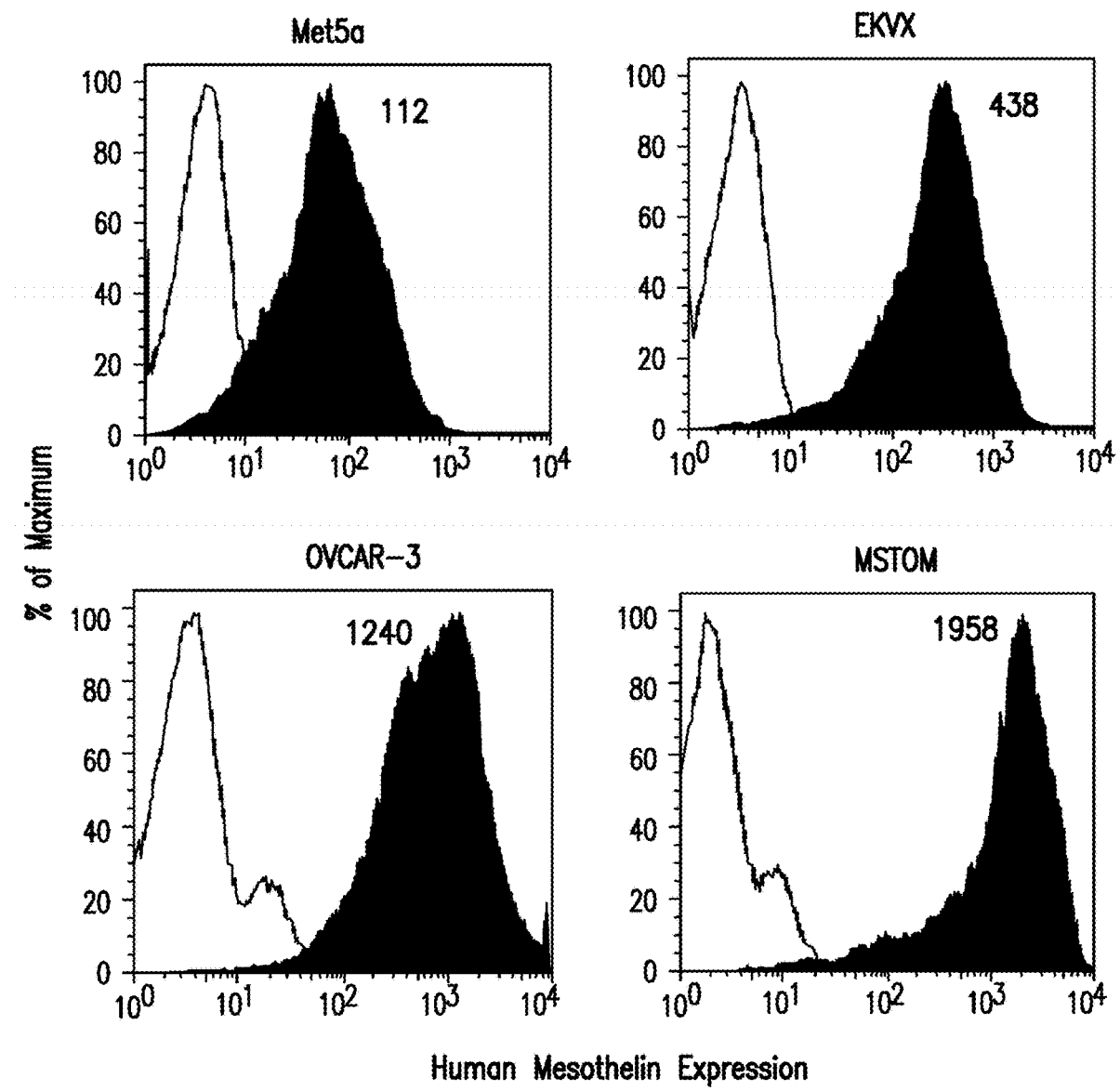

FIG. 28 depicts target cell lines expressing varying levels of human mesothelin.

Figure 29A:
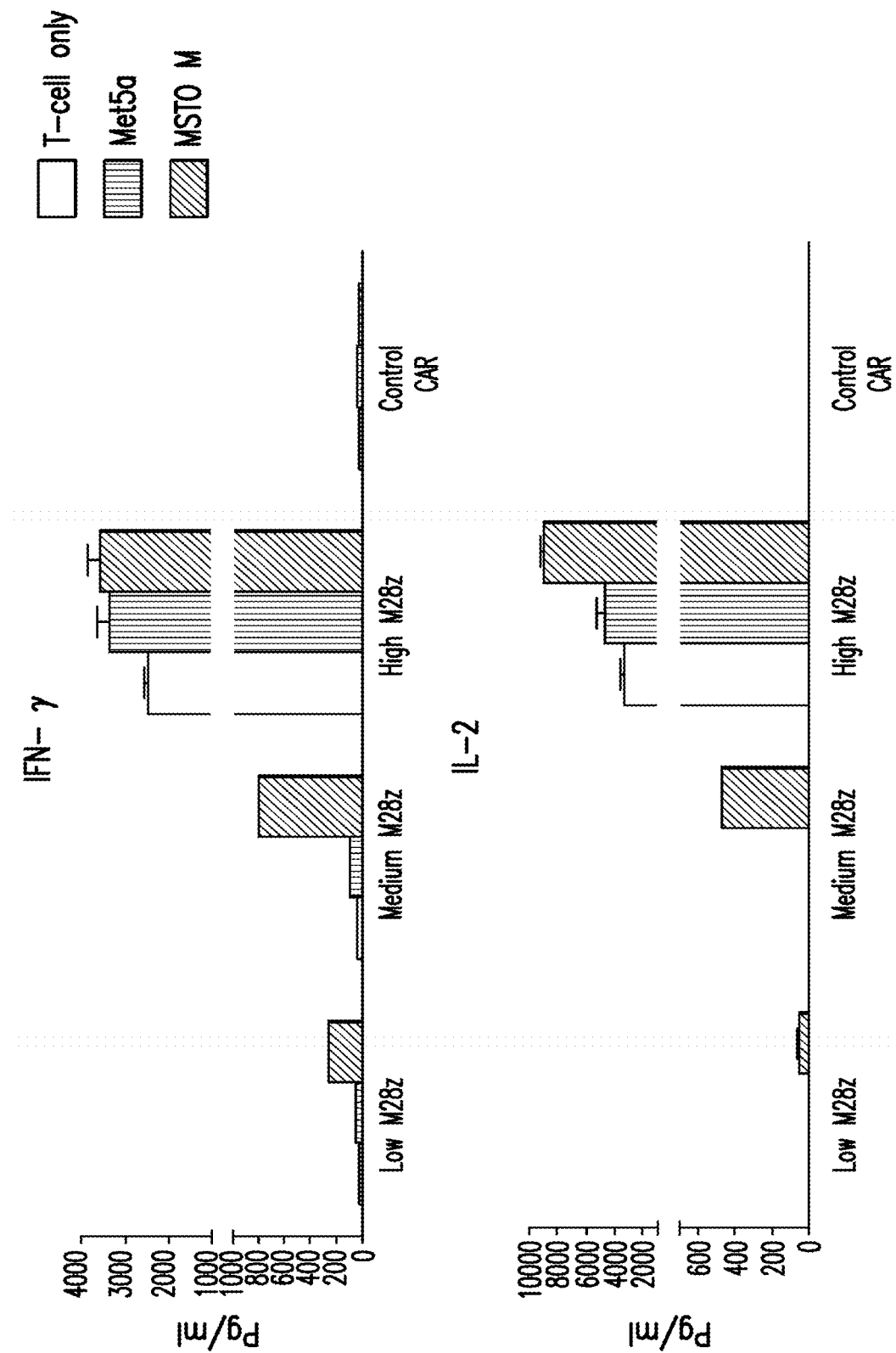

FIGS. 29A and B depict cytokine production of M28z$^+$ T cells against target cells expressing varying levels of human mesothelin.

Figure 30:
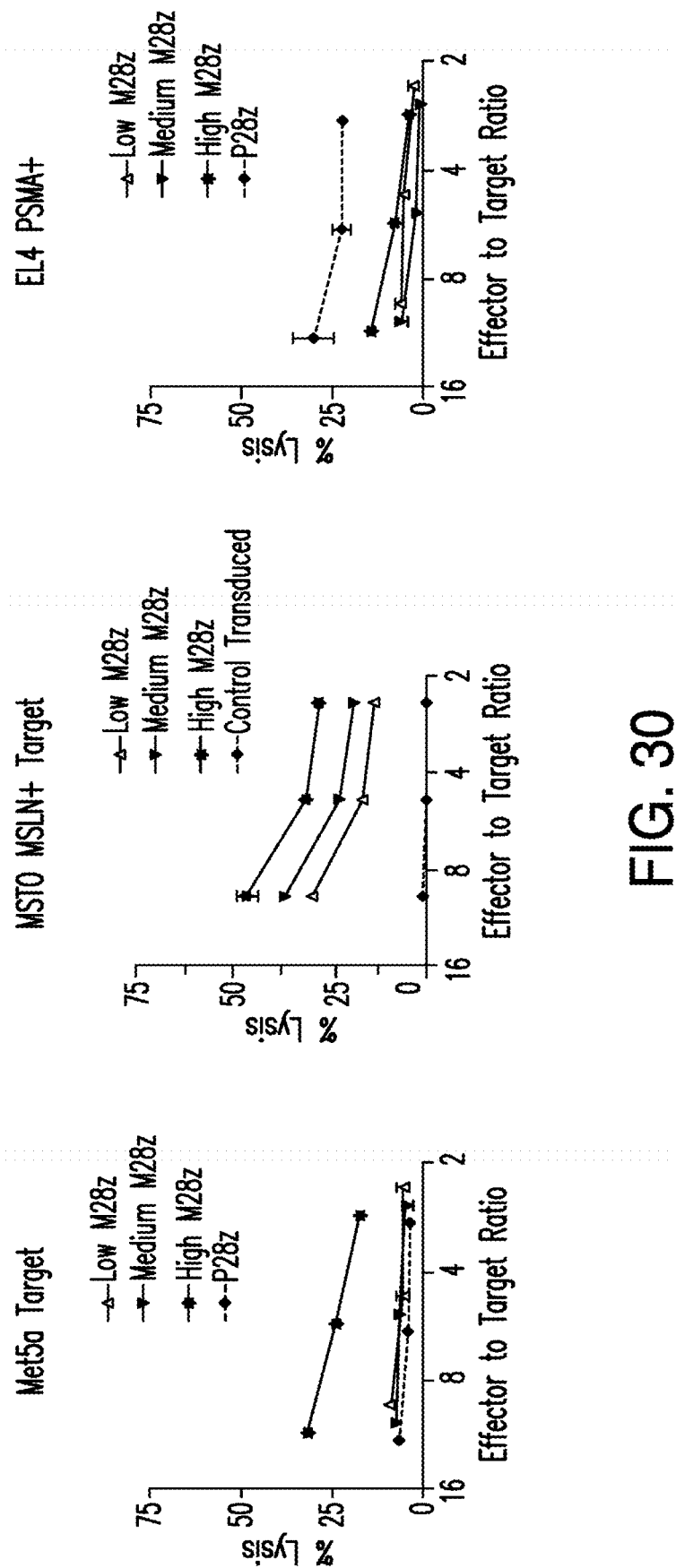

FIG. 30 depicts cytotoxicity of M28z$^+$ T cells against target cells expressing varying levels of human mesothelin.

FIGS. 31A-31C depict cytokine production and cytotoxicity of M28z+ T cells against target cells expressing varying levels of human mesothelin (MSLN). (A) MSTO-211H cells expressing different levels of MSLN. (B) CTL analysis on MSTO-211H cells expressing different levels of MSLN. (C) cytokine production on MSTO-211H cells expressing different levels of MSLN.

Figure 32:
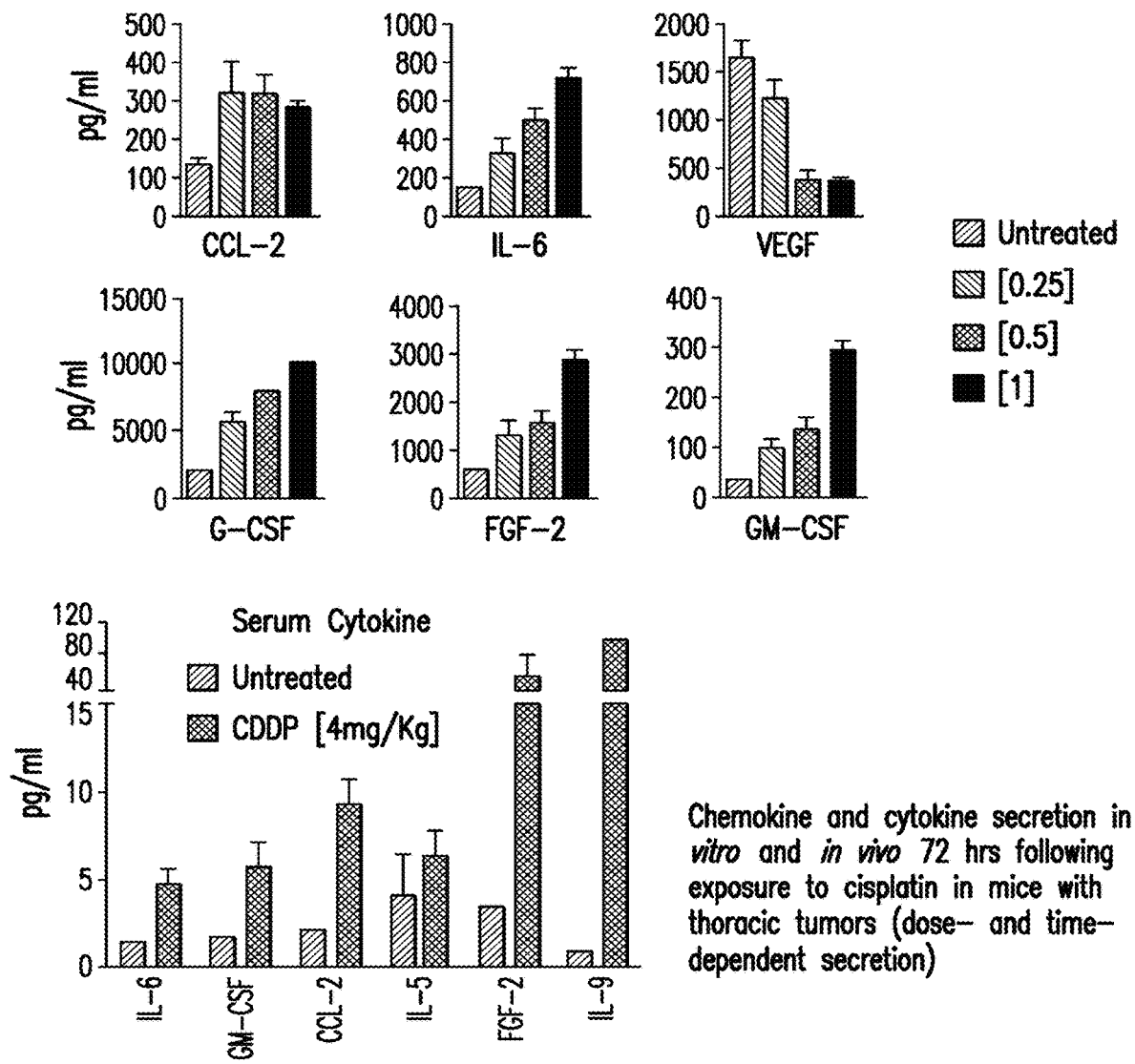
Figure 32:
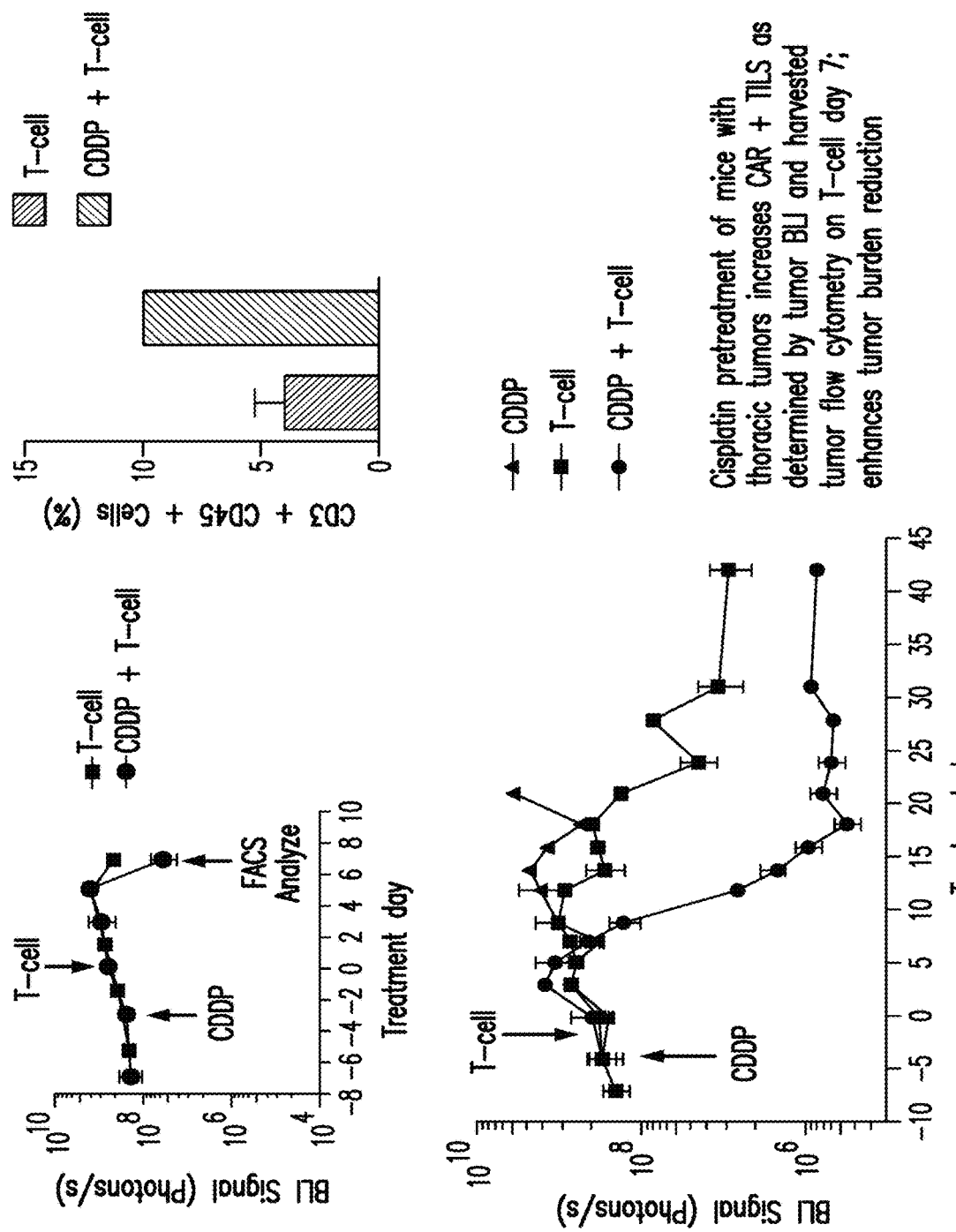

FIG. 32 depicts cisplatin pretreatment promoted the efficacy of a presently disclosed MSLN-specific CAR-expressing T-cell.

Figure 33:
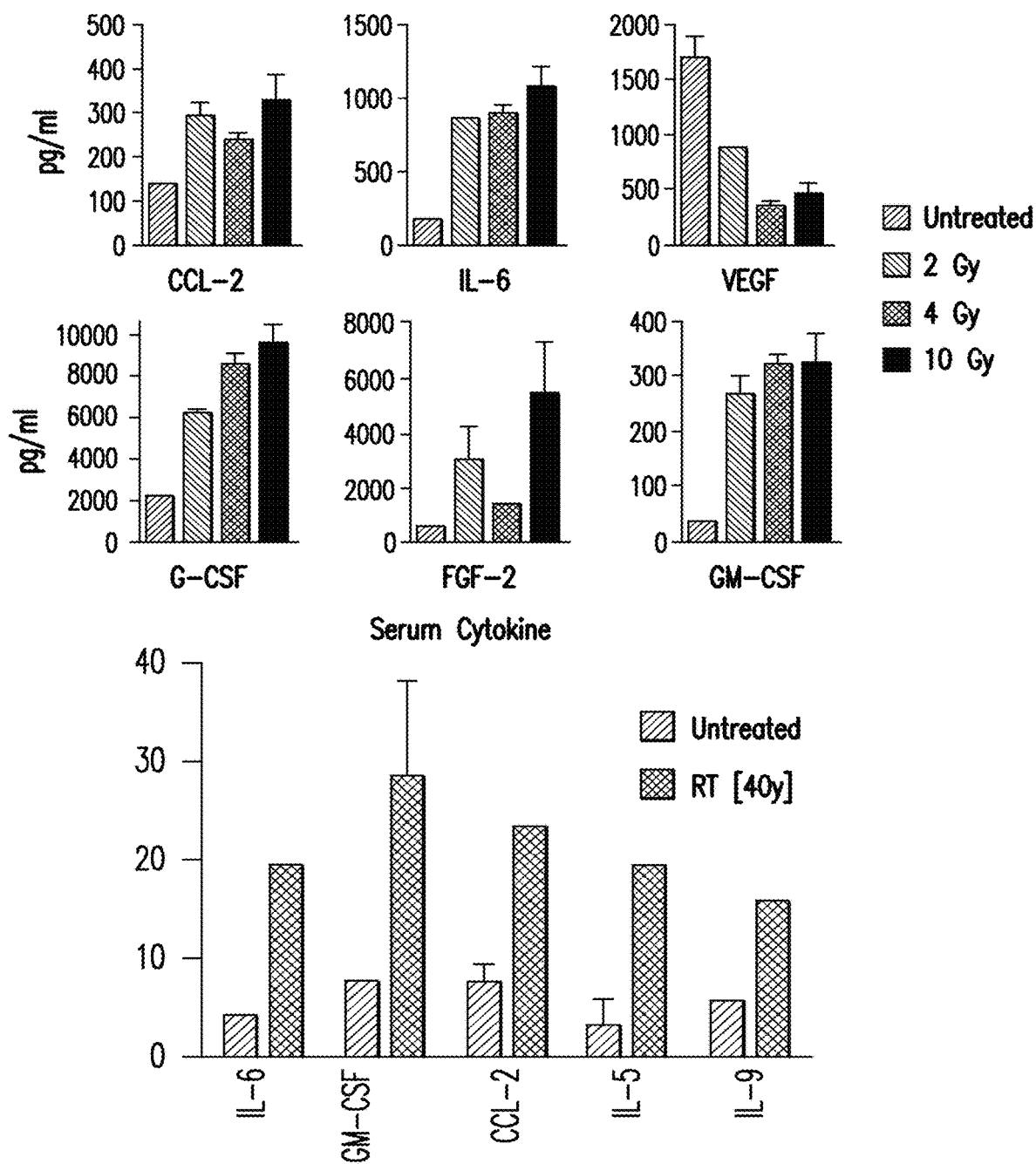

FIG. 33 depicts radiation therapy promoted the efficacy of a presently disclosed MSLN-specific CAR-expressing T-cell. Chemokine and cytokine secretion in vitro (A) and in vivo (B) 72 h following exposure to hemithoracic radiation therapy (HTRT) in mice with thoracic tumors.

Figure 34:
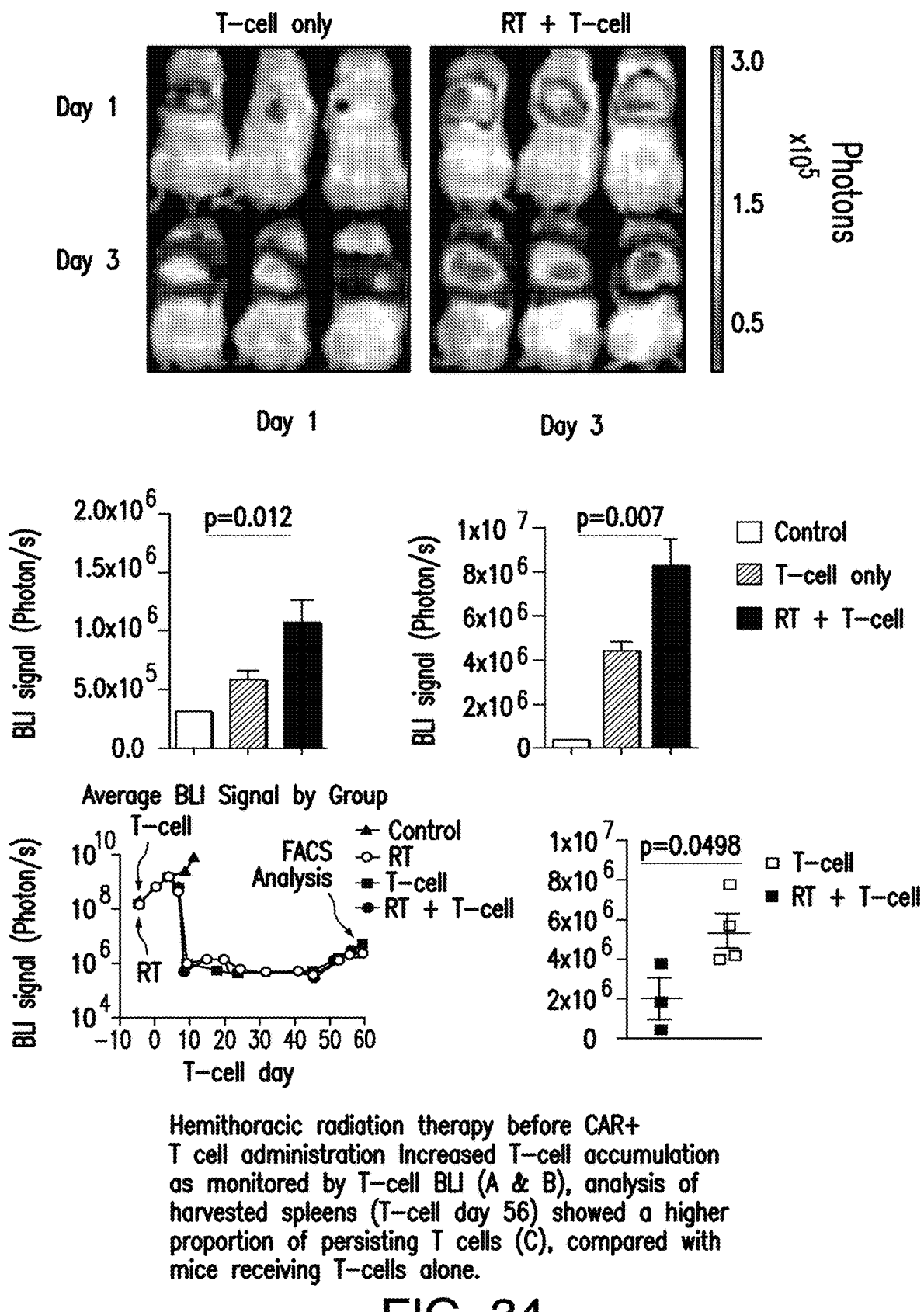
Figure 34:
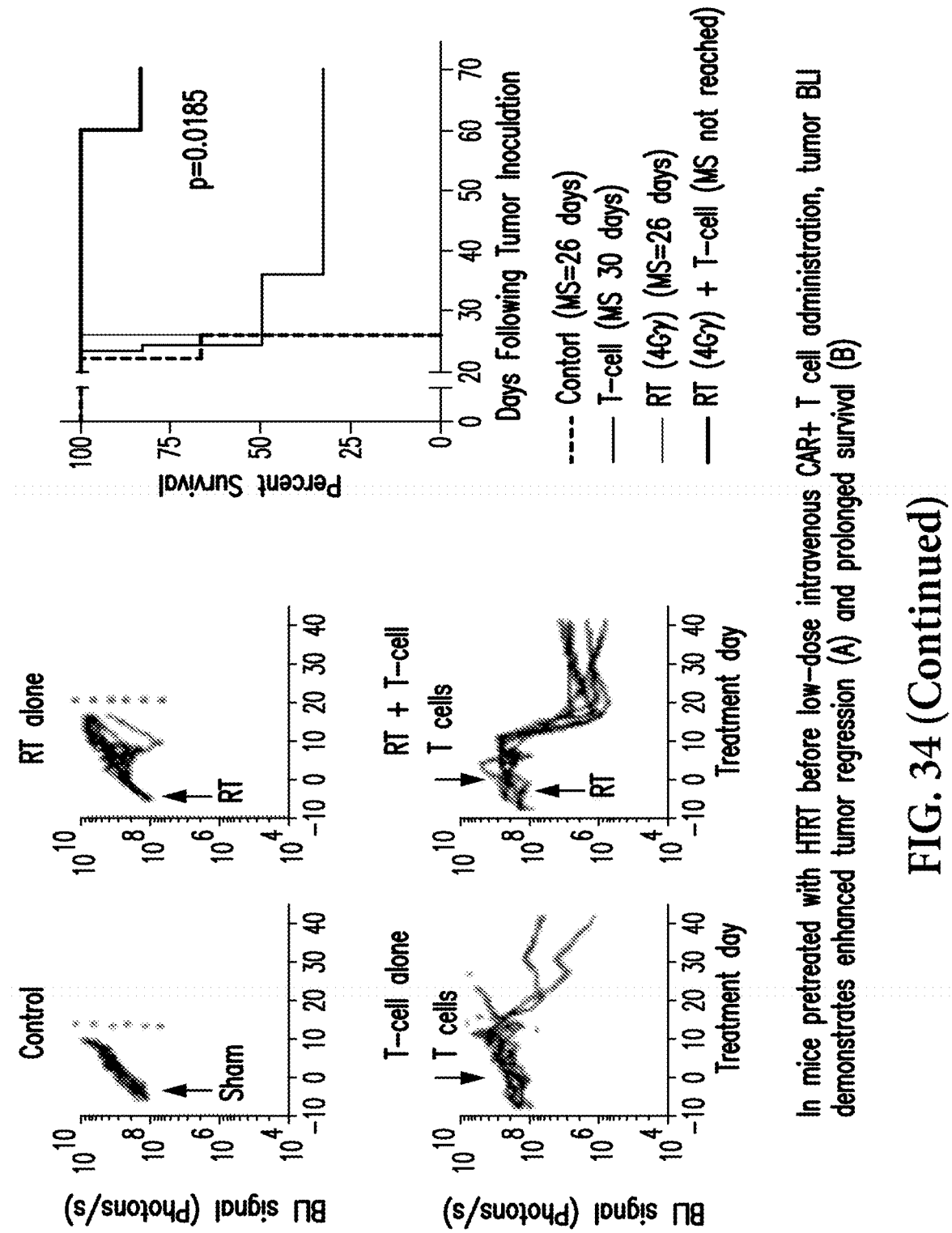

FIG. 34 depicts radiation therapy promoted the efficacy of a presently in its entity disclosed MSLN-specific CAR-expressing T-cell. Hemithoracic radiation therapy before CAR+ T cell administration increased T-cell accumulation as monitored by T-cell BLI, analysis of harvested spleens (T-cell day 56) showed a higher proportion of persisting T cells, compared with mice receiving T cells alone.

FIGS. 35A-35E depict Regional administration of MSLN CAR-transduced T cells results in superior antitumor efficacy. (A) Antigen-specific effector function of MSLN-CAR-transduced T cells as shown by lysis of MSLN-expressing, but not PSMA-expressing, target cells measured by chromium-release assays. (B and D) Tumor BLI of NOD/SCID/γcnull mice bearing pleural tumor. Tumor-bearing mice were treated with either 1×105 (1×) or 3×106 (30×) M28z T cells intravenously (E:T, 1:3000 or 100, respectively), compared with 1×105 (1×) or 3×105 (3×) M28z T cells intrapleurally (E:T, 1:3000 or 1000, respectively). Death is depicted by an asterisk (*). (C and E) Kaplan-Meier survival analysis demonstrates superior efficacy with intrapleural administration (solid blue line), compared with intravenous administration (dashed blue line). Median survival was not reached for intrapleural administration of M28z; median survival for intravenous administration was 27 days (1×) and 86 days (30×). Control mice treated with pleural P28z (black line) had a median survival of 27 to 42 days (n=4-10 per group). Survival curves were analyzed with Log-rank test. $P<0.01$; *$P<0.001$.

FIGS. 36A-36E depict intrapleurally administered M28z+ T cells display early, robust proliferation of both CD4+ and CD8+ subsets. (A) Serial T-cell BLI in tumor-bearing mice. Intravenously administered M28z+ T cells display delayed but equivalent accumulation in the progressing pleural tumor. (B) Average effLuc-luciferase signal intensities from sequential T-cell BLI. Intrapleurally administered T cells (blue lines) display an earlier and sustained accumulation, with maximal T-cell signal at day 5. Intravenously administered T cells show delayed accumulation, with maximal signal at day 7. (C) E:T ratios reflect M28z T-cell accumulation in parallel with tumor burden at 6 h and days 1, 3, and 7, confirming the findings of T-cell BLI. Intravenous administration shows delayed T-cell accumulation, lower E:T ratios, and decreased CD8+ T cell infiltration. (D) FACS analysis at day 7 displays an equal accumulation of CD4+ and CD8+ T-cell subsets within the tumor and spleen after intrapleural administration, compared with decreased tumor accumulation of CD8+ T cells and equal distribution of CD4+ and CD8+ T cells in the spleen after intravenous administration. (E) A decrease in CD62L expression was observed in both CD4+ and CD8+ T cells following intrapleural administration. Error bars represent ±SEM. *$P<0.05$, $P<0.01$, *$P<0.001$ by Student's t test.

Figure 37C:
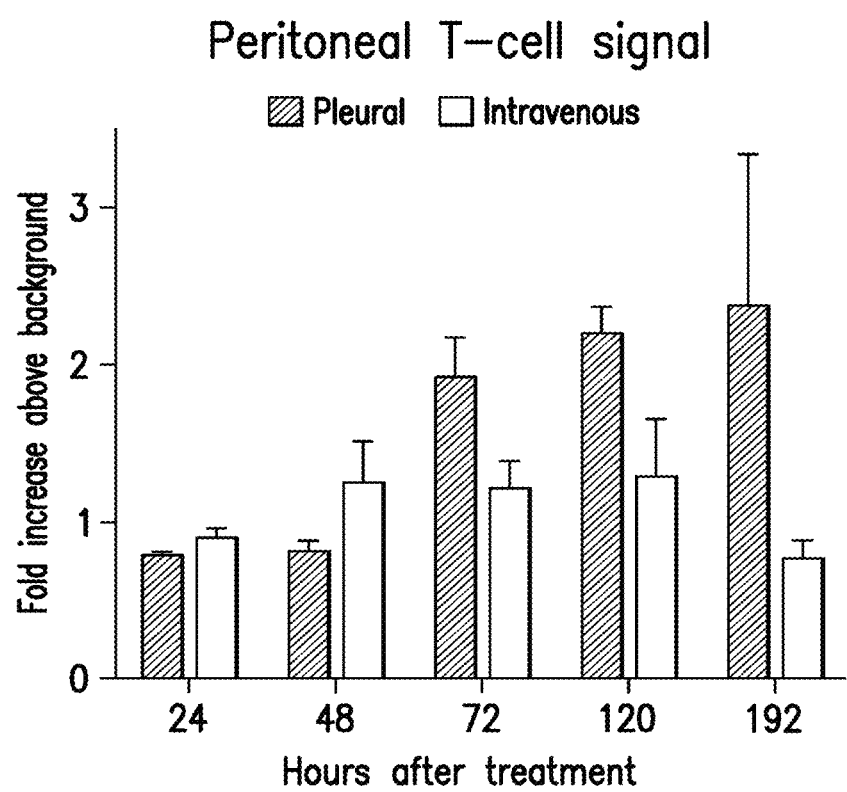

FIGS. 37A-37C depict intrapleurally administered M28z+ T cells display efficient systemic trafficking and accumulation in extrapleural tumor in an antigen-specific manner. (A) Serial tumor and T-cell BLI with dual luciferase imaging, demonstrating systemic trafficking and extrapleural tumor accumulation. Mice with established ffluc+ MSLN+ tumor in the right flank and pleural cavity and MSLN-tumor in the left flank received Gaussia-luciferase+ M28z T cells intrapleurally. A representative mouse with tumor in the flanks and pleural cavity before T-cell administration (left). T-cell BLI 15 days after T-cell administration (center) demonstrates residual T cells in the pleural cavity and accumulation in the MSLN+ right-flank tumor (center). One day later, tumor BLI shows a reduced burden in the MSLN+ right-flank tumor, compared with the MSLN-left-flank tumor (right). (B and C) Intrapleurally administered M28z+ T cells show early and robust accumulation in MSLN+ intraperitoneal tumor, compared with intravenously administered T cells. (C) Quantification of the fold increase in signal intensity of the peritoneal cavity in tumor-bearing mice displays enhanced T-cell accumulation with intrapleural administration, compared with intravenous administration (n=3 per group, error bars represent ±SEM).

FIGS. 38A and 38B depict intrapleurally administered M28z T cells eradicate pleural tumor and establish long-term CD4+ predominant persistence. (A) CD28 costimulation facilitates tumor eradication following a single dose of T cells. In total, 1×10$^5$ CAR+Mz, M28z, or P28z (negative control) T cells were intrapleurally administered into mice bearing established tumors. (Left) Tumor burden. (Right) Kaplan-Meier survival curve. Median survival of the Mz and M28z groups (at least 9 mice per group) was 63 days and median survival not reached, respectively. Survival curve was analyzed by log-rank test. **$P<0.01$. (B) CD28 costimulation enhances CAR+ T-cell persistence. Absolute CAR+ T-cell counts (per mL of peripheral blood) at 50 days after intrapleural administration of 3×10$^6$ CAR+ T cells. Error bars represent ±SEM, *$P<0.05$ by Student's t test.

Figure 39:
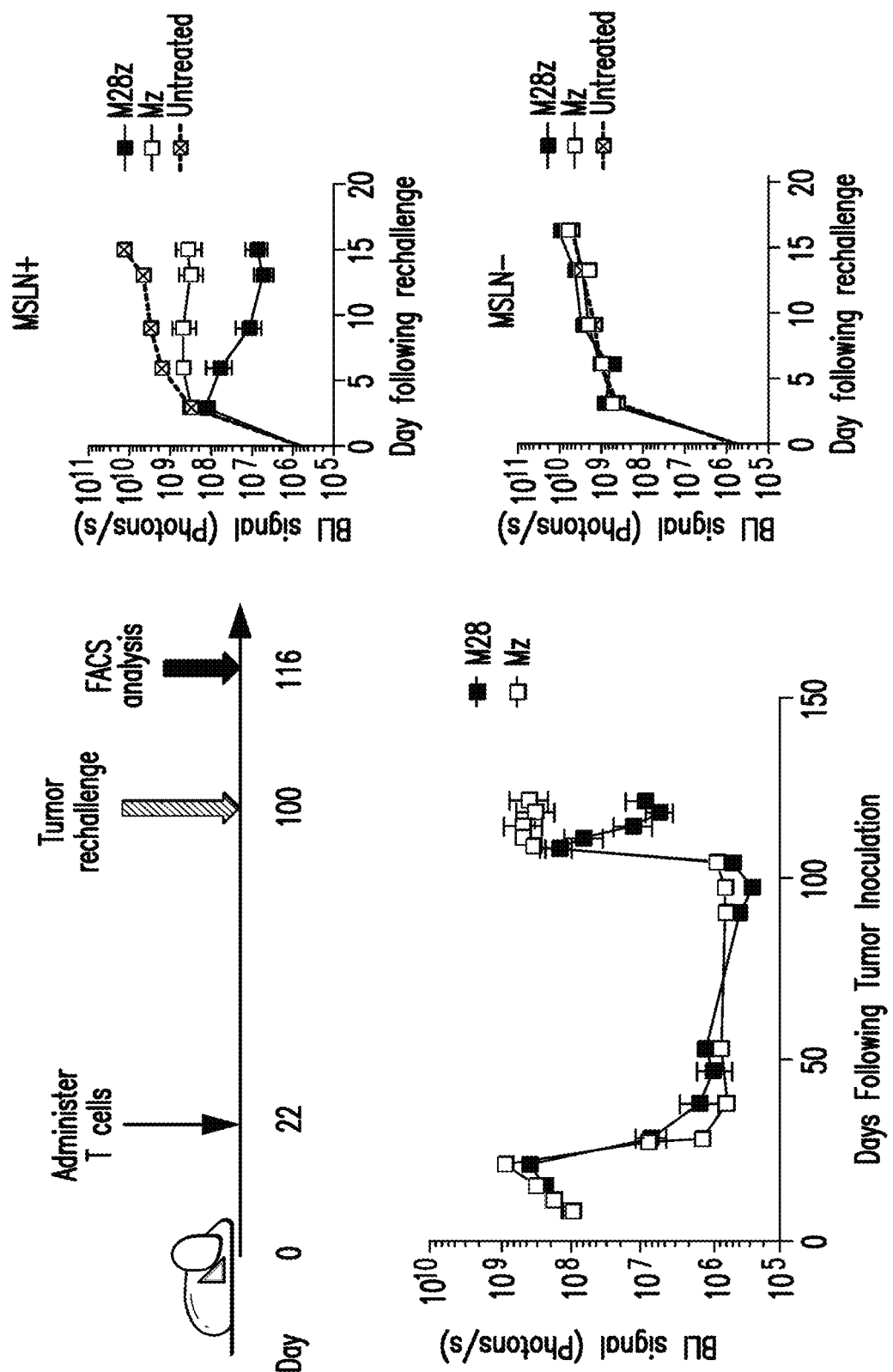

FIG. 39 represents tumor BLI of mice rechallenged with MSLN+ and MSLN– tumor. Eighty-seven days after pleural tumor eradication, following administration of a single dose of 3×10$^5$ M28z or Mz T cells, 1×10$^6$ MSLN+ or MSLN– tumor cells were injected into the peritoneal cavity. Following tumor rechallenge, Mz T cells prevent tumor growth, whereas M28z T cells promote tumor regression.

FIGS. 40A-40F depict CD4+M28z T cells augment CD8+ accumulation that is enhanced with preactivation. (A-C) Unsorted M28z and Mz or bead-sorted CD4+ and CD8+ T cells were assayed. M28z CD4+ T cells show (A) higher cytokine secretion (from 4- to 14-fold; ***$P<0.001$ by Student's t test) and (B) profound T-cell expansion without exogenous IL-2. (C) CD4+M28z activation facilitates robust CD8+M28z T-cell accumulation upon repeated antigen stimulation in vitro. (D) Antigen-activated CD4+M28z activation facilitates robust CD8+M28z T-cell accumulation in vivo. Isolated CD8+ effLuc M28z T cells were intrapleurally administered to MSLN+ pleural tumor-bearing mice with either CD4+M28z (n=6) or CD4+ control-transduced T cells (n=6) and were serially imaged. One representative mouse (n=6 per group; left) displays increased CD8+M28z T-cell accumulation in the presence of CD4+M28z. (E) The average accumulation of CD8+ CAR+ T cells was calculated at the indicated intervals (P values as shown calculating fold increase from 16 to 72 hours, n=6 per group). (F) Preactivation of M28z CD4+ enhances CD8+ proliferation, compared with simultaneous activation of CD4+. Bead-sorted CD8+Mz or M28z T cells were cocultured with either corresponding Mz or M28z CD4+ or preactivated CD4+ T cells (activated on MSLN+ tumor cells 24 h before the assay). Preactivation of M28z CD4+ enhances the accumulation of CD8+ to a greater degree than does CD8+ and CD4+ concurrent stimulation.

FIGS. 41A-41E depict CD4+ MSLN CAR+ T cells demonstrate efficient cytolytic function that is granzyme/perforin dependent. (A) CD4+M28z T cells show a delayed but similar cytotoxicity as CD8+M28z T cells. (B) CD28 costimulation enhances CD4+-mediated cytotoxicity. (C) Cytokine-rich supernatants obtained from stimulated CD4+ M28z CAR+ T cells enhance cytotoxicity of both CD8M28z and CD4M28z T cells. (D) CAR T-cell lytic function is dependent on release of cytotoxic granules. Bulk, CD4, or CD8 M28z and Mz T cells were cocultured for 18 h in the presence or absence of the chelating agent ethylene glycol tetraacetic acid (EGTA). (A-D) Cytotoxicity of bead-purified CD4+ or CD8+Mz and M28z T cells. (E, left) CD4+ CAR T cells express granzyme B, but with delayed kinetics, compared with CD8+ CAR T cells. Intracellular FACS analysis for granzymes B was performed on resting PBMCs, PHA-stimulated blasts, and M28z, Mz, and P28z T cells stimulated with MSLN+ for 4 or 18 h.(E, right) CD28 costimulation enhances granzyme B expression. Histograms show expression at 18 h after MSLN+ stimulation. Error bars represent ±SEM, *P<0.05 by Student's t test.

Figure 42A:
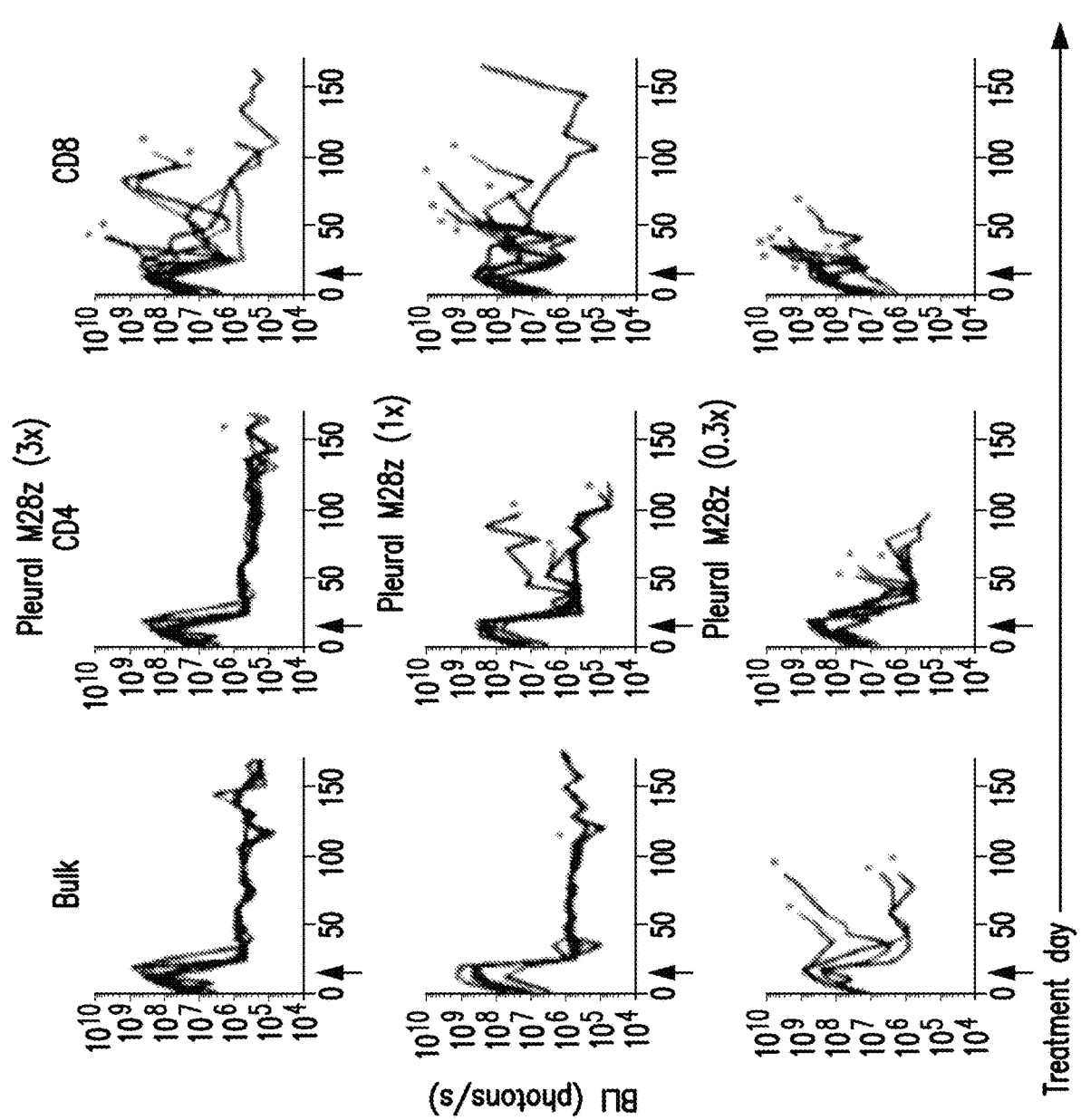

FIGS. 42A-42C depict intrapleurally administered CD4+ M28z CAR T cells are efficacious when administered alone in vivo; mediate enhanced efficacy, compared with CD8+ M28z T cells; and establish long-term functional persistence. (A) BLI tracking the progression of tumor burden. Eighteen days after tumor injection, mice received either $3 \times 10^5$ (3×), $1 \times 10^5$ (1×), or $3 \times 10^4$ (0.3×) CAR+ T cells of bulk M28z (n=5), bead-sorted CD4+, CD8+M28z (n=7), or P28z (n=4). (B) Kaplan-Meier survival curves. At all doses, CD4+M28z CAR+ T cells were efficacious, compared with CD8+ CAR+ T cells. The antitumor efficacy of CD4+ CAR+ T cells was comparable to that of unsorted CAR+ T cells. *P<0.05; P<0.01; *P<0.001 by Student's t test. Raw data and P values are provided in the Supplementary Materials. (C) Tumor BLI of mice rechallenged with tumor. At 196 days after intrapleural administration of a single dose of $3 \times 10^5$ (3×) unsorted (bulk) M28z or CD4+-sorted M28z T cells, $1 \times 10^6$ MSLN+ tumor cells were injected into the peritoneal cavity. Persisting CD4+ M28z T cells prevented tumor growth.

FIGS. 43A and 43B depict mesothelin-targeted CAR T cells demonstrate antigen-specific effector function. (B) FACS analysis of tumor cell lines used for in vitro analysis of CAR T-cell effector function. (C) M28z CAR T cells secreted a 2- to 5-fold greater amount of Th1 cytokines.

FIG. 44 represents intracellular FACS analysis for granzymes A and B, which was performed on resting PBMCs, PHA-stimulated blasts, and M28z CAR T cells stimulated with MSLN+, here shown following 18 h coculture.

Figure 45A:
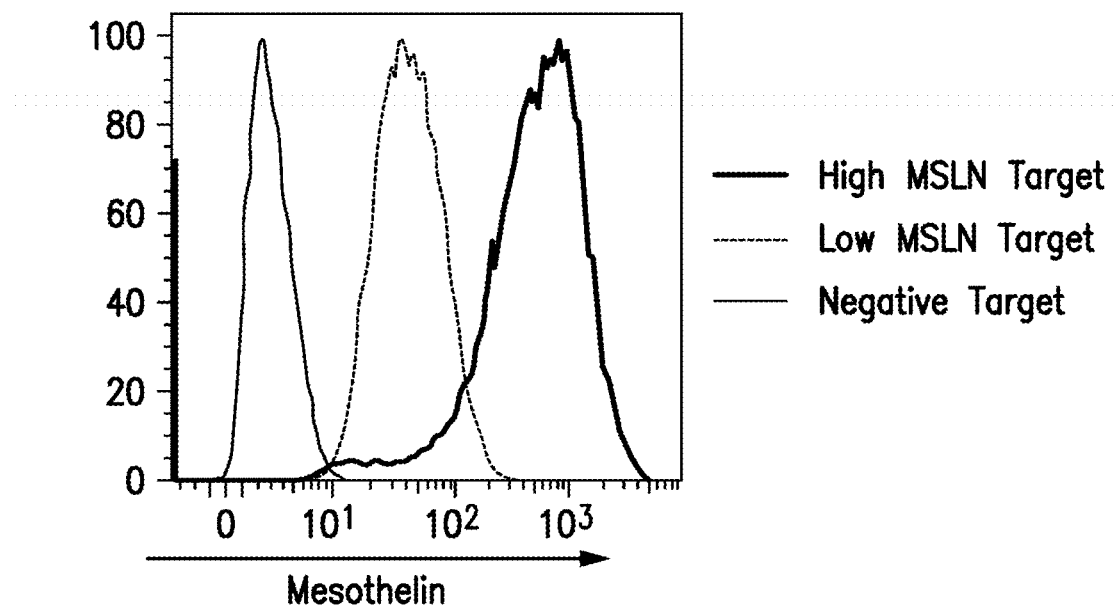
Figure 45B:
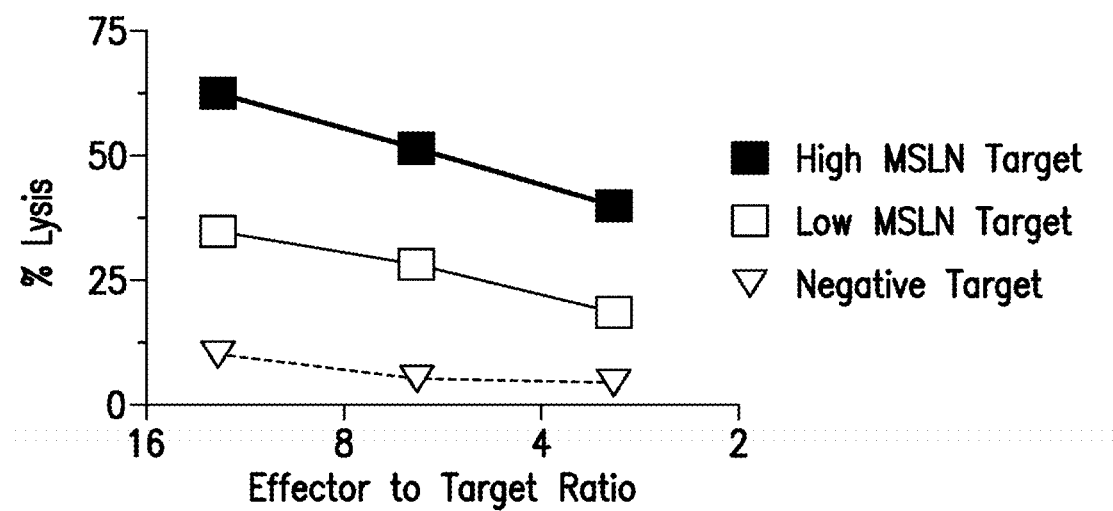

FIGS. 45A and 45B depict CAR T cell cytolytic function is proportional to level of target antigen expression. (A) Surface mesothelin expression by MSTO-211H mesothelioma tumor cells transduced with either a low (gray) or high (black) level of mesothelin. Isotype staining is included for reference. (B) Cytolytic function of M28z CAR T cells measured by chromium release following 18 hr coculture of T cells and either mesothelin low or high targets at the indicated effector to target ratios.

FIGS. 46A and 46B depict Gating strategy for flow cytometry. (A) For in vitro and in vivo analyses using sorted CD4 and CD8 CAR T cells, all samples were sorted to >95% purity. (B) T cell phenotype analysis was performed with appropriate untransduced controls (to determine CAR positive gate) and with isotype controls to set gates for CD62L and CD45RA.

FIGS. 47A-47E depict chimeric antigen receptors (CARs) with CD28 or 4-1BB costimulation exhibit equivalent effector cytokine secretion and proliferation in vitro upon initial antigen stimulation. (A) First- and second-generation CARs. (B) Mesothelin (MSLN)-targeted CARs contain the CD3ζ endodomain either alone (Mz, first-generation CAR) or in combination with the CD28 (M28z) or 4-1BB (MBBz) costimulatory domain (second-generation CAR). A prostate-specific membrane antigen (PSMA)-directed CAR with CD28 costimulation (P28z) as well as PSMA-expressing targets (PSMA+) are included in experiments as negative controls. CYT, cytoplasmic domain; LS, leader sequence; LTR, long terminal repeat; SA, splice acceptor; SD, splice donor; $T_M$, transmembrane. (C-E) Antigen-specific effector functions of CAR-transduced T cells. (C) Lysis of MSLN-expressing targets (MSLN+), but not PSMA+ targets, as measured by chromium-release assays. (D) 4-1BB and CD28 costimulations enhance cytokine secretion, as assessed by Luminex assay, after coculture of CAR T cells with MSLN+ cells. (E) M28z and MBBz CARs facilitate robust T-cell accumulation after stimulation with MSLN+ cells. Data represent the mean±SEM (C, E) of three replicates or are plotted as individual points (D). ***P<0.001, comparing costimulated CAR T cells (M28z or MBBz) with the first-generation receptor (Mz), by Student's t test; significance was determined using the Bonferroni correction for multiple comparisons.

Figure 48A:
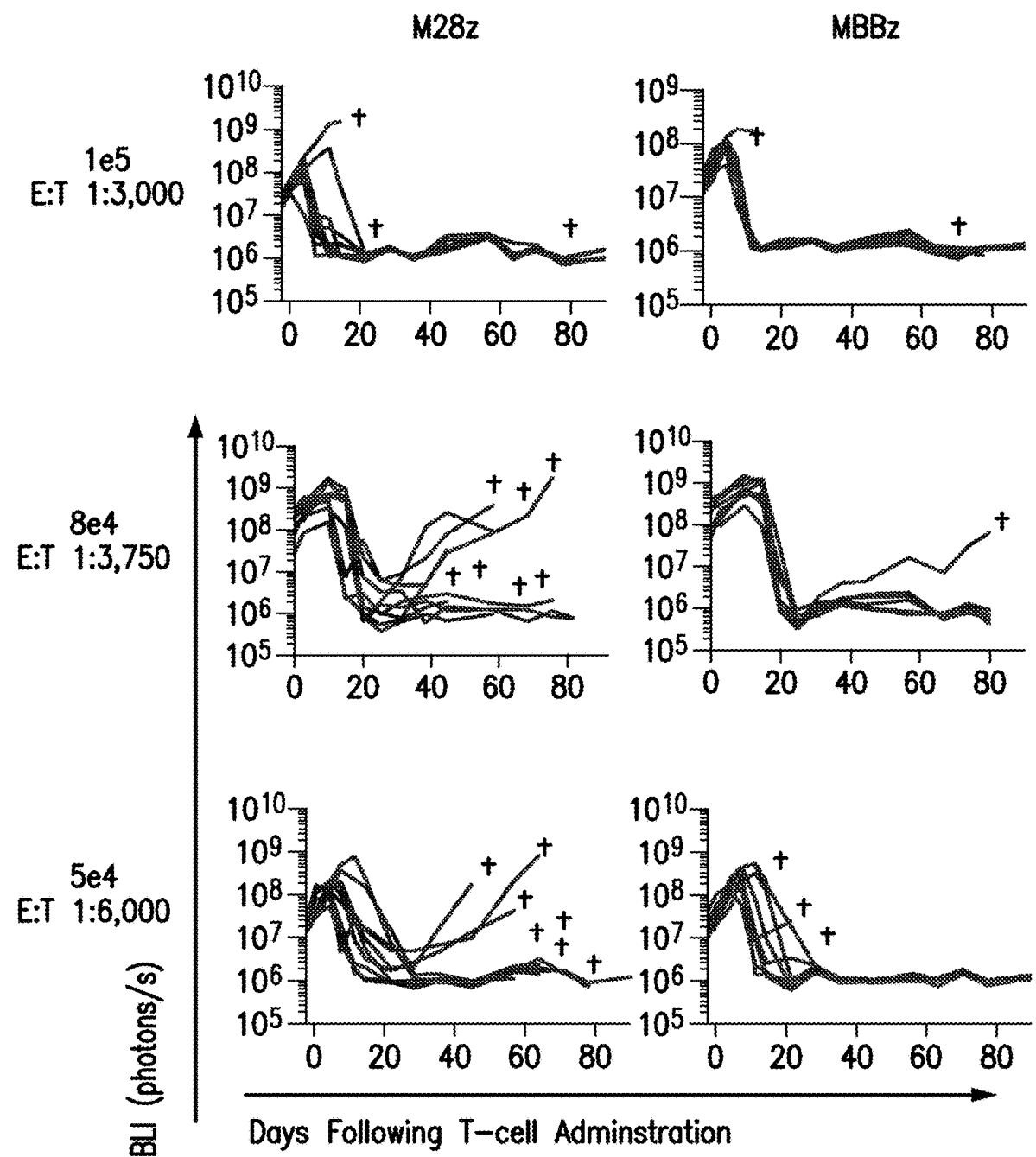
Figure 48B:
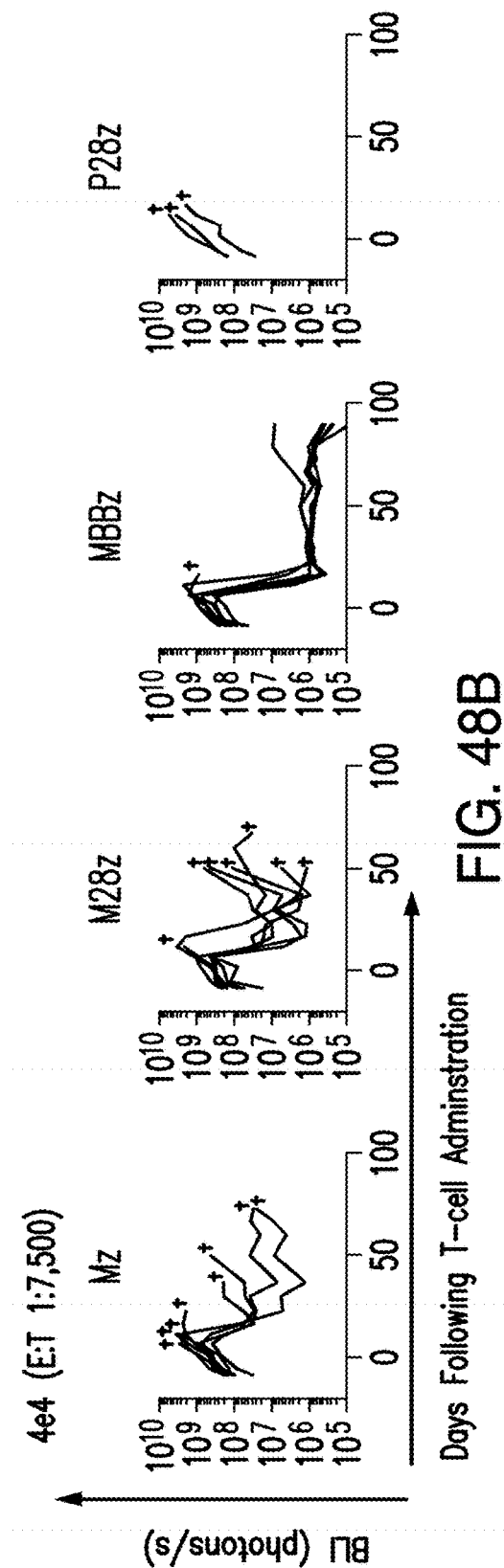
Figure 48C:
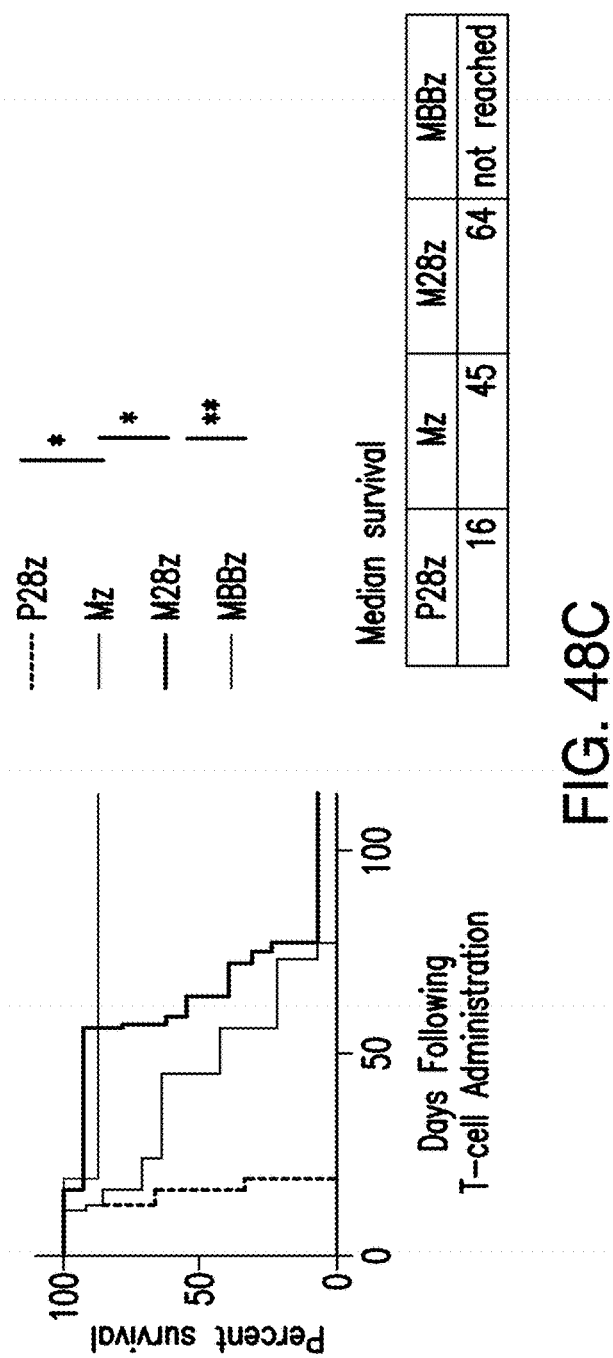

FIGS. 48A-48C depict mice treated with M28z and MBBz CAR T cells demonstrate tumor eradication at a higher dose whereas treatment with lower doses results in higher rate of tumor relapse with M28z. (A) In vivo bioluminescence imaging (BLI) was used to monitor tumor burden (firefly luciferase+ MSLN+) in NOD/SCID/$\gamma_c^{null}$ mice. Mice with established pleural tumor were treated with a single dose of 1e5 (E:T 1:3,000), 8e4 (E:T1:3,750), or 5e4 (E:T 1:6,000) M28z or MBBz CAR T cells. The (t) symbol indicates the death of a mouse. Two similar experiments with the same donor are combined for the illustration. (B) Mice were treated with 4e4 CAR T cells (E:T 1:7,500). The 1$^{st}$ generation Mz CAR and negative control P28z are included. (C) Kaplan-Meier survival analysis comparing the in vivo efficacy of intrapleural administration of 4e4 Mz (n=13, red), M28z (n=15, blue), MBBz (n=8, green), and P28z (n=3, black) CAR T cells. Median survival in days following T-cell administration. The survival curve was analyzed using the log-rank test. *P<0.05; **P<0.01.

Figure 49C:
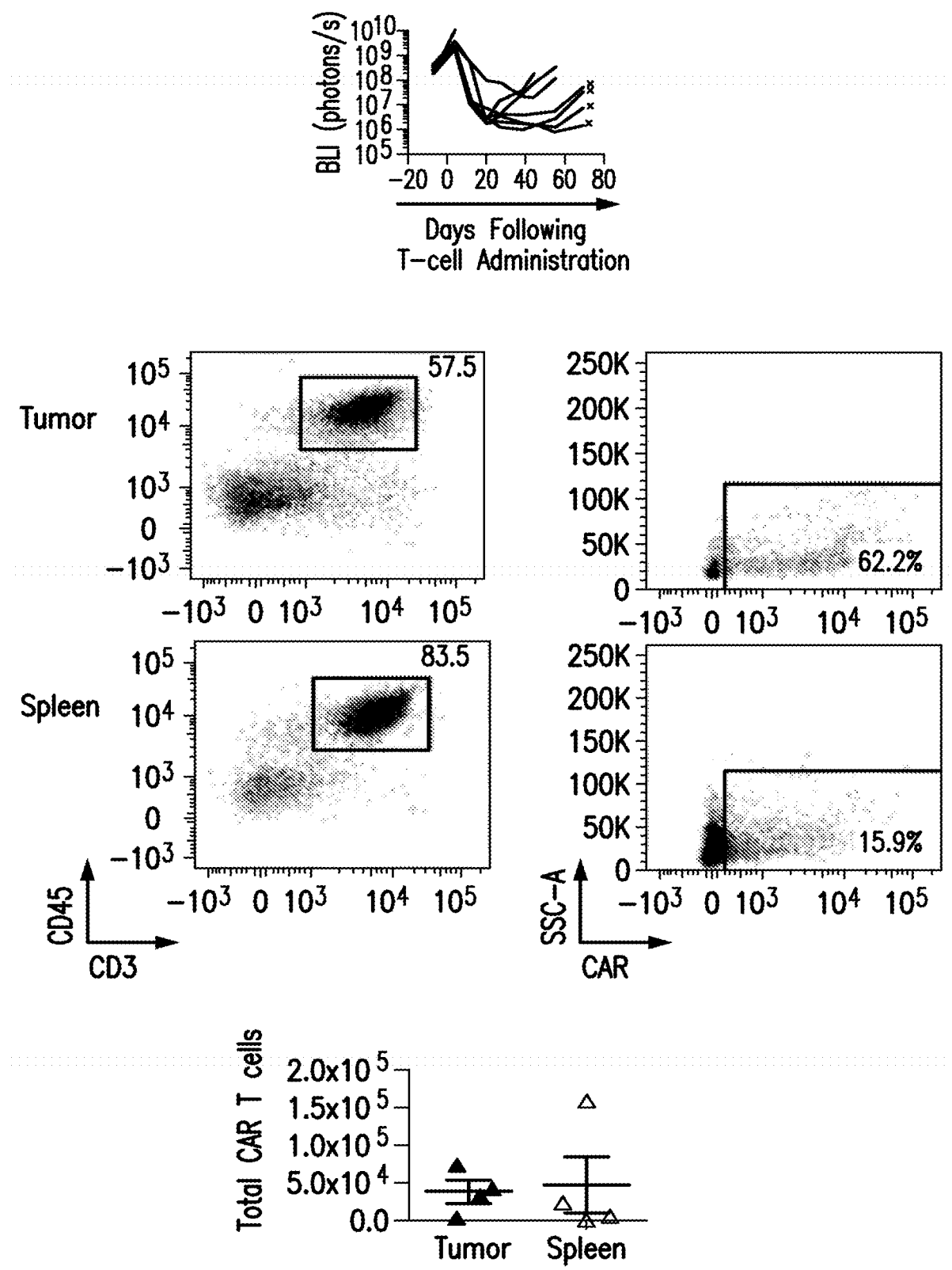

FIGS. 49A-49C depict M28z- and MBBz-treated mice demonstrate similar early and long-term CAR T-cell accumulation, and M28z-treated mice with progressing tumors contain persisting CAR T cells. (A) CD28 and 4-1BB costimulation enhance intratumoral CAR T-cell accumulation to equal extents. The left panels show the results of tumor BLI after after administration of a single dose of 8e$^4$ CAR T cells. After 6 days, T cells were harvested from the tumor; x denotes mice whose T-cell counts are represented as data points. The right panel shows absolute CAR T cells per gram of tumor tissue (*P<0.05). Student's t tests were performed and statistical significance was determined using the Bonferroni correction for multiple comparisons. (B) CD28 and 4-1BB costimulation enhance CAR T-cell persistence, as measured in the spleen, to equal extents. Absolute CAR T cells per spleen are shown 73 days after intrapleural administration of CAR T cells (8e$^4$). The left panels show the results of tumor BLI; x denotes mice whose T-cell counts are represented as data points (*P<0.05). Student's t tests were performed and statistical significance was determined using the Bonferroni correction for multiple comparisons. (C) Mice treated with a low dose of M28z T cells ($4e^4$) display tumor recurrence with persisting CAR T cells in the spleen and tumor. The left panel shows the results of tumor BLI. Spleen and tumor from mice denoted by an x were harvested and used for FACs analysis (middle panel) and T-cell quantification (right panel).

FIGS. 50A-50D depict CAR T cells become exhausted following in vivo antigen exposure, although MBBz CAR T cells preferentially retain effector cytokine secretion and cytotoxicity. (A) Six days after intrapleural administration of CAR T cells, M28z and MBBz CAR T cells were isolated from the tumor and spleen and subjected to ex vivo antigen stimulation. (B) Chromium-release assay upon ex vivo stimulation demonstrates a decrease in M28z but persistent MBBz cytolytic function (E:T ratio 1:5) (C) Cytokine secretion measurements demonstrate decreases in effector cytokine secretion by CAR T cells, although MBBz CAR T cells are better able to retain secretion. (D) RT-PCR measurements of GzB, IFN-γ, and IL-2 expression by harvested CAR T cells correlate well with protein level measurements in panels (A) and (B). Data represent the fold-change relative to the mRNA expression of unstimulated M28z CAR T cell in vitro. Data represent the mean±SEM of three individual wells per condition. Student's t tests were performed, and statistical significance was determined using the Bonferroni correction for multiple comparisons (*P<0.05; P<0.01; *P<0.001). Results are reproduced in two separate cohorts of mice used for each of the two experiments.

FIGS. 51A-51E depict CAR T cells become exhausted upon repeated antigen stimulation in vitro, although MBBz CAR T cells preferentially retain effector cytokine secretion and cytotoxicity in vitro and upon tumor rechallenge in vivo. (A) Both M28z and MBBz CAR T cells retain proliferative capacity in vitro upon repeated antigen stimulation. T cells were also tested for cytotoxicity by chromium-release assay and for cytokine secretion by Luminex assay (B-D). (B) (Left) CAR T cells demonstrate equal killing at the first stimulation and loss of cytolytic function upon repeated antigen stimulation, although MBBz CAR T cells are better able to retain cytolytic function as measured by chromium-release assay. (C) Cytotoxic granule release as measured by CD107a expression (shown at the third stimulation) correlates with chromium release assay (B). Data represent the mean±SD (triplicates) of the fold-change relative to the CD107a MFI of unstimulated CAR T cells. (D) Cytokine secretion measurements similarly demonstrate loss of CAR T-cell effector function upon repeated antigen encounter; again, MBBz CAR T cells are better able to preserve their function. (E) Although equally persistent, MBBz CAR T cells demonstrate superior functional persistence. Twenty-eight days after pleural tumor eradication (following a single dose of $1e^5$ CAR T cells), $1e^6$ MSLN+ tumor cells were injected into the pleural cavity (tumor rechallenge). MBBz CAR T cells prevented tumor growth in all mice, whereas tumor growth and death were observed in 2 of 4 mice initially treated with M28z CAR T cells. Student's t tests were performed and statistical significance was determined using the Bonferroni correction (*P<0.05; ***P<0.001). Data represent the mean±SEM of three replicates or are plotted as individual points.

FIGS. 52A-52F depict PD-1 receptor and its ligands are upregulated in vivo. (A) Tumor-infiltrating M28z and MBBz CAR T cells express inhibitory receptors 6 days after their administration, but MBBz CAR T cells express lower levels of PD-1. (B) Mean fluorescence intensity (MFI) of PD-1 receptor expression of tumor-infiltrating CAR T cells (TIL) 6 days after intrapleural administration. (C) Relative expression of PD-1 mRNA in CD4 and CD8 subsets of tumor-infiltrating CAR T cells 6 days after intrapleural administration. Data are represented in fold-change relative to the PD-1 mRNA expression of unstimulated M28z T cells. (D) Tumor-infiltrating M28z CAR T cells isolated from progressing tumors express inhibitory receptors PD-1, Tim-3, and Lag-3. (E) Single-cell tumor suspensions harvested from mice treated with M28z CAR T cells express high levels of PD-1 binding ligands. (F) In vitro cultured mesothelioma tumor cells express the ligands (PD-L1, PD-L2) for the PD-1 receptor, and expression is further upregulated following incubation for 24 h with IFN-γ and TNF-α.

FIGS. 53A-53D depict PD-L1 inhibits CAR T-cell effector function. (A) 3T3 fibroblasts were transduced to either express mesothelin alone (MSLN+, left) or coexpress MSLN in addition to PD-L1 (MSLN+PD-L1+, right). (B-D) M28z and MBBz CAR T-cell effector functions were assessed after stimulation with 3T3 MSLN+ or MSLN+PD-L1+ targets. PD-L1 inhibits M28z and MBBz CAR T-cell accumulation upon repeated antigen stimulation (B), cytolytic function following two stimulations with MSLN+ PD-L1+ tumor cells (C), and Th1 effector cytokine secretion upon the first stimulation (D). Data represent the mean±SEM of three replicates or are plotted as individual points.

Figure 54:
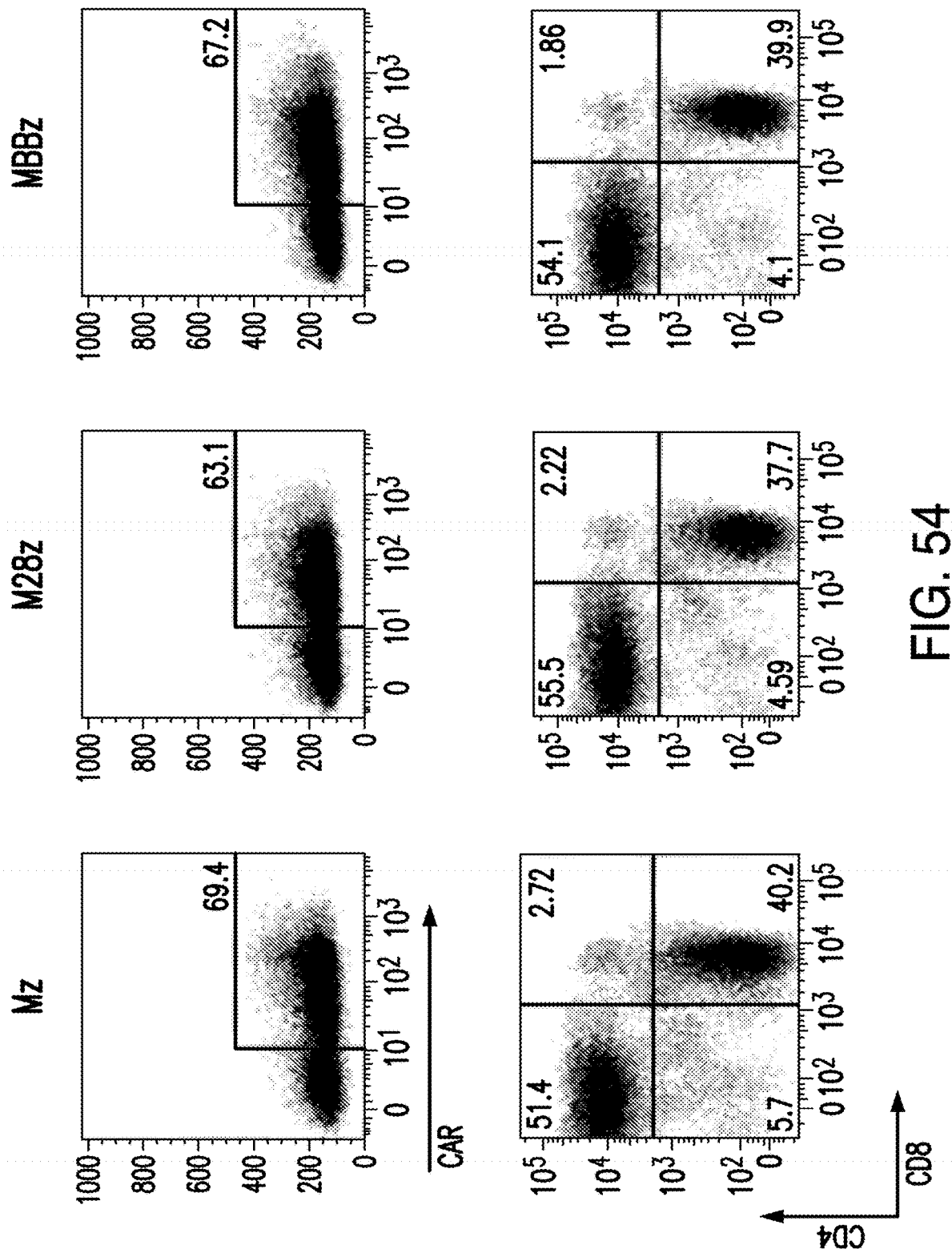

FIG. 54 represents efficient retroviral transduction of human T cells to express Mz, M28z, and MBBz CARs. (Top) Shown is representative FACS analysis 4 days after gene transfer. Fluorescence minus one staining was used to set positive gates after a live/dead stain excluded nonviable cells. All experiments used T cells with 50% to 70% CAR transduction efficiency; transduction percentages between T-cell groups were within 5% of each other. (Bottom) Both CD4+ and CD8+ T-cell subsets were efficiently transduced. CD4+ and CD8+ percentages after gating for CAR T cells are shown.

Figure 55:
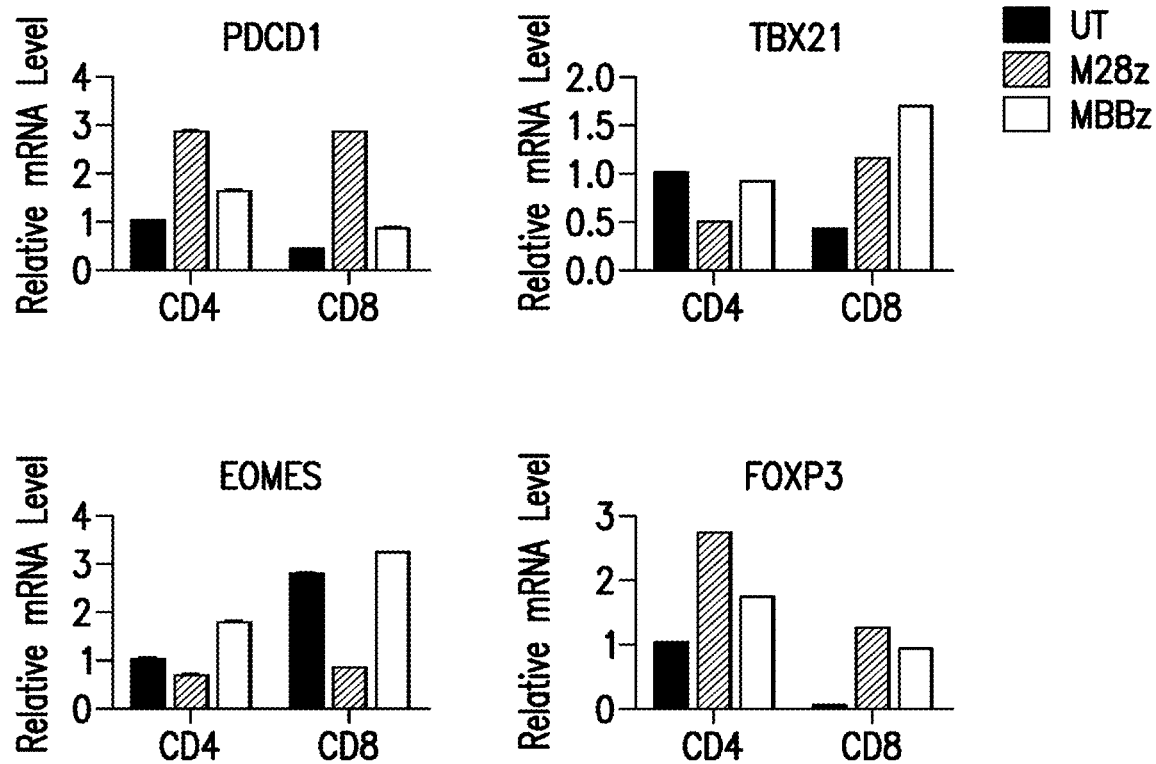

FIG. 55 represents MBBz CAR T cells express a less exhausted, more potent phenotype compared to M28z CAR T cells. 4-1BB- and CD28-costimulated T cells were expanded with repeated antigen stimulation, and mRNA was extracted and subjected to RT-PCR analysis 20 h after the third stimulation. Data are represented in fold change relative to the mRNA expression of CD4+ unstransduced T cells. MBBz CAR T cells express higher levels of EOMES (Eomesodermin) and TBX21 (T-bet), and lower levels of PDCD1 (PD-1) and FOXP3 (Foxp3). All comparisons were significant at P<0.001. Results were similar in 3 separate experiments using different donors.

Figure 56:
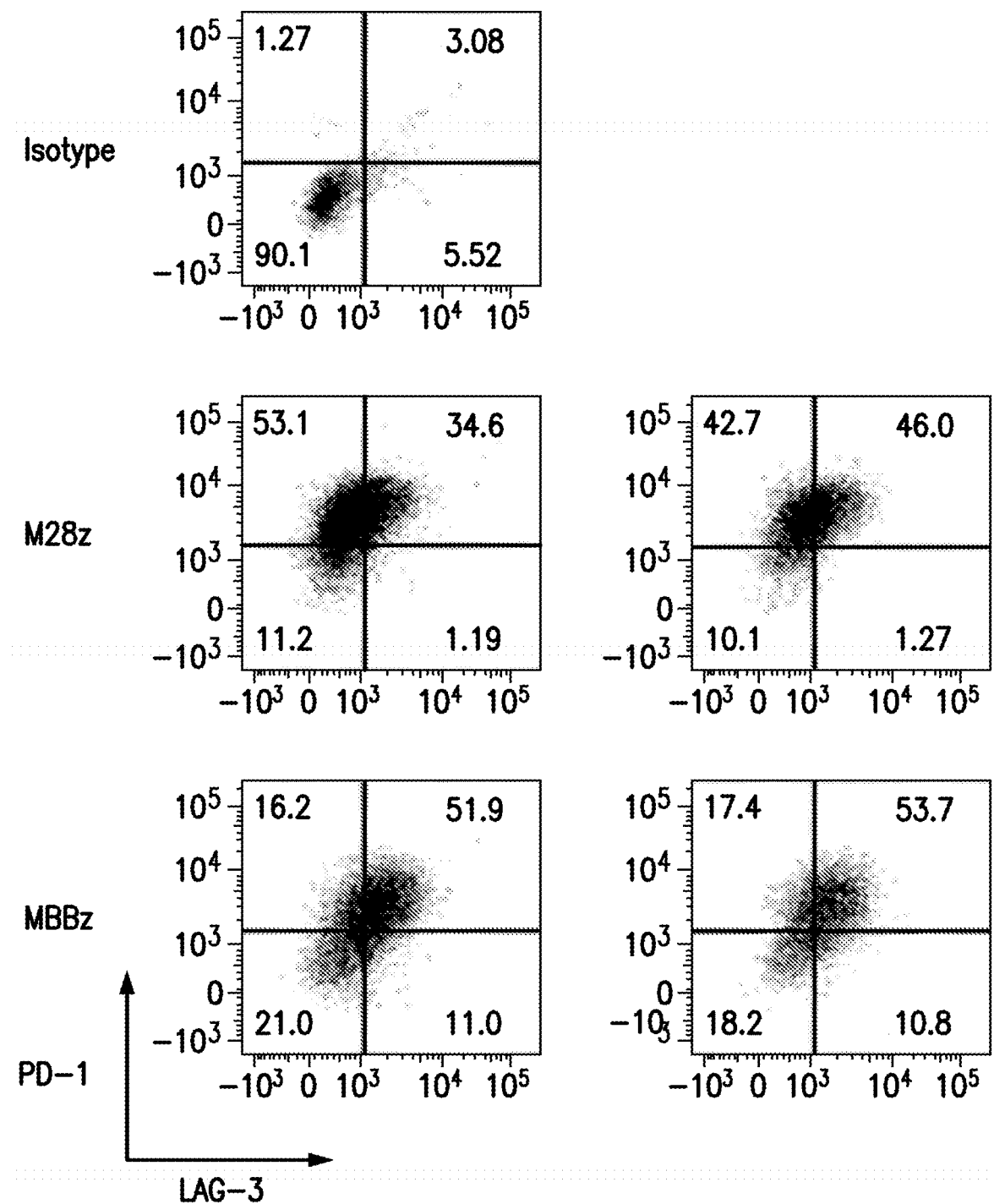
Figure 56:
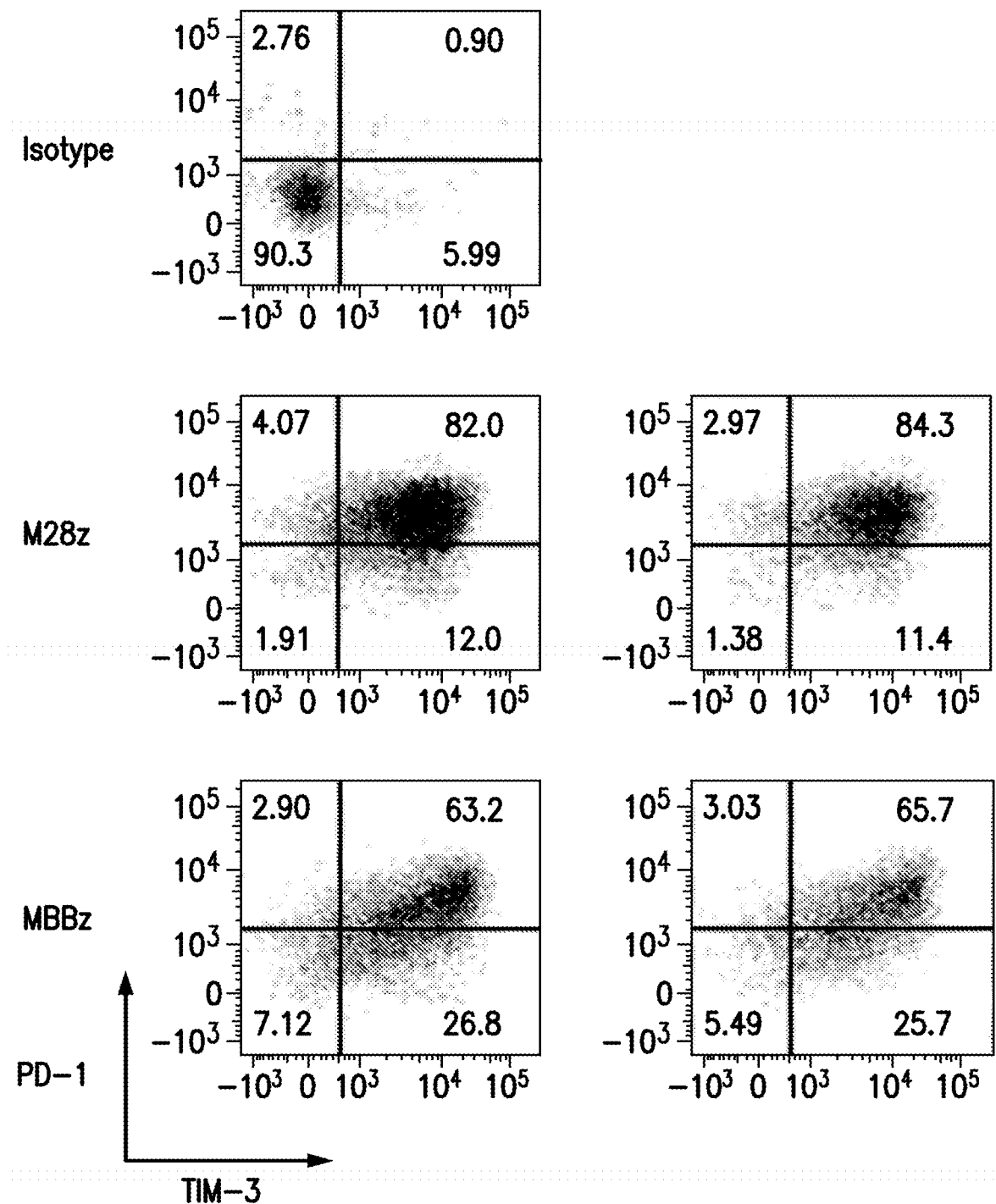

FIG. 56 represents M28z and MBBz CAR T cells coexpress PD-1 along with other inhibitory receptors. Tumor-infiltrating M28z and MBBz CAR T cells were harvested 6 days following intrapleural administration to pleural tumor bearing mice. Cells were costained with antibodies for PD-1 and either Lag-3 (left) or Tim-3 (right) and analyzed by flow cytometry. Isotype staining controls (top) were used to establish positive gates.

Figure 57:
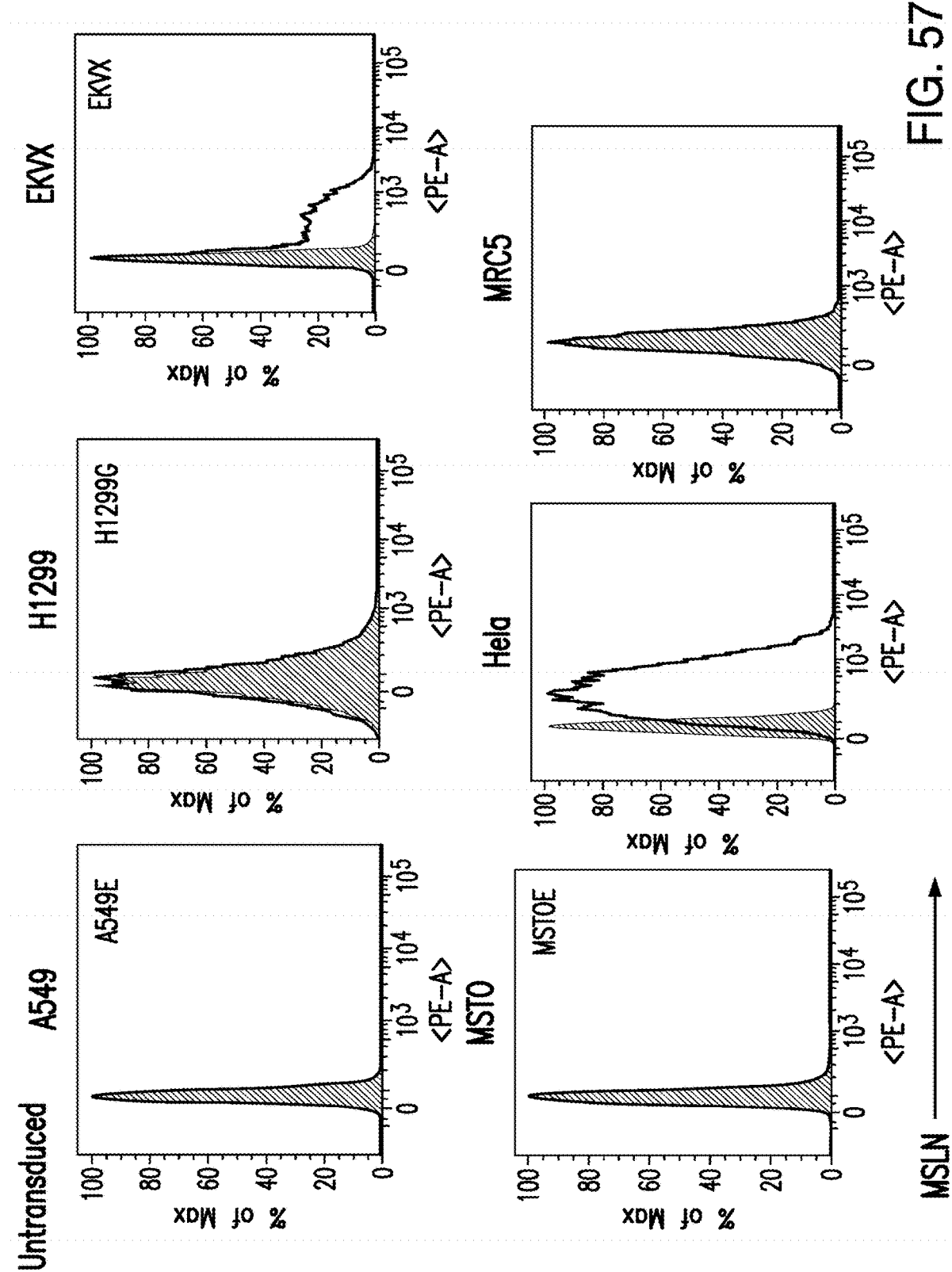
Figure 57:
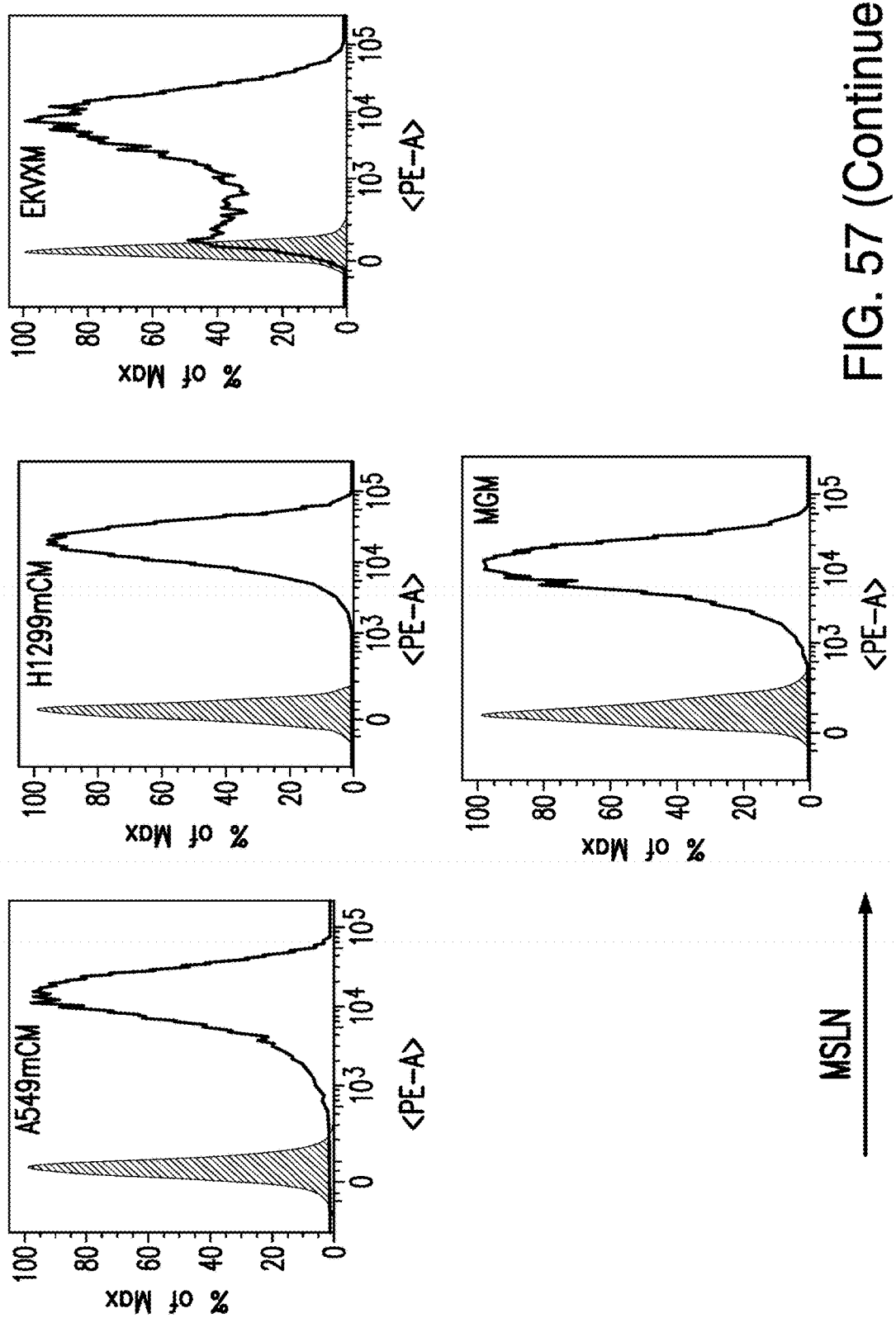

FIG. 57 depicts MSLN expression on various cancer and normal cells.

Figure 58:
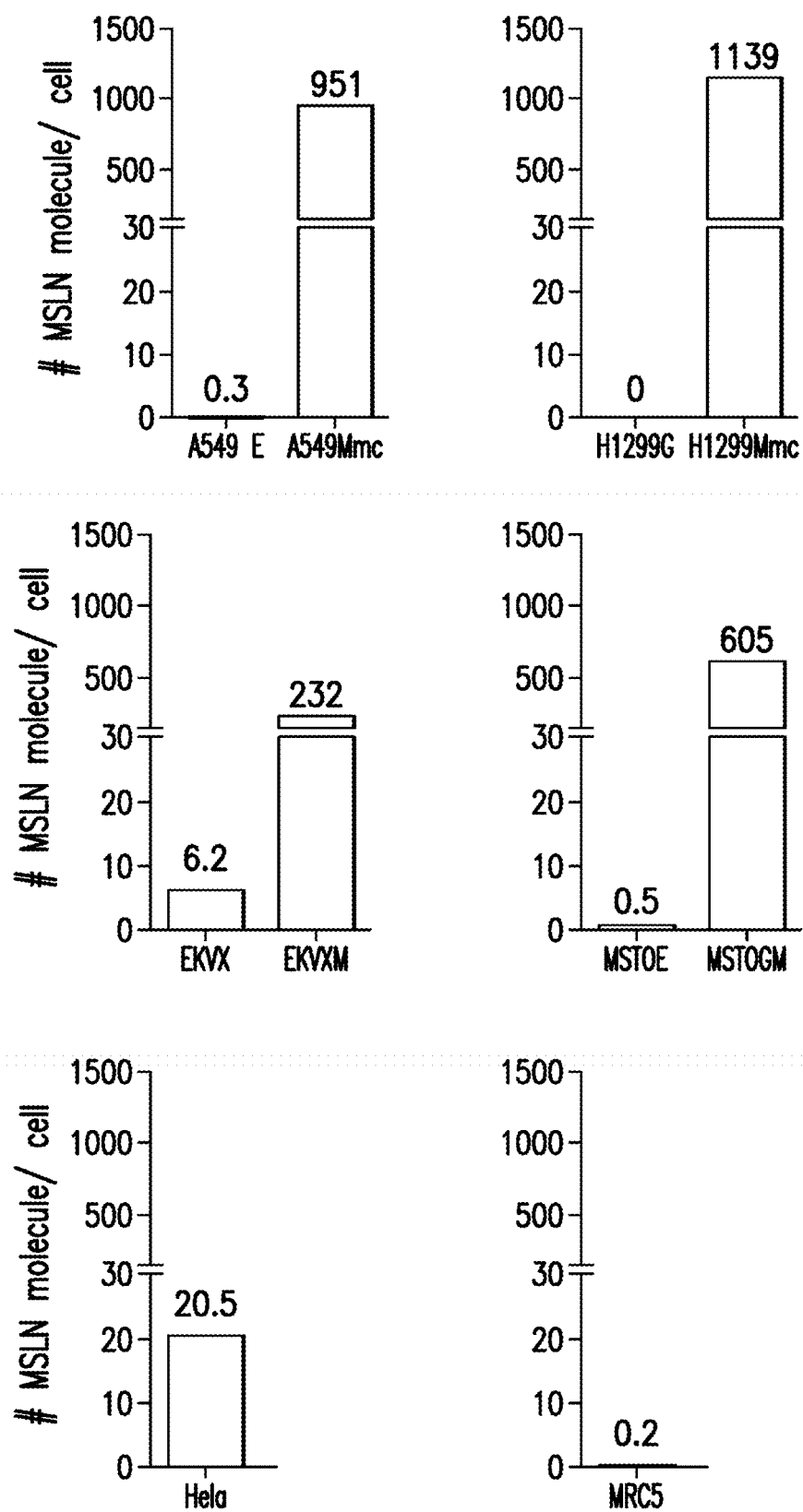

FIG. 58 depicts quantification of MSLN molecules per cell on various cancer and normal cells.

Figure 59:
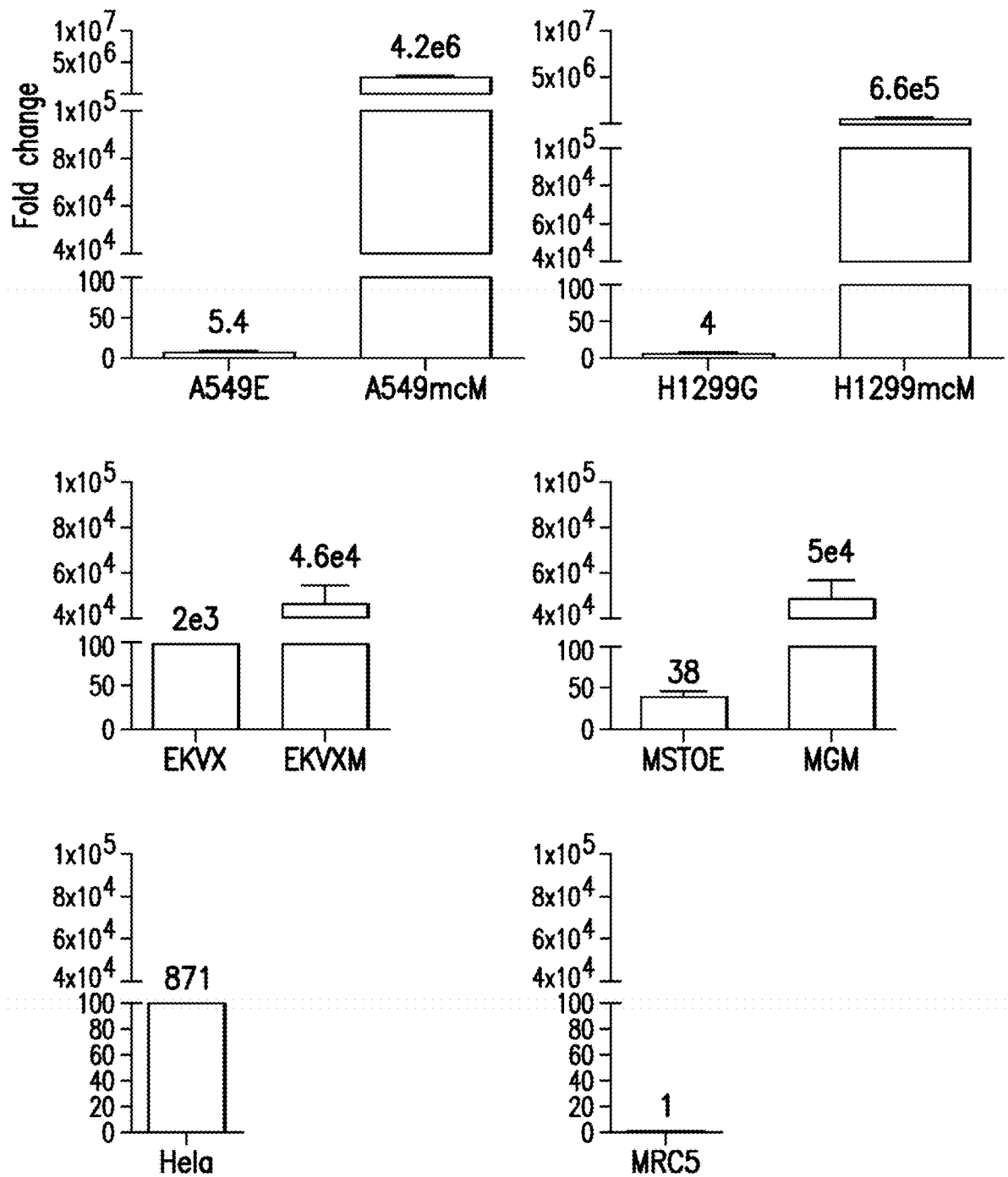

FIG. 59 depicts mRNA MSLN expression level on various cancer and normal cells.

Figure 60:
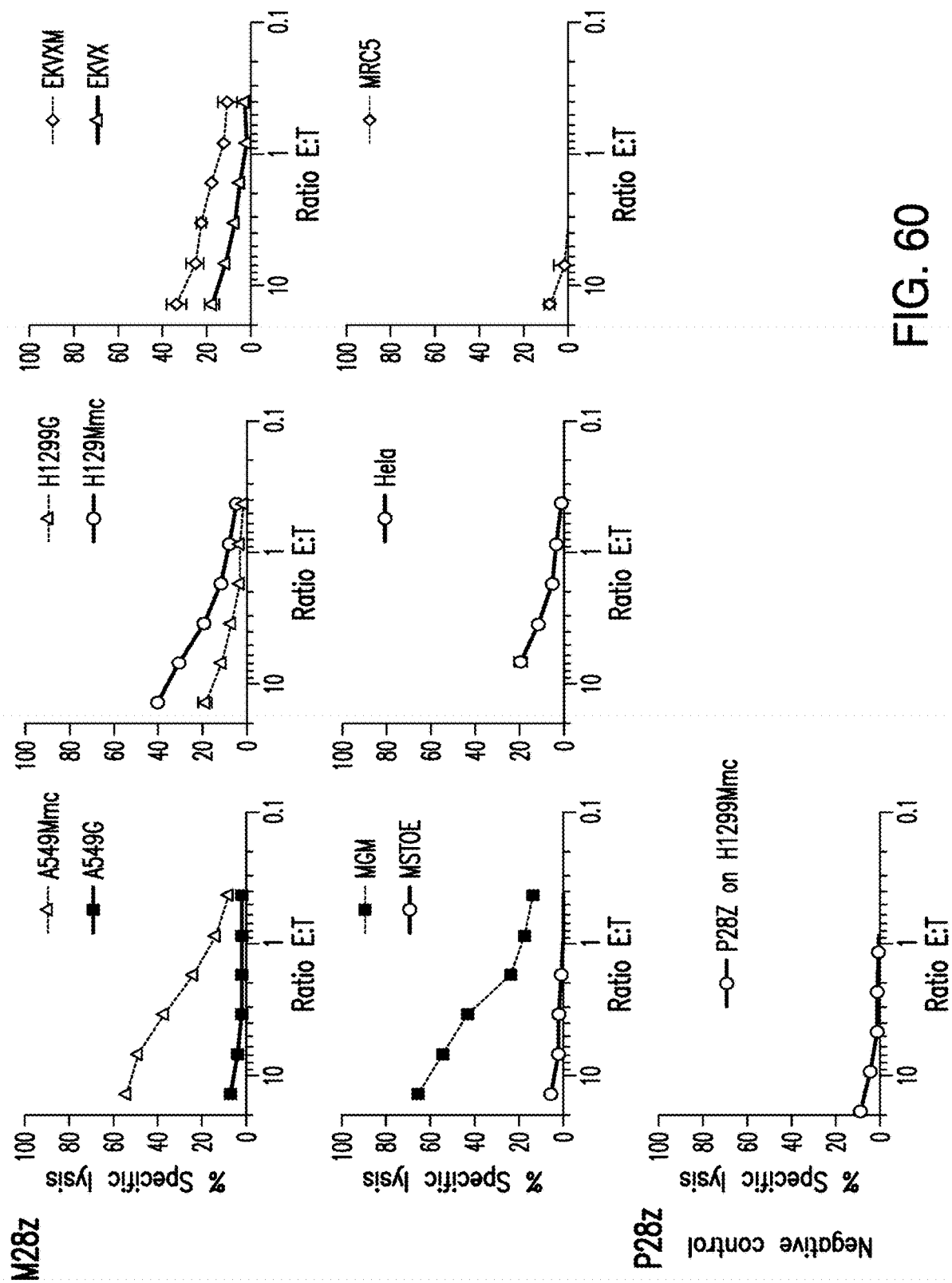

FIG. 60 depicts cytotoxicity of M28z CAR T cells on various cancer and normal cells.

Figure 61:
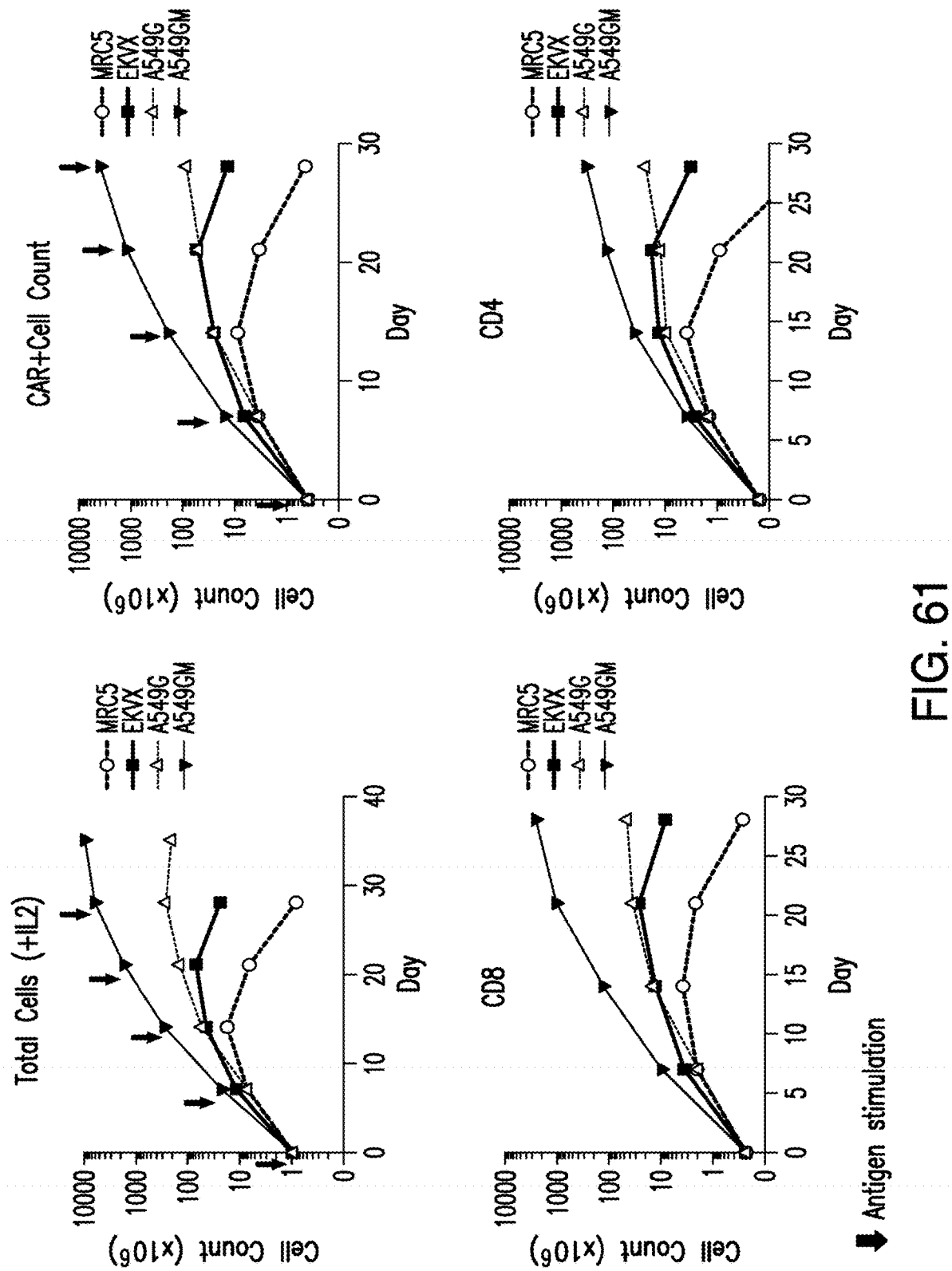

FIG. 61 depicts CAR T-cell accumulation after repeated antigen stimulation in the presence of exogenous IL-2.

Figure 62:
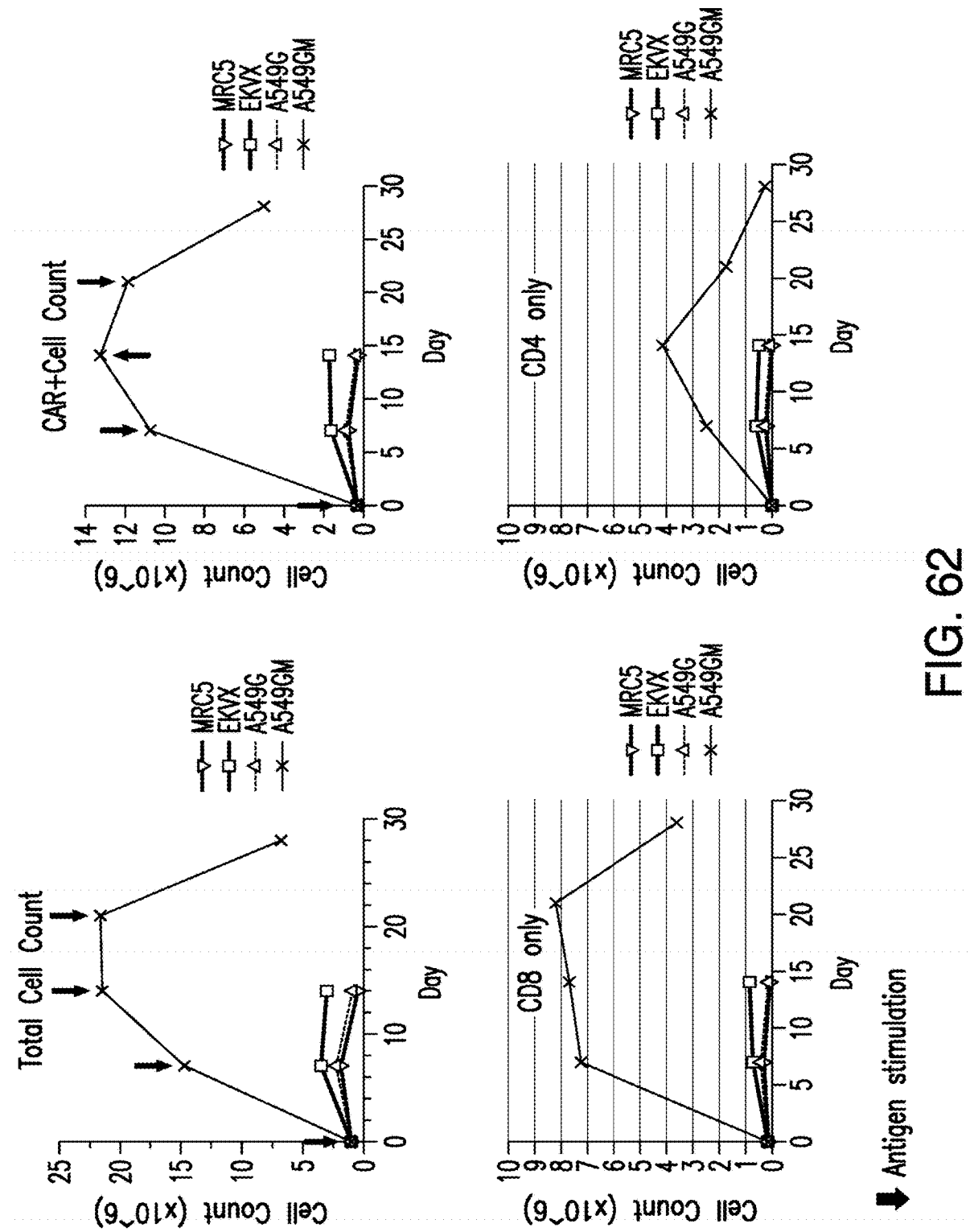

FIG. 62 depicts CAR T-cell accumulation after repeated antigen stimulation in the absence of exogenous IL-2.

Figure 63A:
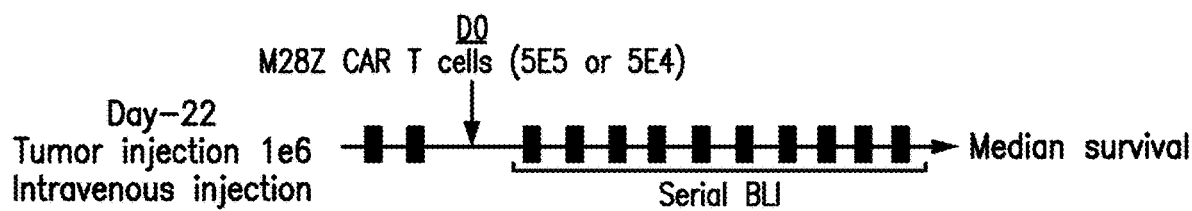
Figure 63B:
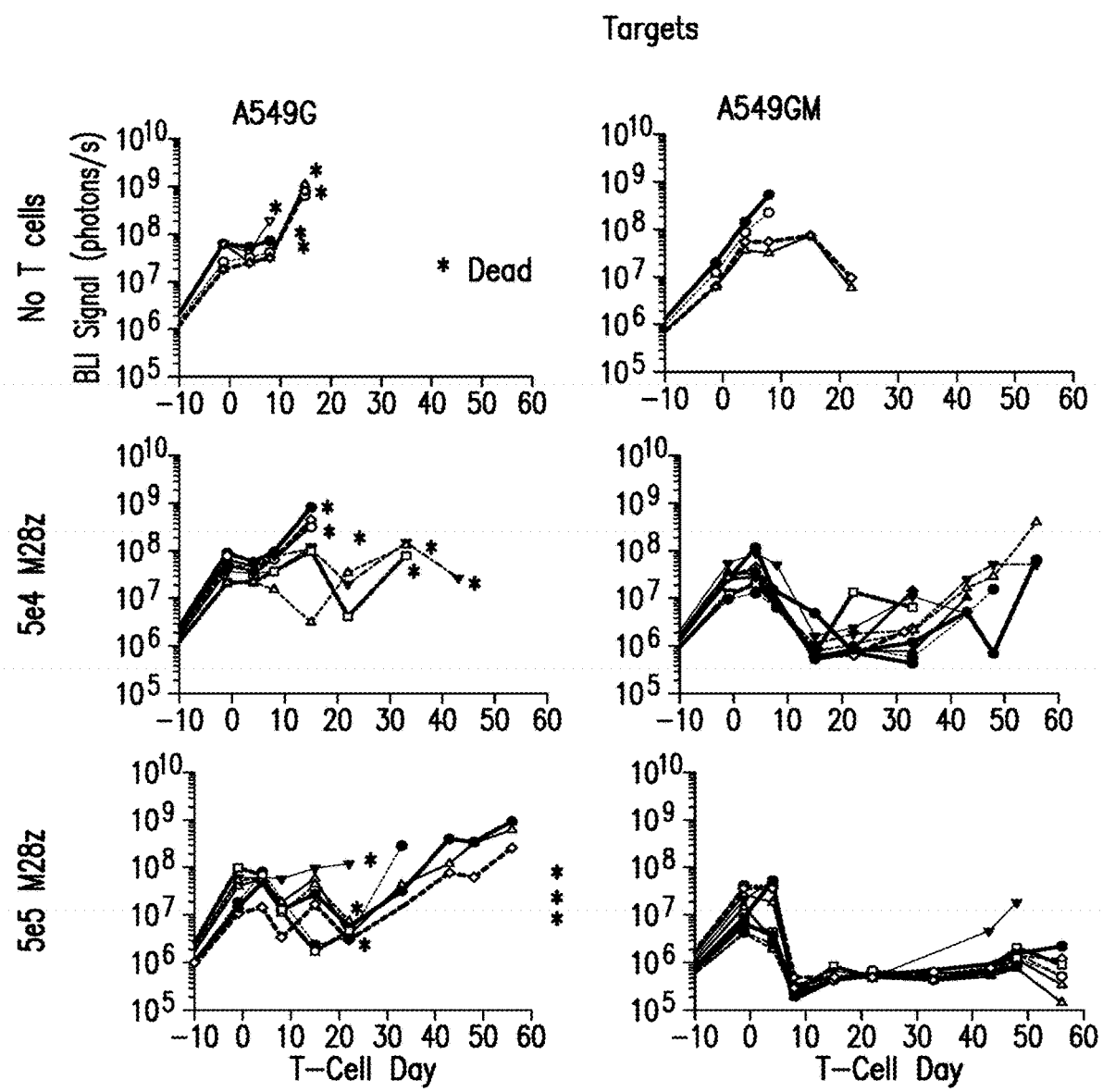

FIGS. 63A-63C depict in vivo efficacy of M28z CAR T cells in lung cancer model. (A) study design. (B) Tumor growth analysis by bioluminescence (BLI). (C) Survival analysis.

FIGS. 64A-64D depict in vivo accumulation of M28z CAR T cells in lung cancer model. (A) study design. (B-D) T-cell accumulation analysis by BLI.

DETAILED DESCRIPTION OF THE INVENTION

The presently disclosed subject matter generally provides mesothelin-targeted chimeric antigen receptors (CARs). In one non-limiting example, the CAR comprises an extracellular antigen-binding domain, a transmembrane domain and an intracellular domain, where the extracellular antigen-binding domain specifically binds to human mesothelin with a binding affinity ($K_d$) of from about 1 nM to about 25 nM. The presently disclosed subject matter also provides immunoresponsive cells (e.g., T cell, a Natural Killer (NK) cell, a cytotoxic T lymphocyte (CTL), a regulatory T cell, a human embryonic stem cell, and a pluripotent stem cell from which lymphoid cells may be differentiated) expressing the mesothelin-targeted CARs, and methods of using such immunoresponsive cells for treating neoplasia and other pathologies. Malignant cells have developed a series of mechanisms to protect themselves from immune recognition and elimination. The present approach provides immunogenicity within the tumor microenvironment for tumor eradication, and represents a significant advance over conventional adoptive T cell therapy.

I. Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 1000 cells expressing similar or different phenotypes.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')$_2$, and Fab. F(ab')$_2$, and Fab fragments that lack the Fc fragment of intact antibody, clear more rapidly from the circulation, and may have less non-specific tissue binding of an intact antibody (Wahl et al., J Nucl. Med. 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. In one non-limiting example, the linker comprises amino acids having the sequence set forth in SEQ ID NO: 17 as provided below.

[SEQ ID NO: 17]
GGGGSGGGGSGGGGS

In one embodiment, the nucleotide sequence encoding the amino acid sequence of SEQ ID NO: 17 is set forth in SEQ ID NO: 18, which is provided below:

[SEQ ID NO: 18]
GGAGGTGGAGGCTCAGGAGGAGGAGGCAGTGGAGGTGGTGGGTCA.

In another embodiment, the nucleotide sequence encoding the amino acid sequence f SEQ ID NO:17 is set forth in SEQ ID NO: 19, which is provided below.

[SEQ ID NO: 19]
GGTGGAGGCGGTTCAGGCGGAGGTGGCTCTGGCGGTGGCGGATCA

Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hyrbidoma (Larchmt) 2008

27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chern 2003 25278(38):36740-7; Xie et al., Nat Biotech 1997 15(8):768-71; Ledbetter et al., Crit Rev Immunol 997 17(5-6):427-55; Ho et al., BioChim Biophys Acta 2003 1638(3):257-66).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')$_2$" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

As used herein, the term "expression vector" refers to a recombinant nucleic acid sequence, i.e. recombinant DNA molecule, containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes. Methods for calculating the affinity of an antibody for an antigen are known in the art, comprising use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay).

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between e-3 and e-100 indicating a closely related sequence.

As used herein, the term "analog" refers to a structurally related polypeptide or nucleic acid molecule having the function of a reference polypeptide or nucleic acid molecule.

As used herein, the term "ligand" refers to a molecule that binds to a receptor. In particular, the ligand binds a receptor on another cell, allowing for cell-to-cell recognition and/or interaction.

As used herein, the term "disease" refers to any condition or disorder that damages or interferes with the normal function of a cell, tissue, or organ. Examples of diseases include neoplasia or pathogen infection of cell.

As used herein, the term "effective amount" refers to an amount sufficient to have a therapeutic effect. In one embodiment, an "effective amount" is an amount sufficient to arrest, ameliorate, or inhibit the continued proliferation, growth, or metastasis (e.g., invasion, or migration) of a neoplasia.

As used herein, the term "endogenous" refers to a nucleic acid molecule or polypeptide that is normally expressed in a cell or tissue.

As used herein, the term "exogenous" refers to a nucleic acid molecule or polypeptide that is not endogenously present in the cell, or not present at a level sufficient to achieve the functional effects obtained when over-expressed. The term "exogenous" would therefore encompass any recombinant nucleic acid molecule or polypeptide expressed in a cell, such as foreign, heterologous, and over-expressed nucleic acid molecules and polypeptides.

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "immunoresponsive cell" refers to a cell that functions in an immune response or a progenitor, or progeny thereof.

As used herein, the term "modulate" refers positively or negatively alter. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "isolated cell" refers to a cell that is separated from the molecular and/or cellular components that naturally accompany the cell.

As used herein, the term "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, the term "pathogen" refers to a virus, bacteria, fungi, parasite or protozoa capable of causing disease.

Exemplary viruses include, but are not limited to, Retroviridae (e.g. human immunodeficiency viruses, such as HIV-1 (also referred to as HDTV-III, LAVE or HTLV-IIILAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Naira viruses); Arenaviridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Exemplary bacteria include, but are not limited to, *Pasteurella, Staphylococci, Streptococcus, Escherichia coli, Pseudomonas species*, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia*, and *Actinomyces israelli*.

As used herein, the term "receptor" refers to meant a polypeptide, or portion thereof, present on a cell membrane that selectively binds one or more ligand.

As used herein, the term "recognize" is meant selectively binds to a target. A T cell that recognizes a virus typically expresses a receptor that binds an antigen expressed by the virus.

As used herein, the term "reference" or "control" is meant a standard of comparison. For example, the level of scFv-antigen binding by a cell expressing a CAR and an scFv may be compared to the level of scFv-antigen binding in a corresponding cell expressing CAR alone.

As used herein, the term "secreted" is meant a polypeptide that is released from a cell via the secretory pathway through the endoplasmic reticulum, Golgi apparatus, and as a vesicle that transiently fuses at the cell plasma membrane, releasing the proteins outside of the cell.

As used herein, the term "specifically binds" or "specifically binds to" or "specifically target" is meant a polypeptide or fragment thereof that recognizes and binds a biological molecule of interest (e.g., a polypeptide), but which does not substantially recognize and bind other molecules in a sample, for example, a biological sample, which naturally includes a polypeptide of the invention.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, non-human primates, rodents, and the like (e.g., which is to be the recipient of a particular treatment, or from whom cells are harvested).

II. Chimeric Antigen Receptor (CAR)

Chimeric antigen receptors (CARs) are engineered receptors, which graft or confer a specificity of interest onto an immune effector cell. CARs can be used to graft the specificity of a monoclonal antibody onto a T cell; with transfer of their coding sequence facilitated by retroviral vectors.

There are three generations of CARs. "First generation" CARs are typically composed of an extracellular antigen binding domain (e.g., a single-chain variable fragments (scFv)) fused to a transmembrane domain, fused to cytoplasmic/intracellular domain of the T cell receptor chain. "First generation" CARs typically have the intracellular domain from the CD3 ξ-chain, which is the primary transmitter of signals from endogenous TCRs. "First generation" CARs can provide de novo antigen recognition and cause activation of both CD4$^+$ and CD8$^+$ T cells through their CD3ζ chain signaling domain in a single fusion molecule, independent of HLA-mediated antigen presentation. "Second generation" CARs add intracellular domains from various co-stimulatory molecules (e.g., CD28, 4-1BB, ICOS, OX40) to the cytoplasmic tail of the CAR to provide additional signals to the T cell. "Second generation" CARs comprise those that provide both co-stimulation (e.g., CD28 or 4-1BB) and activation (CD3ξ). Preclinical studies have indicated that "Second Generation" CARs can improve the anti-tumor activity of T cells. For example, robust efficacy of "Second Generation" CAR modified T cells was demonstrated in clinical trials targeting the CD19 molecule in patients with chronic lymphoblastic leukemia (CLL) and acute lymphoblastic leukemia (ALL). "Third generation" CARs comprise those that provide multiple co-stimulation (e.g., CD28 and 4-1BB) and activation (CD3ζ).

In accordance with the presently disclosed subject matter, the CARs comprise an extracellular antigen-binding domain, a transmembrane domain and an intracellular domain, where the extracellular antigen-binding domain binds to human mesothelin with a dissociation constant ($K_d$) of from about 1 nM to about 25 nM. In a specific non-limiting embodiment, the extracellular antigen-binding domain is a scFv. In a specific non-limiting embodiment, the extracellular antigen-binding domain is a Fab, which is optionally crosslinked. In a specific non-limiting embodiment, the extracellular binding domain is a F(ab)$_2$. In a specific non-limiting embodiment, any of the foregoing molecules may be comprised in a fusion protein with a heterologous sequence to form the extracellular antigen-binding domain.

Mesothelin (MSLN) is an immunogenic cell surface antigen[27,28] that is highly expressed in solid cancers[28-33]. MSLN is involved in cell proliferation[34], adhesion[35,36], invasion[37-39], cell signaling[35], and metastasis[40]. Studies have demonstrated that serum soluble MSLN-related peptide (SMRP) secreted by MSLN-expressing tumors can be measured in both humans[32,33,41-47] and mice, and has been shown to correlate with therapy response and prognosis. In normal tissues, MSLN is expressed only in the pleura, pericardium, and peritoneum, at low levels[28,48]. The anti-MSLN recombinant immunotoxin SS1P has shown in vivo specificity and significant antitumor activity in patients[49,50]. In a pancreatic cancer vaccine trial, patients with survival advantage had consistent CD8$^+$ T cell responses to MSLN associated with vaccine-induced delayed-type hypersensitivity response[51]. Specific T cell epitopes derived from MSLN were shown to activate human T cells to efficiently lyse human tumors expressing MSLN[52]. Thus, there is strong supportive evidence that adoptive immunotherapy targeting MSLN can target MSLN-expressing tumors.

In certain non-limiting embodiments, MSLN is human mesothelin having the sequence with a NCBI Reference No: AAV87530.1 (SEQ ID NO: 43), or fragments thereof.

SEQ ID NO:43 is provided below:

```
                                              [SEQ ID NO: 43]
MALPTARPLL GSCGTPALGS LLFLLFSLGW VQPSRTLAGE

TGQEAAPLDG VLANPPNISSLSPRQLLGFP CAEVSGLSTE

RVRELAVALA QKNVKLSTEQ LRCLAHRLSE

PPEDLDALPLDLLLFLNPDA FSGPQACTHF FSRITKANVD

LLPRGAPERQ RLLPAALACW GVRGSLLSEADVRALGGLAC

DLPGRFVAES AEVLLPRLVS CPGPLDQDQQ EAARAALQGG

GPPYGPPSTWSVSTMDALRG LLPVLGQPII RSIPQGIVAA

WRQRSSRDPS WRQPERTILR PRFRREVEKTACPSGKKARE

IDESLIFYKK WELEACVDAA LLATQMDRVN AIPFTYEQLD

VLKHKLDELYPQGYPESVIQ HLGYLFLKMS PEDIRKWNVT

SLETLKALLE VNKGHEMSPQ VATLIDRFVKGRGQLDKDTL

DTLTAFYPGY LCSLSPEELS SVPPSSIWAV RPQDLDTCDP

RQLDVLYPKARLAFQNMNGS EYFVKIQSFL GGAPTEDLKA

LSQQNVSMDL ATFMKLRTDA VLPLTVAEVQKLLGPHVEGL

KAEERHRPVR DWILRQRQDD LDTLGLGLQG GIPNGYLVLD

LSVQEALSGTPCLLGPGPVL TVLALLLAST LA
```

In certain non-limiting embodiments, the extracellular antigen-binding domain of a CAR has a high binding specificity as well as high binding affinity to human MSLN. For example, in such embodiments, the extracellular antigen-binding domain of the CAR (embodied, for example, in a scFv or an analog thereof) binds to human MSLN with a dissociation constant ($K_d$) of about 25 nM or less. In some embodiments, the $K_d$ is about 24 nM, about 23 nM, about 22 nM, about 21 nM or 25 about 20 nM or less. In other embodiments, the $K_d$ is about 15 nM or less, such as about 14 nM, about 13 nM, about 12 nM or about 11 nM. In other embodiments, the $K_d$ is about 10 nM or less, such as about 9 nM, about 8 nM, about 7 nM or about 6 nM. In other embodiments, the $K_d$ is about 5 nM or less, such as about 4 nM, about 3 nM, about 2.5 nM, about 2 nM or about 1 nM or less. In some embodiments, the $K_d$ is about 1 to about 20 nM, such as about 2.5 to about 15 nM, or about 5 to about 10 nM. In some embodiments, $K_d$ is from about 1 nM to about 25 nM, from about 1 nM to about 20 nM, from about 1 nM to about 15 nM, from about 1 nM to about 10 nM, from about 5 nM to about 10 nM, from about 1 nM to about 5 nM, or from about 1 nM to about 2 nM. In certain embodiments, the extracellular antigen-binding domain comprises a human anti-mesothelin antibody or an antigen-binding portion thereof described in U.S. Pat. No. 8,357,783, which is herein incorporated by reference in its entirety. In some embodiments, the extracellular antigen-binding domain is derived from a heavy chain variable region and a light chain variable region of an antibody that binds to human mesothelin, e.g., antibody m912 as disclosed in Feng (2009), which is herein incorporated by reference in its entirety. Antibody m912 was isolated from a human Fab library by panning against recombinant mesothelin. In other embodiments, extracellular antigen-binding domain is derived from Fab's (e.g., from human or mouse Fab libraries).

Binding of the extracellular antigen-binding domain (embodiment, for example, in a scFv or an analog thereof) of a presently disclosed CAR to human MSLN can be confirmed by, for example, enzyme-linked immunosorbent assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or a scFv) specific for the complex of interest. For example, the scFv can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography. In certain embodiments, the MSLN targeted extracellular antigen-binding domain is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet). In one embodiment, the MSLN-targeted human scFv is labeled with GFP.

In certain non-limiting embodiments, the extracellular antigen-binding domain of a presently disclosed CAR recognizes or binds to human MSLN with a MSLN level of about 1,000 or more MSLN binding sites/cell. In certain embodiments, the extracellular antigen-binding domain of a presently disclosed CAR recognizes or binds to human MSLN with a MSLN level of from about 1,000 to about 50,000 MSLN binding sites/cell. In some embodiments, the extracellular antigen-binding domain of a presently disclosed CAR does not recognize or bind to human MSLN with a MSLN expression level of less than 1,000 MSLN binding sites/cell, e.g., the human MSLN expressed normal tissues, e.g., normal pleura, pericardium, and peritoneum tissues. In certain embodiments, the extracellular antigen-binding domain of a presently disclosed CAR does not recognize or bind to human MSLN with a MSLN expression level of more than 50,000 MSLN binding sites/cell. In one embodiment, a human scFV comprised in a presently disclosed CAR recognizes or binds to human MSLN with a MSLN expression level of from about 1,000 to about 50,000 MSLN binding sites/cell. In one embodiment, a human scFV comprised in a presently disclosed CAR does not recognize or bind to human MSLN with a MSLN expression level of more than 50,000 or less than 1,000 MSLN binding sites/cell.

In certain embodiments, the extracellular antigen-binding domain comprises a heavy chain variable region comprising amino acids having the sequence set forth in SEQ ID NO:1 as provided below.

```
                                               [SEQ ID NO: 1]
QVQLQESGPGLVKPSETLSLTCTVSGGSVSSGSYYWSWIRQPPGKGLE

WIGYIYYSGSTNYNPSLKSRVTISVDTSKNQFSLKLSSVTAADTAVYY

CAREGKNGAFDIWGQGTMVTVSSASTKGPSVFPLAPSSKSTSGGTAAL

GCLVKDYFPEPVTVSWNSGALTSGVHTFPAVLQSSGLYSLSSVVTVPS

SSLGTQTYICNVNHKPSNTKVDKKVEPKSCDKTSGQAG
```

The nucleic acid sequence encoding the amino acid sequence of SEQ ID NO:1 is set forth in SEQ ID NO:2 as provided below.

```
[SEQ ID NO: 2]
caggtgcagctgcaggagtccggcccaggactggtgaagccttcggagaccctgtccctc    60 acctgcactgtctctggtggctccgtcagcagtggtagttactactggagctggatccgg   120 cagccccagggaagggactggagtggattgggtatatctattacagtgggagcaccaac    180 tacaaccctccctcaagagtcgagtcaccatatcagtagacacgtccaagaaccagttc    240 tccctgaagctgagctctgtgaccgctgcggacacggccgtgtattactgtgcgagagag   300 gggaagaatggggcttttgatatctggggccaagggacaatggtcaccgtctcttcagcc   360 tccaccaagggcccatcggtcttccccctggcaccctcctccaagagcacctctggggc    420 acagcggccctgggctgcctggtcaaggactacttccccgaaccggtgacggtgtcgtgg   480 aactcaggcgccctgaccagcggcgtgcacaccttcccggctgtcctacagtcctcagga   540 ctctactccctcagcagcgtggtgaccgtgccctccagcagcttgggcacccagacctac   600 atctgcaacgtgaatcacaagcccagcaacaccaaggtggacaagaaagttgagcccaaa   660 tcttgtgacaaaactagtggccaggccggccac                              693
```

In some embodiments, the extracellular antigen-binding domain comprises a light chain variable region comprising amino acids having the sequence set forth in SEQ ID NO:3 as provided below.

```
[SEQ ID NO: 3]
DIQMTQSPSSLSASVGDRVTITCRASQSISSYLNWYQQKPGKAPKLLI
YAASSLQSGVPSGFSGSGSGTDFTLTISSLQPEDFATYYCQQSYSTPL
TEGGGTKVEIKRTVAAPSVFIFPPSDEQLKSGTASVVCLLNNEYPREA
KVQWKVDNALQSGNSQESVTEQDSKDSTYSLSSTLTLSKADYEKHKVY
ACEVTHQGLSSPVTKSFNRGEC
```

The nucleic acid sequence encoding the amino acid sequence of SEQ ID NO:3 is set forth in SEQ ID NO:4 as provided below.

In some embodiments, the extracellular antigen-binding domain comprises a light chain variable region comprising amino acids having the sequence set forth in SEQ ID NO:5 as provided below.

```
[SEQ ID NO: 5]
RHQMTQSPSSLSASVGDRVTITCRASQSISSYLNWYQQKPGKAPKLLIYA
ASSLQSGVPSGFSGSGSGTDFTLTISSLQPEDFATYYCQQSYSTPLTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC
```

In certain embodiments, the extracellular antigen-binding domain of a presently disclosed CAR comprises a single-chain variable fragment (scFv). In one specific embodiment,

```
[SEQ ID NO: 4]
gacatccagatgacccagtctccatcctccctgtctgcatctgtaggagacagagtcacc   60 atcacttgccgggcaagtcagagcattagcagctatttaaattggtatcagcagaaacca  120 gggaaagcccctaagctcctgatctatgctgcatccagtttgcaaagtggggtcccatca  180 gggttcagtggcagtggatctgggacagatttcactctcaccatcagcagtctgcaacct  240 gaagattttgcaacttactactgtcaacagagttacagtaccccgctcactttcggcgga  300 gggaccaaggtggagatcaaacgaactgtggctgcaccatctgtcttcatcttcccgcca  360 tctgatgagcagttgaaatctggaactgcctctgttgtgtgcctgctgaataacttctat  420 cccagagaggccaaagtacagtggaaggtggataacgcccctccaatcgggtaactcccag  480 gagagtgtcacagagcaggacagcaaggacagcacctactgcctcagcagcaccctgacg  540 ctgagcaaagcagactacgagaaacacaaactctacgcctgcgaagtcacccatcagggc  600 ctgagctcgcccgtcacaaagagcttcaacaggggagagt
``` the extracellular antigen-binding domain of a presently disclosed CAR comprises a human scFV. In one embodiment, the human scFV comprises a heavy chain variable region comprising amino acids 1-119 of SEQ ID NO:1. In another embodiment, the human scFV comprises a heavy chain variable region comprising amino acids having the sequence set forth in SEQ ID NO:6 as provided below.

[SEQ ID NO: 6]
QVQLQESGPGLVKPSETLSLTCTVSGGSVSSGSYYWSWIRQPPGKGLEWI
GYIYYSGSTNYNPSLKSRVTISVDTSKNQFSLKLSSVTAADTAVYYCARE
GKNGAFDIWGQGTMVTVSSS

In one embodiment, the human scFV comprises a light chain variable region comprising amino acids 1-107 of SEQ ID NO:3. In one embodiment, the human scFV comprises a light chain variable region comprising amino acids 1-107 of SEQ ID NO:5.

In certain embodiments, the human scFV comprises amino acids having the sequence set forth in SEQ ID NO:7 as provided below.

[SEQ ID NO: 7]
Q V Q L Q E S G P G L V K P S E T L S L T C T V S G G S V S S G S Y Y W S
W I R Q P P G K G L E W I G Y I Y Y S G S T N Y N P S L K S R V T I S V D
T S K N Q F S L K L S S V T A A D T A V Y Y C A R E G K N G A F D I W G Q
G T M V T V S S S G G G G S G G G G S G G G G S R H Q M T Q S P S S L S A
S V G D R V T I T C R A S Q S I S S Y L N W Y Q Q K P G K A P K L L I Y A
A S S L Q S G V P S R F S G S G S G T D F T L T I S S L Q P E D F A T Y Y
C Q Q S Y S T P L T F G G G T K V E I K G Q A G H H H H H H G D Y K D D D
D K G

In one embodiment, the nucleic acid sequence encoding the amino acid sequence of SEQ ID NO:7 is set forth in SEQ ID NO:8 as provided below.

[SEQ ID NO: 8]
atggccttaccagtgaccgccttgctcctgccgctggccttgctgctcc
acgccgccaggccgcaggtgcagctgcaggagtccggcccaggactggt
gaagccttcggagaccctgtccctcacctgcactgtctctggtggctcc
gtcagcagtggtagttactactggagctggatccggcagcccccaggga
agggactggagtggattgggtatatctattacagtgggagcaccaacta
caaccctccctcaagagtcgagtcaccatatcagtagacacgtccaag
aaccagttctccctgaagctgagctctgtgaccgctgcggacacggccg
tgtattactgtgcgagagaggggaagaatggggcttttgatatctgggg
ccaagggacaatggtcaccgtctcttcaggtggaggcggttcaggcgga
ggtggctctggcggtggcggatcacgacatcagatgacccagtctccat
cctcctgtctgcatctgtaggagacagagtcaccatcacttgccgggc
aagtcagagcattagcagctatttaaattggtatcagcagaaaccaggg
aaagcccctaagctcctgatctatgctgcatccagtttgcaaagtgggg
tcccatcaaggttcagtggcagtggatctgggacagatttcactctcac
catcagcagtctgcaacctgaagattttgcaacttactactgtcaacag agttacagtacccccgctcactttcggcggagggaccaaggtggagatca aacggactgcggccgca In another embodiment, the nucleic acid sequence encoding the amino acid sequence of SEQ ID NO:7 is set forth in SEQ ID NO:9 as provided below. The nucleic acid sequence as set forth in SEQ ID NO:9 is synthetically optimized for codon usage, which can increase the expression of the CAR.

[SEQ ID NO: 9]
ATGGCGCTGCCGGTGACCGCGCTGCTGCTGCCGCTGGCGCTGCTGCTG

CATGCGGCGCGCCCGCAGGTGCAGCTGCAGGAAAGCGGCCCGGGCCTG

GTGAAACCGAGCGAAACCCTGAGCCTGACCTGCACCGTGAGCGGCGGC

AGCGTGAGCAGCGGCAGCTATTATTGGAGCTGGATTCGCCAGCCGCCG

GGCAAAGGCCTGGAATGGATTGGCTATATTTATTATAGCGGCAGCACC

AACTATAACCCGAGCCTGAAAAGCCGCGTGACCATTAGCGTGGATACC

AGCAAAAACCAGTTTAGCCTGAAACTGAGCAGCGTGACCGCGGCGGAT

ACCGCGGTGTATTATTGCGCGCGCGAAGGCAAAAACGGCGCGTTTGAT

ATTTGGGGCCAGGGCACCATGGTGACCGTGAGCAGCGGCGGCGGCGGC

AGCGGCGGCGGCGGCAGCGGCGGCGGCGGCAGCCGCCATCAGATGACC

CAGAGCCCGAGCAGCCTGAGCGCGAGCGTGGGCGATCGCGTGACCATT

ACCTGCCGCGCGAGCCAGAGCATTAGCAGCTATCTGAACTGGTATCAG

CAGAAACCGGGCAAAGCGCCGAAACTGCTGATTTATGCGGCGAGCAGC

CTGCAGAGCGGCGTGCCGAGCCGCTTTAGCGGCAGCGGCAGCGGCACC

GATTTTACCCTGACCATTAGCAGCCTGCAGCCGGAAGATTTTGCGACC

TATTATTGCCAGCAGAGCTATAGCACCCCGCTGACCTTTGGCGGCGGC

ACCAAAGTGGAAATTAAACGCACCGCGGCGGCG

In yet another embodiment, nucleic acid sequence encoding the amino acid sequence of SEQ ID NO:7 is set forth in SEQ ID NO:10 as provided below. The nucleic acid sequence as set forth in SEQ ID NO: 10 is synthetically optimized for codon usage, which can increase the expression of the CAR.

[SEQ ID NO: 10]
```
atggccCTCCCGGTAACGGCTCTGCTGCTTCCACTCGCACTGCTCTTG
CATGCTGCCAGACCACAGGTCCAGCTGCAGGAGAGTGGGCCTGGACTG
GTTAAGCCGAGTGAGACACTTTCCTTGACGTGCACTGTGAGCGGGGA
AGTGTGTCCTCAGGTAGTTATTACTGGTCCTGGATTCGCCAGCCACCA
GGAAAGGGACTGGAGTGGATAGGTTATATCTATTATTCTGGCAGCACT
AATTACAATCCTTCTCTCAAAAGTAGGGTGACAATTTCAGTGGATACT
TCCAAAAATCAGTTTAGTCTGAAGCTCAGCTCTGTGACAGCTGCTGAT
ACTGCAGTTTACTACTGCGCCAGGGAGGGGAAGAATGGCGCCTTCGAT
ATTTGGGGACAGGGCACTATGGTGACTGTATCAAGCGGAGGCGGTGGC
AGCGGCGGGGAGGGAGTGGAGGCGGCGGGTCTCGACATCAGATGACA
CAGAGCCCATCATCACTTAGCGCCAGCGTTGGCGACCGGGTTACGATA
ACATGCAGGGCTTCCCAATCTATCAGTTCTTATCTGAACTGGTATCAG
CAGAAACCAGGTAAGGCCCCCAAGCTGCTCATCTACGCAGCCTCATCC
CTGCAGAGCGGCGTCCCTAGTCGATTTTCCGGTAGTGGGTCAGGGACA
GATTTTACCCTGACTATCAGTTCACTGCAGCCCGAGGACTTCGCGACA
TACTATTGCCAACAGTCCTATAGTACACCCTTGACATTTGGCGGCGGG
ACTAAAGTAGAAATTAAACGCACCgcggccgca
```

In certain embodiments, the extracellular antigen-binding domain comprises a heavy chain variable region CDR1 comprising amino acids having the sequence set forth in SEQ ID NO:11 or conservative modifications thereof, a heavy chain variable region CDR2 comprising amino acids having the sequence set forth in SEQ ID NO: 12 or conservative modifications thereof, and a heavy chain variable region CDR3 comprising amino acids having the sequence set forth in SEQ ID NO: 13 or conservative modifications thereof. In some embodiments, the extracellular antigen-binding domain comprises a light chain variable region CDR1 comprising amino acids having the sequence set forth in SEQ ID NO: 14 or conservative modifications thereof, a light chain variable region CDR2 comprising amino acids having the sequence set forth in SEQ ID NO:15 or conservative modifications thereof, and a light chain variable region CDR3 comprising amino acids having the sequence set forth in SEQ ID NO:16 or conservative modifications thereof. In one non-limiting, exemplary embodiment, the extracellular antigen-binding domain is a human scFv derived from a fully human anti-MSLN antibody m912 as disclosed in Feng et al., *Mol. Cancer Therapy* (2009); 8(5):1113-1118, which is incorporated by referenced herewith.

SEQ ID NOs: 11-16 are provided below:

[SEQ ID NO: 11]
GGSVSSGSYY

[SEQ ID NO: 12]
IYYSGST

[SEQ ID NO: 13]
AREGKNGAFDIW

[SEQ ID NO: 14]
QSISSY

[SEQ ID NO: 15]
AASS

[SEQ ID NO: 16]
QQSYSTPLTF

As used herein, the term "conservative sequence modifications" refers to amino acid modifications that do not significantly affect or alter the binding characteristics of the presently disclosed CAR (e.g., the extracellular antigen-binding domain) comprising the amino acid sequence. Such conservative modifications include amino acid substitutions, additions and deletions. Modifications can be introduced into the human scFv of the presently disclosed subject matter by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (l) above) using the functional assays described herein. In certain embodiments, no more than one, no more than two, no more than three, no more than four, no more than five residues within a specified sequence or a CDR region are altered.

In certain non-limiting embodiments, an extracellular antigen-binding domain of the CAR can comprise a linker connecting the heavy chain variable region and light chain variable region of the extracellular antigen-binding domain. As used herein, the term "linker" refers to a functional group (e.g., chemical or polypeptide) that covalently attaches two or more polypeptides or nucleic acids so that they are connected to one another. As used herein, a "peptide linker" refers to one or more amino acids used to couple two proteins together (e.g., to couple $V_H$ and $V_L$ domains). In one non-limiting example, the linker comprises amino acids having the sequence set forth in SEQ ID NO:17 as provided below.

[SEQ ID NO: 17]
GGGGSGGGGSGGGGS

In one embodiment, the nucleotide sequence encoding the amino acid sequence of SEQ ID NO: 17 is set forth in SEQ ID NO: 18, which is provided below:

[SEQ ID NO: 18]
GGAGGTGGAGGCTCAGGAGGAGGAGGCAGTGGAGGTGGTGGGTCA

In another embodiment, the nucleotide sequence encoding the amino acid sequence f SEQ ID NO:17 is set forth in SEQ ID NO: 19, which is provided below.

[SEQ ID NO: 19]
GGTGGAGGCGGTTCAGGCGGAGGTGGCTCTGGCGGTGGCGGATCA

In addition, the extracellular antigen-binding domain can comprise a leader or a signal peptide that directs the nascent protein into the endoplasmic reticulum. Signal peptide or leader can be essential if the CAR is to be glycosylated and anchored in the cell membrane. The signal sequence or leader can be a peptide sequence (about 5, about 10, about 15, about 20, about 25, or about 30 amino acids long) present at the N-terminus of newly synthesized proteins that directs their entry to the secretory pathway. In non-limiting examples, the leader is covalently joined to the 5' terminus of the extracellular antigen-binding domain. In one embodiment, the leader comprises a CD8 polypeptide comprising amino acids having the sequence set forth in SEQ ID NO:20 as provided below.

[SEQ ID NO: 20]
MALPVTALLLPLALLLHAARP

The nucleotide sequence encoding the amino acid sequence of SEQ ID NO:20 is set forth in SEQ ID NO:21, which is provided below:

[SEQ ID NO: 21]
ATGGCCCTGCCAGTAACGGCTCTGCTGCTGCCACTTGCTCTGCTCCTC

CATGCAGCCAGGCC

In certain non-limiting embodiments, the transmembrane domain of the CAR comprises a hydrophobic alpha helix that spans at least a portion of the membrane. Different transmembrane domains result in different receptor stability. After antigen recognition, receptors cluster and a signal is transmitted to the cell. In accordance with the presently disclosed subject matter, the transmembrane domain of the CAR can comprise a CD8 polypeptide, a CD28 polypeptide, a CD3 ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, a synthetic peptide (not based on a protein associated with the immune response), or a combination thereof.

In one embodiment, the transmembrane domain comprises a CD8 polypeptide. The CD8 polypeptide can have an amino acid sequence that is at least about 85%, about 90%, about 95%, about 96%, about 97%, about 98%, about 99% or about 100% homologous to the sequence having a NCBI Reference No: NP_001139345.1 (SEQ ID NO:22) (homology herein may be determined using standard software such as BLAST or FASTA) as provided below, or fragments thereof, and/or may optionally comprise up to one or up to two or up to three conservative amino acid substitutions. In non-limiting embodiments, the CD8 polypeptide can have an amino acid sequence that is a consecutive portion of SEQ ID NO:22 which is at least 20, or at least 30, or at least 40, or at least 50, and up to 235 amino acids in length. Alternatively or additionally, in non-limiting various embodiments, the CD8 polypeptide has an amino acid sequence of amino acids 1 to 235, 1 to 50, 50 to 100, 100 to 150, 150 to 200, or 200 to 235 of SEQ ID NO:22. In one embodiment, the CAR of the presently disclosed subject matter is Mz, whose transmembrane domain comprises a CD8 polypeptide. In another embodiment, the CAR of the presently disclosed subject matter is MBBz, whose transmembrane domain comprises a CD8 polypeptide. In one non-limiting embodiment, a presently disclosed CAR comprises a transmembrane domain that comprises a CD8 polypeptide having amino acids 137 to 209 of SEQ ID NO: 22.

[SEQ ID NO: 22]
MALPVTALLLPLALLLHAARPSQFRVSPLDRTWNLGETVELKCQVLLS

NPTSGCSWLFQPRGAAASPTFLLYLSQNKPKAAEGLDTQRFSGKRLGD

TFVLTLSDFRRENEGYYFCSALSNSIMYFSHFVPVFLPAKPTTTPAPR

PPTPAPTIASQPLSLRPEACRPAAGGAVHTRGLDFACDIYIWAPLAGT

CGVLLLSLVITLYCNHRNRRRVCKCPRPVVKSGDKPSLSARYV

In accordance with the presently disclosed subject matter, a "CD8 nucleic acid molecule" refers to a polynucleotide encoding a CD8 polypeptide.

In one embodiment, the transmembrane domain of the presently disclosed CAR comprises a CD28 polypeptide. The CD28 polypeptide can have an amino acid sequence that is at least about 85%, about 90%, about 95%, about 96%, about 97%, about 98%, about 99% or 100% homologous to the sequence having a NCBI Reference No: P10747 or NP_006130 (SEQ ID No:23), or fragments thereof, and/or may optionally comprise up to one or up to two or up to three conservative amino acid substitutions. In non-limiting embodiments, the CD28 polypeptide can have an amino acid sequence that is a consecutive portion of SEQ ID NO:23 which is at least 20, or at least 30, or at least 40, or at least 50, and up to 220 amino acids in length. Alternatively or additionally, in non-limiting various embodiments, the CD28 polypeptide has an amino acid sequence of amino acids 1 to 220, 1 to 50, 50 to 100, 100 to 150, 150 to 200, or 200 to 220 of SEQ ID NO:23. In one embodiment, the CAR of the presently disclosed subject matter is M28z, which comprises a transmembrane domain comprising a CD28 polypeptide, and an intracellular domain comprising a co-stimulatory signaling region that comprises a CD28 polypeptide. In one embodiment, the CD28 polypeptide comprised in the transmembrane domain and the intracellular domain of M28z has an amino acid sequence of amino acids 117 to 220 of SEQ ID NO:23.

SEQ ID NO:23 is provided below:

[SEQ ID NO: 23]
1   MLRLLLALNL FPSIQVTGNK ILVKQSPMLV AYDNAVNLSC KYSYNLFSRE FRASLHKGLD

61  SAVEVCVVYG NYSQQLQVYS KTGFNCDGKL GNESVTFYLQ NLYVNQTDIY FCKIEVMYPP

121 PYLDNEKSNG TIIHVKGKHL CPSPLFPGPS KPFWVLVVVG GVLACYSLLV TVAFIIFWVR

181 SKRSRLLHSD YMNMTPRRPG PTRKHYQPYA PPRDFAAYRS

In accordance with the presently disclosed subject matter, a "CD28 nucleic acid molecule" refers to a polynucleotide encoding a CD28 polypeptide. In one embodiment, the CD28 nucleic acid molecule encoding the CD28 polypeptide comprised in the transmembrane domain and the intracellular domain (e.g., the co-stimulatory signaling region) of M28z comprises a nucleotide sequence as set forth in SEQ ID NO:24 as provided below.

[SEQ ID NO: 24]
```
ATTGAAGTTATGTATCCTCCTCCTTACCTAGACAATGAGAAGAGCAAT

GGAACCATTATCCATGTGAAAGGGAAACACCTTTGTCCAAGTCCCCTA

TTTCCCGGACCTTCTAAGCCCTTTTGGGTGCTGGTGGTGGTTGGTGGA

GTCCTGGCTTGCTATAGCTTGCTAGTAACAGTGGCCTTTATTATTTTC

TGGGTGAGGAGTAAGAGGAGCAGGCTCCTGCACAGTGACTACATGAAC

ATGACTCCCCGCCGCCCCGGGCCCACCCGCAAGCATTACCAGCCCTAT

GCCCCACCACGCGACTTCGCAGCCTATCGCTCC
```

In certain non-limiting embodiments, a CAR can also comprise a spacer region that links the antigen binding domain to the transmembrane domain. The spacer region can be flexible enough to allow the antigen binding domain to orient in different directions to facilitate antigen recognition. The spacer region can be the hinge region from IgG1, or the CH$_2$CH$_3$ region of immunoglobulin and portions of CD3.

In certain non-limiting embodiments, an intracellular domain of the CAR can comprise a CD3 ζ polypeptide, which can activate or stimulate a cell (e.g., a cell of the lymphoid lineage, e.g., a T cell). CD3 ζ comprises 3 ITAMs, and transmits an activation signal to the cell (e.g., a cell of the lymphoid lineage, e.g., a T cell) after antigen is bound. The CD3ζ polypeptide can have an amino acid sequence that is at least about 85%, about 90%, about 95%, about 96%, about 97%, about 98%, about 99% or about 100% homologous to the sequence having a NCBI Reference No: NP_932170 (SEQ ID No: 25), or fragments thereof, and/or may optionally comprise up to one or up to two or up to three conservative amino acid substitutions. In non-limiting embodiments, the CD3ζ polypeptide can have an amino acid sequence that is a consecutive portion of SEQ ID NO: 25 which is at least 20, or at least 30, or at least 40, or at least 50, and up to 164 amino acids in length. Alternatively or additionally, in non-limiting various embodiments, the CD3ζ polypeptide has an amino acid sequence of amino acids 1 to 164, 1 to 50, 50 to 100, 100 to 150, or 150 to 164 of SEQ ID NO:25. In one embodiment, the CD3ζ polypeptide has an amino acid sequence of amino acids 52 to 164 of SEQ ID NO: 25. In one embodiment, the CAR of the presently disclosed subject matter is Mz, whose intracellular domain comprises a CD3ζ polypeptide having an amino acid sequence of amino acids 52 to 164 of SEQ ID NO:25. In one embodiment, the CAR of the presently disclosed subject matter is M28z, whose intracellular domain comprises a CD3 ζ polypeptide having an amino acid sequence of amino acids 52 to 164 of SEQ ID NO:25. In one embodiment, the CAR of the presently disclosed subject matter is MBBz, whose intracellular domain comprises a CD3 ζ polypeptide having an amino acid sequence of amino acids 52 to 164 of SEQ ID NO: 25.

SEQ ID NO: 25 is provided below:

[SEQ ID NO: 25]
```
  1 MKWKALFTAA ILQAQLPITE AQSFGLLDPK LCYLLDGILF IYGVILTALF LRVKFSRSAD

61 APAYQQGQNQ LYNELNLGRR EEYDVLDKRR GRDPEMGGKP QRRKNPQEGL YNELQKDKMA

121 EAYSEIGMKG ERRRGKGHDG LYQGLSTATK DTYDALHMQA LPPR
```

In accordance with the presently disclosed subject matter, a "CD3 ζ nucleic acid molecule" refers to a polynucleotide encoding a CD3ζ polypeptide. In one embodiment, the CD3ζ nucleic acid molecule encoding the CD3ζ polypeptide comprised in the intracellular domain of the presently disclosed CARs (e.g., Mz, M28z, or MBBz) comprises a nucleotide sequence as set forth in SEQ ID NO: 26 as provided below.

[SEQ ID NO: 26]
```
AGAGTGAAGTTCAGCAGGAGCGCAGACGCCCCCGCGTACCAGCAGGGC

CAGAACCAGCTCTATAACGAGCTCAATCTAGGACGAAGAGAGGAGTAC

GATGTTTTGGACAAGAGACGTGGCCGGGACCCTGAGATGGGGGGAAAG

CCGAGAAGGAAGAACCCTCAGGAAGGCCTGTACAATGAACTGCAGAAA

GATAAGATGGCGGAGGCCTACAGTGAGATTGGGATGAAAGGCGAGCGC

CGGAGGGGCAAGGGGCACGATGGCCTTTACCAGGGTCTCAGTACAGCC

ACCAAGGACACCTACGACGCCCTTCACATGCAGGCCCTGCCCCCTCGC

TAA
```

In certain non-limiting embodiments, an intracellular domain of the CAR further comprises at least one co-stimulatory signaling region comprising at least one co-stimulatory molecule, which can provide optimal lymphocyte activation. As used herein, "co-stimulatory molecules" refer to cell surface molecules other than antigen receptors or their ligands that are required for an efficient response of lymphocytes to antigen. The at least one co-stimulatory signaling region can include a CD28 polypeptide, a 4-1BB polypeptide, an OX40 polypeptide, an ICOS polypeptide, a PD-1 polypeptide, a CTLA-4 polypeptide, a LAG-3 polypeptide, a 2B4 polypeptide, a BTLA polypeptide, a synthetic peptide (not based on a protein associated with the immune response), or a combination thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen binds to its CAR molecule. Co-stimulatory ligands, include, but are not limited to CD80, CD86, CD70, OX40L, 4-1BBL, CD48, TNFRSF14, and PD-L1. As one example, a 4-1BB ligand (i.e., 4-1BBL) may bind to 4-1BB (also known as "CD137") for providing an intracellular signal that in combination with a CAR signal induces an effector cell function of the CAR$^+$ T cell. CARs comprising an intracellular domain that comprises a co-stimulatory signaling region comprising 4-1BB, ICOS or DAP-10 are disclosed in U.S. Pat. No. 7,446,190 (e.g., the nucleotide sequence encoding 4-1BB is set forth in SEQ ID No: 15, the nucleotide sequence encoding ICOS is set forth in SEQ ID No: 16, and the nucleotide sequence encoding DAP-10 is set forth in SEQ ID No: 17 in U.S. Pat. No. 7,446,190), which is herein incorporated by reference in its entirety. In some embodiments, the intracellular domain of the CAR comprises a co-stimulatory signaling region that comprises two co-stimulatory molecules: CD28 and 4-1BB (see Sadelain, et al., Cancer Discovery, OF1-11, (2013)), or CD28 and OX40.

4-1BB can act as a tumor necrosis factor (TNF) ligand and have stimulatory activity. The 4-1BB polypeptide can have an amino acid sequence that is at least about 85%, about 90%, about 95%, about 96%, about 97%, about 98%, about 99% or 100% homologous to the sequence having a NCBI Reference No: P41273 or NP_001552 (SEQ ID NO:27) or fragments thereof, and/or may optionally comprise up to one or up to two or up to three conservative amino acid substitutions. In non-limiting embodiments, the 4-1BB polypeptide can have an amino acid sequence that is a consecutive portion of SEQ ID NO: 27 which is at least 20, or at least 30, or at least 40, or at least 50, and up to 255 amino acids in length. Alternatively or additionally, in non-limiting various embodiments, the 4-1BB polypeptide has an amino acid sequence of amino acids 1 to 255, 1 to 50, 50 to 100, 100 to 150, 150 to 200, or 200 to 255 of SEQ ID NO: 27. In one embodiment, the CAR of the presently disclosed subject matter is MBBz, whose intracellular domain comprises a 4-1BB polypeptide.

SEQ ID NO: 27 is provided below:

```
                                                                    [SEQ ID NO: 27]
  1 MGNSCYNIVA TLLLVLNFER TRSLQDPCSN CPAGTFCDNN RNQICSPCPP NSFSSAGGQR

61 TCDICRQCKG VFRTRKECSS TSNAECDCTP GFHCLGAGCS MCEQDCKQGQ ELTKKGCKDC

121 CFGTFNDQKR GICRPWTNCS LDGKSVLVNG TKERDVVCGP SPADLSPGAS SVTPPAPARE

181 PGHSPQIISF FLALTSTALL FLLFFLTLRF SVVKRGRKKL LYIFKQPFMR PVQTTQEEDG

241 CSCRFPEEEE GGCEL
```

In accordance with the presently disclosed subject matter, a "4-1BB nucleic acid molecule" refers to a polynucleotide encoding a 4-1BB polypeptide.

An OX40 polypeptide can have an amino acid sequence that is at least about 85%, about 90%, about 95%, about 96%, about 97%, about 98%, about 99% or 100% homologous to the sequence having a NCBI Reference No: P43489 or NP_003318 (SEQ ID No: 28), or fragments thereof, and/or may optionally comprise up to one or up to two or up to three conservative amino acid substitutions.

SEQ ID NO: 28 is provided below:

```
                                                                    [SEQ ID NO: 28]
  1 MCVGARRLGR GPCAALLLLG LGLSTVTGLH CVGDTYPSND RCCHECRPGN GMVSRCSRSQ

61 NTVCRPCGPG FYNDVVSSKP CKPCTWCNLR SGSERKQLCT ATQDTVCRCR AGTQPLDSYK

121 PGVDCAPCPP GHFSPGDNQA CKPWTNCTLA GKHTLQPASN SSDAICEDRD PPATQPQETQ

181 GPPARPITVQ PTEAWPRTSQ GPSTRPVEVP GGRAVAAILG LGLVLGLLGP LAILLALYLL

241 RRDQRLPPDA HKPPGGGSFR TPIQEEQADA HSTLAKI
```

In accordance with the presently disclosed subject matter, an "OX40 nucleic acid molecule" refers to a polynucleotide encoding an OX40 polypeptide.

An ICOS polypeptide can have an amino acid sequence that is at least about 85%, about 90%, about 95%, about 96%, about 97%, about 98%, about 99% or 100% homologous to the sequence having a NCBI Reference No: NP_036224 (SEQ ID NO: 29) or fragments thereof, and/or may optionally comprise up to one or up to two or up to three conservative amino acid substitutions.

SEQ ID NO: 29 is provided below:

```
                                                                    [SEQ ID NO: 29]
  1 MKSGLWYFFL FCLRIKVLTG EINGSANYEM FIFHNGGVQI LCKYPDIVQQ FKMQLLKGGQ

61 ILCDLIKTKG SGNTVSIKSL KFCHSQLSNN SVSFFLYNLD HSHANYYFCN LSIFDPPPFK

121 VTLTGGYLHI YESQLCCQLK FWLPIGCAAF VVVCILGCIL ICWLTKKKYS SSVHDPNGEY

181 MFMRAVNTAK KSRLTDVTL
```

In accordance with the presently disclosed subject matter, an "ICOS nucleic acid molecule" refers to a polynucleotide encoding an ICOS polypeptide.

CTLA-4 is an inhibitory receptor expressed by activated T cells, which when engaged by its corresponding ligands (CD80 and CD86; B7-1 and B7-2, respectively), mediates activated T cell inhibition or anergy. In both preclinical and clinical studies, CTLA-4 blockade by systemic antibody infusion, enhanced the endogenous anti-tumor response albeit, in the clinical setting, with significant unforeseen toxicities.

CTLA-4 contains an extracellular V domain, a transmembrane domain, and a cytoplasmic tail. Alternate splice variants, encoding different isoforms, have been characterized. The membrane-bound isoform functions as a homodimer interconnected by a disulfide bond, while the soluble isoform functions as a monomer. The intracellular domain is similar to that of CD28, in that it has no intrinsic catalytic activity and contains one YVKM motif able to bind PI3K, PP2A and SHP-2 and one proline-rich motif able to bind SH3 containing proteins. One role of CTLA-4 in inhibiting T cell responses seem to be directly via SHP-2 and PP2A dephosphorylation of TCR-proximal signaling proteins such as CD3 and LAT. CTLA-4 can also affect signaling indirectly via competing with CD28 for CD80/86 binding. CTLA-4 has also been shown to bind and/or interact with PI3K, CD80, AP2M1, and PPP2R5A.

In accordance with the presently disclosed subject matter, a CTLA-4 polypeptide can have an amino acid sequence that is at least about 85%, about 90%, about 95%, about 96%, about 97%, about 98%, about 99% or about 100% homologous to SEQ ID NO: 30 (homology herein may be determined using standard software such as BLAST or FASTA) or fragments thereof, and/or may optionally comprise up to one or up to two or up to three conservative amino acid substitutions. In non-limiting embodiments, a CTLA-4 polypeptide can have an amino acid sequence that is a consecutive portion of SEQ ID NO: 30 which is at least 20, or at least 30, or at least 40, or at least 50, and up to 223 amino acids in length. Alternatively or additionally, in non-limiting various embodiments, the CTLA-4 polypeptide has an amino acid sequence of amino acids 1 to 223, 1 to 50, 50 to 100, 100 to 140, 141 to 161, 162 to 182, 183 to 223, 141 to 223, 162 to 223, or 183 to 223 of SEQ ID NO: 30. In one embodiment, the CTLA-4 polypeptide has an amino acid sequence of amino acids 183 to 223 of SEQ ID NO: 30. In certain embodiments, the intracellular domain of the CAR comprises a co-stimulatory signaling region comprising a CTLA-4 polypeptide having an amino acid sequence of amino acids 183 to 223 of SEQ ID NO: 30. In certain embodiments, the transmembrane domain of the CAR comprises a CTLA-4 polypeptide having an amino acid sequence of amino acids 162 to 182 of SEQ ID NO: 30.

SEQ ID NO: 30 is provided below:

```
  1 MACLGFQRHK AQLNLATRTW PCTLLFFLLF IPVFCKAMHV AQPAVVLASS RGIASFVCEY

61 ASPGKATEVR VTVLRQADSQ VTEVCAATYM MGNELTFLDD SICTGTSSGN QVNLTIQGLR

121 AMDTGLYICK VELMYPPPYY LGIGNGTQIY VIDPEPCPDS DFLLWILAAV SSGLFFYSFL

181 LTAVSLSKML KKRSPLTTGV YVKMPPTEPE CEKQFQPYFI PIN
```

In accordance with the presently disclosed subject matter, a "CTLA-4 nucleic acid molecule" refers to a polynucleotide encoding a CTLA-4 polypeptide.

PD-1 is a negative immune regulator of activated T cells upon engagement with its corresponding ligands PD-L1 and PD-L2 expressed on endogenous macrophages and dendritic cells. PD-1 is a type I membrane protein of 268 amino acids. PD-1 has two ligands, PD-L1 and PD-L2, which are members of the B7 family. The protein's structure comprises an extracellular IgV domain followed by a transmembrane region and an intracellular tail. The intracellular tail contains two phosphorylation sites located in an immunoreceptor tyrosine-based inhibitory motif and an immunoreceptor tyrosine-based switch motif, that PD-1 negatively regulates TCR signals. SHP-I and SHP-2 phosphatases bind to the cytoplasmic tail of PD-1 upon ligand binding. Upregulation of PD-L1 is one mechanism tumor cells may evade the host immune system. In pre-clinical and clinical trials, PD-1 blockade by antagonistic antibodies induced anti-tumor responses mediated through the host endogenous immune system.

In accordance with the presently disclosed subject matter, a PD-1 polypeptide can have an amino acid sequence that is at least about 85%, about 90%, about 95%, about 96%, about 97%, about 98%, about 99% or about 100% homologous to SEQ ID NO: 31 or fragments thereof, and/or may optionally comprise up to one or up to two or up to three conservative amino acid substitutions. In non-limiting embodiments, a PD-1 polypeptide can have an amino acid sequence that is a consecutive portion of SEQ ID NO: 31 which is at least 20, or at least 30, or at least 40, or at least 50, and up to 288 amino acids in length. Alternatively or additionally, in non-limiting various embodiments, a PD-1 polypeptide has an amino acid sequence of amino acids 1 to 288, 1 to 50, 50 to 100, 100 to 144, 145 to 170, 171 to 191, 192 to 288, 145 to 288, 171 to 288, or 192 to 288 of SEQ ID NO:31. In one embodiment, the PD-1 polypeptide has an amino acid sequence of amino acids 192 to 288 of SEQ ID NO: 31. In certain embodiments, the intracellular domain of the CAR comprises a co-stimulatory signaling region comprising a PD-1 polypeptide having an amino acid sequence of amino acids 192 to 288 of SEQ ID NO: 31. In certain embodiments, the transmembrane domain of the CAR comprises a PD-1 polypeptide having an amino acid sequence of amino acids 171 to 191 of SEQ ID NO: 31.

SEQ ID NO: 31 is provided below:

```
  1 mqipqapwpv vwavlqlgwr pgwfldspdr pwnpptfspa llvvtegdna tftcsfsnts 61 esfvlnwyrm spsnqtdkla afpedrsqpg qdcrfrvtql pngrdfhmsv vrarrndsgt 121 ylcgaislap kaqikeslra elrvterrae vptahpspsp rpagqfqtlv vgvvggllgs 181 lvllvwvlav icsraargti garrtgqplk edpsavpvfs vdygeldfqw rektpeppvp 241 cvpeqteyat lvfpsgmgts sparrgsadg prsaqplrpe dghcswpl
```

In accordance with the presently disclosed subject matter, a "PD-1 nucleic acid molecule" refers to a polynucleotide encoding a PD-1 polypeptide.

Lymphocyte-activation protein 3 (LAG-3) is a negative immune regulator of immune cells. LAG-3 belongs to the immunoglobulin (lg) superfamily and contains 4 extracellular Ig-like domains. The LAG3 gene contains 8 exons. The sequence data, exon/intron organization, and chromosomal localization all indicate a close relationship of LAG3 to CD4. LAG3 has also been designated CD223 (cluster of differentiation 223).

In accordance with the presently disclosed subject matter, a LAG-3 polypeptide can have an amino acid sequence that is at least about 85%, about 90%, about 95%, about 96%, about 97%, about 98%, about 99% or about 100% homologous to SEQ ID NO: 32 or fragments thereof, and/or may optionally comprise up to one or up to two or up to three conservative amino acid substitutions. In non-limiting embodiments, a LAG-3 polypeptide can have an amino acid sequence that is a consecutive portion of SEQ ID NO: 32 which is at least 20, or at least 30, or at least 40, or at least 50, and up to 525 amino acids in length. Alternatively or additionally, in non-limiting various embodiments, a LAG-3 polypeptide has an amino acid sequence of amino acids 1 to 525, 1 to 50, 50 to 100, 100 to 150, 150 to 200, 200 to 250, 250 to 300, 300 to 350, 350 to 400, 400 to 420, 421 to 450, 451 to 471, 472 to 525, 421 to 525, 451 to 525, or 472 to 525 of SEQ ID NO: 32. In one embodiment, the LAG-3 polypeptide has an amino acid sequence of amino acids 472 to 525 of SEQ ID NO: 32. In certain embodiments, the intracellular domain of the CAR comprises a co-stimulatory region comprising a LAG-3 polypeptide having an amino acid sequence of amino acids 472 to 525 of SEQ ID NO: 32. In certain embodiments, the transmembrane domain of the CAR comprises a LAG-3 polypeptide having an amino acid sequence of amino acids 451 to 471 of SEQ ID NO: 32.

SEQ ID NO: 32 is provided below:

In accordance with the presently disclosed subject matter, a "LAG-3 nucleic acid molecule" refers to a polynucleotide encoding a LAG-3 polypeptide.

Natural Killer Cell Receptor 2B4 (2B4) mediates non-MHC restricted cell killing on NK cells and subsets of T cells. To date, the function of 2B4 is still under investigation, with the 2B4-S isoform believed to be an activating receptor, and the 2B4-L isoform believed to be a negative immune regulator of immune cells. 2B4 becomes engaged upon binding its high-affinity ligand, CD48. 2B4 contains a tyrosine-based switch motif, a molecular switch that allows the protein to associate with various phosphatases. 2B4 has also been designated CD244 (cluster of differentiation 244).

In accordance with the presently disclosed subject matter, a 2B4 polypeptide can have an amino acid sequence that is at least about 85%, about 90%, about 95%, about 96%, about 97%, about 98%, about 99% or about 100% homologous to SEQ ID NO: 33 or fragments thereof, and/or may optionally comprise up to one or up to two or up to three conservative amino acid substitutions. In non-limiting embodiments, a 2B4 polypeptide can have an amino acid sequence that is a consecutive portion of SEQ ID NO: 33 which is at least 20, or at least 30, or at least 40, or at least 50, and up to 370 amino acids in length. Alternatively or additionally, in non-limiting various embodiments, a 2B4 polypeptide has an amino acid sequence of amino acids 1 to 370, 1 to 50, 50 to 100, 100 to 150, 150 to 215, 216 to 229, 230 to 250, 251 to 370, 216 to 370, 230 to 370, or 251 to 370 of SEQ ID NO: 33. In one embodiment, the 2B4 polypeptide has an amino acid sequence of amino acids 251 to 370 of SEQ ID NO: 33. In certain embodiments, the intracellular domain of the CAR comprises a co-stimulatory signaling region comprising a 2B4 polypeptide having an amino acid sequence of amino acids 251 to 370 of SEQ ID NO: 33. In certain embodiments, the transmembrane domain of the CAR comprises a 2B4 polypeptide having an amino acid sequence of amino acids 230 to 250 of SEQ ID NO: 33.

```
  1 mweaqflgll flqplwvapv kplqpgaevp vvwaqegapa qlpcsptipl qdlsllrrag 61 vtwqhqpdsg ppaaapghpl apgphpaaps swgprprryt vlsvgpgglr sgrlplqpry 121 qldergrqrg dfslwlrpar radageyraa vhlrdralse rlrlrlgqas mtasppgslr 181 asdwvilncs fsrpdrpasv hwfrnrgqgr vpvresphhh laesflflpq vspmdsgpwg 241 ciltyrdgfn vsimynltvl glepptpltv yagagsrvgl perlpagvgt rsfltakwtp 301 pgggpdllvt gdngdftlrl edvsqaqagt ytchihlqeq qlnatvtlai itvtpksfgs 361 pgslgkllce vtpvsgqerf vwssldtpsq rsfsgpwlea qeaqllsqpw qcqlyqgerl 421 lgaavyftel sspgaqrsgr apgalpaghl llflilgvls llllvtgafg fhlwrrqwrp 481 rrfsaleqgi hppqaqskie eleqepepep epepepepep epeql
```

SEQ ID NO: 33 is provided below:

```
  1 mlgqvvtlil llllkvyqgk gcqgsadhvv sisgvplqlq pnsiqtkvds iawkkllpsq
 61 ngfhhilkwe ngslpsntsn drfsfivknl sllikaaqqq dsglyclevt sisgkvqtat
121 fqvfvfesll pdkvekprlq gqgkildrgr cqvalsclvs rdgnvsyawy rgskliqtag
181 nltyldeevd ingthtytcn vsnpvswesh tlnltqdcqn ahqefrfwpf lviivilsal
241 flgtlacfcv wrrkrkekqs etspkeflti yedvkdlktr rnheqeqtfp gggstiysmi
301 qsqssaptsq epaytlysli qpsrksgsrk rnhspsfnst iyevigksqp kaqnparlsr
361 kelenfdvys
```

In accordance with the presently disclosed subject matter, a "2B4 nucleic acid molecule" refers to a polynucleotide encoding a 2B4 polypeptide.

B- and T-lymphocyte attenuator (BTLA) expression is induced during activation of T cells, and BTLA remains expressed on Th1 cells but not Th2 cells. Like PD1 and CTLA4, BTLA interacts with a B7 homolog, B7H4. However, unlike PD-1 and CTLA-4, BTLA displays T-Cell inhibition via interaction with tumor necrosis family receptors (TNF-R), not just the B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses. BTLA activation has been shown to inhibit the function of human CD8+ cancer-specific T cells. BTLA has also been designated as CD272 (cluster of differentiation 272).

In accordance with the presently disclosed subject matter, a BTLA polypeptide can have an amino acid sequence that is at least about 85%, about 90%, about 95%, about 96%, about 97%, about 98%, about 99% or about 100% homologous to SEQ ID NO: 34 or fragments thereof, and/or may optionally comprise up to one or up to two or up to three conservative amino acid substitutions. In non-limiting embodiments, a BTLA polypeptide can have an amino acid sequence that is a consecutive portion of SEQ ID NO: 34 which is at least 20, or at least 30, or at least 40, or at least 50, and up to 289 amino acids in length. Alternatively or additionally, in non-limiting various embodiments, a BTLA polypeptide has an amino acid sequence of amino acids 1 to 289, 1 to 50, 50 to 100, 100 to 134, 135 to 157, 158 to 178, 179 to 289, 135 to 289, 158 to 289, or 179 to 289 of SEQ ID NO: 34. In one embodiment, the BTLA polypeptide has an amino acid sequence of amino acids 179 to 289 of SEQ ID NO: 34. In certain embodiments, the intracellular domain of the CAR comprises a co-stimulatory signaling region comprising a BTLA polypeptide having an amino acid sequence of amino acids 179 to 289 of SEQ ID NO: 34. In certain embodiments, the transmembrane domain of the CAR comprises a BTLA polypeptide having an amino acid sequence of amino acids 158 to 178 of SEQ ID NO: 34.

SEQ ID NO: 34 is provided below:

In accordance with the presently disclosed subject matter, a "BTLA nucleic acid molecule" refers to a polynucleotide encoding a BTLA polypeptide.

In one embodiment, the CAR is Mz, which comprises an extracellular antigen binding region comprising an extracellular antigen-binding domain that specifically binds to human mesothelin, a transmembrane domain comprising a CD8 polypeptide, and an intracellular domain comprising a CD3 ζ polypeptide (see, for example, FIG. 2). Mz also comprises a leader covalently joined to the 5' terminus of the extracellular antigen-binding domain. The leader comprises a CD8 polypeptide comprising amino acids having the sequence set forth in SEQ ID NO: 20.

Figure 24:
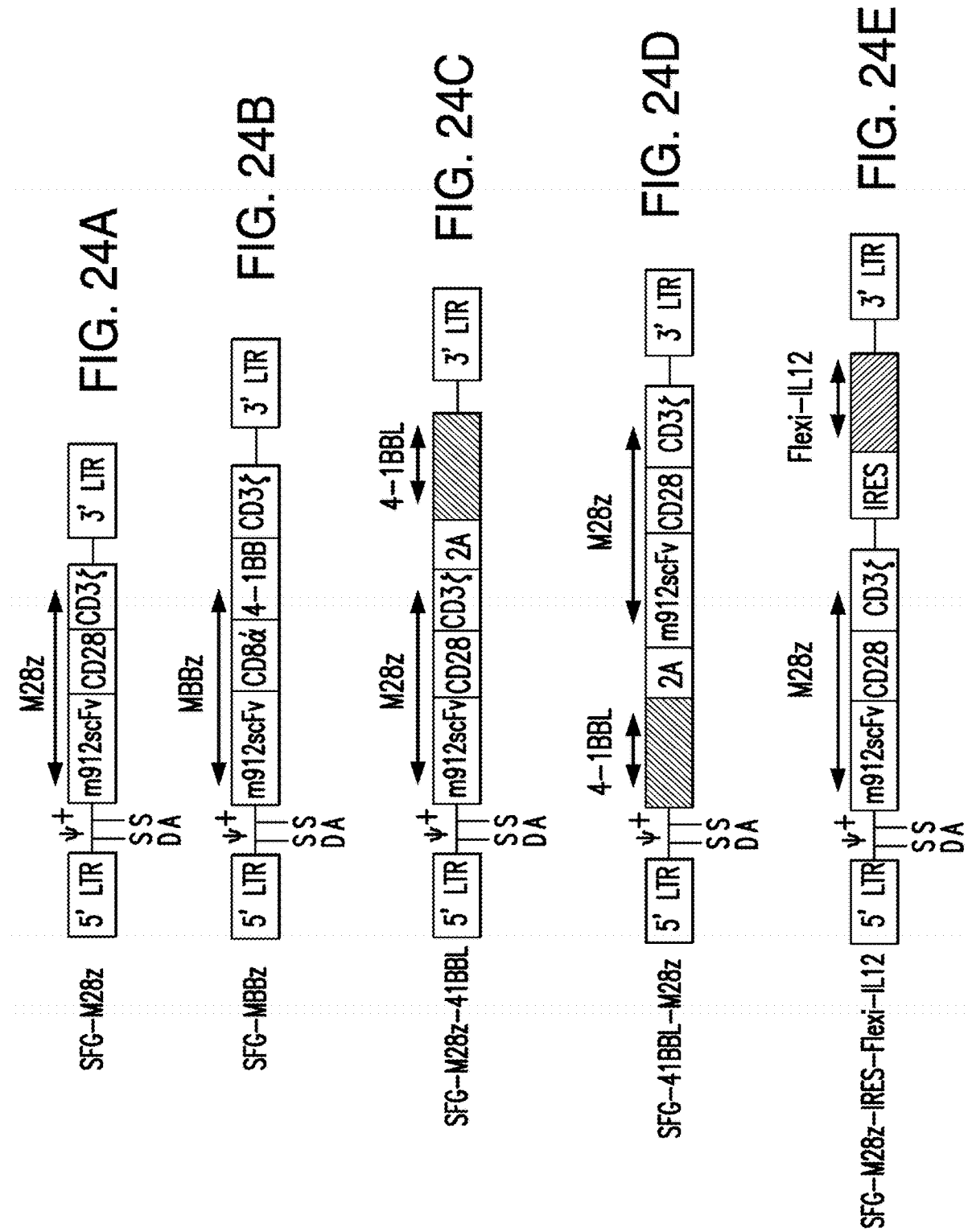

In one embodiment, the CAR is M28z, which comprises an extracellular antigen binding region that specifically binds to human mesothelin, a transmembrane domain comprising a CD28 polypeptide, and an intracellular domain comprising a CD3ζ polypeptide and a co-stimulatory signaling region comprising a CD28 polypeptide (see, for example, FIG. 2). M28z also comprises a leader covalently joined to the 5' terminus of the extracellular antigen-binding domain. The leader comprises a CD8 polypeptide comprising amino acids having the sequence set forth in SEQ ID NO: 20. In some embodiments, the CAR comprises M28z and a co-stimulatory ligand that is IL-12, e.g., M28z+IL-12 as shown in FIG. 24E. IL-12 can be covalently joined to the 3' terminus of the intracellular domain of M28z. In some embodiments, the CAR comprises M28z and a co-stimulatory ligand that is 4-1BBL, e.g., M28z+4-1BBL as shown in FIGS. 24C and 24D. 4-1BBL can be covalently joined to the 5' terminus of the extracellular antigen-binding domain of M28z, as shown in FIG. 24D. Alternatively, 4-1BBL can be covalently joined to the 3' terminus of the intracellular domain of M28z, as shown in FIG. 24C.

In one embodiment, the CAR is MBBz, which comprises an extracellular antigen binding region that specifically binds to human mesothelin, a transmembrane domain comprising a CD8 polypeptide, and an intracellular domain comprising a CD3ζ polypeptide and a co-stimulatory signaling region comprising a 4-1BB polypeptide (see, for example, FIGS. 19 and 24B). MBBz also comprises a leader covalently joined to the 5' terminus of the extracellular

```
  1 MKTLPAMLGT GKLFWVFFLI PYLDIWNIHG KESCDVQLYI KRQSEHSILA GDPFELECPV
 61 KYCANRPHVT WCKLNGTTCV KLEDRQTSWK EEKNISFFIL HFEPVLPNDN GSYRCSANFQ
121 SNLIESHSTT LYVTDVKSAS ERPSKDEMAS RPWLLYRLLP LGGLPLLITT CFCLFCCLRR
181 HQGKQNELSD TAGREINLVD AHLKSEQTEA STRQNSQVLL SETGIYDNDP DLCFRMQEGS
241 EVYSNPCLEE NKPGIVYASL NHSVIGPNSR LARNVKEAPT EYASICVRS
``` antigen-binding domain. The leader comprises a CD8 polypeptide comprising amino acids having the sequence set forth in SEQ ID NO: 20.

In some embodiments, the CAR of the presently disclosed subject matter can further comprise an inducible promoter, for expressing nucleic acid sequences in human cells. Promoters for use in expressing CAR genes can be a constitutive promoter, such as ubiquitin C (UbiC) promoter.

MSLN-specific CARs have shown efficacy against ovarian cancer, malignant pleural mesothelioma (MPM), and triple-negative breast cancer (TNBC) in both in vitro and in vivo settings[54-58]. Two Phase I clinical trials have used anti-MSLN CAR-transduced T cells. An NCI Phase I clinical trial (NCT01583686) treats metastatic or unresectable cancers that express MSLN with CAR T cells, in combination with myeloablative chemotherapy and/or aldesleukin (an IL-2 analogue) to augment CAR T cell persistence. A University of Pennsylvania Phase I clinical trial (NCT01355965) gives mesothelioma patients 1 to 3 doses of RNA-transfected, MSLN-targeted CAR T cells. In the latter study, a human anti-mouse antibody (HAMA) response was observed in the third treated patient (*Cancer Immunol Res* Apr. 7, 2013). Unlike the MSLN CARs in the NCI and U Penn clinical trials, in one embodiment, the presently disclosed MSLN-targeted CAR is derived from a human Fab[53], and thus, affords a much decreased risk of immunogenicity, compared with CARs derived from murine antibodies (see (see Maus et al., *Cancer Immunol Res* (2003); 1(1):26-31), which reports that the potential immunogenicity of CARs derived from murine antibodies may be a safety issue for mRNA CARs). The presently disclosed MSLN-targeted CARs can transduce both CD4$^+$ and CD8$^+$ T cells, and thus, transduction of a patient's T cells with CARs generates both helper and CTL responses, resulting in a sustained anti-tumor response.

III. Immunoresponsive Cells

The presently disclosed subject matter provides immunoresponsive cells expressing a CAR that comprises an extracellular antigen-binding domain, a transmembrane domain and an intracellular domain, where the extracellular antigen-binding domain specifically binds to human mesothelin, as described above. The presently disclosed subject matter also provides methods of using such cells for the treatment of a disease that, e.g., requires an enhanced immune response. The immunoresponsive cells of the presently disclosed subject matter can be cells of the lymphoid lineage. The lymphoid lineage, comprising B, T and natural killer (NK) cells, provides for the production of antibodies, regulation of the cellular immune system, detection of foreign agents in the blood, detection of cells foreign to the host, and the like. Non-limiting examples of cells of the lymphoid lineage include T cells, Natural Killer (NK) cells, cytotoxic T lymphocytes (CTLs), regulatory T cells, embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, T helper cells, cytotoxic T cells, memory T cells (including central memory T cells, stem-cell-like memory T cells (or stem-like memory T cells), and two types of effector memory T cells: e.g., TEM cells and TEMRA cells), Regulatory T cells (also known as suppressor T cells), Natural killer T cells, Mucosal associated invariant T cells, and γδ T cells. In some embodiments, the CAR-expressing T cells express Foxp3 to achieve and maintain a T regulatory phenotype. Natural killer (NK) cells can be lymphocytes that are part of cell-mediated immunity and act during the innate immune response. NK cells do not require prior activation in order to perform their cytotoxic effect on target cells. Cytotoxic T cells (CTL or killer T cells) are a subset of T lymphocytes capable of inducing the death of infected somatic or tumor cells.

The immunoresponsive cells of the presently disclosed subject matter can express an extracellular antigen-binding domain (e.g., a human scFV, a Fab that is optionally cross-linked, or a F(ab)$_2$) that specifically binds to human mesothelin, for the treatment or prevention of a neoplasia. Such immunoresponsive cells can be administered to a subject (e.g., a human subject) in need thereof for the treatment or prevention of a solid tumor (e.g. mesothelioma, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, and/or cholangiocarcinoma). In one embodiment, the immunoresponsive cell is a T cell. The T cell can be a CD4$^+$ T cell or a CD8$^+$ T cell. In one embodiment, the T cell is a CD4$^+$ T cell.

A presently disclosed immunoresponsive cell can further comprise at least one exogenous co-stimulatory ligand, such that the immunoresponsive cell co-expresses or is induced to co-express exogenously the mesothelin-specific CAR and the at least one exogenous co-stimulatory ligand. The interaction between the mesothelin-specific CAR and at least one co-stimulatory ligand provides a non-antigen-specific signal important for full activation of an immunoresponsive cell (e.g., T cell). Co-stimulatory ligands include, without limitation, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. TNF superfamily members include, without limitation, nerve growth factor (NGF), CD40L (CD40L)/CD154, CD137L/4-1BBL, TNF-α, CD134L/OX40L/CD252, CD27L/CD70, Fas ligand (FasL), CD30L/CD153, tumor necrosis factor beta (TNFβ)/lymphotoxin-alpha (LTα), lymphotoxin-beta (LTβ), CD257/B cell-activating factor (BAFF)/Blys/THANK/Tall-1, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, without limitation, CD80 and CD86, both ligands for CD28, PD-L1/(B7-H1) that ligands for PD-1.

In some embodiments, the at least one co-stimulatory ligand is selected from the group consisting of 4-1BBL, CD80, CD86, CD70, OX40L, CD48, TNFRSF14, PD-L1, and combinations thereof. In one embodiment, the co-stimulatory ligand is 4-1BBL. In one non-limiting embodiment, an immunoresponsive cell co-expresses M28z and 4-1BBL, e.g., M28z+4-1BBL as shown in FIGS. 24C and 24D. 4-1BBL can be covalently joined to the 5' terminus of the extracellular antigen-binding domain of M28z, as shown in FIG. 24D. Alternatively, 4-1BBL can be covalently joined to the 3' terminus of the intracellular domain of M28z, as shown in FIG. 24C.

An OX40L polypeptide can have an amino acid sequence that is at least about 85%, about 90%, about 95%, about 96%, about 97%, about 98%, about 99% or 100% homologous to the sequence having a NCBI Reference No: BAB18304 or NP_003317 (SEQ ID NO: 35), or fragments thereof, and/or may optionally comprise up to one or up to two or up to three conservative amino acid substitutions.

SEQ ID NO: 35 is provided below:

```
  1 mervqpleen vgnaarprfe rnklllvasv igglglllcf tyiclhfsal qvshrypriq 61 sikvqfteyk kekgfiltsq kedeimkvqn nsviincdgf ylislkgyfs qevnislhyq 121 kdeeplfqlk kvrsvnslmv asltykdkvy lnvttdntsl ddfhvnggel ilihqnpgef 181 cvl
```

In accordance with the presently disclosed subject matter, an "OX40L nucleic acid molecule" refers to a polynucleotide encoding an OX40L polypeptide.

Furthermore, a presently disclosed immunoresponsive cell can further comprise at least one exogenous cytokine, such that the immunoresponsive cell co-expresses or is induced to co-express exogenously the mesothelin-specific CAR and the at least one cytokine. In some embodiments, the at least one cytokine is selected from the group consisting of IL-2, IL-3, IL-6, IL-7, IL-11, IL-12, IL-15, IL-17, and IL-21. In one embodiment, the cytokine is IL-12. In one non-limiting embodiment, an immunoresponsive cell co-expresses M28z and IL-12, e.g., M28z+IL-12 as shown in FIG. 24E. IL-12 can be covalently joined to the 3' terminus of the intracellular domain of M28z.

Additionally, the immunoresponsive cells can express a second CAR that binds to an antigen different than human mesothelin. CARs that can be used as a second CAR in combination with the mesothelin-specific CAR in the presently disclosed subject matter include those described in Sadelain, et al., "The Basic Principles of Chimeric Antigen Receptor Design." Cancer Discovery, OF1-11, (2013), Chicaybam, et al., (2011), Brentjens et al. Nature Medicine 9:279-286 (2003), and U.S. Pat. No. 7,446,190, which are herein incorporated by reference in their entireties, e.g., CD19-targeted CARs (see U.S. Pat. No. 7,446,190; U.S. 2013/0071414,), HER2-targeted CARs (see Ahmed, et al., Clin Cancer Res., 2010), MUC16-targeted CARs (see Chekmasova, et al., 2011), prostate-specific membrane antigen (PSMA)-targeted CARs (for example, Zhong, et al., Molecular Therapy, 18(2):413-420 (2010), all of which are herein incorporated by reference in their entireties. Immunoresponsive cells expressing two or more antigen recognizing receptors (e.g., CARs) are described in WO 2014/055668, which is herein incorporated by reference in its entirety.

The antigen can be a tumor or pathogen antigen. Any suitable tumor antigen (antigenic peptide) is suitable for use in the tumor-related embodiments described herein. Sources of tumor antigen include, but are not limited to cancer proteins. The antigen can be expressed as a peptide or as an intact protein or portion thereof. The intact protein or a portion thereof can be native or mutagenized. Suitable antigens include, but are not limited to, prostate specific membrane antigen (PSMA) and prostate stem cell antigen (PCSA). In some embodiments, the tumor antigen can be carbonic anhydrase IX (CA1X), carcinoembryonic antigen (CEA), CD5, CD7, CD10, CD19, CD20, CD22, CD30, CD33, CD34, CD38, CD41, CD44, CD49f, CD56, CD74, CD123, CD133, CD138, an antigen of a cytomegalovirus (CMV) infected cell (e.g., a cell surface antigen), epithelial glycoprotein2 (EGP 2), epithelial glycoprotein-40 (EGP-40), epithelial cell adhesion molecule (EpCAM), receptor tyrosine-protein kinases erb-B2,3,4, folate-binding protein (FBP), fetal acetylcholine receptor (AChR), folate receptor-a, Ganglioside G2 (GD2), Ganglioside G3 (GD3), human Epidermal Growth Factor Receptor 2 (HER-2), human telomerase reverse transcriptase (hTERT), Interleukin-13 receptor subunit alpha-2 (IL-13Rα2), κ-light chain, kinase insert domain receptor (KDR), Lewis A (CA19.9), Lewis Y (LeY), L1 cell adhesion molecule (L1CAM), melanoma antigen family A, 1 (MAGE-AI), Mucin 16 (Muc-16), Mucin 1 (Muc-1), NKG2D ligands, cancer-testis antigen NY-ESO-1, oncofetal antigen (h5T4), prostate stem cell antigen (PSCA), prostate-specific membrane antigen (PSMA), tumor-associated glycoprotein 72 (TAG-72), vascular endothelial growth factor R2 (VEGF-R2), Wilms tumor protein (WT-1), type 1 tyrosine-protein kinase transmembrane receptor (ROR1), or a combination thereof.

Suitable pathogenic antigens for use in the treatment of pathogen infection or other infectious disease, for example, in an immunocompromised subject include, without limitation, viral antigens present in Cytomegalovirus (CMV), Epstein Barr Virus (EBV), Human Immunodeficiency Virus (HIV), and influenza virus. The immunoresponsive cells that include a second CAR targeting a viral antigen can be used for treating viral diseases. In one non-limiting embodiment, the presently disclosed mesothelin-targeted CAR and a second CAR that binds to a CMV antigen are co-expressed in the immunoresponsive cells (e.g., cytotoxic T lymphocytes) can be used for treating CMV.

The mesothelin-specific or mesothelin-targeted human lymphocytes that can be used in the methods of the presently disclosed subject matter include, without limitation, peripheral donor lymphocytes, e.g., those disclosed in Sadelain, M., et al. 2003 Nat Rev Cancer 3:35-45 (disclosing peripheral donor lymphocytes genetically modified to express CARs), in Morgan, R. A., et al. 2006 Science 314:126-129 (disclosing peripheral donor lymphocytes genetically modified to express a full-length tumor antigen-recognizing T cell receptor complex comprising the c and 3 heterodimer), in Panelli, M. C., et al. 2000 *J Immunol* 164:495-504; Panelli, M. C., et al. 2000 *J Immunol* 164:4382-4392 (disclosing lymphocyte cultures derived from tumor infiltrating lymphocytes (TILs) in tumor biopsies), and in Dupont, J., et al. 2005 Cancer Res 65:5417-5427; Papanicolaou, G. A., et al. 2003 *Blood* 102:2498-2505 (disclosing selectively in vitro-expanded antigen-specific peripheral blood leukocytes employing artificial antigen-presenting cells (AAPCs) or pulsed dendritic cells). The immunoresponsive cells (e.g., T cells) can be autologous, non-autologous (e.g., allogeneic), or derived in vitro from engineered progenitor or stem cells.

Assays may be used to compare the influence of co-stimulatory signaling on enhancing MSLN CAR-transduced T cell proliferation, effector function, and accumulation upon repeated (weekly) antigen stimulation. Peripheral blood lymphocytes (PBL) may be harvested from healthy volunteers under an IRB-approved protocol and transduced. Gene transfer efficiency may be monitored by FACS analysis to quantify the fraction of GFP$^+$ (transduced) T cells and/or by quantitative PCR. Using a well-established coc-ultivation system,[16,25,98] it may be determined whether fibroblast AAPCs expressing MSLN (vs MSLN– controls) direct cytokine release from transduced T cells (cell supernatant LUMINEX assay for IL-2, IL-4, IL-10, IFN-γ, TNF-α, and GM-CSF), T cell proliferation (by CFSE labeling), and T cell survival (by Annexin V staining). The influence of CD80 and/or 4-1BBL on T cell survival, proliferation, and efficacy may be evaluated. T cells may be exposed to repeated stimulation by MSLN$^+$ target cells and determine whether T cell proliferation and cytokine response remained similar or diminished with repeated stimulation. The Mz, M28z, MBBz, M28z$^+$4-1BBL, and M28z-IL-12 CAR constructs may be compared side by side under strictly equivalent conditions. Cytotoxicity assays with multiple E:T ratios may be conducted using chromium-release assays. Statistical analysis may be optionally performed with 2-way ANNOVA, followed by pairwise multiple comparison procedures, where data may be expressed as mean±SEM. The CD4 and CD8 T cell subtypes (activated effector, central memory, effector memory) may be identified to determine what conditions favor maintenance or expansion of the central memory phenotype.

In one non-limiting example, in two or more mice each with and without MSLN-expressing TNBC tumors from the same cell line, transduced (Mz/M28z/MBBz/M28z+4-1BBL) and untransduced T cells may be injected systemically by tail vein injection. Before the administration, T cells may be CFSE labeled, transduced with Gaussia Luciferase, and quantified for their emission. At 24 h and 7, 40, and 70 days, T cell trafficking and persistence in the TME may be assessed by BLI for T cells and flow cytometry of harvested tumor from euthanized mice (4 mice at each time point), and may be further confirmed by IHC analysis. To determine the specific influence of MSLN expression on T cell trafficking, mice may be injected with an equal number of MSLN-expressing tumor cells in the right mammary pad and MSLN-negative tumor cells in the left mammary pad, and T cells may be administered systemically. Mice with imaging-positive TNBC may be injected with a 1:1 mixture of untransduced and targeted T cells systemically. Untransduced T cells may be labeled with Click Beetle luciferase, and targeted T cells may be labeled with Gaussia-luciferase and followed with BLI to characterize their pharmacodynamics in relation to MSLN$^+$ TNBC cells. T cell persistence and proliferation may be distinguished by CFSE labeling of T cells, determined by flow cytometry after mice are euthanized.

In one non-limiting example, to study the specificity and efficacy of targeted T cells, SMRP and imaging-positive mice with metastatic TNBC (either pleural metastatic disease or systemic metastatic disease) may be divided into 4 groups of 36 mice each. Mice may be treated with control T cells delivered systemically (group 1) or intrapleurally (group 2) or with MSLN-targeted T cells delivered systemically (group 3) or intrapleurally (group 4). Control T cells may be transduced with hrGFP vectors. T cells in doses from 1 million cells to 5 million cells may be delivered. Tumor burden may be monitored by serial BLI and by measuring SMRP, in addition to monitoring for weight loss and cachexia. Three mice from each group may be sacrificed at 7, 21, 40, and 70 days after T cell administration for histological examination and IHC analysis. Harvested tissue may be analyzed by flow cytometry for persistence of targeted T cells and for phenotype. The T cell therapy efficacy evaluation parameters are tumor burden that may be assessed by the number and distribution of tumor nodules (in the pleural cavity=mean chest wall weight of disease/treated mice–mean chest wall weight of control mice), number and burden of metastases in lymph nodes, serum SMRP levels, micrometastatic tumor burden in solid organs as detected by flow cytometry, and long-term survival of mice. The median survival and survival curves of each group of mice may be monitored and measured in a parallel experiment of 12 mice per group.

In certain embodiments, a presently disclosed immunoresponsive cell (e.g., T cell) expresses from about 1 to about 4, from about 2 to about 4, from about 3 to about 4, from about 1 to about 2, from about 1 to about 3, or from about 2 to about 3 vector copy numbers/cell of a presently disclosed mesothelin-specific CAR. For example, a presently disclosed immunoresponsive cell (e.g., T cell) expresses about 1, about 2, about 3, or about 4 vector copy numbers/cell of the mesothelin-specific CAR. In one non-limiting embodiment, a presently disclosed immunoresponsive cell (e.g., T cell) expresses from about 3 to about 4 vector copy numbers/cell of a presently disclosed mesothelin-specific CAR. In certain embodiments, the cytotoxicity and cytokine production of the immunoresponsive cell (e.g., T cell) are proportional to the expression level of the mesothelin-specific CAR in the cell. For example, the higher the CAR expression level in an immunoresponsive cell, the greater cytotoxicity and cytokine production the immunoresponsive cell exhibits. An immunoresponsive cell (e.g., T cell) having a high mesothelin-CAR expression level can induce antigen-specific cytokine production or secretion and/or exhibit cytotoxicity to a tissue or a cell having a low level of mesothelin expression, e.g., about 2,000 or less, about 1,000 or less, about 900 or less, about 800 or less, about 700 or less, about 600 or less, about 500 or less, about 400 or less, about 300 or less, about 200 or less, about 100 or less of mesothelin binding sites/cell. See for example, Examples 4 and 5. Additionally or alternatively, the cytotoxicity and cytokine production of a presently disclosed immunoresponsive cell (e.g., T cell) are proportional to the expression level of human mesothelin in a target tissue or a target cell. For example, the higher the expression level of human mesothelin in the target, the greater cytotoxicity and cytokine production the immunoresponsive cell exhibits. See for example, Example 5.

In certain embodiments, the target cells are heterogeneous MSLN-expressing cells, which are a population of cells comprising low MSLN-expressing cells and high MSLN-expressing cells. The presently disclosed immunoresponsive cell can exhibit increased cytotoxicity and antitumor activity to low MSLN-expressing cells (e.g., about 2,000 or less, about 1,000 or less, about 900 or less, about 800 or less, about 700 or less, about 600 or less, about 500 or less, about 400 or less, about 300 or less, about 200 or less, or about 100 or less MSLN binding sites/cell) in the presence of high MSLN– expressing cells. See for example, Example 2. In certain embodiments, even in the presence of high MSLN-expressing cells, the immunoresponsive cell does not exhibit increased cytotoxicity or nonspecific kill to MSLN-negative cells. Thus, the immunoresponsive cell can exhibit increased cytotoxicity and antitumor activity to low MSLN-expressing cells in the presence of high MSLN– expressing cells while retain safety to MSLN-negative cells.

In certain embodiments, the immunoresponsive cell can express one or more adhesion molecules, which can increase the avidity of the MSLN-specific CAR, especially when the CAR is a low affinity CAR. Non-limiting examples of adhesion molecules include CD2 and VLA-4. CD2 expressed on the immunoresponsive cell can bind to CD58 expressed on a target cell (e.g., a cancerous cell). VLA-4 expressed on the immunoresponsive cell can bind to VCAM-1 on a target cell (e.g., a cancerous cell).

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially. mAbs are particularly useful for identifying markers associated with particular cell lineages and/or stages of differentiation for both positive and negative selections.

A large proportion of terminally differentiated cells can be initially removed by a relatively crude separation. For example, magnetic bead separations can be used initially to remove large numbers of irrelevant cells. Preferably, at least about 80%, usually at least 70% of the total hematopoietic cells will be removed prior to cell isolation.

Procedures for separation include, but are not limited to, density gradient centrifugation; resetting; coupling to particles that modify cell density; magnetic separation with antibody-coated magnetic beads; affinity chromatography; cytotoxic agents joined to or used in conjunction with a mAb, including, but not limited to, complement and cytotoxins; and panning with antibody attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

IV. Vectors

Genetic modification of immunoresponsive cells (e.g., T cells, CTL cells, NK cells) can be accomplished by transducing a substantially homogeneous cell composition with a recombinant DNA or RNA construct. In one embodiment, the vector is a retroviral vector (e.g., gamma retroviral or lentiviral) is employed for the introduction of the DNA or RNA construct into the host cell genome. For example, a polynucleotide encoding the mesothelin-specific CAR can be cloned into a retroviral vector and expression can be driven from its endogenous promoter, from the retroviral long terminal repeat, or from an alternative internal promoter.

Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide mesothelin-specific cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci. USA* 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Transducing viral vectors can be used to express a co-stimulatory ligand (e.g., 4-1BBL and IL-12) in an immunoresponsive cell. Preferably, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263 267, 1996; and Miyoshi et al., Proc. Natl. Acad. Sci. U.S.A. 94:10319, 1997). Other viral vectors that can be used include, for example, adeno-viral, lentiviral, and adeno-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

In one non-limiting example, a vector encoding a presently disclosed MSLN-targeted CAR is a retroviral vector, e.g., a SGF γ-retroviral vector, which is Moloney murine leukemia-based retroviral vector, such as a SGF γ-retroviral vector encoding M28z as shown in FIGS. 24A and 26. The nucleotide sequence of SFG-ICAS9-P2A-M28z plasmid DNA is set forth in SEQ ID NO: 36, which is provided below:

SEQ ID NO: 36

```
CATGCTCGAGGGAGTGCAGGTGGAGACTATCTCCCCAGGAGACGGGCGCACCTTCCCCAAGCGCGGCCAGACCTGCGTGG
TGCACTACACCGGGATGCTTGAAGATGGAAAGAAAGTTGATTCCTCCCGGGACAGAAACAAGCCCTTTAAGTTTATGCTA
GGCAAGCAGGAGGTGATCCGAGGCTGGGAAGAAGGGGTTGCCCAGATGAGTGTGGGTCAGAGAGCCAAACTGACTATATC
TCCAGATTATGCCTATGGTGCCACTGGGCACCCAGGCATCATCCCACCACATGCCACTCTCGTCTTCGATGTGGAGCTTC
TAAAACTGGAATCTGGCGGTGGATCCGGAGTCGACGGATTTGGTGATGTCGGTGCTCTTGAGAGTTTGAGGGGAAATGCA
GATTTGGCTTACATCCTGAGCATGGAGCCCTGTGGCCACTGCCTCATTATCAACAATGTGAACTTCTGCCGTGAGTCCGG
GCTCCGCACCCGCACTGGCTCCAACATCGACTGTGAGAAGTTGCGGCGTCGCTTCTCCTCGCTGCATTTCATGGTGGAGG
TGAAGGGCGACCTGACTGCCAAGAAAATGGTGCTGGCTTTGCTGGAGCTGGCGCGGCAGGACCACGGTGCTCTGGACTGC
TGCGTGGTGGTCATTCTCTCTCACGGCTGTCAGGCCAGCCACCTGCAGTTCCCAGGGGCTGTCTACGGCACAGATGGATG
CCCTGTGTCGGTCGAGAAGATTGTGAACATCTTCAATGGGACCAGCTGCCCCAGCCTGGGAGGGAAGCCCAAGCTCTTTT
TCATCCAGGCCTGTGGTGGGGAGCAGAAAGACCATGGGTTTGAGGTGGCCTCCACTTCCCCTGAAGACGAGTCCCCTGGC
AGTAACCCCGAGCCAGATGCCACCCCGTTCCAGGAAGGTTTGAGGACCTTCGACCAGCTGGACGCCATATCTAGTTTGCC
CACACCCAGTGACATCTTTGTGTCCTACTCTACTTTCCCAGGTTTTGTTTCCTGGAGGGACCCCAAGAGTGGCTCCTGGT
ACGTTGAGACCCTGGACGACATCTTTGAGCAGTGGGCTCACTCTGAAGACCTGCAGTCCCTCCTGCTTAGGGTCGCTAAT
GCTGTTTCGGTGAAAGGGATTTATAAACAGATGCCTGGTTGCTTTAATTTCCTccggaaaaaacttttctttaaaacatc
aGGATCTGGAGCAACAAACTTCTCACTACTCAAACAAGCAGGTGACGTGGAGGAGAATCCCGGCCCAATGGCCCTGCCAG
TAACGGCTCTGCTGCTGCCACTTGCTCTGCTCCTCCATGCAGCCAGGCCTCAGGTTCAGCTTCAGGAGAGTGGCCCAGGC
CTGGTGAAGCCAAGTGAGACTCTCAGCTTGACTTGCACAGTTTCTGGAGGCAGTGTCTCCTCAGGCAGCTATTATTGGTC
CTGGATTCGGCAGCCCCTGGGAAAGGCCTGGAGTGGATTGGGTACATATATTACAGTGGCAGCACAAATTACAATCCAT
CCCTGAAGTCTCGAGTAACTATCAGTGTGGACACAAGCAAGAATCAGTTTTCACTCAAACTGTCTTCTGTGACTGCTGCT
GACACTGCTGTTTATTATTGTGCCAGGGAGGGGAAAAATGGGGCATTTGATATTTGGGGTCAGGGCACAATGGTGACAGT
CAGCTCTGGAGGTGGAGGCTCAGGAGGAGGAGGCAGTGGAGGTGGTGGGTCACGCCATCAGATGACTCAGTCCCCcTCCA
GTCTTTCTGCCTCAGTTGGGGATAGAGTGACCATCACATGCAGAGCAAGTCAGAGCATATCATCCTATCTGAACTGGTAC
CAGCAGAAGCCAGGGAAAGCCCCCAAATTGCTGATTTATGCAGCCTCAAGTCTCCAGAGTGGGGTGCCAAGCAGGTTCTC
AGGCAGTGGCAGTGGGACAGATTTCACATTGACAATCAGCTCCCTCCAACCTGAAGATTTTGCCACCTACTATTGCCAGC
AATCCTACAGCACGCCCCTGACTTTTGGAGGTGGCACAAAGGTAGAGATCAAGAGGACTGCGGCCGCAATTGAAGTTATG
TATCCTCCTCCTTACCTAGACAATGAGAAGAGCAATGGAACCATTATCCATGTGAAAGGGAAACACCTTTGTCCAAGTCC
CCTATTTCCCGGACCTTCTAAGCCCTTTTGGGTGCTGGTGGTGGTTGGTGGAGTCCTGGCTTGCTATAGCTTGCTAGTAA
CAGTGGCCTTTATTATTTTCTGGGTGAGGAGTAAGAGGAGCAGGCTCCTGCACAGTGACTACATGAACATGACTCCCCGC
CGCCCCGGGCCCACCCGCAAGCATTACCAGCCCTATGCCCCACCACGCGACTTCGCAGCCTATCGCTCCAGAGTGAAGTT
CAGCAGGAGCGCAGACGCCCCCGCGTACCAGCAGGGCCAGAACCAGCTCTATAACGAGCTCAATCTAGGACGAAGAGAGG
AGTACGATGTTTTGGACAAGAGACGTGGCCGGGACCCTGAGATGGGGGGAAAGCCGAGAAGGAAGAACCCTCAGGAAGGC
CTGTACAATGAACTGCAGAAAGATAAGATGGCGGAGGCCTACAGTGAGATTGGGATGAAAGGCGAGCGCCGGAGGGGCAA
GGGGCACGATGGCCTTTACCAGGGTCTCAGTACAGCCACCAAGGACACCTACGACGCCCTTCACATGCAGGCCCTGCCCC
CTCGCTAACAGCCACTCGAGGATCCGGATTAGTCCAATTTGTTAAAGACAGGATATCAGTGGTCCAGGCTCTAGTTTTGA
CTCAACAATATCACCAGCTGAAGCCTATAGAGTACGAGCCATAGATAAAATAAAAGATTTTATTTAGTCTCCAGAAAAAG
GGGGGAATGAAAGACCCCACCTGTAGGTTTGGCAAGCTAGCTTAAGTAACGCCATTTTGCAAGGCATGGAAAATACATA
ACTGAGAATAGAGAAGTTCAGATCAAGGTCAGGAACAGATGGAACAGCTGAATATGGGCCAAACAGGATATCTGTGGTAA
GCAGTTCCTGCCCCGGCTCAGGGCCAAGAACAGATGGAACAGCTGAATATGGGCCAAACAGGATATCTGTGGTAAGCAGT
TCCTGCCCCGGCTCAGGGCCAAGAACAGATGGTCCCCAGATGCGGTCCAGCCCTCAGCAGTTTCTAGAGAACCATCAGAT
```

```
GTTTCCAGGGTGCCCCAAGGACCTGAAATGACCCTGTGCCTTATTTGAACTAACCAATCAGTTCGCTTCTCGCTTCTGTT

CGCGCGCTTCTGCTCCCCGAGCTCAATAAAAGAGCCCACAACCCCTCACTCGGGGCGCCAGTCCTCCGATTGACTGAGTC

GCCCGGGTACCCGTGTATCCAATAAACCCTCTTGCAGTTGCATCCGACTTGTGGTCTCGCTGTTCCTTGGGAGGGTCTCC

TCTGAGTGATTGACTACCCGTCAGCGGGGGTCTTTCACATGCAGCATGTATCAAAATTAATTTGGTTTTTTTtCTTAAGT

ATTTACATTAAATGGCCATAGTACTTAAAGTTACATTGGCTTCCTTGAAATAAACATGGAGTATTCAGAATGTGTCATAA

ATATTTCTAATTTTAAGATAGTATCTCCATTGGCTTTCTACTTTTTCTTTTATTTTTTTTGTCCTCTGTCTTCCATTTGT

TGTTGTTGTTGTTTGTTTGTTTGTTGGTTGGTTGGTTAAtTTTTTTTTAAAGATCCTACACTATAGTTCAAGCTAG

ACTATTAGCTACTCTGTAACCCAGGGTGACCTTGAAGTCATGGGTAGCCTGCTGTTTTAGCCTTCCCACATCTAAGATTA

CAGGTATGAGCTATCATTTTTGGTATATTGATTGATTGATTGATTGATGTGTGTGTGTGATTGTGTTTGTGTGTGA

TTGTGTATATGTGTGTATGGTTGTGTGTGATTGTGTGTATGTATGTTTGTGTGTGATTGTGTGTGTGTGATTGTGCATGT

GTGTGTGTGATTGTGTTTATGTGTATGATTGTGTGTGTGTGTGTGTGTGTGTGTGTGTGTGTGTGTGTTG

TGTATATATATTTATGGTAGTGAGAGGCAACGCTCCGGCTCAGGTGTCAGGTTGGTTTTTGAGACAGAGTCTTTCACTTA

GCTTGGAATTCACTGGCCGTCGTTTTACAACGTCGTGACTGGGAAAACCCTGGCGTTACCCAACTTAATCGCCTTGCAGC

ACATCCCCTTTCGCCAGCTGGCGTAATAGCGAAGAGGCCCGCACCGATCGCCCTTCCCAACAGTTGCGCAGCCTGAATG

GCGAATGGCGCCTGATGCGGTATTTTCTCCTTACGCATCTGTGCGGTATTTCACACCGCATATGGTGCACTCTCAGTACA

ATCTGCTCTGATGCCGCATAGTTAAGCCAGCCCCGACACCCGCCAACACCCGCTGACGCGCCCTGACGGGCTTGTCTGCT

CCCGGCATCCGCTTACAGACAAGCTGTGACCGTCTCCGGGAGCTGCATGTGTCAGAGGTTTTCACCGTCATCACCGAAAC

GCGCGAGACGAAAGGGCCTCGTGATACGCCTATTTTTATAGGTTAATGTCATGATAATAATGGTTTCTTAGACGTCAGGT

GGCACTTTTCGGGGAAATGTGCGCGGAACCCCTATTTGTTTATTTTTCTAAATACATTCAAATATGTATCCGCTCATGAG

ACAATAACCCTGATAAATGCTTCAATAATATTGAAAAAGGAAGAGTATGAGTATTCAACATTTCCGTGTCGCCCTTATTC

CCTTTTTTGCGGCATTTTGCCTTCCTGTTTTTGCTCACCCAGAAACGCTGGTGAAAGTAAAAGATGCTGAAGATCAGTTG

GGTGCACGAGTGGGTTACATCGAACTGGATCTCAACAGCGGTAAGATCCTTGAGAGTTTTCGCCCCGAAGAACGTTTTCC

AATGATGAGCACTTTTAAAGTTCTGCTATGTGGCGCGGTATTATCCCGTATTGACGCCGGGCAAGAGCAACTCGGTCGCC

GCATACACTATTCTCAGAATGACTTGGTTGAGTACTCACCAGTCACAGAAAAGCATCTTACGGATGGCATGACAGTAAGA

GAATTATGCAGTGCTGCCATAACCATGAGTGATAACACTGCGGCCAACTTACTTCTGACAACGATCGGAGGACCGAAGGA

GCTAACCGCTTTTTTGCACAACATGGGGATCATGTAACTCGCCTTGATCGTTGGGAACCGGAGCTGAATGAAGCCATAC

CAAACGACGAGCGTGACACCACGATGCCTGTAGCAATGGCAACAACGTTGCGCAAACTATTAACTGGCGAACTACTTACT

CTAGCTTCCCGGCAACAATTAATAGACTGGATGGAGGCGGATAAAGTTGCAGGACCACTTCTGCGCTCGGCCCTTCCGGC

TGGCTGGTTTATTGCTGATAAATCTGGAGCCGGTGAGCGTGGGTCTCGCGGTATCATTGCAGCACTGGGGCCAGATGGTA

AGCCCTCCCGTATCGTAGTTATCTACACGACGGGGAGTCAGGCAACTATGGATGAACGAAATAGACAGATCGCTGAGATA

GGTGCCTCACTGATTAAGCATTGGTAACTGTCAGACCAAGTTTACTCATATATACTTTAGATTGATTTAAAACTTCATTT

TTAATTTAAAAGGATCTAGGTGAAGATCCTTTTTGATAATCTCATGACCAAAATCCCTTAACGTGAGTTTTCGTTCCACT

GAGCGTCAGACCCCGTAGAAAAGATCAAAGGATCTTCTTGAGATCCTTTTTTTCTGCGCGTAATCTGCTGCTTGCAAACA

AAAAAACCACCGCTACCAGCGGTGGTTTGTTTGCCGGATCAAGAGCTACCAACTCTTTTTCCGAAGGTAACTGGCTTCAG

CAGAGCGCAGATACCAAATACTGTTCTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTCGTGTCTTACCGGGTTGGACTCAAGA

CGATAGTTACCGGATAAGGCGCAGCGGTCGGGCTGAACGGGGGGTTCGTGCACACAGCCCAGCTTGGAGCGAACGACCTA

CACCGAACTGAGATACCTACAGCGTGAGCTATGAGAAAGCGCCACGCTTCCCGAAGGGAGAAAGGCGGACAGGTATCCGG

TAAGCGGCAGGGTCGGAACAGGAGAGCGCACGAGGGAGCTTCCAGGGGAAACGCCTGGTATCTTTATAGTCCTGTCGGG

TTTCGCCACCTCTGACTTGAGCGTCGATTTTTGTGATGCTCGTCAGGGGGCGGAGCCTATGGAAAAACGCCAGCAACGC

GGCCTTTTTACGGTTCCTGGCCTTTTGCTGGCCTTTTGCTCACATGTTCTTTCCTGCGTTATCCCCTGATTCTGTGGATA
```

```
ACCGTATTACCGCCTTTGAGTGAGCTGATACCGCTCGCCGCAGCCGAACGACCGAGCGCAGCGAGTCAGTGAGCGAGGAA
GCGGAAGAGCGCCCAATACGCAAACCGCCTCTCCCCGCGCGTTGGCCGATTCATTAATGCAGCTGGCACGACAGGTTTCC
CGACTGGAAAGCGGGCAGTGAGCGCAACGCAATTAATGTGAGTTAGCTCACTCATTAGGCACCCCAGGCTTTACACTTTA
TGCTTCCGGCTCGTATGTTGTGTGGAATTGTGAGCGGATAACAATTTCACACAGGAAACAGCTATGACCATGATTACGCC
AAGCTTTGCTCTTAGGAGTTTCCTAATACATCCCAAACTCAAATATATAAAGCATTTGACTTGTTCTATGCCCTAGGGGG
CGGGGGGAAGCTAAGCCAGCTTTTTTtAACATTTAAAATGTTAATTCCATTTTAAATGCACAGATGTTTTTATTTCATAA
GGGTTTCAATGTGCATGAATGCTGCAATATTCCTGTTACCAAAGCTAGTATAAATAAAAATAGATAAACGTGGAAATTAC
TTAGAGTTTCTGTCATTAACGTTTCCTTCCTCAGTTGACAACATAAATGCGCTGCTGAGAAGCCAGTTTGCATCTGTCAG
GATCAATTTCCCATTATGCCAGTCATATTAATTACTAGTCAATTAGTTGATTTTTATTTTTGACATATACATGTGAAAGA
CCCCACCTGTAGGTTTGGCAAGCTAGCTTAAGTAACGCCATTTTGCAAGGCATGGAAAAATACATAACTGAGAATAGAAA
AGTTCAGATCAAGGTCAGGAACAGATGGAACAGCTGAATATGGGCCAAACAGGATATCTGTGGTAAGCAGTTCCTGCCCC
GGCTCAGGGCCAAGAACAGATGGAACAGCTGAATATGGGCCAAACAGGATATCTGTGGTAAGCAGTTCCTGCCCCGGCTC
AGGGCCAAGAACAGATGGTCCCCAGATGCGGTCCAGCCCTCAGCAGTTTCTAGAGAACCATCAGATGTTTCCAGGGTGCC
CCAAGGACCTGAAATGACCCTGTGCCTTATTTGAACTAACCAATCAGTTCGCTTCTCGCTTCTGTTCGCGCGCTTCTGCT
CCCCGAGCTCAATAAAAGAGCCCACAACCCCTCACTCGGCGCGCCAGTCCTCCGATTGACTGAGTCGCCCGGGTACCCGT
GTATCCAATAAACCCTCTTGCAGTTGCATCCGACTTGTGGTCTCGCTGTTCCTTGGGAGGGTCTCCTCTGAGTGATTGAC
TACCCGTCAGCGGGGGTCTTTCATTTGGGGGCTCGTCCGGGATCGGGAGACCCCTGCCCAGGGACCACCGACCCACCACC
GGGAGGTAAGCTGGCCAGCAACTTATCTGTGTCTGTCCGATTGTCTAGTGTCTATGACTGATTTTATGCGCCTGCGTCGG
TACTAGTTAGCTAACTAGCTCTGTATCGGCGGACCCGTGGTGGAACTGACGAGTTCGGAACACCCGGCCGCAACCCTGG
GAGACGTCCCAGGGACTTCGGGGGCCGTTTTTGTGGCCCGACCTGAGTCCTAAAATCCCGATCGTTTAGGACTCTTTGGT
GCACCCCCCTTAGAGGAGGGATATGTGGTTCTGGTAGGAGACGAGAACCTAAAACAGTTCCCGCCTCCGTCTGAATTTTT
GCTTTCGGTTTGGGACCGAAGCCGCGCCGCGCGTCTTGTCTGCTGCAGCATCGTTCTGTGTTGTCTCTGTCTGACTGTGT
TTCTGTATTTGTCTGAAAATATGGGCCCGGGCTAGCCTGTTACCACTCCCTTAAGTTTGACCTTAGGTCACTGGAAAGAT
GTCGAGCGGATCGCTCACAACCAGTCGGTAGATGTCAAGAAGAGACGTTGGGTTACCTTCTGCTCTGCAGAATGGCCAAC
CTTTAACGTCGGATGGCCGCGAGACGGCACCTTTAACCGAGACCTCATCACCCAGGTTAAGATCAAGGTCTTTTCACCTG
GCCCGCATGGACACCCAGACCAGGTCCCCTACATCGTGACCTGGGAAGCCTTGGCTTTTGACCCCCCTCCCTGGGTCAAG
CCCTTTGTACACCCTAAGCCTCCGCCTCCTCTTCCTCCATCCGCCCCGTCTCTCCCCCTTGAACCTCCTCGTTCGACCCC
GCCTCGATCCTCCCTTTATCCAGCCCTCACTCCTTCTCTAGGCGCCCCCATATGGCCATATGAGATCTTATATGGGCAC
CCCCGCCCCTTGTAAACTTCCCTGACCCTGACATGACAAGAGTTACTAACAGCCCCTCTCTCCAAGCTCACTTACAGGCT
CTCTACTTAGTCCAGCACGAAGTCTGGAGACCTCTGGCGGCAGCCTACCAAGAACAACTGGACCGACCGGTGGTACCTCA
CCCTTACCGAGTCGGCGACACAGTGTGGGTCCGCCGACACCAGACTAAGAACCTAGAACCTCGCTGGAAAGGACCTTACA
CAGTCCTGCTGACCACCCCCACCGCCCTCAAAGTAGACGGCATCGCAGCTTGGATACACGCCGCCCACGTGAAGGCTGCC
GACCCCGGGGGTGGACCATCCTCTAGACTGC
```

A SFG γ-retroviral vector encoding M28z can be constructed by inserting two DNA fragments into a 6.7 kb NotI/BglII of the SFG backbone. The backbone encodes the following: (1) the entire SFG γ-retroviral vector except for a region encompassing the SA and 5'UTR of the Mo-MLV env encoding mRNA; (2) the CDS of the human CD28 signaling domain fused to the human CD3ζ signaling domain.

DNA fragment 1 can be a 1.5 kb BglI/BspEI fragment derived from plasmid construct SFG-iCAS9-41BBL-NY28z. This fragment encodes a region encompassing the SA and 5'UTR of the Mo-MLV env encoding mRNA fused to the CDS of iCASP9 lacking eight amino acids of the C-terminus and the stop codon. The iCASP9 CDS can be derived by de novo synthesis from Blue 50 Heron Bio.

DNA fragment 2 can be a 0.89 kb BspEI/NotI fragment derived from a 0.979 kb PCR product. This fragment encodes the C-terminal CDS of iCASP9 (without the stop codon) fused to GSG-P2A-CD8a leader_m912 scFv. This PCR product can be synthesized from SFG-TK-2A-M28z as a template using the following primers:

(1.) iCASP9-2A Left primer:

[SEQ ID NO: 37]
gcgctccggaaaaaacttttctttaaaacatc aggatctggagcaac aaacttc (2.) CD28 Right primer: ggtgtttcccttttcacatgg [SEQ ID NO: 38].

The amino acid sequence of P2A is set forth in SEQ ID NO: 39, which is provided below:

[SEQ ID NO: 39]
ATNFSLLKQAGDVEENPGP

The nucleotide sequence encoding the amino acid sequence of SEQ ID NO: 39 is set forth in SEQ ID NO: 40, which is provided below:

[SEQ ID NO: 40]
GCAACAAACTTCTCACTACTCAAACAAGCAGGTGACGTGGAGGAGAAT

CCCGGCCC

SFG-TK_2A_M28z template can be derived using the SFG-Hsvtk_P2A_P28z backbone and the CD8a leader_m912 scFv sequence in SFG-M28z_ires_hrGFP by overlap-extension PCR. The CD8a leader_m912 scFv sequence in SFG-M28z_ires_hrGFP can be derived by de novo synthesis from Blue Heron Bio using an expression optimized codon table.

SFG/TK_2A_P28z can be derived from SFG/TP28z.3 using a 3 piece ligation—
(1) a 1462 bp BglI/BssHII fragment derived from SFG-TP28z.3 encoding a region of the Mo-MLV vector containing the splice acceptor site fused to the HSV-TK gene;
(2) a 880 bp BssHII/NotI fragment derived from PCR product encoding the 3' end of the HSV-TK gene without the stop codon_GSG 2A_CD8a signal peptide J591 ScFv; and
(3) a 6652 bp NotI/BssHII fragment derived from SFG-TP28z.3 encoding the rest of the transmembrane_CD28_zeta chain of the chimeric antigen receptor plus the remainder of the retroviralvector backbone.

The PCR product can be amplified using a previously constructed plasmid DNA encoding the GSG_P2A_CD28z as a template. The following primers can be utilized:

(1) Forward HSVTK_linker_GSG_P2A:

[SEQ ID NO: 41]
GCGCGCGCGCACGTTTGCCCGGGAGATGGGGGAGGCTAACGGATCTGG

AGCAACAAACTTC; and (2) Reverse- P28z R:

[SEQ ID NO: 42]
ggtgtttcccttttcacatgg

SFG-iC9-41BBL-NY28z can be generated by inserting two fragments into a 6.8 kb AgeI/NotI backbone derived from SFG-Hsvtk_2A_P28z: (1) a 1.7 kb AgeI/SacII fragment derived from pUC(-mcs)-CBNI encoding the Mo-MLV S D and 5' UTR of the env mRNA fused to the entire CDS of iCASP9 and the N-terminal 4-1BBL fused in frame with the gsg_P2A cleavage peptide; and (2) a 1.5 kb SacIV/AgeI fragment derived from pUC(-mcs)-CBNII encoding the remaining C-terminal 4-1BBL CDS fused via another GSG_P2A cleavage peptide to an scFv targeting the NYESO-1 antigen.

Both pUC(-mcs)-CBNI and pUC(-mcs)-CBNII can be obtained from Blue Heron Bio and the inserts generated by de novo gene synthesis.

Non-viral approaches can also be employed for the expression of a protein in cell. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucleases, or TALE nucleases). Transient expression may be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g. the elongation factor 1 α enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

V. Polypeptides and Analogs and Polynucleotides

Also included in the presently disclosed subject matter are extracellular antigen-binding domains that specifically binds to human mesothelin (e.g., a scFv, such as a scFv derived from antibody m912, a Fab, or a (Fab)$_2$), CD3ζ, CD8, CD28, 4-1BB, 4-1BBL, IL-12, Mz, M28z, MBBz polypeptides or fragments thereof, and polynucleotides encoding thereof that are modified in ways that enhance their anti-neoplastic activity when expressed in an immunoresponsive cell. The presently disclosed subject matter provides methods for optimizing an amino acid sequence or a nucleic acid sequence by producing an alteration in the sequence. Such alterations may comprise certain mutations, deletions, insertions, or post-translational modifications. The presently disclosed subject matter further comprises analogs of any naturally-occurring polypeptide of the presently disclosed subject matter. Analogs can differ from a naturally-occurring polypeptide of the presently disclosed subject matter by amino acid sequence differences, by post-translational modifications, or by both. Analogs of the presently disclosed subject matter can generally exhibit at least about 85%, about 90%, about 91%, about 92%, about 93%, about 94%, about 95%, about 96%, about 97%, about 98%, about 99% or more identity with all or part of a naturally-occurring amino, acid sequence of the presently disclosed subject matter. The length of sequence comparison is at least 5, 10, 15, 20, 25, 50, 75, 100 or more amino acid residues. Again, in an exemplary approach to determining the degree of identity, a BLAST program may be used, with a probability score between $e^{-3}$ and $e^{-100}$ indicating a closely related sequence. Modifications comprise in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the presently disclosed subject matter by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amina acids, e.g., D-amino acids or non-naturally occurring or synthetic amino acids, e.g., beta (β) or gamma (γ) amino acids.

In addition to full-length polypeptides, the presently disclosed subject matter also provides fragments of any one of the polypeptides or peptide domains of the presently disclosed subject matter. A fragment can be at least 5, 10, 13, or 15 amino acids. In some embodiments, a fragment is at least 20 contiguous amino acids, at least 30 contiguous amino acids, or at least 50 contiguous amino acids. In some embodiments, a fragment is at least 60 to 80, 100, 200, 300 or more contiguous amino acids. Fragments of the presently disclosed subject matter can be generated by methods known to those of ordinary skill in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the presently disclosed subject matter. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. The protein analogs can be relatively resistant to in vivo degradation, resulting in a more prolonged therapeutic effect upon administration. Assays for measuring functional activity include, but are not limited to, those described in the Examples below.

In accordance with the presently disclosed subject matter, the polynucleotides encoding an extracellular antigen-binding domain that specifically binds to human mesothelin (e.g., a scFV (e.g., a scFv derived from antibody m912), a Fab, or a (Fab)$_2$), CD3ζ, CD8, CD28, 4-1BB, 4-1BBL, IL-12, Mz, M28z, and MBBz can be modified by codon optimization. Codon optimization can alter both naturally occurring and recombinant gene sequences to achieve the highest possible levels of productivity in any given expression system. Factors that are involved in different stages of protein expression include codon adaptability, mRNA structure, and various cis-elements in transcription and translation. Any suitable codon optimization methods or technologies that are known to ones skilled in the art can be used to modify the polynucleotides of the presently disclosed subject matter, including, but not limited to, OptimumGene™, Encor optimization, and Blue Heron.

In certain embodiments, the extracellular antigen-binding domain of a presently disclosed CAR is a scFv derived from m912 antibody. Codon optimization of the m912 antibody is performed based on four different algorithms (e.g., Blue Heron and Encore algorithms). The codon optimization sequences obtained from all four algorithms are blended, and all CPGs and BAM-H1 are removed for optimal cloning. The codon optimized nucleotide sequence is about 70% homologous to the original m912 scFv. In order to obtain efficient expression in an immunoresponsive cell (e.g., human primary T cells), the codon optimized nucleotide sequence is ligated to a human CD8 leader, e.g, a polynucleotide encoding SEQ ID NO:20. The CD8 leader provides optimal signal cleavage preceding ScFv heavy chain (QVQL). Codon optimization optimize mesothelin CAR expression in an immunoresponsive cell, e.g., multiple human donor primary T cells, with good transduction efficiency. Multiple CAR vector copy numbers in multiple donors T cells are tested for functional efficiency, specificity and sensitivity against multiple hematological and solid cancer cells with varying mesothelin expression. The codon optimized m912-based mesothelin CAR with a vector copy number of 1-4 (more specifically, about 3-4) provides highly efficient cytotoxicity against high mesothelin expressing targets, yet minimal reactivity against low mesothelin expressing targets, i.e. normal tissue, which is a key feature accomplished for vector safety without compromising efficiency. The above-described innovative genetic engineering in generating a specific mesothelin CAR that is reactive against cancer cells expressing high mesothelin while sparing normal tissue expressing low mesothelin is optimal for use as clinical vector for cancer therapy while assuring safety.

VI. Administration

Mesothelin-specific CARs and immunoresponsive cells expressing thereof of the presently disclosed subject matter can be provided systemically or directly to a subject for treating or preventing a neoplasia, pathogen infection, infectious disease, inflammatory disease, or graft rejection. In one embodiment, the MSLN-specific CARs and immunoresponsive cells expressing thereof are directly injected into an organ of interest (e.g., an organ affected by a neoplasia). Alternatively, the MSLN-specific CARs and immunoresponsive cells expressing thereof are provided indirectly to the organ of interest, for example, by administration into the circulatory system (e.g., the tumor vasculature). Expansion and differentiation agents can be provided prior to, during or after administration of cells and compositions to increase production of T cells in vitro or in vivo.

MSLN-specific CARs and immunoresponsive cells expressing thereof of the presently disclosed subject matter can be administered in any physiologically acceptable vehicle, normally intravascularly, although they may also be introduced into bone or other convenient site where the cells may find an appropriate site for regeneration and differentiation (e.g., thymus). Usually, at least $1\times10^5$ cells will be administered, eventually reaching $1\times10^{10}$ or more. A cell population comprising immunoresponsive cells expressing a MSLN-specific CAR can comprise a purified population of cells. Those skilled in the art can readily determine the percentage of immunoresponsive cells in a cell population using various well-known methods, such as fluorescence activated cell sorting (FACS). The ranges of purity in cell populations comprising genetically modified immunoresponsive cells expressing a MSLN-specific CAR can be from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. Dosages can be readily adjusted by those skilled in the art (e.g., a decrease in purity may require an increase in dosage). The immunoresponsive cells can be introduced by injection, catheter, or the like. If desired, factors can also be included, including, but not limited to, interleukins, e.g. IL-2, IL-3, IL 6, IL-11, IL-7, IL-12, IL-15, IL-21, as well as the other interleukins, the colony stimulating factors, such as G-, M- and GM-CSF, interferons, e.g., gamma.-interferon.

Compositions of the presently disclosed subject matter comprise pharmaceutical compositions comprising immunoresponsive cells expressing a MSLN-specific CAR and a pharmaceutically acceptable carrier. Administration can be autologous or non-autologous. For example, immunoresponsive cells expressing a MSLN-specific CAR and compositions comprising thereof can be obtained from one subject, and administered to the same subject or a different, compatible subject. Peripheral blood derived T cells of the presently disclosed subject matter or their progeny (e.g., in vivo, ex vivo or in vitro derived) can be administered via localized injection, including catheter administration, systemic injection, localized injection, intravenous injection, or parenteral administration. When administering a pharmaceutical composition of the presently disclosed subject matter (e.g., a pharmaceutical composition comprising immunoresponsive cells expressing a MSLN-specific CAR), it will generally be formulated in a unit dosage injectable form (solution, suspension, emulsion).

VII. Formulations

Immunoresponsive cells expressing a MSLN-specific CAR and compositions comprising thereof of the presently disclosed subject matter can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions comprising immunoresponsive cells expressing a MSLN-specific CAR of the presently disclosed subject matter in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin. According to the present invention, however, any vehicle, diluent, or additive used would have to be compatible with the immunoresponsive cells expressing a MSLN-specific CAR of the presently disclosed subject matter.

The compositions can be isotonic, i.e., they can have the same osmotic pressure as blood and lacrimal fluid. The desired isotonicity of the compositions of the presently disclosed subject matter may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the immunoresponsive cells as describe in the presently disclosed subject matter. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of the immunoresponsive cells of the presently disclosed subject matter is the quantity of cells necessary to achieve an optimal effect. The quantity of cells to be administered will vary for the subject being treated. In certain embodiments, from about $10^4$ to about $10^{10}$, e.g., from about $10^4$ to about $10^5$, from about $10^4$ to about $10^6$, from about $10^5$ to about $10^6$, from about $10^6$ to about $10^7$, from about $10^7$ to about $10^8$, from about $10^8$ to about $10^9$, from about $10^9$ to about $10^{10}$, from about $10^5$ to about $10^9$, or from about $10^6$ to about $10^8$ of the presently disclosed immunoresponsive cells are administered to a subject. More effective cells may be administered in even smaller numbers. In certain embodiments, at least about $1\times10^4$, at least about $1\times10^5$, from about $1\times10^4$ to about $1\times10^5$ (e.g., about $1\times10^4$, $2\times10^4$, $3\times10^4$, $4\times10^4$, $5\times10^4$, $6\times10^4$, $7\times10^4$, $8\times10^4$, $9\times10^4$, or $1\times10^5$), from about $1\times10^5$ to about $1\times10^6$ (e.g., $1\times10^5$, $2\times10^5$, $3\times10^5$, $4\times10^5$, $6\times10^5$, $7\times10^5$, $8\times10^5$, $9\times10^5$, or $1\times10^6$), or from about $1\times10^6$ to about $1\times10^7$ (e.g., $1\times10^6$, $2\times10^6$, $3\times10^6$, $4\times10^6$, $5\times10^6$, $7\times10^6$, $8\times10^6$, $9\times10^6$ or $1\times10^7$) of the presently disclosed immunoresponsive cells are administered to a subject.

In certain embodiments, at least about $1\times10^8$, about $2\times10^8$, about $3\times10^8$, about $4\times10^8$, and about $5\times10^8$ immunoresponsive cells of the presently disclosed subject matter are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods of the presently disclosed subject matter. Typically, any additives (in addition to the active cell(s) and/or agent(s)) are present in an amount of from about 0.001% to about 50% by weight) solution in phosphate buffered saline, and the active ingredient is present in the order of micrograms to milligrams, such as from about 0.0001 wt % to about 5 wt %, from about 0.0001 wt % to about 1 wt %, from about 0.0001 wt % to about 0.05 wt %, from about 0.001 wt % to about 20 wt %, from about 0.01 wt % to about 10 wt %, or from about 0.05 wt % to about 5 wt %. For any composition to be administered to an animal or human, and for any particular method of administration, toxicity should be determined, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

VIII. Methods of Treatment

Tumor Microenvironment.

Tumors have a microenvironment that is hostile to the host immune response involving a series of mechanisms by malignant cells to protect themselves from immune recognition and elimination. This "hostile tumor microenvironment" comprises a variety of immune suppressive factors including infiltrating regulatory CD4+ T cells (Tregs), myeloid derived suppressor cells (MDSCs), tumor associated macrophages (TAMs), immune suppressive cytokines including IL-10 and TGF-β, and expression of ligands targeted to immune suppressive receptors expressed by activated T cells (CTLA-4 and PD-1). These mechanisms of immune suppression play a role in the maintenance of tolerance and suppressing inappropriate immune responses, however within the tumor microenvironment these mechanisms prevent an effective anti-tumor immune response. Collectively these immune suppressive factors can induce either marked anergy or apoptosis of adoptively transferred CAR modified T cells upon encounter with targeted tumor cells.

Challenges in Tumor Immunology.

Effective tumor immunity requires recognition of tumor antigens and unopposed tumor elimination by immune effector cells. Tumor antigens must contain peptide epitopes that are presented by the tumor and can be recognized by specific cytotoxic T lymphocytes (CTLs). The primed CTLs must expand to a sufficient number and migrate to tumor sites, wherein they mature into effectors to perform their functions, which are enhanced by helper T cells and dampened by Tregs and inhibitory macrophages.

Targeted T Cell Therapy with Engineered T Lymphocytes.

T cell engineering is a groundbreaking strategy to potentially resolve many previously observed shortcomings of earlier immunotherapeutic approaches. Within the past year, researchers have reported dramatic complete remissions in relapsed[10,11], chemorefractory leukemia and metastatic melanoma[12-14], obtained with autologous peripheral blood T cells targeted to a defined antigen (CD19 and NY-ESO-1, respectively).

Rationale for a Genetic Approach:

Cell engineering can be used to redirect T cells toward tumor antigens and to enhance T cell function. One impetus for genetic T cell modification is the potential to enhance T cell survival and expansion and to offset T cell death, anergy, and immune suppression. The genetic targeting of T cells can also be refined to prevent undesired destruction of normal tissues.

Figure 1:
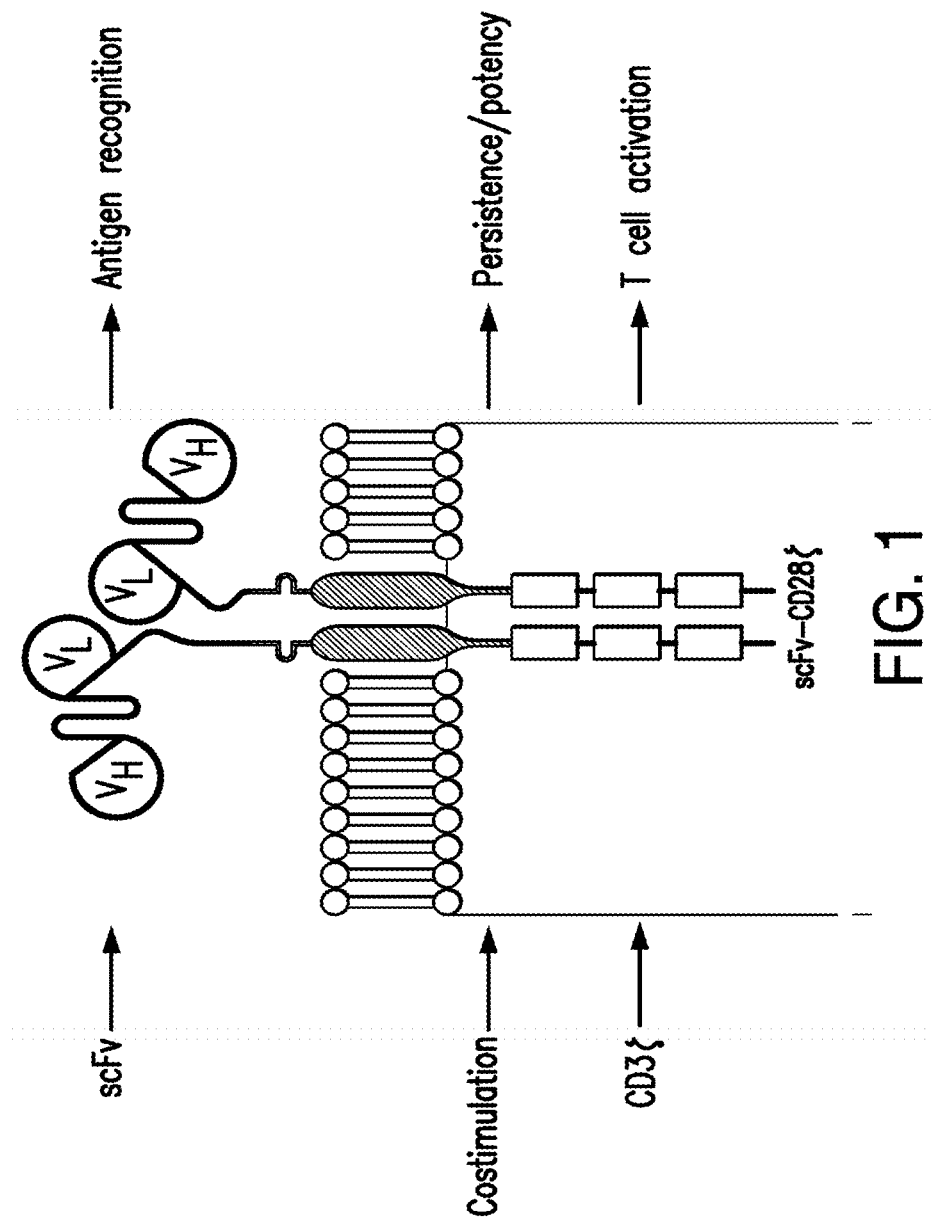
FIG. 1 depicts the "Second Generation" CARs.

Chimeric Antigen Receptors (CARs):

Tumor-specific T cells can be generated by the transfer of genes that encode CARs[15-20]. Second-generation CARs comprise a tumor antigen-binding domain fused to an intracellular signaling domain capable of activating T cells and a co-stimulatory domain designed to augment T cell potency and persistence[21] (see FIG. 1). CAR design can therefore reconcile antigen recognition with signal transduction, two functions that are physiologically borne by two separate complexes, the TCR heterodimer and the CD3 complex. The CAR's extracellular antigen-binding domain is usually derived from a murine monoclonal antibody (mAb) or from receptors or their ligands. Antigen recognition is therefore not MHC-restricted[22-23] and is therefore applicable to any patient expressing the target antigen, using the same CAR. Antigen binding by the CARs triggers phosphorylation of immunoreceptor tyrosine-based activation motifs (ITAMs) in the intracellular domain, initiating a signaling cascade required for cytolysis induction, cytokine secretion, and proliferation. Because MHC restriction of antigen recognition is bypassed, the function of CAR-targeted T cells is not affected by HLA downregulation or defects in the antigen-processing machinery.

T Cell Requirements for Expansion and Survival:

Proliferation of tumor-specific T cells is needed ex vivo and is arguably desirable in vivo. T cell proliferation must be accompanied by T cell survival to permit absolute T cell expansion and persistence. To proliferate in response to antigen, T cells must receive two signals. One is provided by TCR recognition of antigenic peptide/MHC complexes displayed on the surface of antigen-presenting cells (APCs)[19]. The other is provided by a T cell co-stimulatory receptor, such as the CD28 or 4-1BB receptors. Whereas the cytolytic activity of T cells does not require concomitant co-stimulation, there is a critical need for the provision of co-stimulatory signals to sustain the antitumor functions of adoptively transferred T cells, as previously demonstrated[17,21,24-26].

Immune Monitoring:

Lymphocytes are multifunctional "drugs" that exhibit dynamically evolving effects after infusion. Upon antigen encounter, tumor-specific T cells activate and/or release a variety of proteins that can trigger tumor killing, T cell proliferation, and recruitment or immunomodulation of other immune cells. Thus, measuring which proteins are secreted from which cells, in what quantity, and at what time point yields profound insights into why a particular patient is or is not responding and provides critical feedback for designing more-effective trials. These assay systems will permit direct and meaningful comparisons of clinical approaches and thus help design rational, next-generation therapeutic strategies.

For treatment, the amount administered is an amount effective in producing the desired effect. An effective amount can be provided in one or a series of administrations. An effective amount can be provided in a bolus or by continuous perfusion.

An "effective amount" (or, "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

For adoptive immunotherapy using antigen-specific T cells, cell doses in the range of about $10^6$ to about $10^{10}$ (e.g., about $10^9$) are typically infused. Upon administration of the immunoresponsive cells into the subject and subsequent differentiation, the immunoresponsive cells are induced that are specifically directed against one specific antigen (e.g., human mesothelin). "Induction" of T cells can include inactivation of antigen-specific T cells such as by deletion or anergy. Inactivation is particularly useful to establish or reestablish tolerance such as in autoimmune disorders. The immunoresponsive cells of the presently disclosed subject matter can be administered by any methods known in the art, including, but not limited to, pleural administration, intravenous administration, subcutaneous administration, intranodal administration, intratumoral administration, intrathecal administration, intrapleural administration, intraperitoneal administration, and direct administration to the thymus. In one embodiment, the immunoresponsive cells and the compositions comprising thereof are pleurally administered to the subject in need.

The presently disclosed subject matter provides various methods of using the immunoresponsive cells (e.g., T cells) expressing a mesothelin-specific CAR. For example, the presently disclosed subject matter provides methods of reducing tumor burden in a subject. In one non-limiting example, the method of reducing tumor burden comprises administering an effective amount of the presently disclosed immunoresponsive cell to the subject, thereby inducing tumor cell death in the subject. The presently disclosed immunoresponsive cell can reduce the number of tumor cells, reduce tumor size, and/or eradicate the tumor in the subject. The tumor can be a solid tumor. Non-limiting examples of solid tumor include mesothelioma, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, and cholangiocarcinoma.

The presently disclosed subject matter also provides methods of increasing or lengthening survival of a subject having neoplasia. In one non-limiting example, the method of increasing or lengthening survival of a subject having neoplasia comprises administering an effective amount of the presently disclosed immunoresponsive cell to the subject, thereby increasing or lengthening survival of the subject. The method can reduce or eradicate tumor burden in the subject. Additionally, the presently disclosed subject matter provides methods for increasing an immune response in a subject, comprising administering the presently disclosed immunoresponsive cell to the subject. The presently disclosed subject matter further provides methods for treating or preventing a neoplasia in a subject, comprising administering the presently disclosed immunoresponsive cell to the subject.

As used herein, the term "neoplasia" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells). In one embodiment, the neoplasia is a solid tumor. The neoplasia can a primary tumor or primary cancer. In addition, the neoplasia can be in metastatic status.

Cancers whose growth may be inhibited using the immunoresponsive cells of the presently disclosed subject matter comprise cancers typically responsive to immunotherapy. Non-limiting examples of cancers for treatment include mesothelioma, lung cancer (e.g. non-small cell lung cancer), pancreatic cancer, ovarian cancer, breast cancer (e.g., metastatic breast cancer, metastatic triple-negative breast cancer), colon cancer, pleural tumor, glioblastoma, esophageal cancer, gastric cancer, synovial sarcoma, thymic carcinoma, endometrial carcinoma, stomach cancer, and cholangiocarcinoma. Additionally, the presently disclosed subject matter comprises refractory or recurrent malignancies whose growth may be inhibited using the immunoresponsive cells of the presently disclosed subject matter.

Examples of other neoplasias or cancers that may be treated using the methods of the presently disclosed subject matter include bone cancer, intestinal cancer, liver cancer, skin cancer, cancer of the head or neck, melanoma (cutaneous or intraocular malignant melanoma), renal cancer (e.g. clear cell carcinoma), throat cancer, prostate cancer (e.g. hormone refractory prostate adenocarcinoma), blood cancers (e.g. leukemias, lymphomas, and myelomas), uterine cancer, rectal cancer, cancer of the anal region, bladder cancer, brain cancer, stomach cancer, testicular cancer, carcinoma of the fallopian tubes, carcinoma of the endometrium, carcinoma of the cervix, carcinoma of the vagina, carcinoma of the vulva, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, include Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, hepatoma, nile duct carcinoma, choriocarcinoma, seminoma, embryonal carcinoma, Wilm's tumor, cervical cancer, uterine cancer, testicular cancer, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

Additionally, the presently disclosed subject matter provides methods of increasing immune-activating cytokine production in response to a cancer cell or a pathogen in a subject. In one non-limiting example, the method comprises administering the presently disclosed immunoresponsive cell to the subject. The immune-activating cytokine can be granulocyte macrophage colony stimulating factor (GM-CSF), IFN-α, IFN-β, IFN-γ, TNF-α, IL-2, IL-3, IL-6, IL-11, IL-7, IL-12, IL-15, IL-21, interferon regulatory factor 7 (IRF7), and combinations thereof. In certain embodiments, the immunoresponsive cells including a mesothelin-specific CAR of the presently disclosed subject matter increase the production of GM-CSF, IFN-γ, and/or TNF-α.

The presently disclosed subject matter provides therapies that are particularly useful for treating solid tumors (e.g., mesothelioma, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, and cholangiocarcinoma). Solid tumors can be primary tumors or tumors in metastatic state. Certain solid tumors are heterogeneous MSLN expressing tumors, e.g., breast cancer (e.g., TNBC), lung cancer, ovarian cancer, pancreatic cancer, esophagus cancer, colon cancer, gastric cancer, and malignant pleural mesothelioma (MPM). Heterogeneous MSLN expressing cells (e.g., tumor cells) are a population of cells comprising low MSLN-expressing cells and high MSLN-expressing cells. The presently disclosed immunoresponsive cell can exhibit increased cytotoxicity and antitumor activity to low MSLN-expressing cells (e.g., about 2,000 or less, about 1,000 or less, about 900 or less, about 800 or less, about 700 or less, about 600 or less, about 500 or less, about 400 or less, about 300 or less, about 200 or less, or about 100 or less MSLN binding sites/cell), in the presence of high MSLN− expressing cells. See for example, Example 2. In certain embodiments, even in the presence of high MSLN-expressing cells, immunoresponsive cell does not exhibit increased cytotoxicity or nonspecific kill to MSLN-negative cells. Thus, the immunoresponsive cell can exhibit exhibit increased cytotoxicity and antitumor activity to low MSLN-expressing cells in the presence of high MSLN-expressing cells while retain safety to MSLN-negative cells.

Suitable human subjects for therapy typically comprise two treatment groups that can be distinguished by clinical criteria. Subjects with "advanced disease" or "high tumor burden" are those who bear a clinically measurable tumor. A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in the presently disclosed subject matter is administered to these subjects to elicit an anti-tumor response, with the objective of palliating their condition. Ideally, reduction in tumor mass occurs as a result, but any clinical improvement constitutes a benefit. Clinical improvement comprises decreased risk or rate of progression or reduction in pathological consequences of the tumor.

A second group of suitable subjects is known in the art as the "adjuvant group." These are individuals who have had a history of neoplasia, but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasia. Features typical of high-risk subgroups are those in which the tumor has invaded neighboring tissues, or who show involvement of lymph nodes.

Another group has a genetic predisposition to neoplasia but has not yet evidenced clinical signs of neoplasia. For instance, women testing positive for a genetic mutation associated with breast cancer, but still of childbearing age, can wish to receive one or more of the antigen-binding fragments described herein in treatment prophylactically to prevent the occurrence of neoplasia until it is suitable to perform preventive surgery.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

Furthermore, the presently disclosed subject matter provides methods for treating subjects with a pathogen infection (e.g., viral infection, bacterial infection, fungal infection, parasite infection, or protozoal infection). The presently disclosed subject matter is particularly useful for enhancing an immune response in an immunocompromised subject. Exemplary viral infections susceptible to treatment using a method of the invention include, but are not limited to, Cytomegalovirus (CMV), Epstein Barr Virus (EBV), Human Immunodeficiency Virus (HIV), and influenza virus infections. Accordingly, the presently disclosed subject matter provides a method of treating or preventing a pathogen infection in a subject, the method comprising administering an effective amount of the immunoresponsive cells expressing a mesothelin-specific CAR of the presently disclosed subject matter.

In accordance with the presently disclosed subject matter, the above-described various methods can comprise administering at least one immunomodulatory agent. Non-limiting examples of immunomodulatory agents include immunostimulatory agents, checkpoint immune blockade agents, radiation therapy agents, and chemotherapy agents. In certain embodiments, the immunomodulatory agent is an immunostimulatory agent. Non-limiting examples of immunostimulatory agents include IL-12, and agonist costimulatory monoclonal antibodies. In one embodiment, the immunostimulatory agent is IL-12. In certain embodiments, the immunoresponsive cell of the presently disclosed subject matter in combination with anti-IL-12 antibody can be used to treat breast cancer (BC), e.g., metastatic triple-negative breast cancer (TNBC). Non-limiting examples of agonist costimulatory monoclonal antibodies include anti-4-1BB antibodies, anti-OX40 antibodies, and anti-ICOS antibodies. In one embodiment, the agonist costimulatory monoclonal antibody is an anti-4-1BB antibody.

An essential aspect of the presently disclosed subject matter is to not merely generate tumor-targeted (e.g., mesothelin-specific) T cells for adoptive therapy but to enhance T cell function through the design of improved antigen receptors and through intervention in the host microenvironment by immunomodulation using IL-12. Among all immunotherapeutic approaches, IL-12, a multifunctional cytokine, has been considered to be one of the most promising approaches to treat BC[59-61]. IL-12 is considered a master regulator of adaptive type 1 cell-mediated immunity, the critical pathway involved in antitumor responses[62]. IL-12 modulates antitumor responses at various levels, including polarization of CD4 T cells toward a Th1 phenotype[63], boosting of T cell and NK effector functions[64], remodeling the innate immune response[65], and regulating tumor angiogenesis[66]. The immunomodulating and antiangiogenic functions of IL-12 have provided the rationale for using this cytokine in combination with the immunoresponsive cell of the presently disclosed subject matter for treating cancers, e.g., BC (e.g., TNBC). Among 148 clinical trials including administration of IL-12 to patients with cancer (36 of which were reported recently), successful phase II studies with intraperitoneal[67,68] or subcutaneous[69,70] IL-12 have shown that paracrine secretion of IL-12, generated by gene transfer, can induce immunity against the tumor locally and at a distant site. Although several studies have documented the anticancer effectiveness of IL-12 in preclinical models of breast cancer (BC)[59,61,71], the significant toxicity resulting from administration of recombinant human IL-12 observed in several clinical trials in advanced cancers precludes its clinical use. To overcome this limitation, a number of groups have demonstrated that intratumoral delivery of IL-12, using adenoviral vectors, induces tumor regression and T cell activation in preclinical models of BC[72],7[3]. More recently, Sabel et al. used polylactic acid microspheres to release IL-12 into the tumor and found that the antitumor response was mediated primarily by NK cells[74]. Others have used mesenchymal stromal cells to locally deliver IL-12 to mouse BC[75]. A phase I trial of paclitaxel and trastuzumab, in combination with IL-12, in patients with HER2/neu-expressing malignancies showed an impressive synergy between IL-12 and trastuzumab for stimulation of NK-cell cytokine secretion[76]. Therefore, IL-12 can have considerable promise as an anticancer agent, and its use as a co-stimulant in an adoptive T cell therapy approach is well-justified.

In certain embodiments, the immunomodulatory agent is a checkpoint immune blockade agent. Non-limiting examples of checkpoint immune blockade agents include anti-PD-L1 antibodies, anti-CTLA-4 antibodies, anti-PD-1 antibodies, anti-LAG3 antibodies, anti-B7-H3 antibodies, and anti-TIM3 antibodies. In one embodiment, the checkpoint immune blockade agent is an anti-PD-L1 antibody. In certain embodiments, the immunoresponsive cell of the presently disclosed subject matter in combination with anti-PD-L1 antibody can be used to treat breast cancer (BC), e.g., TNBC.

Programmed cell death ligand 1 (PD-L1/B7-H4/CD274) is an inhibitory signal typically expressed in actively inflamed tissues, serving as a negative feedback loop to limit T cell activation. PD-L1 expression is typically absent from uninflamed normal tissues (including breast[77]) and is instead most prevalent in cancer tissues, particularly in those with an inflammatory infiltrate[78]. This association with inflammation is likely due to PD-L1 upregulation upon tumor cell exposure to T cell-secreted cytokines generated upon T cell activation. This pattern of expression is exhibited by BCs, with 50%-75% of BC specimens staining positive for PD-L1[79-81] and with expression strongly associated with severe lymphocytic infiltrate[80]. BC-infiltrating T cells also expressed PD-L1 in 54% of patients.[81] BCs may also innately express PD-L1 secondary to oncogenic signaling. Activation of the PI(3)K pathway results in PD-L1 protein upregulation in BC cells, and PI(3)K activation in patient tumors significantly correlates with PD-L1 expression[82]. The expression of PD-1 by activated T cells spatially and temporally links ligand with receptor expression within the immunosuppressive TME. Expression of PD-L1 in BC tissues suggests it as an immunotherapeutic target for these patients. Efficacy of PD-L1/PD-1 blockade in multiple preclinical cancer models (including breast[83]) paved the way for phase I trials using PD-L1- or PD-1-targeting antibodies for patients with advanced cancers. A phase I study (using a PD-1 antibody) demonstrated efficacy only in PD-L1+ patients[84]. Genetically engineered T cells offer unique advantages for overcoming co-inhibitory checkpoints and the typical lack of co-stimulation found within the TME. CAR-expressing T cells are indeed engineered to optimize their co-stimulatory requirements to support T cell expansion, survival, and function.

In some embodiments, the immunomodulatory agent is a radiation therapy agent. The localized, radiation-induced immunological milieu not only can provide the preconditions to enhance the engraftment of targeted T cells in the tumor (thereby eliminating the need for systemic lymphodepleting regimens), but that the immunological responses resulting from a combination of radiation therapy and adoptive T cell therapy also enhance abscopal antitumor efficacy. In radiation-resistant tumors, 4-1BB co-stimulatory signaling in CAR T cells can overcome immunoinhibition. In some embodiments, the immunomodulatory agent is a chemotherapy agents, including, but not limited to, cisplatin.

Cisplatin-induced secretion of chemokines and cytokines can promote MSLN– targeted and endogenous T-cell responses.

Studies have shown that patients with lung adenocarcinoma (LAC) and malignant pleural mesothelioma (MPM) who present with high levels of cytotoxic tumor infiltrating lymphocytes (cTILs) and low levels of regulatory T cells (Tregs) have a better prognosis and longer progression-free survival (Servais, et al., Clin Cancer Res (May 1, 2012); 18:2478-2489; Kachala et al., Clin Cancer Res (2013); 20(4); 1020-8). An adoptive T-cell therapy using a MSLN-targeted CAR can be used to promote cTILs in LAC and MPM. Servais (2012) and Kachala (2013) report that MSLN is over-expressed and promotes aggressiveness in LAC and MPM—justifying the choice of MSLN as a target for CAR T-cell therapy. The higher proportion of TILs following cisplatin and radiation therapy are associated with improved outcomes both in mouse models and in patients (FIGS. 32, 33 and 34).

Tumor radiation- and cisplatin therapy-induced tumoral and abscopal immunomodulation can provide the preconditioning required for better engraftment of adoptively transferred T cells; T-cell co-stimulatory strategies to exploit the tumor and stromal immunomodulation can potentiate the antitumor efficacy of both endogenous and adoptively transferred T cells.

Additionally, the above-described various methods of using the immunoresponsive cells (e.g., T cells) expressing a mesothelin-specific CAR, e.g., for treating cancer in a subject, or for reducing tumor burden in a subject, can be combined with cancer cell antigen modulation. Immunoresponsive cells (e.g., T cells) expressing a mesothelin-specific CAR can target and kill the MSLN expressed on the membrane (referred to as "cell membrane MSLN") of a tumor or cancerous cell but not cytoplasmic MSLN. Certain tumors or cancers (e.g., lung cancer, and mesothelioma) have low cell membrane MSLN, but high cytoplasmic MSLN. Cancer cell antigen modulation can increase the expression of cell membrane MSLN in a tumor or cancerous cell, which can make the tumor or cancerous cell more likely be targeted by the CAR-expressing immunoresponsive cell, and thus, more susceptible to the killing by the immunoresponsive cell. In one embodiment, the cancer cell antigen modulation is radiation.

Further modification can be introduced to the mesothelin-specific CAR-expressing immunoresponsive cells (e.g., T cells) to avert or minimize the risks of immunological complications (known as "malignant T-cell transformation"), e.g., graft versus-host disease (GvHD), or when healthy tissues express the same target antigens as the tumor cells, leading to outcomes similar to GvHD. A potential solution to this problem is engineering a suicide gene into the CAR-expressing T cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In one embodiment, the suicide gene is an EGFRt polypeptide. The EGFRt polypeptide can enable T cell elimination by administering anti-EGFR monoclonal antibody (e.g., cetuximab). EGFRt can be covalently joined to the 3' terminus of the intracellular domain of the MSLN-specific CAR (e.g., Mz, M28z, MBBz), as shown in FIG. 25. The suicide gene can be included within the vector comprising nucleic acids encoding the presently disclosed mesothelin-specific CARs. In this way, administration of a prodrug designed to activate the suicide gene (e.g., a prodrug (e.g., AP1903 that can activates iCasp-9) during malignant T-cell transformation (e.g., GVHD) triggers apoptosis in the suicide gene-activated CAR-expressing T cells.

In addition, the presently disclosed subject matter provides a method of preventing or treating an inflammatory disease in a subject. In one non-limiting example, the method comprises administering the presently disclosed immunoresponsive cell to the subject. In one embodiment, the immunoresponsive cell is an immunoinhibitory cell. In one non-limiting example, the immunoinhibitory cell is a regulatory T cell. In one embodiment, the inflammatory disease is pancreatitis. In one embodiment, the subject is a human. In one specific embodiment, the subject is a recipient of an organ transplant, e.g., a recipient of a pancreas transplant.

Furthermore, the presently disclosed subject matter provides a method of preventing graft rejection in a subject who is a recipient of an organ transplant. In one non-limiting example, the method comprises administering the presently disclosed immunoresponsive cell to the subject. In one embodiment, the immunoresponsive cell is an immunoinhibitory cell. In one non-limiting example, the immunoinhibitory cell is a regulatory T cell. In one embodiment, the subject is a human. In a further embodiment, the subject is a recipient of a pancreas transplant.

A presently disclosed mesothelin-specific CAR can be transduced into an immunoinhibitory cell, e.g., a regulatory T cell. The transduced immunoinhibitory cell can be administered to a subject (e.g., a human) having inflammatory conditions or an inflammatory disease. In some embodiments, the inflamed site or the site of the inflammatory disease has a high expression level of mesothelin, which is recognized by the presently disclosed MSLN-CAR. The inflammatory condition can be extreme, e.g., severe pancreatitis. In addition, the transduced immunoinhibitory cell can be administered to a subject who is a recipient of an organ transplant.

Additionally, a presently disclosed MSLN-specific CAR as well as a second CAR targeting an MHC antigen can be co-transduced into an immunoinhibitory cell (e.g., regulatory T cell) so that the immunoinhibitory cell can specifically collect at the site of the transplanted pancreas. In one example, a MHC class I subject receives a pancreas transplant from a MHC class II donor; the regulatory T cells of the recipient are transduced with the presently disclosed MSLN-specific CAR and a second CAR targeting a MHC class II antigen, and thus, the transduced regulatory T cells of the recipient collect/pool at the site of the transplanted pancreas and avoid graft or organ rejection.

IX. Kits

The presently disclosed subject matter provides kits for the treatment or prevention of a neoplasia, pathogen infection, immune disorder or allogeneic transplant. In one embodiment, the kit comprises a therapeutic or prophylactic composition containing an effective amount of an immunoresponsive cell comprising a mesothelin-specific CAR in unit dosage form. In particular embodiments, the cells further comprise a co-stimulatory ligand. In some embodiments, the kit comprises a sterile container which contains a therapeutic or prophylactic vaccine; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired, the immunoresponsive cell is provided together with instructions for administering the cell to a subject having or at risk of developing a neoplasia, pathogen infection, immune disorder or allogeneic transplant. The instructions will generally include information about the use of the composition for the treatment or prevention of neoplasia, pathogen infection, immune disorder or allogeneic transplant. In other embodiments, the instructions include at least one of the following: description of the therapeutic agent; dosage schedule and administration for treatment or prevention of a neoplasia, pathogen infection, immune disorder or allogeneic transplant or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Examples

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1—Working Example

1. Introduction

Cancer antigen targeted T-cell therapy using chimeric antigen receptors (CARs) has enjoyed recent clinical success in treating hematologic malignancies. Translating CAR T cell therapy to solid tumors poses several obstacles that must be overcome to achieve clinical benefit. Solid tumors are restricted within anatomical compartments that impede efficient T-cell trafficking, typically lack expression of co-stimulatory ligands, and express negative regulators of T cell function. Therefore, elimination of solid tumors relies on the successful infiltration of T cells able to surmount tumor-mediated immunosuppression.

Engineering activating co-stimulatory signaling into antigen-specific chimeric receptors can counteract the immunosuppressive tumor microenvironment to ensure T-cell proliferation and survival. The ability of co-stimulatory signaling to enhance anti-tumor efficacy is attributed to a concerted effort among $CD4^+$ and $CD8^+$ T cell subsets. Traditionally, $CD8^+$ T cells are thought to play the primary role in eliminating cancer cells while $CD4^+$ T cells provide the helper cytokines necessary for $CD8^+$ effector formation and prevention of $CD8^+$ T cell exhaustion. More recently, the appreciation that $CD4^+$ T cells can themselves mediate potent anti-tumor efficacy highlights an evolving role for this subset in tumor immunotherapy. Chimeric antigen receptors may be uniquely suited for effective recruitment of $CD4^+$ T cells into all aspects of the antitumor response. CAR T cells recognize cell surface tumor antigen, bypassing the need for MHC Class II expression lacking in the majority of tumors. In addition, their antibody-derived antigen recognition domain provides the high binding affinity necessary for $CD4^+$ T cell mediated lysis.

To promote efficient T cell delivery to tumor in an orthotopic model of pleural mesothelioma, T cells was directed administered into the pleural cavity. It was hypothesized that pleurally administered $CD4^+$ CAR T cells would be able to directly lyse tumor and in concert with an enhanced proliferative capacity imparted by CD28 co-stimulation should themselves mediate all functions necessary for in vivo tumor elimination. This Example demonstrates efficient $CD4^+$ mediated tumor cell lysis equal in magnitude to $CD8^+$ CAR T cells and a unique ability of $CD4^+$ CAR T cells to secrete IL-2 and expand upon repeated in vitro antigen stimulations. Pleurally administered $CD4^+$ T cells genetically targeted to mesothelin undergo a robust proliferation and sole transfer of these cells results in rejection of large established pleural tumor. Furthermore, $CD4^+$ CAR T cells migrate out of the pleural cavity and establish long-term tumor immunity, as demonstrated by their ability to generate a response to extrapleural tumor rechallenge. Altogether, both in vitro and in vivo studies support the use of regional CAR T-cell administration to overcome obstacles posed by solid tumors. This Example demonstrates that generation of multifunctional $CD4^+$ T cells capable of T-cell help and cytotoxicity provides a particular advantage to the use of CAR+ T cell therapy for the treatment of solid tumors.

2. Materials and Methods

Cell Lines

MSTO-211H (human pleural mesothelioma) and EL4 (murine thymoma) were both obtained from American Type Culture Collection, ATCC. MSTO-211H cells were retrovirally transduced to express the green fluorescent protein/firefly luciferase fusion protein (MSTO GFP-ffLuc+) to facilitate noninvasive in vivo bioluminescent imaging. These cells were then transduced with the human MSLN-variant 1 (isolated from a human ovarian cancer cell line (OVCAR-3)) subcloned into a SFG retroviral vector to generate MSTO $MSLN^+$ GFP-ffLuc$^+$.

Gammaretroviral Vector Construction and Viral Production

To generate mesothelin-specific chimeric antigen receptors, a fusion protein encoding a fully human scFv, m912, ligated to a human CD8 leader peptide at its N-terminus was engineered. Using gammaretroviral vectors as backbone constructs, this scFv was exchanged to generate first (SFG-Mz) and second generation (SFG-M28z) mesothelin-specific constructs by directional cloning using a NcoI site located 5' of the scFv and a NotI site located 3' of the scFv. An internal ribosomal entry site was inserted to facilitate bicistronic expression of CARs with humanized recombinant green fluorescent protein (hrGFP) reporter gene. SFG-Mz, SFG-M28z, and SFG-P28z were then transfected into 293T H29 packaging cell lines and this viral supernatant was used to transduce and generate stable 293T RD114 cell lines.

T-Cell Isolation, Gene Transfer, and CD4/CD8 Isolation

Peripheral blood leukocytes were isolated from the blood of healthy volunteer donors under an institutional review board-approved protocol. PHA-activated peripheral blood mononuclear cells (PBMC) were isolated by low-density centrifugation on Lymphoprep (Accurate Chemical & Scientific Corporation, NY). Two days after isolation, PBMCs were transduced with 293T produced supernatant containing Mz, M28z, or P28z vectors for 1 hour on plates coated with 15 μg/ml retronectin (Takara Biomedical, Otsu, Japan) daily for 2 days. After allowing 3 d for vector expression, transduced PBMCs were maintained in 20 units/ml IL-2. Transduction efficiencies were determined by flow cytometry.

Pure populations of CD4 and CD8 T-cells were obtained through negative selection protocols using Dynabeads® Untouched™ Human CD4 & CD8 T Cells isolation kits, as per the manufacture's instructions (Invitrogen, CA). Isolated cells were either used immediately in experiments or cultured in RPMI 1640 supplemented with 10% FBS, 100 units/mL penicillin, 100 g/mL streptomycin. For in vivo experiments, media was also supplemented with 20 units/mL of IL-2.

Cytotoxicity Assays

Cytotoxicity of T cells transduced with a chimeric antigen receptor or vector control were determined by a standard $^{51}$Cr-release assays. In 96 well round bottom plates, $1\times10^6$ total T cells in 200 ul of RPMI with 10% FCS, 100 units/mL penicillin, and 100 ug/mL streptomycin were serially diluted 1:2 in 100 ul of media. Target cells were incubated with 100 μCi $^{51}$Cr per $1\times10^6$ cells for 2 hours and resuspended at a final concentration of $5\times10^3$ cells/100 μl. After three washes with media, 100 μl of the target cells were added to the T-cells and incubated for 4 to 24 hours in a 5% $CO_2$ humidified incubator at 37° C. For experiments using MSLN-stimulated CD4 cells, CD4 effectors and targets were incubated in a total volume of 100 ul for four hours and was added to the cytotoxicity assay as described above with effectors and targets suspended in 100 ul for a total volume of 200 ul. In experiments adding exogenous IL-2, cells were incubated in a final media with a final concentration of 10-40 units/mL. Supernatants were collected, plated on 96-well Lumina plates (PerkinElmer, Calif.) and measured on a PerkinElmer TopCount (PerkinElmer, Calif.). Spontaneous $^{51}$Cr release was evaluated in target cells incubated with medium alone and maximal $^{51}$Cr release was determined with target cells incubated in 100 ul of 0.2% Triton-X 100. Percent specific lysis was calculated as follows: [(cpm experimental release−cpm spontaneous release)/(cpm maximal release−cpm spontaneous release)]×100. Data are reported as the mean of triplicate measurements+/− SEM and were analyzed with Microsoft Excel (Microsoft Corp., WA) or GraphPad Prism (GraphPad Software, Inc., CA).

T-Cell Isolation, Gene Transfer, and CD4/CD8 Isolation

Human primary T lymphocytes were isolated from the blood of healthy volunteer donors under an institutional review board-approved protocol. PHA-activated peripheral blood mononuclear cells (PBMC) were isolated by low-density centrifugation on Lymphoprep (Accurate Chemical & Scientific Corporation, NY). Two days after isolation, PBMCs were transduced using retroviral vectors encoding for M28zG, M2zG, or human recombinant green fluorescent protein (hrGFP) in 6-well non-tissue culture plates (Falcon, Becton Dickinson, N.J.) coated with 15 μg/ml retronectin (Takara Biomedical, Otsu, Japan) as per the manufacturer's instructions, with viral supernatants daily for 2 days by spinoculation at 3000 rpm at 24° C. for 1 hour. Transduced PBMCs were maintained in RPMI-1640 supplemented with 10% FBS, 100 units/mL penicillin, 100 μg/mL streptomycin, and 20 units/ml IL-2. Pure populations of CD4 and CD8 T-cells were obtained through negative selection protocols using Dynabeads® Untouched™ Human CD4 & CD8 T Cells isolation kits, as per the manufacture's instructions (Invitrogen, CA). Isolated cells were either used immediately in experiments or cultured in RPMI 1640 supplemented with 10% FBS, 100 units/mL penicillin, 100 g/mL streptomycin. For in vivo experiments, media was also supplemented with 20 units/mL of IL-2.

Orthotopic Pleural Mesothelioma Animal Model and Adoptive T-Cell Therapy

To develop the orthotopic mouse model of pleural mesothelioma, female NOD/SCID gamma (Taconic, N.Y.) at 6-10 weeks of age were utilized. All procedures were performed under approved Institutional Animal Care and Use Committee protocols. Mice were anesthetized using inhaled isoflurane and oxygen and administered bupivacaine for analgesia. Direct intrapleural injection of $1\times10^5$-$1\times10^6$ tumor cells in 200 μL serum-free media via a right thoracic incision was performed to establish orthotopic MPM tumors as previously described[35,37,39,40]. $3\times104$-$3\times10^6$ transduced T cells were adoptively transferred into tumor bearing mice with in an injection of 200 μL of serum-free media into the thoracic cavity of mice by direct pleural injection or systemically by tail vein injection. For experiments with the administration of exogenous IL-2, mice were treated were administered three intraperitoneal doses of 100,000 units IL-2 daily beginning the day following adoptively transferred T-cell administration.

Cytokine Detection Assays

Cytokine release assays were performed by coculturing $5\times10^5$-$5\times10^3$ T cells transduced with M28zG, M2zG, or control vector with 5×103 target cells in 200 ul of media in 96-well round bottom plates as triplicates. After 6-24 hours of co-culture supernatants were collected. Cytokine levels were determined using multiplex bead Human Cytokine Detection kits (EMD Millipore Corp., MA) for IL-2, IL-4, IL-6, IL-10, IL-17, MIP-1, MCP-1, RANTES, GM-CSF, TNF-α, and, IFN-γ on a Luminex IS 100 system. Values represent the mean of the triplicate wells and error bars represent standard error of measurement (SEM). Resulting data was analyzed with IS 2.3 software (Luminex Corp, TX), Microsoft Excel (Microsoft Corp., WA), and GraphPad Prism (GraphPad Software, Inc., CA).

T-Cell Proliferation Assays $1\times10^6$-$3\times10^6$ T-cells transduced with M28zG, M2zG, or hrGFP were stimulated over irradiated MSTO-211H cells with or without MSLN expression were that were plated in 6-well tissue culture plates at a density of $1\times10^5$-$3\times10^5$ cells/3 mL/well. Fresh RPMI-1640 media supplemented with 10% FBS, 100 units/mL penicillin, 100 ug/mL streptomycin, and 20-40 units/ml IL-2. Cells were counted every 7 days and then overlaid on irradiated MSTO-211H cells with or without MSLN expression. Cell number versus time was plotted for each T-cell group and phenotypes determined by flow cytometry.

Histology and Immunostaining

Histopathological evaluation of tumors was performed following hematoxylin and eosin staining of paraffin-embedded, 4% paraformaldehyde fixed tissue samples. For angiogenesis, CD34 rat monoclonal antibody (5 ug/ml, eBioscience) was incubated for 7 hours, followed by 16 minutes with (1:200) biotinylated rabbit anti-rat IgG (Vector Labs, Cat. #BA-4000). Rat IgG2a (5 ug/ml) was used as an appropriate isotype negative control. For lymphangiogenesis, goat polyclonal LYVE-1 antibody (1 µg/ml; R&D Systems) was incubated for 3 hours, followed by 60 minutes with biotinylated rabbit anti-goat IgG (ABC kit from Vector labs). The protocols for immunofluorescence detection using Tyramide-Alexa Fluor 488 (Invitrogen) or Tyramide-Alexa Fluor 568(Invitrogen) for CD34 and LYVE-1, respectively, were established and performed at the MSKCC Molecular Cytology Core Facility using a Discovery XT automatic processor (Ventana Medical Systems). Immunohistochemistry for human MSLN was performed with a mouse anti-human MSLN IgG (1:100, Vector Labs, CA) using the Ventana platform.

Quantitative and T-Cell Bioluminescence Imaging

In vivo BLI in tumor-bearing mice was performed using a single intraperitoneal dose of 150 mg/kg D-Luciferin. Mice were imaged with the Xenogen IVIS 100 Imaging System (Caliper Life Sciences, MA), 20 minutes following D-Luciferin injection. Images were acquired for 5-30 seconds depending on signal strength. BLI data were analyzed using Living Image 2.60 software and BLI signal reported as total flux (photons/s). BLI flux (photon/s) was then determined as the average of ventral and dorsal images with Microsoft Excel (Microsoft Corp., WA) and analyzed with GraphPad Prism (GraphPad Software, Inc., CA).

T-cells transduced with M28zG and an enhanced firefly luciferase reporter gene were adoptively transferred into mice by a single intrapleural injection. Following transfer, T-cells were imaged with a single intravenous a single intraperitoneal dose of 150 mg/kg D-Luciferin and imaged for 120 seconds 20 minutes after injection with a Xenogen IVIS 100 Imaging system.

3. Results

Mesothelin-Targeted CD28 Co-Stimulation Enhances CAR T Cell Function

Figure 2A:
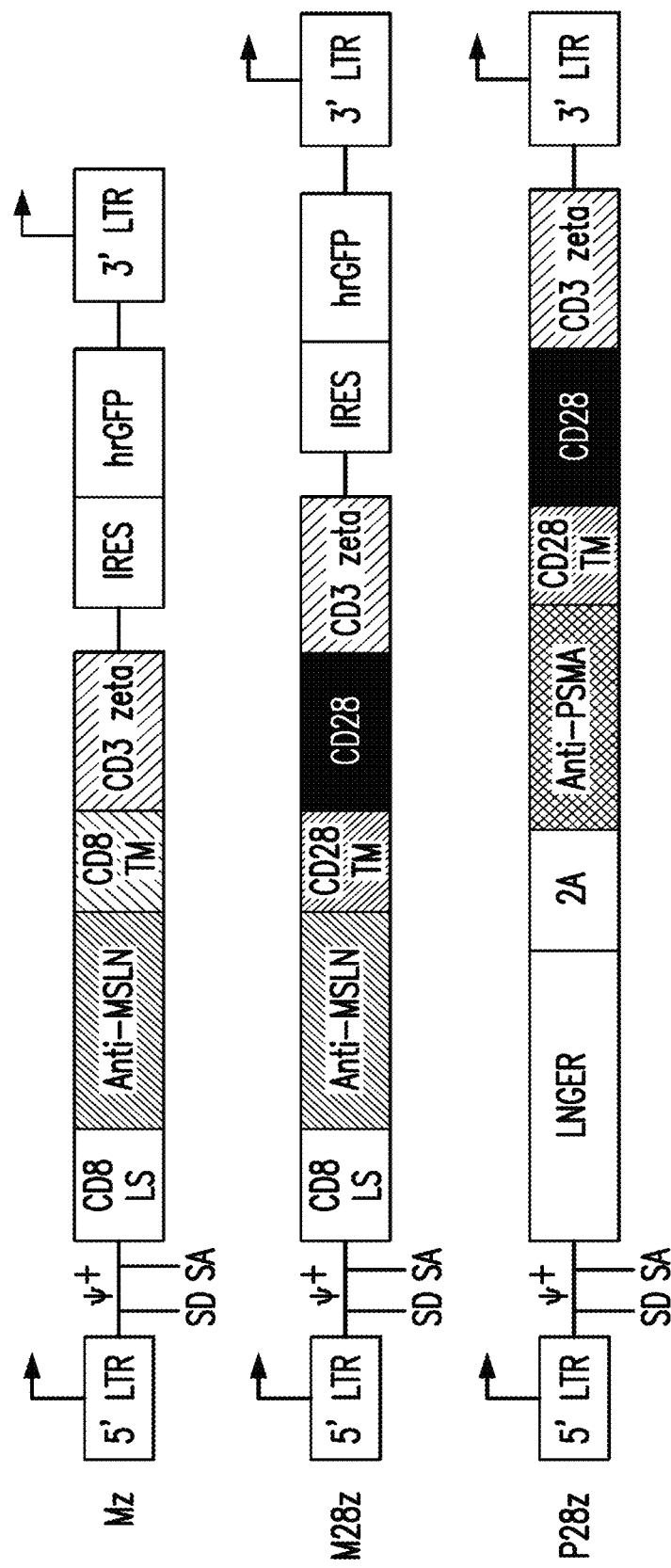
FIGS. 2A-2F depict in vitro effector function of mesothelin-specific constructs. (A) Generation of mesothelin-specific constructs. Anti-mesothelin constructs contain either the CD3 ζ endodomain alone (Mz) or in combination with the CD28 co-stimulatory domain (M28z). A PSMA-directed CAR (P28z) with CD28 co-stimulation was included in experiments as a negative control. (B) Both $CD4^+$ and $CD8^+$ T-cell subsets are efficiently transduced with CARs. Transduction percentages represent reporter gene expression as measured by flow cytometry. M28z and Mz CAR were detected via green fluorescent protein (GFP) reporter gene expression. T cells expressing the P28z CAR were detected via low-affinity nerve growth factor (LNGFR) reporter gene expression. Untransduced cells were used to set positive gates after a live/dead stain excluded nonviable cells. $CD4^+$ and $CD8^+$ percentages are reported after gating for $CAR^+$ cells. (C) Mesothelin-specific T cells demonstrate antigen-specific lysis. T cells were incubated at indicated effector/target ratios with 51Cr-loaded MSTO-211H target cells transduced to over-express mesothelin (MSTO $MSLN^+$) and target cell lysis (chromium release) was measured. Error bars represent s.e.m. of the mean of three replicates. (D) CD28 co-stimulation enhances antigen-specific cytokine secretion. Control transduced or T cells transduced with Mz or M28z were stimulated with either un-transduced MSTO-211H cells (MSTO Empty) or MSTO $MSLN^+$ cells and cytokines were measured using Luminex bead array. (E) CD28 co-stimulation facilitates robust T-cell accumulation upon repeated antigen stimulation. T cells were co-cultured with MSTO Empty or MSTO $MSLN^+$ tumor cells (arrows indicate re-stimulation with freshly irradiated tumor cells). Left, antigen stimulation without the addition of exogenous IL-2. Right, exogenous IL-2 added (20 IU/mL). Absolute $CAR^+$ T-cell numbers were calculated at indicated time intervals using manual hemocytometer counts corrected by $GFP^+$ percentage determined by flow cytometry. Error bars represent s.e.m. of the mean of three replicates. (F) T cells transduced with mesothelin-specific CARs attain a 62L-effector phenotype upon successive antigenic stimulations. Serial multicolor flow cytometric analysis of $CAR^+$ T cells following each antigen stimulation.
Figure 2B:
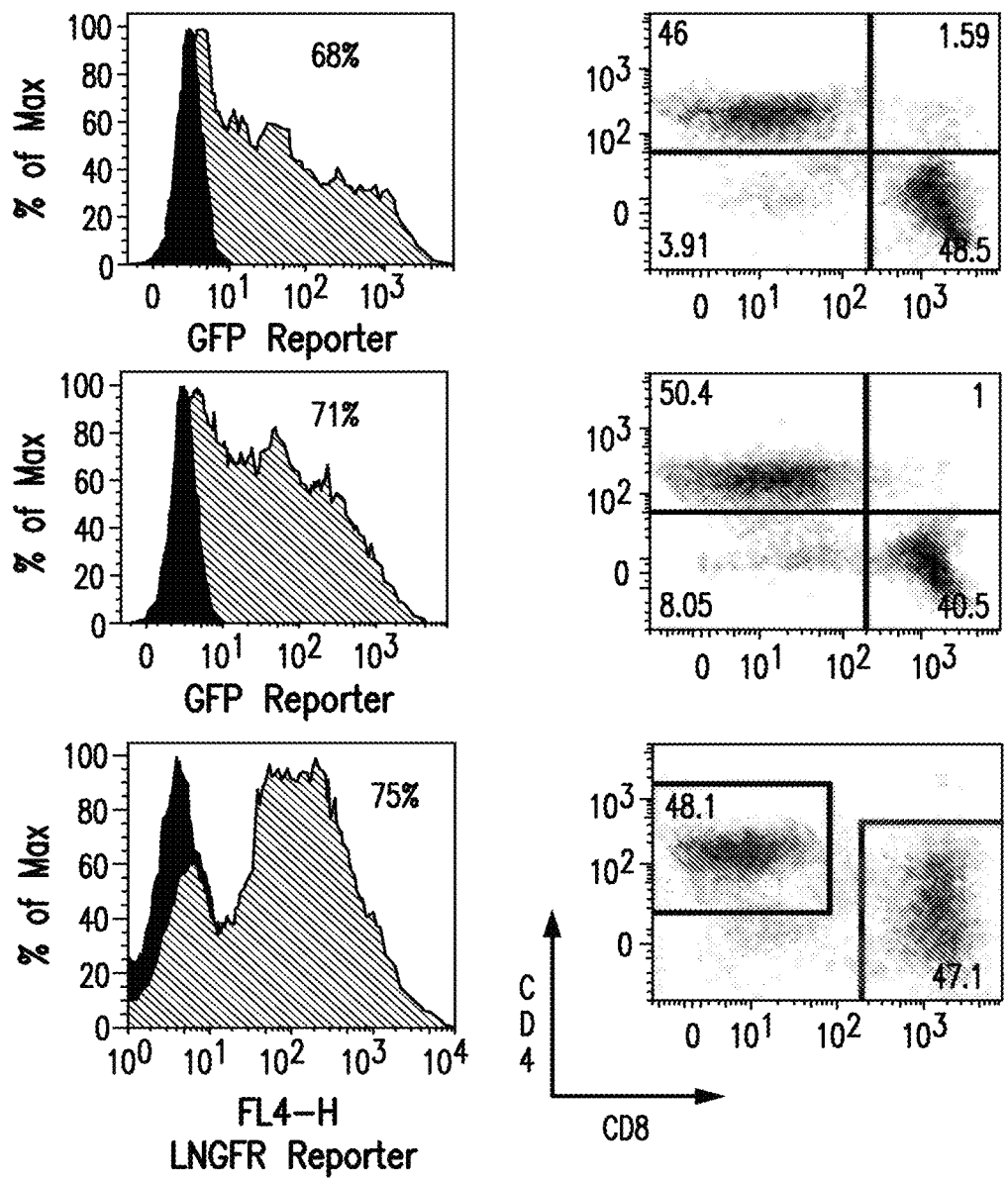

To generate mesothelioma-reactive T cells, peripheral blood human T cells were retrovirally transduced with mesothelin-specific chimeric antigen receptors (CARs). Mesothelin-specific antigen recognition was provided by the m912 scFv fused to downstream T-cell signaling domains providing either CD3ζ signaling alone (Mz) or in tandem with CD28 co-stimulatory signaling (M28z) (FIG. 2A). Mz and M28z transduction efficiency was monitored through a GFP reporter transgene linked to CAR expression by an IRES element. GFP signal was highly correlated with protein-L binding to the human scFv of the CAR demonstrating its reliability as a reporter. A negative control conferring specificity to an irrelevant antigen was included in all experiments. Both CD4$^+$ and CD8$^+$ subsets of primary human T cells were efficiently transduced with chimeric receptors to equivalent frequencies of 60-70% for experiments (FIG. 2B).

Figure 2C:
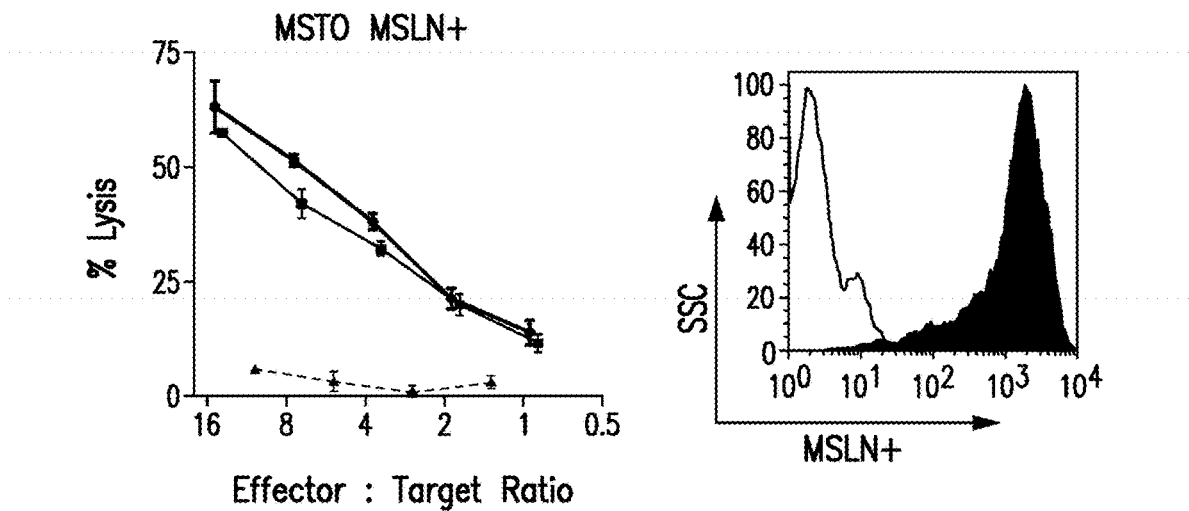

To assess mesothelin-specific effector functions of Mz and M28z CAR transduced T cells, in vitro T-cell responses in three standard assays were investigated. As a target cell line, MSTO-211H mesothelioma cancer cell line (which lacks expression of endogenous CD80/86 co-stimulatory ligands) transduced to overexpress mesothelin (MSTO MSLN$^+$) was used. In a chromium release assay to measure cytotoxicity, Mz and M28z CAR T cells demonstrated equivalent mesothelin-specific lysis upon 18 hour coculture with MSTO MSLN+ tumor cells (FIG. 2C). The observation of equal lysis when comparing $1^{st}$ and $2^{nd}$ generation receptors reproduces data available for other chimeric receptors.

Figure 2D:
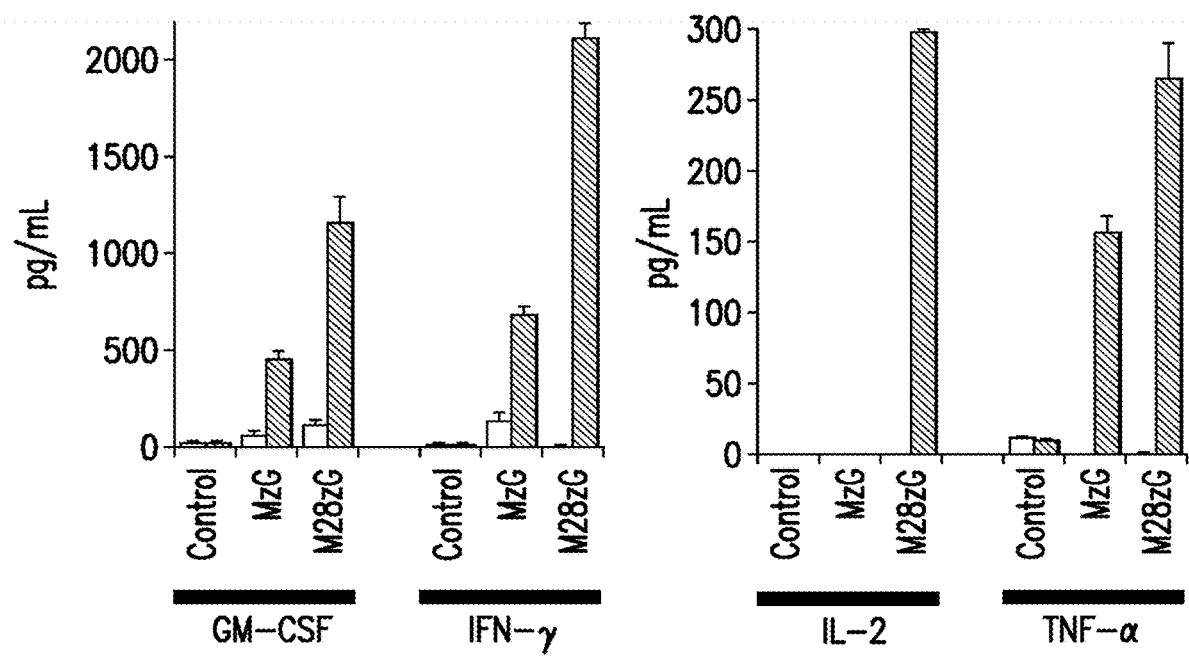

The beneficial effects of co-stimulation were typically seen when measuring cytokine secretion and proliferation, findings confirmed in model system. M28z CAR T cells secreted an approximately two-fold greater amount of GM-CSF, IFN-γ, and TNF-α when compared to Mz T cells. IL-2 secretion, a cytokine crucial for T-cell survival and proliferation, was uniquely provided by the M28z receptor (FIG. 2D). T cells transduced with a negative control receptor and mesothelin-specific cells stimulated by mesothelin-negative tumor cells did not demonstrate cytotoxicity nor secrete cytokines, demonstrating the need for antigen specificity for all anti-tumor effector functions.

Figure 2E:
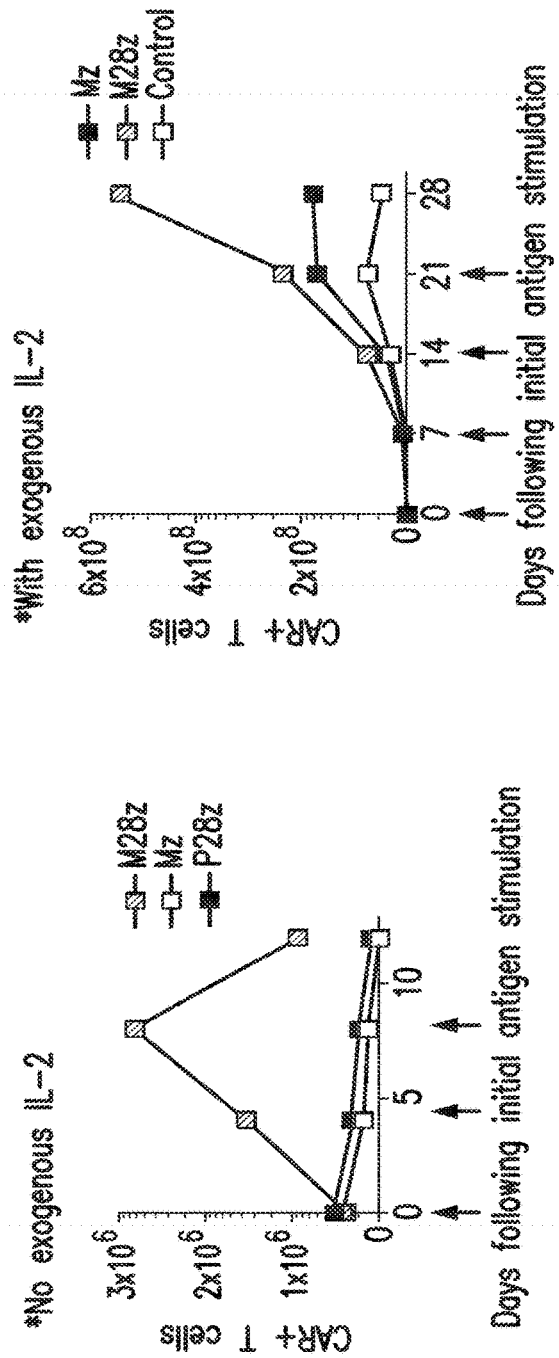
Figure 2F:
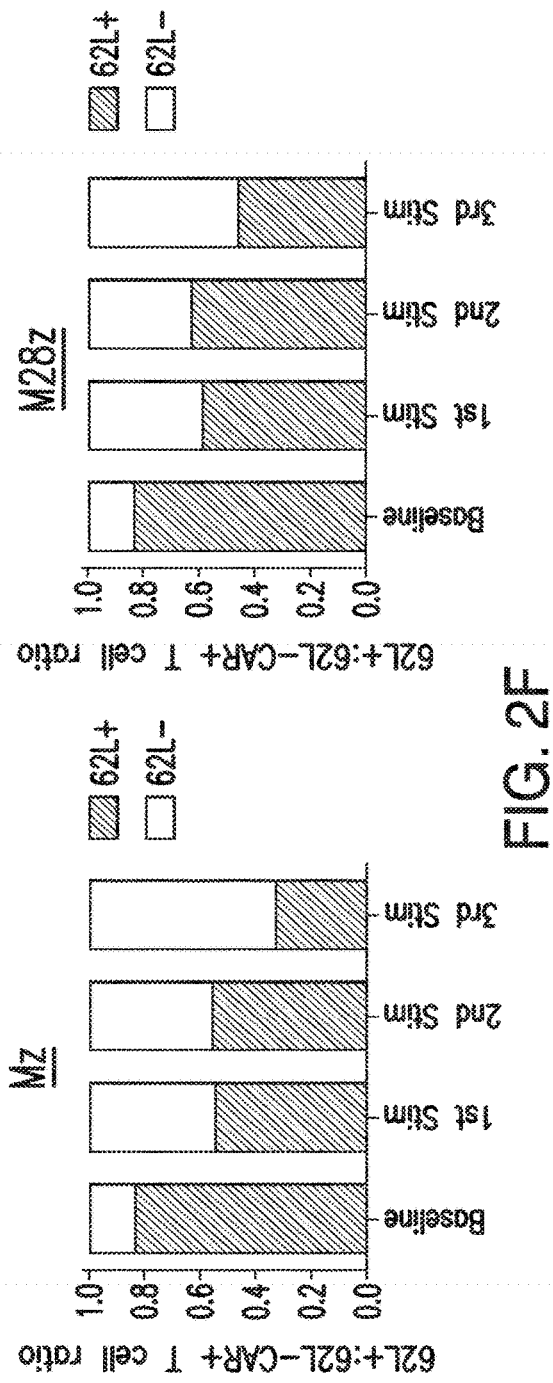

To assess whether CD28 co-stimulation provided in cis to antigen recognition can provide T-cell accumulation in the absence of tumor cell co-stimulatory ligand expression, the expansion of Mz and M28z CAR T cells upon repeated antigen stimulation with MSTO MSLN$^+$ tumor cells was quantified. In the presence of exogenous IL-2, T cells transduced with mesothelin-specific receptors expanded, with CD28 costimulated cells achieving a 180 fold expansion after four weeks in culture with weekly antigen stimulation. This robust proliferative response was 3 fold greater than that achieved by Mz CAR T cells (FIG. 2E, left). Furthermore, in the absence of exogenous IL-2, a model system providing a more vigorous test of T-cell ability to survive and proliferate, only M28z CAR T cells were able to accumulate. Co-stimulated T cells were able to survive and proliferate upon two successive antigen stimulations before undergoing cell death-induced decline in T cell number seen following the third stimulation (FIG. 2E, right). Mz and M28z CAR T cells were enriched for GFP positivity upon successive stimulation and attained an effector/differentiated L-selectin negative T-cell phenotype upon successive stimulation (FIG. 2F).

Pleurally Administered M28z Transduced T Cells Eradicate Pleura Tumor

Figure 3B:
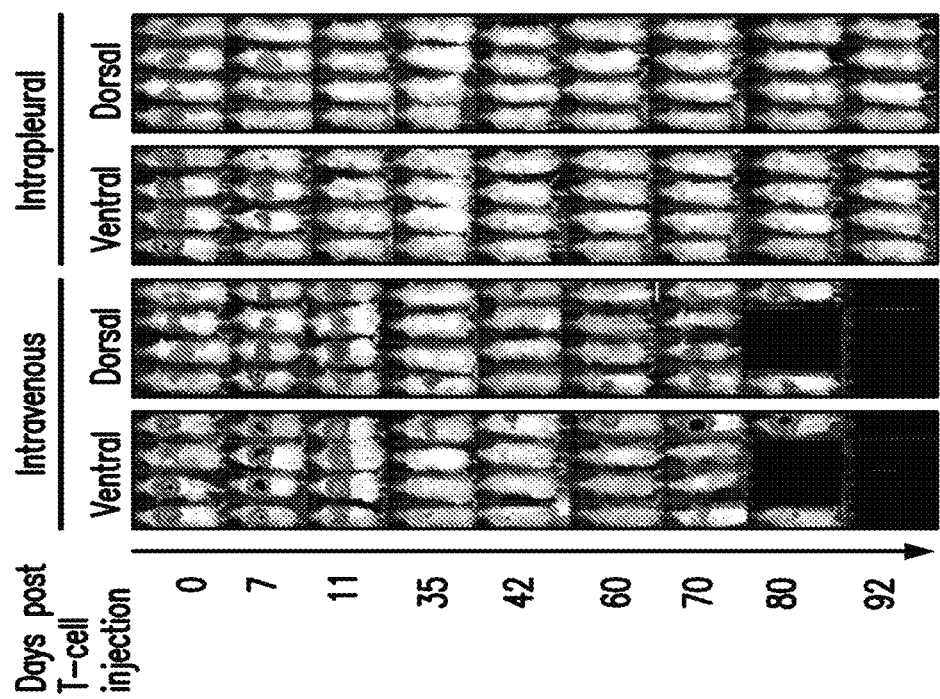
FIGS. 3A-3E depict eradication of established $MSLN^+$ pleural tumor following intrapleural administration of M28z T cells. (A) Mouse model of orthotopic malignant pleural mesothelioma recapitulates human disease. Magnetic resonance image and photograph of macroscopic lesions in mice injected with $1\times10^5$ MSTO MSLN+ tumor cells 5 weeks after tumor inoculation (top left and right image respectively). All mice have tumor growing along the pleural and diaphragmatic surfaces and encasing the mediastinal structures. Bottom, representative hematoxylin and eosin (H&E) stain of chest wall sections demonstrating early chest wall invasion by the tumor (bottom left) as well as sustained mesothelin expression (bottom right). (B) Serial in vivo tumor bioluminescence imaging (BLI) of NOD/SCID/$\gamma_c^{null}$ mice (NSG) mice bearing pleural tumor. MSTO $MSLN^+$ tumor cells co-express green fluorescent protein/firefly-luciferase fusion protein (GFP/Luc) to allow imaging. Following establishment of intrapleural tumor, mice were treated with adoptive transfer of either $3\times10^6$ M28z T lymphocytes intravenously or $3\times10^5$ M28z T lymphocytes (a 10-fold lower dose) intrapleurally, and $3\times10^5$ T cells bearing the human PSMA-targeting chimeric antigen receptor P28z were pleurally injected as a negative control. Shown are 4 representative mice from each group. Mice were imaged both ventrally and dorsally. BLI signal intensities are shown in photons/second. (C) BLI tumor signal quantified per animal every week over a period of 100 days. Each line corresponds to one animal, with each dot representing the average photon count of the ventral and dorsal acquisition per animal at a given time point. (D) Kaplan-Meier survival analysis comparing intravenously administered M28z T cells (n=4, blue dashed line) have decreased survival compared with intrapleurally administered $M28z^+$ T cells (n=7, blue line) (92d vs. nd, p=0.02). Results confirmed on multiple repeat experiments. (E) Treatment of animals after tumor inoculation.
Figure 3A:
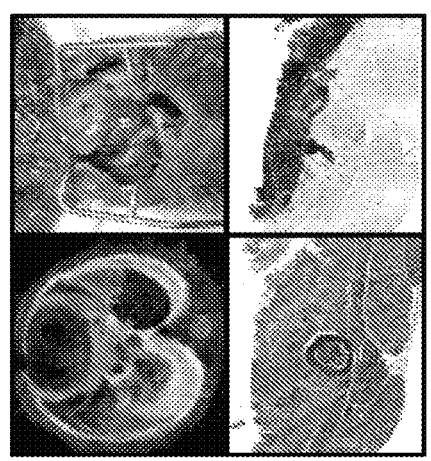
Figure 3C:
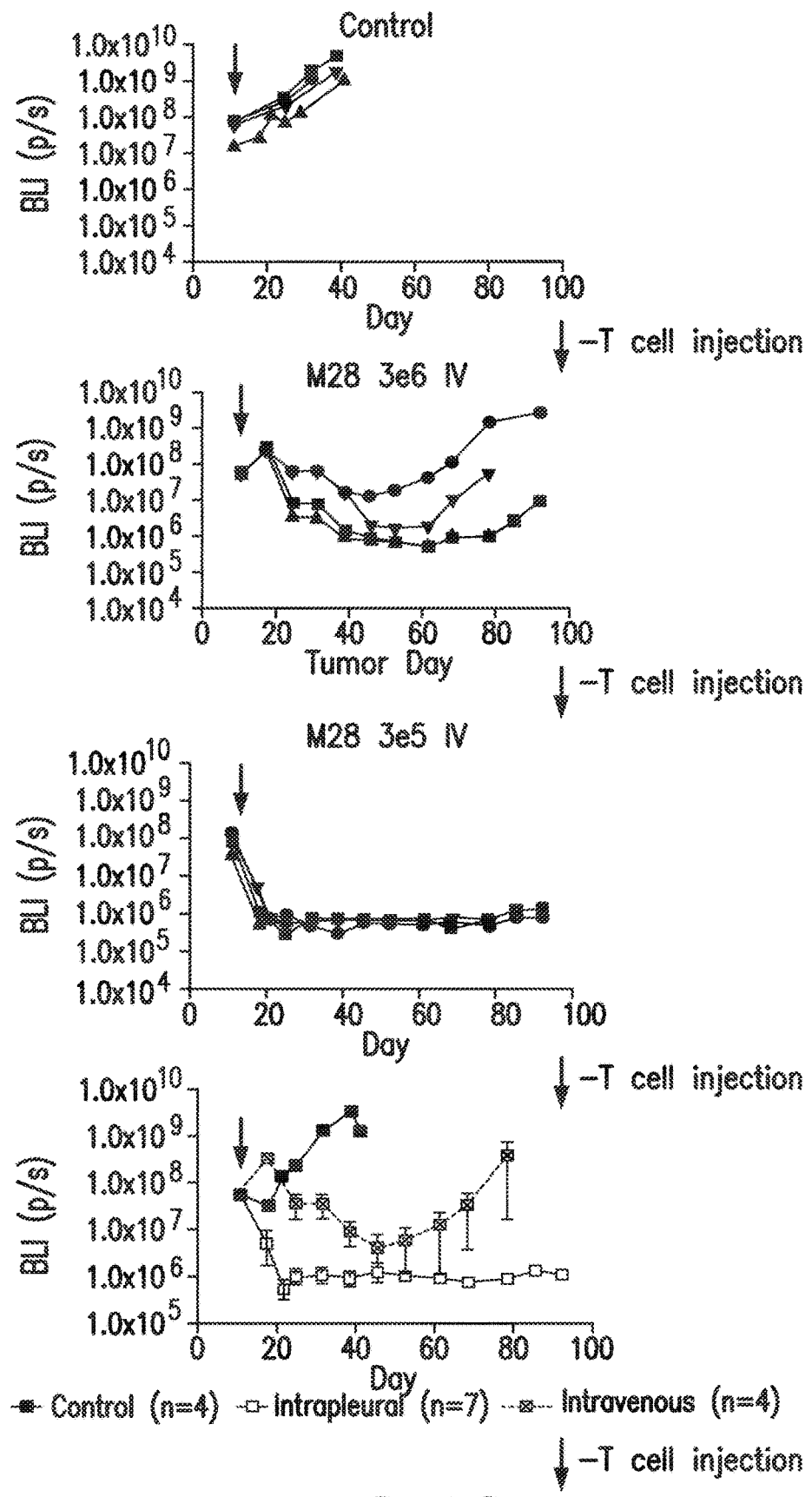

To investigate the potency of M28z T cells in vivo, an orthotopic model of malignant pleural mesothelioma using MSTO-211H tumor cells as previously described was developed. Tumor cells were inoculated directly into the pleural cavity, and given sufficient time (>10 days) to establish a large tumor burden prior to initiation of therapy. Tumor spreaded locally along the pleural surface (MRI, FIG. 3A top left), compressed mediastinal structures (FIG. 3A, top right), and invaded the chest wall (FIG. 3A, bottom). This pattern recapitulated human disease. Serial BLI was used to confirm tumor establishment prior to initiating adoptive T-cell therapy, and was used subsequently to measure response to therapy. In this experiment, animals were treated 12 days after tumor inoculation with either a single intravenous infusion of 3×10$^6$ or a single pleural administration of 3×10$^5$ mesothelin-targeted T cells. In control mice treated with 3×10$^5$ PSMA-targeted T cells, which, did not lyse MSLN$^+$ tumor targets in vitro (FIG. 2B), the tumor burden steadily progressed until the mice die (FIGS. 3B and 3C). Treatment with intravenous M28z T cells resulted in a delayed, short-lived reduction in the tumor burden, followed by terminal tumor progression (FIG. 3B), yielding a modest 44-d survival advantage (P=0.0051, FIG. 3D). Pleurally administered M28z T cells induced major responses. Tumor burdens were significantly lower by day 7 and at baseline by T cell day 11 (FIG. 3B). Median survival was not reached in this group (p=0.0013 compared to IV). Two of 7 treated animals were tumor free 200 days after pleural administration of M28z T cells, but no animals in any of the other treatment or control groups achieved complete tumor clearance (FIG. 3C). The other four mice treated initially showed marked tumor regression before relapsing with antigen negative tumor cells 100 days after T cell therapy (FIG. 3B).

Pleurally Administered T-Cell Expansion is Robust and Antigen Specific

Figure 4A:
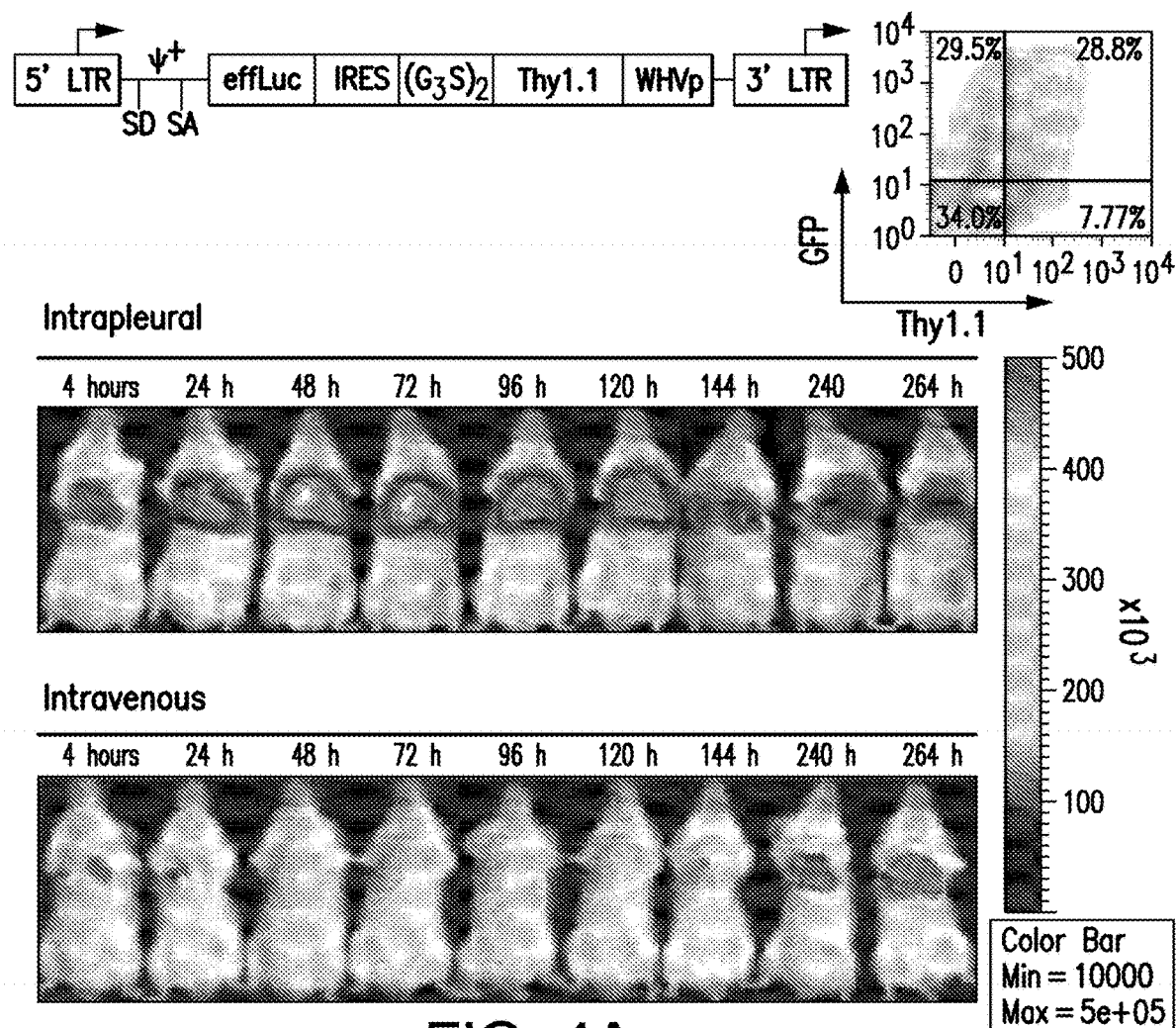
FIGS. 4A-4F depict robust, tumor antigen-dependent, in vivo accumulation of pleurally administered $M28z^+$ T cells. (A) Comparative in vivo T-cell BLI of adoptively transferred T cells in MSTO MSLN+ tumor-bearing NSG mice on 0 to 10 d after pleural or intravenous administration of $1\times10^6$ T cells co-transduced with enhanced firefly luciferase (effLuc) (vector shown at top) and M28z CAR. T cells were administered 1 week after the intrapleural injection of $1\times10^6$ MSTO $MSLN^+$ tumor cells. One representative mouse per group (n=3-4) is shown. (B) EffLuc-luciferase signal intensities from sequential BLI after T cell transfer for a 10-d period. Each line represents the average signal of 3-4 mice, with each dot showing the average photon count of the ventral and dorsal acquisition per animal per group at a given time point. Notably, pleurally administered $effLuc^+$ M28z T cells display an increased and sustained luminescence compared to intravenously administered $effLuc^+$M28z T cells which show initial pulmonary retention and delayed signal emission within the tumor in the pleural cavity. (C) Multicolor flow cytometric analysis of a tumor single-cell suspension prepared from representative animals 3 d after either pleural or intravenous M28z T cell administration. Cells were stained with antibodies for human CD3 and CAR positivity was determined by the GFP reporter expression, further analysis included CD4/CD8/CD62L/CD45RA. (D) Immunohistochemistry of M28z T cells. (E) Absolute tumor infiltrating M28z T cell numbers (total cell counts using countbright beads). Shown bar graphs represent the mean±s.e.m. of three mice per group showing a robust accumulation of M28z T cells 7 days following pleural administration. Mice treated with intravenous T cells at the same dose demonstrate less accumulation within the pleural tumor. (F) Absolute tumor infiltrating M28z T cells numbers in spleen 3 days and 7 days following pleural administration.
Figure 4B:
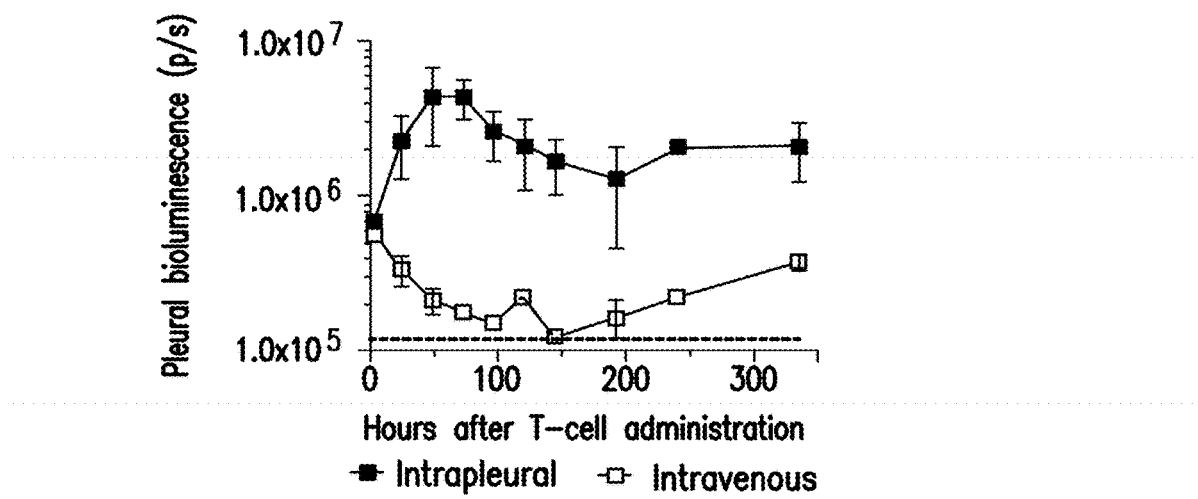
Figure 4C:
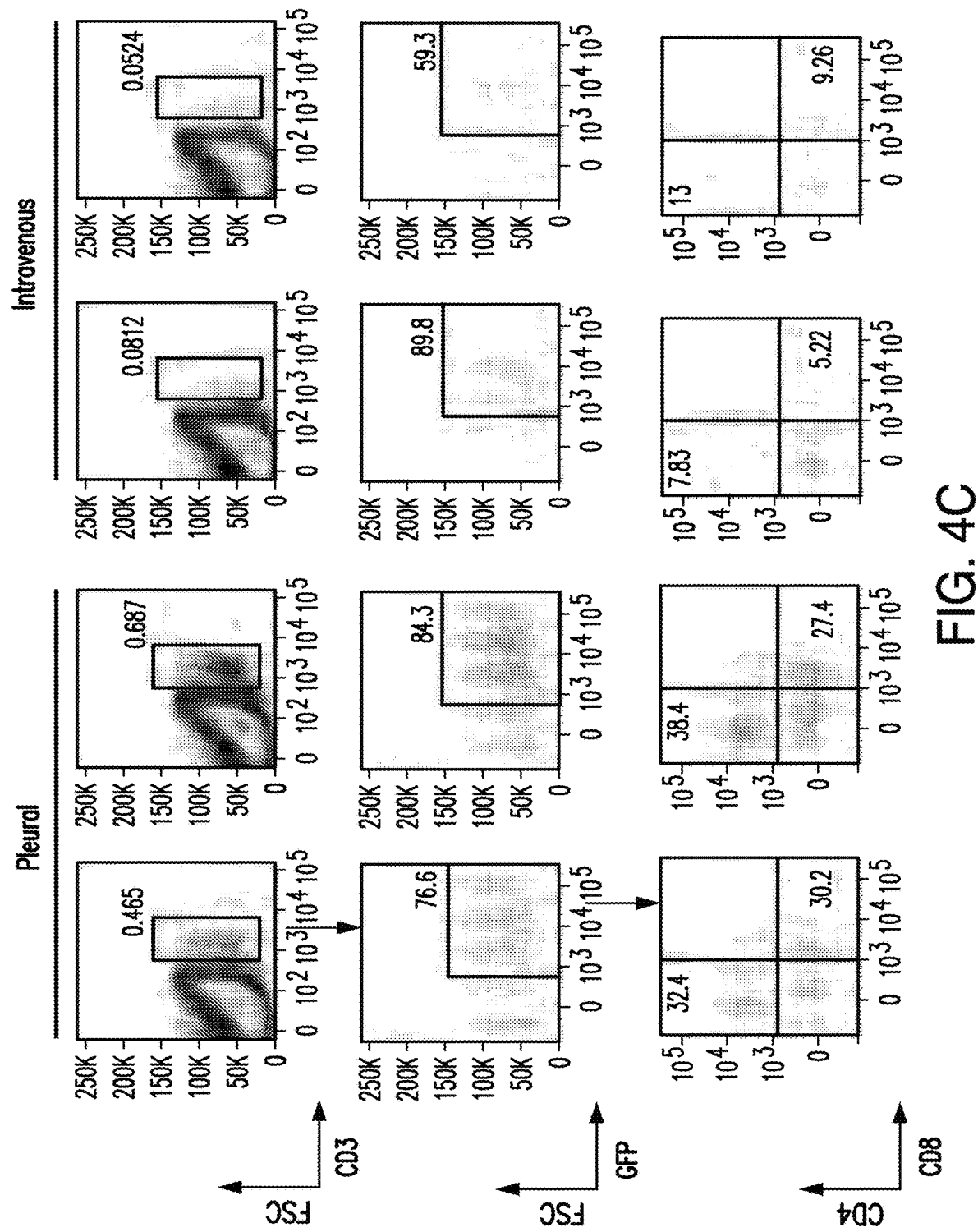
Figure 4D:
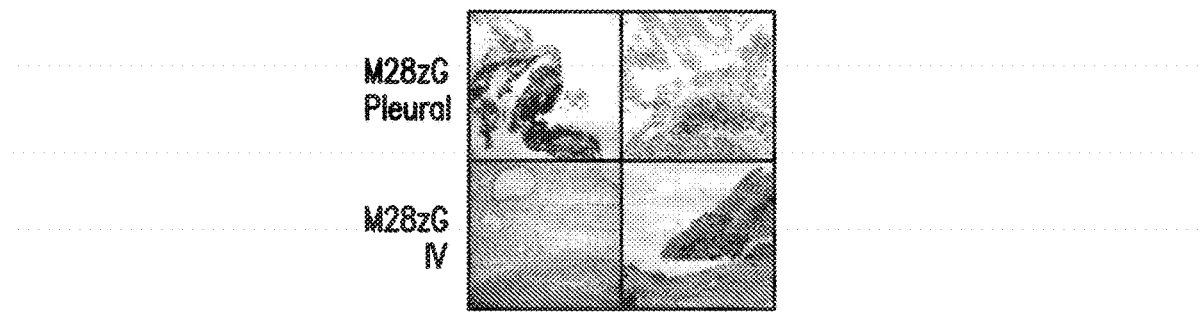
Figure 4E:
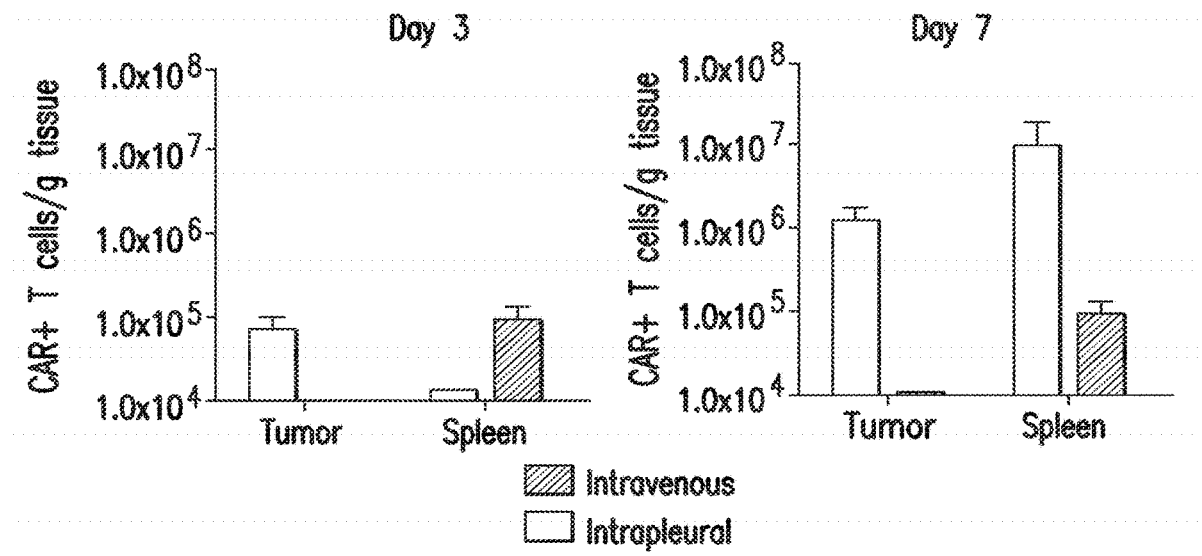
Figure 4F:
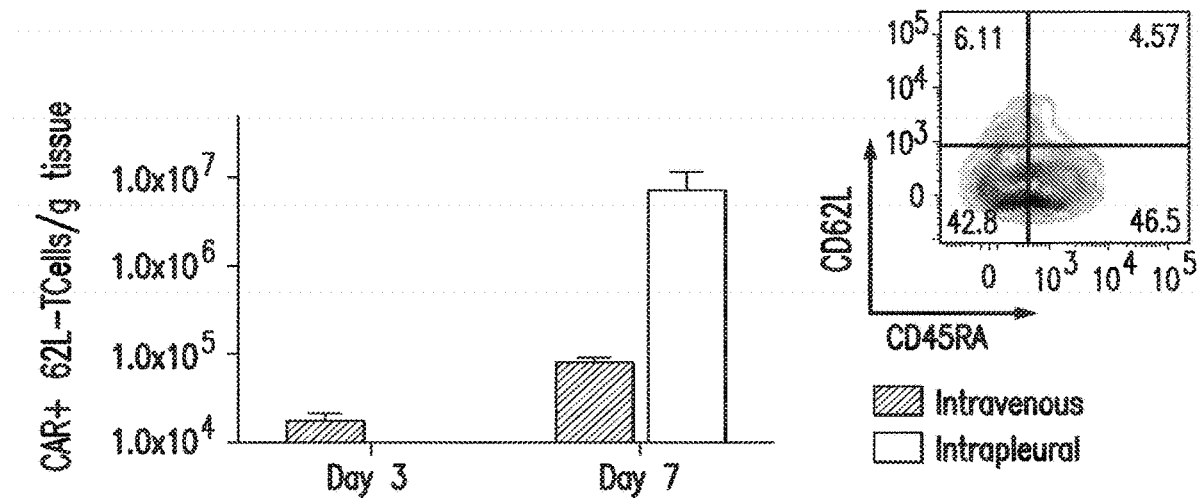

These observations led to investigation on whether there was a difference in T-cell expansion and tumor localization between intrapleural and intravenous administration. To this end, the previously described animal model was used where tumor is confined to the pleural space. All mice were treated with T cells that where transduced to coexpress both M28z$^+$ and an enhanced firefly luciferase (effLuc) to allow for in vivo imaging of CAR-transduced T cells (FIG. 4A). Large differences in tissue distribution and bioluminescent signals of M28z effLuc$^+$ lymphocytes were observed 4 hours after adoptive transfer of 1×10$^6$ M28z$^+$ effLuc$^+$ T cells in both treatment groups (FIG. 4B). The four hour bioluminescent signal comparing both groups showed a profound 10 fold increase in pleural T-accumulation with local administration when compared to intravenous. Intravenously administered T cells showed initial lung retention and a modest T-cell accumulation appreciated 8-10 days after administration. Conversely, pleurally administered T cells showed profound and sustained antigen specific accumulation for up to 2 weeks when compared to effLuc-transduced T cells alone (data not shown). Flow cytometric analyses, T-cell counts and immunohistochemistry determined that the T cell number was highly concordant with bioluminescent signal intensities (FIGS. 4C to 4E). In addition, pleurally administered T cells egressed from the pleural cavity by day 7 following infusion and circulated to extrapleural sites, including the spleen (FIG. 4F) and lung (data not shown).

M28z Costimulated CAR T Cells Demonstrate Potent Anti-Tumor Efficacy and T-Cell Persistence To investigate the proliferative capacity provided by CD28 co-stimulation in vivo, pleural tumor bearing mice were treated with Mz, M28z, or control transduced T cells at a low dose of 3×10$^5$ CAR$^+$ T cells. As before, T cells were injected directly into the pleural cavity following 18 days of tumor growth. In control mice treated with 3×10$^4$ PSMA-targeted T cells, the tumor burden steadily progressed until mortality (median survival 36 d). Treatment with an equal dose of Mz CAR$^+$ T cells prolonged survival by 63 d (FIG. 4a) and eradicated tumor in 20% of mice. Tumor bioluminescence demonstrates a mixed response in tumor burden. Treatment with M28z receptor transduced T cells induced an almost uniform reduction in tumor bioluminescence to background emission, suggesting eradication in the majority of M28z treated mice. Median survival was not reached in this group (p=0.01 vs. Mz). 60% of mice treated with M28z T cells were tumor free greater than 200 days following T cell infusion, as confirmed on gross inspection. The other mice initially showed marked tumor regression before relapsing and survived for a mean of 125 days. At higher T cell doses, complete tumor eradication was observed in both groups, reflecting the equal cytolytic potency of both receptors and demonstrating the importance of CD28 co-stimulation induced T cell proliferation at an initially low T cell effector to tumor cell ratio.

Serial assessment of CAR$^+$ T cell counts in the peripheral blood of treated mice demonstrated a strong correlation between anti-tumor efficacy and enhanced T cell survival. M28z treated mice demonstrated enhanced T-cell persistence at all weekly measurements, including at late timepoints days 40 and 50 following T-cell infusion (FIG. 6B). Similar results were obtained at three separate T-cell doses (3×10$^6$, 1×10$^6$, and 3×10$^5$) administered CAR$^+$ T cells) and upon absolute CAR$^+$ T cell quantitation in the spleen at days 14 and 55 following T cell infusion.

Phenotype assessment of persisting T cells demonstrated progressive enrichment in CD4+ T cells that was statistically significant 30 days following T-cell infusion in both Mz and M28z treated mice. This finding was consistently observed regardless of T cell dose or tissue analyzed (spleen or blood). This enrichment was more pronounced for Mz treated mice, suggesting two alternative explanations for a differential role of CD4$^+$ and CD8$^+$ T cell subsets in CAR efficacy. Either the greater absolute amount of predominant CD4$^+$ T cells were responsible for enhanced M28z efficacy or it is the ability of CD28 co-stimulation to maintain a significant proportion of CD8$^+$ T cells which are ultimately responsible for anti-tumor efficacy. In order to address these two possibilities, CD4$^+$ and CD8$^+$ CAR transduced T cells were compared head-to-head with respect to their anti-tumor efficacy in vitro and in vivo.

Figure 6A:
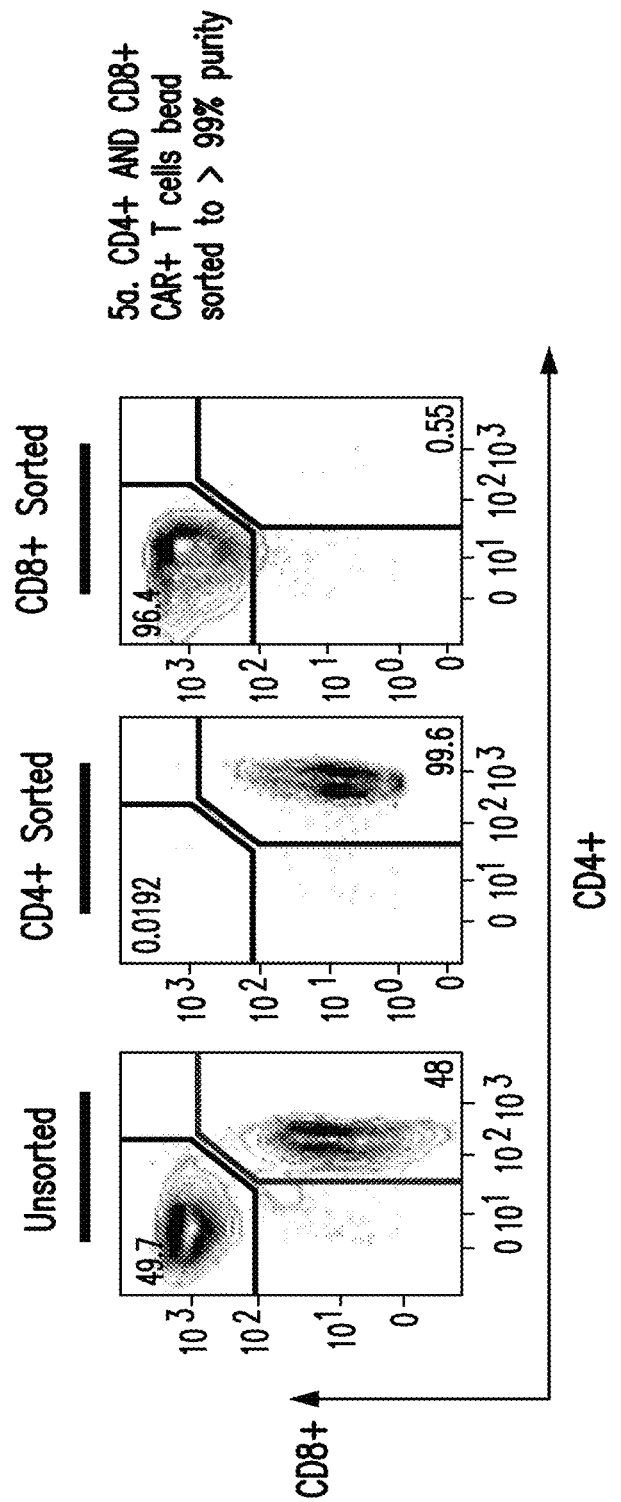

CD4$^+$ CAR T Cells Demonstrate a Potent Cytotoxicity that is Dependent on CD28 Co-Stimulatory Signaling To compare the effector functions of CD4$^+$ and CD8$^+$ CAR T cells, both T-cell subsets were purified to a >98% purity (FIG. 6A). Following 4 h of co-culture, CD8$^+$ T cells were the only subset demonstrating cytotoxicity (FIG. 6B, left); however, following 18 h co-culture, CD4$^+$ M28z T cells mediated equivalent cytotoxicity when compared to CD8$^+$ M28z T cells.

Since CD28 co-stimulation can enhance cytolysis either through IL-2 induced potentiation of T-cell cytotoxicity or TNF-α secretion, a cytokine able to directly induce tumor cell apoptosis, the role of CD28 co-stimulation in CAR mediated cytotoxicity was assessed. CD28 co-stimulatory signaling enhanced lysis by CD4$^+$ M28z CAR T cells by 13-16% at multiple effector to target ratios (p<0.0001), but did not consistently enhance lysis by CD8$^+$ CAR T cells (p=0.07).

Figure 6D:
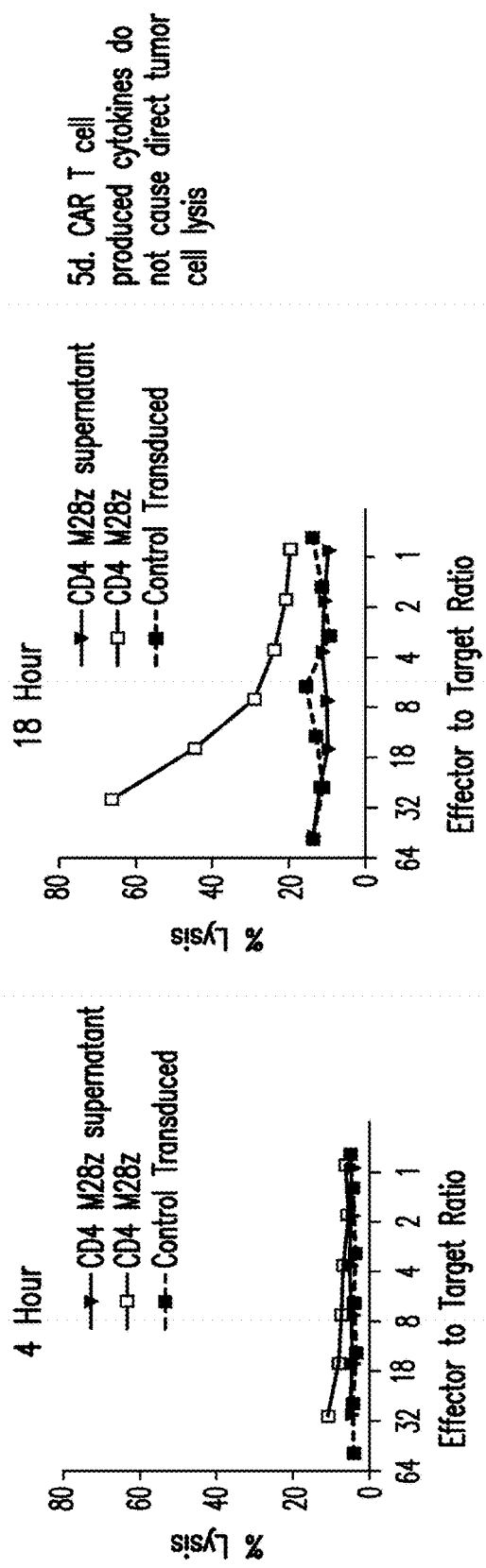

To determine the mechanism by which CD28 signaling enhances CAR T-cell cytotoxicity, CD4$^+$ M28z CAR T cells with mesothelin-expressing tumor cells were stimulated and supernatant transfer cytotoxicity assays were performed. Transfer of only supernatant or transfer of supernatant in addition to control transduced T cells did not result in detectable lysis (FIG. 6D). As a positive control, CD4$^+$ M28z lysed mesothelin-positive targets. In contrast, transfer of cytokine-rich supernatant (cytokine concentrations confirmed by Luminex assay) obtained from stimulated CD4$^+$ M28z T cells enhanced cytotoxicity of both CD4$^+$ M28z (5 to 23% enhancement, p<0.0001) and CD8$^+$ M28z CAR T cells (5 to 30% enhancement, p<0.001). Paralleling the observation that co-stimulation enhances CD4$^+$ CAR T cell lysis with delayed kinetics, supernatant enhanced lysis to a smaller degree following short-term 4 h coculture (2.5 to 4% for CD4$^+$, 1.0 to 4.4% for CD8$^+$, data not shown).

Thus, CD28 co-stimulatory signaling provided in cis to antigen recognition promotes generation of cytotoxic CAR T cell effectors with delayed kinetics and most prominently in the CD4$^+$ T cell subset.

CAR$^+$ T Cell Mediated Cytotoxicity is Granzyme/Perforin Pathway Dependent

Figure 7A:
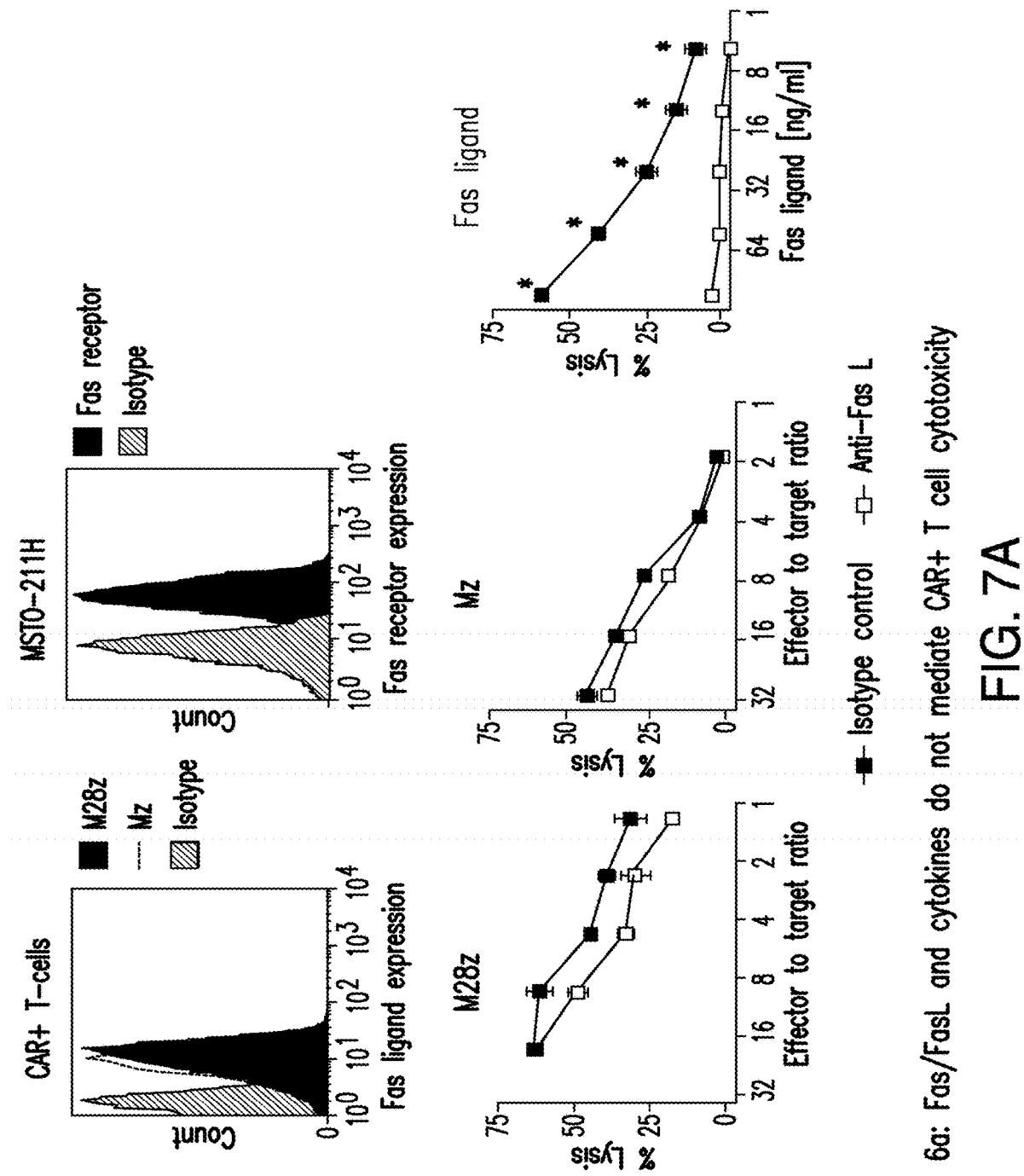

Having excluded direct lysis of tumor targets by cytokine rich supernatant, which of two cell-contact dependent (Fas/FasL or granzyme/peforin pathway) lytic mechanisms are responsible for CAR T cell cytotoxicity was studied. Antibody blockade of Fas ligand/Fas receptor interaction did not reduce target cell lysis by either Mz or M28z CAR T cells (p>0.05, FIG. 7A, bottom). Flow cytometry confirmed Fas ligand expression by CAR T cells and Fas receptor expression on MSTO MSLN$^+$ tumor (FIG. 7A, top). MSTO MSLN$^+$ cells were susceptible to FasL mediated cytotoxicity and the αFasL Ab used in experiments blocked this effect (FIG. 7A, bottom right).

Blockade of granzyme release by addition of calcium chelator EGTA to T cell/tumor cell coculture reduced CAR mediated lysis in all groups tested (p<0.0001, FIG. 7B), demonstrating CAR T cell cytotoxicity is perforin/granzyme pathway dependent. The observed reduction in cytotoxicity using equal concentrations of EGTA (4 mM) varied among groups. The most prominent reduction in lysis was seen in Mz (mean reduction 27.6% vs. 17.6% for M28z) and CD8$^+$ (29.4% CD8$^+$ Mz vs. 15.3% CD4$^+$ Mz; 24.2% for CD8$^+$ M28z vs. 11.1% for CD4$^+$ M28z) T cell groups.

Figure 7B:
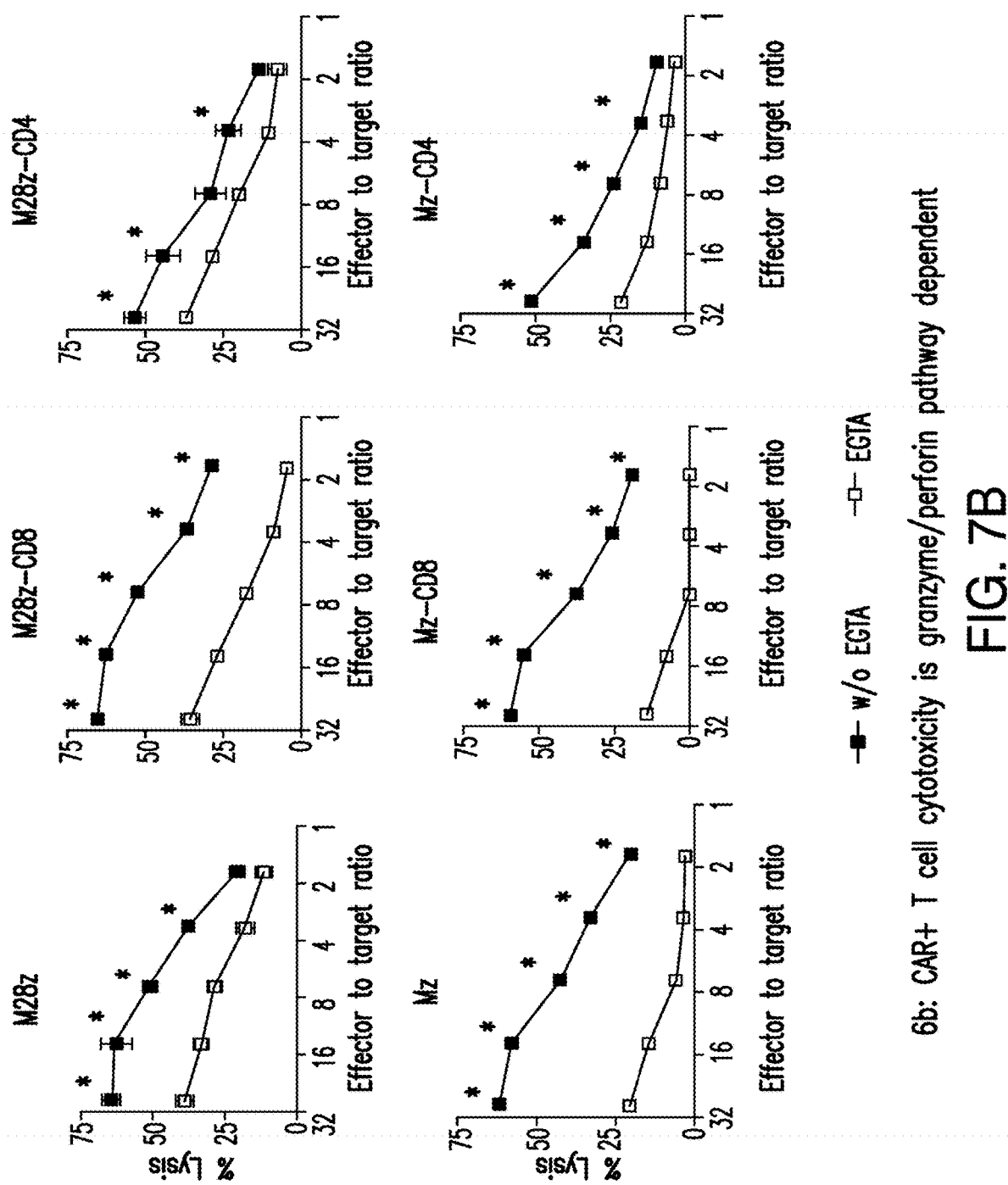
Figure 7D:
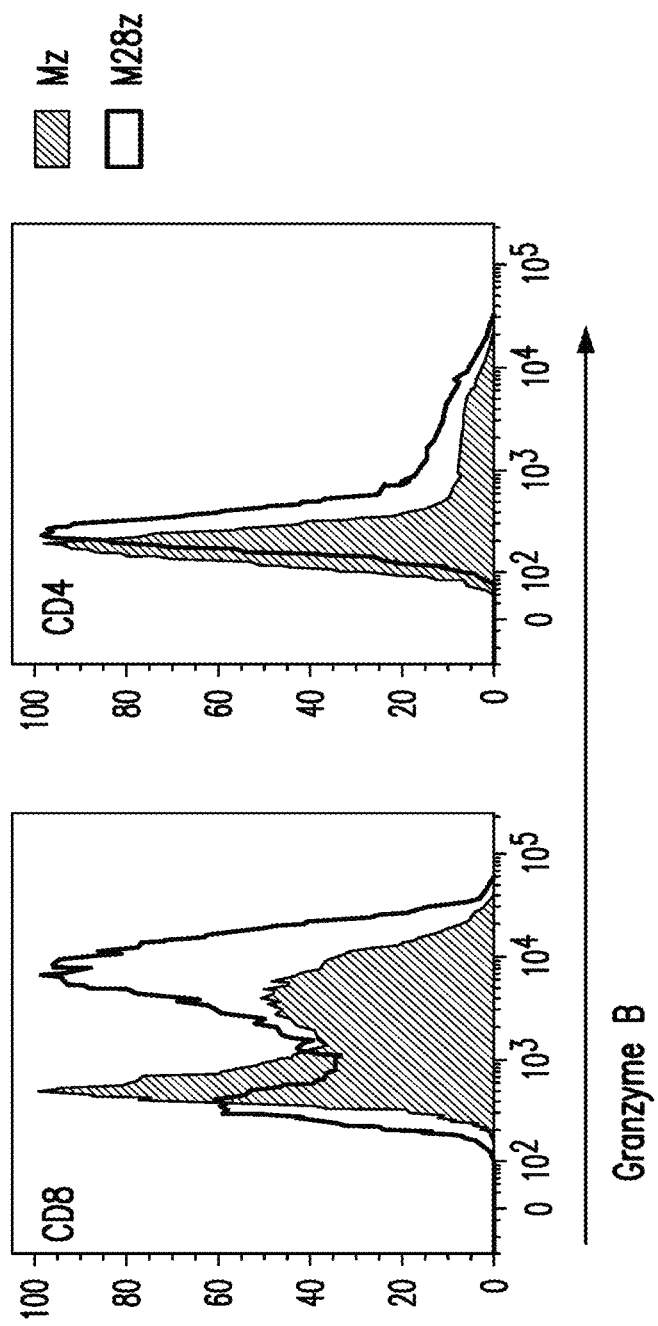

Intracellular flow cytometry were performed to correlate results of cytotoxicity assays with expression of granzymes A and B, two of the primary mediators of perforin-granzyme induced lysis. Expression of granzymes A and B in resting PBMCs was primarily restricted to CD8$^+$ T cells, in concordance with previous studies (FIG. 7C). Granzyme A expression was not significantly altered following PHA stimulation and mesothelin-specific stimulation of CAR transduced T cells. In contrast, granzyme B was characterized by inducible expression. Following PHA stimulation, approximately 75% of both CD4$^+$ and CD8$^+$ T cells stained positive and at 18 h following stimulation with mesothelin-expressing tumor cells, granzyme B was expressed in >95% of CD4$^+$ and CD8$^+$ M28z CAR T cells. In order to compare CD4$^+$ and CD8$^+$ T cells with respect to the kinetics of granzyme B expression, cells were stimulated for either 4 or 18 h and granzyme B MFI was quantified. CD8$^+$ M28z T cells demonstrated a 1.8-fold increase in MFI following 4 h coculture and further up-regulated granzyme B expression an additional 0.8 fold over the final 12 h. CD4$^+$ M28z T cells, however, up-regulated granzyme B expression to a much greater degree over the final 12 h of culture (1.5 fold over 4 h, an additional 2.2 fold over the final 12 h, similar results obtained in two other independent experiments). These findings may reflect the delayed kinetics of cytotoxicity observed with CD4$^+$ CAR T cells as demonstrated in FIG. 6B. Furthermore, CD28 co-stimulatory signaling enhanced granzyme B expression in both CD4$^+$ and CD8$^+$ T cell subsets (FIG. 7D, expression following 18 h coculture), possibly reflecting the enhanced cytotoxicity seen with CD4$^+$ M28z T cells (when compared to CD4$^+$ Mz T cells, FIG. 6C) and the relative resistance of M28z T cells to granzyme release blockade (FIG. 7B).

CD28 Co-Stimulation Provides Superior Cytokine Secretion and Proliferation in CD4$^+$ T Cells To assess the relative contribution of CD28 co-stimulation on in vitro T-cell cytokine and proliferative responses to antigen activation on T-cell subpopulations, CD4$^+$, CD8$^+$ and bulk T cells transduced with either Mz or M28z with mesothelin expressing tumor cells were activated and the secretion of Th1 cytokines as well as antigen specific proliferation were quantified. Compared to CD8$^+$ T cells, CD4$^+$ T cells transduced with Mz showed increased levels of Th1 cytokine secretion, this difference was augmented with CD28 co-stimulation seen in the M28z T cells (FIG. 2A). As expected, recurrent stimulation in the absence of co-stimulatory ligands did not induce T cell expansion in either CD4$^+$ or CD8$^+$ Mz T cell populations and rapidly induced a decline in T cell number after the first stimulation in the absence of exogenous IL-2 (FIG. 2B). In contrast, co-stimulation endowed CD4$^+$ M28z T cells triggered a 20-fold greater mean proliferation by the 3$^{rd}$ stimulation compared to a 2-fold increase in CD8$^+$ M28z T cells.

CD4 M28z CAR T Cells are Efficacious Alone In Vivo and Mediate Enhanced Efficacy when Compared to CD8 M28z CAR T Cells The observations of potent in vitro effector function of CD4$^+$ M28z T cells led to hypothesis that CD4$^+$ M28z T cells would demonstrate in vivo efficacy even when administered in the absence of CD8$^+$ T cells. Tumor bearing mice were treated with CD4$^+$ M28z, CD8$^+$ M28z, or bulk unsorted M28z T cells that were administered into the pleural cavity at three different doses following 18 days of tumor growth. In control mice treated with the highest dose of 3×10$^5$ CAR$^+$ T cells, the tumor burden steadily progressed until mice had to be sacrificed (median survival 28 d). Treatment with CD4$^+$ M28z and bulk M28z CAR T cells resulted in tumor eradication in 100% of mice, with mice remaining tumor-free to 200 days of follow-up. CD8$^+$ M28z T cells extended survival above control transduced cells by 83 days (111 vs. 28 d, p=0.003), but resulted in tumor eradication in only 3/7 mice. Treatment with CD4$^+$ M28z CAR T cells significantly extended survival when compared to CD8$^+$ M28z treated mice (ms not reached vs. 111 d, p=0.02). At the lower doses, results were similar when comparing efficacy of CD4$^+$ to CD8$^+$ M28z CAR therapy (at dose 1×10$^5$, 112 vs. 67 d, p=0.04 and at dose 3×10$^4$ 160 VS. 37, p=0.001). These results illustrate that CD4$^+$ CAR T cells, able to mediate lysis in addition to their more traditional functions of cytokine production and proliferation are superior to CD8$^+$ CAR T cell therapy. In addition, the proliferative potential of CD4$^+$ M28z T cells confers ability to reach efficacious E:T ratios even at doses where the initial E:T ratio is 1:10,000.

Functional Persistence of Adoptively Transferred is Predominantly CD4$^+$ Mediated and Augmented by CD28 Co-Stimulation The importance of persisting T cells in continued tumor control by performing a tumor rechallenge experiment was assessed. Mice were initially inoculated with pleural MSTO MSLN$^+$ and administered either 1×10$^5$ Mz or M28z pleural T cells, a dose which almost uniformly eradicates tumor in both groups (FIG. 4). 87 d after initial T-cell injection, either 1×10$^6$ MSLN$^+$ or MSLN$^-$ MSTO tumor cells were administered into the peritoneal cavity and tumor burden was followed by BLI. After an initial increase in tumor burden in all mice, antigen specific control of tumor burden was seen in both the Mz and M28z T cell treated mice with a greater decrease seen in the M28z mice (FIG. 10). The T-cell proliferative response in the mice was examined. Mice from all groups were sacrificed at day 16 post rechallenge and the spleens were harvested as previously described. M28z T cells rechallenged with antigen showed a 4 fold expansion of T-cell numbers compared to antigen negative tumor rechallenge (FIG. 10C). This profound difference in T-cell accumulation within the spleen was predominantly due to CD4$^+$ subpopulation (FIG. 10D).

4. Discussion

Figure 5B:
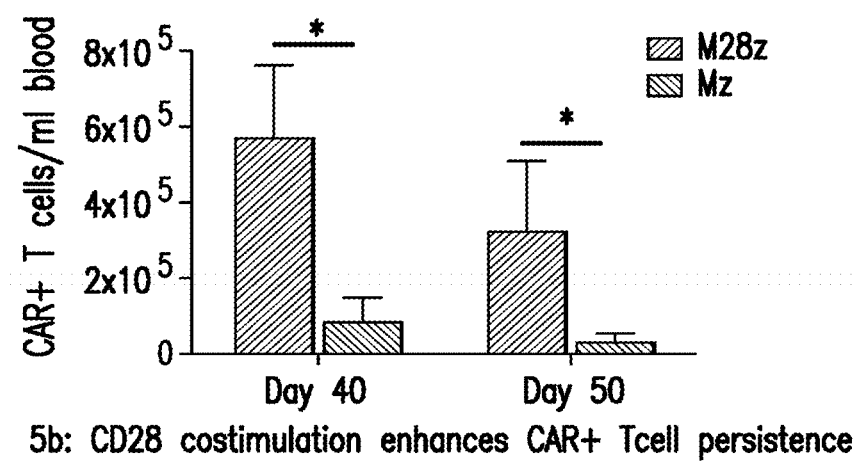
Figure 5C:
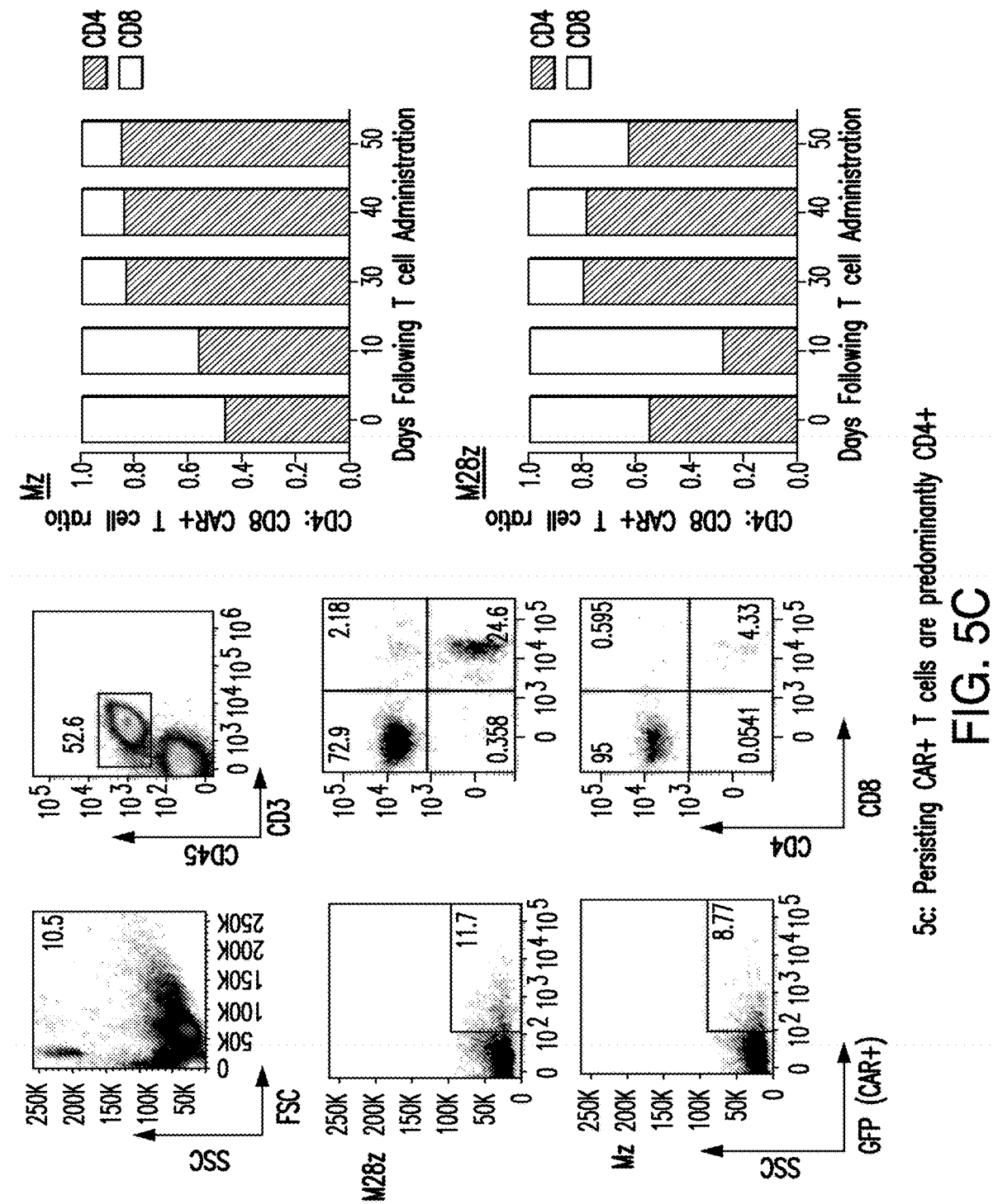
Figure 6E:
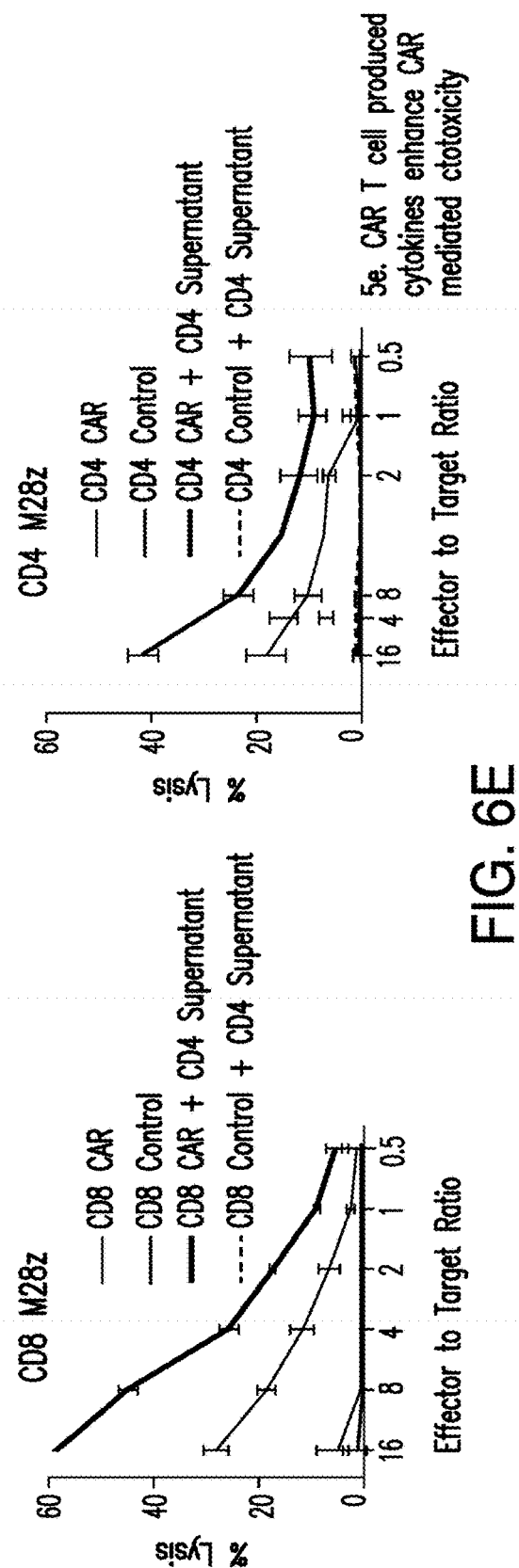
Figure 8A:
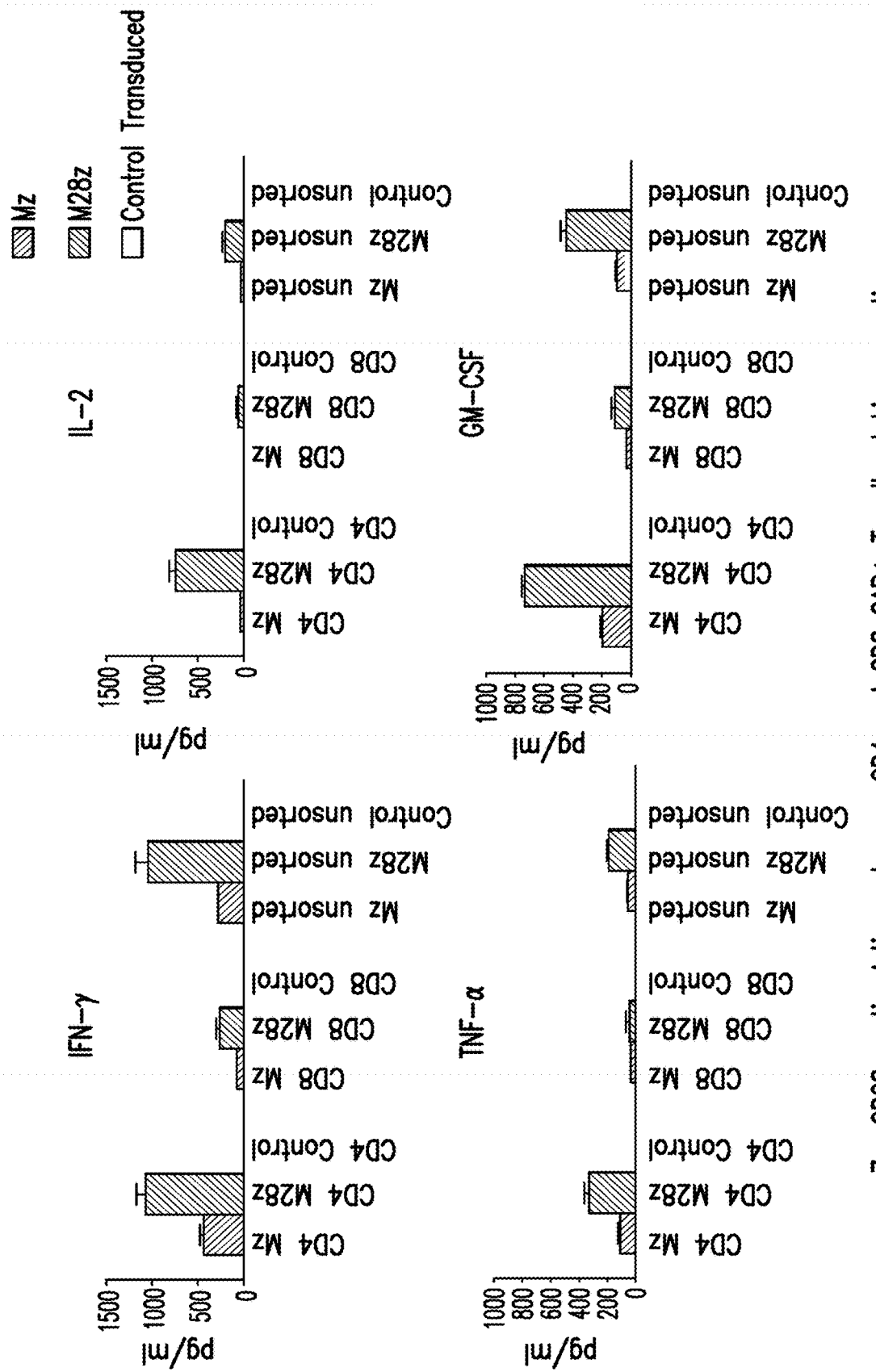
FIGS. 8A and 8B depict CD28 co-stimulatory effect of mesothelin specific CAR+ T-cell is predominantly CD4+ mediated. (A) Enhanced cytokine secretion in M28z T cells is primarily CD4+ mediated. Cytokine release assays were performed for M28z and Mz T cells sorted for CD4+, CD8 subpopulations (as previously described) or an unsorted bulk population. $5\times10^4$ CAR+ T cells were co-cultured with $5\times10^3$ target cells per well in triplicate in 96-well round bottom plates at a final volume of 200 µl per well. After 20 h, co-culture supernatants were collected and cytokine assays were performed using a multiplex Human Cytokine Detection assay to detect IL-2, GM-CSF, TNF-α, and, IFN-γ (Millipore Corp.) Data represent the mean±s.e.m. cytokine levels in three wells per cytokine. (B) Profound T cell expansion capacity of M28z CD4+ T cells without exogenous IL-2. T cell expansion of M28z or Mz-transduced CD4+, CD8+ subpopulations or an unsorted bulk population of T cells cocultured every 4 d with MSLN+ or MSLN− tumor monolayers. Absolute CAR$^+$ T-cell numbers were calculated at indicated time intervals using manual hemocytometer counts corrected by GFP$^+$ percentage determined by flow cytometry. Each dot represents the mean±s.e.m. counts in three wells.
Figure 8B:
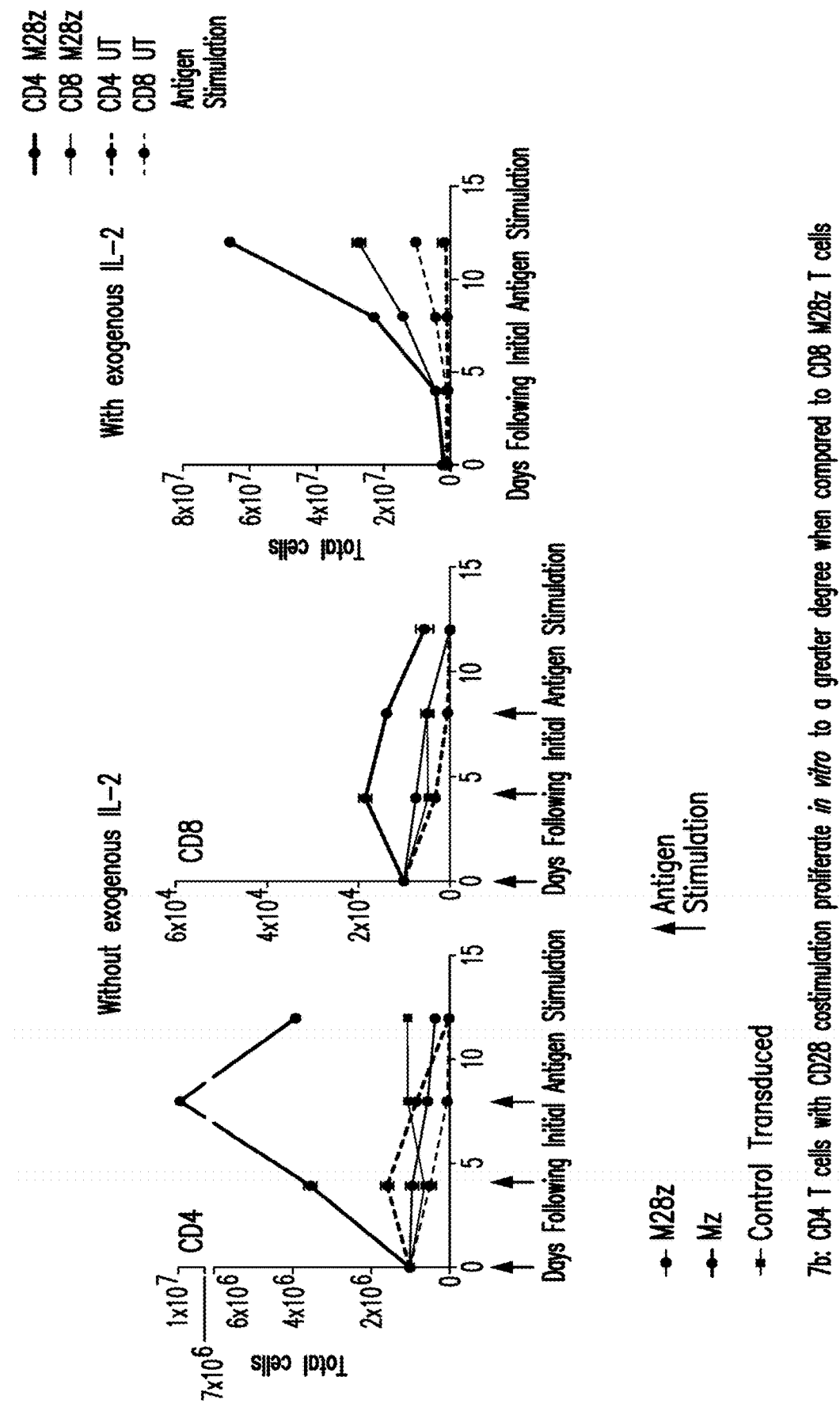

A major goal of cancer immunotherapy is to generate a potent primary immune response and establish T-cell persistence. Solid tumors pose significant challenges to these goals given that they are located within anatomical compartments that impede T-cell trafficking and typically lack expression of co-stimulatory ligands. Using established murine model of pleural mesothelioma, this Example shows that T cells genetically engineered to target cancer antigen and provide co-stimulatory signaling eradicate established pleural mesothelioma in a majority of mice (FIG. 5). This Example demonstrates that the potentiating properties of co-stimulatory signaling are particularly amplified by the CD4 subset, as demonstrated by their superior cytokine secretion and proliferation when compared to CD8$^+$ T cells (FIG. 8). Furthermore, transducing CD4$^+$ T cells with co-stimulated chimeric antigen receptors recruits this subset into the primary cytotoxic response (FIG. 6). The acquisition of cytotoxic potential combined with an ability to retain Th1 helper cytokine secretion forms powerful CD4$^+$ immune effectors able to independently eliminate pleural mesothelioma xenografts (FIG. 10). This anti-tumor efficacy is especially prominent when T cells are administered directly into the pleural cavity, resulting in complete tumor control at dramatically lower T-cell doses when compared with intravenous administration. Pulmonary sequestration is identified as a key impediment to efficient tumor infiltration by intravenously administered T cells (FIG. 4). In contrast, pleural T-cell administration results in early tumor infiltration and a robust proliferation following antigen encounter. Strikingly, regionally administered T cells migrate away from the pleural cavity into the systemic circulation (FIG. 4), and in combination with co-stimulatory signaling, demonstrate long-term functional persistence upon tumor rechallenge 100 days after initial T-cell infusion (FIG. 10). These findings demonstrate that CAR therapy may be particularly useful to overcome the obstacles imposed by solid tumors by successful recruitment of CD4$^+$ T cells as primary mediators of the antitumor efficacy and by using regional administration to achieve potent primary and secondary immunity.

In this Example, pulmonary sequestration was identified as a key impediment limiting efficient T-cell trafficking to solid tumor. Bioluminescent imaging of luciferase-labeled T-cells demonstrates that prolonged pulmonary sequestration of intravenously administered T cells results in a delay in pleural tumor accumulation (FIG. 4). The delay in tumor infiltration by IV T cells was consistent with a delayed regression in tumor burden (FIG. 3). These results corroborate previous studies demonstrating that efficient trafficking and infiltration of peripheral tumors correlates with antitumor efficacy in solid cancers, and suggest pulmonary sequestration as a major reason for poor tumor accumulation of intravenously administered T-cells. Pulmonary sequestration may in part be due to the activation status of the CAR$^+$ transduced T cells which require activation for efficient retroviral transduction. A functional consequence of activation is an increase in affinity of adhesion integrins which bind ligands constitutively expressed by the pulmonary vasculature. In addition to a delay in trafficking seen with IV administration, an absolute decrease in T-cell accumulation within the pleural tumor compared with pleural administration was also observed (FIG. 4). The low level of tumor accumulation may be due to inefficient trafficking of CAR T cells to the peripheral tissues which typically requires additional signals such as downregulation of L-selectin and upregulation of chemokine receptors and adhesion molecules. Consistent with these studies, the majority of CAR transduced T cells at administration are L-selectin positive, and may not be able to efficiently traffic to pleural tumor, a problem that needs to be addressed in future studies. Other strategies aimed at optimizing T cell delivery to solid tumors have overexpressed chemokine receptors to enhance tumor accumulation. Trafficking requirements can be circumvented by the clinically relevant approach of administering T cells regionally, directly into the tumor bearing pleura. Pleural administration bypasses both pulmonary sequestration as well as any trafficking bias intrinsic to the T-cell phenotype. The resulting T-cell activation and potent proliferative response results in increased antitumor efficacy. Importantly, intrapleurally administered T cells are able to egress from the pleural cavity and circulate throughout the periphery, persist at long-term time points up to 200 days, and establish systemic tumor surveillance >100 days following their initial infusion (FIG. 10).

The findings that CD28 costimulated T cells demonstrate superior cytokine secretion and proliferate following repeated antigen exposure in the absence of exogenous IL-2 (FIG. 1), which is consistent with other chimeric receptor-cancer antigen models. M28z CAR T cells eliminated pleural tumor even at low T-cell doses, illustrating the importance of co-stimulation in providing the proliferative capacity necessary to achieve effective T-cell to tumor ratios in vivo. Furthermore, CD28 co-stimulation enhanced T-cell persistence (FIG. 5) and provided superior tumor control upon secondary rechallenge >100 days following their initial administration. Remarkably, M28z T cells underwent a robust proliferation following antigen rechallenge, demonstrating persistent functioning of co-stimulatory signaling (FIG. 10). This underscores the importance of co-stimulation for complete control of large tumor burdens and suggests that co-stimulated T cells are less susceptible to exhaustion in the presence of chronic antigen stimulus. Including co-stimulatory signaling to enhance CAR T cell in vivo proliferation and persistence has recently translated to long-term cancer remission in trials of hematopoietic malignancies. The late relapses of antigen-positive tumors seen in some mice following initial tumor regression suggest CAR T cells administered at low T-cell doses may be negatively regulated by tumor-mediated immunosuppression. Ongoing preclinical studies will address if combining co-stimulatory CAR transfer and targeted reversal of these inhibitory pathways onto the same cell will further improve antitumor efficacy.

Previous studies have reinforced the requirement for both CD4$^+$ and CD8$^+$ T cells for optimal anti-tumor immunity. CD8$^+$ T cells are traditionally thought to play the primary role in eliminating cancer cells whereas CD4$^+$ T cells provide CD8$^+$ T cells with growth factors such as IL-2 that are necessary for optimal function. While the results shown in this Example are consistent with a large body of work supporting the importance of CD4$^+$ T-cell help in priming optimal CD8$^+$ effector formation and in maintaining the CD8$^+$ T cell response to persistent virus or tumor, they also highlight an increasing appreciation that CD4$^+$ T cells can act as primary mediators of antitumor efficacy. In vitro, CD28 co-stimulated CD4$^+$ CAR T cells secrete a greater amount of cytokines (FIG. 8), were uniquely capable of proliferating upon repeated antigen stimulation without exogenous IL-2 supplementation (FIG. 8), and displayed equivalent cytotoxicity when compared to CD8$^+$ T cells (FIG. 6). The acquisition of cytotoxic potential combined with an ability to retain Th1 helper cytokine secretion forms powerful CD4$^+$ immune effectors able to eliminate pleural mesothelioma xenografts following regional administration. This observation is in contrast with previous studies using CAR T cells. The lack of CD4$^+$ CAR T cell efficacy in these studies may be explained by a low level of CAR expression and the use of first generation receptors lacking in co-stimulatory signaling. Since CD4$^+$ T cells require a higher avidity interaction to mediate effector functions when compared to CD8$^+$ T cells and since functional avidity is in part determined by receptor level of expression, the high level of receptor expression obtained in this Example may explain CD4$^+$ potency. Furthermore, because chimeric antigen receptors implement high-affinity scFvs for antigen recognition that further increase avidity, CAR therapy may be uniquely suited for generating multifunctional CD4$^+$ T cells capable of T-cell help and cytotoxicity. Other strategies of raising T-cell avidity have successfully been used to generate cytotoxic CD4+ T cells in antitumor TCR transgenic therapy. The study shown in this Example helps inform an understanding that factors governing functional avidity in addition to environmental cues regulating T-cell response dictate the relative roles of CD4+ vs. CD8+ T cells in antitumor immunity.

The acquisition of cytotoxic activity by CAR transduced CD4+ T cells is especially striking. Recently published studies performed using TCR transgenic models of antitumor immunity also demonstrate the ability of CD4+ T cells to differentiate into cytotoxic effectors. In these reports, the ability of CD4+ T cells to independently eliminate tumors was dependent on attaining lymphopenia in recipient mice. Lymphodepleting regimens are used to improve efficacy of gene-modified T cell therapy, acting in part by increasing the availability of γ-chain cytokines capable of stimulating T-cell expansion and programming cytotoxic differentiation. Other clinical strategies to increase cytokine availability include systemic IL-2 administration, although the efficacy using IV administration is limited by inefficient delivery to the tumor. Genetic modification of T cells holds promise of achieving full activation of tumor-reactive CAR+ T cells without the use of lymphodepletion in a way that efficiently delivers IL-2 to the site of T-cell activation within the tumor microenvironment. In this Example, incorporating CD28 co-stimulatory signaling downstream of antigen recognition enhanced CD4+ T-cell cytotoxicity (FIG. 6) by a perforin/granzyme dependent pathway (FIG. 7), correlating with the ability of costimulated CD4+ CAR T cells to express high levels of granzyme B upon antigen stimulation. This effect was potentiated by secreted cytokines made increasingly available by CD28 signaling; whereas cytokines were incapable of mediating direct tumor lysis, the addition of a cytokine rich supernatant to CD4+ T cells led to enhanced cytotoxicity (FIG. 6). These findings are supported by other studies demonstrating an IL-2 dependent role in the ability of co-stimulation to produce cytotoxic CD4+ cells. Given their robust IL-2 production, co-stimulated CD4+ T cells are in a unique position to serve as powerful immune effectors, especially when outfitted with CAR receptors that provide high avidity interactions with tumor antigen.

In conclusion, this Example provides evidence supporting the use of regional CAR T-cell administration to overcome obstacles posed by solid tumors. Successful recruitment of CD4+ T cells into all aspects of antitumor immunity provides a particular advantage to the use of CAR+ T cell therapy for the treatment of solid tumors.

Example 2—Targeted T Cell Therapy for Metastatic Breast Cancer

Figure 13E:
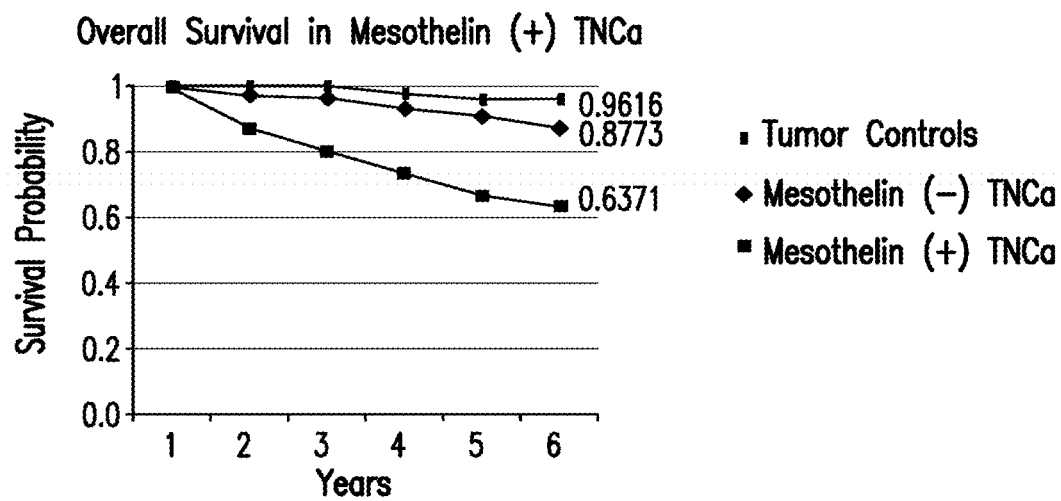
Figure 13F:
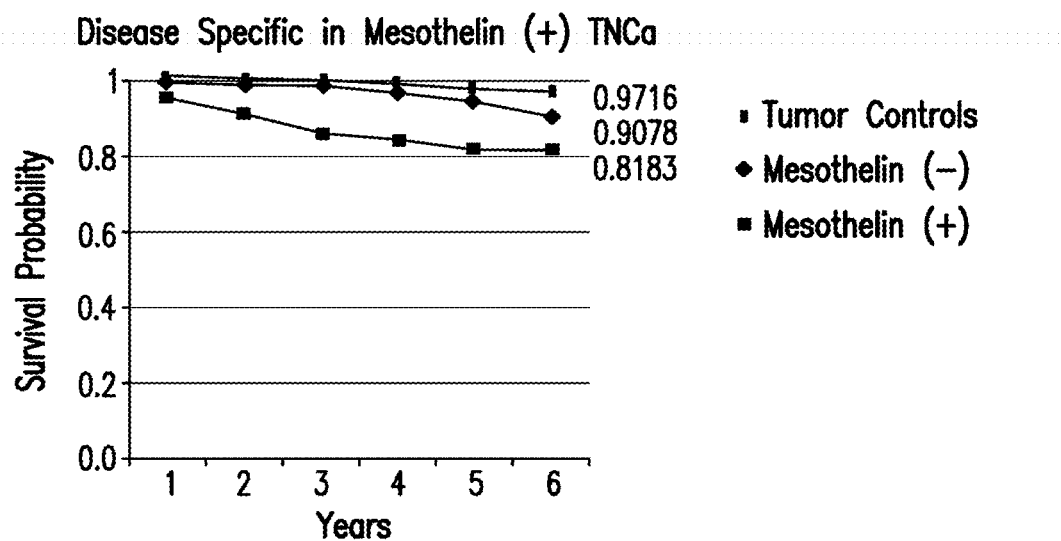

1. MSLN Expression in TNBC Correlates with Aggressiveness:

the expression of MSLN in tissue microarrays of 226 TNBCs and 88 non-TNBCs was evaluated. The analysis revealed that MSLN over-expression was significantly more frequent in TNBCs than in non-TNBCs (36% vs 16%, respectively; p=0.0006; FIG. 12). Patients with MSLN-positive TNBC developed more distant metastases with shorter intervals (see Table 1) and had significantly lower overall and disease-free survival than patients with MSLN-negative TNBC, indicating that MSLN expression is a marker of aggressiveness. The results show that patients with MSLN+ TNBC are a potential population for trials of MSLN-targeted therapies. With a median follow-up of 5.3 years (range, 0.7-8.2), the 5-year Kaplan-Meier survival estimates showed that TNBC had a significantly shorter overall probability of survival, at 0.82 (95% CI: 0.75-0.87), compared with 0.959 (95% CI: 0.895-0.984) for non-TNBC (FIG. 13A). Among patients with TNBC, MSLN positivity correlated with significantly shorter overall survival (OS) (0.659 [95% CI: 0.515-0.770] vs. 0.913 [95% CI: 0.838-0.954]) (FIG. 13B), as well as significantly shorter disease-free survival (DFS) (0.665 [95% CI: 0.536-0.766] vs. 0.865 [95% CI: 0.785-0.916]) (FIG. 13C). The negative survival impact of MSLN is independent of lymph node status (log rank test, p=0.0003). Node-positive/MSLN+ TNBC cases fared the worst (5-year OS probability, 0.564 [95% CI: 0.348-0.733]), compared with node-positive/MSLN− TNBC cases (0.865 [95% CI: 0.699-0.943]) (FIG. 13D). Within TNBC patients, mesothelin positive patients had decreased overall survival (p=0.001); decreased disease-specific survival (p=0.08); increased frequency of distant metastases (OR 2.9, p=0.011); decreased mean interval to distant metastases (19 vs. 35 months, p=0.006); decreased mean survival (24 vs. 53 months, p=0.001), as shown in FIGS. 13E and 14F.

TABLE 1

|  | TNBC MSLN (+) | TNBC MSLN (−) | Non-TNBC |
|---|---|---|---|
| Distant Metastasis (+) | 16/70* (23%) | 12/128* (9%) | 8/88 (9%) |
| Interval to Metastasis (mo) (95% CI) | 19.2 (13.5-24.9) | 35.2 (23.8-46.6) | 35 (28.7-41.3) |
| Bone | 2 (13%) | 2 (17%) | 6 (75%) |
| Brain | 10 (63%) | 4 (33%) | 2 (25%) |
| Liver | 2 (13%) | 2 (17%) | 4 (50%) |

Serum SMRP as a Marker of Tumor Burden Progression:

Published data have established the role of serial measurement of serum SMRP (a standard clinical test for mesothelioma patients) as a marker of tumor burden progression, e.g., as a marker of progression in patients with esophageal and lung adenocarcinoma (FIG. 14). Therefore, serum SMRP measurement is a standard clinical laboratory test that can be readily applied to the TNBC patient population.

MSLN-Specific CARs:

a MSLN-targeted CAR derived from a human MSLN antibody (scFv) and an eGFP reporter gene separated by an IRES linker (Mz) was created, as described in Example 1. As described in Example 1, the cytoplasmic domain of the CD28 receptor was incorporated to construct a second-generation M28z CAR to enhance T cell proliferation, cytokine secretion, and survival. The vector constructs were successfully transduced into both CD4 and CD8 subsets of human T cells, as detected by the eGFP reporter gene. In vitro cytotoxicity using standard chromium-release assays, where MSLN-targeting or control T cells were incubated with a MSLN+ cancer cells, showed efficacious and specific kill of an MSLN+ cells by both the Mz- and the M28z-transduced T cells. M28z CAR T cells secreted an approximately 2-fold greater amount of GM-CSF, IFN-γ, and TNF-α, compared with Mz T cells. Secretion of IL-2, a cytokine crucial for T cell survival and proliferation, is uniquely provided by the M28z. In the presence of exogenous IL-2, T cells transduced with MSLN-specific receptors expanded, with CD28-costimulated cells achieving a proliferative response 3-fold greater than that achieved by Mz CAR T cells. Furthermore, in the absence of exogenous IL-2, only M28z CAR T cells were able to accumulate upon repeated antigen stimulation.

CAR+ T Cell-Mediated Cytotoxicity is Granzyme/Perforin Pathway Dependent:

as described in Example 1, which of two cell-contact-dependent (Fas/FasL or granzyme/perforin pathway) lytic mechanisms are responsible for CAR T cell cytotoxicity was determined. Antibody blockade of Fas ligand/Fas receptor interaction did not reduce target cell lysis by either Mz or M28z CAR T cells (p>0.05). Flow cytometry confirmed Fas ligand expression by CAR T cells and Fas receptor expression on MSLN+ tumor. MSLN+ cells were susceptible to FasL-mediated cytotoxicity, and the FasL antibody used in experiments blocked this effect. In contrast, blockade of granzyme release by addition of calcium chelator ethylene glycol tetraacetic acid (EGTA) to T cell/tumor cell coculture reduced CAR-mediated lysis in both Mz and M28z, as well as both CD4 and CD8, subsets (p<0.0001)-demonstrating that CAR T cell cytotoxicity is perforin/granzyme dependent.

Development of Mouse Models:

To facilitate investigation of pleural and systemic targeted therapy for MSLN-expressing TNBC, three distinct animal models were developed and validated by the inventors[85-90]. The resulting tumors anatomically resemble human disease for either orthotopic or metastatic pleural pulmonary lesions (FIGS. 15A, B&C, respectively). These animal models were validated for the use of noninvasive bioluminescent imaging (BLI)[85-89,91-93] to track the progression of tumors by using eGFP+, MSLN+, and firefly luciferase+ cell lines. These tumors retained the expression of MSLN, even at late stages of disease (data not shown). Importantly, mice inoculated with tumor and imaged weekly with optimized protocols for BLI secreted serum SMRP, a reliable serum biomarker, and correlated with tumor burden measurement and progression (FIGS. 15A, B&C, bottom). Shown in the insets are mice with metastases demonstrated by BLI or MRI.

Antitumor Efficacy of a Single Low Dose of M28z CAR+ T Cells in an MSLN-Expressing Lung Metastasis Mouse Model:

A single dose of intravenous M28z-transduced T cells, following 22 days of metastatic tumor growth, effectively decreased tumor burden, as seen by an increase in median survival, compared with control mice (p<0.05 vs. control) (FIG. 16)-therefore demonstrating the ability of systemically administered M28z T cells to eradicate multiple tumor lesions in a lung metastasis model.

Figure 3D:
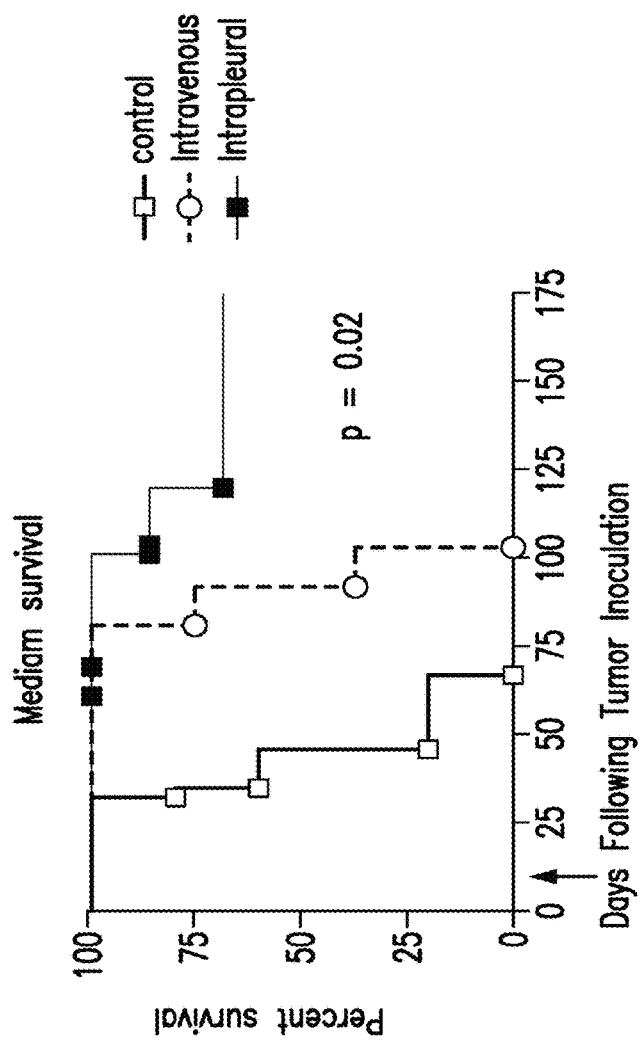
Figure 3E:
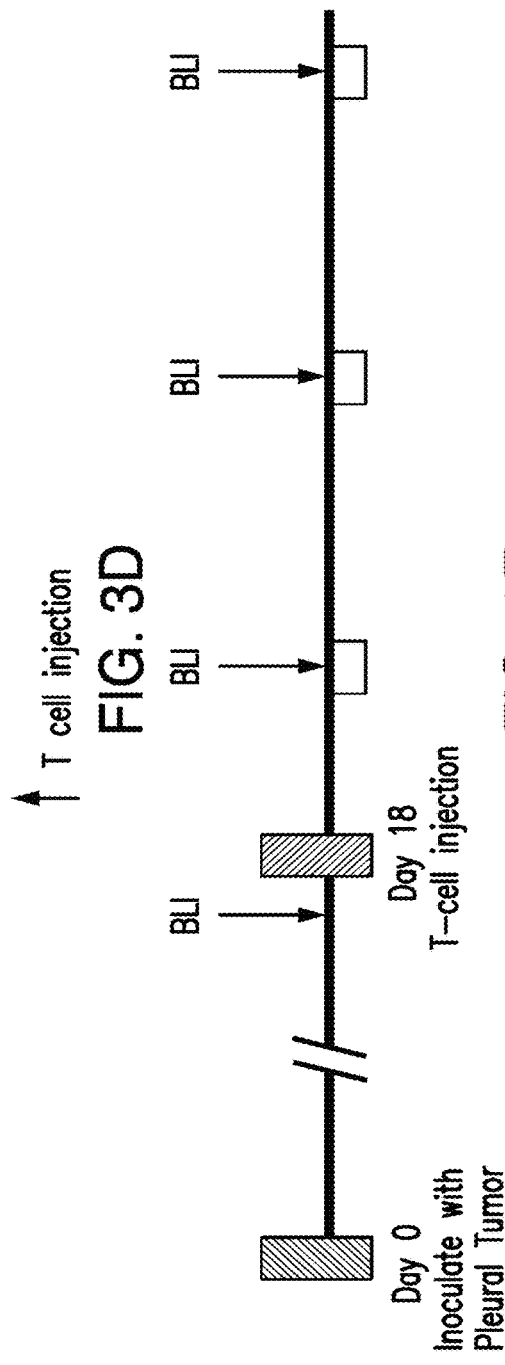
Figure 17A:
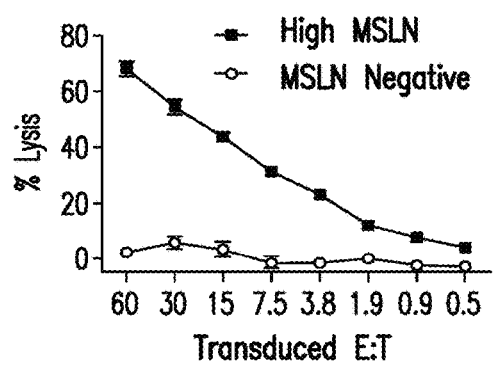
Figure 17B:
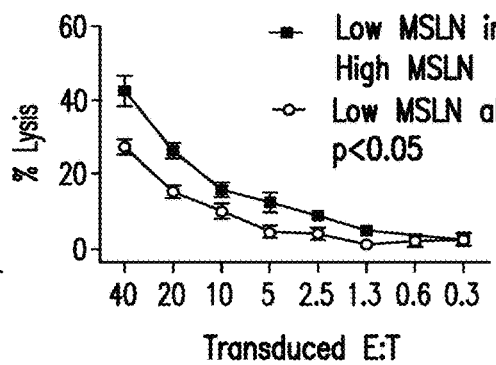
Figure 17C:
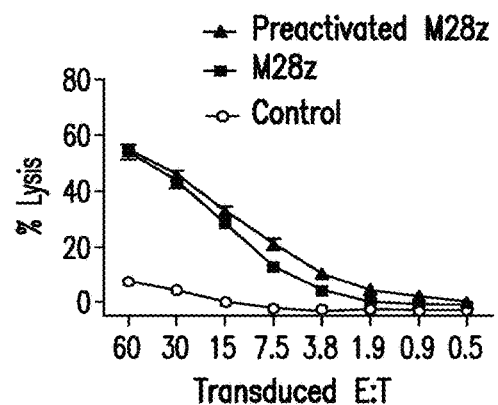
Figure 17D:
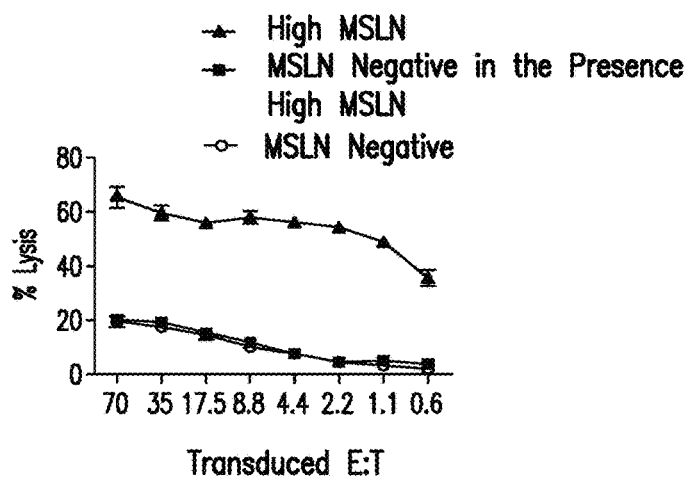

Regionally Administered M28z-Transduced T Cells Eradicate Pleural Tumor:

As described in Example 1, following establishment of large metastatic pleural tumor burden, animals were treated 18 days after tumor inoculation (FIG. 3E) with either a single intravenous infusion or a single intrapleural administration of MSLN-targeted T cells. In mice treated with pleurally administered control transduced T cells, the tumor burden steadily progressed (FIG. 17B) until the mice died (FIG. 3C). Treatment with a lower dose of intravenous M28z T cells resulted in a delayed reduction in the tumor burden (FIGS. 3B and C), yielding a survival advantage (p=0.005; FIG. 3D). Pleurally administered M28z T cells induced major responses. Tumor burdens were significantly lower by day 7 and at baseline by T day 11 (FIG. 3B). Median survival was not reached with the majority of mice achieving tumor eradication (FIG. 17D).

Figure 10A:
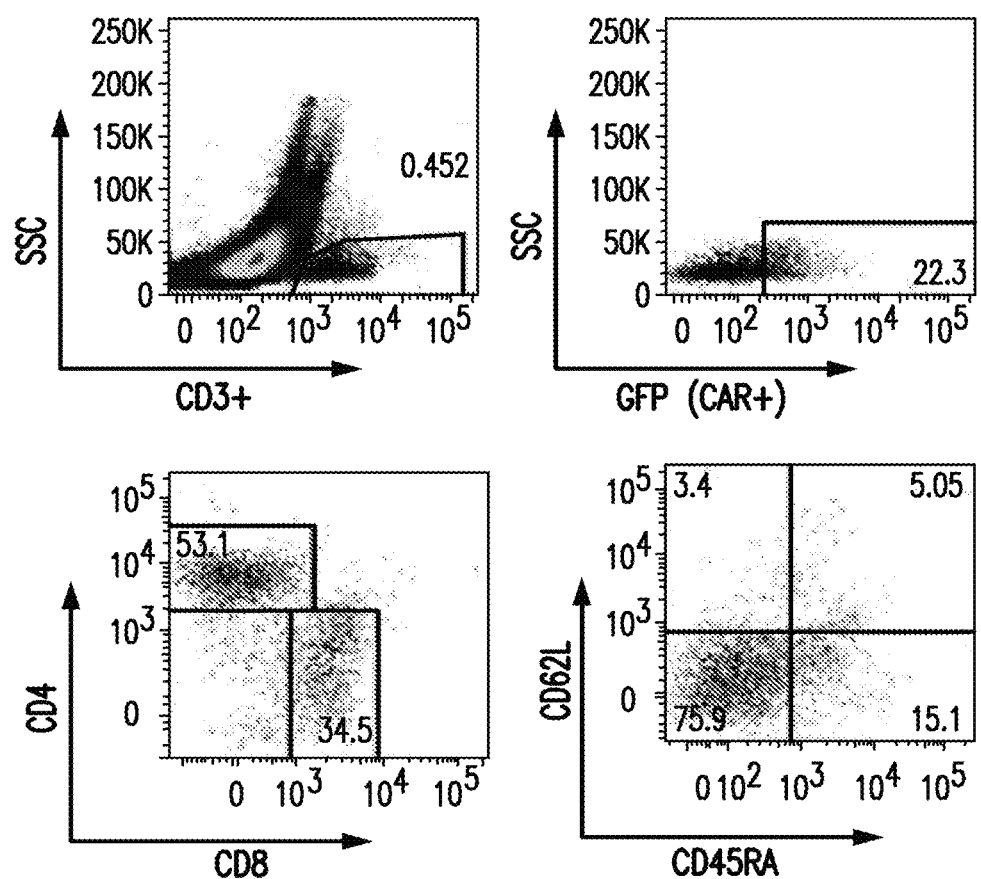
Figure 10B:
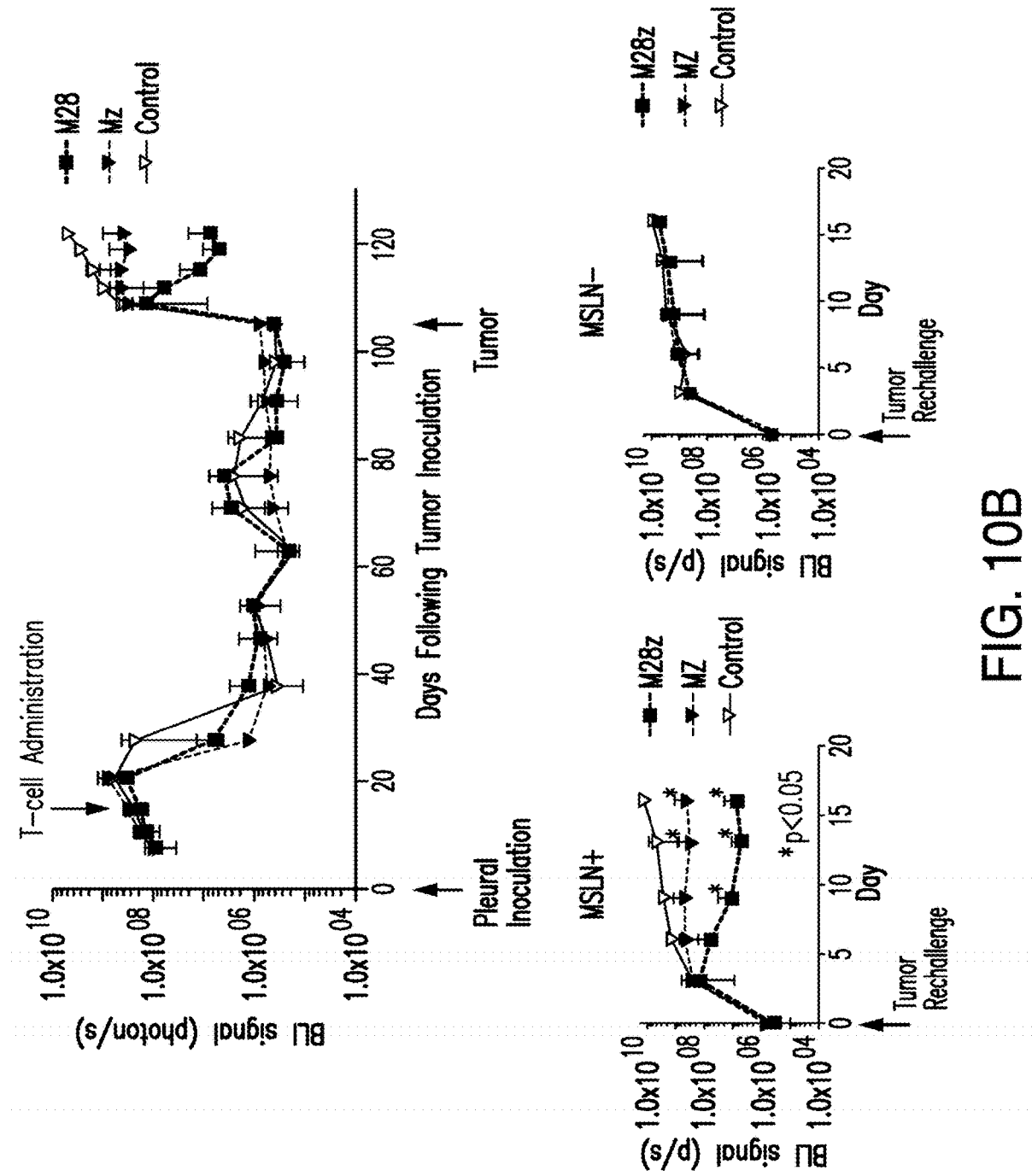

M28z CAR T Cells Demonstrate Potent Antitumor Efficacy, and T Cell Functional Persistence is Augmented by CD28 Co-Stimulation:

As described in Example 1, in mice with established pleural MSLN+ tumor that were administered either Mz or M28z pleural T cells, following tumor eradication, both groups displayed CAR T cell persistence of both CD4 and CD8 subsets (FIG. 10A). Eighty-seven days after initial T cell injection, either MSLN+ or MSLN− tumor cells were administered into the peritoneal cavity, and tumor burden was followed by BLI (FIG. 10E, top). Antigen-specific control of tumor burden was seen in both the Mz- and M28z T cell-treated mice, with a greater decrease seen in the M28z-treated mice (FIGS. 10C and 10E). Mice were sacrificed at day 16 after rechallenge, and their spleens were harvested. M28z T cells rechallenged with antigen-positive tumor showed a 4-fold expansion of T cells, compared with antigen-negative tumor (FIG. 10D). This demonstrates that CAR T cells are able to persist in the periphery and display proliferation when rechallenged with tumor, an effect that is augmented by CD28 co-stimulation.

M28z T Cells Mediate Antigen-Specific Bystander Killing of Low-MSLN-Expressing Targets:

Given the heterogeneity of MSLN expression in certain solid cancers, including in TNBC, the cytotoxicity of M28z T cells against heterogeneous MSLN-expressing targets was evaluated. After 16 h of coculture with MRC-5 lung fibroblasts (MSLN−), M28z T cells demonstrated no lysis (FIG. 17A). The cytotoxicity of M28z T cells against MSLN-expressing targets, composed of a 1:1 mixture of a cell line naturally expressing low levels of MSLN (low MSLN) and a cell line transduced to express high levels of MSLN (high MSLN) was evaluated. To examine the specific lysis, only low MSLN cell lines were labeled with $^{51}$Chromium and were mixed with unlabeled, high MSLN cells and subsequently cocultured with either M28z or control T cells. After 16 h of coculture, specific cytolysis of low MSLN cells by M28z T cells in the presence of high MSLN targets (FIG. 17B) was observed, exceeding the lysis of low MSLN cell lines alone by approximately 5%-15% at each effector to target ratio (p<0.05). Importantly, compared with nonactivated M28z T cells, antigen preactivated M28z T cells did not demonstrate any increased cytotoxicity or nonspecific kill against low MSLN cells or MSLN-negative tumors (FIGS. 17C and 17D). Thus, M28z T cells demonstrate augmented antigen-specific cytolysis against low MSLN cells in the presence of high MSLN tumor.

MSLN-Targeted CAR T Cell In Vivo Trafficking Demonstrated by T Cell BLI:

As described in Example 1, to determine T cell in vivo trafficking and proliferation, double transduction of human T cells with the M28z CAR and enhanced firefly luciferase (effLuc) were optimized. Pleurally administered T cells displayed increasing intensity only in tumor-bearing mice, compared with nontumor-bearing mice, signifying MSLN-specific T cell proliferation (FIG. 4A, dorsal & ventral). Comparatively, systemically administered M28zG-effluc+ T cells displayed lung retention immediately after administration, with increasing pleural signal emission after a few days (FIG. 4B). The monitoring of T cell response by the use noninvasive imaging was optimized, allowing visualization of trafficking as well as quantification of T cell proliferation in response to antigen.

MSLN-Specific CARs with 4-1BB Co-Stimulatory Domain to Investigate Efficacy Against Cancer Cells Expressing Inhibitors of T Cell Function:

To investigate the influence of cancers that typically express inhibitory proteins in order to evade the immune system, cells that express PD-L1 (the black in FIG. 18, compared with isotype control, in red) and secrete inhibitory cytokines such as TGF-β were characterized and confirmed by ELISA. Thus, these cells permit to model the in vivo antitumor efficacy of CAR T cells within an inhibitory TME. To study the ability of CAR T cells to overcome tumor-mediated inhibition, receptors that, upon antigen recognition, provide 4-1BB co-stimulatory signaling (MBBz; FIG. 19) were provided. Primary human T cells were efficiently transduced with MSLN-specific CARs to frequencies of 60%-70%.

MSLN-Targeted CD28 and 4-1BB Co-Stimulation Enhances CAR T Cell Function in the Presence of Tumor-Secreted Immunosuppressive Proteins:

3T3 mouse fibroblast cells to express either MSLN (3T3 MSLN$^+$; FIG. 20A, top) or both MSLN and PD-L1 (3T3 MSLN$^+$ PD-L1$^+$; FIG. 20A, bottom) were engineered and exogenous TGF-β were added to T cell/3T3 MSLN$^+$ cocultures (FIG. 21A) as a surrogate for an adverse TME. Upon stimulation with 3T3 MSLN$^+$ PD-L1$^+$ (unfilled shapes; 3T3 MSLN$^+$, filled-in shapes), co-stimulated CAR$^+$ T cells secreted a lower amount of cytokines, compared with stimulation with 3T3 MSLN$^+$. However, co-stimulated T cells continued to secrete a greater amount of cytokines than Mz T cells even in the presence of PD-L1 ($p<0.005$). Furthermore, blockade of PD-L1/PD-1 ligation with 10 ug/mL of PD-L1 blocking antibody rescued cytokine secretion for all T cell groups (rescue shown with blue filled-in shapes; $p<0.02$, comparing Mz with PD-L1 blockade to Mz without blockade; $p=0.02$ for IFN-γ for MBBz; $p<0.02$ for M28z, unpaired t tests), further demonstrating the specificity of PD-L1-mediated inhibition and suggesting a role for PD-L1/PD-1 axis blockade in enhancing CAR T cell therapy. With regard to proliferation, only M28z and MBBz CAR T cells were able to expand in the presence of PD-L1 overexpression ($p<0.05$, at 7 and 14 days). Similar to PD-L1-mediated inhibition, the addition of TGF-β also decreased cytokine secretion of all CAR T cell groups, but once again costimulated CAR$^+$ T cells continued to secrete a greater amount of cytokines, compared with Mz CAR+ T cells ($p<0.003$; FIG. 21B). In response to MSLN-specific stimulation in the presence of TGF-β, MBBz CAR T cells were still able to expand upon two successive stimulations ($p<0.002$; FIG. 21C). It was demonstrated that co-stimulatory signaling enhanced CAR T cell function even in the presence of prominent tumor-expressed inhibitory proteins.

IL-12 as a Costimulant in Adoptive T Cell Therapy:

It was characterized that M28zIL12 CAR construct, when transduced into T cells, secreted IL-12. Both M28z and M28zIL12 cells, but not untransduced cells, mediated specific lysis of MSLN$^+$ cancer cells with approximately the same effect (FIG. 22). Using an ELISA/LUMINEX assay, it was shown that, upon coculture with antigen-expressing tumor cells, IL-12 CAR T cells enhanced the secretion of Th1 cytokines (IFN-γ, TNFα, and GM-CSF) (FIG. 23) and inhibited the production of Th2 cytokines (IL-13, IL-4, and IL-5) compared with M28z CAR T cells.

Example 3—Generation of Retroviral Vector SFG-iCASP9-2A-M28z

The SFG vector employed both the 5' and 3' long terminal repeats (LTR) of the Mo-MuLV for the expression of the iCASP9-2A-M28z CAR. The transcription of the iCASP9-2A-M28z CAR was under the control of enhancer and promoter sequences present in the U3 region of the 5'LTR and of the polyadenylation site present in the R region of the 3'LTR. Additionally, the vector retained the ψ+ sequences necessary for efficient encapsidation of recombinant retroviral genomes into viral particles and the retroviral splice donor and acceptor sequences used for the generation of the subgenomic retroviral RNA that codes for the env protein in Mo-MLV. The iCASP9-2A-M28z sequence was inserted so its initiation codon was at the position normally occupied by the viral env ATG in the subgenomic viral transcript. It was shown by Northern blot analyses that this cloning strategy increased the ratio of spliced to unspliced vector RNA per vector copy by four-fold relative to a conventional gammaretroviral vector (Krall and Kohn, 1996, Expression levels by retroviral vectors based upon the N2 and the MFG backbones. Gene Ther 3, 365).

SFG-iCASP9-2A-M28z (as shown in FIGS. 31 and 32) was constructed by inserting two DNA fragments into a 6.7 kb NotI/BglII of the SFG backbone. The backbone encodes the following: (1) the entire SFG γ-retroviral vector except for a region encompassing the SA and 5'UTR of the Mo-MLV env encoding mRNA; and (2) the CDS of the human CD28 signaling domain fused to the human CD3 ζ signaling domain.

DNA fragment 1 was a 1.5 kb BglII/BspEI fragment derived from plasmid construct SFG-iC9-41BBL-NY28z. This fragment encoded a region encompassing the SA and 5'UTR of the M0-MLV env encoding mRNA fused to the CDS of iCASP9 lacking eight amino acids of the C-terminus and the stop codon. The iCASP9 CDS was derived by de novo synthesis from Blue Heron Bio.

DNA fragment 2 was a 0.89 kb BspEI/NotI fragment derived from a 0.979 kb PCR product. This fragment encoded the C-terminal CDS of iCASP9 (without the stop codon) fused to GSG-P2A-CD8a leader_m912 scFv. This PCR product was synthesized from SFG-TK-2A-M28z as a template using the following primers:

(1) iCASP9-2A Left primer:
[SEQ ID NO: 37]
gcgctccggaaaaaactttattaaaacatc aggatctggagcaaca aacttc (2) CD28 Right primer:
[SEQ ID NO: 38]
ggtgtttcccttcacatgg.

The amino acid sequence of P2A is set forth in SEQ ID NO: 39, which is provided below:

[SEQ ID NO: 39]
ATNFSLLKQAGDVEENPGP

The nucleotide sequence encoding the amino acid sequence of SEQ ID NO: 39 is set forth in SEQ ID NO: 40, which is provided below:

[SEQ ID NO: 40]
GCAACAAACTTCTCACTACTCAAACAAGCAGGTGACGTGGAGGAGAAT

CCCGGCCC

SFG-TK_2A_M28z template was derived using the SFG-Hsvtk_P2A_P28z backbone and the CD8a leader_m912 scFv sequence in SFG-M28z_ires_hrGFP by overlap-extension PCR. The CD8a leader_m912 scFv sequence in SFG-M28z_ires_hrGFP was derived by de novo synthesis from Blue Heron Bio using an expression optimized codon table.1. Generation of the SFG-Hsvtk_P2A_P28z retroviral vectorSFG/TK_2A_P28z was derived from SFG/TP28z.3 using a 3 piece ligation—(1) a 1462 bp BglI/BssHII fragment derived from SFG-TP28z.3 encoding a region of the Mo-MLV vector containing the splice acceptor site fused to the HSV-TK gene; (2) a 880 bp BssHII/NotI fragment derived from PCR product encoding the 3' end of the HSV-TK gene without the stop codon_GSG 2A_CD8a signal peptide J591 ScFv; and (3) a 6652 bp NotI/BssHII fragment derived from SFG-TP28z.3 encoding the rest of the transmembrane_CD28_zeta chain of the chimeric antigen receptor plus the remainder of the retroviralvector backbone. The PCR product was amplified using a previously constructed plasmid DNA encoding the GSG_P2A CD28z as a template. The following primers were utilized: (1) Forward HSVTK_linker_GSG_P2A: GCGCGCGCGCACGTTTGCCCGGGAGATGGGG-GAGGCTAACGG ATCTGGAGCAACAAACTTC [SEQ ID NO: 41] (2) Reverse-P28z R: ggtgtttcccttcacatgg [SEQ ID NO: 42]

2. Generation of the retroviral vector SFG-iC9-41BBL-NY28zSFG-iC9-41BBL-NY28z was generated by inserting two fragments into a 6.8 kb AgeI/NotI backbone derived from SFG-Hsvtk_2A_P28z: (1) 1.7 kb AgeI/SacII fragment derived from pUC(-mcs)-CBNI encoding the Mo-MLV S D and 5' UTR of the env mRNA fused to the entire CDS of iCASP9 and the N-terminal 4-1BBL fused in frame with the gsg_P2A cleavage peptide; and (2.) 1.5 kb SacI/AgeI fragment derived from pUC(-mcs)-CBNII encoding the remaining C-terminal 4-1BBL CDS fused via another GSG_P2A cleavage peptide to an scFv targeting the NYESO-1 antigen.

Both pUC(-mcs)-CBNI and pUC(-mcs)-CBNII were obtained from Blue Heron Bio and the inserts generated by de novo gene synthesis.

Figure 29B:
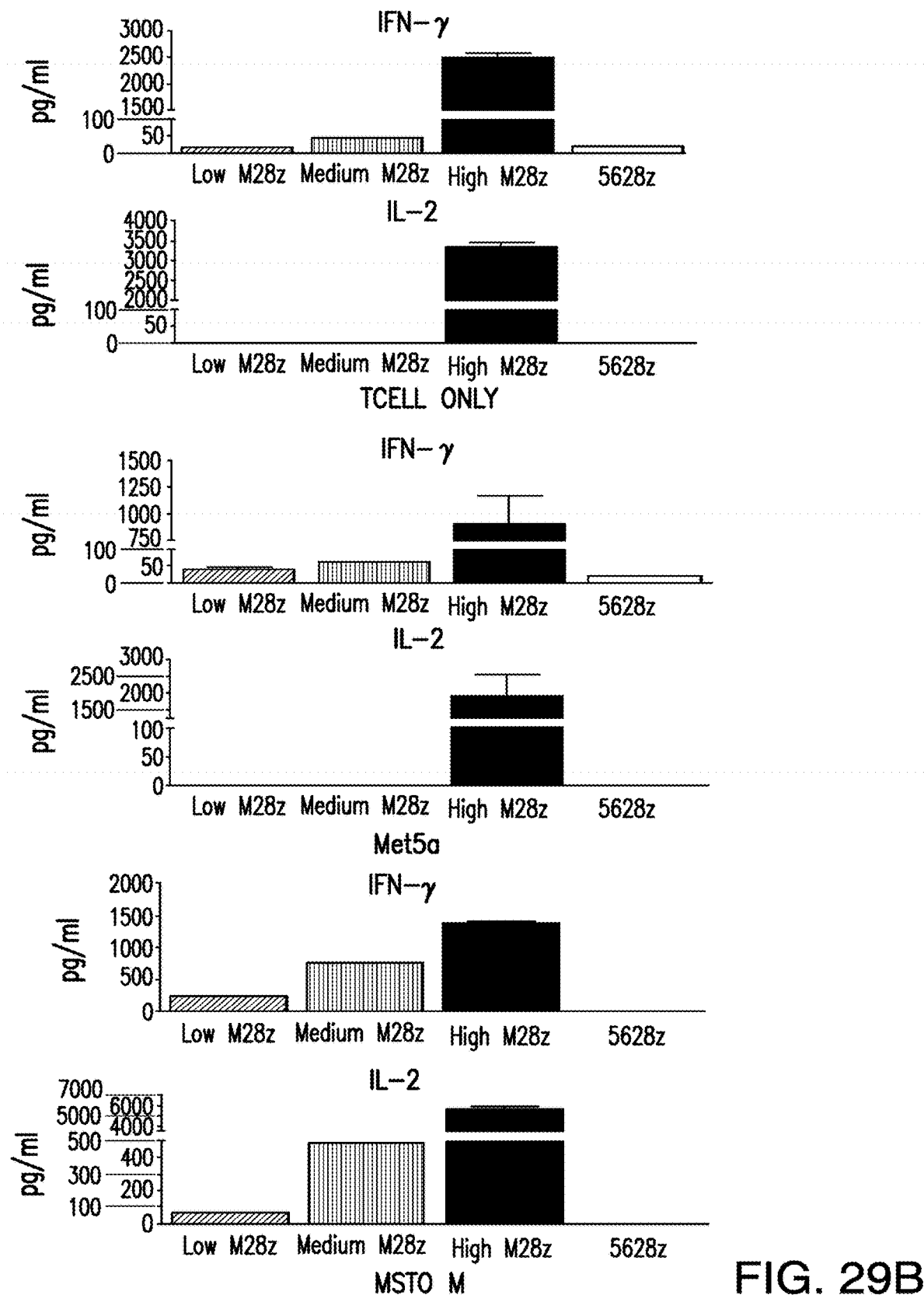

Example 4—CAR Expression Level is Associated with Efficacy of CAR-Expressing T Cells T cells populations with varying expression levels of M28z CAR using subclones of 293T packaging cell lines were generated. A second generation CAR targeting a CD marker was used as a negative control (control CAR). A retroviral construct coding for M28z is shown in FIG. 27A. As shown in FIG. 27A, the construct comprises a reporter, GFP. CD3$^+$ human T cells were transduced with M28z and the control CAR. T cells expressed different levels of M28z, as shown in FIG. 27B. T cells with a M28z expression level of about 4 or more vector copy numbers/cell were categorized as "high M28z". T cells with a M28z expression level of from about 1 to about 4 vector copy numbers/cell were categorized as "medium M28zT", and cells with a M28z expression level of less than about 1 vector copy numbers/cell were categorized as "low M28z". Vector copy numbers of untransduced and transduced T cells were measured by quantitative PCR, as shown in FIG. 27C. Four target cell lines expressing varying levels of surface mesothelin were generated: Met5a, EKVX, MSTO M and OVCAR-3. Met5a was a human mesothelial cell line immortalized with SV40 large T antigen. EKVX was a lung cancer cell line naturally expressing mesothelin. MSTO M was the MSTO-211H cell line transduced to overexpress human mesothelin. OVCAR-3 was an ovarian cancer line naturally expressing mesothelin. As shown in FIG. 28, among these four target cell lines, MSTO M had the highest expression level of human mesothelin, and Met5a had the lowest expression level of human mesothelin. The four target cell lines were co-cultured with either M28z$^+$ T cells or the control CAR$^+$ T cells. Cytokine production or secretion of M28z$^+$ T cells in the four target cell lines was evaluated. As shown in FIGS. 29A and 29B, only T cells with the highest expression level of M28z displayed antigen-specific cytokine secretion to Met5a target cells, which had the lowest expression level of human mesothelin among the four tested cell lines. Increasing expression levels of M28z CAR resulted in dose-dependent cytokine secretion to MSTO target cells, which had the highest expression level of human mesothelin among the four tested cell lines. In pairwise comparisons using Bonferroni correction, cytokine secretion was significantly higher ($p<0.05$) in (1) high expression level of M28z versus all three other effectors for both the T cell only and Met5a targets; and (2) all between group comparisons in the case of the MSTO M target cells.

In addition, the cytotoxicity of M28z$^+$ T cells against the four target cell lines was evaluated by standard $^{51}$Cr-release assays. T cells expressing various density of M28z CAR, Met5a target cells, MSTO MSLN+ target cells, and EL4PSMA+ MSLN− target cells were incubated for 18 hours at different E:T ratios. EL4PSMA+ MSLN− target cells were used as negative control. As shown in FIG. 30, only the T cells with a high expression level of M28z exhibited cytotoxicity against Met5a target cells, which had the lowest expression level of human mesothelin among the four tested cell lines. In addition, as shown in FIG. 30, the expression level of CAR determined the degree of cytotoxicity against MSTO target cells, which had the highest expression level of human mesothelin among the four tested cell lines.

Example 5—Mesothelin Expression Level is Associated with to Efficacy of CAR-Expressing T Cells A single mesothelioma cell line (MSTO 211-H) was used and transduced with a low or high level of human MSLN, as shown in FIG. 31A. The cytotoxicity of M28z$^+$ T cells was determined by standard $^{51}$Cr-release assays as described above, and the results are shown in FIG. 31B. The cytokine production was determined by cytokine secretion assay, and the results are shown in FIG. 31C. As shown in FIGS. 31B and 31C, the cytotoxicity and cytokine production of the M28z$^+$ T cells were proportional to the expression level of human MSLN. For example, the higher the expression level of human MSLN, the greater cytotoxicity and cytokine production the T cells.

Example 6—Generation of MSLN-Specific CAR with Optional Expression Levels

A scFv derived from m912 antibody was obtained. Codon optimization of the m912 antibody was performed based on four different algorithms (e.g., Blue Heron and Encore algorithms). The codon optimization sequences obtained from all four algorithms were blended, and all CPGs and BAM-H1 were removed for optimal cloning. The codon optimized nucleotide sequence was about 70% homologous to the original m912 scFv. In order to obtain efficient expression in an immunoresponsive cell (e.g., human primary T cells), the codon optimized nucleotide sequence was ligated to a human CD8 leader, e.g., a polynucleotide encoding SEQ ID NO:20. The CD8 leader provided optimal signal cleavage preceding ScFv heavy chain (QVQL).

Codon optimization optimized mesothelin CAR expression in an immunoresponsive cell, e.g., multiple human donor primary T cells, with good transduction efficiency. Multiple CAR vector copy numbers in multiple donors T cells were tested for functional efficiency, specificity and sensitivity against multiple hematological and solid cancer cells with varying mesothelin expression. The codon optimized m912-based mesothelin CAR with a vector copy number of 1-4 provided highly efficient cytotoxicity against high mesothelin expressing targets, yet minimal reactivity against low mesothelin expressing targets, i.e. normal tissue, which is a key feature accomplished for vector safety without compromising efficiency. The above-described innovative genetic engineering in generating a specific mesothelin CAR that is reactive against cancer cells expressing high mesothelin while sparing normal tissue expressing low mesothelin is optimal for use as clinical vector for cancer therapy while assuring safety.

Example 7—Regional Delivery of Mesothelin-Targeted CAR T Cell Therapy Generates Potent and Long-Lasting CD4-Dependent Tumor Immunity—Update of Example 1

1. Abstract

Translating the recent success of CAR T cell therapy for hematological malignancies to solid tumors will necessitate overcoming several obstacles, including inefficient T cell tumor infiltration and insufficient functional persistence. Taking advantage of an orthotopic model that faithfully mimics human pleural malignancy, two routes of administration of mesothelin-targeted T cells using the M28z CAR were evaluated. It was found that intrapleurally administered CAR T cells vastly outperformed systemically infused T cells, requiring 30-fold fewer M28z T cells to induce long-term complete remissions. After intrapleural T cell administration, prompt in vivo antigen-induced T cell activation allowed robust CAR T cell expansion and effector differentiation, resulting in enhanced antitumor efficacy and functional T cell persistence for 200 days. Regional T cell administration also promoted efficient elimination of extrathoracic tumor sites. This therapeutic efficacy was dependent on early CD4+ T cell activation associated with a higher intratumoral CD4/CD8 cell ratios and CD28-dependent CD4+ T cell-mediated cytotoxicity. In contrast, intravenously delivered CAR T cells, even when accumulated at equivalent numbers in the pleural tumor, did not achieve comparable activation, tumor eradication, or persistence. The ability of intrapleurally administered T cells to circulate and persist supports the concept of delivering optimal CAR T cell therapy through "regional distribution centers." On the basis of these results, a phase 1 clinical trial is in progress to evaluate the safety of intrapleural administration of mesothelin-targeted CAR T cells in patients with primary or secondary pleural malignancies.

1. Introduction

Pleural malignancies, both primary (malignant pleural mesothelioma, MPM) and metastatic (from lung and breast cancers), affect more than 150,000 patients per year in the U.S. alone[108]. MPM is a regionally aggressive disease with limited treatment options[109]. Studies have reported on the better prognosis of having higher levels of tumor-infiltrating lymphocytes in MPM[110-113], suggesting that T cell-based immunotherapy may be beneficial to patients with MPM[114].

Targeted immunotherapies utilizing CARs to redirect and reprogram patient T cells have recently shown encouraging results in some B cell malignancies, especially acute lymphoblastic leukemia and non-Hodgkin lymphomall,[11,115,116,117.] CARs are synthetic receptors that retarget T cells to tumor surface antigens[21,118]. The advent of second generation CARs, which combine activating and costimulatory signaling domains, has enabled the design of potent T cells that can mediate complete responses in patients with chemo refractory CD19+ malignancies[11,115,116,117.] The therapeutic potential of CAR therapies against solid cancers remains unknown. One critical aspect of devising a CAR therapy for any solid tumor is the identification of a valid target antigen. Mesothelin (MSLN) is a cell surface molecule associated with regional invasion, a characteristic of MPM where it is overexpressed in more than 90% of epithelioid MPM[37]. In the inventors' clinicopathological studies systematically evaluating MSLN expression and intensity, strong to intermediate MSLN expression was found in 69% of lung adenocarcinoma (n=1209)[119], 36% of triple-negative breast cancer (n=355) and 46% of esophageal adenocarcinoma (n=125)[47]. MSLN expression was consistently associated with tumor aggressiveness and decreased survival[37,47,119]. Collectively, these observations support targeting MSLN in MPM and other solid cancers[114,120-122]

Mesothelin-targeted CARs have previously shown activity in a subcutaneous model of mesothelioma[55,56,123]. Targeted T cell therapies have however not been studied in orthotopic models. To this end, a clinically relevant MPM mouse model that recapitulates characteristic features of the human disease[37,85,86] was established. The established pleural tumors encase lung and mediastinal structures with regional invasion, show extensive lymphangiogenesis and develop mediastinal lymph node metastases. This model not only addressed whether CAR T cells could eradicate tumor but also studied two potential routes of T cell administration: the conventional systemic intravenous and regional intrapleural administration. It was hypothesized that systemic delivery may be superior owing to better infiltration of diffuse pleural disease, mediastinal lymph nodes and occasional metastatic sites, which we could model. Surprisingly, it was found that regional, i.e. intra-pleural T cell administration, was vastly superior, not only against pleural disease but also against disseminated tumor sites. This observation prompted investigation of the basis for such therapeutic efficacy.

In this example, the therapeutic potential of regional CAR T-cell therapy for solid tumors was reported and the importance of early-antigen activation of CD4+ CAR T cells to achieve enhanced antitumor efficacy was underscored. Furthermore, the findings, which demonstrate the clear benefit of regional therapy in a clinically relevant disease model, are immediately translatable for the treatment of MPM and metastatic pleural tumors.

3. Materials and Methods

Study Design

The purpose of this study was to create an optimal T cell immunotherapy for solid malignancies. Mesothelin-targeted chimeric antigen receptors that, when transduced into human T cells, provide tumor antigen recognition and antigen-specific effector function, were designed. In vitro, (i) cytotoxicity, (ii) cytokine secretion, and (iii) T cell proliferation were analyzed. In vivo experiments analyzed strategies for optimizing T-cell therapy using live imaging of both T cells and tumor. Immunodeficient mice with human cancer cells and human T cells were used in order to validate and facilitate the translation of our M28z CAR to the clinic, as previously did for CD19 (Brentjens, N M, 2003) and PSMA (Gade, C R, 2005). The study of mechanistic interactions between CAR T cells and the endogenous immune system would be best studied in an immunocompetent mouse model, which would however have to utilize a murine CAR differing from its clinically relevant counterpart. The experimental procedures were approved by the Institutional Animal Care and Use Committee of Memorial Sloan-Kettering Cancer Center (MSKCC). Each experiment was performed multiple times using different donor T cells (T cells were never pooled). The presented data used a representative experiment (with sample replicates of more than three) to avoid confounding variables such as differences due to transduction efficiencies, donor-related variability, and E:T ratios.

Cell Lines

MSTO-211H (human pleural mesothelioma) and EL4 (murine thymoma) cells were retrovirally transduced to express the GFP/firefly luciferase fusion protein (MSTO GFP-ffLuc+). These cells were then transduced with the human MSLN-variant 1 subcloned into a SFG retroviral vector to generate MSTO MSLN+ GFP-ffLuc+.

Gamma-Retroviral Vector Construction and Viral Production

To generate MSLN-specific CARs, a fusion protein encoding a fully human scFv, m912 (kindly provided by D. Dimitrov, NCI-Frederick)[53] linked to the human CD8 leader peptide and the CD8/CD3ζ or CD28/CD3ζ sequences as previously described was engineered[17]. Within the SFG gamma-retroviral vector backbone (kindly provided by I Riviere, MSKCC), an internal ribosomal entry site was inserted to facilitate bicistronic expression of CARs with humanized recombinant GFP reporter gene. The Mz, M28z, and P28z-encoding plasmids were then transfected into 293T H29 packaging cell lines as previously described[20].

T-Cell Isolation, Gene Transfer, and CD4/CD8 Isolation

Peripheral blood leukocytes were isolated from the blood of healthy volunteer donors under an institutional review board-approved protocol. PHA-activated PBMCs were isolated by low-density centrifugation on Lymphoprep. Two days after isolation, PBMCs were transduced with 293T RD114-produced supernatant containing Mz, M28z, or P28z vectors for 1 h on plates coated with 15 μg/mL retronectin daily for 2 days. After allowing 3 days for vector expression, transduced PBMCs were maintained in 20 units/mL IL-2. Transduction efficiencies were determined by flow cytometric analysis. Pure populations of CD4+ and CD8+ T cells were obtained through negative selection protocols using Dynabeads Untouched Human CD4 and CD8 T-cell isolation kits.

Cytotoxicity Assays

The cytotoxicity of T cells transduced with a CAR or vector control was determined by standard $^{51}$Cr-release assays as previously described[153]

Orthotopic Pleural Mesothelioma Animal Model and In Vivo Assessments

To develop the orthotopic mouse model of pleural mesothelioma, female NOD/SCID gamma mice at 6 to 10 weeks of age were used. All procedures were performed under approved Institutional Animal Care and Use Committee protocols. Mice were anesthetized using inhaled isoflurane and oxygen and were administered bupivacaine for analgesia. Direct intrapleural injection of $1\times10^5$ to $1\times10^6$ tumor cells in 200 μL of serum-free media via a right thoracic incision was performed to establish orthotopic MPM tumors, as previously described[85,86,92,154]. In total, $3\times10^4$ to $3\times10^6$ transduced T cells were adoptively transferred into tumor-bearing mice, with 200 μL of serum-free media, into the thoracic cavity of mice by direct intrapleural injection or systemically by tail vein injection. Peripheral blood was obtained by retro-orbital bleeding.

Cytokine Detection Assays

Cytokine-release assays were performed by coculturing $5\times10^5$ to $5\times10^3$ T cells transduced with M28z, Mz, or control vector with $5\times10^3$ target cells in 200 uL of media in 96-well round-bottom plates as triplicates. After 6 to 24 h of coculture, supernatants were collected. Cytokine levels were determined using multiplex bead Human Cytokine Detection kit.

T-Cell Proliferation Assays

In total, $1\times10^6$ to $3\times10^6$ T cells transduced with M28z, Mz, or P28z were stimulated over irradiated MSTO-211H cells with or without MSLN expression and were plated in 6- or 24-well tissue culture plates at a density of $1\times10^5$ to $3\times10^5$ cells/well. Proliferation assays were performed in the absence or presence of 20 U/mL exogenous IL-2, as noted. Cells were counted every 4 or 7 days and then overlaid on irradiated MSTO-211H cells with or without MSLN expression. Cell number versus time was plotted for each T-cell group, and phenotypes were determined by flow cytometric analysis.

Histologic Analysis and Immunostaining

Histopathologic evaluation of tumors was performed after hematoxylin and eosin staining of paraffin-embedded, 4% paraformaldehyde-fixed tissue samples. Immunohistochemical analysis for human MSLN was performed with a mouse anti-human MSLN IgG. Human anti-CD3 staining was performed with a mouse anti-human CD3 IgG.

Flow Cytometry

Human MSLN expression was detected using a PE-conjugated or APC-conjugated anti-human MSLN rat $IgG_{2a}$. T-cell phenotypes were determined with monoclonal antibodies for CD3, CD4, CD8, CD62L, CD25, CD27 and CD45RA. Subsequent flow cytometry for GFP, MSLN expression, and T-cell phenotype analysis was performed on an LSRII cytometers and analyzed using FlowJo analysis software. Mouse tissues were processed as follows: tissues were weighed and harvested into ice-cold RPMI-1640. The tissues were manually morselized with a scalpel and then mechanically disaggregated through 40-100 um filters. Samples were resuspended and $2\times10^6$ events were recorded on FACS.

Quantitative and T-Cell BLI In Vivo

BLI in mice was performed using a single intraperitoneal dose of 150 mg/kg d-Luciferin for firefly or effLuc reporter gene (Kindly provided by Dr Patrick Hwu, Texas)[86,155]. Cells transduced with M28z and a Gaussia luciferase reporter gene were imaged with a single intravenous dose of 15 ug native coelentereazine resuspended in 150 ul of propylene glycol:PBS (1:1)[156]. BLI data were analyzed using Living Image 2.60 software and BLI signal reported as total flux (photons/s). BLI flux (photon/s) was then determined as the average of ventral and dorsal images with Microsoft Excel (Microsoft Corp., WA) and analyzed with GraphPad Prism (GraphPad Software, Inc., CA).

Statistical Methods

Data are presented as means+/−SD or SEM as stated in the figure legends. Results were analyzed by unpaired Student't t test (two-tailed) with Bonferroni correction for multiple comparisons where applicable. Survival curves were analyzed with log-rank test. Statistical significance was defined as $P<0.05$. All statistical analysis were performed with Prism software version 6.0 (GraphPad).

4. Results

Mz- and M28z-Transduced T Cells Specifically Respond to MSLN+ Target Cells

Figure 35A:
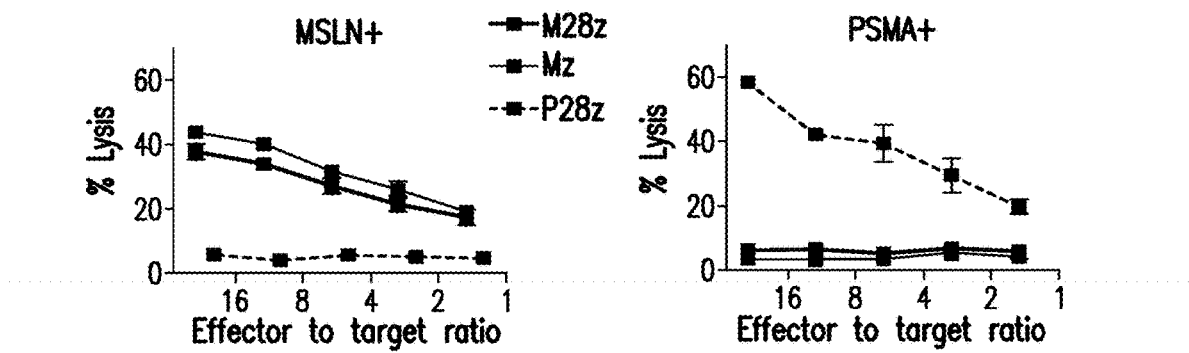

Two CARs incorporating a human MSLN-specific scFv[53] and either CD3ζ or CD28/CD3ζ signaling domains (Mz and M28z, FIG. 2A) were constructed. The P28z CAR, specific for prostate-specific membrane antigen (PSMA)[17], served as a negative control for alloreactivity and xenoreactivity. Both CD4+ and CD8+ human peripheral blood T lymphocytes were effectively transduced using the SFG gamma-retroviral vector (60-75% transduction, FIG. 2B). MSLN− transduced MSTO-211H (MSLN+) and PSMA-transduced EL-4 mouse lymphoma cells (MSLN−) cells provided MSLN positive and negative targets used for in vitro experiments (FIG. 43A). Mz- and M28z-transduced T cells demonstrated similar MSLN-specific lysis in vitro. (FIG. 35A). P28z CAR T cells did not lyse MSTO MSLN+ and mesothelin-targeted CARs did not lyse EL4 PSMA+. As expected for second generation CARs[15], M28z CAR T cells secreted a 2- to 5-fold greater amount of Th1 cytokines (FIG. 43B) and afforded greater T cell accumulation upon repeated exposure to MSLN+ cells in the absence or presence of exogenous IL-2 (FIG. 2E). Based on these findings, we proceeded to evaluate the therapeutic potential of M28z in mice bearing established pleural tumors.

Regional Delivery of M28z T Cells is More Potent than the Systemic Route

Figure 35B:
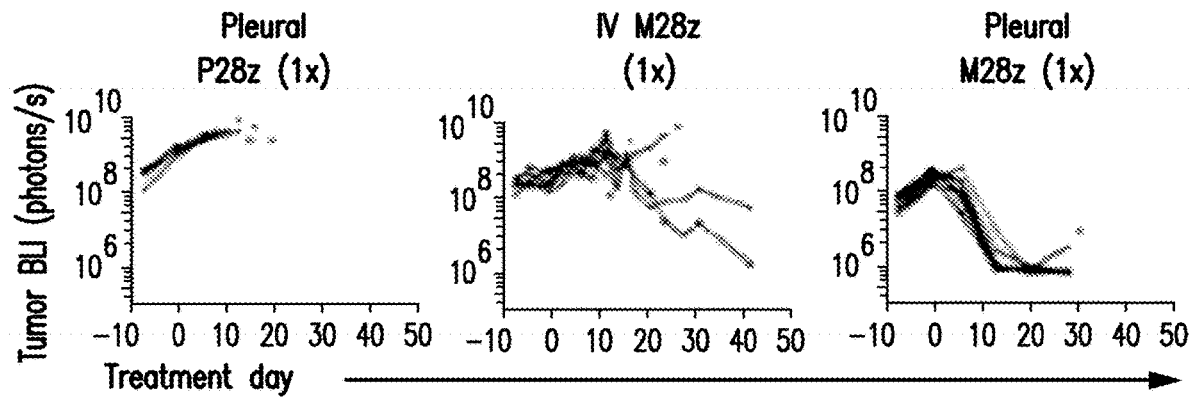
Figure 35C:
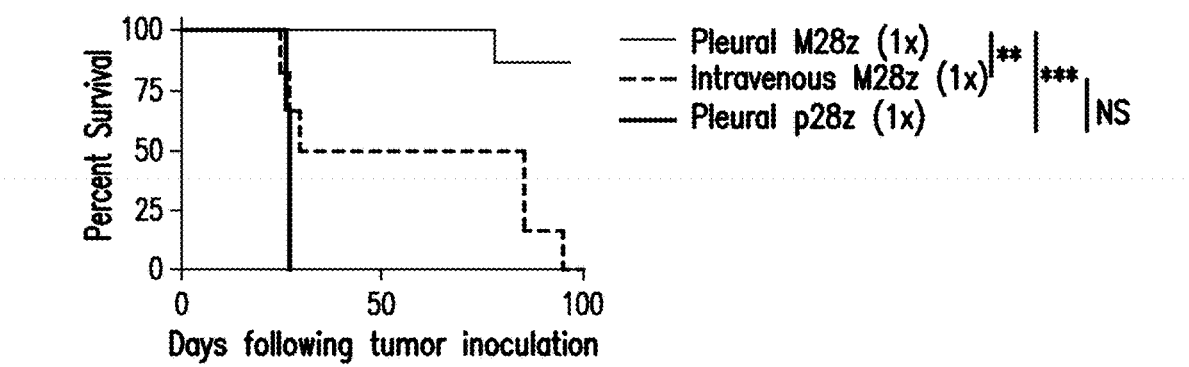
Figure 35D:
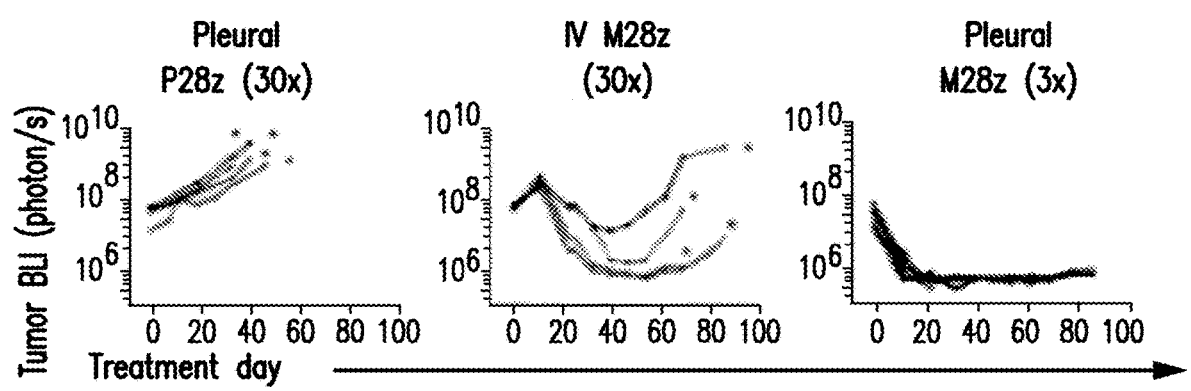
Figure 35E:
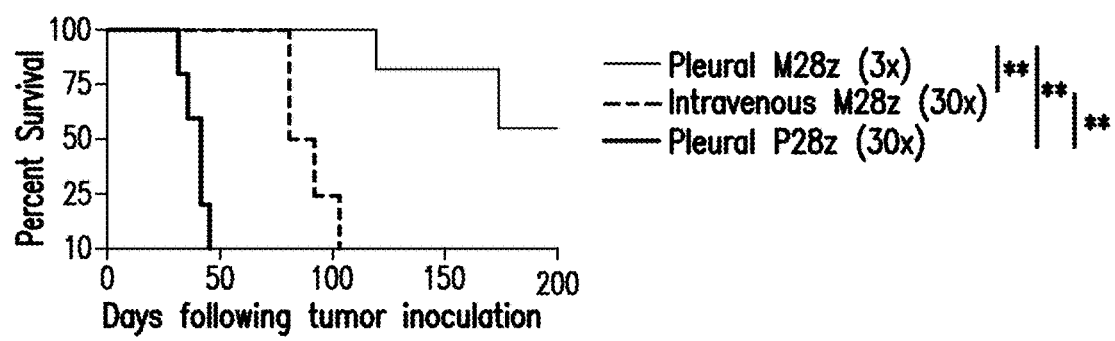

In an orthotopic model of MPM previously established by the inventors' laboratory[37,85,86,93], serial bioluminescence imaging (BLI) using firefly-luciferase (fLuc)-transduced MSTO-211H was used to confirm establishment of tumor, equalize tumor burden across intervention groups before initiation of T cell therapy, and measure response to therapy. Mice with established pleural tumor were treated 12 days after tumor inoculation with either a single intravenous or intra-pleural administration of 1×10$^5$ M28z CAR T cells (Effector to target [E:T] ratio of 1:3000, estimated from tumor burden quantification as previously described)[85,86]. P28z CAR or untransduced T cells were administered at the same dose to demonstrate antigen-specificity and control for alloreactivity and xenoreactivity. Treatment with intravenous M28z T cells at this dose resulted in marginal antitumor efficacy (FIG. 35B), hardly exceeding P28z control T cells (FIG. 35C, broken blue line vs. solid black line, MS. 27 vs. 25 days, respectively). In contrast, intra-pleurally administered M28z T cells induced major responses. Tumor burdens were significantly lower by day 7, becoming undetectable by day 11 (FIG. 35B). Median survival was not reached by day 100 (FIG. 35C). Treatment with a higher dose of intravenous M28z T cells (3×10$^6$, a 30-fold increase, E:T 1:100) reduced tumor burden but did not avert eventual tumor progression (FIGS. 2B and 35D), yielding a modest 44-day survival advantage (FIG. 35E, broken blue line). In contrast, a 10-fold lower dose of M28z CAR T cells (3×10$^5$, E:T 1:1000) administered intra-pleurally rapidly decreased tumor burden within 10 days of administration (FIGS. 2B and 35D) and did not reach median survival by day 200 (solid blue line, FIG. 35E). Experimental results were similar with T cells from 3 different donors, arguing against a significant impact of alloreactivity, if any.

Unlike Systemic Delivery, Intra-Pleural T Cell Administration Promotes Prompt M28z T Cell Expansion and Differentiation The long-term tumor-free survival observed with regional CAR T-cell therapy, even at a dose 30-fold lower than that used intravenously, prompted us to investigate T cell tumor infiltration, expansion, and persistence following intra-pleural vs intravenous administration. To this end, the inventors first performed tumor and T cell noninvasive, quantitative BLI. All mice were treated with a single dose of T cells (1×10$^6$) co-expressing M28z and enhanced firefly luciferase (effLuc). Within 24 h of administration, intra-pleural delivery resulted in a rapid increase in pleural M28z T cell accumulation, 10-fold greater than via intravenous delivery (FIG. 36A). This rapid and sustained accumulation occurred with M28z (FIG. 36B, blue line) but not P28z T cells. Intravenously administered M28z T cells yielded signal comparable to intra-pleurally delivered T cells after 5 to 7 days. Rising T cell BLI signal paralleled tumor burden regression recorded by concomitant tumor BLI decrease. Serial immuno-histochemical analyses confirmed the T cell accumulation kinetics (FIG. 4D). Further flow cytometric analysis of the T cell to tumor cell ratio revealed a similar accumulation of CAR T cells at initial time points (day 3-5) when comparing the two routes of administration, which however diverged thereafter, steadily increasing in the case of intra-pleurally delivered T cells but diminishing in the systemically treated mice (FIG. 36C). Consistent with differential acquisition of effector functions, we observed marked differences in the pleural CD4/CD8 ratio and the pattern of CD62L expression (L-selectin), a marker down-regulated upon T-cell activation and effector memory formation[124]. While intra-pleural administration maintained a balanced CD4/CD8 ratio, intravenous administration resulted in significantly lesser CD8+ accumulation (FIGS. 36C and 36D). The equal distribution of CD4+ and CD8+ T cells seen within the spleen of these mice indicates that the reduced intra-tumoral CD8+ accumulation is not due to a systemic absence of CD8+ T cells. Furthermore, most intravenously administered CD4+ T cells demonstrated a non-activated (CD62L+) T-cell phenotype 1 week after administration. In contrast, a large proportion of intra-pleurally administered CD4+ T cells exhibited an activated CD62L− phenotype (FIG. 36F). CD8+M28z T cells showed a similar reduction in CD62L expression in either case (FIG. 36F), establishing that differential activation primarily affected the activation of CD4+ T cells and the concomitant accumulation of CD8+ T cells.

Regionally Primed M28z T Cells Support Potent, Systemic, Tumor Specific Responses To assess whether intrapleurally administered T cells provide systemic tumor protection, the inventors treated mice bearing MSLN+ pleural tumor expressing firefly luciferase as well as MSLN+ and MSLN− flank tumors (right MSLN+ and left MSLN−, FIG. 37A, left) with intrapleural M28z T cells expressing Gaussia luciferase. Fifteen days after T cell administration, BLI with coelenterazine demonstrated residual T cells in the pleural cavity and T-cell accumulation in the MSLN+ right-flank tumor (FIG. 37A, center) but not the MSLN− left-flank tumor. Tumor imaging with D-Luciferin on the following day showed eradication of pleural tumor, regression of the MSLN+ right-flank tumor and progression of the MSLN− left-flank tumor (FIG. 37A, right). Furthermore, it was investigated whether intra-pleurally administered CAR T cells could traffic to the peritoneal cavity, a potential site of mesothelioma dissemination. In this dual pleural/peritoneal disease model, intra-pleurally administered M28z T cells rapidly accumulated (days 1-2) and at a higher number than intravenously administered T cells (FIGS. 37B and 37C).

Intrapleurally Administered M28z T Cells Remain Functional for at Least 100 Days Having demonstrated rapid activation of regionally dispensed M28z T cells and their efficient extra-thoracic redistribution, their persistence and function were further examined. After establishing large pleural tumor burdens over 18 days, Mz, M28z or P28z T cells were administered into the pleural cavity at a low dose of $3\times10^5$ CAR+ T cells (E:T, 1:1000). Treatment with M28z T cells induced a uniform reduction in tumor bioluminescence to background emission levels, as well as long-term tumor-free survival (median survival not reached vs. 63 days in Mz vs. 36 days in P28z, P=0.01, FIG. 38). Serial assessment of CAR+ T cell counts in the peripheral blood of treated mice demonstrated increased T-cell persistence in M28z-treated mice when compared to Mz treated mice (50 days after T-cell infusion; FIG. 38B). Similar results of T-cell persistence were obtained using 3 separate T-cell doses ($3\times10^6$, $1\times10^6$, and $3\times10^5$ administered CAR+ T cells). Phenotype assessment of persisting T cells demonstrated progressive and predominant enrichment in CD4+ T cells 30 days after T-cell infusion in both Mz- and M28z-treated mice (FIG. 5C). This gradual CD4+ enrichment was observed at all 3 T cell doses in both spleen and blood.

Next, the functional status of persisting T cells was assessed by performing a tumor re-challenge experiment. Mice with established MSLN+ pleural tumors were intrapleurally administered either $3\times10^5$ Mz or M28z T cells to eradicate pleural tumor and promote long term survival. Eighty-seven days after initial T-cell injection, either MSLN+ or MSLN− tumor cells ($1\times10^6$) were administered into the peritoneal cavity to long-term survivors and tumor burden was monitored using BLI. At the time of rechallenge, persisting T cells were predominantly effector memory (CD45RA-CD62L-) cells (FIG. 10A) as evidenced by FACS analysis in representative mice. After an initial increase in tumor burden in all mice, antigen-specific control of tumor burden was seen in both the Mz and M28z T-cell-treated mice, most markedly in M28z-treated mice (FIG. 39). Then, the T cell proliferative response on tumor challenge was examined. Mice from all groups were sacrificed 16 days after rechallenge, and spleens were harvested for FACS analysis. Mice initially treated with M28z T cells and rechallenged with MSLN+ tumor showed a 4-fold higher T cell expansion than those rechallenged with MSLN− tumor (FIG. 10C). The greater T cell accumulation was predominantly attributable to the CD4+ subpopulation in the M28z group (FIG. 10D).

Figure 40A:
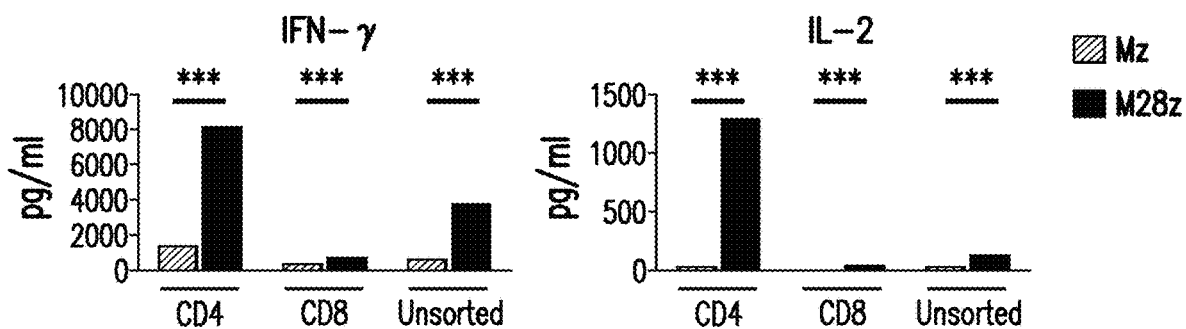
Figure 40B:
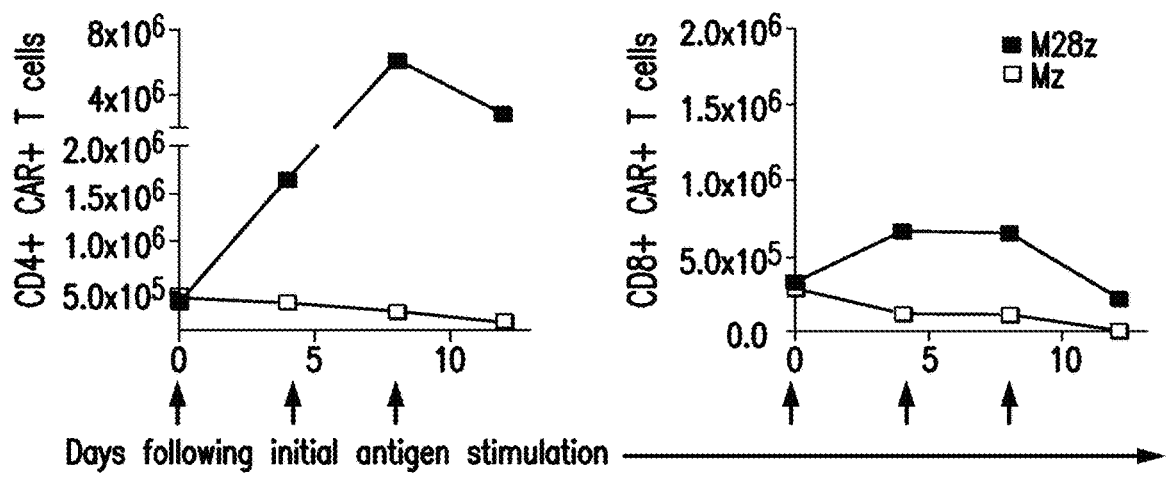
Figure 40C:
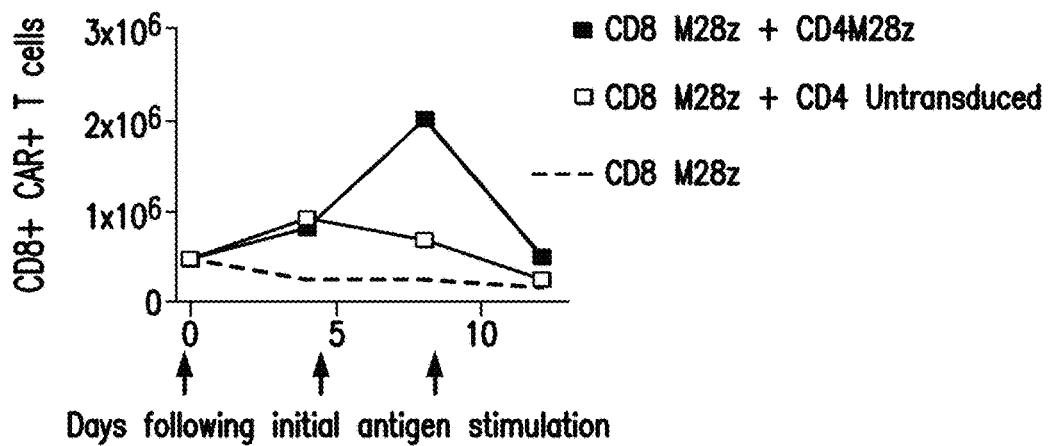

Early Antigen Activation of CD4+M28z T Cells is Essential for Enhancing CAR T Cell Efficacy To assess the relative contribution of CD28 costimulation to CD4+ and CD8+ cytokine and proliferative responses, CD4+, CD8+, and bulk T cells transduced with either Mz or M28z were stimulated with MSLN+ tumor cells and the secretion of Th1 cytokines and proliferation were quantified. Compared with CD8+ T cells, CD4+ T cells transduced with Mz had increased levels of Th1 cytokine secretion (FIG. 40A). CD28-costimulated CD4+ T cells secreted 11- to 50-fold higher levels of cytokines than CD8+ T cells, showing that cytokine secretion is strongly enhanced in CD28-costimulated T cells, particularly in CD4+ T cells. As expected, repeated stimulation with MSLN+ targets did not induce T-cell expansion in either the CD4+ or CD8+Mz T-cell population and rather rapidly induced a decline in T cell number upon antigen stimulation in the absence of exogenous IL-2 (FIG. 40B). In contrast, CD4+M28z T cells expanded >20-fold greater mean proliferation by the third stimulation, compared with a 2-fold increase in CD8+M28z T cells (P<0.001). The importance of CD4+ CAR T cells in supporting M28z CAR T-cell function was further demonstrated by the robust accumulation of CD8+M28z T cells when cocultured with CD4+M28z T cells and stimulated by MSLN+ targets (3-fold greater accumulation; P<0.001; FIG. 40C). To further confirm the potentiating function of CD4+ M28z CAR T cells in vivo, CD8+M28z CAR T cells were transduced with effLuc (to monitor T-cell accumulation in pleural tumor-bearing mice). CD8+M28z CAR T cells had significantly enhanced in vivo accumulation when administered with CD4+M28z T cells, as determined by tracking of T-cell signal emission by BLI (2.3-vs. 1.2-fold increase in T-cell bioluminescent signal at 72 h; FIGS. 40D-E).

The enhanced anti-tumor efficacy of pleurally administered M28z T cells could be explained by an earlier antigen-activation of CD4+M28z T cells which may lead to optimal cytokine secretion to sustain the expansion of both the CD4+ and CD8+ CAR T-cell subsets. In order to demonstrate the influence of early antigen-activation, we performed in vitro accumulation experiments described above utilizing pre-activated CD4+M28z T cells (pre-activated once on MSLN+ tumor cells 24 hrs prior). CD4+ CAR T-cell pre-activation resulted in an enhancement in both CD4+ and CD8+ accumulation in vitro compared to the experimental condition where CD4+ T cells are antigen exposed simultaneously with CD8+ T cells (FIG. 40F).

Figure 41A:
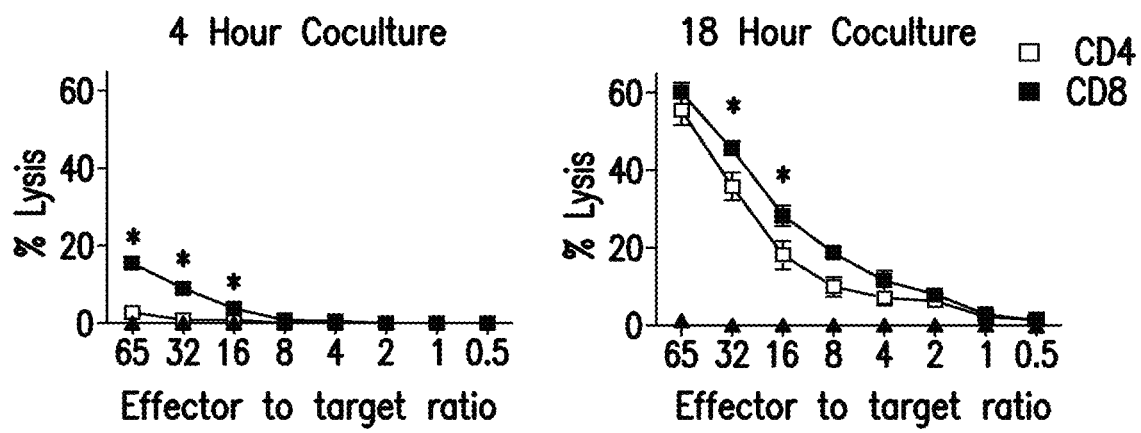
Figure 41B:
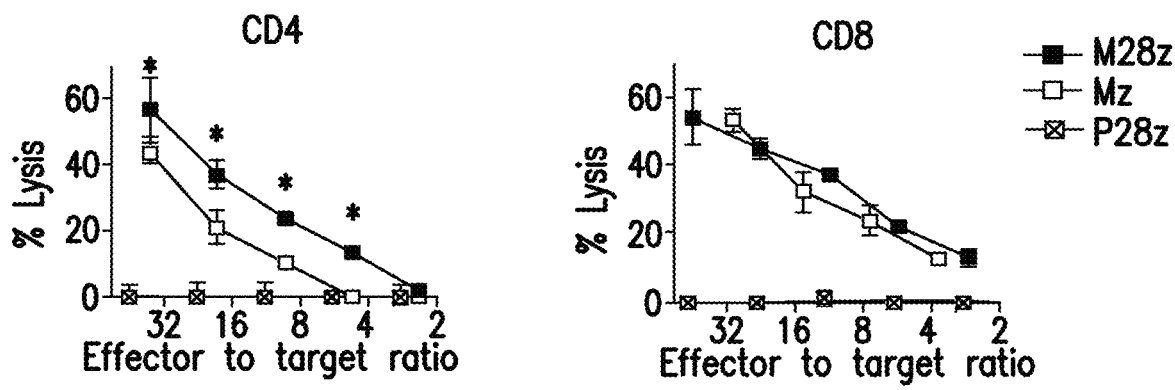
Figure 41C:
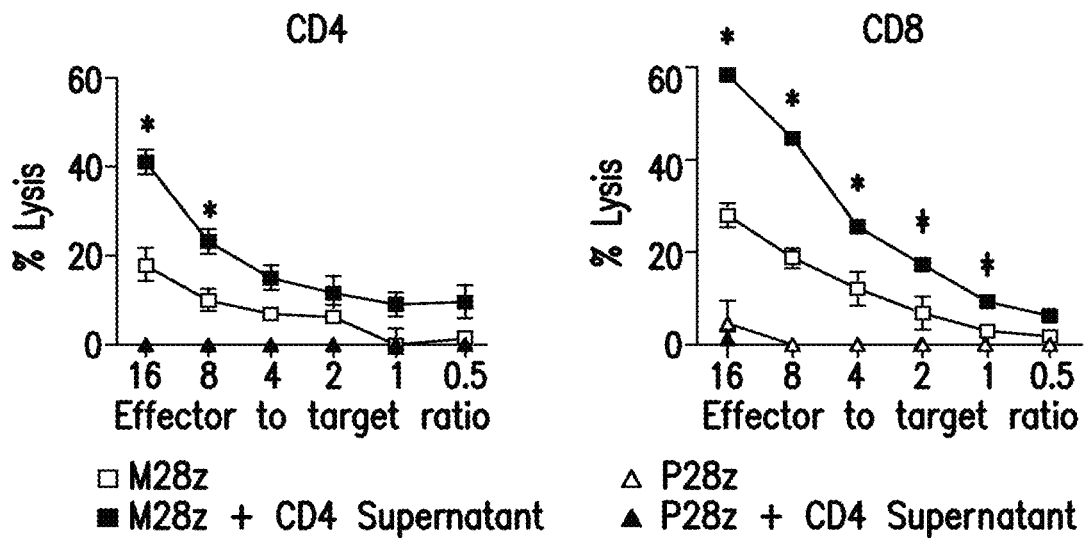
Figure 41D:
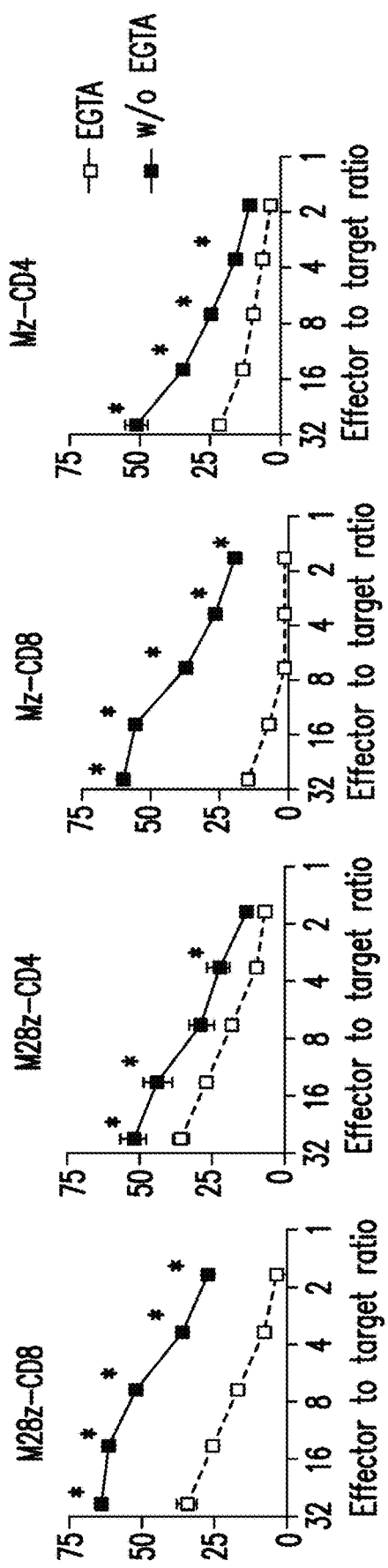

CD4+ CAR T cells demonstrate CD28-dependent granzyme/perforin-mediated cytotoxicity The cytotoxic potential of M28z CAR T cells was investigated. Purified CD8+ T cells demonstrated rapid cytotoxicity over 4 hrs (FIG. 41A, left). CD4+M28z+ T cells had lower rapid cytotoxic potential but reached equivalent levels to CD8+M28z+ T cells by 18 hrs. CD28 costimulatory signaling enhanced lysis by CD4+M28z CAR T cells by 13-16% at multiple E:T ratios (P<0.001; FIG. 41B) but did not consistently enhance CD8+ T cell-mediated cytolysis (P=0.07). Transfer of cytokine-rich supernatant obtained from stimulated CD4+M28z T cells added at the time of $^{51}$Cr-release assay enhanced the cytotoxicity of both CD4+M28z T cells (5%-23% enhancement; P<0.0001; FIG. 41C) and CD8+M28z CAR T cells (5%-30% enhancement; P<0.001). Transfer of supernatant alone or addition of supernatant to P28z control T cells did not result in lysis (FIG. 41C). Therefore, it was concluded that the M28z CAR favors formation of cytotoxic CD4+ T cell effectors and helps CD8+ T cell cytotoxicity in CD4-dependent manner.

Figure 41E:
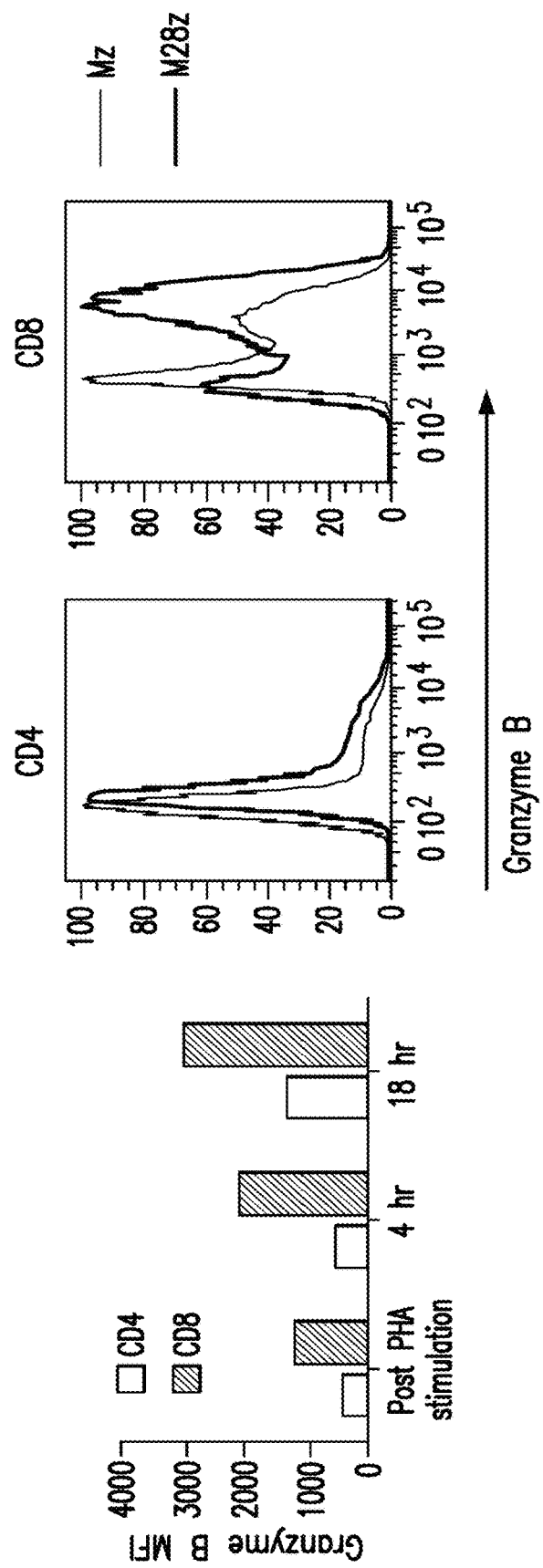

With direct lysis of tumor targets by cytokine-rich supernatant excluded, it was determined which of two cell contact-dependent lytic mechanisms (Fas receptor/Fas ligand or granzyme/perforin pathway) were responsible for CAR T-cell cytotoxicity. Antibody blockade of Fas ligand/Fas receptor (FasL/FasR) interaction did not reduce target cell lysis by either Mz or M28z CAR T cells (P>0.05; FIG. 7A, left and middle). Flow cytometric analysis confirmed FasL expression by CAR T cells and FasR expression on MSLN+ tumor (FIG. 7A). MSLN+ cells are indeed susceptible to FasL-mediated cytotoxicity, and the αFasL antibody used in these experiments blocked this effect (FIG. 45A, right). Blockade of granzyme release by the addition of the calcium chelator EGTA to T-cell/tumor-cell coculture reduced CAR-mediated lysis in all groups tested (FIG. 41D), demonstrating that CAR T-cell cytotoxicity is dependent on the perforin/granzyme pathway. The most prominent reduction in lysis was seen in the Mz (mean reduction, 27.6% vs. 17.6% for M28z) and CD8+(29.4% for CD8+Mz vs. 15.3% for CD4+Mz; 24.2% for CD8+M28z vs. 11.1% for CD4+M28z) T cell groups. Expression of granzymes A and B in resting peripheral blood mononuclear cells (PBMCs) was primarily restricted to CD8+ T cells, in concordance with the results of previous studies (FIGS. 41E and 44C). Granzyme A expression is not significantly altered following PHA stimulation and MSLN-specific stimulation of CAR transduced T cells (FIG. 44). Granzyme B was expressed in >95% of CD4+ and CD8+M28z CAR T cells within 18 h after stimulation with MSLN-expressing tumor cells. CD8+M28z T cells had a 1.8-fold increase in MFI after 4-h coculture, and granzyme B expression was further upregulated to 2.6-fold during the final 12 h. With CD4+M28z T cells, however, granzyme B expression was upregulated to a much greater degree during the final 12 h of culture (1.5-fold during the first 4 h, to 3.7-fold during the final 12 h). These findings may explain the delayed lysis kinetics displayed by CD4+ CAR T cells. Furthermore, M28z enhanced granzyme B expression in both CD4+ and CD8+ T-cell subsets (FIG. 41E, expression following 18 h of coculture), possibly explaining the enhanced cytotoxicity seen with CD4+M28z T cells compared with CD4+Mz T cells (FIG. 41B).

Regionally Administered CD4+ CAR T Cells are Efficacious Alone and Mediate Functional Persistence The observations of a potent CD4+M28z in vitro effector function and CD4+ predominant long-term immunity lead to hypothesis that CD4+M28z T cells would demonstrate in vivo efficacy in the absence of CD8+ T cells. Tumor-bearing mice were treated with CD4+M28z, CD8+M28z, or bulk unsorted M28z T cells administered into the pleural cavity at 3 different doses following 18 days of tumor growth (FIGS. 42A and 42B). In P28z treated mice, the tumor burden steadily progressed until mice had to be sacrificed (median survival, 28 days). Treatment with CD4+M28z and bulk M28z CAR T cells ($3\times10^5$; E:T, 1:1000) resulted in tumor eradication in 100% of mice, with mice remaining tumor free through 200 days of follow-up. Treatment with CD8+M28z T cells extended survival by 83 days only (111 vs. 28 days; P=0.003; FIG. 42B) and achieved tumor eradication in only 3 of 7 mice. Even at the lower doses, CD4+M28z CAR T cells had higher efficacy than CD8+ CAR T cells ($1\times10^5$: E:T, 1:3000, 112 vs. 67 days [P=0.04]; $3\times10^4$: E:T, 1:10000, 160 vs. 37 days [P=0.001]). These results illustrate that CD4+ CAR T cells alone are superior to CD8+ CAR T cells alone, although they are not as effective as combined CD4+ and CD8+ T cells.

Finally, to address whether CD4+ T cells can establish long-term functional persistence when administered without CD8+ T cells, we performed peritoneal tumor re-challenge in mice 196 days after initial intra-pleural administration of CD4+ sorted or bulk M28z T cells. Although there was an initial increase in tumor burden with persisting CD4+M28z T cells compared to the bulk population containing both CD4+ and CD8+, tumors then regressed, and subsequent tumor growth was controlled for >4 weeks (FIG. 42C).

5. Discussion

An orthotopic MPM model that faithfully mimics human disease[37,85,86,93] was used to evaluate two routes of administration to treat malignant pleural disease with MSLN-targeted T cells. It was found that intra-pleurally administered CAR T cells vastly out-performed systemically infused T cells, inducing long-term complete remissions with less than 30-fold fewer M28z CAR T cells. Regionally administered CAR T cells displayed rapid and robust T-cell expansion, resulting in effective T cell differentiation and systemic tumor immunity. This superior efficacy was dependent on early CD4+ T cell activation and associated with a higher intra-tumoral CD4/CD8 cell ratio and long-term memory. In contrast, intravenously delivered CAR T cells, even when accumulated at equivalent numbers in the pleural tumor, did not achieve comparable activation, tumor eradication or persistence. The translational relevance of these findings is further increased by the use of human T cells and CARs as these will be utilized in clinical studies based on the results reported herein.

In this study, MSLN-targeted CAR T cells were intra-pleurally administered to mice bearing established pleural tumors (12-18 days post-inoculation, control mice die by day 25-36). Using tumor and T cell noninvasive imaging, we demonstrated that intra-pleurally administered CAR T cells (1) efficiently infiltrate throughout the tumor in the chest, (2) become potent effector cells that eradicate pleural tumor at doses 30-fold lower than those used in intravenous therapy, and (3) migrate out of the pleural cavity, circulate, and accumulate in extra-thoracic tumor sites. While the immediate location of regionally administered cells evidently circumvents the obligate circulation and transient pulmonary sequestration of intravenously administered T cells, the intra-pleurally administered T cells differed from systemically recruited T cells in 1) the level of CD8 T cell accumulation and 2) the rapidity of kinetics of effector differentiation, as reflected by CD62L down-regulation. The initial lack of pleural CD8+ T cell accumulation is not caused by overall CD8+T cell disappearance, as CD8+ T cells persisted in the spleen of mice over 7 days after intravenous administration. Their poor recruitment could be in part due to suboptimal expression of chemokine receptor or adhesion molecules required for their trafficking. However, even though pleural accumulation may be enhanced by forced expression of transduced CCR-2 in CAR T cells[55], regional therapy with CAR T cells bypasses trafficking restrictions, if any, and enables, without additional T cell engineering, highly efficient redistribution to other tumor locations with greater efficacy than intravenously administered T cells. Furthermore, a single dose of regional CAR T-cell therapy established long-term tumor immunity (up to 200 days after T cell administration), providing effective protection against tumor re-challenge.

This systemic benefit of regional CAR T-cell therapy is reminiscent of the abscopal effect of loco-regional radiation therapy[125,126] and intra-tumoral oncolytic viral therapy[127] for solid malignancies, in which a local inflammatory response may generate specific immunity and effectively impact distant tumor sites. Intrapleurally administered CAR T cells migrate out of the pleural cavity and are directly visualized at extrapleural tumor sites as early as 24 to 72 h after administration. Thus early T-cell activation has a beneficial effect on CAR T-cell biodistribution. The rapid acquisition of a CD62L-phenotype may account for their efficient subsequent trafficking to metastatic sites[124]. The extensive lymphovascularity of pleural mesothelioma[86] in our orthotopic model, which contrasts with that of flank tumors, which typically undergo central necrosis upon growth, may contribute to such efficient T cell activation and redistribution.

The remarkable ability of intrapleurally administered T cells to circulate and persist within the periphery opens new avenues of treatment for metastatic cancers with accessible tumor sites, which may serve as "regional charging and distribution centers" for CAR T cell therapy. These include cancers that metastasize to the pleural cavity, such as lung and breast cancers, as well as those that metastasize to the peritoneal cavity, such as pancreatic and ovarian cancers. In addition to intrapleural or intraperitoneal administration, our findings raise the prospect that other regional adoptive T cell therapy approaches such as hepatic artery infusion, regional limb perfusion or intracranial administration[128-130] may provide superior efficacy. More conservatively, these regional and/or intratumoral delivery approaches are highly applicable to other MSLN-expressing sold cancers, which include ovarian, pancreatic, colorectal, lung, triple-negative breast, esophageal, gastric, cholangio and thymic cancer[37,47,119,58,131-135]. This approach may at the very least decrease the T cell dose requirement, presenting an advantage when high numbers of CAR T cells are not attainable (due to low-yield apheresis, poor ex vivo expansion or low transduction) and may even obviate the need for systematic apheresis.

The early infiltration and activation of the CD4+ T-cell subset is essential to the observed benefits of regional administration. M28z CAR T cells were multifunctional, displaying potent CD4+ T-cell cytotoxicity as well as helper function supporting T cell effector formation, survival and proliferation. The dual functionality of CD4+ T cells is most clearly demonstrated by the ability of CD4+ effectors to independently eliminate pleural mesothelioma xenografts following regional administration. Their key role in helper function is further supported by the enhanced CD8+ T cell subset observed following pleural administration compared to intravenous administration and the importance of early-antigen activated CD4+ T cells for achieving a CD8+ T-cell proliferative burst. The lesser ability of intravenously administered T cells to achieve potent accumulation of both CD4+ and CD8+ subsets, suggests that M28z CAR T cells are negatively impacted by their delayed arrival at the tumor site.

The critical role of CD28 costimulation provided through the CAR is revealed in several ways. M28z T cells eliminated large pleural tumors even at low T-cell doses. The intrapleural T cell doses we used ($3 \times 10^5$ M28z T cells in most experiments) is a markedly lower dose than used in other mesothelioma xenografts studies[55,56,123], and is comparable to doses used in current clinical trials for hematologic malignancies[11,116] and solid tumors[136,137] (see Table 2).

TABLE 2

CAR T cell doses in preclinical and clinical studies*.

| Reference | Type of study | Tumor | Route of administration | T-cell dose |
|---|---|---|---|---|
| Current study | Preclinical | Orthotopic MPM | Pleural | $3 \times 10^5$ CAR+ |
| 20 | Preclinical | Flank MPM | Intravenous, intraperitoneal and intratumoral | $20 \times 10^6$ CAR+ |
| 22 | Preclinical | Flank MPM | Intravenous | $20 \times 10^6$ CAR+ |
| 43* | Clinical | MPM | Intravenous | $3.5 \times 10^6$ CAR+** |
| 42 | Clinical | Glioblastoma | Intravenous | $8 \times 10^5$ CAR+ |
| 9 | Clinical | B cell acute lymphoblastic leukemia | Intravenous | $7 \times 10^5$ CAR+ |

*This clinical trial uses electroporation of mRNA to express CAR. Other clinical and preclinical studies use either retroviral (current study[11,136]) or lentiviral[55,123] vectors transduce CAR.
**Mouse doses equivalent to human doses used in clinical trials calculated using formulas available from National Cancer Institute (http://dtp.nci.nih.gov).

Compared to Mz T cells, M28z T cells provided superior tumor control and robust proliferation upon tumor rechallenge >100 days after intrapleural administration. The potentiating properties of CD28 signaling are particularly notable in the CD4+ subset, as demonstrated by their superior cytokine secretion and proliferation, relative to CD8+ T cells. Interestingly, the CD28/CD3 ζ CAR was essential to induce efficient CD4+ T cell-mediated cytotoxicity by a perforin/granzyme-dependent pathway. It is well established that CD4+ T cells require a higher-avidity interaction to mediate effector functions compared to CD8+ T cells[138,139]. CD28/CD3 ζ CAR engineering may thus be particularly suited for generating multifunctional CD4+ T cells that are capable of T cell help and cytotoxicity[140].

The enhanced localization and activation of mesothelin-targeted CAR T cells in the vicinity of normal tissues that express low levels of mesothelin may increase the hypothetical risk of "on-target off-tumor" toxicities such as pleuritis and pericarditis. However, mesothelin expression is markedly higher in tumor tissues compared to normal tissues, as previously reported.[47,91,119] Since CAR T cell activation is stronger in the presence of higher antigen density, CAR T cells are expected to more strongly respond to tumor than to the normal tissue. This is supported by the inventors' in vitro studies using an isogenic target (FIGS. 46A and 46B) and others[54,140]. It is also noteworthy that histopathological studies in mice treated with mesothelin-targeted CAR T cells did not reveal inflammatory changes in the pleura or pericardium. Furthermore, clinical studies targeting mesothelin with immunotoxins have not shown toxicity to normal tissues in over 100 patients[122,141,142]. The reported toxicity observed in a patient treated with mesothelin-targeted CAR T cells (an anaphylactic shock) was due to an antibody response to the CAR, which comprises a murine scFv[143]. M28z CAR is comprised of human sequences only[53]. Nonetheless, it was believed that additional strategies are necessary to limit or prevent reactivity against normal tissue. While lymphotoxic corticosteroids can sometimes eliminate CAR T cells[117], the inventors will proceed to the clinic utilizing a suicide gene[94]. Suicide genes such as iCaspase-9[94], EGFR mutation[144] and herpes simplex virus thymidine kinase-[145] mediate rapid T cell elimination following administration of a prodrug or antibody. The inventors may also pursue, if necessary, alternative strategies designed to prevent reactivity against normal tissues utilizing combinatorial antigen recognition or inhibitory receptors[146-148]. Another strategy to limit CAR T cell toxicity is to transiently express the CAR using mRNA electroporation[56,149], albeit at the expense of CAR T cell persistence and requiring multiple T-cell administrations to attain efficacy.

In this study, immunodeficient mice with human cancer cells and human T cells were used in order to facilitate direct clinical translation of our findings and the human-based CAR vectors to clinical trials as previously did for CD19- and PSMA-targeted CAR T-cell therapies[15,16,117]. The interactions between adoptively transferred cells and the endogenous immune system investigated in an immunocompetent mouse model will extend the significance of our observations.

Based on the data presented herein, a phase I clinical trial was designed to evaluate the safety of intrapleural administration of MSLN-targeted CAR T cells. Patients with primary pleural malignancy or secondary pleural malignancies from lung and breast cancers overexpressing MSLN, which the inventors have shown to have more aggressive disease[91,119], will be enrolled on this trial. MSLN-targeted CAR T cells will be delivered through intrapleural catheters, an approach developed to be the standard of care in managing patients with malignant pleural effusions[150]. The regional administration of biological agents such as cytokines[151] and oncolytic virus[152] has been previously translated to the clinic with success. This study strongly supports that regional CAR T cell administration to subjects with MPM will result in greater T cell anti-tumor potency with reduced T cell doses, owing in part to early CD4+ T cell activation and the systemic benefits that ensue.

Example 8—CAR T Cells Resist Tumor-Mediated Inhibition

1. Abstract

Using a clinically relevant, orthotopic mouse model of pleural mesothelioma, the inventors demonstrate that T cells expressing CD28 or 4-1BB-based second generation CARs although persistent, are functionally inhibited within the tumor microenvironment. While CD28 and 4-1BB CARs conferred similar proliferation and persistence of CAR T cells; the latter more durably retained their cytotoxic and cytokine secretion functions, resulting in improved survival in mice given low T-cell doses.

2. Introduction

Chimeric antigen receptors (CARs) are synthetic receptors that retarget T cells to tumor surface antigens[157,158]. First-generation receptors link an antibody-derived tumor-binding element that is responsible for antigen recognition to either CD3zeta or Fc receptor signaling domains, which trigger T-cell activation. The advent of second-generation CARs, which combine activating and costimulatory signaling domains, has led to encouraging results in patients with chemorefractory B-cell malignancies[159-163]. The translation of this clinical success to solid tumors, which has not yet been accomplished, will require overcoming additional obstacles, including achieving sufficient T-cell infiltration into tumors and resisting tumor immune escape. To overcome the limitations of tumor infiltration and delayed activation observed with systemic T-cell administration, the inventors recently demonstrated the merits of regional administration of mesothelin-specific CAR T cells in a clinically relevant model of pleural mesothelioma[164]. Mesothelin (MSLN) is a tumor-associated cell-surface antigen, which was selected on the basis of its overexpression in several cancers and our observations of its association with tumor aggressiveness and decreased survival in mesothelioma, lung and breast cancer patients[165-172]. Regional administration of MSLN-targeted CAR T cells eradicates primary tumor and establishes long-term systemic immunosurveillance at 30-fold lower doses than intravenous administration[64]. These results are encouraging for the treatment of solid malignancies and prompted the inventors to initiate a phase I clinical trial of intrapleural administration of mesothelin-targeted CAR T cells (NCT02414269). As the inventors modeled low-level tumor infiltration, they found and report here that CAR T cells can be susceptible to tumor cell-mediated immune-inhibition, resulting in impaired T-cell function and diminished tumor rejection.

In this report, the inventors have established the presence and kinetics of tumor-mediated inhibition of CAR T cells. By performing a comprehensive serial analysis of T-cell effector functions, the inventors have established that even costimulated CAR T cells currently in clinical trials are subject to inhibition of their cytolytic and cytokine secretion functions upon repeated antigen encounter in vivo. The differing abilities of alternative costimulatory strategies (4-1BB vs. CD28) to withstand immuno inhibition was further highlighted.

3. Materials and Methods

General Purpose

The purpose of this study was to characterize the mechanisms of tumor-mediated T-cell inhibition, to enhance the efficacy of T-cell immunotherapy for solid malignancies. The inventors designed MSLN-targeted CARs that, when transduced into human T cells, provide tumor antigen recognition and antigen-specific effector function activation. The inventors also designed signaling domains that provide costimulatory signaling and/or coinhibitory blockade. In vitro, cytotoxicity, cytokine secretion, and T-cell proliferation were analyzed. In vivo experiments analyzed strategies for optimizing T-cell therapy, by use of clinically relevant mouse models of orthotopic MPM and metastatic lung cancer. Human cancer cells and human T cells were used to validate and facilitate the translation of our M28z CAR to the clinic, as previously demonstrated for CD19[214] and PSMA[215] CAR T cells. The experimental procedures were approved by the Institutional Animal Care and Use Committee of Memorial Sloan Kettering Cancer Center (MSKCC). Each experiment was performed multiple times, using different donor T cells. To avoid confounding variables—such as differences due to transduction efficiencies, donor-related variability, and E:T ratios—the data presented herein using a representative experiment, with sample replicates of more than 3.

Cell Lines

MSTO-211H human pleural mesothelioma cells (ATCC, Manassas, Va.) were retrovirally transduced to express GFP and firefly luciferase fusion protein (MSTO GFP-ffLuc+). These cells were then transduced with the human MSLN variant 1 subcloned into an SFG retroviral vector to generate MSTO MSLN$^+$ GFP-ffLuc$^+$. Similarly, A549 cells and 3T3 murine fibroblasts were transduced with human MSLN variant 1 alone to generate A549 MSLN+ and 3T3 MSLN+ cell lines. 3T3 cells were also cotransduced with PD-L1 (Origene cDNA subcloned into SFG vector) to generate 3T3 MSLN+ PDL1+ cells.

γ-Retroviral Vector Construction and Viral Production

To generate MSLN-specific CARs, the inventors engineered a cDNA encoding for a fully human scFv m912 specific for MSLN (provided by D. Dimitrov, National Cancer Institute at Frederick)[186], linked to the human CD8 leader domain and the CD8/CD3ζ, CD28/CD3ζ, or CD8/4-1BB/CD3ζ domain, as previously described[216]. The control PSMA-specific CAR was generated similarly, using a previously characterized PSMA-targeting scFv[215]. The CAR sequence was inserted into the SFG γ-retroviral vector (provided by I. Riviere, MSKCC) and linked to a P2A sequence to induce coexpression of the LNGFR reporter (truncated low-affinity nerve growth factor receptor). The CAR encoding plasmids were then transfected into 293T H29 packaging cell lines to produce the retrovirus, as previously described[219].

T-Cell Isolation, Gene Transfer, and CD4/CD8 Isolation

Peripheral blood leukocytes were isolated from the blood of healthy volunteer donors under an institutional review board-approved protocol. Peripheral blood mononuclear cells (PBMCs) were isolated by low-density centrifugation on Lymphoprep (Stem Cell Technology, Vancouver, Canada) and activated with phytohemagglutinin (2 ug/mL; Remel, Lenexa, Kans.). Two days after isolation, PBMCs were transduced with 293T RD114-produced retroviral particles encoding for CARs and spinoculated for 1 h at 3000 rpm on plates coated with retronectin (15 μg/mL; r-Fibronectin, Takara, Tokyo, Japan). After 1 day, transduced PBMCs were maintained in IL-2 (20 UI/mL; Novartis, Basel, Switzerland). Transduction efficiencies were determined by flow cytometric analysis. Pure populations of CD4+ and CD8+ CAR+ T cells, were obtained by flow cytometric-based sorting (BD Aria Sorter).

Flow Cytometry

Human MSLN expression was detected using a phycoerythrin- or allophycocyanin-conjugated anti-human MSLN rat IgG2a (R&D Systems, Minneapolis, Minn.). Expression of costimulation or inhibitory proteins on tumor cells was analyzed using the following antibodies: 4-1BBL (PE, clone 5F4; BioLegend, San Diego, Calif.), MHC HLA-DR (PE, clone L203; R&D Systems), PD-L1 (APC, clone MIH1; eBioscience, San Diego, Calif.), PD-L2 (APC, clone MIH18; eBioscience), and galectin-9 (APC, clone 9M13; BioLegend). T-cell phenotype and transduction efficiency were determined with monoclonal antibodies for CD3, CD4, CD8, and CD69m LNGFR. Expression of T-cell inhibitory receptors was analyzed using PD1 (APC, eBioJIU5; eBioscience), TIM-3 (PE, clone 344823; R&D Systems), and Lag-3 (PE, clone C9B7W; BioLegend). Cell staining was analyzed using a BD LSRII flow cytometer (BD, Franklin Lakes, N.J.) and FlowJo analysis software.

T-Cell Functional Assays

The cytotoxicity of T cells transduced with a CAR or vector control was determined by standard $^{51}$Cr-release assays, as previously described[220]. To perform the luciferase-activity assay, CAR+ T cells and MSTO-211H cells expressing MSLN and firefly luciferase were incubated for 18 h at different E:T ratios. Tumor-cell quantity was determined by BLI using IVIS 100/lumina II, after the addition of 100 uL of D-luciferin (15 mg/mL) per well, and was compared to the signal emitted by the tumor cells alone. CD107a and intracellular staining were performed after incubation of effector cells and irradiated MSTO-211H MSLN tumor cells for 18 h in 24-well plates at a ratio of 5:1. For the CD107a assay, 5 uL of CD107a-PeCy7 antibody (BD Biosciences, San Jose, Calif.) and Golgi STOP (4 uL/6 mL; BD Biosciences) were added at the time of stimulation. For intracellular staining, Golgi Plug (1 uL/1 mL; BD Biosciences) was added at the time of stimulation. After incubation, effector cells were stained for CD4, CD8, LNGFR, and CD3 marker, then fixed and permeabilized in accordance with the manufacturer's instructions (Cytofix/Cytoperm Kit; BD Biosciences). Staining for intracellular cytokines was performed using granzyme B-APC, perforin-PE, and IFN-γ-FITC antibodies (BD Biosciences).

Cytokine-release assays were performed by coculturing $3 \times 10^4$ to $5 \times 10^3$ T cells with target cells in a 1:1 to 5:1 ratio, in 200 μL of medium, in 96-well round-bottomed plates as triplicates. After 6 to 24 h of coculture, supernatants were collected. Cytokine levels were determined using a multiplex bead Human Cytokine Detection kit, in accordance with the manufacturer's instructions (Millipore, Darmstadt, Germany).

To analyze the proliferation capacity of T cells, $1 \times 10^6$ CAR+ T cells were stimulated over irradiated MSTO-211H or 3T3 cells with or without MSLN expression (and, in the case of 3T3, with or without PD-L1). Proliferation assays were performed in the absence of exogenous IL-2. Cells were counted every 7 days and then overlaid on irradiated target cells for repeated stimulations. The CAR+ T cell number versus time was plotted for each T-cell group.

Orthotopic Pleural Mesothelioma Animal Model and Ex Vivo Experiments

To develop the orthotopic mouse model of pleural mesothelioma, female NOD/SCIDγ mice (The Jackson Laboratory, Bar Harbor, Me.) aged 4 to 6 weeks were used. All procedures were performed under approved Institutional Animal Care and Use Committee protocols. Mice were anesthetized using inhaled isoflurane and oxygen, with bupivacaine administered for analgesia. Direct intrapleural injection of $1 \times 10^5$ to $1 \times 10^6$ tumor cells in 200 μL of serum-free medium via a right thoracic incision was performed to establish orthotopic MPM tumors, as previously described[164,171,188]. In total, $3 \times 10^4$ to $1 \times 10^5$ transduced T cells (in 200 μL of serum-free medium) were adoptively transferred into tumor-bearing mice, either into the thoracic cavity by direct intrapleural injection or systemically by tail vein injection. Tumor growth was monitored and quantified in vivo by BLI performed 20 min after a single intraperitoneal dose of D-luciferin (150 mg/kg; Perkin Elmer, Waltham, Mass.). BLI data were analyzed using Living Image software (version 2.60); BLI signal was reported as total flux (photons per second), which represents the average of ventral and dorsal flux. To analyze the functional capacity of CAR T cells ex vivo, tumor tissues and mouse spleen were processed as follows: Tissues were weighed and harvested into ice-cold RPMI 1640. The tissues were manually morselized with a scalpel and then mechanically disaggregated through 40- to 100-μm filters. Next, samples were analyzed by FACS for phenotyping, or CAR+CD4+ or CD8+ T cells were sorted using a FACS Aria sorter then rested for 24 h in RPMI with IL-2 (60 UI/mL), and $^{51}$Cr-release and cytokine-release assays were performed as described above.

Histologic Analysis and Immunostaining

Histopathologic evaluation of tumors was performed after H&E staining of paraffin-embedded, 4% paraformaldehyde-fixed tissue samples. Immunohistochemical analysis for human MSLN was performed with mouse anti-human MSLN immunoglobulin G, as previously described[168,170,172].

Quantitative Real-Time PCR

The mRNA from CD4+ LNGFR+ or CD8+ LNGFR+ sorted T cells were extracted and reverse transcribed into cDNA using MACS One-Step cDNA kit (MACS molecular, Miltenyi Biotech Inc, Auburn, USA). Quantitative Real Time PCR (RT-PCR) was performed with Taqman® method using Applied Biosystems® 7500 systems (Foster, Calif., USA), Taqman® Universal PCR Mastermix and Taqman® probes labeled with 6-carboxyfluorescein (FAM-MBG) and designed by life technologies: Tbet (Hs00203436_m1); Eomes (Hs00172872_m1); Granzyme B (Hs01554355_m1); IFNγ (Hs00989291_m1); IL-2 (Hs00174114_m1); PD-1 (Hs01550088_m1). The comparative threshold cycle ($C_T$) of the gene of interest was used and normalized to the β2m housekeeping gene using the following formula ΔCt (sample)=Ct (gene of interest)−Ct (β2m). Then, the $2^{-\Delta\Delta Ct}$ method was used to analyze the relative fold change expression compared to control condition and calculated as follow: $2^{-\Delta\Delta ct}=2^{\wedge}(\Delta Ct(sample)-\Delta Ct(control))$.

Statistical Methods

Data were analyzed using Prism (version 6.0; GraphPad Software, La Jolla, Calif.) software and are presented as mean±SEM, as stated in the figure legends. Results were analyzed using the unpaired Student's t test (two-tailed), with the Bonferroni correction used for multiple comparisons, when applicable. Survival curves were analyzed using the log-rank test. Statistical significance was defined as $P<0.05$. All statistical analyses were performed with Prism software.

4. Results

Figure 47A:
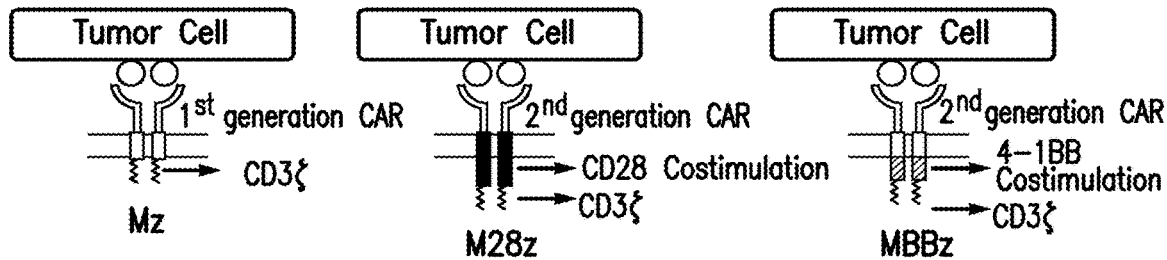
Figure 47B:
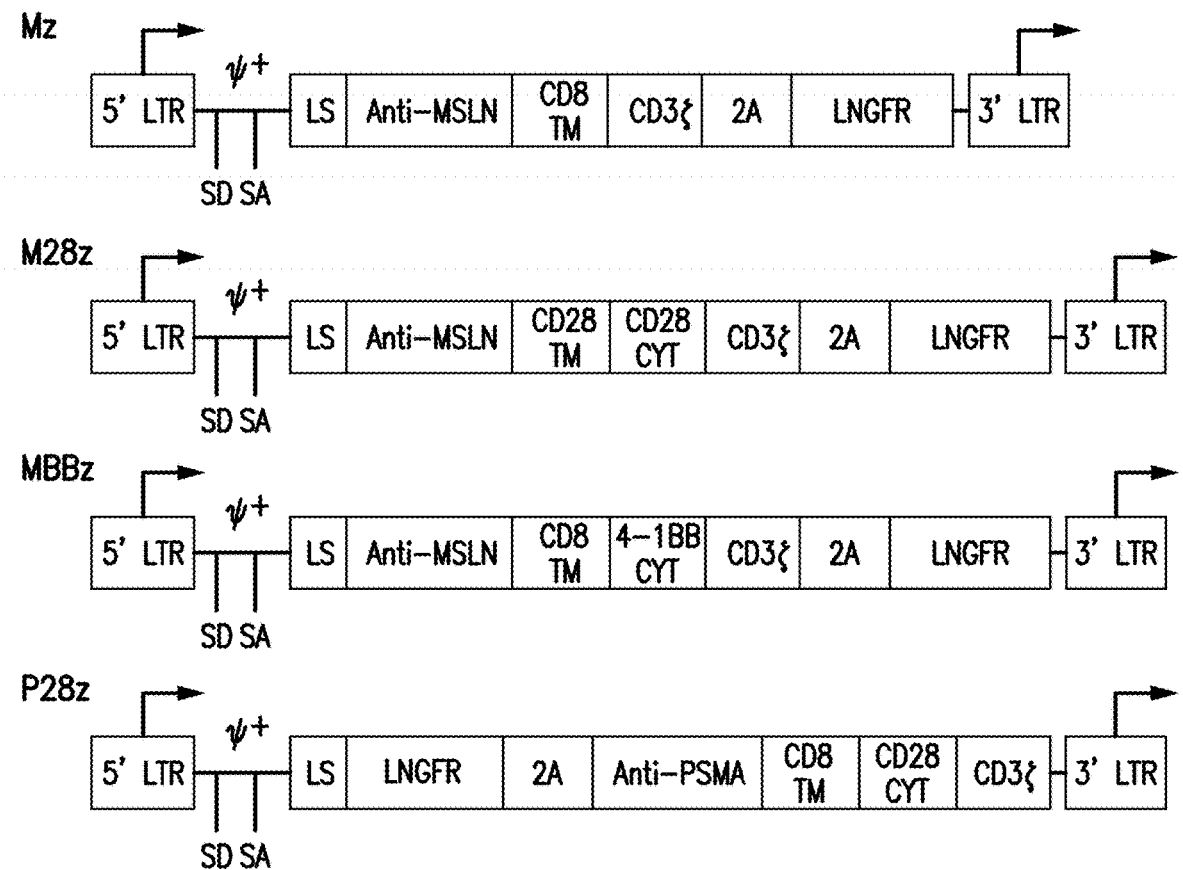
Figure 47C:
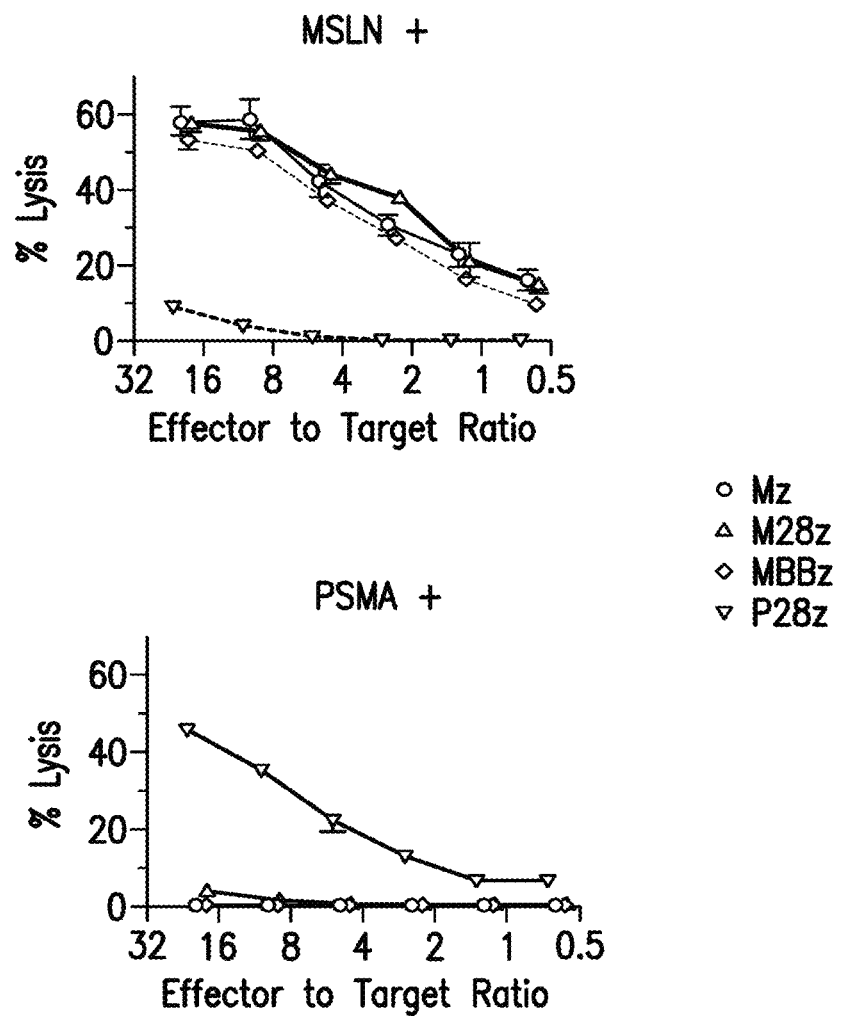
Figure 47D:
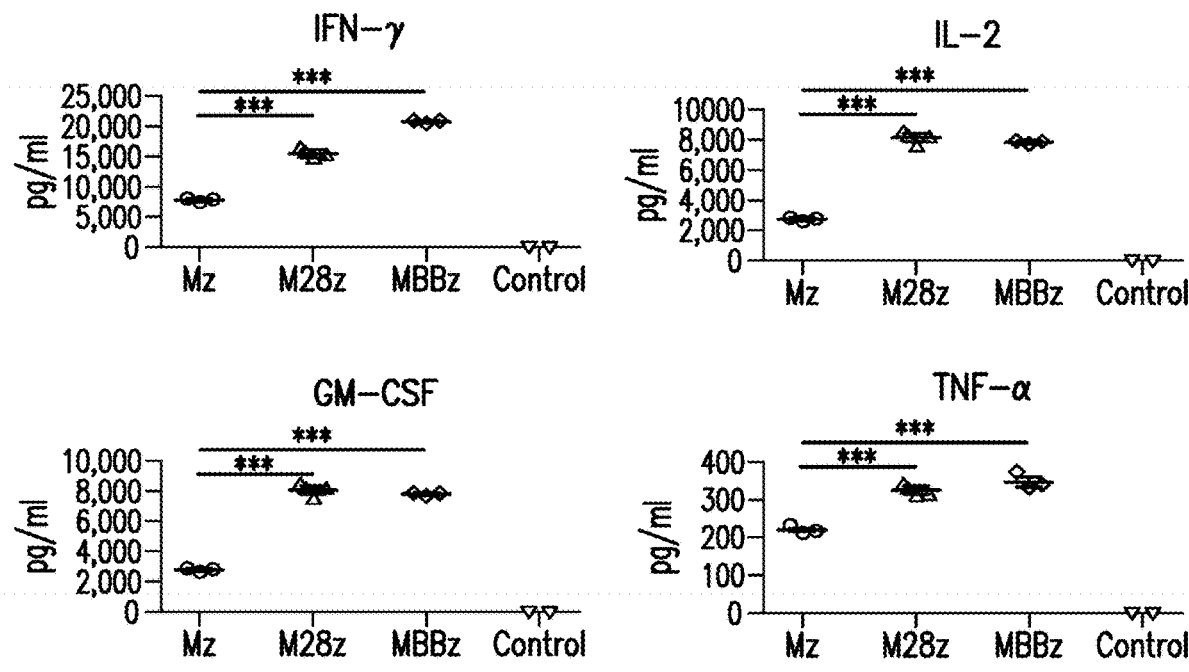
Figure 47E:
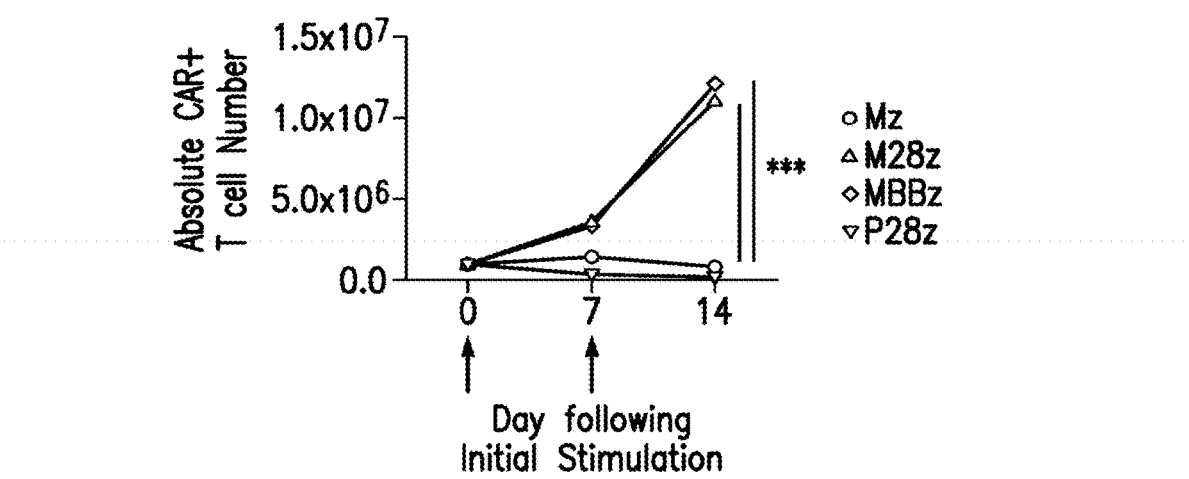

CARs with CD28 or 4-1BB Costimulation Exhibit Equivalent Effector Cytokine Secretion and Proliferation In Vitro Upon Initial Antigen Stimulation Three CARs that incorporated a human MSLN-specific scFv[186] and either CD3ξ, CD28/CD3 ξ or 4-1BB/CD3 ξ signaling domains (Mz, M28z, MBBz) were constructed (FIGS. 47A and 47B). The P28z CAR, which is specific for prostate-specific membrane antigen (PSMA), served as a negative effector to control for alloreactivity and xenoreactivity. Both CD4+ and CD8+ human peripheral blood T lymphocytes were effectively transduced using the SFG-retroviral vector (50%-70% transduction) (FIG. 54). MSLN-transduced MSTO-211H cells (MSLN+) and PSMA-transduced EL-4 mouse lymphoma cells (MSLN−) served as MSLN-positive and -negative targets in the in vitro experiments. Mz−, M28z−, and MBBz-transduced T cells demonstrated similar MSLN− specific lysis in vitro (FIG. 47C). P28z CAR T cells did not lyse MSTO MSLN+ cells, and MSLN-targeted CARs did not lyse EL4 PSMA+ cells-demonstrating that lysis is antigen specific. Validating the functionality of costimulatory signaling[187], M28z and MBBz CAR T cells secreted 2- to 15-fold higher levels of Th1 cytokines (FIG. 47D) and achieved 14-fold greater T-cell accumulation upon repeated exposure to MSLN+ cells when compared to Mz in the absence of exogenous IL-2 (FIG. 47E). Having established antigen specificity and validated the functionality of costimulatory signaling domains, we proceeded to evaluate the therapeutic potential of MSLN− targeted CAR T cells in mice bearing established pleural tumors.

M28z is More Prone to Allowing Tumor Relapse than MBBz

In an orthotopic model of malignant pleural mesothelioma (MPM) previously established by our laboratory[171,188-190], serial bioluminescence imaging (BLI) with firefly-luciferase (ffLuc)-transduced MSTO-211H cells was used to confirm the establishment of tumor, to equalize tumor burden across intervention groups before the initiation of T-cell therapy, and to measure the response to therapy. Both M28z and MBBz CAR T cells intrapleurally administered at a single dose of $1\times10^5$ (effector to target [E:T] ratio of 1:3000, estimated from tumor burden quantification)[189] were able to eradicate established pleural tumors in the majority of mice (FIG. 48A, top). Since the goal in this study was to investigate the effect of tumor-induced immuno inhibition on T-cell exhaustion, CAR T cells were administered to mice bearing established pleural tumors at successively lower doses. It was hypothesized that at these lower doses, T cells would be especially susceptible to exhaustion as they must retain function upon repeated antigen encounters within an inhibitory environment in order to eliminate tumor. It is at these lower doses that the inventors began to see tumor relapse, especially within the M28z cohort (FIG. 48A, middle and bottom). At the lowest dose tested of $4\times10^4$ (E:T, 1:7,500), mice treated with intrapleural Mz (1$^{st}$ generation CAR, no costimulatory signaling included) CAR T cells showed an unsustainable response in terms of tumor burden (FIG. 48B), and median survival was 29 days longer than that in the P28z-treated controls (median survival, 45 vs. 16 days, P28z represents a xenoreactivity and alloreactivity control targeting the PSMA antigen) (FIG. 48B). Mice treated with M28z CAR T cells had a more uniform reduction in tumor burden and survived longer (median survival, 64 days) than mice treated with first-generation CAR T cells; however, all mice treated with M28z CAR T cells eventually died of progressing tumor. It was confirmed that tumor outgrowth was not caused by tumor antigen escape (recurring tumors in all tested mice were found to be MSLN+ by flow cytometric and histologic analysis; data not shown). In contrast, intrapleurally administered MBBz CAR T cells induced tumor eradication within 20 days of treatment, and the vast majority of mice (7 of 8) remained tumor free for >100 days (median survival was not reached by day 100).

MBBz Surpasses M28z CAR T Cells at Low T-Cell Doses

Improvements in CAR T-cell efficacy afforded by costimulatory signaling are typically attributed to improvements in CAR T-cell proliferation and/or persistence[158]. As expected, M28z and MBBz CAR T cells achieved enhanced intratumoral T-cell accumulation, compared with Mz CAR T cells (9-fold greater for M28z, 12-fold greater for MBBz) (FIG. 49A). Surprisingly, despite the differences in efficacy between M28z and MBBz CAR T cells, similar numbers of tumor-infiltrating T cells were observed between the two groups (FIG. 49A). Furthermore, M28z and MBBz CAR T cells were equally persistent at long-term time points (FIG. 49B). Tumor tissue and spleen from M28z-treated mice that initially had a treatment response but then died of progressing tumor contained circulating T cells as well as tumor-infiltrating T cells, including CAR positive cells (FIG. 49C). This finding demonstrates that the mere persistence of T cells that can effectively traffic to the tumor is not sufficient to eliminate tumor and that the T-cell functional status within the tumor microenvironment may be the more critical determinant of clinical outcome. It was therefore hypothesized that even costimulated T cells may become exhausted within tumor, especially at low T-cell doses that correspond to low effector:target ratios. Furthermore, MBBz CAR T cells, which were as persistent as M28z CAR T cells, may be better able to resist exhaustion and retain T-cell effector function in order to eliminate a large tumor burden.

Mesothelin CAR T Cells Become Exhausted Following In Vivo Antigen Exposure

Figure 50C:
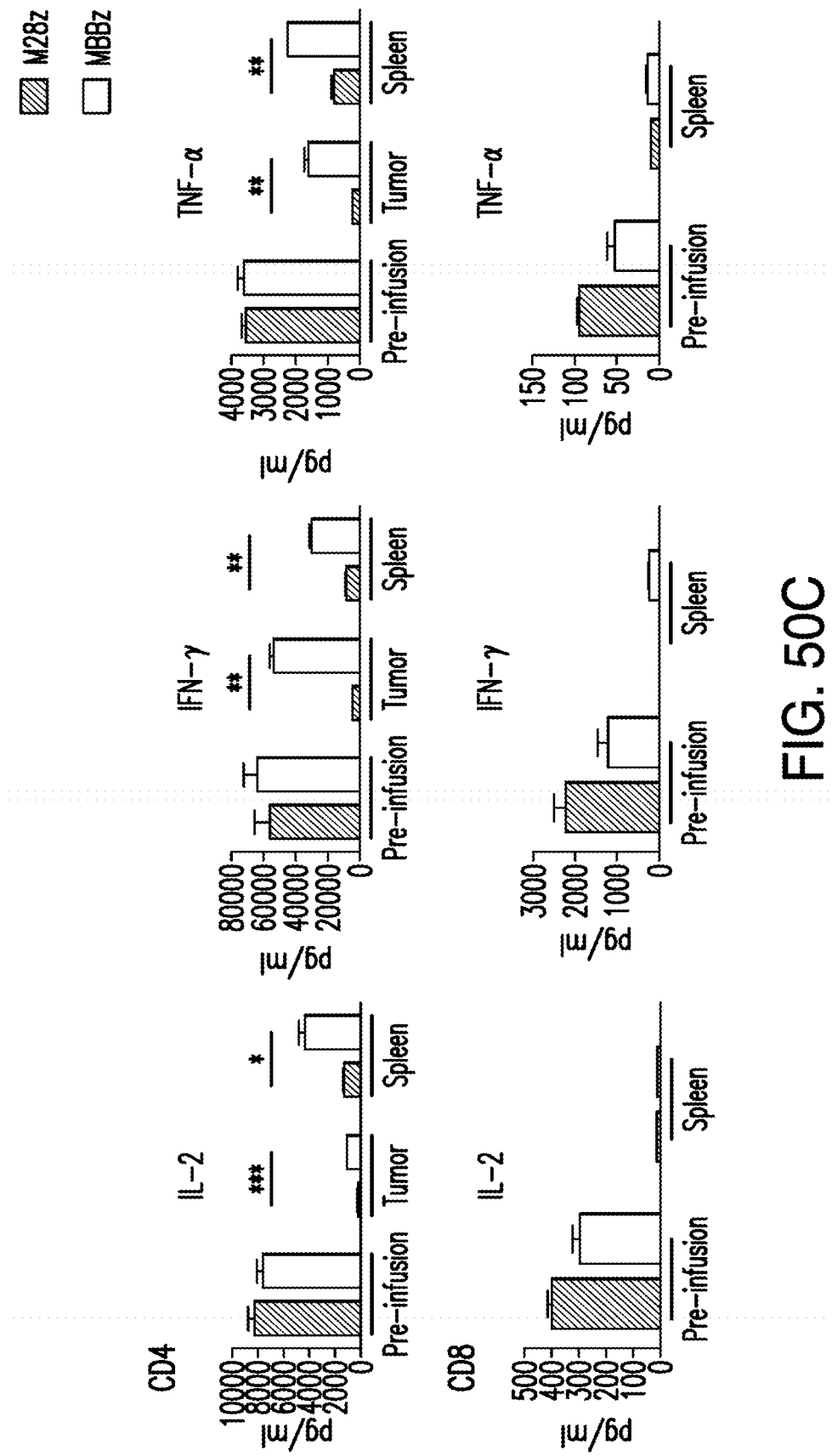
Figure 50D:
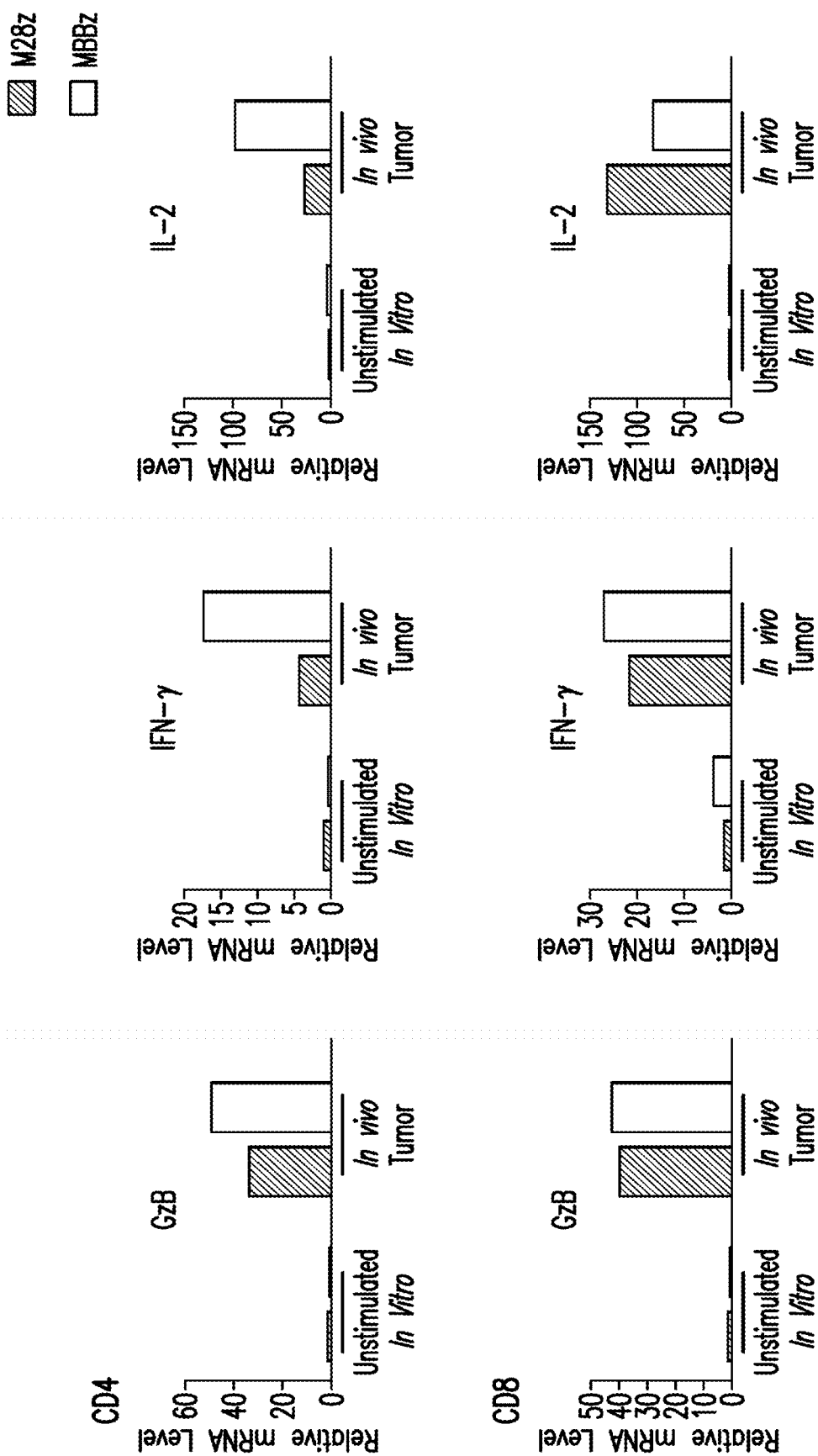

To assess whether there is ongoing immuno inhibition of CAR T cells and to compare the relative abilities of M28z and MBBz CAR T cells to overcome tumor-mediated immuno inhibition, $1\times10^6$ CAR T cells were injected into the pleural cavities of MSTO MSLN+ tumor-bearing mice, allowed sufficient time for repeated antigen encounter and T-cell activation (confirmed by forward- and side-scatter and upregulation of the activation marker CD69), and then performed ex vivo stimulation of harvested CD4 or CD8 CAR tumor-infiltrating or splenic T cells with MSLN+ targets (schematic shown in FIG. 50A). Uninjected in vitro resting T cells ("preinfusion cells") were used to establish the baseline level of function (before antigen exposure). Compared with resting M28z CD8+ CAR T cells, T cells exposed to MSLN antigen in vivo had lower levels of cytolytic function (FIG. 50A) (preinfusion cell lysis, 20.5%; tumor-infiltrating T-cell lysis, 13.1%; splenic T-cell lysis, 8.7%). In contrast, MBBz CAR T cells retained cytolytic function (preinfusion cell lysis, 18.3%; tumor-infiltrating T-cell lysis, 37.2%; splenic T-cell lysis, 22.2%). Sorted CD4+ CAR T cells demonstrated a similar pattern of results. Cytokine levels upon ex vivo stimulation of tumor-infiltrating and splenic CAR T cells were also measured and a decrease in Th1 cytokine secretion for CD4+M28z CAR T cells exposed in vivo to MSLN+ antigen was also observed. CD4+ MBBz CAR T cells also demonstrated a decrease in Th1 cytokine secretion, although these cells were better able to retain cytokine secretion when compared with M28z CAR T cells (FIG. 50B). CD8+ T cell supernatants contained significantly lower levels of cytokines, compared with CD4+ T cell supernatants (a finding previously observed in our model[164]. CD8+ T cells also had a decreased ability to secrete cytokines upon in vivo antigen exposure; CD8+ MBBz CAR T cells preferentially retained their ability to secrete IFN-γ. Next, mRNA levels of T cells harvested from tumor and spleen on day 3 after administration were assessed, and it was found that the in vivo expression levels of GzB, IL-2, and IFN-γ were mostly greater for CD4+ and CD8+ MBBz CAR T cells than for M28z CAR T cells, with the exception of IL-2 expression in the CD8+ subset (FIG. 50C).

MBBz CAR T Cells Show Delayed Exhaustion In Vivo

Figure 51A:
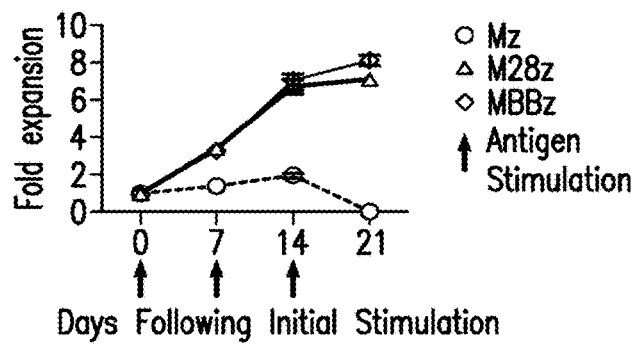
Figure 51B:
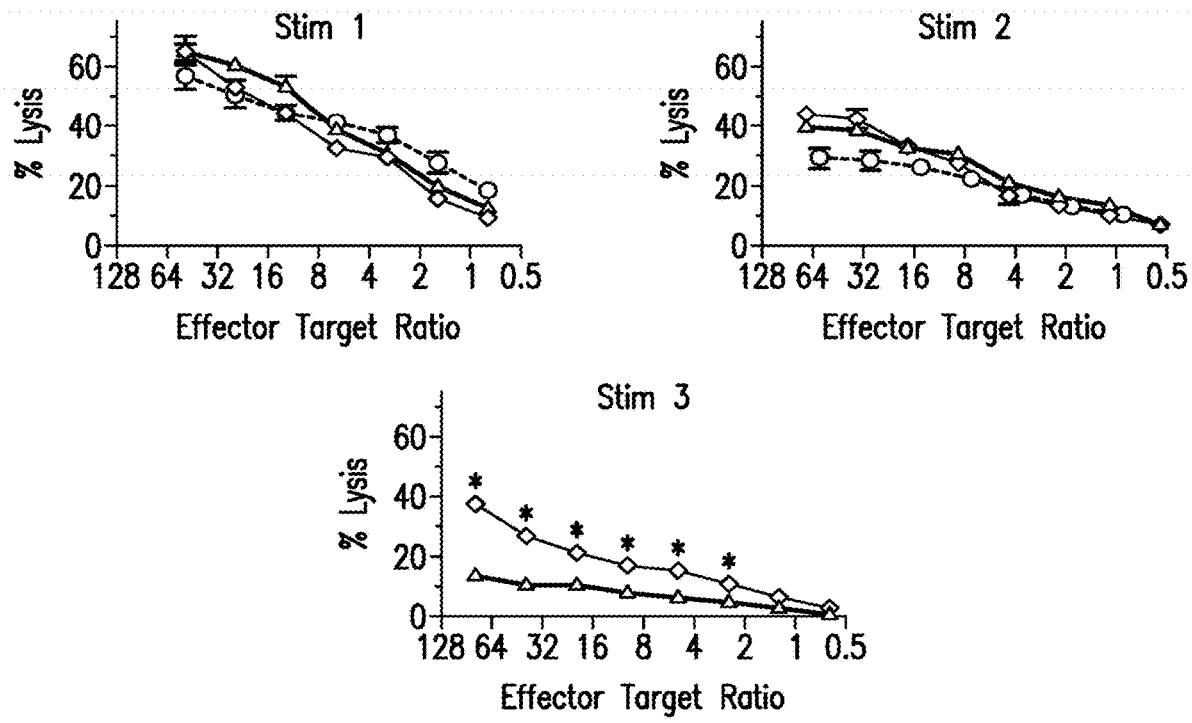
Figure 51C:
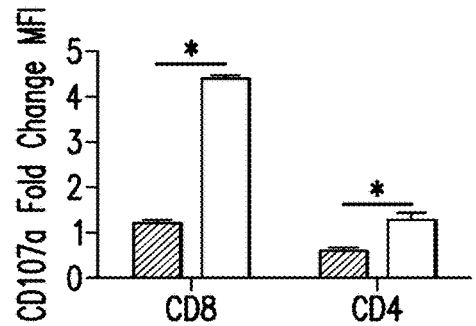
Figure 51D:
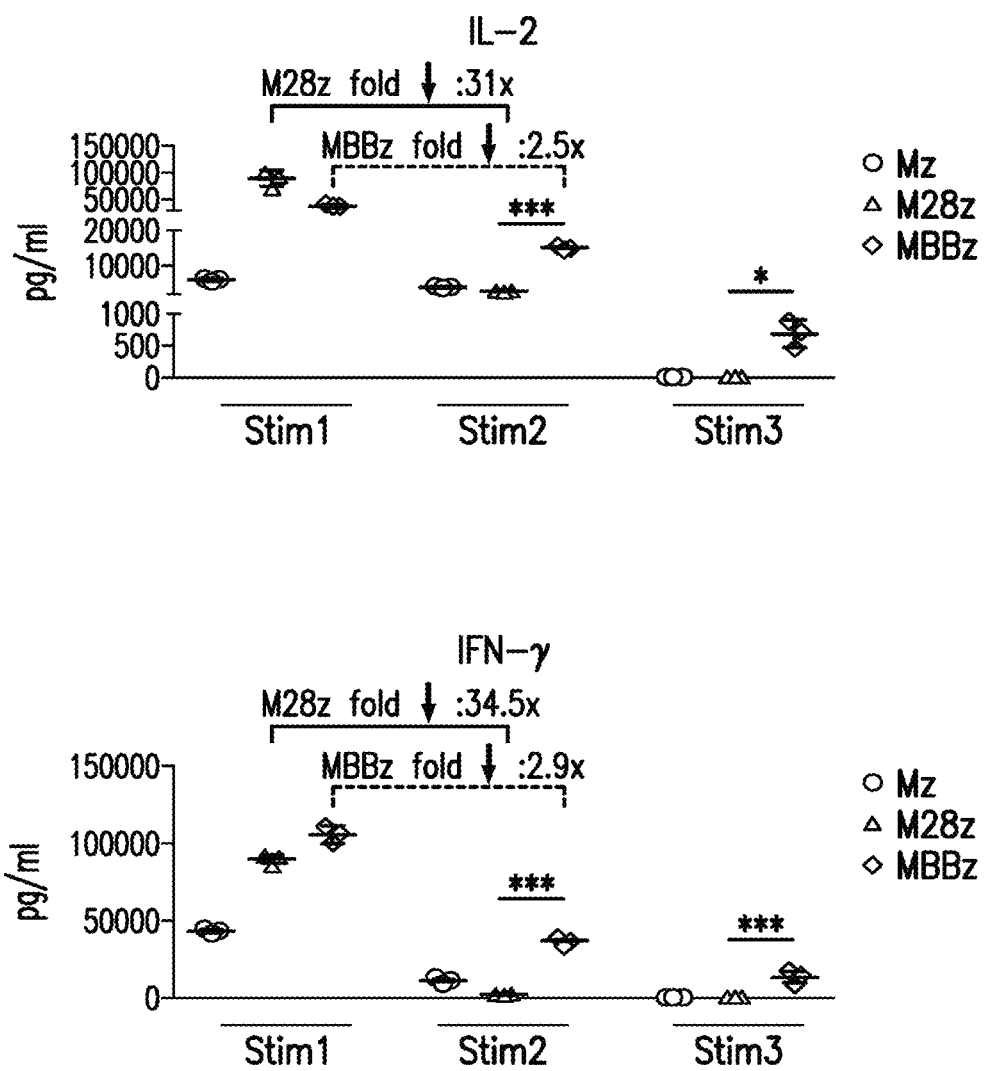
Figure 51E:
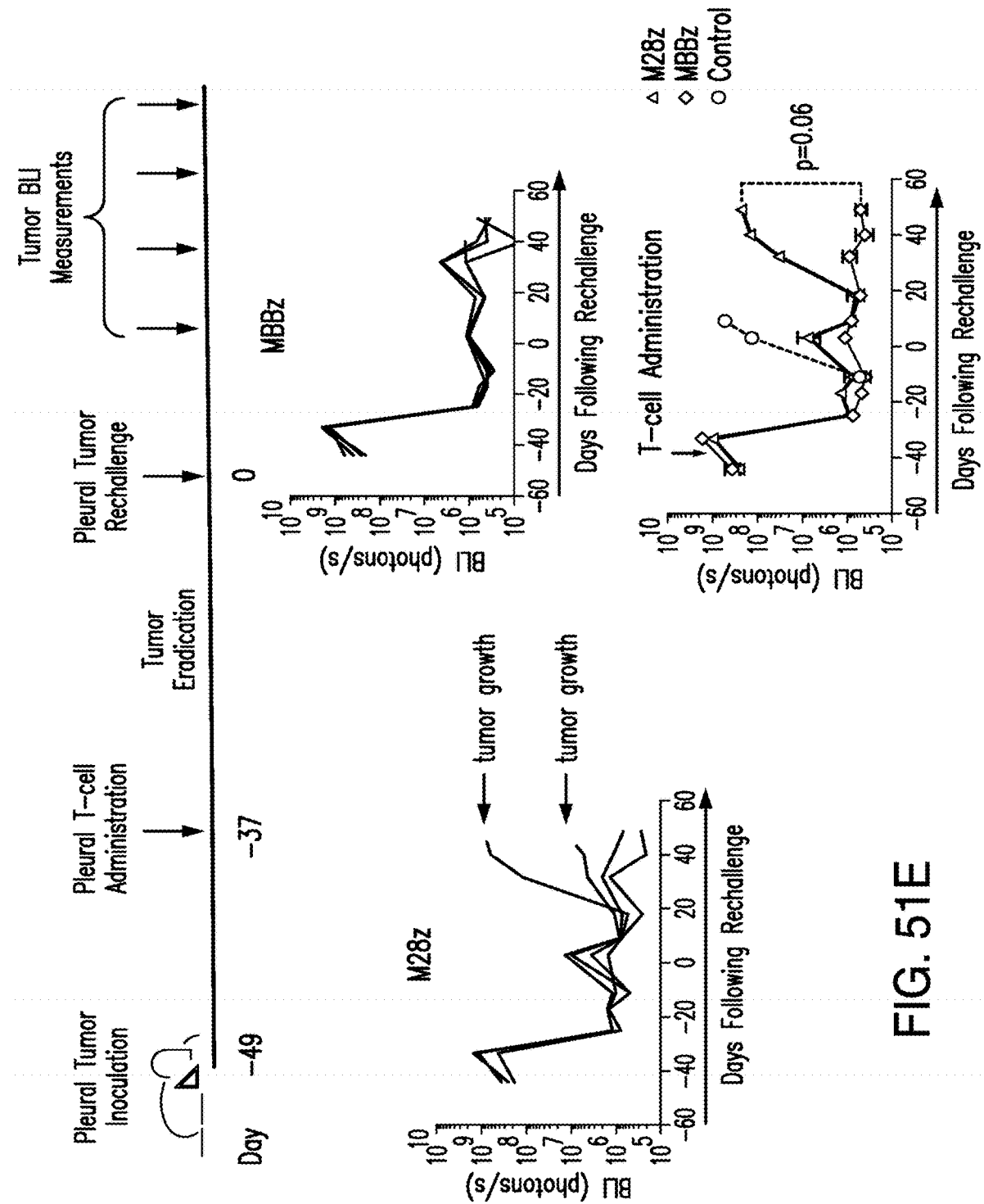

Having demonstrated inhibition of both the cytolytic function and effector cytokine secretion in costimulated CAR T cells exposed to antigen in vivo, the inventors reasoned that repeated antigen stimulation may, similar to models of chronic infection, play a role in T-cell inhibition and that differing abilities to retain function upon repeated antigen encounter might explain enhanced efficacy of MBBz CAR T cells. Therefore, Mz, M28z, and MBBz CAR T cells were tested for their ability to withstand repeated antigen encounter in an in vitro model system, wherein cells were assessed for proliferation, cytolytic function, and cytokine secretion upon MSLN+ antigen stimulation every 7 days. M28z and MBBz CAR T cells had similar abilities to expand upon serial MSLN+ stimulation, expanding to levels 14-fold greater than those of Mz CAR T cells; they lost the ability to expand following the third stimulation (FIG. 51). Both MBBz and M28z CAR T cells lost cytolytic function upon repeated antigen stimulation, although MBBz CAR T cells were better able to retain lytic function. Whereas lysis was equal among the three T-cell groups at the first stimulation, by the third stimulation, M28z lytic function was inhibited to a more pronounced level, such that MBBz CAR T cells had enhanced tumor lysis at multiple E:T ratios (FIG. 51B, right). Lytic function (as assessed by a degranulation assay measuring CD107a expression) at the third stimulation correlated with the results of chromium-release assays (FIG. 51C). Next, Th1 cytokine secretion was measured, and again, similar levels between M28z and MBBz CAR T cells at the first stimulation, as well as a successive decrease with each stimulation were noted. As with cytotoxicity, MBBz CAR T cells preferentially retained cytokine secretion; cytokine concentrations decreased >30-fold for M28z and only around 2-fold for MBBz CAR T cells, when levels at the first and second stimulations were compared (FIG. 51D). It was then confirmed the differences in cytokine production by measuring intracellular levels of cytokines at the second stimulation (data not shown). Reverse-transcriptase PCR analysis of CAR T cells at the time of antigen stimulation revealed that MBBz CAR T cells expressed markers that correlate with lower levels of exhaustion and inhibition, compared with M28z CAR T cells: MBBz CAR T cells expressed higher levels of Tbet and Eomesodermin and lower levels of PD1 and FoxP3 (FIG. 55). The inventors then sought to test the in vivo function of persisting CAR T cells that had already been exposed to tumor antigen, hypothesizing that, although quantitative persistence is equal between M28z and MBBz CAR T cells, MBBz CAR T cells would demonstrate enhanced function upon tumor rechallenge. Mice with established MSLN+ pleural tumors were administered intrapleural M28z or MBBz CAR T cells (at a dose of $1 \times 10^5$, E:T ratio 1:3000) to eradicate pleural tumor (FIG. 51E). Twenty days after the initial T-cell injection, tumor rechallenge was performed by injecting MSLN+ tumor cells ($1 \times 10^6$) into the pleural cavity of survivors; tumor burden was monitored using BLI. Persisting MBBz CAR T cells were better able to control tumor burden (4 of 4 MBBz-treated mice had a BLI signal at baseline levels vs. 2 of 4 M28z-treated mice) (FIG. 51E).

Tumor Cell PD-L1 Inhibits Mesothelin CAR T-Cell Effector Functions

Figure 52C:
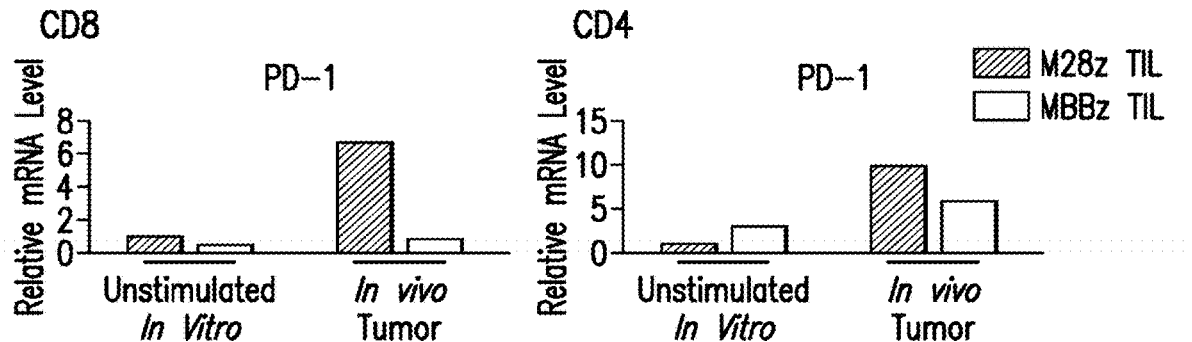
Figure 52D:
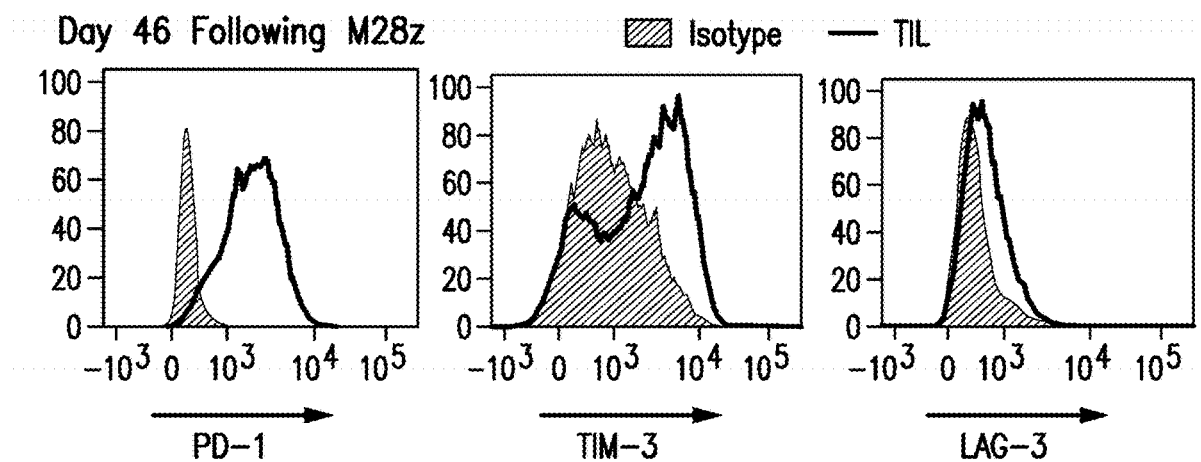
Figure 52E:
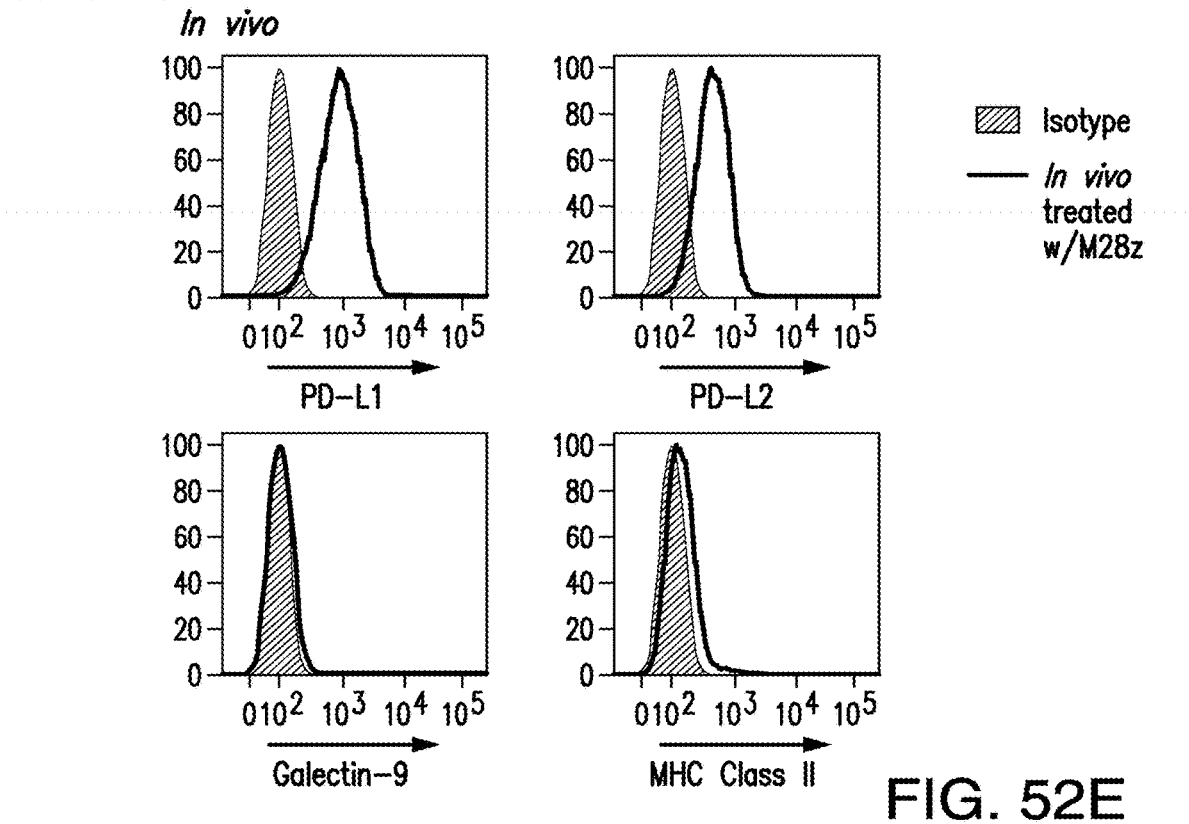
Figure 52F:
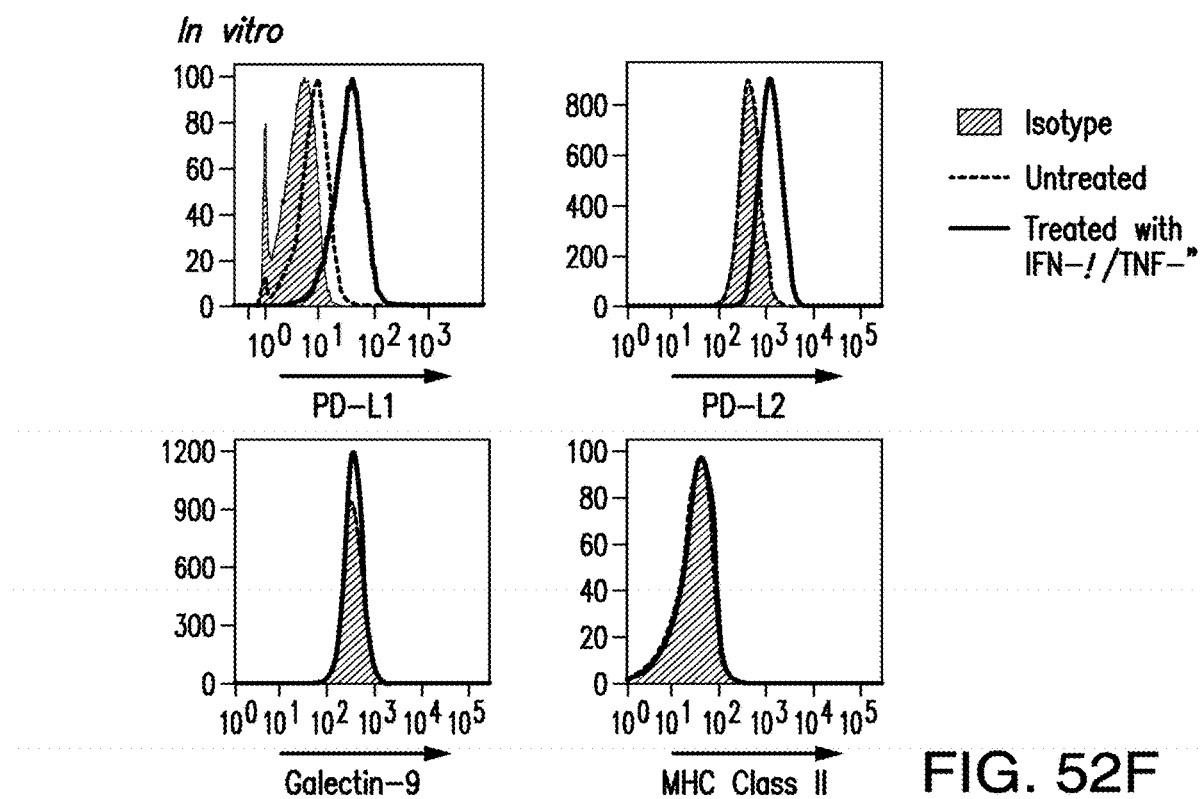
Figure 53A:
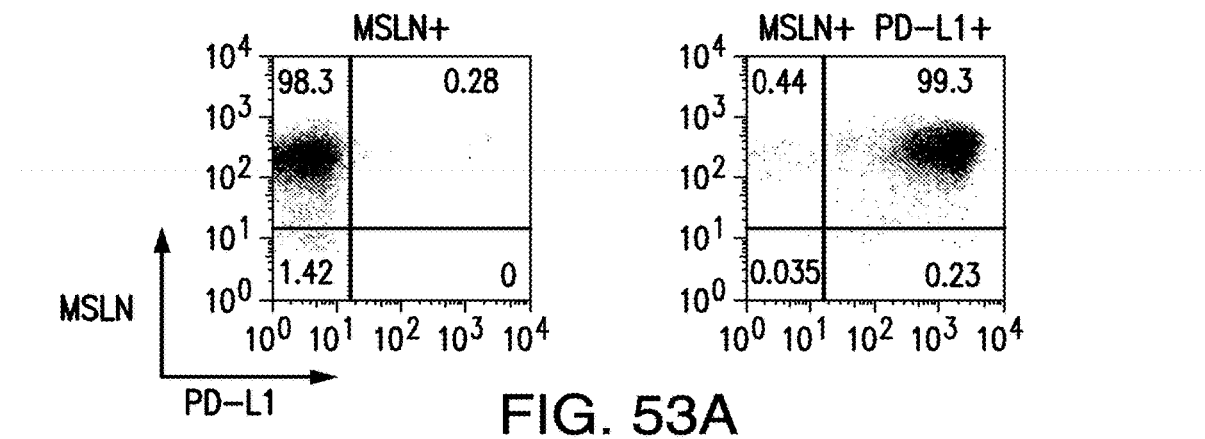
Figure 53B:
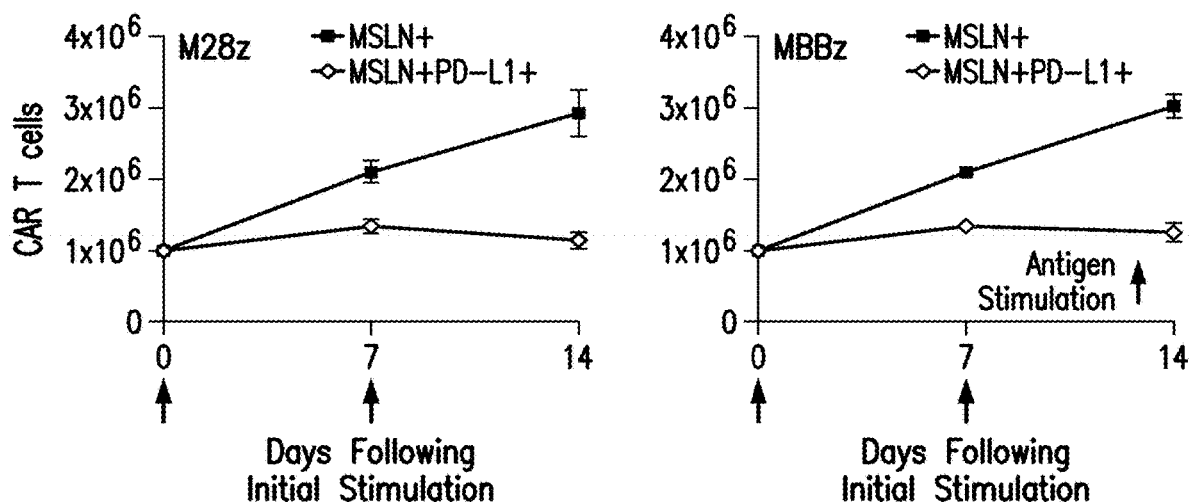
Figure 53C:
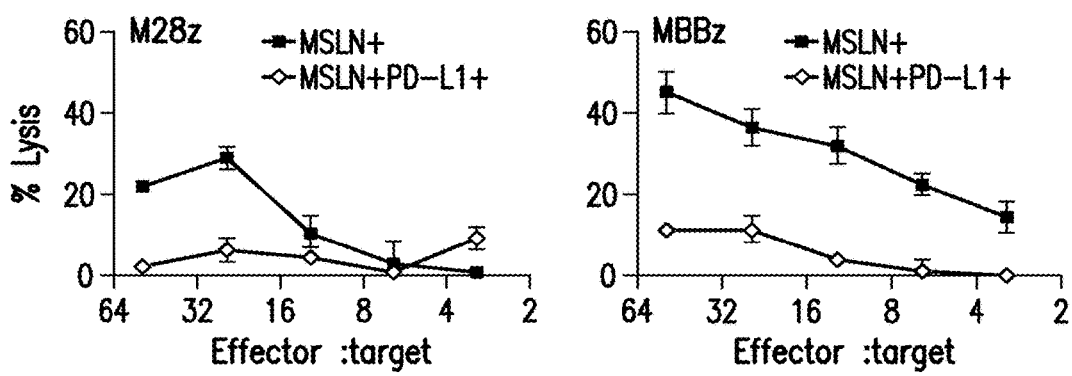
Figure 53D:
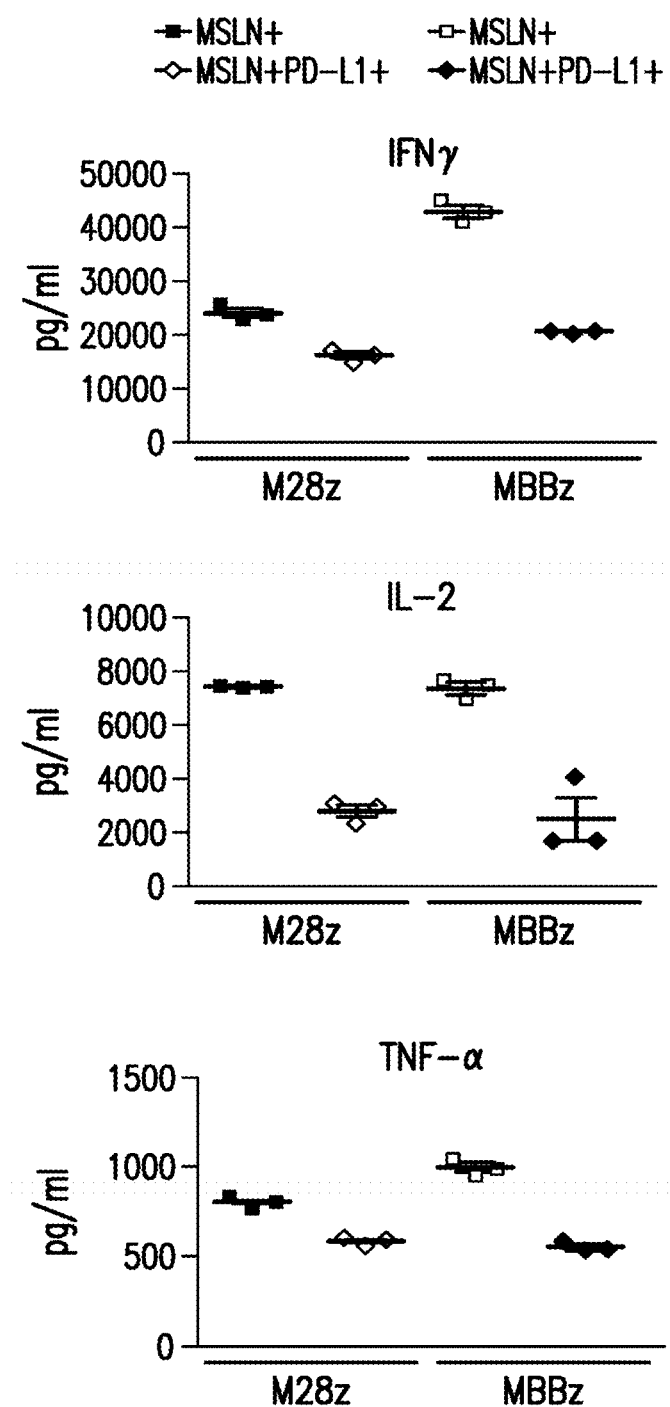

Having established that CAR T cells were inhibited by the in vivo tumor environment and that MBBz CAR T cells were better able to overcome this inhibition—at least in part because of their ability to retain function upon repeated antigen encounter—the inventors next sought to assess the role that inhibitory receptor and ligand pathways play in the model. The inventors started by staining tumor-infiltrating T cells, in M28z-treated mice with tumor progression, for the expression of well-known pathways of inhibition. We found high levels of expression of PD-1, Tim-3, and LAG-3 (FIG. 52A). Tumor-infiltrating MBBz CAR T cells harvested 6 days after administration demonstrated upregulation of inhibitory receptors as well, although they expressed significantly lower levels of PD-1 receptor at both the protein and the mRNA level (FIGS. 52B-52D). CD4+ T cells expressed higher levels of PD-1, compared with CD8+ T cells. A significant fraction of both M28z and MBBz CAR T cells were observed to coexpress PD-1 and LAG-3 or PD-1 and Tim-3, which suggests that multiple inhibitory pathways could be functioning simultaneously (FIG. 56). Next, tumor-expressed ligands: PD-L1 and PD-L2 (ligands for PD-1), galectin-9 (ligand for Tim-3), and MHC class II (ligand for LAG-3) were assessed. Only PD-1 ligands were expressed on pleural tumor cells harvested after intrapleural administration of M28z CAR T cells (FIG. 52E). As reported elsewhere[173,174], coculture of tumor cells with IFN-γ and TNF-α (at concentrations similar to those secreted by T cells in FIGS. 47 and 51) resulted in a similar level of upregulation of PD-L1 and PD-L2 expression on tumor cells (FIG. 52F), reflecting an adaptation of tumor cells to resist immune attack ("adaptive immunoresistance"). The unique presence of expression of both PD-1 receptor and ligand in vivo suggests that this pathway may play a significant inhibitory role. As some studies have suggested that costimulation may be sufficient to overcome inhibition by PD-1[191-193], the inventors next assessed whether overexpressed PD-L1 can inhibit CAR T-cell function in an in vitro model of PD-L1-mediated immuno inhibition (using 3T3 mouse fibroblasts transduced with either MSLN alone [MSLN+] or both MSLN and PD-L1 [MSLN+PD-L1+]) (FIG. 53A). In both M28z and MBBz CAR T cells, PD-L1 overexpression resulted in decreased accumulation upon successive stimulation (FIG. 53B) and Th1 effector cytokine secretion (FIG. 53D). Although tumor-cell lysis was not inhibited upon initial stimulation (data not shown), chromium release assay performed with 3T3s as targets following two stimulations against MSTO MSLN+ tumor cells demonstrates decreased lytic function in both M28z and MBBz CAR T cells, a higher extent of decrease in M28z CAR T cells (FIG. 53C). This result may be due to the differential upregulation of PD-1 on M28z and MBBz CAR T cells following exposure to MSTO MSLN+ tumor cells.

5. Discussion

The study presented herein demonstrates that even T cells expressing second generation CARs are inhibited upon in vivo antigen exposure within the tumor microenvironment. That several other studies report that costimulation alone can overcome tumor-expressed inhibitory signaling may be explained by their reliance on in vitro studies, their use of immuno sensitive in vivo models, and their administration of high T-cell doses that do not reflect the burdens of established solid tumors seen in patients[191-193]. In the experiments, higher T-cell doses result in tumor eradication regardless of a CD28 or 4-1BB costimulatory domain. It is at the lower T-cell doses (and resulting lower effector:target ratios) that the effect of exhaustion becomes apparent. These findings illustrate the importance of using clinically relevant in vivo models and T-cell doses that are similar to those used in patient trials. The intrapleural T-cell doses used ($4 \times 10^4$ to $1 \times 10^5$ per mouse equivalent to $1.2 \times 10^5$ to $3 \times 10^6$/Kg in human) are markedly lower doses than those used in other mesothelioma xenografts studies[194,195] and are comparable to those used in current clinical trials for hematologic malignancies[159,162] and solid tumors[196,197]. Therefore, the experimental strategy presented herein is particularly suited to characterize the role of exhaustion in CAR T-cell therapy.

In this report, although both 4-1BB and CD28 costimulatory signaling enhanced T-cell persistence to a similar degree—at lower E:T ratios, only treatment with 4-1BB-costimulated T cells eradicated tumor. 4-1BB-costimulated T cells, while still sensitive to tumor-mediated inhibition, were relatively resistant to decline in T-cell cytolytic function and cytokine secretion both following in vivo antigen exposure and upon repeated antigen stimulation in vitro. The resistance of 4-1BB signaling to immuno inhibition is associated with a more potent phenotype (PD-1$^{lo}$Tbet$^{hi}$, Eomesodermin$^{hi}$)[198-202], which has been linked to less exhaustion and a more robust cytotoxic effector response in other tumor models and the analogous model of chronic viral infection. This suggests that the criteria for selecting a particular costimulatory signaling strategy among the options available (i.e. 4-1BB, CD28, OX40L, 4-1BBL, CD27, etc.) should extend beyond T-cell persistence to "functional persistence," which is defined as the ability of T cells to function upon repeated antigen stimulation either initially within the tumor microenvironment or as may occur upon antigen rechallenge after control of primary tumor burden. As with the inventors' already published work supporting regional CAR T-cell therapy,[164] administering T cells of with high functional persistence enables single administrations of low T-cell doses which may serve to limit cytokine release syndromes yet still eradicate primary tumor. It is important to note that one should not conclude from these experiments that 4-1BB is the de facto costimulation agent to be used for patient therapy—the superior signaling pathway will depend on the unique patterns of costimulatory and coinhibitory ligand expression by the tumor, the antigen expression level or density, the affinity of scFv for the tumor antigen, the distance of the tumor epitope from the membrane, and variations in construct design (such as spacer and transmembrane domains)[158,203,207]. These variables—and not qualitative differences in signaling—may ultimately explain the variability seen in preclinical trials, which alternately conclude that 4-1BB or CD28 is superior, depending on the context. Indeed, the 4-1BB and CD28 constructs used in this report are sufficiently different in their transmembrane domains that conclusions determining the optimal costimulatory domain should not be made from this study.

Example 9—Efficacy of M28z CAT T Cells on Cells with Variable MSLN Expressions

The MSLN expression on cancer cells (e.g., A549, H1299 and EKVX lung cancer cells, MSTO mesothelioma cells and Hela cells) and normal cells (e.g., MRC5 cells) were evaluated by FACS. The results are shown in FIG. 57. The number of MSLN molecules per cell was quantified by quantibrite beads FACS analysis. The results are shown in FIG. 58. As shown in FIGS. 57 and 58, the MSLN-transduced A549Mmc and H1299Mmc cells had the highest MSLN expression, followed by MSLN-transduced EKVXM and MSTOGM (or "MGM") cells. Next, the MSLN mRNA expression analysis was performed on these lung and mesothelioma cells. The mRNA was extracted from cultured tumor cells and synthesized into cDNA. Taqman assay was performed for MSLN and B2-microglobulin was used as internal control. The results are represented in fold change relative to the MSLN mRNA expression in MRC-5 cells, as shown in FIG. 59. Consistent with the MSLN expression levels shown in FIGS. 57 and 58, the MSLN-transduced A549Mmc and H1299Mmc cells had the highest MSLN mRNA level, followed by MSLN-transduced EKVXM and MGM cells.

The cytotoxicity of T cells transduced with M28z CAR was determined by standard 51Cr-release assays, as previously described[220]. M28z CAR transduced T cells and cells with variable MSLN expression levels were incubated for 18 hours at different E:T ratios. P28z targeting PSMA antigen was used as a negative control. The results are shown in FIG. 60. As shown in FIG. 60, M28z CAR T cell cytotoxicity was MLSN antigen-dependent and proportional to the MSLN expression level. For example, the cytotoxicity of M28z CAR T cells on A549Mmc cells that had the highest MSLN expression level was the highest among all the tested cells. It was also noted that M28z CAR T cell cytotoxicity was not exactly proportional to the MSLN antigen intensity on the cell surface as the cytotoxicity may be influenced by several other factors, e.g., the amount of intracellular MSLN, expression of costimulatory or coinhibitory ligands on the cancer cell, cell size, duration of cancer cell/T-cell incubation in culture (which in turn influences coinhibitory ligand expression) and confluence of the cancer cells plated.

Example 10—Proliferation Capacity of M28z CAR T Cells

CAR T cell accumulation after repeated antigen stimulation in the presence of exogenous IL-2 as well as in the absence of IL-2 was determined. M28z CAR T cells were stimulated multiple times with varying cell lines expressing different level of MSLN (MRC5, EKVX, A549G, and A549GM) in the presence of IL-2. Ratio 10:1 was used and T cells were counted 7 days after stimulation. The results are shown in FIGS. 61 and 62. As shown in FIGS. 61A and 61B, CAR T-cell accumulation was proportional to the level of MSLN on tumor cells.

Example 11—In Vivo Efficacy of M28z CAR T Cells in Lung Cancer Model

To assess the efficacy of M28z CAR transduced T cells against lung cancer cells expressing low or high MSLN antigen expression in an orthotopic lung cancer model, immunodeficient NSG mice were injected intravenously with 1e6 A549 cells expressing the GFP-Firefly luciferase and either a low or high MSLN expression (A549G or A549GM respectively). Twenty-two days after tumor establishment, mice were treated intravenously with a single dose of 5e4 or 5e5 M28z CAR T cells (FIG. 63A). Anti-tumor efficacy was monitored by serial assessment of tumor burden by tumor bioluminescence imaging (BLI) (FIG. 63B) and Kaplan-Meier survival analysis (FIG. 63C). M28z CAR T cells were effective against high MSLN expressing cancer cells (A549GM) at both doses. M28z T cells were effective in delaying tumor burden progression and prolonging survival against low MSLN expressing A549G cells only at a higher dose of the two doses tested. Both doses used are much lower doses compared to conventional CAR T-cell experiments published. As a conclusion, M28z T cells were effective in controlling tumor burden in mice with low MSLN expressing cells (A549G) and eradicate tumors in mice with high antigen expressing cells (A549GM).

Figure 64A:
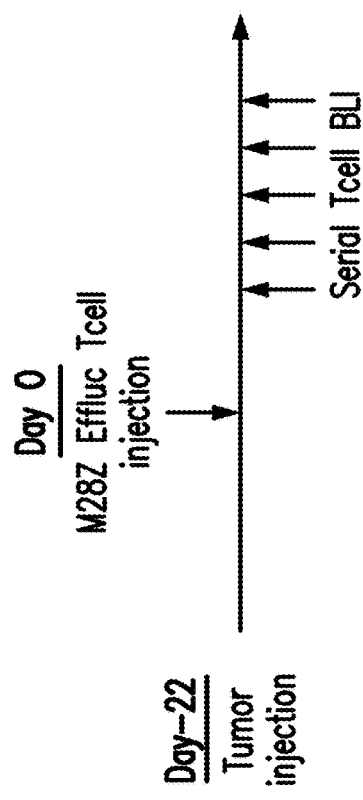
Figure 64B:
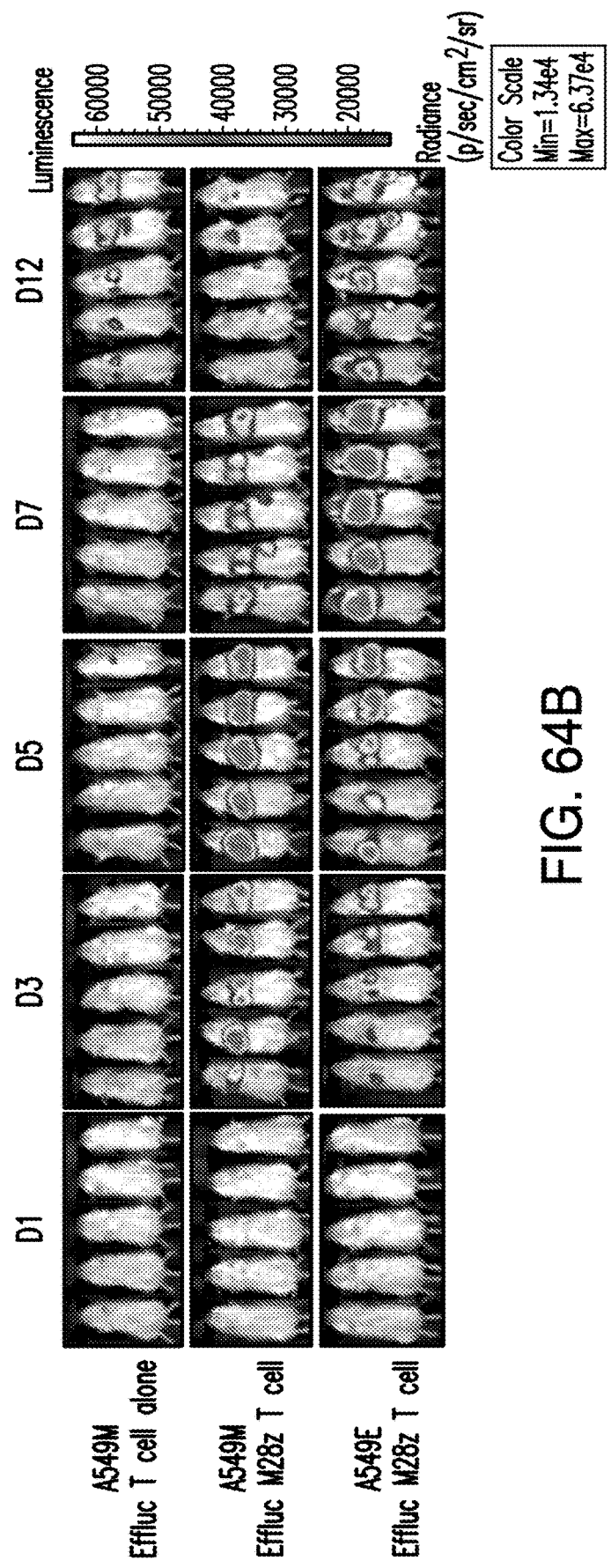
Figures 64C, 64D:
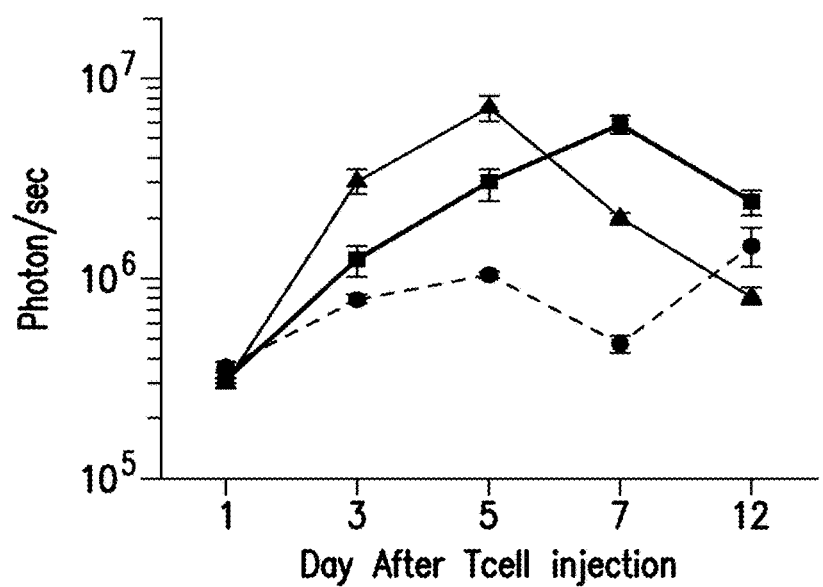

Immunodeficient NSG mice were injected intravenously with 1e6 A549E or A549 M cells (low and high MSLN expression respectively, no GFP-Luciferase) to establish lung cancer (FIG. 64A). Twenty-two days after tumor establishment, mice were treated intravenously with a single dose of 2e6 M28z CAR T-cell cotransduced with enhanced firefly luciferase (Effluc) to monitor T-cell accumulation in vivo. T-cell BLI was performed on days 1, 3, 5, 7 and 12 after T-cell injection (FIG. 64A). As shown in FIGS. 64B-64D, CAR T cells accumulated in a rapid fashion in mice with high MSLN expression (A549M), reached their peak by day 5 (at which time tumor is being eliminated) and then showed decreased accumulation. CAR T-cell accumulation progressed relatively at a low pace in mice with low MSLN expressing tumors (A549E), reached their peak on day 7. Thus, M28z CAR T-cell accumulation was dependent upon antigen expression level in lung cancer tumors.

REFERENCES

1. Carey, L., Winer, E., Viale, G., Cameron, D. & Gianni, L. Triple-negative breast cancer: disease entity or title of convenience? *Nature reviews. Clinical oncology* 7, 683-692 (2010).
2. Rakha, E. A., Reis-Filho, J. S. & Ellis, I. O. Basal-like breast cancer: a critical review. *J Clin Oncol* 26, 2568-2581 (2008).
3. Smid, M., et al. Subtypes of breast cancer show preferential site of relapse. *Cancer Res* 68, 3108-3114 (2008).
4. Dent, R., et al. Triple-negative breast cancer: clinical features and patterns of recurrence. *Clin Cancer Res* 13, 4429-4434 (2007).
5. Liedtke, C., et al. Response to neoadjuvant therapy and long-term survival in patients with triple-negative breast cancer. *J Clin Oncol* 26, 1275-1281 (2008).
6. Kuo, W. H., et al. Molecular characteristics and metastasis predictor genes of triple-negative breast cancer: a clinical study of triple-negative breast carcinomas. *PLoS One* 7, e45831 (2012).
7. Yau, C., et al. A multigene predictor of metastatic outcome in early stage hormone receptor-negative and triple-negative breast cancer. *Breast Cancer Res* 12, R85 (2010).
8. Kim, S. T., et al. Tumor-infiltrating Lymphocytes, Tumor Characteristics, and Recurrence in Patients With Early Breast Cancer. *Am J Clin Oncol* (2012).
9. Li, C. H., et al. Activation of regulatory T cells instigates functional down-regulation of cytotoxic T lymphocytes in human breast cancer. *Immunologic research* 51, 71-79 (2011).
10. Brentjens, R. J., et al. Safety and persistence of adoptively transferred autologous CD19-targeted T cells in patients with relapsed or chemotherapy refractory B-cell leukemias. *Blood* 118, 4817-4828 (2011).
11. Brentjens, R. J., et al. CD19-targeted T cells rapidly induce molecular remissions in adults with chemotherapy-refractory acute lymphoblastic leukemia. *Science translational medicine* 5, 177ra138 (2013).
12. Hunder, N. N., et al. Treatment of metastatic melanoma with autologous CD4+ T cells against NY-ESO-1. *N. Engl. J. Med.* 358, 2698-2703 (2008).
13. Rosenberg, S. A., Restifo, N. P., Yang, J. C., Morgan, R. A. & Dudley, M. E. Adoptive cell transfer: a clinical path to effective cancer immunotherapy. *Nat. Rev. Cancer* 8, 299-308 (2008).
14. Dudley, M. E., et al. Adoptive cell therapy for patients with metastatic melanoma: evaluation of intensive myeloablative chemoradiation preparative regimens. *J Clin Oncol* 26, 5233-5239 (2008).
15. Brentjens, R. J., et al. Genetically targeted T cells eradicate systemic acute lymphoblastic leukemia xenografts. *Clin. Cancer Res.* 13, 5426-5435 (2007).
16. Gade, T. P., et al. Targeted elimination of prostate cancer by genetically directed human T lymphocytes. *Cancer Res.* 65, 9080-9088 (2005).
17. Maher, J., Brentjens, R. J., Gunset, G., Riviere, I. & Sadelain, M. Human T-lymphocyte cytotoxicity and proliferation directed by a single chimeric TCRzeta/CD28 receptor. *Nat. Biotechnol.* 20, 70-75 (2002).
18. Kershaw, M. H., et al. Gene-engineered T cells as a superior adjuvant therapy for metastatic cancer. *J Immunol* 173, 2143-2150 (2004).
19. Sadelain, M., Brentjens, R. & Riviere, I. The promise and potential pitfalls of chimeric antigen receptors. *Curr Opin Immunol* (2009).
20. Hollyman, D., et al. Manufacturing validation of biologically functional T cells targeted to CD19 antigen for autologous adoptive cell therapy. *J Immunother* 32, 169-180 (2009).
21. Sadelain, M., Brentjens, R. & Riviere, I. The basic principles of chimeric antigen receptor design. *Cancer discovery* 3, 388-398 (2013).
22. Riviere, I., Sadelain, M. & Brentjens, R. J. Novel strategies for cancer therapy: the potential of genetically modified T lymphocytes. *Curr Hematol Rep* 3, 290-297 (2004).
23. Stephan, M. T., et al. T cell-encoded CD80 and 4-1BBL induce auto- and transco-stimulation, resulting in potent tumor rejection. *Nat. Med.* 13, 1440-1449 (2007).
24. Krause, A., et al. Antigen-dependent CD28 signaling selectively enhances survival and proliferation in genetically modified activated human primary T lymphocytes. *J Exp Med* 188, 619-626 (1998).
25. Gong, M. C., et al. Cancer patient T cells genetically targeted to prostate-specific membrane antigen specifically lyse prostate cancer cells and release cytokines in response to prostate-specific membrane antigen. *Neoplasia.* 1, 123-127 (1999).
26. Lyddane, C., et al. Cutting Edge: CD28 controls dominant regulatory T cell activity during active immunization. *J. Immunol.* 176, 3306-3310 (2006).
27. Ho, M., et al. Humoral immune response to mesothelin in mesothelioma and ovarian cancer patients. *Clin Cancer Res* 11, 3814-3820 (2005).
28. Hassan, R. & Ho, M. Mesothelin targeted cancer immunotherapy. *Eur J Cancer* 44, 46-53 (2008).
29. Zervos, M. D., Bizekis, C. & Pass, H. I. Malignant mesothelioma 2008. *Curr Opin Pulm Med* 14, 303-309 (2008).
30. Palumbo, C., Bei, R., Procopio, A. & Modesti, A. Molecular targets and targeted therapies for malignant mesothelioma. *Current medicinal chemistry* 15, 855-867 (2008).
31. Roe, O. D., et al. Mesothelin-related predictive and prognostic factors in malignant mesothelioma: a nested case-control study. *Lung Cancer* 61, 235-243 (2008).
32. Pass, H. I., et al. Soluble mesothelin-related peptide level elevation in mesothelioma serum and pleural effusions. *Ann Thorac Surg* 85, 265-272; discussion 272 (2008).
33. Rodriguez Portal, J. A., et al. Serum Levels of Soluble Mesothelin-Related Peptides in Malignant and Nonmalignant Asbestos-Related Pleural Disease: Relation with Past Asbestos Exposure. *Cancer Epidemiol Biomarkers Prev* (2009).
34. Bharadwaj, U., Li, M., Chen, C. & Yao, Q. Mesothelin-induced pancreatic cancer cell proliferation involves 35. Uehara, N., Matsuoka, Y. & Tsubura, A. Mesothelin promotes anchorage-independent growth and prevents anoikis via extracellular signal-regulated kinase signaling pathway in human breast cancer cells. *Mol Cancer Res* 6, 186-193 (2008).
34. ... alteration of cyclin E via activation of signal transducer and activator of transcription protein 3. *Mol Cancer Res* 6, 1755-1765 (2008).
36. Kaneko, O., et al. A Binding Domain on Mesothelin for CA125/MUC16. *J Biol Chem* 284, 3739-3749 (2009).
37. Servais, E. L., et al. Mesothelin overexpression promotes mesothelioma cell invasion and MMP-9 secretion in an orthotopic mouse model and in epithelioid pleural mesothelioma patients. *Clin Cancer Res* (2012); 18:2478-2489.
38. Wang, Y., Wang, L., Li, D., Wang, H. B. & Chen, Q. F. Mesothelin promotes invasion and metastasis in breast cancer cells. *J Int Med Res* 40, 2109-2116 (2012).
39. Wang, L., et al. Clinicopathological significance of mesothelin expression in invasive breast cancer. *J Int Med Res* 40, 909-916 (2012).
40. Wu, J. M., et al. Heterogeneity of breast cancer metastases: comparison of therapeutic target expression and promoter methylation between primary tumors and their multifocal metastases. *Clin Cancer Res* 14, 1938-1946 (2008).
41. Robinson, B. W., et al. Soluble mesothelin-related protein—a blood test for mesothelioma. *Lung Cancer* 49 Suppl 1, S109-S111 (2005).
42. Tajima, K., et al. ERC/mesothelin as a marker for chemotherapeutic response in patients with mesothelioma. *Anticancer Res* 28, 3933-3936 (2008).
43. Park, E. K., et al. Soluble mesothelin-related protein in an asbestos-exposed population: the dust diseases board cohort study. *Am J Respir Crit Care Med* 178, 832-837 (2008).
44. Segawa, T., et al. MESOMARK kit detects C-ERC/mesothelin, but not SMRP with C-terminus. *Biochem Biophys Res Commun* 369, 915-918 (2008).
45. Amati, M., et al. Profiling tumor-associated markers for early detection of malignant mesothelioma: an epidemiologic study. *Cancer Epidemiol Biomarkers Prev* 17, 163-170 (2008).
46. van den Heuvel, M. M., Korse, C. M., Bonfrer, J. M. & Baas, P. Non-invasive diagnosis of pleural malignancies: the role of tumour markers. Lung *Cancer* 59, 350-354 (2008).
47. Rizk, N. P., et al. Tissue and Serum Mesothelin Are Potential Markers of Neoplastic Progression in Barrett's Associated Esophageal Adenocarcinoma. *Cancer Epidemiol Biomarkers Prev* 21, 482-486 (2012).
48. Bera, T. K. & Pastan, I. Mesothelin is not required for normal mouse development or reproduction. *Mol Cell Biol* 20, 2902-2906 (2000).
49. Kelly, R. J., Sharon, E., Pastan, I. & Hassan, R. Mesothelin-targeted agents in clinical trials and in preclinical development. *Mol Cancer Ther* 11, 517-525 (2012).
50. Hassan, R., et al. Phase I study of SS1P, a recombinant anti-mesothelin immunotoxin given as a bolus I. V. infusion to patients with mesothelin-expressing mesothelioma, ovarian, and pancreatic cancers. *Clin Cancer Res* 13, 5144-5149 (2007).
51. Thomas, A. M., et al. Mesothelin-specific CD8(+) T cell responses provide evidence of in vivo cross-priming by antigen-presenting cells in vaccinated pancreatic cancer patients. *J. Exp. Med.* 200, 297-306 (2004).
52. Yokokawa, J., et al. Identification of novel human CTL epitopes and their agonist epitopes of mesothelin. *Clin Cancer Res* 11, 6342-6351 (2005).
53. Feng, Y., et al. A novel human monoclonal antibody that binds with high affinity to mesothelin-expressing cells and kills them by antibody-dependent cell-mediated cytotoxicity. *Mol Cancer Ther* (2009); 8:1113-1118.
54. Lanitis, E., et al. Redirected antitumor activity of primary human lymphocytes transduced with a fully human anti-mesothelin chimeric receptor. *Mol Ther* 20, 633-643 (2012).
55. Moon, E. K., et al. Expression of a functional CCR2 receptor enhances tumor localization and tumor eradication by retargeted human T cells expressing a mesothelin-specific chimeric antibody receptor. *Clin Cancer Res* 17, 4719-4730 (2011).
56. Zhao, Y., et al. Multiple injections of electroporated autologous T cells expressing a chimeric antigen receptor mediate regression of human disseminated tumor. *Cancer Res* 70, 9053-9061 (2010).
57. Riese, M. J., et al. Enhanced effector responses in activated CD8+ T cells deficient in diacylglycerol kinases. *Cancer Res* 73, 3566-3577 (2013).
58. Tchou, J., et al. Mesothelin, a novel immunotherapy target for triple negative breast cancer. *Breast Cancer Res Treat* 133, 799-804 (2012).
59. Boggio, K., et al. Ability of systemic interleukin-12 to hamper progressive stages of mammary carcinogenesis in HER2/neu transgenic mice. *Cancer Res* 60, 359-364 (2000).
60. Czerniecki, B. J., et al. Targeting HER-2/neu in early breast cancer development using dendritic cells with staged interleukin-12 burst secretion. *Cancer Res* 67, 1842-1852 (2007).
61. Nanni, P., et al. Combined allogeneic tumor cell vaccination and systemic interleukin 12 prevents mammary carcinogenesis in HER-2/neu transgenic mice. *J Exp Med* 194, 1195-1205 (2001).
62. Del Vecchio, M., et al. Interleukin-12: biological properties and clinical application. *Clin Cancer Res* 13, 4677-4685 (2007).
63. Wesa, A., Kalinski, P., Kirkwood, J. M., Tatsumi, T. & Storkus, W. J. Polarized type-1 dendritic cells (DC1) producing high levels of IL-12 family members rescue patient TH1-type antimelanoma CD4+ T cell responses in vitro. J Immunother 30, 75-82 (2007).
64. Curtsinger, J. M., Lins, D. C. & Mescher, M. F. Signal 3 determines tolerance versus full activation of naive CD8 T cells: dissociating proliferation and development of effector function. J Exp Med 197, 1141-1151 (2003).
65. Chmielewski, M., Kopecky, C., Hombach, A. A. & Abken, H. IL-12 release by engineered T cells expressing chimeric antigen receptors can effectively Muster an antigen-independent macrophage response on tumor cells that have shut down tumor antigen expression. *Cancer Res* 71, 5697-5706 (2011).
66. Voest, E. E., et al. Inhibition of angiogenesis in vivo by interleukin 12. *J Natl Cancer Inst* 87, 581-586 (1995).
67. Lenzi, R., et al. Phase I study of intraperitoneal recombinant human interleukin 12 in patients with Mullerian carcinoma, gastrointestinal primary malignancies, and mesothelioma. *Clin. Cancer Res.* 8, 3686-3695 (2002).
68. Lenzi, R., et al. Phase II study of intraperitoneal recombinant interleukin-12 (rhIL-12) in patients with peritoneal carcinomatosis (residual disease <1 cm) associated with ovarian cancer or primary peritoneal carcinoma. *J. Transl. Med.* 5, 66 (2007).

69. Mahvi, D. M., et al. Intratumoral injection of IL-12 plasmid DNA—results of a phase I/IB clinical trial. *Cancer Gene Ther.* 14, 717-723 (2007).
70. Kang, W. K., et al. Interleukin 12 gene therapy of cancer by peritumoral injection of transduced autologous fibroblasts: outcome of a phase I study. *Hum. Gene Ther.* 12, 671-684 (2001).
71. Brunda, M. J., et al. Antitumor and antimetastatic activity of interleukin 12 against murine tumors. *J Exp Med* 178, 1223-1230 (1993).
72. Gyorffy, S., Palmer, K., Podor, T. J., Hitt, M. & Gauldie, J. Combined treatment of a murine breast cancer model with type 5 adenovirus vectors expressing murine angiostatin and IL-12: a role for combined anti-angiogenesis and immunotherapy. *J Immunol* 166, 6212-6217 (2001).
73. Bramson, J. L., et al. Direct intratumoral injection of an adenovirus expressing interleukin-12 induces regression and long-lasting immunity that is associated with highly localized expression of interleukin-12. *Hum Gene Ther* 7, 1995-2002 (1996).
74. Sabel, M. S., Su, G., Griffith, K. A. & Chang, A. E. Intratumoral delivery of encapsulated IL-12, IL-18 and TNF-alpha in a model of metastatic breast cancer. *Breast Cancer Res Treat* 122, 325-336 (2010).
75. Eliopoulos, N., Francois, M., Boivin, M. N., Martineau, D. & Galipeau, J. Neo-organoid of marrow mesenchymal stromal cells secreting interleukin-12 for breast cancer therapy. *Cancer Res* 68, 4810-4818 (2008).
76. Bekaii-Saab, T. S., et al. A phase I trial of paclitaxel and trastuzumab in combination with interleukin-12 in patients with HER2/neu-expressing malignancies. *Molecular cancer therapeutics* 8, 2983-2991 (2009).
77. Dong, H., et al. Tumor-associated B7-H1 promotes T-cell apoptosis: a potential mechanism of immune evasion. *Nature medicine* 8, 793-800 (2002).
78. Spranger, S., et al. Up-Regulation of PD-L1, IDO, and Tregs in the Melanoma Tumor Microenvironment Is Driven by CD8+ T Cells. *Science translational medicine* 5, 200ra 116 (2013).
79. Brown, J. A., et al. Blockade of programmed death-1 ligands on dendritic cells enhances T cell activation and cytokine production. *Journal of immunology* 170, 1257-1266 (2003).
80. Ghebeh, H., et al. The B7-H1 (PD-L1) T lymphocyte-inhibitory molecule is expressed in breast cancer patients with infiltrating ductal carcinoma: correlation with important high-risk prognostic factors. *Neoplasia* 8, 190-198 (2006).
81. Ghebeh, H., et al. FOXP3+ Tregs and B7-H1+/PD-1+T lymphocytes co-infiltrate the tumor tissues of high-risk breast cancer patients: Implication for immunotherapy. *BMC cancer* 8, 57 (2008).
82. Crane, C. A., et al. PI(3) kinase is associated with a mechanism of immunoresistance in breast and prostate cancer. *Oncogene* 28, 306-312 (2009).
83. Ge, Y., Xi, H., Ju, S. & Zhang, X. Blockade of PD-1/PD-L1 immune checkpoint during DC vaccination induces potent protective immunity against breast cancer in hu-SCID mice. *Cancer letters* 336, 253-259 (2013).
84. Topalian, S. L., et al. Safety, activity, and immune correlates of anti-PD-1 antibody in cancer. *The New England journal of medicine* 366, 2443-2454 (2012).
85. Servais, E. L., et al. An in vivo platform for tumor biomarker assessment. *PLoS One* 6, e26722 (2011).
86. Servais, E. L., Colovos, C., Kachala, S. S. & Adusumilli, P. S. Pre-clinical mouse models of primary and metastatic pleural cancers of the lung and breast and the use of bioluminescent imaging to monitor pleural tumor burden. *Current protocols in pharmacology/editorial board, S. J. Enna* Chapter 14, Unit14 21 (2011).
87. Adusumilli, P. S., et al. Real-time diagnostic imaging of tumors and metastases by use of a replication-competent herpes vector to facilitate minimally invasive oncological surgery. *FASEB J.* 20, 726-728 (2006).
88. Adusumilli, P. S., et al. Virally-directed fluorescent imaging (VFI) can facilitate endoscopic staging. *Surg. Endosc.* 20, 628-635 (2006).
89. Eisenberg, D. P., et al. Real-time intraoperative detection of breast cancer axillary lymph node metastases using a green fluorescent protein-expressing herpes virus. *Ann. Surg.* 243, 824-830 (2006).
90. Eisenberg, D. P., et al. Real-time intraoperative detection of breast cancer axillary lymph node metastases using a green fluorescent protein-expressing herpes virus. *Ann Surg* 243, 824-830; discussion 830-822 (2006).
91. Servais, E. L., et al. Mesothelin overexpression promotes mesothelioma cell invasion and MMP-9 secretion in an orthotopic mouse model and in epithelioid pleural mesothelioma patients. *Clin Cancer Res* 18, 2478-2489 (2012).
92. Adusumilli, P. S., et al. Intraoperative localization of lymph node metastases with a 5 replication-competent herpes simplex virus. *J. Thorac. Cardiovasc. Surg.* 132, 1179-1188 (2006).
93. Adusumilli, P. S., et al. Imaging and therapy of malignant pleural mesothelioma using replication-competent herpes simplex viruses. *J. Gene Med.* 8, 603-615 (2006).
94. Di Stasi, A., et al. Inducible apoptosis as a safety switch for adoptive cell therapy. *N Engl J Med* 365, 1673-1683 (2011).
95. Davila, M. L., Kloss, C. C., Gunset, G. & Sadelain, M. CD19 CAR-targeted T cells induce long-term remission and B Cell Aplasia in an immunocompetent mouse model of B cell acute lymphoblastic leukemia. *PLoS One* 8, e61338 (2013).
96. Wolchok, J. D., et al. Nivolumab plus ipilimumab in advanced melanoma. *N Engl J Med* 369, 122-133 (2013).
97. Hamid, O., et al. Safety and tumor responses with lambrolizumab (anti-PD-1) in melanoma. *N Engl J Med* 369, 134-144 (2013).
98. Latouche, J. B. & Sadelain, M. Induction of human cytotoxic T lymphocytes by artificial antigen-presenting cells. *Nat. Biotechnol.* 18, 405-409 (2000).
99. Papanicolaou, G. A., et al. Rapid expansion of cytomegalovirus-specific cytotoxic T lymphocytes by artificial antigen-presenting cells expressing a single HLA allele. *Blood* 102, 2498-2505 (2003).
100. Pegram, H. J., et al. Tumor-targeted T cells modified to secrete IL-12 eradicate systemic tumors without need for prior conditioning. *Blood* (2012).
101. Pegram, H. J., et al. Tumor-targeted T cells modified to secrete IL-12 eradicate systemic tumors without need for prior conditioning. *Blood* 119, 4133-4141 (2012).
102. Lee, J. C., et al. In vivo inhibition of human CD19-targeted effector T cells by natural T regulatory cells in a xenotransplant murine model of B cell malignancy. *Cancer Res* 71, 2871-2881 (2011).
103. Santos, E. B., et al. Sensitive in vivo imaging of T cells using a membrane-bound Gaussia princeps luciferase. *Nat Med* 15, 338-344 (2009).
104. Ponomarev, V., et al. Imaging TCR-dependent NFAT-mediated T-cell activation with positron emission tomography in vivo. *Neoplasia* 3, 480-488 (2001).

105. Song, X., Davidian, M. & Tsiatis, A. A. A semiparametric likelihood approach to joint modeling of longitudinal and time-to-event data. *Biometrics* 58, 742-753 (2002).
106. Pogoda, K., Niwinska, A., Murawska, M. & Pienkowski, T. Analysis of pattern, time and risk factors influencing recurrence in triple-negative breast cancer patients. *Med Oncol* 30, 388 (2013).
107. Baselga, J., et al. Randomized phase II study of the anti-epidermal growth factor receptor monoclonal antibody cetuximab with cisplatin versus cisplatin alone in patients with metastatic triple-negative breast cancer. *J Clin Oncol* 31, 2586-2592 (2013).
108. Antony V B, Loddenkemper R, Astoul P, Boutin C, Goldstraw P, Hott J, Rodriguez Panadero F, Sahn S A. Management of malignant pleural effusions. Eur Respir J. 2001; 18:402-419.
109. Robinson B W, Musk A W, Lake R A. Malignant mesothelioma. Lancet. 2005; 366:397-408.
110. Anraku M, Cunningham K S, Yun Z, Tsao M S, Zhang L, Keshavjee S, Johnston M R, de P M. Impact of tumor-infiltrating T cells on survival in patients with malignant pleural mesothelioma. J Thorac Cardiovasc Surg. 2008; 135:823-829.
111. Yamada N, Oizumi S, Kikuchi E, Shinagawa N, Konishi-Sakakibara J, Ishimine A, Aoe K, Gemba K, Kishimoto T, Torigoe T, Nishimura M. CD8+ tumor-infiltrating lymphocytes predict favorable prognosis in malignant pleural mesothelioma after resection. Cancer Immunol Immunother. 2010; 59:1543-1549.
112. Suzuki K, Kadota K, Sima C S, Sadelain M, Rusch V W, Travis W D, Adusumilli P S. Chronic inflammation in tumor stroma is an independent predictor of prolonged survival in epithelioid malignant pleural mesothelioma patients. Cancer Immunol Immunother. 2011; 60:1721-1728.
113. Bograd A J, Suzuki K, Vertes E, Colovos C, Morales E A, Sadelain M, Adusumilli P S. Immune responses and immunotherapeutic interventions in malignant pleural mesothelioma. Cancer Immunol Immunother. 2011; 60:1509-1527.
114. Adusumilli P S. Translational immunotherapeutics: Chemoimmunotherapy for malignant pleural mesothelioma. Cancer. 2014
115. Kochenderfer J N, Dudley M E, Carpenter R O, Kassim S H, Rose J J, Telford W G, Hakim F T, Halverson D C, Fowler D H, Hardy N M, Mato A R, Hickstein D D, Gea-Banacloche J C, Pavletic S Z, Sportes C, Maric I, Feldman S A, Hansen B G, Wilder J S, Blacklock-Schuver B, Jena B, Bishop M R, Gress R E, Rosenberg S A. Donor-derived CD19-targeted T cells cause regression of malignancy persisting after allogeneic hematopoietic stem cell transplantation. Blood. 2013; 122:4129-4139.
116. Grupp S A, Kalos M, Barrett D, Aplenc R, Porter D L, Rheingold S R, Teachey D T, Chew A, Hauck B, Wright J F, Milone M C, Levine B L, June C H. Chimeric antigen receptor-modified T cells for acute lymphoid leukemia. N Engl J Med. 2013; 368:1509-1518.
117. Davila M L, Riviere I, Wang X, Bartido S, Park J, Curran K, Chung S S, Stefanski J, Borquez-Ojeda O, Olszewska M, Qu J, Wasielewska T, He Q, Fink M, Shinglot H, Youssif M, Satter M, Wang Y, Hosey J, Quintanilla H, Halton E, Bernal Y, Bouhassira D C, Arcila M E, Gonen M, Roboz G J, Maslak P, Douer D, Frattini M G, Giralt S, Sadelain M, Brentjens R. Efficacy and toxicity management of 19-28z CAR T cell therapy in B cell acute lymphoblastic leukemia. Science translational medicine. 2014; 6:224ra225.
118. Jensen M C, Riddell S R. Design and implementation of adoptive therapy with chimeric antigen receptor-modified T cells. Immunol Rev. 2014; 257:127-144.
119. Kachala S S, Bograd A J, Villena-Vargas J, Suzuki K, Servais E L, Kadota K, Chou J, Sima C S, Vertes E, Rusch V W, Travis W D, Sadelain M, Adusumilli P S. Mesothelin overexpression is a marker of tumor aggressiveness and is associated with reduced recurrence-free and overall survival in early-stage lung adenocarcinoma. Clin Cancer Res. 2014; 20:1020-1028.
120. Villena-Vargas J, Adusumilli P S. Mesothelin-targeted immunotherapies for malignant pleural mesothelioma. Annals of cardiothoracic surgery. 2012; 1:466-471.
121. Pastan I, Hassan R. Discovery of Mesothelin and Exploiting It as a Target for Immunotherapy. *Cancer Res.* 2014
122. Hassan R, Miller A C, Sharon E, Thomas A, Reynolds J C, Ling A, Kreitman R J, Miettinen M M, Steinberg S M, Fowler D H, Pastan I. Major cancer regressions in mesothelioma after treatment with an anti-mesothelin immunotoxin and immune suppression. Science translational medicine. 2013; 5:208ra147.
123. Carpenito C, Milone M C, Hassan R, Simonet J C, Lakhal M, Suhoski M M, Varela-Rohena A, Haines K M, Heitjan D F, Albelda S M, Carroll R G, Riley J L, Pastan I, June C H. Control of large, established tumor xenografts with genetically retargeted human T cells containing CD28 and CD137 domains. Proc Natl Acad Sci USA. 2009; 106:3360-3365.
124. Sallusto F, Lenig D, Forster R, Lipp M, Lanzavecchia A. Two subsets of memory T lymphocytes with distinct homing potentials and effector functions. Nature. 1999; 401:708-712.
125. Reits E A, Hodge J W, Herberts C A, Groothuis T A, Chakraborty M, Wansley E K, Camphausen K, Luiten R M, de Ru A H, Neij ssen J, Griekspoor A, Mesman E, Verreck F A, Spits H, Schlom J, van Veelen P, Neefjes J J. Radiation modulates the peptide repertoire, enhances MHC class I expression, and induces successful antitumor immunotherapy. J Exp Med. 2006; 203:1259-1271.
126. Formenti S C, Demaria S. Systemic effects of local radiotherapy. Lancet Oncol. 2009; 10:718-726.
127. Zamarin D, Holmgaard R B, Subudhi S K, Park J S, Mansour M, Palese P, Merghoub T, Wolchok J D, Allison J P. Localized oncolytic virotherapy overcomes systemic tumor resistance to immune checkpoint blockade immunotherapy. Science translational medicine. 2014; 6:226ra232.
128. Kitahara T, Watanabe O, Yamaura A, Makino H, Watanabe T, Suzuki G, Okumura K. Establishment of interleukin 2 dependent cytotoxic T lymphocyte cell line specific for autologous brain tumor and its intracranial administration for therapy of the tumor. Journal of neurooncology. 1987; 4:329-336.
129. Sigurdson E R, Ridge J A, Kemeny N, Daly J M. Tumor and liver drug uptake following hepatic artery and portal vein infusion. J Clin Oncol. 1987; 5:1836-1840.
130. Thom A K, Alexander H R, Andrich M P, Barker W C, Rosenberg S A, Fraker D L. Cytokine levels and systemic toxicity in patients undergoing isolated limb perfusion with high-dose tumor necrosis factor, interferon gamma, and melphalan. J Clin Oncol. 1995; 13:264-273.
131. Kawamata F, Kamachi H, Einama T, Homma S, Tahara M, Miyazaki M, Tanaka S, Kamiyama T, Nishihara H, Taketomi A, Todo S. Intracellular localization of meso- 132. Einama T, Homma S, Kamachi H, Kawamata F, Takahashi K, Takahashi N, Taniguchi M, Kamiyama T, Furukawa H, Matsuno Y, Tanaka S, Nishihara H, Taketomi A, Todo S. Luminal membrane expression of mesothelin is a prominent poor prognostic factor for gastric cancer. Br J Cancer. 2012; 107:137-142.
133. Hassan R, Laszik Z G, Lerner M, Raffeld M, Postier R, Brackett D. Mesothelin is overexpressed in pancreaticobiliary adenocarcinomas but not in normal pancreas and chronic pancreatitis. Am J Clin Pathol. 2005; 124:838-845.
134. Frierson H F, Jr, Moskaluk C A, Powell S M, Zhang H, Cerilli L A, Stoler M H, Cathro H, Hampton G M. Large-scale molecular and tissue microarray analysis of mesothelin expression in common human carcinomas. Hum Pathol. 2003; 34:605-609.
135. Argani P, Iacobuzio-Donahue C, Ryu B, Rosty C, Goggins M, Wilentz R E, Murugesan S R, Leach S D, Jaffee E, Yeo C J, Cameron J L, Kern S E, Hruban R H. Mesothelin is overexpressed in the vast majority of ductal adenocarcinomas of the pancreas: identification of a new pancreatic cancer marker by serial analysis of gene expression (SAGE) Clin Cancer Res. 2001; 7:3862-3868.
136. Louis C U, Savoldo B, Dotti G, Pule M, Yvon E, Myers G D, Rossig C, Russell H V, Diouf O, Liu E, Liu H, Wu M F, Gee A P, Mei Z, Rooney C M, Heslop H E, Brenner M K. Antitumor activity and long-term fate of chimeric antigen receptor-positive T cells in patients with neuroblastoma. Blood. 2011; 118:6050-6056.
137. Beatty G L, Haas A R, Maus M V, Torigian D A, Soulen M C, Plesa G, Chew A, Zhao Y, Levine B L, Albelda S M, Kalos M, June C H. Mesothelin-specific chimeric antigen receptor mRNA-engineered T cells induce anti-tumor activity in solid malignancies. Cancer *Immunol* Res. 2014; 2:112-120.
138. Engels B, Chervin A S, Sant A J, Kranz D M, Schreiber H. Long-term persistence of CD4(+) but rapid disappearance of CD8(+) T cells expressing an MHC class I-restricted TCR of nanomolar affinity. Mol Ther. 2012; 20:652-660.
139. Zhao Y, Bennett A D, Zheng Z, Wang Q J, Robbins P F, Yu L Y, Li Y, Molloy P E, Dunn S M, Jakobsen B K, Rosenberg S A, Morgan R A. High-affinity TCRs generated by phage display provide CD4+ T cells with the ability to recognize and kill tumor cell lines. J Immunol. 2007; 179:5845-5854.
140. Stone J D, Aggen D H, Schietinger A, Schreiber H, Kranz D M. A sensitivity scale for targeting T cells with chimeric antigen receptors (CARs) and bispecific T-cell Engagers (BiTEs) Oncoimmunology. 2012; 1:863-873.
141. Hassan R, Cohen S J, Phillips M, Pastan I, Sharon E, Kelly R J, Schweizer C, Weil S, Laheru D. Phase I clinical trial of the chimeric anti-mesothelin monoclonal antibody MORAb-009 in patients with mesothelin-expressing cancers. Clin Cancer Res. 2010; 16:6132-6138.
142. Hassan R, Kindler H L, Jahan T, Bazhenova L, Reck M, Thomas A, Pastan I, Parno J, O'Shannessy D J, Fatato P, Maltzman J D, Wallin B A. Phase II clinical trial of amatuximab, a chimeric anti-mesothelin antibody with pemetrexed and cisplatin in advanced unresectable pleural mesothelioma. Clin Cancer Res. 2014
143. Maus M V, Haas A R, Beatty G L, Albelda S M, Levine B L, Liu X, Zhao Y, Kalos M, June C H. T cells expressing chimeric antigen receptors can cause anaphylaxis in humans. Cancer Immunol Res. 2013; 1:26-31.
144. Wang X, Chang W C, Wong C W, Colcher D, Sherman M, Ostberg J R, Forman S J, Riddell S R, Jensen M C. A transgene-encoded cell surface polypeptide for selection, in vivo tracking, and ablation of engineered cells. Blood. 2011; 118:1255-1263.
145. Cooper L J, Ausubel L, Gutierrez M, Stephan S, Shakeley R, Olivares S, Serrano L M, Burton L, Jensen M C, Forman S J, DiGiusto D L. Manufacturing of gene-modified cytotoxic T lymphocytes for autologous cellular therapy for lymphoma. Cytotherapy. 2006; 8:105-117.
146. Kloss C C, Condomines M, Cartellieri M, Bachmann M, Sadelain M. Combinatorial antigen recognition with balanced signaling promotes selective tumor eradication by engineered T cells. Nat Biotechnol. 2013; 31:71-75.
147. Fedorov V D, Sadelain M, Kloss C C. Novel approaches to enhance the specificity and safety of engineered T cells. Cancer J. 2014; 20:160-165.
148. Fedorov V D, Themeli M, Sadelain M. PD-1- and CTLA-4-based inhibitory chimeric antigen receptors (iCARs) divert off-target immunotherapy responses. Science translational medicine. 2013; 5:215ra172.
149. Beatty G L, Haas A R, Maus M V, Torigian D A, Soulen M C, Plesa G, Chew A, Zhao Y, Levine B L, Albelda S M, Kalos M, June C H. Mesothelin-Specific Chimeric Antigen Receptor mRNA-Engineered T Cells Induce Antitumor Activity in Solid Malignancies. Cancer Immunol Res. 2014
150. Suzuki K, Servais E L, Rizk N P, Solomon S B, Sima C S, Park B J, Kachala S S, Zlobinsky M, Rusch V W, Adusumilli P S. Palliation and pleurodesis in malignant pleural effusion: the role for tunneled pleural catheters. J Thorac Oncol. 2011; 6:762-767.
151. van Herpen C M, van der Laak J A, de Vries I J, van Krieken J H, de Wilde P C, Balvers M G, Adema G J, De Mulder P H. Intratumoral recombinant human interleukin-12 administration in head and neck squamous cell carcinoma patients modifies locoregional lymph node architecture and induces natural killer cell infiltration in the primary tumor. Clin Cancer Res. 2005; 11:1899-1909.
152. Carpenter S G, Carson J, Fong Y. Regional liver therapy using oncolytic virus to target hepatic colorectal metastases. Semin Oncol. 2010; 37:160-169.
153. McCoy J L, Herberman R B, Rosenberg E B, Donnelly F C, Levine P H, Alford C. 51 Chromium-release assay for cell-mediated cytotoxicity of human leukemia and lymphoid tissue-culture cells. National Cancer Institute monograph. 1973; 37:59-67.
154. Stiles B M, Adusumilli P S, Bhargava A, Stanziale S F, Kim T H, Chan M K, Huq R, Wong R, Rusch V W, Fong Y. Minimally invasive localization of oncolytic herpes simplex viral therapy of metastatic pleural cancer. Cancer Gene Ther. 2006; 13:53-64.
155. Rabinovich B A, Ye Y, Etto T, Chen J Q, Levitsky H I, Overwijk W W, Cooper L J, Gelovani J, Hwu P. Visualizing fewer than 10 mouse T cells with an enhanced firefly luciferase in immunocompetent mouse models of cancer. Proc Natl Acad Sci USA. 2008; 105:14342-14346.
156. Na I K, Markley J C, Tsai J J, Yim N L, Beattie B J, Klose A D, Holland A M, Ghosh A, Rao U K, Stephan M T, Serganova I, Santos E B, Brentjens R J, Blasberg R G, Sadelain M, van den Brink M R. Concurrent visualization of trafficking, expansion, and activation of T lymphocytes and T-cell precursors in vivo. Blood. 2010; 116:e18-25.
157. Sadelain M, Riviere I, and Brentjens R. Targeting tumours with genetically enhanced T lymphocytes. Nat Rev Cancer. 2003; 3(1):35-45.

158. Sadelain M, Brentjens R, and Riviere I. The basic principles of chimeric antigen receptor design. *Cancer discovery*. 2013; 3(4):388-98.

159. Brentjens R J, Davila M L, Riviere I, Park J, Wang X, Cowell L G, Bartido S, Stefanski J, Taylor C, Olszewska M, et al. CD19-targeted T cells rapidly induce molecular remissions in adults with chemotherapy-refractory acute lymphoblastic leukemia. *Science translational medicine*. 2013; 5(177): 177ra38.

160. Brentjens R J, Riviere I, Park J H, Davila M L, Wang X, Stefanski J, Taylor C, Yeh R, Bartido S, Borquez-Ojeda O, et al. Safety and persistence of adoptively transferred autologous CD19-targeted T cells in patients with relapsed or chemotherapy refractory B-cell leukemias. *Blood*. 2011; 118(18):4817-28.

161. Davila M L, Riviere I, Wang X, Bartido S, Park J, Curran K, Chung S S, Stefanski J, Borquez-Ojeda O, Olszewska M, et al. Efficacy and toxicity management of 19-28z CAR T cell therapy in B cell acute lymphoblastic leukemia. *Science translational medicine*. 2014; 6(224): 224ra25.

162. Grupp S A, Kalos M, Barrett D, Aplenc R, Porter D L, Rheingold S R, Teachey D T, Chew A, Hauck B, Wright J F, et al. Chimeric antigen receptor-modified T cells for acute lymphoid leukemia. *N Engl J Med*. 2013; 368(16): 1509-18.

163. Kalos M, Levine B L, Porter D L, Katz S, Grupp S A, Bagg A, and June C H. T cells with chimeric antigen receptors have potent antitumor effects and can establish memory in patients with advanced leukemia. *Science translational medicine*. 2011; 3(95):95ra73.

164. Adusumilli P S, Cherkassky L, Villena-Vargas J, Colovos C, Servais E, Plotkin J, Jones D R, and Sadelain M. Regional delivery of mesothelin-targeted CAR T cell therapy generates potent and long-lasting CD4-dependent tumor immunity. *Science translational medicine*. 2014; 6(261):261ra151.

165. Argani P, Iacobuzio-Donahue C, Ryu B, Rosty C, Goggins M, Wilentz R E, Murugesan S R, Leach S D, Jaffee E, Yeo C J, et al. Mesothelin is overexpressed in the vast majority of ductal adenocarcinomas of the pancreas: identification of a new pancreatic cancer marker by serial analysis of gene expression (SAGE). *Clin Cancer Res*. 2001; 7(12):3862-8.

166. Frierson H F, Jr., Moskaluk C A, Powell S M, Zhang H, Cerilli L A, Stoler M H, Cathro H, and Hampton G M. Large-scale molecular and tissue microarray analysis of mesothelin expression in common human carcinomas. *Hum Pathol*. 2003; 34(6):605-9.

167. Gubbels J A, Belisle J, Onda M, Rancourt C, Migneault M, Ho M, Bera T K, Connor J, Sathyanarayana B K, Lee B, et al. Mesothelin-MUC 16 binding is a high affinity, N-glycan dependent interaction that facilitates peritoneal metastasis of ovarian tumors. *Mol Cancer*. 2006; 5(1):50.

168. Kachala S S, Bograd A J, Villena-Vargas J, Suzuki K, Servais E L, Kadota K, Chou J, Sima C S, Vertes E, Rusch V W, et al. Mesothelin overexpression is a marker of tumor aggressiveness and is associated with reduced recurrence-free and overall survival in early-stage lung adenocarcinoma. *Clin Cancer Res*. 2014; 20(4):1020-8.

169. Li M, Bharadwaj U, Zhang R, Zhang S, Mu H, Fisher W E, Brunicardi F C, Chen C, and Yao Q. Mesothelin is a malignant factor and therapeutic vaccine target for pancreatic cancer. *Mol Cancer Ther*. 2008; 7(2):286-96.

170. Rizk N P, Servais E L, Tang L H, Sima C S, Gerdes H, Fleisher M, Rusch V W, and Adusumilli P S. Tissue and serum mesothelin are potential markers of neoplastic progression in Barrett's associated esophageal adenocarcinoma. *Cancer epidemiology, biomarkers & prevention: a publication of the American Association for Cancer Research, cosponsored by the American Society of Preventive Oncology*. 2012; 21(3):482-6.

171. Servais E L, Colovos C, Rodriguez L, Bograd A J, Nitadori J, Sima C, Rusch V W, Sadelain M, and Adusumilli P S. Mesothelin overexpression promotes mesothelioma cell invasion and MMP-9 secretion in an orthotopic mouse model and in epithelioid pleural mesothelioma patients. *Clinical cancer research: an official journal of the American Association for Cancer Research*. 2012; 18(9):2478-89.

172. Tozbikian G, Brogi E, Kadota K, Catalano J, Akram M, Patil S, Ho A Y, Reis-Filho J S, Weigelt B, Norton L, et al. Mesothelin expression in triple negative breast carcinomas correlates significantly with basal-like phenotype, distant metastases and decreased survival. *PLoS One*. 2014; 9(12):e114900.

173. McGray A J, Hallett R, Bernard D, Swift S L, Zhu Z, Teoderascu F, Vanseggelen H, Hassell J A, Hurwitz A A, Wan Y, et al. Immunotherapy-induced CD8(+) T Cells Instigate Immune Suppression in the Tumor. *Molecular therapy: the journal of the American Society of Gene Therapy*. 2014; 22(1):206-18.

174. Spranger S, Spaapen R M, Zha Y, Williams J, Meng Y, Ha T T, and Gajewski T F. Up-regulation of PD-L1, IDO, and T(regs) in the melanoma tumor microenvironment is driven by CD8(+) T cells. *Science translational medicine*. 2013; 5(200):200ra116.

175. Moon E K, Wang L C, Dolfi D V, Wilson C B, Ranganathan R, Sun J, Kapoor V, Scholler J, Pure E, Milone M C, et al. Multifactorial T-cell hypofunction that is reversible can limit the efficacy of chimeric antigen receptor-transduced human T cells in solid tumors. *Clin Cancer Res*. 2014; 20(16):4262-73.

176. Hodi F S, O'Day S J, McDermott D F, Weber R W, Sosman J A, Haanen J B, Gonzalez R, Robert C, Schadendorf D, Hassel J C, et al. Improved survival with ipilimumab in patients with metastatic melanoma. *The New England journal of medicine*. 2010; 363(8):711-23.

177. Wolchok J D, Kluger H, Callahan M K, Postow M A, Rizvi N A, Lesokhin A M, Segal N H, Ariyan C E, Gordon R A, Reed K, et al. Nivolumab plus ipilimumab in advanced melanoma. *N Engl J Med*. 2013; 369(2):122-33.

178. Topalian S L, Hodi F S, Brahmer J R, Gettinger S N, Smith D C, McDermott D F, Powderly J D, Carvajal R D, Sosman J A, Atkins M B, et al. Safety, activity, and immune correlates of anti-PD-1 antibody in cancer. *The New England journal of medicine*. 2012; 366(26):2443-54.

179. Ji R R, Chasalow S D, Wang L, Hamid O, Schmidt H, Cogswell J, Alaparthy S, Berman D, Jure-Kunkel M, Siemers N O, et al. An immune-active tumor microenvironment favors clinical response to ipilimumab. *Cancer Immunol Immunother*. 2012; 61(7):1019-31.

180. Rizvi N A, Hellmann M D, Snyder A, Kvistborg P, Makarov V, Havel J J, Lee W, Yuan J, Wong P, Ho T S, et al. Cancer immunology. Mutational landscape determines sensitivity to PD-1 blockade in non-small cell lung cancer. *Science*. 2015; 348(6230):124-8.

181. Hamid O, Schmidt H, Nissan A, Ridolfi L, Aamdal S, Hansson J, Guida M, Hyams D M, Gomez H, Bastholt L, et al. A prospective phase II trial exploring the association between tumor microenvironment biomarkers and clinical activity of ipilimumab in advanced melanoma. *Journal of translational medicine*. 2011; 9(204.

182. Nesbeth Y C, Martinez D G, Toraya S, Scarlett U K, Cubillos-Ruiz J R, Rutkowski M R, and Conejo-Garcia J R. CD4+ T cells elicit host immune responses to MHC class II-negative ovarian cancer through CCL5 secretion and CD40-mediated licensing of dendritic cells. *Journal of immunology.* 2010; 184(10):5654-62.

183. Spear P, Barber A, and Sentman C L. Collaboration of chimeric antigen receptor (CAR)-expressing T cells and host T cells for optimal elimination of established ovarian tumors. *Oncoimmunology.* 2013; 2(4):e23564.

184. John L B, Devaud C, Duong C P, Yong C S, Beavis Pa., Haynes N M, Chow M T, Smyth M J, Kershaw M H, and Darcy P K. Anti-PD-1 antibody therapy potently enhances the eradication of established tumors by gene-modified T cells. *Clin Cancer Res.* 2013; 19(20):5636-46.

185. Strome S E, Dong H, Tamura H, Voss S G, Flies D B, Tamada K, Salomao D, Cheville J, Hirano F, Lin W, et al. B7-H1 blockade augments adoptive T-cell immunotherapy for squamous cell carcinoma. *Cancer research.* 2003; 63(19):6501-5.

186. Feng Y, Xiao X, Zhu Z, Streaker E, Ho M, Pastan I, and Dimitrov D S. A novel human monoclonal antibody that binds with high affinity to mesothelin-expressing cells and kills them by antibody-dependent cell-mediated cytotoxicity. *Mol Cancer Ther.* 2009; 8(5):1113-8.

187. Brentjens R J, Santos E, Nikhamin Y, Yeh R, Matsushita M, La Perle K, Quintas-Cardama A, Larson S M, and Sadelain M. Genetically targeted T cells eradicate systemic acute lymphoblastic leukemia xenografts. *Clin Cancer Res.* 2007; 13(18 Pt 1):5426-35.

188. Servais E L, Colovos C, Kachala S S, and Adusumilli P S. Pre-clinical mouse models of primary and metastatic pleural cancers of the lung and breast and the use of bioluminescent imaging to monitor pleural tumor burden. *Current protocols in pharmacology/editorial board, SJ Enna.* 2011; Chapter 14 (Unit14 21.

189. Servais E L, Suzuki K, Colovos C, Rodriguez L, Sima C, Fleisher M, Rusch V W, Sadelain M, and Adusumilli P S. An in vivo platform for tumor biomarker assessment. *PLoS One.* 2011; 6(10):e26722.

190. Adusumilli P S, Stiles B M, Chan M K, Mullerad M, Eisenberg D P, Ben-Porat L, Huq R, Rusch V W, and Fong Y. Imaging and therapy of malignant pleural mesothelioma using replication-competent herpes simplex viruses. *The journal of gene medicine.* 2006; 8(5):603-15.

191. Carter L, Fouser L A, Jussif J, Fitz L, Deng B, Wood C R, Collins M, Honjo T, Freeman G J, and Carreno B M. PD-1:PD-L inhibitory pathway affects both CD4(+) and CD8(+) T cells and is overcome by IL-2. *European journal of immunology.* 2002; 32(3):634-43.

192. Freeman G J, Long A J, Iwai Y, Bourque K, Chernova T, Nishimura H, Fitz L J, Malenkovich N, Okazaki T, Byrne M C, et al. Engagement of the PD-1 immunoinhibitory receptor by a novel B7 family member leads to negative regulation of lymphocyte activation. *The Journal of experimental medicine.* 2000; 192(7): 1027-34.

193. Koehler H, Kofler D, Hombach A, and Abken H. CD28 costimulation overcomes transforming growth factor-beta-mediated repression of proliferation of redirected human CD4+ and CD8+ T cells in an antitumor cell attack. Cancer research. 2007; 67(5):2265-73.

194. Carpenito C, Milone M C, Hassan R, Simonet J C, Lakhal M, Suhoski M M, Varela-Rohena A, Haines K M, Heitjan D F, Albelda S M, et al. Control of large, established tumor xenografts with genetically retargeted human T cells containing CD28 and CD137 domains. *Proc Natl Acad Sci USA.* 2009; 106(9):3360-5.

195. Zhao Y, Moon E, Carpenito C, Paulos C M, Liu X, Brennan A L, Chew A, Carroll R G, Scholler J, Levine B L, et al. Multiple injections of electroporated autologous T cells expressing a chimeric antigen receptor mediate regression of human disseminated tumor. *Cancer Res.* 2010; 70(22):9053-61.

196. Louis C U, Savoldo B, Dotti G, Pule M, Yvon E, Myers G D, Rossig C, Russell H V, Diouf O, Liu E, et al. Antitumor activity and long-term fate of chimeric antigen receptor-positive T cells in patients with neuroblastoma. *Blood.* 2011; 118(23):6050-6.

197. Beatty G L, Haas A R, Maus M V, Torigian D A, Soulen M C, Plesa G, Chew A, Zhao Y, Levine B L, Albelda S M, et al. Mesothelin-specific chimeric antigen receptor mRNA-engineered T cells induce anti-tumor activity in solid malignancies. *Cancer Immunol Res.* 2014; 2(2):112-20.

198. Curran M A, Geiger T L, Montalvo W, Kim M, Reiner S L, Al-Shamkhani A, Sun J C, and Allison J P. Systemic 4-1BB activation induces a novel T cell phenotype driven by high expression of Eomesodermin. *J Exp Med.* 2013; 210(4):743-55.

199. Hirschhorn-Cymerman D, Budhu S, Kitano S, Liu C, Zhao F, Zhong H, Lesokhin A M, Avogadri-Connors F, Yuan J, Li Y, et al. Induction of tumoricidal function in CD4+ T cells is associated with concomitant memory and terminally differentiated phenotype. *J Exp Med.* 2012; 209(11):2113-26.

200. Song C, Sadashivaiah K, Furusawa A, Davila E, Tamada K, and Banerjee A. Eomesodermin is required for antitumor immunity mediated by 4-1BB-agonist immunotherapy. Oncoimmunology. 2014; 3(1):e27680.

201. Schietinger A, Delrow J J, Basom R S, Blattman J N, and Greenberg P D. Rescued tolerant CD8 T cells are preprogrammed to reestablish the tolerant state. Science. 2012; 335(6069):723-7.

202. Kao C, Oestreich K J, Paley M A, Crawford A, Angelosanto J M, Ali M A, Intlekofer A M, Boss J M, Reiner S L, Weinmann A S, et al. Transcription factor T-bet represses expression of the inhibitory receptor PD-1 and sustains virus-specific CD8+ T cell responses during chronic infection. *Nature immunology.* 2011; 12(7):663-71.

203. James S E, Greenberg P D, Jensen M C, Lin Y, Wang J, Till B G, Raubitschek A A, Forman S J, and Press O W. Antigen sensitivity of CD22-specific chimeric TCR is modulated by target epitope distance from the cell membrane. *Journal of immunology.* 2008; 180(10):7028-38.

204. James S E, Greenberg P D, Jensen M C, Lin Y, Wang J, Budde L E, Till B G, Raubitschek A A, Forman S J, and Press O W. Mathematical modeling of chimeric TCR triggering predicts the magnitude of target lysis and its impairment by TCR downmodulation. *Journal of immunology.* 2010; 184(8):4284-94.

205. Watanabe K, Terakura S, Martens A C, van Meerten T, Uchiyama S, Imai M, Sakemura R, Goto T, Hanajiri R, Imahashi N, et al. Target Antigen Density Governs the Efficacy of Anti-CD20-CD28-CD3 zeta Chimeric Antigen Receptor-Modified Effector C D8+ T Cells. *Journal of immunology.* 2015; 194(3):911-20.

206. Hombach A A, Schildgen V, Heuser C, Finnern R, Gilham D E, and Abken H. T cell activation by antibody-like immunoreceptors: the position of the binding epitope within the target molecule determines the efficiency of activation of redirected T cells. *Journal of immunology.* 2007; 178(7):4650-7.

207. Chmielewski M, Hombach A, Heuser C, Adams G P, and Abken H. T cell activation by antibody-like immunoreceptors: increase in affinity of the single-chain fragment domain above threshold does not increase T cell activation against antigen-positive target cells but decreases selectivity. *Journal of immunology.* 2004; 173 (12):7647-53.

208. Foster A E, Dotti G, Lu A, Khalil M, Brenner M K, Heslop H E, Rooney C M, and Bollard C M. Antitumor activity of EBV-specific T lymphocytes transduced with a dominant negative TGF-beta receptor. *Journal of immunotherapy.* 2008; 31(5):500-5.

209. Bollard C M, Rossig C, Calonge M J, Huls M H, Wagner H J, Massague J, Brenner M K, Heslop H E, and Rooney C M. Adapting a transforming growth factor beta-related tumor protection strategy to enhance antitumor immunity. *Blood.* 2002; 99(9):3179-87.

210. Long A H, Haso W M, Shern J F, Wanhainen K M, Murgai M, Ingaramo M, Smith J P, Walker A J, Kohler M E, Venkateshwara V R, et al. 4-1BB costimulation ameliorates T cell exhaustion induced by tonic signaling of chimeric antigen receptors. *Nat Med.* 2015.

211. Barber D L, Wherry E J, Masopust D, Zhu B, Allison J P, Sharpe A H, Freeman G J, and Ahmed R. Restoring function in exhausted CD8 T cells during chronic viral infection. *Nature.* 2006; 439(7077):682-7.

212. Mueller S N, and Ahmed R. High antigen levels are the cause of T cell exhaustion during chronic viral infection. *Proceedings of the National Academy of Sciences of the United States of America.* 2009; 106(21):8623-8.

213. Riese M J, Wang L C, Moon E K, Joshi R P, Ranganathan A, June C H, Koretzky G A, and Albelda S M. Enhanced effector responses in activated CD8+ T cells deficient in diacylglycerol kinases. *Cancer Res.* 2013; 73(12):3566-77.

214. Brentjens R J, Latouche J B, Santos E, Marti F, Gong M C, Lyddane C, King P D, Larson S, Weiss M, Riviere I, et al. Eradication of systemic B-cell tumors by genetically targeted human T lymphocytes co-stimulated by CD80 and interleukin-15. *Nat Med.* 2003; 9(3):279-86.

215. Gade T P, Hassen W, Santos E, Gunset G, Saudemont A, Gong M C, Brentjens R, Zhong X S, Stephan M, Stefanski J, et al. Targeted elimination of prostate cancer by genetically directed human T lymphocytes. *Cancer research.* 2005; 65(19):9080-8.

216. Zhong X S, Matsushita M, Plotkin J, Riviere I, and Sadelain M. Chimeric antigen receptors combining 4-1BB and CD28 signaling domains augment PI3kinase/AKT/Bcl-X L activation and CD8+ T cell-mediated tumor eradication. *Mol Ther.* 2010; 18(2):413-20.

217. Markley J C, and Sadelain M. IL-7 and IL-21 are superior to IL-2 and IL-15 in promoting human T cell-mediated rejection of systemic lymphoma in immunodeficient mice. *Blood.* 2010; 115(17):3508-19.

218. Papapetrou E P, Tomishima M J, Chambers S M, Mica Y, Reed E, Menon J, Tabar V, Mo Q, Studer L, and Sadelain M. Stoichiometric and temporal requirements of Oct4, Sox2, Klf4, and c-Myc expression for efficient human iPSC induction and differentiation. *Proceedings of the National Academy of Sciences of the United States of America.* 2009; 106(31): 12759-64.

219. Hollyman D, Stefanski J, Przybylowski M, Bartido S, Borquez-Ojeda O, Taylor C, Yeh R, Capacio V, Olszewska M, Hosey J, et al. Manufacturing validation of biologically functional T cells targeted to CD19 antigen for autologous adoptive cell therapy. *J Immunother.* 2009; 32(2):169-80.

220. McCoy J L, Herberman R B, Rosenberg E B, Donnelly F C, Levine P H, and Alford C. 51 Chromium-release assay for cell-mediated cytotoxicity of human leukemia and lymphoid tissue-culture cells. *National Cancer Institute monograph.* 1973; 37(59-67.

From the foregoing description, it will be apparent that variations and modifications may be made to the invention described herein to adopt it to various usages and conditions. Such embodiments are also within the scope of the following claims.

All patents and publications and sequences referred to by accession or reference number mentioned in this specification are herein incorporated by reference to the same extent as if each independent patent and publication and sequence was specifically and individually indicated to be incorporated by reference.

What is claimed is:

1. A method of reducing mesothelin-expressing tumor burden in a subject and/or increasing survival of a subject having a mesothelin-expressing neoplasm, comprising administering to the subject in need thereof an effective amount of T cells comprising a chimeric antigen receptor (CAR), wherein the CAR comprises an extracellular antigen-binding domain, a transmembrane domain, and an intracellular domain, wherein the extracellular antigen-binding domain specifically binds to human mesothelin comprises: (a) a heavy chain variable region comprising a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 13; and (b) a light chain variable region comprising a CDR1 comprising the amino acid sequence set forth in SEQ ID NO:14, a CDR2 comprising the amino acid sequence set forth in SEQ ID NO:15, and a CDR3 comprising the amino acid sequence set forth in SEQ ID NO: 16.

2. The method of claim 1, wherein the extracellular antigen-binding domain recognizes human mesothelin with a mesothelin expression level of about 1,000 or more mesothelin binding sites/cell.

3. The method of claim 1, wherein (a) the heavy chain variable region comprises an amino acid sequence that is at least about 95% identical to amino acids 1-119 of SEQ ID NO: 1, wherein SEQ ID NOS: 11, 12, and 13 are invariable; and/or (b) the light chain variable region comprises an amino acid sequence that is at least about 95% identical to amino acids 1-107 of SEQ ID NO:3, wherein SEQ ID NOS: 14, 15, and 16 are invariable.

4. The method of claim 1, wherein (a) the heavy chain variable region comprises amino acids 1-119 of SEQ ID NO: 1, and/or (b) the light chain variable region comprises amino acids 1-107 of SEQ ID NO:3.

5. The method of claim 1, wherein the extracellular antigen-binding domain comprises the heavy chain variable region sequence and the light chain variable region sequence of an scFv consisting of the amino acid sequence set forth in SEQ ID NO:7.

6. The method of claim 1, wherein the extracellular antigen-binding domain comprises a single-chain variable fragment (scFv).

7. The method of claim 6, wherein the scFv is a human scFv.

8. The method of claim 6, wherein the scFv comprises the amino acid sequence set forth in SEQ ID NO: 7.

9. The method of claim 1, wherein a linker is positioned between the heavy chain variable region and the light chain variable region.

10. The method of claim 9, wherein the linker comprises the amino acid sequence set forth in SEQ ID NO: 17.

11. The method of claim 1, wherein the transmembrane domain comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, a BTLA polypeptide, or a combination thereof.

12. The method of claim 11, wherein the transmembrane domain comprises a CD28 polypeptide.

13. The method of claim 1, wherein the intracellular domain comprises a CD3ζ polypeptide.

14. The method of claim 1, wherein the intracellular domain further comprises at least one co-stimulatory signaling region.

15. The method of claim 14, wherein the at least one co-stimulatory signaling region comprises a CD28 polypeptide, a 4-1BB polypeptide, an OX40 polypeptide, an ICOS polypeptide, or a combination thereof.

16. The method of claim 1, wherein the intracellular domain comprises (i) a CD3ζ polypeptide and a co-stimulatory signaling domain comprising a CD28 polypeptide, or (ii) a CD3ζ polypeptide and a co-stimulatory signaling domain comprising a 4-1BB polypeptide.

17. The method of claim 1, wherein the T cell is selected from the group consisting of a cytotoxic T lymphocyte (CTL), a regulatory T cell, and combinations thereof.

18. The method of claim 1, wherein the T cell is a $CD4^+$ T cell or a $CD8^+$ T cell.

19. The method of claim 1, wherein the method reduces the number of tumor cells, reduces tumor size, and/or eradicates the tumor in the subject.

20. The method of claim 1, wherein the tumor or neoplasm is a solid tumor.

21. The method of claim 20, wherein the solid tumor is selected from the group consisting of mesothelioma, lung cancer, pancreatic cancer, ovarian cancer, breast cancer, colon cancer, pleural tumor, glioblastoma, esophageal cancer, gastric cancer, synovial sarcoma, thymic carcinoma, endometrial carcinoma, stomach cancer, cholangiocarcinoma, and a combination thereof.

22. The method of claim 1, wherein the cells are administered to the subject intrapleurally.

23. The method of claim 1, wherein the effective amount is at least about $1 \times 10^5$ of the cells.

24. The method of claim 1, further comprising administering at least one immunomodulatory agent.

25. The method of claim 24, wherein the at least one immunomodulatory agent is selected from the group consisting of immunostimulatory agents, checkpoint immune blockade agents, radiation therapy agents, chemotherapy agents, and combinations thereof.

26. The method of claim 25, wherein the immunostimulatory agent is selected from the group consisting of IL-12, an agonist costimulatory monoclonal antibody, and combinations thereof.

27. The method of claim 26, wherein the immunostimulatory agent is IL-12.

28. The method of claim 26, wherein the agonist costimulatory monoclonal antibody is selected from the group consisting of an anti-4-1BB antibody, an anti-OX40 antibody, an anti-ICOS antibody, and combinations thereof.

29. The method of claim 28, wherein the agonist costimulatory monoclonal antibody is an anti-4-1BB antibody.

30. The method of claim 25, wherein the checkpoint immune blockade agent is selected from the group consisting of anti-PD-L1 antibodies, anti-CTLA-4 antibodies, anti-PD-1 antibodies, anti-LAG3 antibodies, anti-B7-H3 antibodies, anti-TIM3 antibodies, and combinations thereof.

31. The method of claim 30, wherein the checkpoint immune blockade agent is an anti-PD-L1 antibody.

\* \* \* \* \*